US008465915B2

(12) United States Patent
Song et al.

(10) Patent No.: US 8,465,915 B2
(45) Date of Patent: Jun. 18, 2013

(54) METHOD FOR ISOLATION OF TRANSCRIPTION TERMINATION SEQUENCES

(75) Inventors: Hee-Sook Song, Raleigh, NC (US); Michael Kock, Schifferstadt (DE); Jeffrey A. Brown, Apex, NC (US); Linda Patricia Loyall, Mannheim (DE); Liqun Xing, Chapel Hill, NC (US); Hongmei Jia, Apex, NC (US); John McMillan, Raleigh, NC (US); Lesley Ireland, Morrisville, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 1437 days.

(21) Appl. No.: 11/659,126

(22) PCT Filed: Jul. 30, 2005

(86) PCT No.: PCT/EP2005/008285
§ 371 (c)(1),
(2), (4) Date: Feb. 1, 2007

(87) PCT Pub. No.: WO2006/013072
PCT Pub. Date: Feb. 9, 2006

(65) Prior Publication Data

US 2007/0243543 A1 Oct. 18, 2007

Related U.S. Application Data

(60) Provisional application No. 60/598,001, filed on Aug. 2, 2004, provisional application No. 60/696,209, filed on Jul. 1, 2005.

(51) Int. Cl.
*C12Q 1/68* (2006.01)

(52) U.S. Cl.
USPC ........ 435/6.1

(58) Field of Classification Search
None
See application file for complete search history.

(56) References Cited

U.S. PATENT DOCUMENTS 5,168,064 A * 12/1992 Bennett et al. ........ 435/411
5,358,649 A * 10/1994 MacLennan et al. ........ 435/6
6,127,604 A * 10/2000 Dale et al. ........ 800/298
6,248,581 B1 * 6/2001 Gicquel et al. ........ 435/320.1

FOREIGN PATENT DOCUMENTS

WO WO-01/73087 10/2001
WO WO 0173087 A1 * 10/2001

OTHER PUBLICATIONS

Padidam et al. (Biotechniques. Aug. 2001;31(2):328-30, 332-4).*

Hasegawa, et al., "In Vitro Analysis of Transcription Initiation and Termination from the *Lhcb1* Gene Family in *Nicotiana sylvestris*: Detection of Transcription Termination Sites", Plant Journal, 2003, vol. 33, pp. 1063-1072.

Yonaha, et al., "Specific Transcriptional Pausing Activates Polyadenylation in a Coupled in Vitro System", *Molecular Cell*, 1999, vol. 3, pp. 593-600.

Liu, et al., "Real-Time Monitoring in Vitro Transcription Using Molecular Beacons", Analytical Biochemistry, 2002, vol. 300, pp. 40-45.

Matzke, et al., "Homology-Dependent Gene Silencing in Transgenic Plants: Epistatic Silencing Loci Contain Multiple Copies of Methylated Transgenes", Mol. Gen. Genet., 1994, vol. 244, pp. 219-229.

An, et al., "Functional Analysis of the 3' Control Region of the Potato Wound-Inducible Proteinase Inhibitor II Gene", Plant Cell, 1989, vol. 1, pp. 115-122.

Yonaha, et al., "Transcriptional Termination and Coupled Polyadenylation in Vitro", EMBO Journal, 2000, vol. 19, No. 14, pp. 3770-3777.

Padidam, et al., "Elimination of Transcriptional Interference between Tandem Genes in Plant Cells", BioTechniques, 2001, vol. 31, No. 2, pp. 328-334.

Ali, S., et al., "The 3' Non-Coding Region of a C4 Photosynthesis Gene Increases Transgene Expression When Combined with Heterologous Promoters", Plant Molecular Biology, 2001, vol. 46, pp. 325-333.

"*Oryza sativa* chromosome 10 clone OSJNBb0089A17,* Sequencing in Progress *, 12 Unordered Pieces", EMBL Database Accession No. AC079890, Sep. 19, 2000.

"*Oryza sativa* Genomic DNA, Chromosome 6, BAC Clone: OJ1226_A12, Working Draft Sequence, 1 Ordered Pieces", EMBL Database Accession No. AP004008, Aug. 21, 2001.

* cited by examiner

*Primary Examiner* — Christopher M. Babic
(74) *Attorney, Agent, or Firm* — Novak Druce Connolly Bove + Quigg LLP

(57) ABSTRACT

The invention relates to efficient, high-throughput methods, systems, and DNA constructs for identification and isolation of transcription termination sequences. The invention relates further to specific terminator sequences identified by the methods isolated from rice.

16 Claims, 22 Drawing Sheets

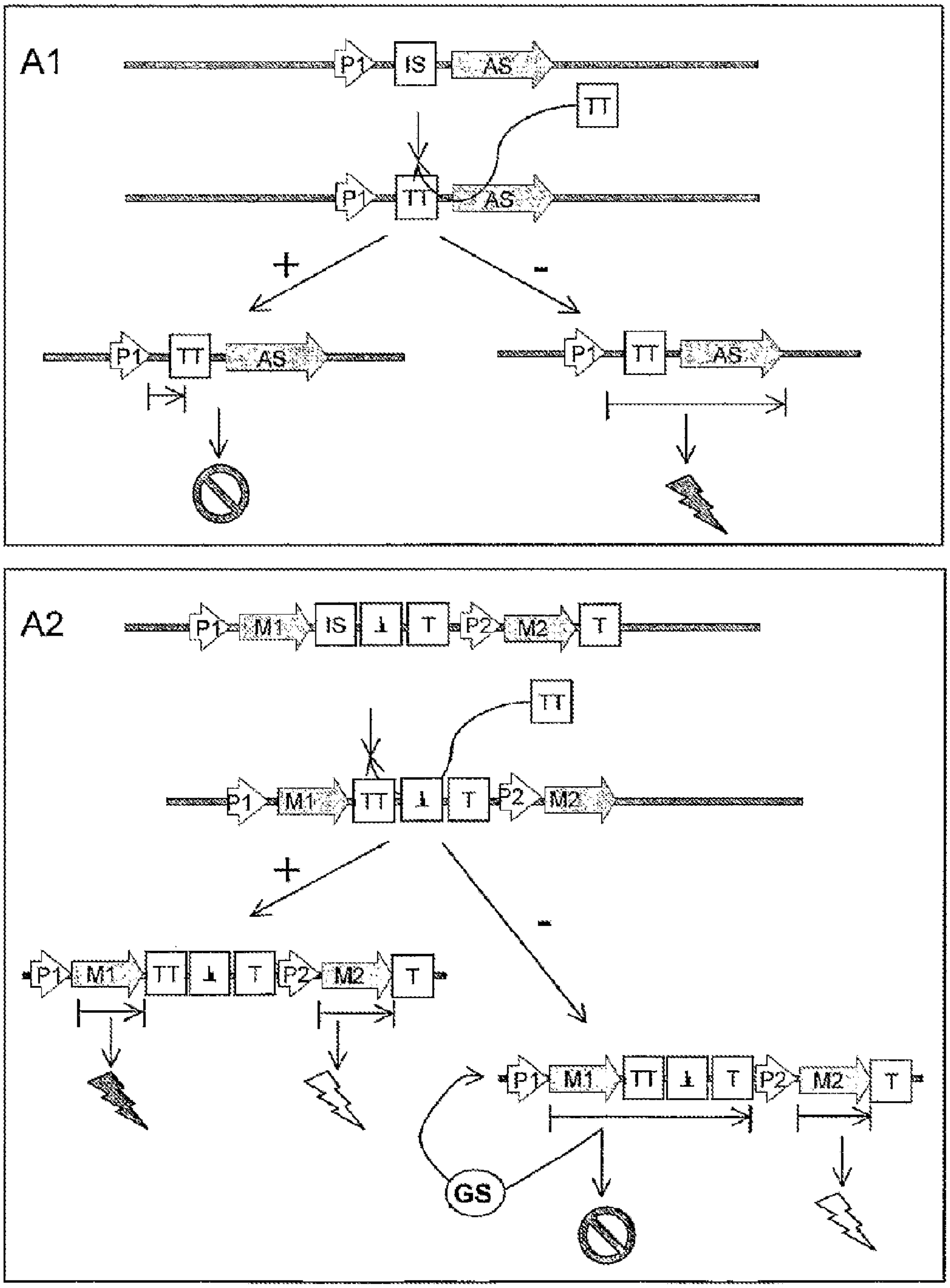
Fig. 1-A

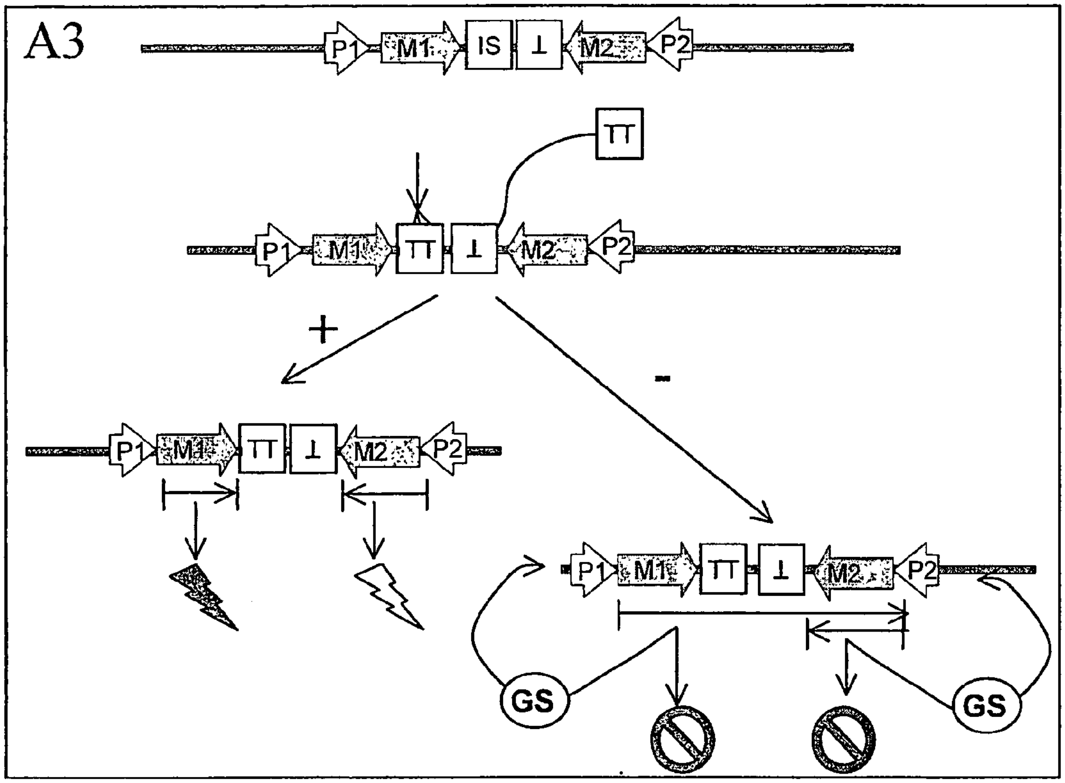
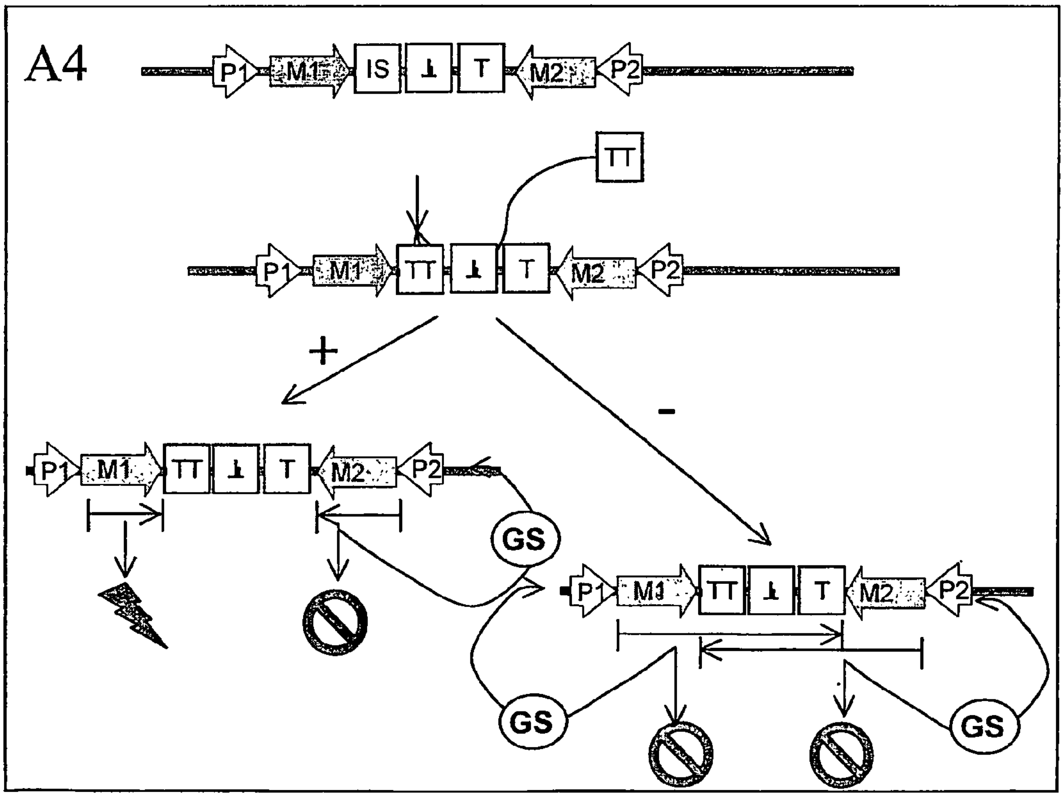
Fig. 1-B

Lo484-pENTR-A1-inv-35s-GFP-E9

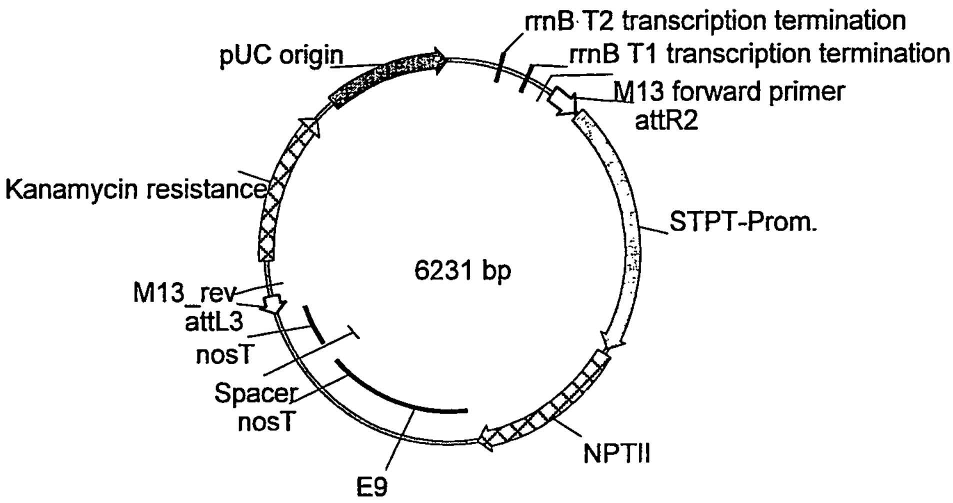
Lo522a-pENTR-C1-R2-STPT-nptII-E9-IRnos-L3
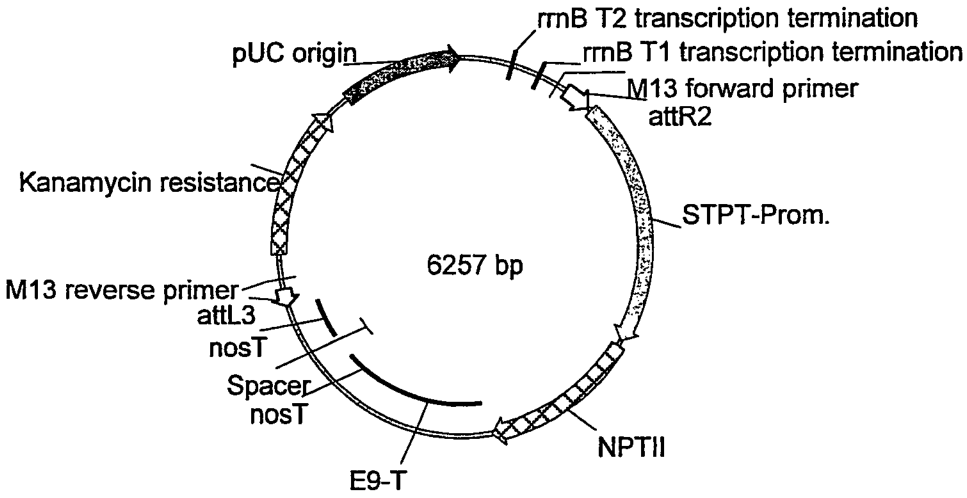
Lo522b-pENTR-C1-R2-STPT-nptII-E9-IRnos-L3
Fig. 6

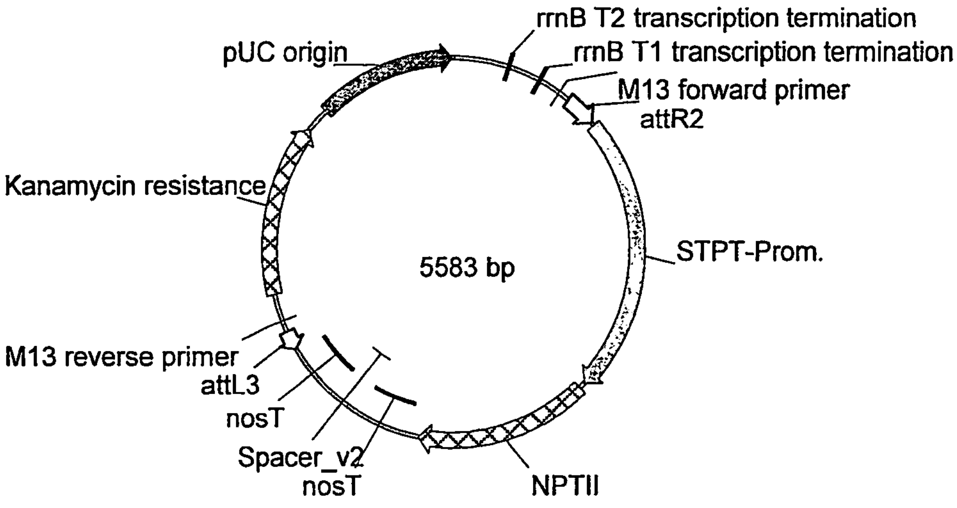
Lo503b-pENTR-C1-R2-STPT-nptII-IRnos-L3
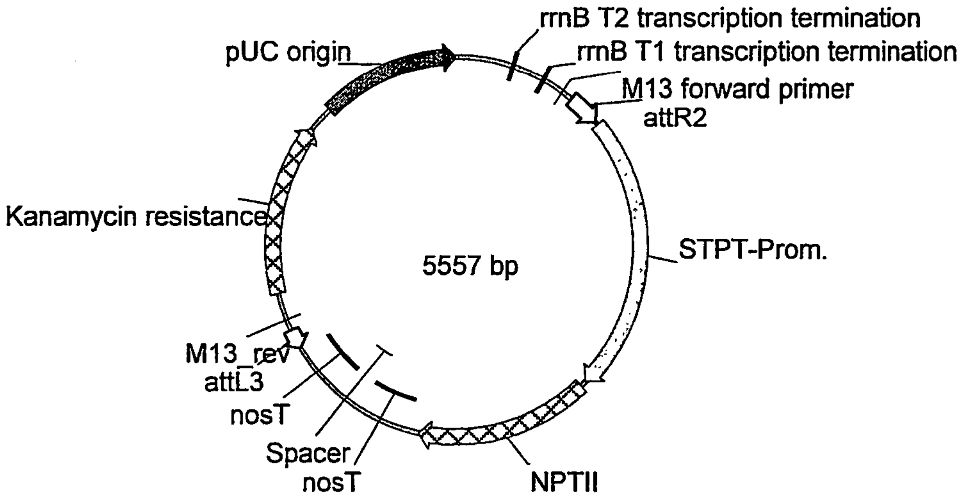
Lo503a-pENTR-C1-R2-STPT-nptII-IRnos-L3
Fig. 7

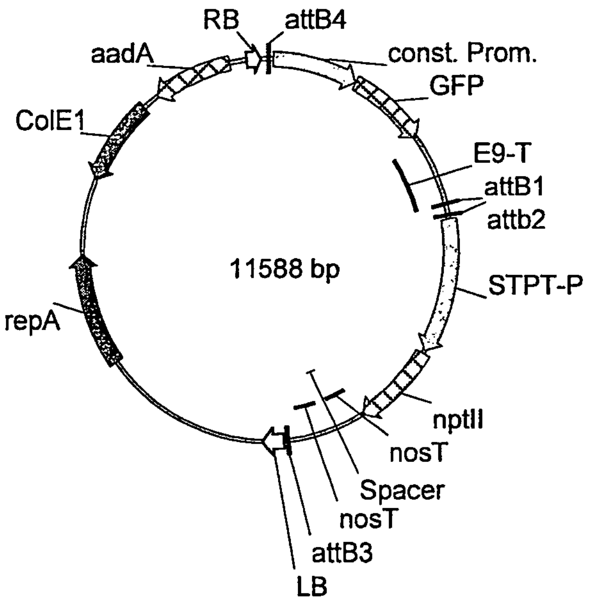
Lo523a-pSun1-R4-Lo484::Lo376::Lo503a-R3
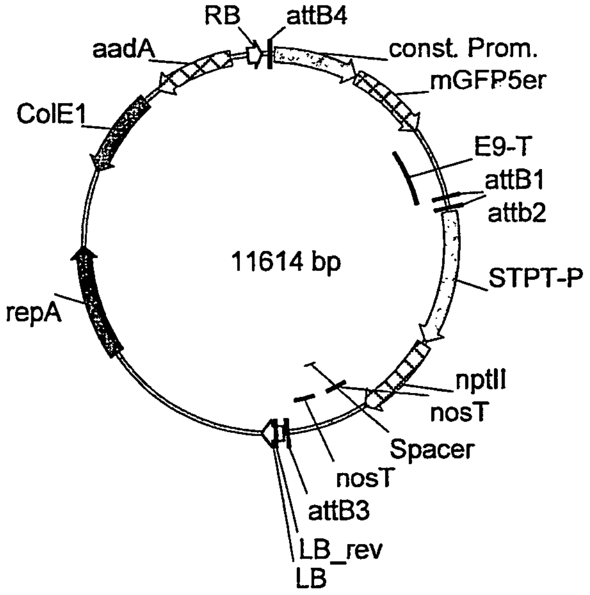
Lo523b-pSun1-R4-Lo484::Lo376::Lo503b-R3
Fig. 8

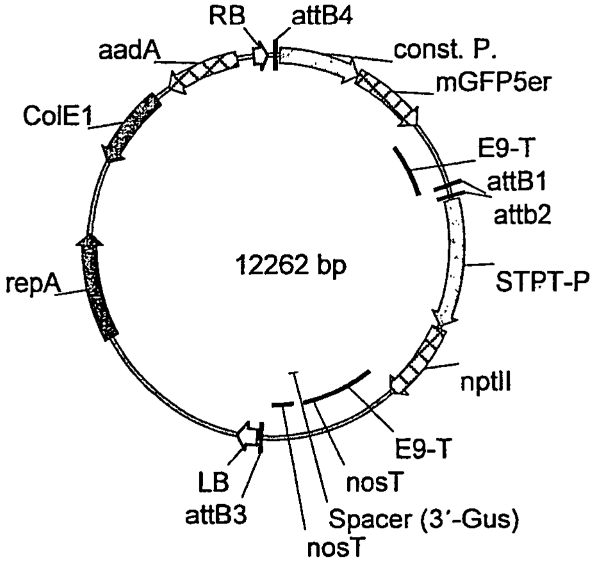
Lo546a-pSun1-R4-Lo484::Lo376::Lo522a-R3
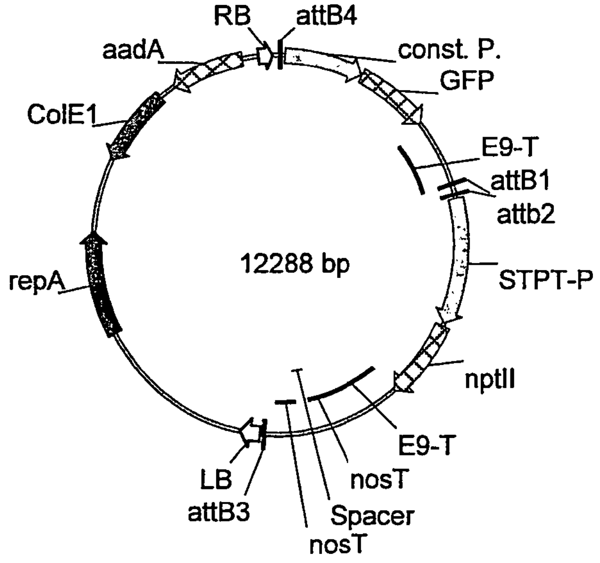
Lo546b-pSun1-R4-Lo484::Lo376::Lo522b-R3
Fig. 9

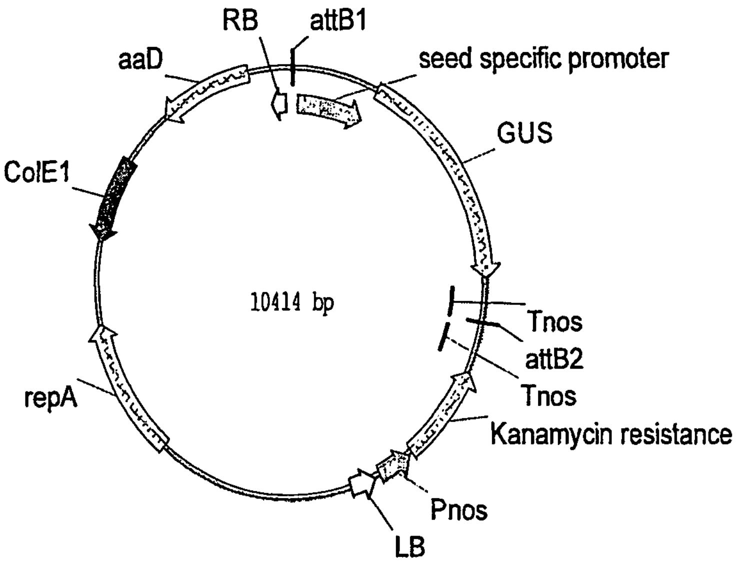
Lo239-pSUN3-GWs-B1-BnAK700::GUS::nosT-B2
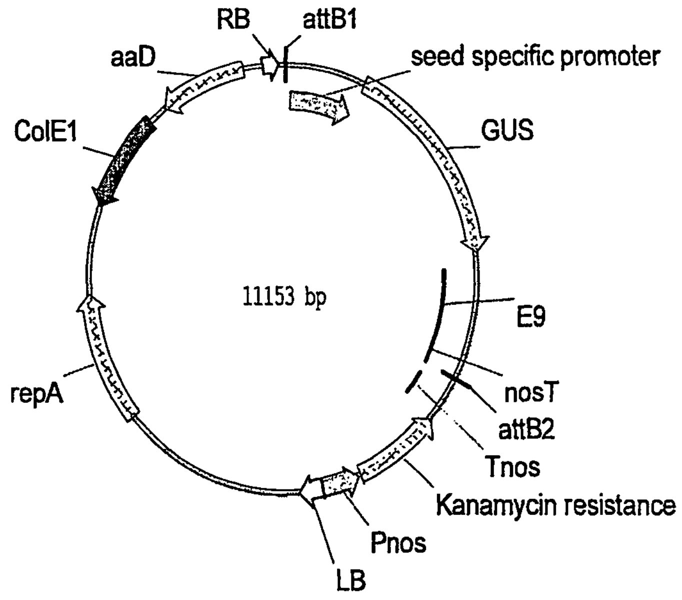
Lo657 5-pSun3-GWs-B1-BnAK700::GUS::E9::nosT-B2
Fig.10

A
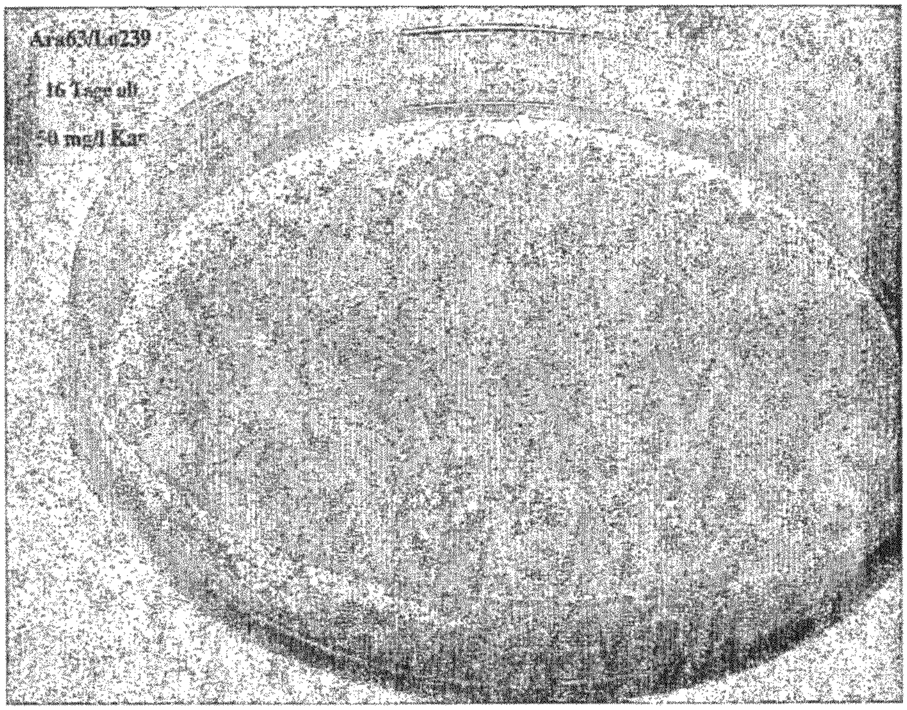
B
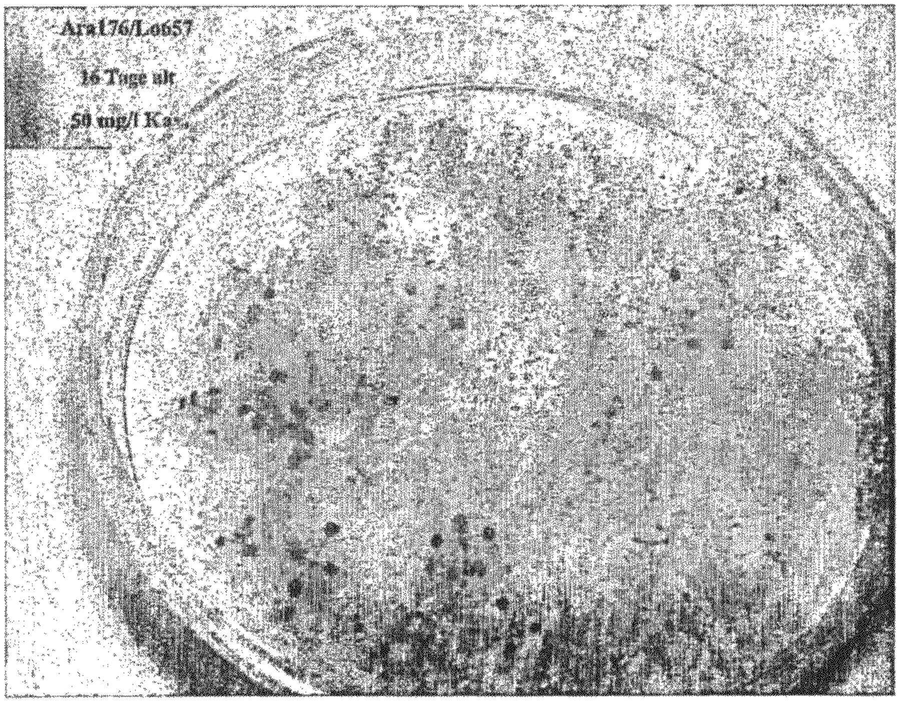
Fig. 11

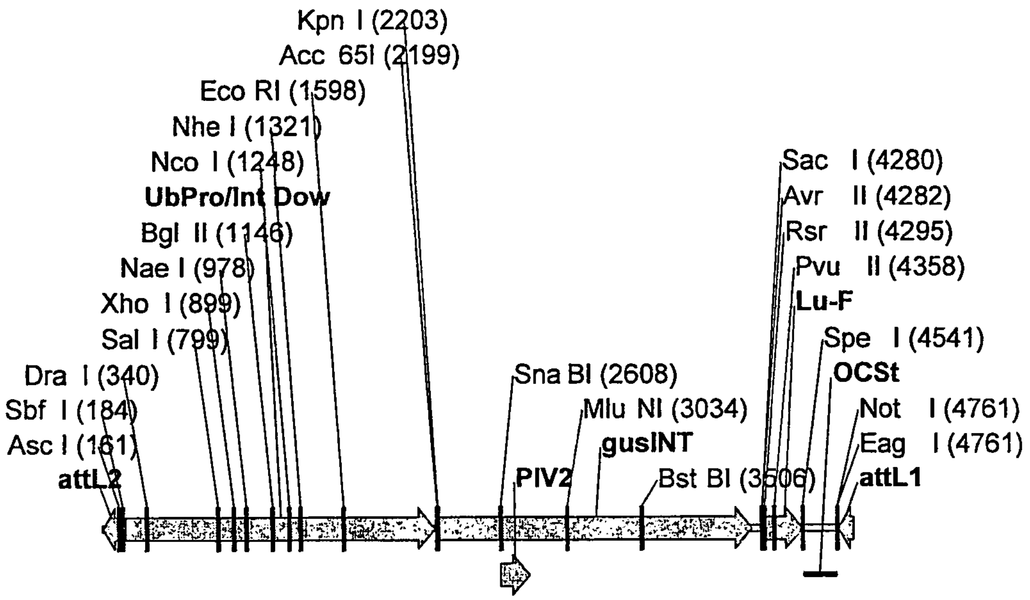
Fragment of pTOI 03
4811 bp (molecule 7155 bp)
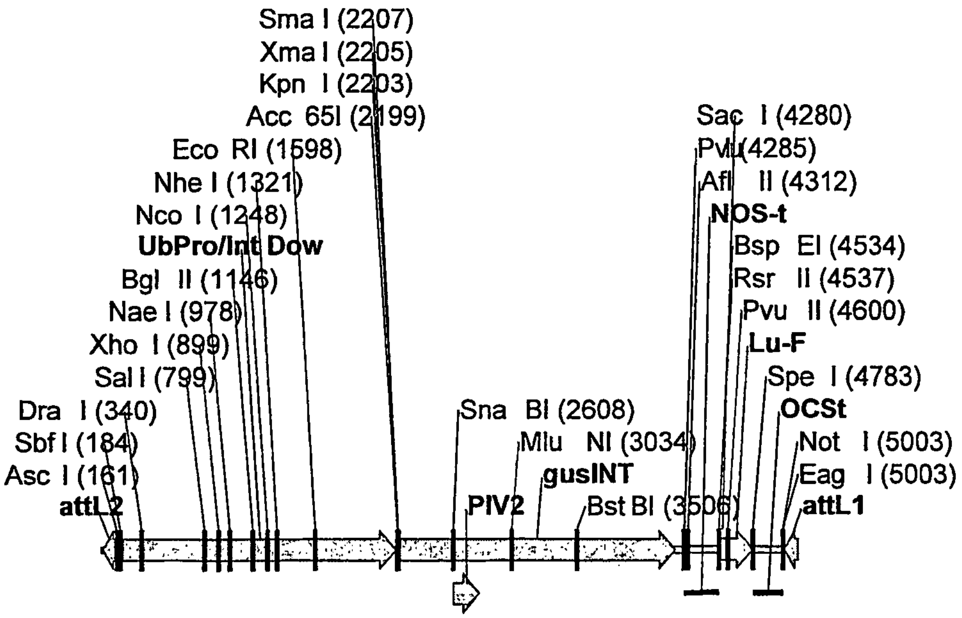
Fragment of pTOI 04
5053 bp (molecule 7397 bp)
Fig. 19

A
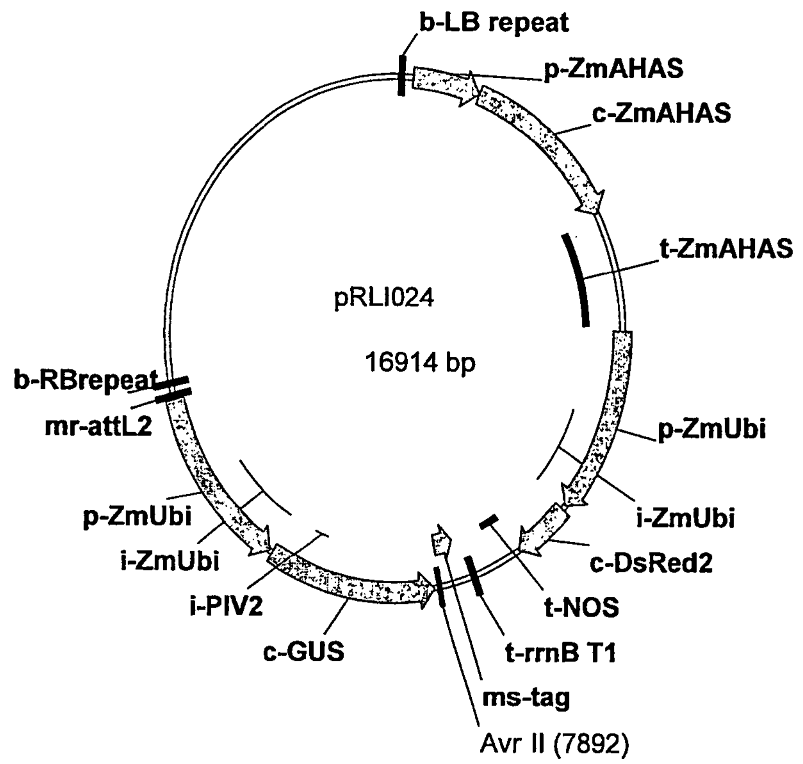
B
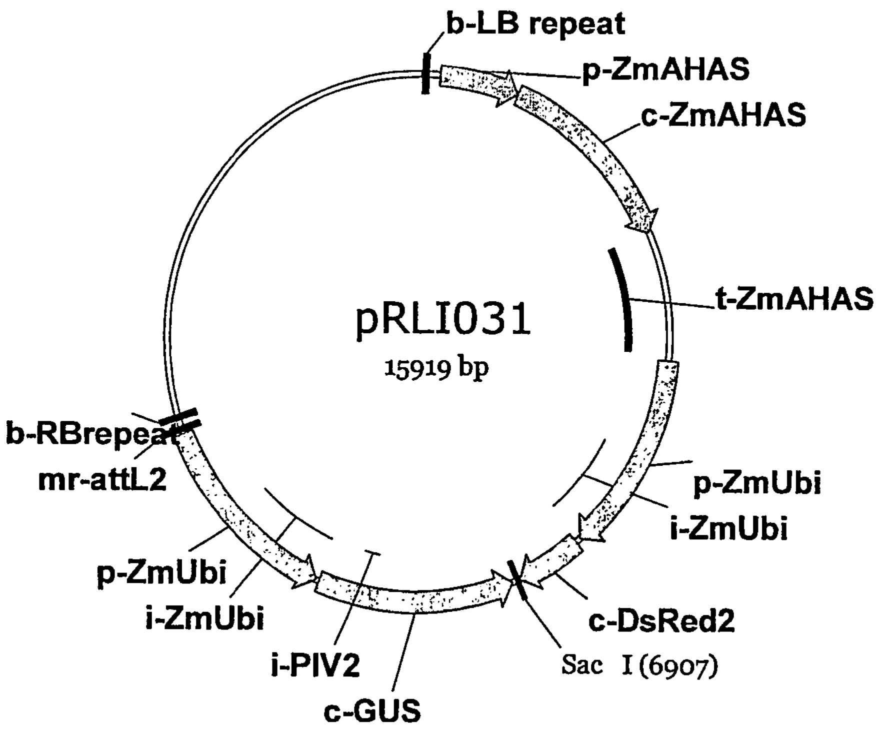
Fig. 21

METHOD FOR ISOLATION OF TRANSCRIPTION TERMINATION SEQUENCES

RELATED APPLICATIONS

This application is a national stage application (under 35 U.S.C. 371) of PCT/EP2005/008285 filed Jul. 30, 2005, which claims benefit of U.S. Provisional application 60/598,001 filed Aug. 2, 2004 and U.S. Provisional application 60/696,209 filed Jul. 1, 2005.

SUBMISSION ON COMPACT DISC

The contents of the following submission on compact discs are incorporated herein by reference in its en tirety: two copies of the Sequence Listing (COPY 1 and COPY 2) and a computer readable form copy of the Sequence Listing (CRF COPY), all on compact disc, each containing: file name: Sequence listing—13987-00036-U.S., date recorded: Jan. 31, 2007, size: 328 KB.

FIELD OF THE INVENTION

The invention relates to efficient, high-throughput methods, systems, and DNA constructs for identification and isolation of transcription termination sequences.

BACKGROUND OF THE INVENTION

The aim of plant biotechnology is the generation of plants with advantageous novel properties, such as pest and disease resistance, resistance to environmental stress (e.g., water-logging, drought, heat, cold, light-intensity, day-length, chemicals, etc.), improved qualities (e.g., high yield of fruit, extended shelf-life, uniform fruit shape and color, higher sugar content, higher vitamins C and A content, lower acidity, etc.), or for the production of certain chemicals or pharmaceuticals (Dunwell 2000). Furthermore resistance against abiotic stress (drought, salt) and/or biotic stress (insects, fungal, nematode infections) can be increased. Crop yield enhancement and yield stability can be achieved by developing genetically engineered plants with desired phenotypes.

For all fields of biotechnology, beside promoter sequences, transcription terminator sequences are a basic prerequisite for the recombinant expression of specific genes. In animal systems, a machinery of transcription termination has been well defined (Zhao et al., 1999; Proudfoot, 1986; Kim et al., 2003; Yonaha and Proudfoot, 2000; Cramer et al., 2001; Kuerstem and Goodwin, 2003). Effective termination of RNA transcription is required to prevent unwanted transcription of trait-unrelated (downstream) sequences, which may interfere with trait performance (see below for more details). Especially arrangement of multiple gene expression cassettes in local proximity (e.g., within one T-DNA) is often causing suppression of gene expression of one or more genes in said construct in comparison to independent insertions (Padidam and Cao, 2001). This is causing problems especially in cases were strong gene expression from all cassettes is required Previously efficiency of transcription termination had to be analyzed either by in vitro or in vivo transcription analysis of individual transcription termination sequences, which is a laborious and time-consuming procedure based on trial-and-error (Yonaha and Proudfoot, 1999, 2000; Yarnell and Roberts, 1999). To simplify this process, single nucleotide-recognizing probe such as beacon has been used for in vitro transcription (Liu et al., 2002).

In plants, understanding transcription termination and re-initiation is at the infant stage. There are no clearly defined polyadenylation signal sequences. Hasegawa et al. (2003) were not able to identify conserved polyadenylation signal sequences in both in vitro and in vivo systems in *Nicotiana sylvestris* and to determine the actual length of the primary (non-polyadenylated) transcript. There are vague ideas that weak terminator can generate read-through, which affects the expression of the genes located in neighboring expression cassettes (Padidam and Cao, 2001). Appropriate control of transcription termination will prevent read-through into sequences (e.g., other expression cassettes) localized downstream and will further allow efficient recycling of RNA polymerase II, which will improve gene expression.

Prediction of functional, efficient transcription termination sequences by bioinformatics is not feasible alternative since virtually no conserved sequences exist which would allow for such a prediction. Prediction of the efficiency in transcription termination of such sequences is even more beyond. Furthermore, experimental determination of the actual length and sequence of the primary transcript is difficult since these structures are highly instable being rapidly converted into polyadenylated transcripts (Hasegawa et al., 2003).

Production of genetically modified cells and organisms (such as plants) requires appropriate recombinant DNA in order to introduce genes of interest. The recombinant DNA contains more than one expression cassette, in general. The expression cassette is composed of promoter, gene of interest, and terminator. The expression of the gene of interest in the expression cassette can be negatively affected by inappropriate termination of transcription from the neighboring cassette. Transcriptional read-through and/or multiple use of the same transcription termination sequence may have one or more of the following disadvantages:

1. Unwanted expression of downstream sequences may cause undesirable effects (e.g., changes in metabolic profile, gene silencing etc.).
2. Unwanted expression of downstream sequences raises higher hurdles in deregulation proceedings.
3. Multiple use of identical transcription termination sequences may lead to failure of the whole transgenic expression approach by epigenic silencing. Because the present panel of evaluated transcription termination sequences is currently very limited, multiple use of the same transcription termination sequence in one transgenic organism is often unavoidable, which has proofed to result in unintended silencing of the entire transgenic expression constructs (Matzke 1994; Matzke 1989)
4. Enablement of constructs comprising multiple gene expression cassettes without undesired interaction of transcription of different cassettes. Such interactions may—depending on the orientation of the cassettes—include unintended expression (e.g., in case of expression cassettes having the same direction of their reading frames) or unintended gene silencing (e.g., in case of inverted orientation of the cassettes).

In consequence, there is an unsolved demand (especially in the plant biotech area) for tight and alternative transcription termination sequences. There is no easy and reliable screening system to identify "tight" terminators that efficiently terminate transcription. It is therefore an objective of the present invention, to provide a method to easily identify such termination sequences and to provide tight and alternative transcription termination sequences for use on plants. This objective is achieved by this invention.

BRIEF DESCRIPTION OF THE INVENTION

Accordingly, a first embodiment of the invention related to a method for identification and isolation of transcription termination sequences for comprising the steps of:

i) providing a screening construct or screening vector comprising
  a) a promoter sequence, and
  b) one or more insertion sites—preferably a restriction or recombination site—for insertion of DNA sequences, and
  c) at least one additional sequence which causes upon expression under said promoter sequence a readily detectable characteristic,
  wherein insertion of an efficient transcription terminator into said insertion site changes expression of said additional sequences by said promoter sequence in comparison to no insertion, and
ii) providing one or more DNA sequences to be assessed for their transcription termination capability, and
iii) inserting one or more copies of said DNA sequences into said insertion site of said screening construct or screening vector, and
iv) introducing said screening construct or screening vector with said inserted DNA sequences into an in vitro or in vivo transcription system suitable to induce expression from said promoter sequence, and
v) identifying and/or selecting screening construct or screening vector with a changed readily detectable characteristic in comparison to no insertion, and
vi) isolating the inserted DNA sequences from said identified and/or selected screening construct or screening vector for use as transcription termination sequences and—optionally—determining their sequence.

There are various options for localization of said insertion site in relation to said additional sequences. For example the insertion site may preferably be at a position selected from group of:

i) upstream of the additional sequences between said promoter and said additional sequences, and
ii) downstream of the additional sequences, and
iii) in between said additional sequences.

Depending on the localization of the insertion site to said additional sequences several especially preferred embodiments result. In one preferred embodiment method for identification and isolation of transcription termination sequences comprises the steps of:

i) providing a screening construct or screening vector comprising in 5' to 3' direction
  a) a promoter sequence, and
  b) one or more insertion sites—preferably a restriction or recombination site—for insertion of DNA sequences, and
  c) at least one additional sequence which causes upon expression under said promoter sequence a readily detectable characteristic,
  wherein insertion of an efficient transcription terminator into said insertion site suppresses expression of said additional sequences by said promoter sequence in comparison to no insertion, and
ii) providing one or more DNA sequences to be assessed for their transcription termination capability, and
iii) inserting one or more copies of said DNA sequences into said insertion site of said screening construct or screening vector, and
iv) introducing said screening construct or screening vector with said inserted DNA sequences into an in vitro or in vivo transcription system suitable to induce expression from said promoter sequence, and
v) identifying and/or selecting screening constructs or screening vectors with a changed readily detectable characteristic in comparison to no insertion, and
vi) isolating the inserted DNA sequences from said identified and/or selected screening constructs or screening vectors for use as transcription termination sequences and—optionally—determining their sequence.

One or more of the sequences to be assessed for their efficiency in transcription termination may be inserted into the screening vector or screening construct. In the case of insertion of two or more copies, in a preferred embodiment said DNA sequences to be assessed for their transcription termination efficiency are inserted into said insertion site in form of an inverted repeat. Thus, preferably the method for identification and isolation of transcription termination sequences comprises the steps of:

i) providing a screening construct or screening vector comprising in 5' to 3' direction
  a) a promoter sequence, and
  b) at least one additional sequence which causes upon expression under said promoter sequence a readily detectable characteristic, and
  c) one or more insertion sites—preferably a restriction or recombination site—for insertion of DNA sequences,
ii) providing one or more DNA sequences to be assessed for their transcription termination capability, and
iii) inserting at least two copies of a specific DNA sequence of said DNA sequences in form of an inverted repeat into said insertion site of said screening construct or screening vector, wherein insertion of an inverted repeat of an efficient transcription terminator into said insertion site allows expression of said additional sequences by said promoter sequence in comparison to no insertion, and
iv) introducing said screening constructs or screening vectors with said inserted DNA sequences into an in vitro or in vivo transcription system suitable to induce expression from said promoter sequence, and
v) identifying and/or selecting screening constructs or screening vectors with said readily detectable characteristic in comparison to no insertion, and
vi) isolating the inserted DNA sequences from said identified and/or selected screening constructs or screening vectors for use as transcription termination sequences and—optionally—determining their sequence.

In another preferred embodiment of the invention, the method for identification and isolation of transcription termination sequences comprises the steps of:

i) providing a screening construct or screening vector comprising in 5' to 3' direction
  a) a promoter sequence, and
  b) at least one additional sequence which causes upon expression under said promoter sequence a readily detectable characteristic, and embedded into said additional sequences one or more insertion sites—preferably a restriction or recombination site—for insertion of DNA sequences,
  wherein insertion of an efficient transcription terminator into said insertion site suppresses full-length transcription of said additional sequences by said promoter sequence in comparison to no insertion, and
ii) providing one or more DNA sequences to be assessed for their transcription termination capability, and iii) inserting one or more copies of said DNA sequences into said insertion site of said screening construct or screening vector, and iv) introducing said screening constructs or screening vectors with said inserted DNA sequences into an in vitro or in vivo transcription system suitable to induce expression from said promoter sequence, and v) identifying and/or selecting screening constructs or screening vectors with a changed readily detectable characteristic in comparison to no insertion, and vi) isolating the inserted DNA sequences from said identified and/or selected screening constructs or screening vectors for use as transcription termination sequences and—optionally—determining their sequence.

Preferably, the additional sequence is selected from the group consisting of positive selection marker, negative selection marker, counter selection marker, reporter genes, and toxic genes. In case of toxic genes, wherein said toxic gene may for example be a construct for gene silencing of an essential endogenous gene.

Preferably, the DNA sequence to be assessed for their transcription termination efficiency is provided by a method selected from the group consisting of:

i) provision of a selected sequence by amplification from a host genome, and ii) provision of a library of sequences by fragmentation of a host genome.

More preferably, the DNA sequence to be assessed for their transcription termination efficiency is derived from a plant cell.

There various methods for insertion of said sequences into said insertion site. Preferably, the DNA sequences to be assessed for their transcription termination efficiency are inserted into said insertion site by a method selected from the group consisting of:

i) recombinational cloning, and ii) insertion by sequence specific restriction and ligation.

BRIEF DESCRIPTION OF THE DRAWINGS

FIG. 1-A A1: Graphic of preferred Method A: Insertion site (IS) for transcription terminator (TT) to be assessed is localized between promoter (P1) and additional sequences (AS), which are able to cause a readily detectable characteristic. In case of an efficient transcription terminator (+), transcription from the promoter P1 is stopped at said transcription terminator (symbolized by arrow below construct). No expression of the additional sequences occurs and no change in characteristic is caused (symbolized by crossed circle). In case of no efficient transcription termination (−), transcription from the promoter P1 read-through said alleged transcription terminator leading to expression of the additional sequences (symbolized by arrow below construct), thereby causing the change in the characteristic (symbolized by lightening symbol).

Figure 2:
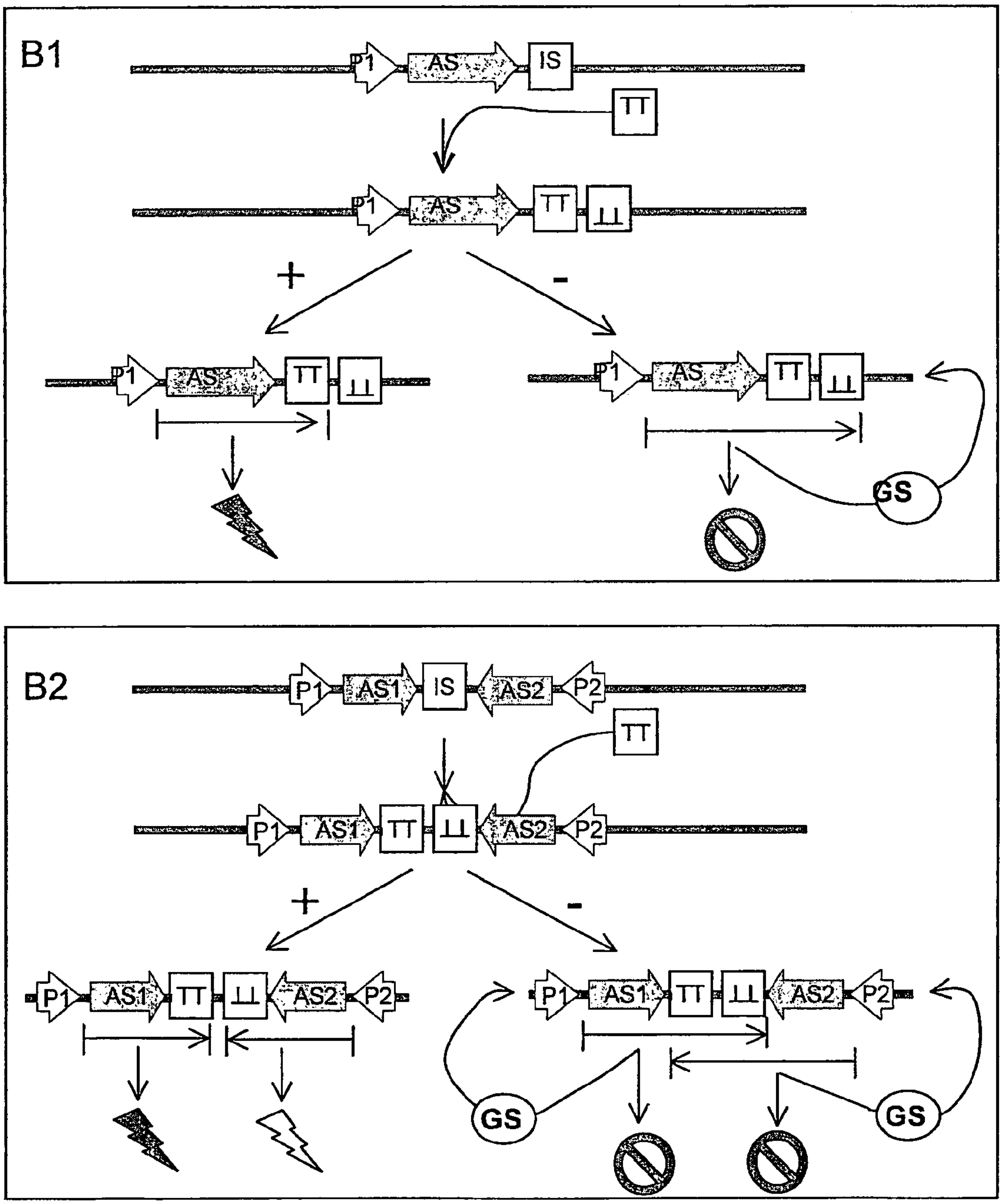

A2: Graphic of preferred Method A based on terminator as additional sequences. Insertion site (IS) for transcription terminator (TT) to be assessed is localized between promoter (P1) and additional sequences which in this case are constituted by an inverted repeat of a known transcription terminator (T). The second copy of said terminator (symbolized by upside letter) down-stream of the promoter is in its functional orientation. In case of an efficient transcription terminator (+), transcription from the promoter P1 is stopped at said transcription terminator (symbolized by arrow below construct) and normal expression of the marker protein (M1) occurs (symbolized by black lightening symbol). In case of no efficient transcription termination (−), transcription from the promoter P1 read-through said alleged transcription terminator leading to expression of the inverted repeat of the known transcription terminator, causing gene silencing (GS) of the Marker M1 expression (symbolized by crossed circle). Preferably, the construct comprises a further expression cassette leading to expression of Marker M2, which functions as a positive control for general presence of the screening construct, bringing about a preferably different second phenotype (symbolized by white lightening symbol).

FIG. 1-B A3: Graphic of preferred Method A based on terminator as additional sequences. Insertion site (IS) for transcription terminator (TT) to be assessed is localized between two expression cassette for different marker genes, which are oriented head to head to eachother. The cassette for the marker M2 is terminated by a known transcription terminator. In case of an efficient termination of transcription by the inserted test terminator (+), transcription from the promoter P1 is stopped at said transcription terminator (symbolized by arrow below construct) and normal expression of the marker proteins (M1) and (M2) occurs (symbolized by black and white lightening symbols). In case of no efficient transcription termination (−), transcription from the promoter P1 read-through said alleged transcription terminator leading to expression of an RNA strand compemenatry to the one expressed from promoter P2, thereby causing hybridization of the transcript of the first marker gene (M1) with the constitutively expressed transcript from the second marker gene (M2). This causes a gene silencing (GS) of both Marker genes M1 and M2 (symbolized by crossed circle).

A4: Graphic of preferred Method A based on terminator as additional sequences. Insertion site (IS) for transcription terminator (TT) to be assessed is localized between promoter (P1) and additional sequences which in this case are constituted by non-transcribed DNA sequence preferably a fragment or a full length sequence of a known transcription terminator. The second expression cassette is oriented head to head to the first cassette and carries a second copy of said DNA sequence, terminator or terminator fragment. In case of an efficient termination of transcription by the inserted test terminator (+), transcription from the promoter P1 is stopped at said transcription terminator (symbolized by arrow below construct) and normal expression of the marker protein (M1) occurs (symbolized by black lightening symbol). In case of no efficient transcription termination (−), transcription from the promoter P1 read-through said alleged transcription terminator leading to expression of the known transcription terminator or transcription terminator fragment, causing hybridization of the transcript of the first marker gene (M1) with the constitutively expressed transcript from the second marker gene (M2) which carries the identical 3' UTR sequence, thereby causing a dose dependent repression of expression of both Marker genes M1 and M2 (symbolized by crossed circle). Preferably, the construct comprises a second marker gene (M2). As the effect of expression repression of both marker genes is dependent on the degree of hybridization between the two classes of transcripts it is possible to screen for intermediary phenotypes, allowing the selection of "weak" candidate terminator sequences or "tight" candidate terminator sequences e.g. by using different screening conditions.

FIG. 2: B1: Graphic of preferred Method B: Insertion site (IS) for transcription terminator (TT) to be assessed is downstream of the additional sequences (AS), which are able to cause a readily detectable characteristic. The transcription terminator (TT) to be assessed is inserted in form of an inverted repeat, wherein the first copy (symbolized by upside letter) downstream of the promoter is in its functional orientation. In case of an efficient transcription terminator (+), transcription from the promoter P1 is stopped at the first copy of the transcription terminator (symbolized by arrow below construct) and normal expression of the additional sequences (AS) occurs (symbolized by black lightening symbol). In case of no efficient transcription termination (–), transcription from the promoter P1 read-through both copies of said alleged transcription terminator leading to expression of the inverted repeat of said transcription terminator, causing gene silencing (GS) of the additional sequences (AS) expression (symbolized by crossed circle).

B2: Preferably, the construct comprises a further expression cassette, wherein AS2 is encoding for a different characteristic than AS1. Both expressions are silenced in case of an inefficient transcription terminator. In case of an efficient terminator, expression of both characteristics (symbolized by black and white lightening symbol, respectively) occurs.

Figure 3:
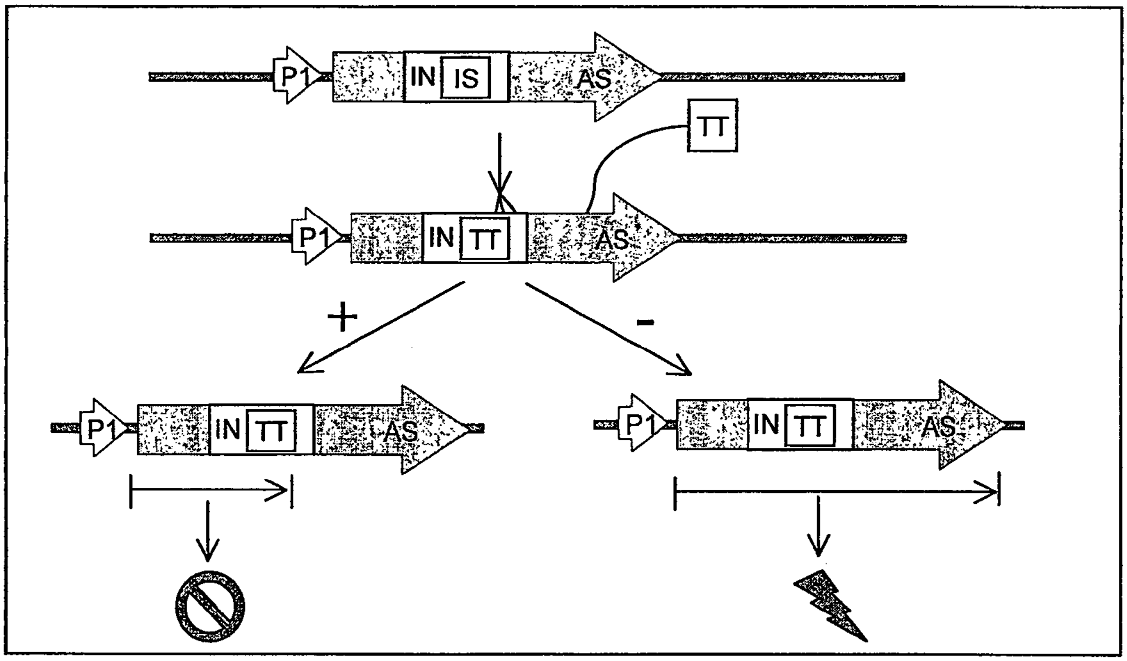

FIG. 3 Graphic of preferred Method C: Insertion site (IS) for transcription terminator (TT) to be assessed is localized in an intron (IN) localized in the additional sequences (AS), which are able to cause a readily detectable characteristic. In case of an efficient transcription terminator (+), transcription from the promoter P1 is stopped at said transcription terminator (symbolized by arrow below construct). No full-length expression of the additional sequences occurs and no change in characteristic is caused (symbolized by crossed circle). In case of no efficient transcription termination (–), transcription from the promoter P1 read-through said alleged transcription terminator leading to full-length expression of the additional sequences (symbolized by arrow below construct), thereby causing the change in the characteristic (symbolized by lightening symbol).

Figure 4:
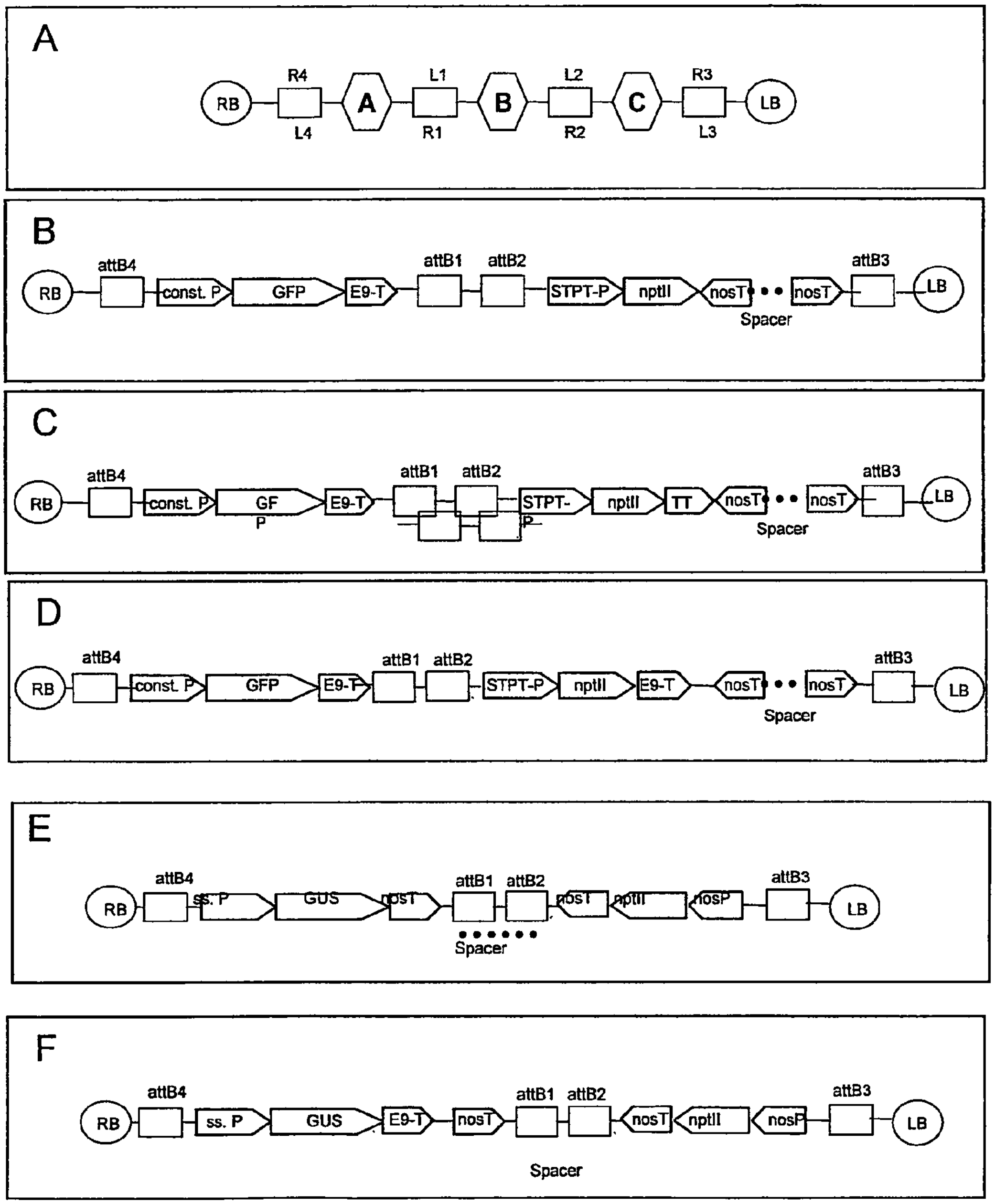

FIG. 4 Schematic presentation of the screening constructs:

A: Lo523 negative control construct: Binary vector corresponding to the screening construct without insertion of an additional transcription terminator sequence. Upon use of this construct for transformation of plant cells the nptII gene will be transcribed. As there is no functional terminator present down-stream of this gene transcription proceeds through the nos terminator IR leading to a transcript with hairpin structure, which causes silencing of nptII gene expression. These cells cannot grow on selective medium containing Kanamycin. By visualization of the constitutively expressed GFP marker gene these non-growing cells can be distinguished from non-transformed cells.

B: Screening construct B: Binary vector containing a first expression cassette with a constitutively expressed reporter gene for selection of transformed from untransformed cells/plants followed by a second expression cassette containing a nptII selection marker driven by a strong constitutive promoter. Down-stream of the nptII gene an IR of the *Agrobacterium* nos terminator sequence is inserted, consisting of a first repeat in antisense direction followed by a short spacer sequence derived from the GUS reporter gene and the second repeat of the nos terminator which is inserted in its functional 5' to 3' direction. The fragments to be tested for transcription terminator activity are to be inserted between the nptII gene and said nos terminator IR.

D: Lo546 positive control construct C: Binary vector derived from construct C where a long fragment of the rbCs E9 terminator sequence is inserted between nptII gene and nos terminator IR. The E9 terminator is believed to act as a highly efficient terminator and will therefore terminate transcription of the nptII gene resulting in normal expression levels of the selection marker which enable the growth of the transformed cells in presence of Kanamycin.

E: Lo239 negative control construct and base construct for insertion of candidate terminator sequences. Use of this binary construct for transformation leads to plants with constitutive expression of the nptII gene, producing transcripts carrying a defined 3'UTR. Upon seed development the expression of the β-Glucuronidase marker is initiated by the seed-specific promotor. The resulting GUS transcripts carry the same defined 3' sequence as the nptII transcripts leading to hybridization between the two transcript classes and thereby causing loss of the phenotype associated with the two marker genes. The seeds cannot grow on selective medium containing Kanamycin and the GUS marker cannot be detected in the seeds.

F: Lo657 positive control construct. Binary vector derived from Lo239 by insertion of a long fragment of the rbCs E9 terminator between the GUS marker gene and the downstream sequences. By efficiently terminating the GUS transcripts which are produced within the cells of the developing seed the resulting transcript carry a different 3' sequence compared to the constitutively expressed nptII transcripts. Both marker cassettes are transcribed and translated without interferences leading to seedlings which are viable on kanamycin selection and allow detection of accumulated GUS protein.

Figure 5:
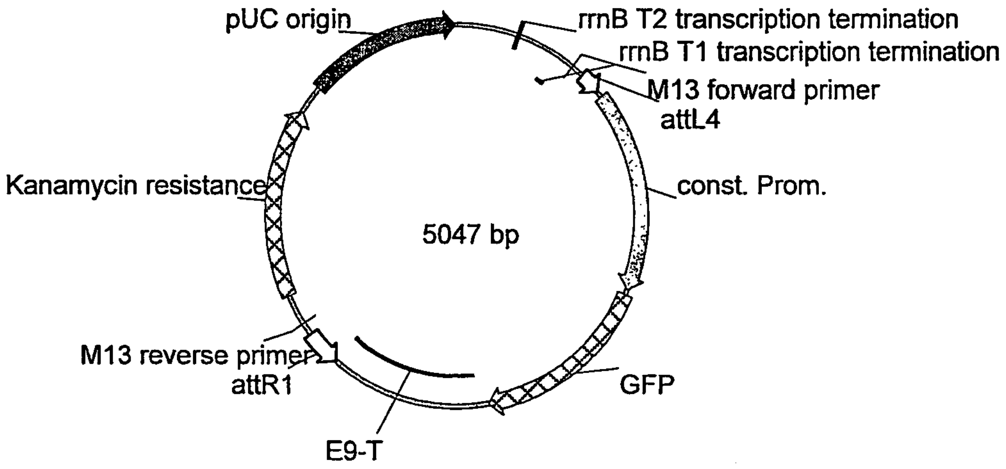

FIG. 5 pENTR construct—position 1 visual marker (reporter gene): Gateway Entry vector A containing the GFP reporter gene under control of a constitutive promoter. The vector is used in combination with the Gateway Entry vector B Lo376 (SEQ ID NO: 76) and the Gateway Entry vector C, Lo522a (Lo522b respectively), for recombination based construction of positive control constructs and in combination with Lo503a (Lo503b respectively) for recombination based construction of binary negative control constructs and the screening construct.

FIG. 6 pENTR constructs for positive controls: The Gateway Entry vectors C contain the nptII selection marker gene under control of the constitutive STPT promoter. 3' to the selection marker a long fragment of the rbCs E9 terminator sequence is inserted in front of a nos terminator IR. The depicted constructs are used in combination with the Gateway Entry vectors A, Lo484, B Lo376 and C, Lo522 (Lo522b respectively), for recombination based construction of binary positive control constructs.

FIG. 7 pENTR constructs for negative controls: The Gateway Entry vectors C contain the nptII selection marker gene under control of the constitutive STPT promoter. 3' to the selection marker a nos terminator IR is inserted. This results in transcription of the nptII Gene and the inverted sequence fragment of the nos terminator followed by the nos terminator sequence in functional 5'-3' orientation, which will by default cause a hairpin structure at the 3' end of the transcript. The depicted constructs are used in combination with the Gateway Entry vectors A, Lo484, B Lo376 and C, Lo522 (Lo522b respectively), for recombination based construction of binary positive control constructs.

FIG. 8 pSUN1 constructs—negative controls: Binary construct derived from the recombination based insertion of the expression cassettes from the respective pENTR vectors into the Gateway Destination vector Lo442 pSUN1-R4R3 (SEQ ID NO: 77).

FIG. 9 pSUN1 constructs—positive controls: Binary construct derived from the recombination based insertion of the expression cassettes from the respective pENTR vectors into the Gateway Destination vector Lo442 pSUN1-R4R3 (SEQ ID NO: 77).

FIG. 10 Binary constructs Lo239-pSUN3-GWs-B1-BnAK700::GUS::nosT-B2 (negative control) and Lo657-pSUN3-GWs-B1-BnAK700::GUS::E9::nosT::B2 (positive control) representing FIGS. 4-E and F. Lo239 is derived from the Gateway based recombination of the pENTR Lo235 carrying the GUS marker cassette with the pSUN destination vector Lo125 pSUN3-GWs-NPTII carrying the nptII cassette. After modification of Lo235 by insertion of a long fragment of the rbCs E9 terminator downstream of the GUS marker gene the resulting Lo654 pENTR-BnAK700::GUS::E9::nosT is used for the Gateway based recombination with Lo125 pSUN3-GWs-NPTII to create the positive control construct Lo657-pSUN3-GWs-B1-BnAK700::GUS::E9::nosT:: B2

FIG. 11 Screening results of negative and positive control constructs: The constructs described in FIG. 10 were used for floral dip transformation of *Arabidopsis thaliana* plants. The harvested seeds were tested for expression of the marker gene nptII by selection on Kanamycin. Whereas the seeds from plants which have been used for transformation with the positive control construct are viable on the selective medium, showing expression of the nptII gene (GUS gene expression is not shown but has been detected by X-Gluc reaction) the negative control construct yields only seeds which are not viable on Kanamycin and show no expression of the Gus marker gene.

Figure 12:
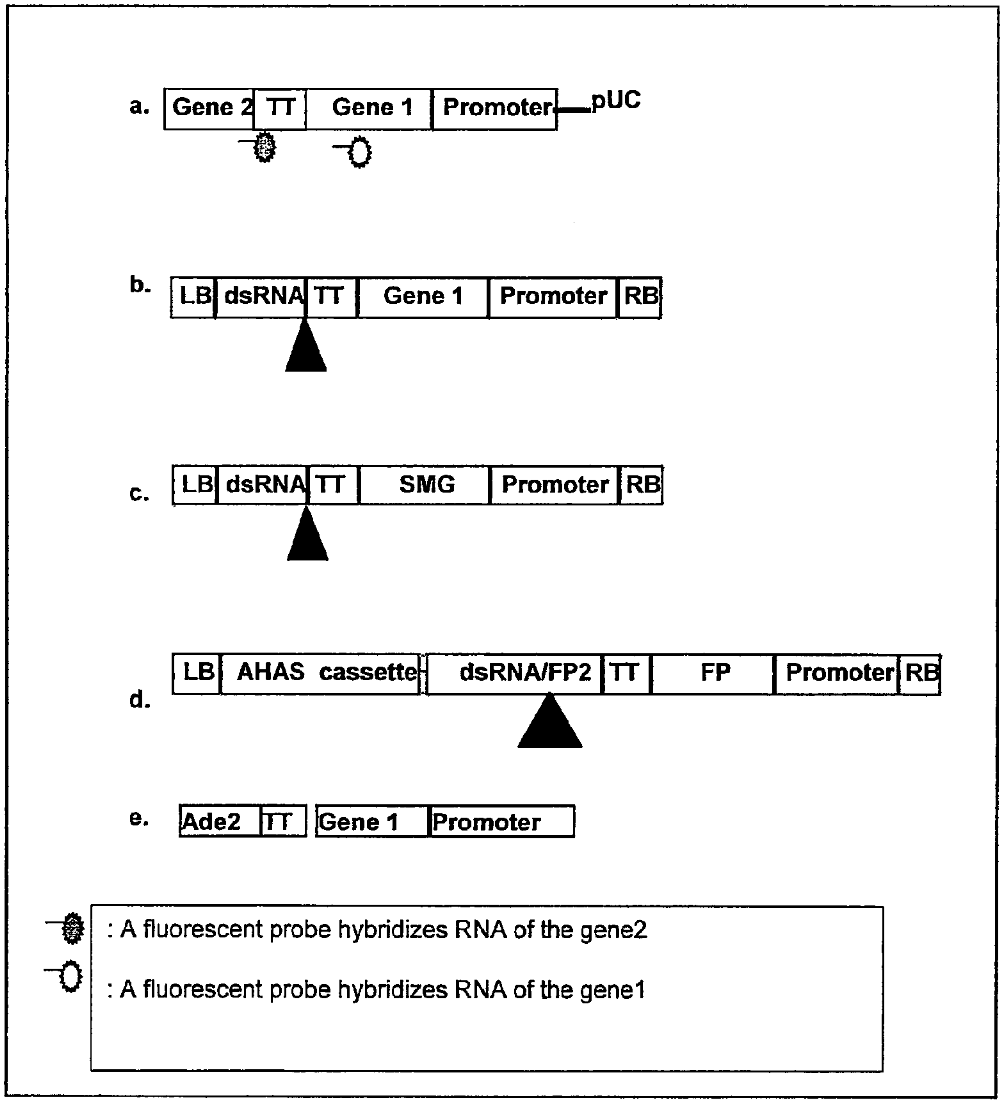

FIG. 12 Diagram of the constructs for identification of transcription terminators of interest (TOI).

(a) The construct for in vitro transcription assays. Gene 1 and 2 prefer to be the sequences that are not homologous to the plant genome.

(b-d) The constructs for in vivo assays. The regions indicated as "dsRNA" are the sequences that generate double-stranded RNA (dsRNA). These dsRNAs down-regulate an essential gene for plant cells (b), negative selection marker gene (SMG) (c), or a reporter gene such as fluorescence protein (FP)

(d) In the construct (d), the DNA downstream of TOI can be another reporter gene or any sequences.

(e) Screening system in yeast: The system allows efficient screening of random sequences. Control vectors contain NOS terminator, truncated NOS, no terminator, or a DNA fragment with unidentified sequence.

Figure 13:
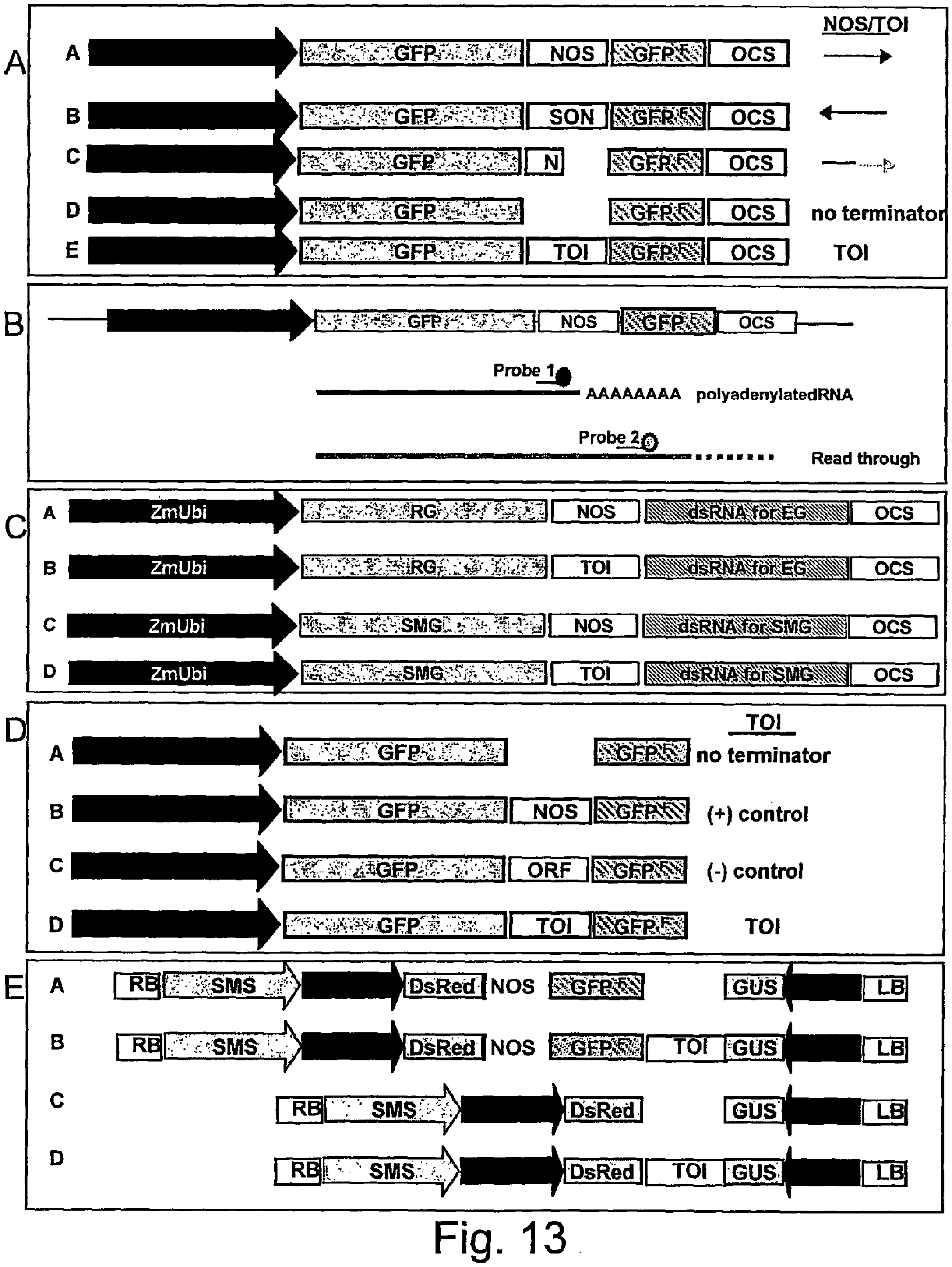

FIG. 13 A: Control constructs (A-D) and a construct containing potential terminator candidate (E). GUS can be replaced with any reporter gene or a non-plant homologous DNA fragment including ATG and stop codon. In the control vectors, four variations are made: (A) 260 bp nopaline synthase terminator (NOS) including polyadenylation site, a cleavage sequence, and approximately 80 bp of nucleotides downstream of the cleavage sequence, (B) reverse orientation of NOS, (C) NOS DNA fragment either including polyadenylation signal and cleavage site or lacking the polyadenylation signal and downstream sequence, and (D) no terminator. Nopaline synthase terminator is replaced with various genomic fragments, which can be selected as potential terminator candidates. $Lu^F$ represents a fragment of luciferase gene (approximately 200 to 300 bp) as a read through region. $Lu^F$ can be replaced with a non-plant homologous DNA fragment (e.g. yeast intergenic sequences). Octopine synthase terminator is located in the end of the cassette to stabilize the transcripts including read through products. These constructs can be built in pUC based vector or a binary vector. TOI stands for terminator of interest. Although the NOS terminator has proven in the screening systems to be of only moderate efficiency, it can be used as kind of control terminator for the evaluation systems described herein.

B: An in vitro screening system. Two single strand fluorescence probes such as beacon probes that hybridize the read through region and polyadenylated RNA. The black bar represents polyadenylated RNA. The gray bar represents read through product. Probe 1 (black star) hybridizes the complementary sequence of the polyadenylated RNA. Probe 2 (gray star) hybridizes the complementary sequence of the read through region.

C: Control constructs (A, C) and constructs containing potential terminator candidates (B, D). RG represents any reporter gene. SMG represents any selectable marker gene. Approximately 260 bp Nopaline Synthase terminator (NOS) is used as a control terminator (A, C). Plant genomic fragment (<1 kb) is cloned between GUS or bar and dsRNA fragment to identify terminator of interest (TOI). Expression of dsRNA for essential gene (EG) causes lethal in plants due to down-regulation of essential gene in the transgenic plants (A, B). Expression of dsRNA for SMG causes lethal under specific selection pressure due to down-regulation of selectable marker gene in the transgenic plants (C, D). However, strong and tight terminator can limit the expression of dsRNA due to low levels or no read through resulting in producing transgenic plants. These constructs can be built in pUC based vector or a binary vector.

D: Control construct (A) is the vector into which control and test sequences were cloned. Positive control vector (B) comprises the NOS terminator sequence downstream of the GUS reporter gene. Negative control vector (C) comprises sequence obtained from an internal portion of a plant-expressible open-reading frame, and therefore should not possess transcriptional termination activity. Vector (D) represents vectors that comprise putative TOI candidates to be tested for terminator activity. These constructs were built into a pUC vector and used for transient analyses of TOI candidate sequences.

E: Control binary vectors (A, C) comprise no insertion of putative terminator sequences downstream of the primary reporter gene, GUS. Test vectors (B, D) comprise putative TOI candidates to be tested for transcriptional termination activity in stably transformed plants. Vectors (A, B) comprise a NOS terminator downstream of the secondary reporter gene, DsRed2; these constructs will be used to determine if efficiency of GUS termination by putative TOIs impacts expression of DsRed2. Vectors (C, D) contain no transcriptional termination sequence for the secondary reporter gene DsRed2, and will be used to test for bidirectional transcriptional termination activity by TOI sequences that are juxtaposed between the 3' ends of the DsRed2 and GUS genes.

Figure 14:
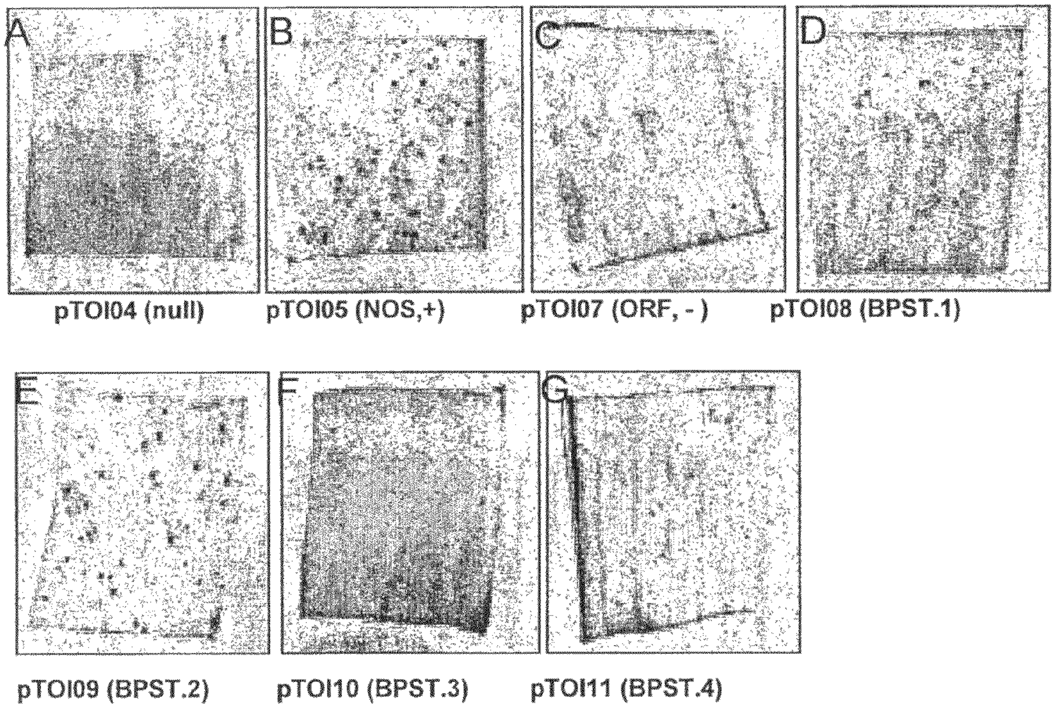

FIG. 14 Maize leaf tissue following transient TOI assays. No GUS staining was observed in vectors that do not comprise a functional transcriptional terminator downstream of the GUS coding sequence (A & C). The presence of a functional terminator rescued GUS expression in the (+) control (B) vector as well as all four TOI candidate sequences (D-G).

Figure 15:
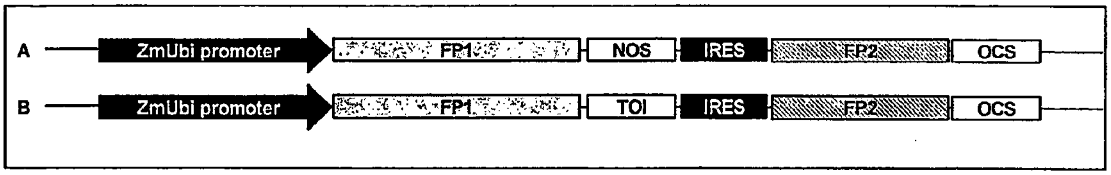

FIG. 15 Control construct (A) and a construct containing potential terminator candidates (B). The constructs are composed of strong constitutive promoter (e.g. maize ubiquitin promoter), FP1 (gene encoding fluorescent protein1), known (A: e.g. NOS) or novel (B) terminator, IRES (e.g. EMCV), FP2 (gene encoding fluorescent protein2), and octopine synthase terminator.

Figure 16:
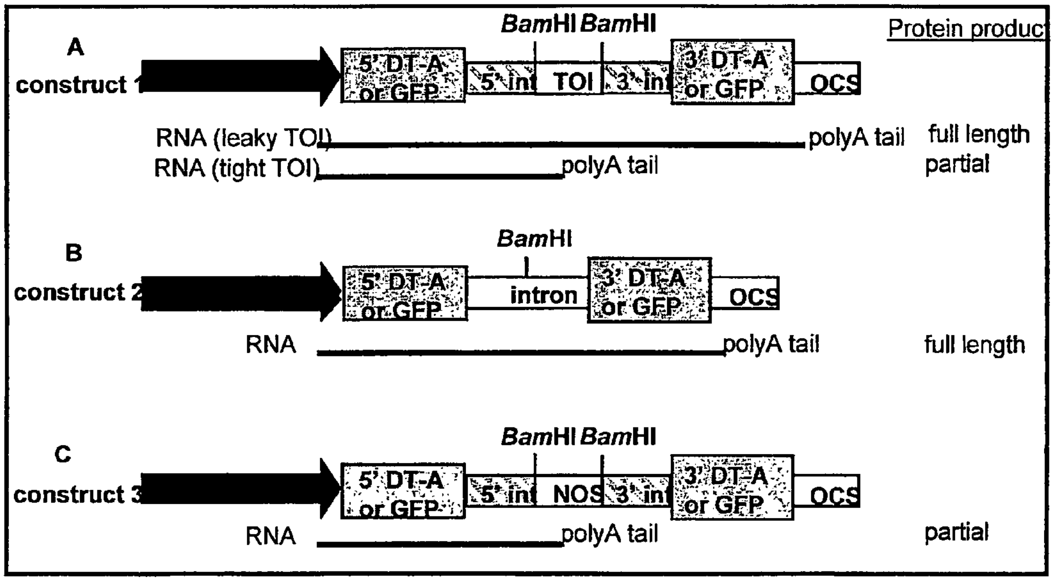

FIG. 16 Terminator of interest (TOI) construct (A) and control constructs (B and C). A TOI is embedded within an intron of a lethal gene or a reporter gene (A). Control constructs will also be built without a TOI embedded in the intron (B) and with a known terminator, NOS, embedded in the intron (C). The lethal gene can be diphtheria toxin fragment A (DT-A) or any known lethal gene for plants in the art. The reporter gene can be green fluorescent protein or any known reporter gene functioning in plants in the art.

Figure 17:
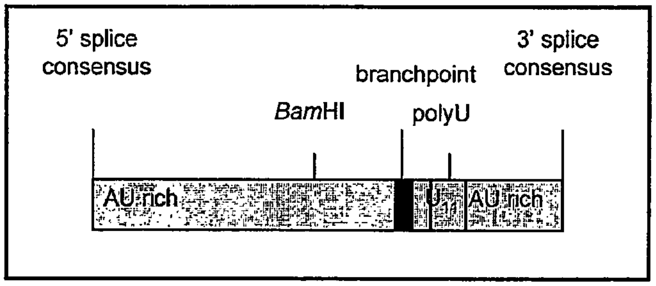

FIG. 17 The modified PIV2 intron. PIV intron contains (1) a consensus 5' recognition sequence (2) high AU content after the 5' splice site, (3) high AU content before the 3' splice site, (4) a consensus 3' recognition sequence, (5) a consensus branchpoint sequence CURAY, (6) a polyU tract between the branchpoint sequence and the 3' splice site.

Figure 18:
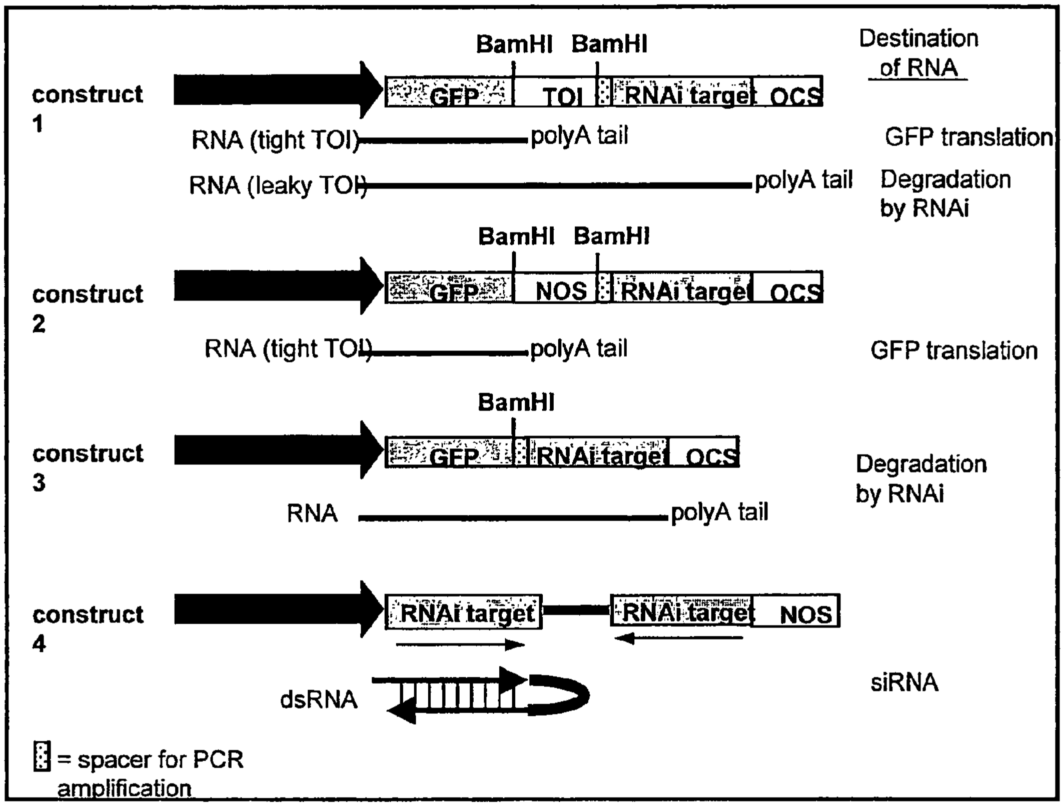

FIG. 18 Terminator of interest (TOI) construct (1), and control constructs (2 and 3). Construct 4 expresses a dsRNA molecule which will target mRNA containing the RNAi target region of constructs 1 (leaky TOI) and construct 3 for degradation. ZmUbi (maize ubiquitin promoter), GFP (green fluorescence protein), OCS (Octopine synthase terminator), NOS (Nopaline synthase terminator), dsRNA (double-stranded RNA), siRNA (small interfering RNA), RNAi (RNA interference; silencing). For constructs 1, 2, and 3, the destination of the RNA produced is shown (translated or degraded) if construct 4 is also expressed in the same plant.

FIG. 19 Schematic drawing of the inserts in vector pTOI3 (SEQ ID NO: 73) and pTOI4 (SEQ ID NO: 73)

Figure 20:
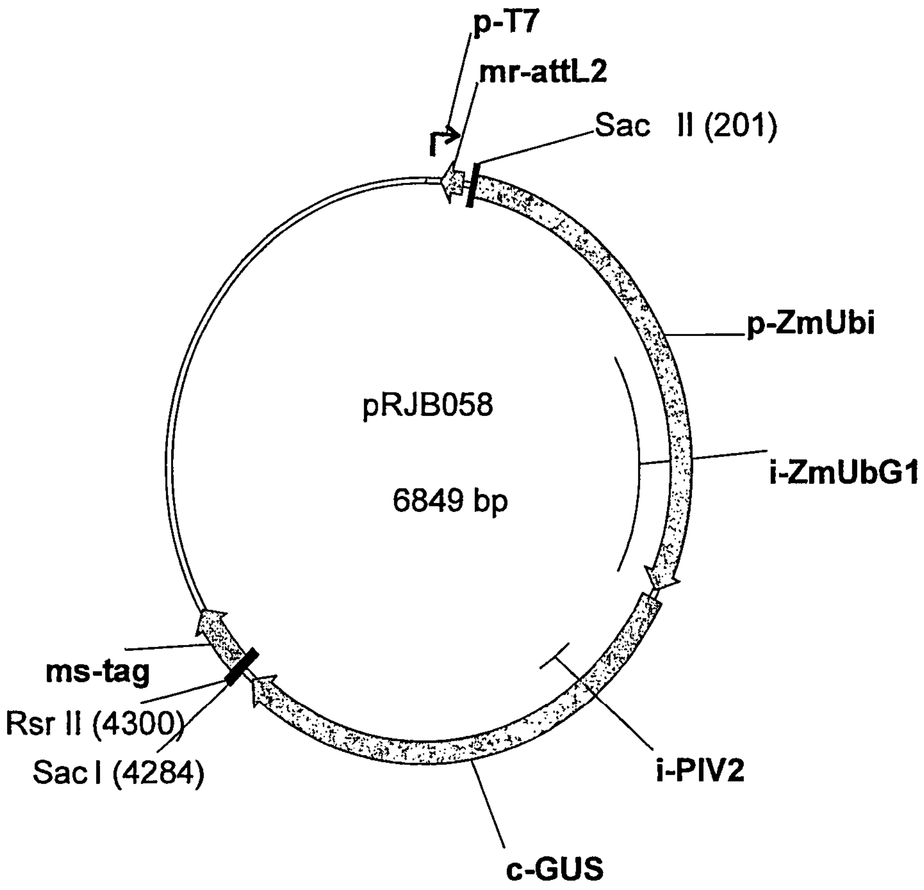

FIG. 20 A map of the pUC based expression vector that was used in transient analyses. Control and putative TOI sequences were cloned into the RsrII-SacI sites of this vector.

FIG. 21 Maps of binary vectors to be used for analysis of TOI activity in stably-transformed plants. A—vectors comprise Nos terminator downstream of DsRed2 reporter gene, and will be used to determine if efficiency of GUS termination by putative TOIs affects expression of DsRed2. TOI sequences were inserted at the AvrII site. B—vectors comprise no terminator for DsRed2 and will be used to assess bidirectional transcriptional termination activity by TOI candidates. TOI sequences will be inserted at SacI site.

GENERAL DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. In the description that follows, a number of terms used in recombinant DNA technology are utilized extensively. In order to provide a clear and consistent understanding of the specification and claims, including the scope to be given such terms, the following definitions are provided.

It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

The term "nucleotide" refers to a base-sugar-phosphate combination. Nucleotides are monomeric units of a nucleic acid sequence (DNA and RNA). The term nucleotide includes ribonucleoside triphosphatase ATP, UTP, CTG, GTP and deoxyribonucleoside triphosphates such as DATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well-known techniques. Detectable labels include, for example, radioactive isotopes, fluorescent labels, chemiluminescent labels, bioluminescent labels and enzyme labels.

The term "nucleic acid" refers to deoxyribonucleotides or ribonucleotides and polymers or hybrids thereof in either single- or double-stranded, sense or antisense form.

Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide".

The phrase "nucleic acid sequence" as used herein refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid which is transcribed and translated in a sequence-specific manner to produce into a particular polypeptide or protein when placed under the control of appropriate regulatory sequences. The coding region is said to encode such a polypeptide or protein.

The term "probe", as used herein, refers to an oligonucleotide, whether occurring naturally as in a purified restriction digest or produced synthetically, recombinantly or by PCR amplification, which is capable of hybridizing to a nucleotide sequence of interest. A probe may be single-stranded or double-stranded. It is contemplated that any probe used in the present invention will be labeled with any "reporter molecule," so that it is detectable in any detection system including, but not limited to enzyme (e.g., ELISA, as well as enzyme-based histochemical assays), fluorescent, radioactive, calorimetric, gravimetric, magnetic, and luminescent systems. It is not intended that the present invention be limited to any particular detection system or label.

The term "oligonucleotide" refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

The term "sense" is understood to mean a nucleic acid having a sequence which is homologous or identical to a target sequence, for example a sequence which binds to a protein transcription factor and which is involved in the expression of a given gene.

According to a preferred embodiment, the nucleic acid comprises a gene of interest and elements allowing the expression of the said gene of interest. The sense RNA can be employed for gene silencing in a co-suppression or sense-suppression gene silencing approach. Expression of genes that when transcribed produce RNA transcripts that are identical or at least very similar to transcripts of endogenous genes can mediate gene silencing in an as yet not fully understood way of inhibition of gene expression referred to as co-suppression (disclosed by Napoli 1990; Jorgensen 1996; Goring 1991; Smith 1990; Van der Krol 1990). The expressed RNA can represent the endogenous target entirely or in part. Translation is nor required, transcription is sufficient. Application in plants is described (Napoli 1990; U.S. Pat. No. 5,034,323).

The term "antisense" is understood to mean a nucleic acid having a sequence complementary to a target sequence, for example a messenger RNA (mRNA) sequence the blocking of whose expression is sought to be initiated by hybridization with the target sequence. To maximize the antisense effects in a plant host, the use of homologous genes is preferred. With homologous is meant obtainable from the same plant species as the plant host. Heterologous, for the purpose of this specification shall mean obtainable from a different plant or non-plant species. Heterologous shall also comprise synthetic analogs of genes, modified in their mRNA encoding nucleic acid sequence to diverge at least 5% of the host gene. Gene silencing by antisense RNA is numerously described in the art (including various applications in plants; e.g. Sheehy 1988; U.S. Pat. No. 4,801,340; Mol 1990). A variation of the antisense approach is the use of $\alpha$-anomeric nucleic acid sequences. Such $\alpha$-anomeric sequences are forming specific double-stranded hybrids with complementary RNA, wherein in contrast to "normal" antisense RNA (or $\beta$-nucleic acids) both strands are in parallel to each other (Gautier 1987).

The term "dsRNAi" or "double-stranded RNA interference" is intended to mean the method of gene silencing by expression of a RNA molecule corresponding to an endogenous gene together with its complementary RNA strand, thus providing two RNA sequences which may form by hybridization a double-stranded RNA structure. The two RNA strands may be on separate molecules or may be part of one molecule, thus forming a so-called self-complementary hairpin structure. Self-complementary hairpin forming RNA structure may be expressed for example from a DNA comprising an "inverted repeat" of a double-stranded DNA fragment. In this context the term "inverted repeat" is intended to mean the orientation of two fragments of double-stranded DNA (which are substantially identical or—preferably identical in sequence) in one double stranded DNA molecule in an inverted orientation (i.e. in a "head" to "head" or "tail" to tail" orientation so that the sense-strand of the first fragment is fused to the antisense strand of the second and vice versa). Preferably, the hairpin forming dsRNA may include a linker (e.g., an intron sequence for example the intron of the ST-LS1 gene from potato; Vancanneyt 1990) connecting the two complementary strands (e.g., as described in WO 99/53050). The method of dsRNAi is well described in the art for various organisms including animal and plant organism (e.g., Matzke 2000; Fire 1998; WO 99/32619; WO 99/53050; WO 00/68374; WO 00/44914; WO 00/44895; WO 00/49035; WO 00/63364). These references and the methods disclosed therein are explicitly incorporated by reference. The phenotype of a dsRNAi expressing cell or organism is similar to that of a knock-out mutant, often resulting in complete gene silencing (Water-house 1998). The term "double-stranded RNA" or "dsRNA" as used herein is intended to mean one or more ribonucleic acid sequences, which because of complementary sequences are theoretically (i.e. according to the base-pairing rules of Watson and Crick) and/or practically (e.g., because of hybridization experiments in vitro and/or in vivo) capable to form double-stranded RNA structures. The person skilled in the art is aware of the fact that formation of a double-stranded RNA structure is an equilibrium between single-stranded and double-stranded forms. Preferably, the relation between double-stranded (i.e. hybridized) and single-stranded (i.e. non-hybridized or dissociated) forms is at least 1:10, preferably at least 1:1, more preferably at least 10:1. One strand of the dsRNA is essentially identical to the sequence of the endogenous gene. Essentially identical in this context means that a 100% identity is not required for efficient gene silencing, but that the dsRNA sequence may comprise insertions, deletions and point mutations in comparison to the target sequence. Preferably the homology between the dsRNA sequence and at least part of the target sequence is at least 60%, preferably at least 80%, more preferably at least 90%, most preferably 100%. Alternatively, an essential identity is one which allows for hybridization of the two sequences under high stringency conditions. The part of the target sequence which is having the homology with the dsRNA has a length of at least 23 bases, preferably at least 50 bases, more preferably at least 100 bases. Said part of the target gene may resemble various part of the gene, but is preferably part which encodes for the mRNA sequence transcribed from said gene.

The term "ribozyme" is intended to mean catalytic RNA-molecules, which are capable to induce sequence-specific cleavage of a target RNA (Tanner 1999). Preparation and use of ribozymes is disclosed in the art (Haseloff 1988; Haselhoff & Gerlach 1988; Steinecke 1992; de Feyter R 1996). Preferred are "hammerhead"-ribozymes (Haselhoff & Gerlach 1988). Disclosed are methods for gene silencing based on customized ribozymes (EP 0 291 533, EP 0 321 201, EP 0 360 257). Use in plants and plant cells is also disclosed (Steinecke 1992; de Feyter 1996). Suitable target sequences are ribozymes can be derived as described (Steinecke 1995) by secondary structure calculation of ribozyme and target sequences and the interaction thereof (Bayley 1992; Lloyd 1994). For example derivatives of the Tetrahymena L-19 IVS RNA can be employed and adapted to virtually any target sequence (U.S. Pat. No. 4,987,071; U.S. Pat. No. 5,116,742). Alternatively, ribozymes can be selected by screening of diversified ribozyme libraries (Bartel. 1993).

The term "gene" refers to a coding region operably joined to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons).

As used herein the term "coding region" when used in reference to a structural gene refers to the nucleotide sequences which encode the amino acids found in the nascent polypeptide as a result of translation of a mRNA molecule.

The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences, which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers, which control or influence the transcription of the gene. The 3'-flanking region may contain sequences, which direct the termination of transcription, posttranscriptional cleavage and polyadenylation.

The term "amplification" refers to any in vitro method for increasing a number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reaction (PCR). One PCR reaction may consist of 5 to 100 "cycles" of denaturation and synthesis of a DNA molecule.

The terms "polypeptide", "peptide", "oligopeptide", "polypeptide", "gene product", "expression product" and "protein" are used interchangeably herein to refer to a polymer or oligomer of consecutive amino acid residues.

The term "isolated" as used herein means that a material has been removed from its original environment. For example, a naturally occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment.

Preferably, the term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. For example, an isolated nucleic acid sequence encoding for a specific trait includes, by way of example, such nucleic acid sequences in cells which ordinarily contain said nucleic acid sequence, wherein said nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

A "complement" of a nucleic acid sequence as used herein refers to a nucleotide sequence whose nucleic acids show total complementarity to the nucleic acids of the nucleic acid sequence.

The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

The term "transgenic" or "recombinant" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed.

Examples of heterologous DNA include reporter genes, transcriptional and translational regulatory sequences, selectable marker proteins (e.g., proteins which confer drug resistance), etc. Preferably, the term 'transgenic' or "recombinant" with respect to a regulatory sequence (e.g., a promoter of the invention) means that said regulatory sequence is covalently joined and adjacent to a nucleic acid to which it is not adjacent in its natural environment.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

"Recombinant polypeptides" or "recombinant proteins" refer to polypeptides or proteins produced by recombinant DNA techniques, i.e., produced from cells transformed by an exogenous recombinant DNA construct encoding the desired polypeptide or protein. Recombinant nucleic acids and polypeptide may also comprise molecules which as such does not exist in nature but are modified, changed, mutated or otherwise manipulated by man.

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed.

The terms "organism", "host", "target organism" or "host organism" are referring to any prokaryotic or eukaryotic organism that can be a recipient of the screening construct or screening vector. A "host," as the term is used herein, includes prokaryotic or eukaryotic organisms that can be genetically engineered. For examples of such hosts, see Maniatis 1989. Included are entire organisms but also organs, parts, cells, cultures, and propagatable material derived therefrom. Preferred are microorganisms, non-human animal and plant organisms. Preferred microorganisms are bacteria, yeasts, algae or fungi.

Preferred bacteria are bacteria of the genus *Escherichia, Corynebacterium, Bacillus, Erwinia, Agrobacterium, Flavobacterium, Alcaligenes, Clostridium, Proionibacterium, Butyrivibrio, Eubacterium, Lactobacillus, Phaeodactylum, Colpidium, Mortierella, Entomophthora, Mucor, Crypthecodinium* or *cyanobacteria*, for example of the genus *Synechocystis*. Especially preferred are microorganisms which are capable of infecting plants and thus of transferring the constructs according to the invention. Preferred microorganisms are those from the genus *Agrobacterium* and, in particular, the species *Agrobacterium tumefaciens.*

Preferred yeasts are *Candida, Saccharomyces, Hansenula* or *Pichia*. Preferred fungi are *Aspergillus, Trichoderma, Ashbya, Neurospora, Fusarium, Beauveria* or other fungi. Plant organisms are furthermore, for the purposes of the invention, other organisms which are capable of photosynthetic activity such as, for example, algae or cyanobacteria, and also mosses. Preferred algae are green algae such as, for example, algae of the genus *Haematococcus, Phaedactylum tricornatum, Volvox* or *Dunaliella.*

Preferred eukaryotic cells and organism comprise plant cells and organisms, animal cells, and non-human animal organism, including eukaryotic microorganism such as yeast, algae, or fungi.

"Non-human animal organisms" includes but is not limited to non-human vertebrates and invertebrates. Preferred are fish species, non-human mammals such as cow, horse, sheep, goat, mouse, rat or pig, birds such as chicken or goose. Preferred animal cells comprise for example CHO, COS, HEK293 cells. Invertebrate organisms include for example nematodes and insects. Insect cells include for example *Drosophila* S2 and *Spodoptera* Sf9 or Sf21 cells.

Preferred nematodes are those which are capable to invade plant, animal or human organism. Preferred namtodes include for example nematodes of the genus *Ancylostoma, Ascaridia, Ascaris, Bunostomum, Caenorhabditis, Capillaria, Chabertia, Cooperia, Dictyocaulus, Haemonchus, Heterakis, Nematodirus, Oesophagostomum, Ostertagia, Oxyuris, Parascaris, Strongylus, Toxascaris, Trichuris, Trichostrongylus, Tfhchonema, Toxocara* or *Uncinaria*. Especially preferred are plant parasitic nematodes such as *Bursaphalenchus, Criconemella, Diiylenchus, Ditylenchus, Globodera, Heicotylenchus, Heterodera, Longidorus, Melodoigyne, Nacobbus, Paratylenchus, Pratylenchus, Radopholus, Rotelynchus, Tylenchus* or *Xiphinema*. Preferred insects comprise those of the genus *Coleoptera, Diptera, Lepidoptera*, and *Homoptera.*

Preferred fungi are *Aspergillus, Trichoderma, Ashbya, Neurospora, Fusarium, Beauveria* or other fungi described in Indian Chem. Engr. Section B. Vol 37, No 1,2 (1995) on page 15, table 6. Especially preferred is the filamentic Hemiascomycete *Ashbya gossypii.*

Preferred yeasts are *Candida, Saccharomyces, Hansenula* or *Pichia*, especially preferred are *Saccharomyces cerevisiae* and *Pichia pastoris* (ATCC Accession No. 201178).

The term "plant" or "plant organism" as used herein refers to a plurality of plant cells which are largely differentiated into a structure that is present at any stage of a plant's development. Such structures include one or more plant organs including, but are not limited to, fruit, shoot, stem, leaf, flower petal, etc. Host or target organisms which are preferred as transgenic organisms are especially plants. Included within the scope of the invention are all genera and species of higher and lower plants of the plant kingdom. Included are furthermore the mature plants, seeds, shoots and seedlings and parts, propagation material and cultures derived therefrom, for example cell cultures. The term "mature plants" is understood as meaning plants at any developmental stage beyond the seedling. The term "seedling" is understood as meaning a young, immature plant in an early developmental stage.

Annual, biennial, monocotyledonous and dicotyledonous plants are preferred host or ganisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacilladophyceae (diatoms) and Euglenophyceae.

Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species max (soybean), alfalfa, pea, lucerne, beans or peanut and many others; and the family of the Cruciferae (Brassicacae), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species thaliana and many others; the family of the Compositae, especially the genus *Lactuca*, very especially the species sativa (lettuce) and many others; the family of the Asteraceae such as sunflower, Tagetes, lettuce or Calendula and many other; the family of the Cucurbitaceae such as melon, pumpkin/squash or zucchini, and linseed. Further preferred are cotton, sugar cane, hemp, flax, chillies, and the various tree, nut and wine species. Very especially preferred are *Arabidopsis thaliana, Nicotiana tabacum, Tagetes erecta, Calendula officinalis, Gycine max, Zea mays, Oryza sativa, Triticum aestivum, Pisum sativum, Phaseolus vulgaris, Hordium vulgare, Brassica napus.*

The term "cell" refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronized or not synchronized, preferably the cells are synchronized.

The term "organ" with respect to a plant (or "plant organ") means parts of a plant and may include (but shall not limited to) for example roots, fruits, shoots, stem, leaves, anthers, sepals, petals, pollen, seeds, etc.

The term "tissue" with respect to a plant (or "plant tissue") means arrangement of multiple plant cells including differentiated and undifferentiated tissues of plants. Plant tissues may constitute part of a plant organ (e.g., the epidermis of a plant leaf) but may also constitute tumor tissues and various types of cells in culture (e.g., single cells, protoplasts, embryos, calli, protocorm-like bodies, etc.). Plant tissue may be in planta, in organ culture, tissue culture, or cell culture.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

The term "structural gene" as used herein is intended to mean a DNA sequence that is transcribed into mRNA which is then translated into a sequence of amino acids characteristic of a specific polypeptide.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

The term "expression" refers to the biosynthesis of a gene product. For example, in the case of a structural gene, expression involves transcription of the structural gene into mRNA and—optionally—the subsequent translation of mRNA into one or more polypeptides.

The term "expression cassette" or "expression construct" as used herein is intended to mean the combination of any nucleic acid sequence to be expressed in operable linkage with a promoter sequence and—optionally—additional elements (like e.g., terminator and/or polyadenylation sequences) which facilitate expression of said nucleic acid sequence.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The term "transcription terminator" or "transcription terminator sequence" as used herein is intended to mean a sequence which leads to or initiates a stop of transcription of a nucleic acid sequence initiated from a promoter. Preferably, a transcription terminator sequences is furthermore comprising sequences which cause polyadenylation of the transcript. A transcription terminator may, for example, comprise one or more polyadenylation signal sequences, one or more polyadenylation attachment sequences, and downstream sequence of various lengths which causes termination of transcription. It has to be understood that also sequences downstream of sequences coding for the 3'-untranslated region of an expressed RNA transcript may be part of a transcription terminator although the sequence itself is not expressed as part of the RNA transcript. Furthermore, a transcription terminator may comprise additional sequences, which may influence its functionality, such a 3'-untranslated sequences (i.e. sequences of a gene following the stop-codon of the coding sequence). Transcription termination may involve various mechanisms including but not limited to induced dissociation of RNA polymerase II from their DNA template. As virtually all biological reactions transcription termination is never of 100% efficiency. The term "transcription termination efficiency" or "efficiency or transcription termination" as used herein is indicating the ratio between the frequencies of stops (or termination) of transcription in the region of said transcription terminator to the frequency of read-through transcription beyond said transcription terminator. The term "tight" or "efficient" in relation to transcription termination sequence as used herein is understood as a transcription termination sequence for which the efficiency of transcription termination is at least 10 (i.e. stop/read-through ratio of 10:1), preferably at least 100 (i.e. stop/read-through ratio of 100:1), more preferably 1000 (i.e. stop/read-through ratio of 1000:1). Transcription may end at one or more specific base pairs within said transcription terminator sequence. In consequence, there might be variability in the length of the transcript. However, preferably transcription termination has a low variability and end to at least 50%, preferably at least 80%, more preferably at least 90% at one specific base pair as judged by the resulting transcript length (excluding the poly-A tail).

The term "operable linkage" or "operably linked" is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. Operable linkage, and an expression construct, can be generated by means of customary recombination and cloning techniques as described (e.g., in Maniatis 1989; Silhavy 1984; Ausubel 1987; Gelvin 1990). However, further sequences which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of promoter and nucleic acid sequence to be expressed, can exist in a vector-integrated form and be inserted into a plant genome, for example by transformation.

The term "transformation" as used herein refers to the introduction of genetic material (e.g., a transgene) into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene (e.g., the uid A gene) as demonstrated herein [e.g., histochemical assay of GUS enzyme activity by staining with X-Gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes.

In contrast, the term "stable transformation" or "stably transformed" refers to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify trans-gene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression which may exhibit variable properties with respect to meiotic stability. Stable transformation also includes introduction of genetic material into cells in the form of viral vectors involving epichromosomal replication and gene expression which may exhibit variable properties with respect to meiotic stability.

Cloning and transformation techniques for manipulation of ciliates and algae are well known in the art (WO 98/01572; Falciatore 1999; Dunahay 1995).

Principally speaking transformation techniques suitable for plant cells or organisms (as described below) can also be employed for animal or yeast organism and cells. Preferred are direct transformation techniques such as calcium phosphate or liposome mediated transformation, or electroporation.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogenes* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" *Agrobacteria; Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria.*

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The terms "homology" or "identity" when used in relation to nucleic acids refers to a degree of complementarity. Homology or identity between two nucleic acids is understood as meaning the identity of the nucleic acid sequence over in each case the entire length of the sequence, which is calculated by comparison with the aid of the program algorithm GAP (Wisconsin Package Version 10.0, University of Wisconsin, Genetics Computer Group (GCG), Madison, USA) with the parameters being set as follows:

| | |
|---|---|
| Gap Weight: 12 | Length Weight: 4 |
| Average Match: 2,912 | Average Mismatch: −2,003 |

Alternatively, a partially complementary sequence is understood to be one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra. When used in reference to a single-stranded nucleic acid sequence, the term "substantially homologous" refers to any probe which can hybridize to the single-stranded nucleic acid sequence under conditions of low stringency as described infra.

The terms "hybridization" and "hybridizing" as used herein includes "any process by which a strand of nucleic acid joins with a complementary strand through base pairing." (Coombs 1994). Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl (see e.g., Anderson 1985). Other references include more sophisticated computations which take structural as well as sequence characteristics into account for the calculation of Tm.

Low stringency conditions when used in reference to nucleic acid hybridization comprise conditions equivalent to binding or hybridization at 68° C. in a solution consisting of 5×SSPE (43.8 g/L NaCl, 6.9 g/L $NaH_2PO_4.H_2O$ and 1.85 g/L EDTA, pH adjusted to 7.4 with NaOH), 1% SDS, 5× Denhardt's reagent [50× Denhardt's contains the following per 500 mL: 5 g Ficoll (Type 400, Pharmacia), 5 g BSA (Fraction V; Sigma)] and 100 μg/mL denatured salmon sperm DNA followed by washing in a solution comprising 0.2×SSPE, and 0.1% SDS at room temperature when a DNA probe of about 100 to about 1000 nucleotides in length is employed.

High stringency conditions when used in reference to nucleic acid hybridization comprise conditions equivalent to binding or hybridization at 68° C. in a solution consisting of 5×SSPE, 1% SDS, 5× Denhardt's reagent and 100 μg/mL denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 80% to 90% homology to the first nucleic acid sequence, then another hybridization condition is said to be equivalent to the hybridization condition of interest if this other hybridization condition also results in hybridization of the first nucleic acid sequence with the other nucleic acid sequences that have from 80% to 90% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions. Those skilled in the art know that whereas higher stringencies may be preferred to reduce or eliminate non-specific binding between the nucleotide sequence of interest and other nucleic acid sequences, lower stringencies may be preferred to detect a larger number of nucleic acid sequences having different homologies to the nucleotide sequence of interest.

The term "recognition sequence" refers to a particular sequences which a protein, chemical compound, DNA, or RNA molecule (e.g., restriction endonuclease, a modification methylase, or a recombinase) recognizes and binds. With respect to a recombinase a recognition sequence will usually refer to a recombination site. For example, the recognition sequence for Cre recombinase is loxP which is a 34 base pair sequence comprised of two 13 base pair inverted repeats (serving as the recombinase binding sites) flanking an 8 base pair core sequence (see Sauer 1994; FIG. 1). Other examples of recognition sequences are the attB, attP, attL, and attR sequences which are recognized by the recombinase enzyme λ Integrase. aftB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis) (see Landy 1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way.

The term "recombinase" is referring to an enzyme which catalyzes the exchange of DNA segments at specific recombination sites.

The term "recombinational cloning" is referring to a method, whereby segments of nucleic acid molecules or populations of such molecules are exchanged, inserted, replaced, substituted or modified, in vitro or in vivo, by action of a site-specific recombinase.

The term "Recombination proteins" refers to polypeptide including excisive or integrative proteins, enzymes, co-factors or associated proteins that are involved in recombination reactions involving one or more recombination sites (Landy 1993).

Repression cassette: is a nucleic acid segment that contains a repressor of a Selectable marker present in the subcloning vector.

The term "site-specific recombinase" as used herein is referring to a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid (see Sauer 1994). Conservative site-specific recombination is distinguished from homologous recombination and transposition by a high degree of specificity for both partners. The strand exchange mechanism involves the cleavage and rejoining of specific DNA sequences in the absence of DNA synthesis (Landy 1989).

The term "vector" is referring to a nucleic acid molecule (preferably DNA) that provides a useful biological or biochemical property to an inserted nucleic acid sequence, preferably allows replication and/or transformation or transfection into host cells and organisms. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), TA Cloning™ brand PCR cloning (Invitrogen Corp., Carlsbad, Calif.), and the like) can also be applied to clone a fragment into a cloning vector to be used according to the present invention. The cloning vector can further contain one or more selectable markers suitable for use in the identification of cells transformed with the cloning vector.

The term "primer" refers to a single stranded or double stranded oligonucleotide that is extended by covalent bonding of nucleotide monomers during amplification or polymerization of a nucleic acid molecule (e.g. a DNA molecule). In a preferred aspect, the primer comprises one or more recombination sites or portions of such recombination sites. Portions of recombination sties comprise at least 2 bases, at least 5 bases, at least 10 bases or at least 20 bases of the recombination sites of interest. When using portions of recombination sites, the missing portion of the recombination site may be provided by the newly synthesized nucleic acid molecule. Such recombination sites may be located within and/or at one or both termini of the primer. Preferably, additional sequences are added to the primer adjacent to the recombination site(s) to enhance or improve recombination and/or to stabilize the recombination site during recombination. Such stabilization sequences may be any sequences (preferably G/C rich sequences) of any length. Preferably, such sequences range in size from 1 to about 1,000 bases, 1 to about 500 bases, and 1 to about 100 bases, 1 to about 60 bases, 1 to about 25, 1 to about 10, 2 to about 10 and preferably about 4 bases. Preferably, such sequences are greater than 1 base in length and preferably greater than 2 bases in length.

The term "template" refers to double stranded or single stranded nucleic acid molecules which are to be amplified, synthesized or sequenced. In the case of double stranded molecules, denaturation of its strands to form a first and a second strand is preferably performed before these molecules will be amplified, synthesized or sequenced, or the double stranded molecule may be used directly as a template. For single stranded templates, a primer complementary to a portion of the template is hybridized under appropriate conditions and one or more polypeptides having polymerase activity (e.g. DNA polymerases and/or reverse transcriptases) may then synthesize a nucleic acid molecule complementary to all or a portion of said template. Alternatively, for double stranded templates, one or more promoters may be used in combination with one or more polymerases to make nucleic acid molecules complementary to all or a portion of the template. The newly synthesized molecules, according to the invention, may be equal or shorter in length than the original template. Additionally, a population of nucleic acid templates may be used during synthesis or amplification to produce a population of nucleic acid molecules typically representative of the original template population.

The term "adapter" refers to an oligonucleotide or nucleic acid fragment or segment (preferably DNA) which comprises one or more recognition sites (e.g., recombination sites or recognition sites for restriction endonucleases) which can be added to a circular or linear DNA molecule as well as other nucleic acid molecules described herein. Such adapters may be added at any location within a circular or linear molecule, although the adapters are preferably added at or near one or both termini of a linear molecule. Preferably, adapters are positioned to be located on both sides (flanking) a particularly nucleic acid molecule of interest. The synthesis of adapters (e.g., by oligonucleotide synthesis, annealing procedures, and or PCR) is a standard technique well known to the person skilled in the art. In accordance with the invention, adapters may be added to nucleic acid molecules of interest by standard recombinant techniques (e.g. restriction digest and ligation). For example, adapters may be added to a circular molecule by first digesting the molecule with an appropriate restriction enzyme, adding the adapter at the cleavage site and reforming the circular molecule which contains the adapter(s) at the site of cleavage. Alternatively, adapters may be ligated directly to one or more and preferably both termini of a linear molecule thereby resulting in linear molecule(s) having adapters at one or both termini. In one aspect of the invention, adapters may be added to a population of linear molecules, (e.g. a cDNA library or genomic DNA which has been cleaved or digested) to form a population of linear molecules containing adapters at one and preferably both termini of all or substantial portion of said population.

Other terms used in the fields of recombinant DNA technology and molecular and cell biology as used herein will be generally understood by one of ordinary skill in the applicable arts.

DETAILED DESCRIPTION OF THE INVENTION

A first subject matter of the invention relates to a method for identification and isolation of transcription termination sequences for comprising the steps of:

i) providing a screening construct or screening vector comprising
   a) a promoter sequence, and
   b) one or more insertion sites—preferably a restriction or recombination site—for insertion of DNA sequences, and
   c) at least one additional sequence which causes upon expression under said promoter sequence a readily detectable characteristic, wherein insertion of an efficient transcription terminator into said insertion site changes expression of said additional sequences by said promoter sequence in comparison to no insertion, and
ii) providing one or more DNA sequences to be assessed for their transcription termination capability, and
iii) inserting one or more copies of said DNA sequences into said insertion site of said screening construct or screening vector, and
iv) introducing said screening construct or screening vector with said inserted DNA sequences into an in vitro or in vivo transcription system suitable to induce expression from said promoter sequence, and
v) identifying and/or selecting screening construct or screening vector with a changed readily detectable characteristic in comparison to no insertion, and
vi) isolating the inserted DNA sequences from said identified and/or selected screening construct or screening vector for use as transcription termination sequences and—optionally—determining their sequence.

By the method of the invention new transcription terminator sequences can be readily identified. The method can be based either on an in vitro or in vivo screening system. The screening method of the invention allows for selection of DNA sequences, screening constructs or screening vectors, and/or cells or organism (preferably plant cells and plant organisms) containing efficient transcription terminator sequences. Previously terminators had to be evaluated sequence-by-sequence. Testing of termination efficiency (tightness) was laborious. The methods of the present invention are time-efficient and very sensitive so that only very tight terminators will be identified. Tight terminators identified by this screening system will be used for the expression cassettes, which will reduce read through between cassettes and increase stability of the transgene expression. Discovery of various terminators of interest will provide opportunity to understand better termination of transcription in planta.

The term "readily detectable characteristic" as used herein is to be understood in the broad sense and may include any change of a characteristic, preferably a phenotypic characteristic. "Change" in this context may include increasing or decreasing said characteristic. In consequence, expression of said additional sequences under control of said promoter may cause increasing or decreasing a phenotypic characteristic. For example expression may cause a herbicide resistance (increased resistance) or may cause a toxic effect by expression of e.g., a toxic gene (decreased viability). Since depending on the localization of the insertion site in relation to said additional sequences (as described below in detail) an efficient transcription terminator may result in increased (preferably initiated) or decreased (preferably silenced) expression of said additional sequences both type of changes can be advantageously employed.

1. Localization of the Insertion Site

The insertion site may have various localizations with respect to the additional sequences which bring about the readily detectable characteristic:

1.1 Variation A:

For example the insertion site may be localized upstream (i.e. in 5' direction) of the additional sequences so that the insertion site is between the promoter sequences and said additional sequences (hereinafter "Variation A"). In case an efficient transcription terminator sequences in inserted into said insertion site transcription, transcription will stop before said additional sequences and no read-through transcription into this additional sequences will occur. In this case an efficient transcription terminator will result in decreased or preferably completely suppressed expression of the additional sequences. Depending whether presence or absence of transcription (i.e. expression) of said additional sequences brings about said readily detectable characteristic (which both is possible depending on the type of additional sequence employed) said readily detectable characteristic diminishes or is expressed. In any case an efficient transcription terminator will cause a changed readily detectable characteristic, which may be suppressed or increased in comparison to a scenario where no sequence is inserted into the insertion site.

Thus in a preferred embodiment of the invention the method for identification and isolation of transcription termination sequences comprises the steps of:

i) providing a screening construct or screening vector comprising in 5' to 3' direction
   a) a promoter sequence, and
   b) one or more insertion sites—preferably a restriction or recombination site—for insertion of DNA sequences, and
   c) at least one additional sequence which causes upon expression under said promoter sequence a readily detectable characteristic, wherein insertion of an efficient transcription terminator into said insertion site suppresses expression of said additional sequences by said promoter sequence in comparison to no insertion, and
ii) providing one or more DNA sequences to be assessed for their transcription termination capability, and
iii) inserting one or more copies of said DNA sequences into said insertion site of said screening construct or screening vector, and
iv) introducing said screening construct or screening vector with said inserted DNA sequences into an in vitro or in vivo transcription system suitable to induce expression from said promoter sequence, and
v) identifying and/or selecting screening constructs or screening vectors with a changed readily detectable characteristic in comparison to no insertion, and
vi) isolating the inserted DNA sequences from said identified and/or selected screening constructs or screening vectors for use as transcription termination sequences and—optionally—determining their sequence.

As described below the additional sequences localized downstream of the insertion site may bring about said readily detectable characteristic only by expression (i.e. transcription) of an RNA (e.g., in cases where said additional sequences are forming an antisense RNA or dsRNA molecule) or by expression (i.e. transcription and translation of a protein). In the latter case it has to be ensured that appropriate translation can occur. This can be ensured by for example avoiding upstream ATG-codons, cloning the sequences in-frame with upstream coding sequences or—preferably—employing IRES sites which may allow efficient translation even in cases where the ATG codon is not close to the 5'-end of the transcript (Vagner 2001; for sequences see e.g., http://ifr31w3.toulouse.inserm.fr/IRESdatabase/).

1.2 Variation B:

In another preferred embodiment of the invention the insertion site may also be arranged downstream (i.e. in 3'-direction) of the additional sequences (hereinafter "Variation B"). For this variation the DNA sequences to be inserted into the insertion sites for evaluation for their transcription termination capability are preferably inserted in form of an inverted repeat. In case the inserted DNA sequence is an efficient transcription terminator only the first copy (i.e. first part) of the inverted repeat will be transcribed and normal expression of the additional sequences will occur. Depending whether presence or absence of transcription (i.e. expression) of said additional sequences brings about said readily detectable characteristic (which both is possible depending on the type of additional sequence employed) said readily detectable characteristic diminishes or is expressed. In any case an efficient transcription terminator will cause a changed readily detectable characteristic, which may be suppressed or increased in comparison to a scenario where no sequence is inserted into the insertion site. However, if only a weak transcription terminator or a sequence with no transcription termination capability at all is inserted the entire inverted repeat (i.e. both copies of the inserted sequence) will be transcribed causing transcription of a RNA comprising a double-stranded hairpin structure (formed by the RNA transcribed from inverted repeat of the inserted DNA sequences). This RNA by means of double-stranded RNA interference (dsRNAi) will cause gene silencing of its own expression (self-suppression or self-silencing) resulting in gene silencing of the expression cassette comprising said additional sequences. In this case an efficient transcription terminator will result in increased expression of the additional sequences and the detectable characteristic will change in just the other direction as in case of an efficient transcription terminator. Thus in a preferred embodiment of the invention the method for identification and isolation of transcription termination sequences comprises the steps of:

i) providing a screening construct or screening vector comprising in 5' to 3' direction
   a) a promoter sequence, and
   b) at least one additional sequence which causes upon expression under said promoter sequence a readily detectable characteristic, and
   c) one or more insertion sites—preferably a restriction or recombination site—for insertion of DNA sequences,
ii) providing one or more DNA sequences to be assessed for their transcription termination capability, and
iii) inserting at least two copies of a specific DNA sequence of said DNA sequences in form of an inverted repeat into said insertion site of said screening construct or screening vector, wherein insertion of an inverted repeat of an efficient transcription terminator into said insertion site allows expression of said additional sequences by said promoter sequence in comparison to no insertion, and
iv) introducing said screening constructs or screening vectors with said inserted DNA sequences into an in vitro or in vivo transcription system suitable to induce expression from said promoter sequence, and
v) identifying and/or selecting screening constructs or screening vectors with said readily detectable characteristic in comparison to no insertion, and
vi) isolating the inserted DNA sequences from said identified and/or selected screening constructs or screening vectors for use as transcription termination sequences and—optionally—determining their sequence.

In a preferred embodiment of this variation two different promoters and two different additional sequences are employed. These two expression cassettes are arranged in a "tail-to-tail" orientation so that transcription initiated from said promoters in running against each other. Preferably the insertion site for the inverted repeat in between the two end (tails) of the two expression cassettes. Insertion of an inverted repeat of weak transcription terminator will result of gene silencing of both additional sequences, while insertion of an efficient transcription terminator results in expression of both additional sequences. In consequence a double-check of the transcription termination efficiency becomes feasible. Preferably one of the sequences is selected from the group of negative selection marker (thus an efficient transcription terminator will result in for example a herbicide or antibiotic resistance). The other additional sequence may be selected from the group of reporter genes (for example GFP or GUS; thus an efficient transcription terminator will result in an easily detectable color).

1.3 Variation C:

In a third preferred embodiment of the invention the insertion site may also be arranged within the additional sequences (for example and preferably embedded into an intron, which is located in said additional sequences) (hereinafter "Variation C"). The full-length transcript of said additional sequence is only made, if the sequence inserted into said insertion site does not control tight transcription termination and expression of said additional sequences will cause a change of said readily detectable characteristic. In case of an efficient transcription terminator inserted into said insertion site no full-length transcript will be produced. Thus in a preferred embodiment of the invention the method for identification and isolation of transcription termination sequences comprises the steps of:

i) providing a screening construct or screening vector comprising in 5' to 3' direction
 a) a promoter sequence, and
 b) at least one additional sequence which causes upon expression under said promoter sequence a readily detectable characteristic, and embedded into said additional sequences one or more insertion sites—preferably a restriction or recombination site—for insertion of DNA sequences,
 wherein insertion of an efficient transcription terminator into said insertion site suppresses full-length transcription of said additional sequences by said promoter sequence in comparison to no insertion, and
ii) providing one or more DNA sequences to be assessed for their transcription termination capability, and
iii) inserting one or more copies of said DNA sequences into said insertion site of said screening construct or screening vector, and
iv) introducing said screening constructs or screening vectors with said inserted DNA sequences into an in vitro or in vivo transcription system suitable to induce expression from said promoter sequence, and
v) identifying and/or selecting screening constructs or screening vectors with a changed readily detectable characteristic in comparison to no insertion, and
vi) isolating the inserted DNA sequences from said identified and/or selected screening constructs or screening vectors for use as transcription termination sequences and—optionally—determining their sequence.

Localization within the additional sequences may be realized by various ways. In an improved embodiment of the invention, the insertion site for the transcription terminator sequences is localized within an intron comprised in said additional sequences. Efficient transcription termination will lead to incomplete transcription of the intron and the additional sequences, thereby preventing the phenotype caused by said additional sequences to occur. The additional sequence to be expressed may be—for example—a toxic gene (such as diphtheria toxin A) or a reporter gene (such as GFP). Additional examples are given below. In case of efficient transcription termination the phenotype corresponding to said sequences is not established. In case of toxic genes only stably transformed cell lines can be established which comprise an efficient transcription terminator sequence.

In another preferred embodiment the insertion site for the transcription termination sequences is localized between a first 5'-part of the additional sequences, which—for example—encodes for a reporter gene (such as GPF) and a 3'-part, which is preferably a non-protein encoding sequence with no homologous sequences in plants (such as for example part of luciferase gene as used in the examples below or sequences of bacteriophage λ). In addition to this screening construct another expression cassette is employed which is expressing an antisense or—preferably—a double-stranded RNA sequence corresponding to said 3'-part sequence. In case of an efficient transcription terminator, transcription of the additional sequence will stop at the terminator site and the 5'-end sequence will not be translated. In case of an inefficient (leaky) transcription terminator transcription will read-through into said 3'-part sequence thereby establishing a target for the antisense- or double-stranded RNA. This will cause degradation of the entire construct, including the region encoding for the marker sequence, thereby "silencing" the related phenotype (e.g., marker signal).

2. The Screening Construct or Screening Vector of the Invention

The screening constructs and screening vectors to be employed for the method of the invention may have various forms. In principle, any form is suitable which allows for expression or transcription of an RNA molecule. In consequence the screening construct or screening vector may be for example an RNA or a DNA molecule, it further may be single-stranded or double-stranded, and it may be linear or circular. Any combination of the before mentioned alternatives is included.

Screening constructs can be advantageously employed in scenarios were no replication is required, such as for example the in vitro screening system described below. However, preferably, a screening vector is employed. Said screening vector may be a RNA vector (such as for example a RNA virus vector) or—preferably—a DNA vector. More preferably the screening vector is a circular double-stranded DNA plasmid vector.

As essential feature the screening construct or screening vector of the invention comprises
a) a promoter sequence, and
b) additional sequences which causes upon expression under said promoter sequence a readily detectable characteristic.

2.1 Promoters for the Invention

The promoter is preferably chosen to be functional in the in vitro or in vivo system where evaluation of said transcription termination sequences is going to be carried out. Preferably, this system is similar or identical to the system where the transcription termination sequence should function in later expression constructs. For example, if a transcription terminator sequence is desired for plant organisms, a transcription system based on plant cells (either an in vitro system such as wheat germ extracts or a in vivo system such as a plant cell or a plant) is employed. In such a case the promoter sequences is preferably a sequence which is able to initiate transcription in plants, preferably an endogenous plant promoter or a promoter derived from a plant pathogen (such as a plant virus or *Agrobacterium*). Various promoters are known to the person skilled in the art for the various transcriptions systems or hosts for which the method of the invention can be employed.

As an illustration, promoters (and if necessary other transcriptional and translational regulatory signals) suitable for a mammalian host may be derived from viral sources, such as adenovirus, bovine papilloma virus, simian virus, or the like, in which the regulatory signals are associated with a particular gene that has a high level of expression. Suitable transcriptional and translational regulatory sequences also can be obtained from mammalian genes, such as actin, collagen, myosin, and metallothionein genes. Illustrative eukaryotic promoters include the promoter of the mouse metallothionein I gene (Hamer 1982), the TK promoter of Herpes virus (McKnight 1982), the SV40 early promoter (Benoist 1981), the Rous sarcoma virus promoter (Gorman 1982), the cytomegalovirus promoter (Foecking 1980), and the mouse mammary tumor virus promoter (see, generally, Etcheverry 1996). Alternatively, a prokaryotic promoter, such as the bacteriophage T3 RNA polymerase promoter, can be used to control expression of the gene of interest in mammalian cells if the prokaryotic polymerase is expressed by an eukaryotic promoter (Zhou 1990; Kaufman 1991).

For expression in plants, plant-specific promoters are preferred. The term “plant-specific promoter” is understood as meaning, in principle, any promoter which is capable of governing the expression of genes, in particular foreign genes, in plants or plant parts, plant cells, plant tissues or plant cultures. In this context, expression can be, for example, constitutive, inducible or development-dependent. The following are preferred:

a) Constitutive Promoters

“Constitutive” promoters refers to those promoters which ensure expression in a large number of, preferably all, tissues over a substantial period of plant development, preferably at all times during plant development. A plant promoter or promoter originating from a plant virus is especially preferably used. The promoter of the CaMV (cauliflower mosaic virus) 35S transcript (Franck 1980; Odell 1985; Shewmaker 1985; Gardner 1986) or the 19S CaMV promoter (U.S. Pat. No. 5,352,605; WO 84/02913) is especially preferred. Another suitable constitutive promoter is the rice actin promoter (McElroy 1990), Rubisco small subunit (SSU) promoter (U.S. Pat. No. 4,962,028), the legumin B promoter (GenBank Acc. No. X03677), the promoter of the nopaline synthase from *Agrobacterium*, the TR dual promoter, the OCS (octopine synthase) promoter from *Agrobacterium*, the ubiquitin promoter (Holtorf S 1995), the ubiquitin 1 promoter (Christensen 1989, 1992; Bruce et al. 1989), the Smas promoter, the cinnamyl alcohol dehydrogenase promoter (U.S. Pat. No. 5,683,439), the promoters of the vacuolar ATPase subunits, the pEMU promoter (Last 1991); the MAS promoter (Velten 1984) and maize H3 histone promoter (Lepetit 1992; Atanassova 1992), the promoter of the *Arabidopsis thaliana* nitrilase-1 gene (GeneBank Acc. No.: U38846, nucleotides 3862 to 5325 or else 5342) or the promoter of a proline-rich protein from wheat (WO 91/13991), and further promoters of genes whose constitutive expression in plants.

b) Tissue-Specific or Tissue-Preferred Promoters

Furthermore preferred are promoters with specificities for seeds, such as, for example, the phaseolin promoter (U.S. Pat. No. 5,504,200; Bustos et al. 1989; Murai 1983; Sengupta-Gopalan 1985), the promoter of the 2S albumin gene (Joseffson 1987), the legumine promoter (Shirsat 1989), the USP (unknown seed protein) promoter (Bäumlein 1991a), the napin gene promoter (U.S. Pat. No. 5,608,152; Stalberg 1996), the promoter of the sucrose binding proteins (WO 00/26388) or the legumin B4 promoter (LeB4; Bäumlein (1991b), the *Arabidopsis oleosin* promoter (WO 98/45461), and the *Brassica* Bce4 promoter (WO 91/13980). Further preferred are a leaf-specific and light-induced promoter such as that from cab or Rubisco (Simpson 1985; Timko 1985); an anther-specific promoter such as that from LAT52 (Twell 1989b); a pollen-specific promoter such as that from Zml3 (Guerrero et al. (1993) Mol Gen Genet 224:161-168); and a microspore-preferred promoter such as that from apg (Twell et al. 1983).

c) Chemically Inducible Promoters

The expression cassettes may also contain a chemically inducible promoter (review article: Gatz 1997), by means of which the expression of the exogenous gene in the plant can be controlled at a particular point in time. Such promoters such as, for example, the PRP1 promoter (Ward 1993), a salicylic acid-inducible promoter (WO 95/19443), a benzenesulfonamide-inducible promoter (EP 0 388 186), a tetracyclin-inducible promoter (Gatz 1991, 1992), an abscisic acid-inducible promoter (EP-A1 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (W0 93/01294) and which is operable in a large number of tissues of both monocots and dicots. Further exemplary inducible promoters that can be utilized in the instant invention include that from the ACE1 system which responds to copper (Mett 1993); or the In2 promoter from maize which responds to benzenesulfonamide herbicide safeners (Hershey 1991; Gatz 994). A promoter that responds to an inducing agent to which plants do not normally respond can be utilized. An exemplary inducible promoter is the inducible promoter from a steroid hormone gene, the transcriptional activity of which is induced by a glucocorticosteroid hormone (Schena 1991).

Particularly preferred are constitutive promoters. Furthermore, further promoters may be linked operably to the nucleic acid sequence to be expressed, which promoters make possible the expression in further plant tissues or in other organisms, such as, for example, *E. coli* bacteria. Suitable plant promoters are, in principle, all of the above-described promoters.

2.2 Additional Sequences for the Invention

The “additional sequence”, which causes upon expression under said promoter sequence a readily detectable characteristic, can be selected from a broad variety of sequences. Selection may depend on various factors, for example, whether insertion of an efficient transcription terminator into said insertion site is expected to result in decreased expression (Variation A or C) or increased expression (Variation B) or the additional sequences in its functional form (i.e., which brings about the readily detectable characteristic).

For expected decreased expression (Variation A and C) it is preferred to employ a sequence which encodes for a selectable marker selected from the group consisting of a reporter gene, a counter selection marker, or a toxic gene. In an preferred embodiment of the in vivo screening systems of the invention, the expression of a toxic gene as the additional sequences will cause a inhibition of growth, propagation and/or or regeneration of said cells or organisms (e.g., plant cells or plants). In consequence, only cells or organisms will survive if an efficient (“tight”) transcription termination sequence is inserted in front of said toxic phenotype causing sequence thereby preventing expression of this growth, propagation and/or or regeneration inhibiting sequences. The surviving cells can be isolated and the transcription terminator sequence can be identified and isolated, e.g., by amplification using PCR followed by sequencing.

For expected increased expression (Variation B) it is preferred to employ a sequence which encodes for a selectable marker selected from the group consisting of a reporter gene, a negative selection marker, or a positive selection marker.

The term “selection marker” refers to any nucleic acid or amino acid sequence which is useful to select and separate cells or organism comprising said selection marker from others not comprising it. Selection marker may comprise sequences which i) allow for separation of cells or organism comprising said marker by conferring a resistance against an otherwise toxic compound (named herein within “negative selection marker”),
ii) allow for separation of cells or organism comprising said marker by conferring a growth advantage to said cells or organism (named herein within “positive selection marker”).

Selection marker may further comprise sequences which allow for separation of cells or organism not comprising said marker by conferring a growth disadvantage to cells or organism comprising said marker (named herein within “counter selection marker” or “toxic gene”).

Selection markers can encode an activity, such as, but not limited to, production of RNA, peptide, or protein, or can provide a binding site for RNA, peptides, proteins, inorganic and organic compounds or compositions and the like. Examples of Selectable markers include but are not limited to:

(a) a DNA segment that encodes a product that provides resistance in a recipient cell or organism against otherwise toxic compounds (“Negative Selection Marker”); (e.g., antibiotics). Negative Selection Markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Especially preferred Negative Selection Markers are those which confer resistance to herbicides. Examples which may be mentioned are:
   - Phosphinothricin acetyltransferases (PAT; also named Bialophos® resistance; bar; de Block 1987; EP 0 333 033; U.S. Pat. No. 4,975,374)
   - 5-enolpyruvylshikimate-3-phosphate synthase (EPSPS) conferring resistance to Glyphosate® (N-(phosphonomethyl)glycine) (Shah 1986)
   - Glyphosate® degrading enzymes (Glyphosate® oxidoreductase; gox),
   - Dalapon® inactivating dehalogenases (deh)
   - sulfonylurea- and imidazolinone-inactivating acetolactate synthases (for example mutated ALS variants with, for example, the S4 and/or Hra mutation
   - Bromoxynil® degrading nitrilases (bxn)
   - Kanamycin- or. G418-resistance genes (NPTII; NPTI) coding e.g., for neomycin phosphotransferases (Fraley et al., 1983)
   - 2-Desoxyglucose-6-phosphate phosphatase ($DOG^R$1-Gene product; WO 98/45456; EP 0 807 836) conferring resistance against 2-desoxyglucose (Randez-Gil et al. 1995).
   - hygromycin phosphotransferase (HPT), which mediates resistance to hygromycin (Vanden Elzen et al. 1985).
   - dihydrofolate reductase (Eichholtz et al. 1987)
   - Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers which confer resistance against the toxic effects imposed by D-amino acids like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Selection Marker suitable in prokaryotic or non-plant eukaryotic systems can also be based on the Selection Markers described above for plants (beside that expression cassettes are based on other host-specific promoters). For mammal cells preferred are resistance against neomycin (G418), hygromycin, Bleomycin, Zeocin Gatignol 1987; Drocourt 1990), puromycin (see, for example, Kaufman 1990a, 1990b). Corresponding selectable marker genes are known in the art (see, for example, Srivastava 1991; Romanos 1995; Markie 1996; Pfeifer 1997; Tucker 1997; Hashida-Okado 1998). For prokaryotes preferred are resistances against Ampicillin, Kanamycin, Spectinomycin, or Tetracyclin. Selectable marker genes can be cloned or synthesized using published nucleotide sequences, or marker genes can be obtained commercially.

(b) a DNA segment that encodes a product that is toxic in a recipient cell or organism (“Counter Selection Marker”). A counter selection marker is especially suitable to select organisms with defined deletions originally comprising said marker (Koprek 1999). Examples for negative selection marker comprise thymidin kinases (TK), cytosine deaminases (Gleave 1999; Perera 1993; Stougaard 1993), cytochrome P450 proteins (Koprek 1999), haloalkan dehalogenases (Naested 1999), iaaH gene products (Sundaresan 1995), cytosine deaminase codA (Schlaman & Hooykaas 1997), or tms2 gene products (Fedoroff & Smith 1993). In general the term “counter selection marker” within the scope of this invention is to be understood in the broad sense including all proteins which either
   i) cause a toxic effect per se on the cell or organism (e.g., a plant cell), or
   ii) convert a non-toxic compound X into a toxic compound Y.

The term “non toxic compound X”, as used herein in intended to mean compounds which in comparison to its conversion product Y—under otherwise identical conditions (i.e. conditions which are identical beside the difference in compound X and Y)—demonstrate a reduced, preferably an absent, biological activity, preferably toxicity. Preferably the toxicity of compound Y is at least two-times, preferably at least five-times, more preferably at least ten-times, most preferably at least one hundred-times the toxicity of the corresponding compound X. Conversion of X to Y can occur by various mechanism including but not limited to hydrolysis, deamination, saporation, dephosphorylation, phosphorylation, oxidation or an other way of activation, metabolization, or conversion. Compound X can for example be an inactive precursor of a plant growth regulator or a herbicide. “Toxicity” or “toxic effect” as used herein means a measurable, negative effect on the physiology of a cell or an organism and may comprise symptoms including but not limited to decreased or impaired growth, decreased or impaired photosynthesis, decreased or impaired cell division, decreased or impaired regeneration or proliferation etc.

The counter selection marker may be an endogenous gene or a heterologous gene or transgene from another organism. The following counter selection marker are given by way of example:

1. Cytosine deaminases (CodA or CDase), wherein compounds like e.g., 5-fluorocytosine (5-FC) is employed as non-toxic compound X. Cytosine deaminases catalyze deamination of cytosine to uracil (Kilstrup 1989; Anderson 1989). 5-FC is concerted to the toxic metabolite ("Y") 5-fluorouracil (5-FU) (Polak 1975). 5-FC is of low toxicity Toxizität (Bennett 1990). In contrast, 5-FU exhibits a strong cytotoxic effect inhibiting RNA- and DNA-synthesis (Calabrisi 1990; Damon 1989).
   Cells of plants and higher mammals do not exhibit a significant CDase-activity and are unable to deaminate 5-FC (Polak 1976; Koechlin 1966). In the context of the present invention, a CDase is introduced as a transgene into the target cell. Introduction can be done prior the screening (e.g., generating a stably transformed cell line or organism). Such cells or organism can then be used as master cell lines or master organism.
   Corresponding CDase sequences, transgenic organisms (including plants) comprising said sequences, and negative selection schemes based on e.g., treatment of these cells or organisms with 5-FC (as non-toxic substance X) are known in the art (WO 93/01281; U.S. Pat. No. 5,358,866; Gleave 1999; Perera 1993; Stougaard 1993; EP-A1595 837; Mullen 1992; Kobayashi 1995; Schlaman 1997; Xiaohui Wang 2001; Koprek 1999; Gallego 1999; Salomon 1998; Thykjaer 1997; Serino 1997; Risseeuw 1997; Blanc 1996; Corneille 2001). Cytosindeaminases and genes encoding the same can be isolated from various organisms, preferably microorganism, like for example *Cryptococcus neoformans, Candida albicans, Torulopsis glabrata, Sporothrix schenckii, Aspergillus, Cladosporium*, and *Phialophora* (Bennett 1990) and from bacteria like e.g., *E.coli* and *Salmonella typhimurium* (Andersen 1989). All these references, the sequences and methods described therein are explicitly incorporated by reference. Especially preferred are the sequences as described by GenBank Acc.-No: S56903, and the modified sequences described in EP-A1 595 873, which were modified to enable expression in eukaryotes.
2. Cytochrome P450 enzymes, especially the bacterial cytochrome P450 SU1 gene product (CYP105A1) from *Streptomyces griseolus* (strain ATCC 11796), wherein substances like the sulfonylurea pro-herbicide R7402 (2-methylethyl-2-3-dihydro-N-[(4,6-dimethoxypyrimidine-2-yl)aminocarbonyl]-1,2-benzoisothiazol-7-sulfonamid-1,1-dioxide) as the non-toxic substance X are employed. Corresponding sequences are negative selection schemes employing e.g., R7402 are described in the art (O'Keefe 1994; Tissier 1999; Koprek 1999; O'Keefe 1991). All these references, the sequences and methods described therein are explicitly incorporated by reference. Especially preferred is the sequence described by GenBank Acc.-No: M32238.
3. Indoleacetic acid hydrolases like e.g., the tms2 gene product from *Agrobacterium tumefaciens*, wherein substances like auxinamide compounds or naphthalacetamide (NAM) are employed as non-toxic compound X (NAM being converted to naphthyacetic acid, a phytotoxic compound). Corresponding sequences and the realization of negative selection schemes (employing NAM as non-toxic compound X) are described in the art (Fedoroff 1993; Upadhyaya 2000; Depicker 1988; Karlin-Neumannn 1991; Sundaresan 1995; Cecchini 1998; Zubko 2000). All these references, the sequences and methods described therein are explicitly incorporated by reference. Especially preferred is the sequence described by GenBank Acc.-No: NC_003308 (Protein_id="NP_536128.1), AE009419, AB016260 (Protein_id="BAA87807.1) and NC002147.
4. Haloalkane dehalogenases (dhIA gene product) e.g., from *Xanthobacter autotropicus* GJ10. This dehalogenase hydrolizes dihaloalkanes like 1,2-dichloroethane (DCE) to halogenated alcohols and inorganic halides (Naested 1999; Janssen 1994; Janssen 1989). All these references, the sequences and methods described therein are explicitly incorporated by reference. Especially preferred is the sequence described by GenBank Acc.-No: M26950.
5. Thymidine kinases (TK), especially virale TKs from virus like Herpes Simplex virus, SV40, Cytomegalovirus, *Varicella zoster* virus, especially preferred is TK from Type 1 Herpes Simplex virus (TK HSV-1), wherein substances like e.g., acyclovir, ganciclovir or 1,2-deoxy-2-fluoro-β-D-arabinofuranosil-5-iodouracile (FIAU) are employed as non-toxic compound X. Corresponding compounds are realization of negative selection schemes (e.g., employing acyclovir, ganciclovir or FIAU) are known in the art (Czako 1994; Wigler 1977; McKnight 1980; McKnight 1980; Preston 1981; Wagner 1981; St. Clair 1987). All these references, the sequences and methods described therein are explicitly incorporated by reference. Especially preferred is the sequence described by GenBank Acc.-No: J02224, V00470, and V00467.
6. Guanine phosphoribosyl transferases, hypoxanthine phosphoribosyl transferases or Xanthin guanine phosphoribosyl transferases, wherein compounds like 6-thioxanthin or allopurinol are employed as non-toxic substance X. Preferred is the guanine phosphoribosyl transferase (gpt) from e.g. *E Coli* (Besnard 1987; Mzoz 1993; Ono 1997), hypoxanthin phosphoribosyl transferases (HPRT; Jolly 1983; Fenwick 1985), xanthin guanine phosphoribosyl transferases (e.g., from *Toxoplasma gondii*; Knoll 1998; Donald 1996). All these references, the sequences and methods described therein are explicitly incorporated by reference Especially preferred is the sequence described by GenBank Acc.-No.: U10247 (*Toxoplasma gondii* HXGPRT), M13422 (*E. coli* gpt) and X00221 (*E. coli* gpt).
7. Purine nucleoside phosphorylases (PNP; DeoD gene product) e.g., from *E coli*, wherein compounds like for example 6-methylpurine deoxyribonucleoside are employed as non-toxic compound X. Suitable compounds and methods for carrying out counter-selection schemes (e.g., employing 6-methylpurine deoxyribonucleoside as non-toxic compound X) are well known to the person skilled in the art (Sorscher 1994). All these references, the sequences and methods described therein are explicitly incorporated by reference. Especially preferred is the sequence described by GenBank Acc.-No.: M60917.
8. Phosphonate monoesterhydrolases, which are suitable to convert physiologically inactive ester derivatives of e.g., the herbicide Glyphosate (e.g., glyceryl-glyphosate) to the active form of the herbicide. Suitable compounds and methods for carrying out counter-selection schemes (e.g., employing glyceryl-glyphosate as non-toxic compound X) are well known to the person skilled in the art (U.S. Pat. No. 5,254,801; Dotson 1996; Dotson 1996). All these references, the sequences and methods described therein are explicitly incorporated by reference. Especially preferred is the sequence described by GenBank Acc.-No.: U44852.

9. Aux-1 and—preferably—Aux-2 gene products e.g. aus derived from the Ti-plasmids of *Agrobacterium* strains (Beclin 1993; Gaudin 1995). The activity of both enzymes causes production of indole acetamide (IAA) in the plant cell. Aux-1 is encoding an indole acetamide synthase (IAMS) converting tryptophan to indole acetamide (VanOnckelen 1986). Aux-2 is encoding indole acetamide hydrolase (IAMH) converting indole acetamide (a compound without phytohormon activity) to the active auxin indole acetic acid (Inze 1984; Tomashow 1984; Schroder 1984). IAMH is furthermore capable to convert various indole amide-type substrates such as naphthyl acetamide, which is converted into the plant growth regulator naphthyl acetic acid (NM). Use of IAMH as counter selection marker is for example disclosed in U.S. Pat. No. 5,180,873. Corresponding enzymes are also described for *A. rhizogenes*, A. *vitis* (Canaday 1992) and *Pseudomonas* savastanoi (Yamada 1985). The use as counter selection marker for selectively killing certain plant tissues (e.g., pollen; U.S. Pat. No. 5,426,041) or transgenic plants (U.S. Pat. No. 5,180,873) is described. Compounds and methods for counter selections (e.g. by employing naphthyl acetamide) are known to the person skilled in the art (see above). All these references, the sequences and methods described therein are explicitly incorporated by reference. Especially preferred is the sequence described by GenBank Acc.-No.: M61151, AF039169 und AB025110.
10. Adenine phosphoribosyl transferases (APRT), wherein compounds such as 4-aminopyrazolo pyrimidine are employed as non-toxic compound X. Suitable compounds and methods for carrying out counter-selection schemes are well known to the person skilled in the art (Wigler 1979; Taylor 1985). All these references, the sequences and methods described therein are explicitly incorporated by reference.
11. Methoxinin dehydrogenases, wherein compounds such as 2-amino-4-methoxy-butanicacid (Methoxinin) are employed as non-toxic compound X, which is converted into the toxic compound methoxyvinylglycine (Margraff 1980).
12. Rhizobitoxine synthases, wherein compound such as 2-amino-4-methoxy-butanicacid (Methoxinin) are employed as non-toxic compound X, which is converted into the toxic compound 2-amino-4-[2-amino-3-hydroxypropyl]-trans-3-butanicacid (Rhizobitoxin) (Owens 1973).
13. 5-Methylthioribose (MTR) kinases, wherein compounds such as 5-trifluoromethyl thioribose (MTR-analogue, "subversives substrate") are employed as non-toxic compound X, which is converted into the toxic compound Y carbothionyldifluoride. MTR-kinase is a key enzyme of the methionine salvage pathway. Corresponding enzyme activities are described in plants, bacteria, and protozoa but not in mammals. MTR kinases from various species can be identified according to defined sequence motives (Sekowska 2001. Corresponding sequences are methods for counter selection (e.g., employing 5-trifluoromethyl thioribose) are known to the person skilled in the art and readily obtainable from sequence databases (e.g., Sekowska 2001; Cornell 1996). All these references, the sequences and methods described therein are explicitly incorporated by reference. Especially preferred is the sequence described by GenBank Acc.-No.: AF212863 or AC079674 and other MTK kinase enzymes as described in WO 03/078629 and DE10212892 hereby incorporated by reference.
14. Alcohol dehydrogenases (Adh) especially plant Adh-1 gene products, where preferably compounds such as allylalcohol is employed as non-toxic compound X, which is converted into the toxic compound (Y) acrolein. Suitable, corresponding compounds and methods for carrying out counter-selection schemes (e.g., employing allyl alcohol) are well known to the person skilled in the art (Wisman 1991; Jacobs 1988; Schwartz 1981). Sequences can be readily derived from sequence databases. All these references, the sequences and methods described therein are explicitly incorporated by reference. Especially preferred is the sequence described by GenBank Acc.-No.: X77943, M12196, AF172282, X04049 or AF253472.
15. Furthermore preferred as counter selection marker are "toxic genes" or "toxic sequences" which per se exhibit and toxic effect on a cell expressing said genes or sequences. Example may include but are not limited to sequences encoding toxic protein such as diphtheria toxin A, Ribonukleases (RNAse e.g., Barnase), ribosome-inhibiting proteins (RIP; such as ricine), magainins, DNAse, phytotoxins, proteins which are able to evoke a hypersensitive reaction, and proteases. Evoking a hypersensitive response (HR) is possible when a pathogen-derived elicitor protein and a corresponding plant-derived receptor protein are expressed simultaneously. Couples of such corresponding elicitor/receptor genes and their applicability to evoke a HR in a transgenic plant, are known in the art, e.g. for *Cladosporium fulvum* avr-genes and *Lycopersicon esculentum* Cf-genes (WO 91/15585) or for *Psuedomonas syringae* avr-genes and *Arabidopsis thaliana* RPM1-genes (Grant 1995).

Additional toxic sequences are those suppressing essential endogenous genes (such as housekeeping genes). The person skilled in the art is aware of various sequences and methods which can be employed to suppress ("silence") gene expression of endogenous genes. The terms "suppression" or "silencing" in relation to a gene, its gene product, or the activity of said gene product is to be understood in the broad sense comprising various mechanism of impairing or reducing the functionality on various levels of expression. Included are for example a quantitative reduction of transcription and translation up to an essentially complete absence of the transcription and/or translation product (i.e. lacking detectability by employing detection methods such as Northern or Western blot analysis, PCR, etc.)

Suitable method of gene silencing may include but shall not be limited to gene silencing by (i) antisense suppression (see above for details),
(ii) sense suppression (co-suppression) (see above for details),
(iii) double-stranded RNA interference (see above for details),
(iv) expression of ribozymes against an endogenous RNA transcript (see above for details),
(v) expression of protein or DNA-binding factors: Expression of an endogenous gene can be "silenced"

also by expression of certain DNA or protein binding factors which interfere with expression or activity of the gene of its gene product. For example artificial transcription factors of the zinc finger type can be adapted to any target sequence and can thus be employed for gene silencing (e.g., by being directed against the promoter region of the target gene). Methods for production of such factors are described (Dreier 2001; Dreier 2000; Beerli 2000a, 2000b; Segal 2000; Kang 2000; Beerli 1998; Kim 1997; Klug 1999; Tsai 1998; Mapp 2000; Sharrocks 1997; Zhang 2000). Furthermore factors can be employed which directly inhibit the gene product (by interacting with the resulting protein). Such protein binding factors may for example be aptameres (Famulok 1999), antibodies, antibody fragments, or single chain antibodies. Their generation is described (Owen 1992; Franken 1997; Whitelam 1996).

(vi) Gene silencing mediating viral expression systems: Gene silencing of endogenous genes can also be mediated employing specific viral expressions systems (Amplikon; Angell 1999). These systems and methods (termed "VIGS"; viral induced gene silencing) are mediating expression of sequences resembling the endogenous gene from a viral vector system. By classifying the expression as "viral" the entire expression (including expression of the homologous endogenous gene) is shot down by plant viral defense mechanism. Corresponding methods are described in the art (Ratcliff 2001; Fagard 2000; Anandalakshmi 1998; Ruiz 1998).

Essential endogenous genes suitable as targets for the method of the invention may for example be genes selected from those coding for enzymes that are essential for cell viability. These so called "housekeeping genes" may for example be selected from genes encoding for proteins such as ATP synthase, cytochrome c, pyruvate kinase, aminoacyl transferase, or phosphate, di-, tri-carboxylkate and 2-oxoglutarate translocators. A list of target enzymes is given in Table 1 by way of example but the invention is not limited to the enzymes mentioned in this table. More detailed listings can be assembled from series as Biochemistry of Plants (Eds. Stumpf & Conn, 1988-1991, Vols. 1-16 Academic Press) or Encyclopedia of Plant Physiology (New Series, 1976, Springer-Verlag, Berlin).

TABLE 1

| EXAMPLES OF TARGET ENZYMES |
|---|
| Enzyme |
| ATP synthase (mitochondrion) |
| adenine nucleotide translocator (mitochondrion) |
| phosphate translocator (mitochondrion) |
| tricarboxylate translocator (mitochondrion) |
| dicarboxylate translocator (mitochondrion) |
| 2-oxo-glutarate translocator (mitochondrion) |
| cytochrome C (mitochondrion) |
| pyruvate kinase |
| glyceraldehyde-3P-dehydrogenase |
| NADPH-cytochrome P450 reductase |
| fatty acid synthase complex |
| glycerol-3P-acyltransferase |
| hydroxymethyl-glutaryl CoA reductase |
| aminoacyl transferase |
| transcription factors |
| elongation factors |

TABLE 1-continued

| EXAMPLES OF TARGET ENZYMES |
|---|
| phytoen desaturase |
| nitrate reductase |
| p-hydroxyphenylpyruvate dioxygenase (HPPD) |
| transketolase |
| (preferably enzymes described and claimed in EP-A1 723 017) |
| ferredoxin oxidoreductase |
| (preferably enzymes described and claimed in EP-A1 1 333 098) |
| S-adenosylmethionin: Mg-protoporphyrin-IX-O-methyltransferase |
| (preferably enzymes described and claimed in EP-A1 1 198 578) |
| dihydrorotase (EC 3.5.2.3) |
| (preferably enzymes described and claimed in EP-A1 1 210 437) |
| phosphoribosyl pyrophosphate synthase |
| (preferably enzymes described and claimed in EP-A1 1 294 925) |
| aspartate carbamyl transferase |
| (preferably enzymes described and claimed in EP-A1 1 259 623) |
| dehydrochinate dehydratase/shikimate dehydrogenase |
| (preferably enzymes described and claimed in EP-A1 1 315 808 |

As housekeeping genes are in general highly conserved, heterologous probes from other (plant) species can be used to isolate the corresponding gene from the species that is to be made resistant Such gene isolations are well within reach of those skilled in the art and, in view of the present teaching require no undue experimentation.

(c) a DNA segment that encodes a product conferring to the recipient cell or organism an advantage by increased or improved regeneration, growth, propagation, multiplication ("Positive Selection Marker"). Genes like isopentenyl transferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma et al. 2000a, 2000b). Additional Positive Selection Markers, which confer a growth advantage to a transformed plant in comparison with a non-transformed one, are described e.g., in EP-A 0 601 092. Growth stimulation selection markers may include (but shall not be limited to)β-glucuronidase (in combination with e.g., a cytokinin glucuronide), mannose-6-phosphate isomerase (in combination with mannose), UDP-galactose4-epimerase (in combination with e.g., galactose), wherein mannose-6-phosphate isomerase in combination with mannose is especially preferred.

(d) a DNA segment that encodes a product that can be readily identified ("reporter genes" or "reporter proteins" or "reporter molecules"; e.g., phenotypic markers such as β-galactosidase, green fluorescent protein (GFP), and cell surface proteins). The term "reporter gene", "reporter protein", or "reporter molecule" is intended to mean any readily quantifiable protein (or the sequence encoding therefore), which via—for example—color or enzyme activity, makes possible an assessment of presence of said protein or expression of said reporter gene. Reporter genes encode readily quantifiable proteins and, via their color or enzyme activity, make possible an assessment of the transformation efficacy, the site of expression or the time of expression. Very especially preferred in this context are genes encoding reporter proteins (Schenborn 1999) such as the green fluorescent protein (GFP) (Sheen 1995; Haseloff 1997; Reichel 1996; Tian 1997; WO 97/41228; Chui 1996; Leffel 1997), the NAN reporter gene (Kavanagh 2002; WO 03/052104), chloramphenicol transferase, a luciferase (Ow 1986; Millar 1992), the aequorin gene (Prasher 1985), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates (Dellaporta 1988; Ludwig 1990), with β-glucuronidase (GUS) being very especially preferred (Jefferson 1987b; 1987a). β-glucuronidase (GUS) expression is detected by a blue color on incubation of the tissue with 5-bromo-4-chloro-3-indolyl-βD-glucuronic acid, bacterial luciferase (LUX) expression is detected by light emission; firefly luciferase (LUC) expression is detected by light emission after incubation with luciferin; and galactosidase expression is detected by a bright blue color after the tissue is stained with 5-bromo-4-chloro-3-indolyl-β-D-galactopyranoside. Reporter genes may also be used as scorable markers as alternatives to antibiotic resistance markers. Such markers are used to detect the presence or to measure the level of expression of the transferred gene. The use of scorable markers in plants to identify or tag genetically modified cells works well only when efficiency of modification of the cell is high.

(e) a DNA segment that encodes a product that inhibits a cell function in a recipient cell;
(f) a DNA segment that inhibits the activity of any of the DNA segments of (a)-(e) above;
(g) a DNA segment that binds a product that modifies a substrate (e.g. restriction endonucleases);
(h) a DNA segment that encodes a specific nucleotide recognition sequence which can be recognized by a protein, an RNA, a DNA or a chemical,
(i) a DNA segment that, when deleted or absent, directly or indirectly confers resistance or sensitivity to cell killing by particular compounds within a recipient cell;
(j) a DNA segment that encodes a product that suppresses the activity of a gene product in a recipient cell;
(k) a DNA segment that encodes a product that is otherwise lacking in a recipient cell (e.g, tRNA genes, auxotrophic markers), and;
(l) a DNA segment that can be used to isolate or identify a desired molecule (e.g., specific protein binding sites).

In a preferred embodiment of the invention, in cases where an efficient transcription terminator would lead to a decreased expression of the additional sequences (especially Method A, where the transcription terminator is inserted between said additional sequences and the promoter), said additional sequences may by an inverted repeat of a known transcription terminator sequence (such as for example the nos terminator) which is localized in a way that the second copy (the copy more downstream from the promoter sequence) is in its "normal" orientation (in which it is constituting a functional transcription terminator). It has to be noted, that such decreased expression of an inverted repeat transcription terminator leads to increased expression (or better not silenced expression) of sequences localized upstream of the insertion site. In case these sequences are encoding for example a marker, an increased resistance or signal can be observed.

Preferably, this transcription terminator (hereinafter "the second transcription terminator") is different from the sequence to be assessed for its transcription termination efficiency. In this case, it is preferred that further sequences are employed which are preferably localized between the promoter and the insertion site and are encoding e.g., for a selection marker or a reporter gene. In such a scenario, an efficient transcription terminator sequence would stop transcription and would not cause transcription of the inverted repeat of said second transcription terminator. In consequence normal expression of the sequences between promoter and insertion site would occur (leading to expression of the selection marker or the reporter gene). In cases, where the sequence inserted into the insertion site is not an effective transcription terminator, transcription will read-through into the inverted repeats of said second transcription terminator. Such a construct would cause its own gene silencing be dsRNAi. In consequence no expression of the sequences between promoter and insertion site would occur (silencing the expression of the selection marker or the reporter gene). Self-affecting gene silencing based on an inverted repeat sequence of an transcription terminator (e.g., NOS terminator) are described (Brummell 2003).

2.3 Other Elements of the Screening Construct or Screening Vector

The screening construct or screening vector may comprise further elements (e.g., genetic control sequences) in addition to a promoter and the additional sequences. The term "genetic control sequences" is to be understood in the broad sense and refers to all those sequences which have an effect on the materialization or the function of the screening construct or screening vector according to the invention. For example, genetic control sequences modify the transcription and translation in prokaryotic or eukaryotic organisms. Genetic control sequences furthermore also encompass the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, N.Y. (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5'-leader sequence (Gallie, 1987) and the like. Furthermore, they may promote tissue specificity (Rouster, 1998).

The screening construct or screening vector may advantageously comprise one or more enhancer sequences, linked operably to the promoter, which make possible an increased recombinant expression of the nucleic acid sequence. Additional advantageous sequences, such as further regulatory elements or additional transcription terminator sequences, may also be inserted at the 3'-end of the nucleic acid sequences to be expressed recombinantly.

In some embodiments of the invention (for example Variation A or C) or screening construct or screening vector can also include a known transcription termination sequence (preferably after the additional sequence), and optionally, a polyadenylation signal sequence. Polyadenylation signals which are suitable as control sequences are plant polyadenylation signals, preferably those which essentially correspond to T-DNA polyadenylation signals from *Agrobacterium tumefaciens*, in particular the OCS (octopine synthase) terminator and the NOS (nopaline synthase) terminator. An expression vector does not necessarily need to contain transcription termination and polyadenylation signal sequences, because these elements can be provided by the cloned gene or gene fragment.

The screening construct or screening vector of the invention may comprise further functional elements. The term functional element is to be understood in the broad sense and refers to all those elements which have an effect on the generation, amplification or function of the screening construct or screening vector according to the invention. Functional elements may include for example (but shall not be limited to) selectable marker genes (including negative, positive, and counter selection marker, see above for details), reporter genes, and 1) Origins of replication, which ensure amplification of the expression cassettes or vectors according to the invention in, for example, *E. coli*. Examples which may be mentioned are ORI (origin of DNA replication), the pBR322 ori or the P15A ori (Maniatis 1989). Additional examples for replication systems functional in *E. coli*, are ColE1, pSC101, pACYC184, or the like. In addition to or in place of the *E. coli* replication system, a broad host range replication system may be employed, such as the replication systems of the P-1 Incompatibility plasmids; e.g., pRK290. These plasmids are particularly effective with armed and disarmed Ti-plasmids for transfer of T-DNA to the plant species host. An expression vector can also include a SV40 origin. This element can be used for episomal replication and rescue in cell lines expressing SV40 large T antigen.
2) Elements which are necessary for *Agrobacterium*-mediated plant transformation, such as, for example, the right and/or—optionally—left border of the T-DNA or the vir region.
3) Cloning Sites: The cloning site can preferably be a multicloning site. Any multicloning site can be used, and many are commercially available.
4) S/MAR (scaffold/matrix attachment regions). Matrix attachment regions (MARs) are operationally defined as DNA elements that bind specifically to the nuclear matrix (nuclear scaffold proteins) in vitro and are proposed to mediate the attachment of chromatin to the nuclear scaffold in vivo. It is possible, that they also mediate binding of chromatin to the nuclear matrix in vivo and alter the topology of the genome in interphase nuclei. When MARs are positioned on either side of a transgene their presence usually results in higher and more stable expression in transgenic organisms (especially plants) or cell lines, most likely by minimizing gene silencing (for reveiw: Allen 2000). Various S/MARS sequences and there effect on gene expression are described (Sidorenko 2003; Allen 1996; Villemure 2001; Mlynarova 2002). S/MAR elements may be preferably employed to reduce unintended gene silencing (Mlynarova 2003). An example for a S/MAR being the chicken lysozyme A element (Stief 1989).
5) Sequences which further modify transcription, translation, and/or transport of an expressed protein. For example the expressed protein may be a chimeric protein comprising a secretory signal sequence. The secretory signal sequence is operably linked to a gene of interest such that the two sequences are joined in the correct reading frame and positioned to direct the newly synthesized polypeptide of interest into the secretory pathway of the host cell. Secretory signal sequences are commonly positioned 5' to the nucleotide sequence encoding the amino acid sequence of interest, although certain secretory signal sequences may be positioned elsewhere in the nucleotide sequence of interest (U.S. Pat. No. 5,037,743, U.S. Pat. No. 5,143,830). Expression vectors can also comprise nucleotide sequences that encode a peptide tag to aid the purification of the polypeptide of interest. Peptide tags that are useful for isolating recombinant polypeptides include poly-Histidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies; see, for example, Luo 1996; Morganti 1996, and Zheng 1997). Nucleic acid molecules encoding such peptide tags are available, for example, from Sigma-Aldrich Corporation (St. Louis, Mo.).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications, patents, and patent applications cited herein are hereby incorporated by reference for all purposes.

2.4. Suitable Vectors for the Invention

As used herein, the terms "vector" and "vehicle" are used interchangeably in reference to nucleic acid molecules that transfer DNA segment(s) from one cell to another. The term "screening vector" as used herein refers to a recombinant DNA molecule comprising at least the above defined elements of said promoter and said additional sequences functional for evaluation of the transcription termination efficiency of an inserted sequence.

The methods of the invention are not limited to the vectors disclosed herein. Any vector which is capable of expressing a nucleic acid sequences, and preferably introducing a nucleic acid sequence of interest into a cell (e.g., a plant cell) is contemplated to be within the scope of this invention. Typically, vectors comprise the above defined essential elements of the invention in combination with elements which allow cloning of the vector into a bacterial or phage host. The vector preferably, though not necessarily, contains an origin of replication which is functional in a broad range of prokaryotic hosts. A selectable marker is generally, but not necessarily, included to allow selection of cells bearing the desired vector. Examples of vectors may be plasmids, cosmids, phages, viruses or *Agrobacteria*. More specific examples are given below for the individual transformation technologies.

Preferred are those vectors which make possible a stable integration of the expression construct into the host genome. In the case of injection or electroporation of DNA into cells (e.g., plant cells), the plasmid used need not meet any particular requirements. Simple plasmids such as those of the pUC series can be used. If intact plants are to be regenerated from the transformed cells, it is necessary for an additional selectable marker gene to be present on the plasmid. A variety of possible plasmid vectors are available for the introduction of foreign genes into plants, and these plasmid vectors contain, as a rule, a replication origin for multiplication in *E. coli* and a marker gene for the selection of transformed bacteria. Examples are pBR322, pUC series, M13 mp series, pACYC 184 and the like.

Preferred vectors for use in the invention include prokaryotic vectors, eukaryotic vectors or vectors which may shuttle between various prokaryotic and/or eukaryotic systems (e.g. shuttle vectors). Preferred eukaryotic vectors comprise vectors, which replicate in yeast cells, plant cells, fish cells, eukaryotic cells, mammalian cells, or insect cells. Preferred prokaryotic vectors comprise vectors which replicate in gram negative and/or gram-positive bacteria, more preferably vectors which replicate in bacteria of the genus *Escherichia, Salmonella, Bacillus, Streptomyces, Agrobacterium, Rhizobium*, or *Pseudomonas*. Most preferred are vectors which replicates in both *E. coli* and *Agrobacterium*. Eukaryotic vectors for use in the invention include vectors which propagate and/or replicate and yeast cells, plant cells, mammalian cells (particularly human cells), fungal cells, insect cells, fish cells and the like. Particular vectors of interest include but are not limited to cloning vectors, sequencing vectors, expression vectors, fusion vectors, two-hybrid vectors, gene therapy vectors, and reverse two-hybrid vectors. Such vectors may be used in prokaryotic and/or eukaryotic systems depending on the particular vector.

In accordance with the invention, any vector may be used to construct a screening vector of the invention. In particular, vectors known in the art and those commercially available (and variants or derivatives thereof) may in accordance with the invention be engineered to include one or more recombination sites for use in the methods of the invention. Such vectors may be obtained from, for example, Invitrogen, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Particular vectors of interest include prokaryotic expression vectors such as pcDNA II, pSL301, pSE280, pSE380, pSE420, pTrcHisA, B, and C, pRSET A, B, and C (Invitrogen, Inc.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Life Technologies, Inc.) and variants and derivatives thereof. Vector donors can also be made from eukaryotic expression vectors such as pFastBac, pFastBacHT, pFastBacDUAL, pSFV, and pTet-Splice (Life Technologies, Inc.), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBsueBacIII, pCDM8, pcDNA1, pZeoSV, pcDNA3 pREP4, pCEP4, and pEBVHis (Invitrogen, Inc.) and variants or derivatives thereof.

Other vectors of particular interest include pUC18, pUC19, pBlueScript, pSPORT, cosmids, phagemids, YAC's (yeast artificial chromosomes), BAC's (bacterial artificial chromosomes), P1 (*E. coli* phage), pQE70, pQE60, pQE9 (quagan), pBS vectors, PhageScript vectors, BlueScript vectors, pNH8A, pNH16A, pNH18A, pNH46A (Strata-gene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Life Technologies, Inc.) and variants or derivatives thereof.

Additional vectors of interest include pTrxFus, pThioHis, pLEX, pTrcHis, pTrcHis2, pRSET, pBlueBacHis2, pcDNA3.1/H is, pcDNA3.1(−)/Myc-His, pSecTag, pEBVHis, pPIC9K, pPIC3.5K, pAO815, pPICZ, pPICZα, pGAPZ, pGAPZα, pBlueBac4.5, pBlue-BacHis2, pMelBac, pSinRep5, pSinHis, pIND, pIND (SP1), pVgRXR, pcDNA2.1. pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λExCell, λgt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2 cp LIC, pBACgus-2 cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21 abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, pig, Signal pig, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-11213, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11'abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of particular interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Preferred vectors for expression in *E. coli* are pQE70, pQE60 und pQE-9 (QIAGEN, Inc.); pBluescript vectors, phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.).

Preferred vectors for expression in eukaryotic, animals systems comprise pWLNEO, pSV2CAT, pOG44, pXT1 and pSG (Stratagene Inc.); pSVK3, pBPV, pMSG und pSVL (Pharmacia Biotech, Inc.). Examples for inducible vectors are pTet-tTak, pTet-Splice, pcDNA4/TO, pcDNA4/TO/LacZ, pcDNA6/TR, pcDNA4/TO/Myc-His/LacZ, pcDNA4/TO/

Myc-His A, pcDNA4/TO/Myc-His B, pcDNA4/TO/Myc-His C, pVgRXR (Invitrogen, Inc.) or the pMAM-Serie (Clontech, Inc.; GenBank Accession No.: U02443).

Preferred vectors for the expression in yeast comprise for example pYES2, pYD1, pTEFI/Zeo, pYES2/GS, pPICZ, pGAPZ, pGAPZalph, pPIC9, pPIC3.5, PHIL-D2, PHIL-SI, pPIC3SK, pPIC9K, and PA0815 (Invitrogen, Inc.).

Preferred vector for plant transformation are described herein below and preferably comprise vectors for *Agrobacterium*-mediated transformation. *Agrobacterium* tumefaciens and *A. rhizogenes* are plant-pathogenic soil bacteria, which genetically transform plant cells. The Ti and Ri plasmids of *A. tumefaciens* and *A. rhizogenes*, respectively, carry genes responsible for genetic transformation of the plant (Kado 1991). Vectors of the invention may be based on the *Agrobacterium* Ti- or R1-plasmid and may thereby utilize a natural system of DNA transfer into the plant genome.

As part of this highly developed parasitism *Agrobacterium* transfers a defined part of its genomic information (the T-DNA; flanked by about 25 bp repeats, named left and right border) into the chromosomal DNA of the plant cell (Zupan 2000). By combined action of the so-called vir genes (part of the original Ti-plasmids) said DNA-transfer is mediated. For utilization of this natural system, Ti-plasmids were developed which lack the original tumor inducing genes ("disarmed vectors"). In a further improvement, the so called "binary vector systems", the T-DNA was physically separated from the other functional elements of the Ti-plasmid (e.g., the vir genes), by being incorporated into a shuttle vector, which allowed easier handling (EP-A1 0 120 516; U.S. Pat. No. 4,940,838). These binary vectors comprise (beside the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art (Miki 1993; Gruber 1993; Moloney 1989). The use of T-DNA for the transformation of plant cells has been studied and described intensively (EP-A1 120 516; Hoekema 1985; Fraley 1985; and An 1985). Various binary vectors are known, some of which are commercially available such as, for example, pBIN19 (Clontech Laboratories, Inc. USA).

Hence, for *Agrobacterium*-mediated transformation the screening construct may be integrated into or the screening vector may consist of specific plasmids, such as shuttle or intermediate vectors, or binary vectors. If a Ti or Ri plasmid is to be used for the transformation, at least the right border, but in most cases the right and left border, of the Ti or Ri plasmid T-DNA is linked to the transgenic expression construct to be introduced in the form of a flanking region. Binary vectors are preferably used. Binary vectors are capable of replication both in *E. coli* and in *Agrobacterium*. They may comprise a selection marker gene and a linker or polylinker (for insertion of e.g the expression construct to be transferred) flanked by the right and left T-DNA border sequence. They can be transferred directly into *Agrobacterium* (Holsters 1978). The selection marker gene permits the selection of transformed *Agrobacteria* and is, for example, the nptII gene, which confers resistance to kanamycin. The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP-A1 0 120 516; Hoekema 1985; An 1985; see also below).

Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101pEHA101 (Hood 1986), EHA105-[pEHA105] (Li 1992), LBA4404[pAL4404] (Hoekema 1983), C58C1[pMP90] (Koncz 1986), and C58C1 [pGV2260] (Deblaere 985). Other suitable strains are *Agrobacterium tumefaciens* C58, a nopaline strain. Other suitable strains are *A. tumefaciens* C58C1 (Van Laerebeke 1974), A136 (Watson et al. 1975) or LBA4011 (Klapwijk 1980). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated. In a preferred embodiment, the *Agrobacterium* strain used to transform the plant tissue pre-cultured with the plant phenolic compound such as acetosyringone. The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen 1991; Scheeren-Groot 1994).

A binary vector or any other vector can be modified by common DNA recombination techniques, multiplied in *E. coli*, and introduced into *Agrobacterium* by e.g., electroporation or other transformation techniques (Mozo 1991). *Agrobacterium* is grown and used as described in the art. The vector comprising *Agrobacterium* strain may, for example, be grown for 3 days on YP medium (5 g/L yeast extract, 10 g/L peptone, 5 g/L Nail, 15 g/L agar, pH 6.8) supplemented with the appropriate antibiotic (e.g., 50 mg/L spectinomycin). Bacteria are collected with a loop from the solid medium and resuspended. For the purpose of this invention, *Agrobacterium* compatible vectors are provided by inserting site-specific recombination sites as described—for example—in the Examples.

After constructing a vector, the vector can be propagated in a host cell to synthesize nucleic acid molecules for the generation of a nucleic acid polymer. Vectors, often referred to as "shuttle vectors," are capable of replicating in at least two unrelated expression systems. To facilitate such replication, the vector should include at least two origins of replication, one effective in each replication system. Typically, shuttle vectors are capable of replicating in a eukaryotic system and a prokaryotic system. This enables detection of protein expression in eukaryotic hosts, the "expression cell type," and the amplification of the vector in the prokaryotic hosts, the "amplification cell type." As an illustration, one origin of replication can be derived from SV40, while another origin of replication can be derived from pBR322. Those of skill in the art know of numerous suitable origins of replication.

After constructing a vector, the vector is typically propagated in a host cell. Vector propagation is conveniently carried out in a prokaryotic host cell, such as *E. coli* or *Bacillus subtilus*. Suitable strains of *E. coli* include BL21 (DE3), BL21 (DE3)pLysS, BL21(DE3)pLysE, DB2, DB3.1, DH1, DH4I, DH5, DH5I, DH5IF, DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), Molecular Biology Labfax (Academic Press 1991)). Suitable strains of *Bacillus subtilus* include BR151, YB886, M1119, M1120, and B170 (see, for example, Hardy 1985). Standard techniques for propagating vectors in prokaryotic hosts are well-known to those of skill in the art (see, for example, Ausubel 1995; Wu 1997).

3. The Sequences to be Assessed as Transcription Terminators

The sequences to be assessed using the method of the invention for their efficiency as transcription terminator sequences may be derived from various sources. In one embodiment of the invention sequences believed to function as transcription terminators may be assessed for their efficiency. Such sequences can be derived from for example regions downstream of the coding sequence of a gene (e.g., comprising the region encoding the 3'-untranslated region and additional downstream genomic sequences), preferably from a region which is surrounding the end of the mRNA transcript. Various of such sequences can be derived from comparison of genomic and cDNA libraries. The corresponding nucleic acid sequences to be inserted into the insertion site of the screening vector or screening construct can be obtained for example by isolation from the corresponding host organism (by the various cloning methods known to the person skilled in the art, e.g., by polymerase chain reaction employing appropriate primer oligonucleotides) or directly by DNA synthesis.

In a preferred embodiment the DNA molecules to be inserted for evaluation is a double-stranded, linear DNA molecule. The ends of said molecules may by blunt (i.e., without 5'- and/or 3' overhangs) or "sticky" (i.e., with 5'- and/or 3' overhangs). Preferably, the ends of the DNA molecule may have overhangs which allow insertion into cleavage sites of restriction endonuclease to facilitate insertion into an insertion site. The length and molecular weight of the DNA molecule may vary. In a preferred embodiment the molecule has a size of about 50 to about 5,000 base pairs, preferably from about 60 to about 2,000 base pairs, more preferably from about 70 to about 1,000 base pairs, most preferably from about 80 to about 500 base pairs.

Beside this educated approach (based on sequences for which some transcription termination efficiency can be presumed) in another preferred embodiment of the invention libraries of DNA sequences are screened to obtain efficient transcription terminator sequences. This embodiment does not require any previous sequence information and is based preferably solely on the phenotype of efficient transcription termination (which is difficult to correlate in practice with sequence information). The library of DNA sequences employed may be a synthetic library or a library of naturally occurring DNA molecules or a mixture of synthetic and naturally occurring DNA molecules. Preferably, the library of DNA molecules is a library of naturally occurring molecules, which may be derived from genomic DNA and/or cDNA of one or more organism. More preferably, the library is derived from the genomic DNA of an organism, preferably a plant organism.

In a preferred embodiment the DNA molecules of the DNA library are double-stranded, linear DNA molecules. The ends of said molecules may by blunt (i.e., without 5'- and/or 3' overhangs) or "sticky" (i.e., with 5'- and/or 3' overhangs). The length and molecular weight of the DNA molecules of the library may vary. In a preferred embodiment the molecules have a size of about 50 to about 5,000 base pairs, preferably from about 60 to about 2,000 base pairs, more preferably from about 70 to about 1,000 base pairs, most preferably from about 80 to about 500 base pairs.

The library of DNA molecules may be derived from the genomic and/or cDNA by various means known to the person skilled in the art. For example, the library may be derived by random shearing of DNA of exhaustive or partial digestion with endonucleases. Preferably, the library is derived by exhaustive digestion with a restriction endonuclease, which has preferably a 4 base recognition site (like, e.g., Sau3A). Following fragmentation (e.g., by restriction), DNA molecules of the preferred molecular weight (as determined above) may be isolated by for example molecular weight exclusion chromatography (size exclusion chromatography using for example Superose™ columns, Amersham Bioscience, Inc.) or gel electrophoresis as known in the art (see for example Ellegren 1989).

In another preferred embodiment of the invention selected sequences can be assessed for their performance as transcription terminator sequences. Such sequences can be, for example, regions downstream of the coding sequence of a gene (e.g., comprising the region encoding the 3'-untranslated region and additional downstream genomic sequences), preferably from a region which is surrounding the end of the mRNA transcript. Such sequences can be derived by in silico search of genome databases, such as for example of *Arabidopsis thaliana* or rice.

In one preferred embodiment, a partial or—preferably—entire plant genome (such as the rice or *Arabidopsis* genome) is screened for potential plant derived terminator candidates. The following criteria are used to identify and determine suitable candidates for transcription terminator sequences which may be further analyzed in the method of the invention:

1. Identification and/or isolation of intergenic regions between paired genes meeting predefined intergenic distance criteria. These genes may preferably have a head-to-tail orientation (i.e. transcription is running in the same direction), or—preferably—a tail-to-tail orientation (i.e. in opposite direction against each other). In the head-to-tail scenario the term "intergenic region" as used herein means the sequence in between (but excluding) the stop-codon of the "tail"-sequence and the start-codon of the "head" sequence, or—if known—the start of the promoter region of the "head" sequence. In the tail-to-tail orientation the term "intergenic region" as used herein means the sequence in between (but excluding) the two stop-codons of the coding sequence. Preferably, intergenic regions from paired genes in tail-to-tail orientation are identified which have a length from about 400 to 3,000 base pairs, preferably from about 700 to about 2,000 base pairs. Identification can be done by various means, including entire genome sequencing (e.g., in case of previously unknown sequences) or in silico screening of already known sequences (such as the *Arabidopsis* or rice genome). Existing database can be employed for this purpose such as the most updated data from The Institute of Genome Research (TIGR;

PUB_tigr_rice_genome_v4.nt (v03212003), PUB_tigr_rice_cds_Oct022003.nt, pubOSest0603 (ncbi)).

2. Identification and/or isolation of intergenic sequences which are flanked on both sides by genes having a high expression level. The term “high expression” or “high expression level” as used in this context means an expression level which is at least 5%, preferably at least 10%, more preferably at least 30%, most preferably at least 50% of the expression level of actin in the same mRNA source (i.e. cell or tissue). Expression may be judged by various means including but not limited to number of ESTs in a non-normalized EST library, Northern-blot analysis, RT-PCR etc. Low expression of one or both genes has been identified as an indicator for gene silencing by read-through transcription. Expression level can be profiled either by experiment (e.g., in vitro or in vivo for example by using expression profiling by chip or microarray technology) or—preferably—in silico by simply counting the number of ESTs for each gene in non-normalized EST/cDNA-libraries which is indicative for expression level.
3. Identification and/or isolation of intergenic sequences which are flanked on both sides by genes having an expression pattern which is preferably independent from the expression pattern of the other paired gene. The term “independent expression pattern” in this context means—for example—that the expression of the first gene is different in its tissue and/or developmental regulation from the expression of the second gene. Dependency and correlation of expression patterns of paired genes has been identified as an indicator for read-through transcription. Expression profiles can be analyzed either by experiment by comparing expression level of said paired genes in various organs or tissues (e.g., in vitro or in vivo for example by using expression profiling by chip technology) or—preferably—in silico by simply counting the number of ESTs for each gene in non-normalized EST/cDNA-libraries which is indicative for expression levels.
4. Identification and/or isolation of intergenic sequences which are flanked on one or—preferably—both sides by genes having a low variability in length of the mRNA transcript derived from said paired genes. Such variability is for example indicated by existence of more than one transcript end in EST, cDNA libraries or databases. Variability in transcript length has been identified as an indicator for low stringency in transcription termination. Variability in transcript length can be analyzed either by experiment (e.g., by RT PCR) or—preferably—in silico by simply analyzing the 3'-ends of EST or cDNA clones in the database.

While the intergenic localization (step 1) is a prerequisite, in a preferred embodiment of the invention each of the criteria 2, 3, 4, and the length of the intergenic region (part of criteria 1) for a certain intergenic sequence is resulting in a criteria score. Addition of said scores (which may be multiplied by certain weight-indicators reflecting the different impact of the criteria) is resulting in a final score which is indicative for the potential of the sequence as a transcription terminator and isolator (see below). This score and the potential can be verified by evaluating the sequence of said intergenic region in one or more screening systems of the invention. The highest weight is given to criteria 2 (high expression profile), followed by criteria 2 (independent expression profile), and criteria 3 (low variability in transcript length). The preferred length for the intergenic regions are indicated below, but seem to have more impact on handling (i.e. in later cloning and transformation procedures) than on functionality of said region.

An intergenic region identified thereby is not only suitable in mono-gene expression cassettes, but is especially suitable in multi-gene expression cassettes not only providing transcription termination for two genes in one sequence, but also allowing efficient “isolation” of said two expression cassettes by minimizing their interference by read-through transcription (thus providing an “isolator”), which has proven to be a serious problem especially in multi-gene expression constructs. The term “isolator” when referring to a sequence (which is preferably localized in between two expression cassettes) as used herein is intended to mean the capability of said sequence to minimize or prevent the influence of one expression cassette on transcription from the other expression cassette, thus isolating the two expression cassettes from each other. Preferred embodiments and additional information for carrying out this method for providing intergenic sequences is given in Example 1.2 below.

Accordingly, another embodiment of the invention is directed to a method for identification and/or isolation intergenic regions—preferably with high transcription termination and/or isolator potential—said method including at least one, preferably at least two, more preferably at least three, most preferably all of the following selection criteria 1. Identification and/or isolation or isolation of intergenic regions between paired genes meeting predefined intergenic distance criteria.
2. Identification and/or isolation of intergenic sequences which are flanked on both sides by genes having a high expression level.
3. Identification and/or isolation of intergenic sequences which are flanked on both sides by genes having an expression pattern which is preferably independent from the expression pattern of the other paired gene a high expression level.
4. Identification and/or isolation of intergenic sequences which are flanked on one or—preferably—both sides by genes having a low variability in length of the mRNA transcript derived from said paired genes.

Preferably the paired genes flanking the intergenic region have tail-to-tail orientation Preferably, intergenic regions from paired genes in tail-to-tail orientation are identified which have a length from about 400 to 3,000 base pairs, preferably from about 700 to about 2,000 base pairs.

Thus, a preferred embodiment of the invention is related to a method for identification and/or isolation of intergenic regions with transcription termination potential said method including at least the steps of a) identification and/or isolation or isolation of intergenic regions between paired genes having an intergenic distance of about 400 to 3,000 base pairs, and
b) identification and/or isolation of intergenic sequences which are flanked on both sides by genes having a high expression level.

More preferably said method further comprising the steps of c) identification and/or isolation of intergenic sequences which are flanked on both sides by genes having an expression pattern which is preferably independent from the expression pattern of the other paired gene, and
d) identification and/or isolation of intergenic sequences which are flanked on one or—preferably—both sides by genes having a low variability in length of the mRNA transcript derived from said paired genes.

Most preferably, the intergenic region a) is localized between genes which have a tail-to-tail localization (i.e. from which expression from said genes is directed in opposite direction against each other) and/or b) has a length measured from the respective stop codons of the flanking genes from about 700 to about 2,000 base pairs.

Based on said method sequences from the rice genome were identified and found to be promising as transcription terminator sequences. Said sequences are described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, and 108.

Another embodiment of the invention is related to the use of said sequences to terminate transcription in a transgenic expression construct. More preferably is the use of said sequences as isolators in multi-gene expression constructs.

Another embodiment of the invention is related to a transgenic expression construct comprising in 5'-3'-direction a) a promoter sequence functional in plants, and b) a nucleic acid sequence of interest of to be expressed operably linked to said promoter a), and c) at least one sequence selected from the group consisting of
   i) the sequences described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, and 108, and
   ii) the sequences having a homology of at least 60%, preferably 80%, more preferably 90%, most preferably 95% with a sequences described by described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, or 108, capable to terminate transcription in a plant cell or organism, and
   iii) the sequences hybridizing under low stringency conditions, preferably under high stringency conditions with a sequences described by described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, or 108 capable to terminate transcription in a plant cell or organism, and
   iv) a fragment of at least 50 consecutive base pairs, preferably at least 100 consecutive base pairs, more preferably at least 250 consecutive base pairs, most preferably at least 500 consecutive base pairs of a sequence described under i), ii), and iii), wherein said sequence c) is heterolog with respect to said promoter a) and/or said nucleic acid of interest b) and is mediating termination of expression of induced from said promoter a).

Another embodiment of the invention is related to a transgenic expression construct comprising at least two expression cassettes having a structure comprising in 5'-3'-direction a1) a first promoter sequence functional in plants, and b1) a first nucleic acid sequence of interest of to be expressed operably linked to said promoter a1), and c) at least one sequence selected from the group consisting of
   i) the sequences described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, and 108, and
   ii) the sequences having a homology of at least 60%, preferably 80%, more preferably 90%, most preferably 95% with a sequences described by described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, or 108, capable to terminate transcription in a plant cell or organism, and
   iii) the sequences hybridizing under low stringency conditions, preferably under high stringency conditions with a sequences described by described by SEQ ID NO: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 92, 93, 107, or 108, capable to terminate transcription in a plant cell or organism, and
   iv) a fragment of at least 50 consecutive base pairs, preferably at least 100 consecutive base pairs, more preferably at least 250 consecutive base pairs, most preferably at least 500 consecutive base pairs of a sequence described under i), ii), and iii), and, b2) a second nucleic acid sequence of interest of to be expressed, and a2) a second promoter sequence functional in plants operably linked to said nucleic acid sequence of interest b2), wherein said sequence c) is heterolog with respect to at least one element selected from promoter a1), promoter a2), nucleic acid of interest b1) and nucleic acid of interest b2), and is mediating termination of expression of induced from said promoters a1) and a2).

Since no protein expression is caused from the above described transcription terminator sequences, a higher degree of variation is acceptable without changing the functionality.

The method of the invention can also be employed to identify regions responsible for transcription termination within larger sequences. This would allow to delete unnecessary sequences and to provide small sequences for transcription termination, which is an important goal in construction gene expression vectors. Large sequences leading to large vectors are linked to inefficient transformation and instability of constructs. Preferably, such identification can be realized by inserting fragments of a larger sequence into a screening vector or screening construct. Such fragments can be derived, for example, by nuclease mediated shorting of 5'- and/or 3'-ends of the larger sequence (by restrictions enzymes or unspecific nucleases such as Bal31). Corresponding methods are well known to the person skilled in the art.

The larger sequence for which one may seek to identify the essential region for transcription termination may for example be the natural region downstream of the coding sequence of the gene, which is the source for the promoter employed in the transgenic expression construct (e.g., comprising the region encoding the 3'-untranslated region and additional downstream genomic sequences), preferably from a region which is surrounding the end of the mRNA transcript. It is advantageous to combine a promoter with its natural transcription terminator (and the heterogeneous sequence of interest in between) to obtain optimal expression results. While formerly either very long 3'-untranslated regions had to be employed to ensure efficient transcriptions termination, or laborious testing of shortened sequences had to be performed, the method of the present invention is allowing for fast and efficient restriction of a potential transcription terminator to its essential elements.

4. Insertion of the DNA Molecules into the Screening Vector

The DNA molecules to be assessed for their transcription termination efficiency may be inserted into the Screening Vector by various means. Preferably, the insertion is realized by one or more methods selected from the group consisting of:

a) Insertion into a restriction site: Various sequence specific endonuclease are known to the person skilled in art which can be employed for carrying out the method of the invention. Suitable endonuclease may be for example type II restriction endonucleases or artificial (e.g., chimeric) nucleases. Preferred are restriction endonucleases which are chosen in a way that only the insertion site is cleaved by said restriction endonuclease. Such restriction endonuclease may preferably include rare cutting endonucleases which have a recognition site of at least 8 base pairs (such as for example Notl) or even homing endonucleases, which have very long recognition sequences (Belfort 1997; Jasin 1996; Internet: http://rebase.neb.com/rebase/rebase.homing.html; Roberts 2001). Examples for preferred homing endonucleases include but are not limited to F-SceI, I-CeuI, I-ChuI, I-DmoI, I-CpaI, I-CpaII, I-CreI, I-CsmI, F-TevI, F-TevII, I-TevI, I-TevII, I-AniI, I-CvuI, I-LlaI, I-NanI, I-MsoI, I-NitI, I-NjaI, I-PakI, I-PorI, I-PpoI, I-ScaI, I-Ssp68031, PI-PkoI, PI-PkoII, PI-PspI, PI-TfuI, PI-TliI. Most preferred are I-CeuI, I-SceI, I-PpoI, PI-PspI, and PI-SceI.

b) Insertion into a recombination site: In a preferred embodiment of the invention, the insertion of DNA segments into the insertion site of the screening construct or screening vector is achieved by the use of recombination proteins, including recombinases and associated co-factors and proteins. Numerous recombination systems from various organisms can also be used, based on the teaching and guidance provided herein. See, e.g., Hoess 1986; Abremski 1986; Campbell, 1992; Qian 1992; Araki 1992). Many of these belong to the integrase family of recombinases (Argos 1986). Perhaps the best studied of these are the Integrase/att system from bacteriophage λ (Landy 1993), the Cre/loxP system from bacteriophage P1 (Hoess 1990), and the FLP/FRT system from the *Saccharomyces cerevisiae* 2μ circle plasmid (Broach 1982)). Detailed method for recombinase mediated cloning, appropriate recombination sites (to be employed as insertion sites), and corresponding recombinases are described e.g., in U.S. Pat. No. 5,888,732, hereby incorporated entirely by reference. A preferred system is the Gateway™ cloning system (Invitrogen, Inc.). Corresponding ready-to-use mixture of lambda integrase with its corresponding co-factors can be obtained from Invitrogen Inc. (Gateway™ LR Clonase™ Plus enzyme).

Also procedures comprising combination of both method can be employed. However, it is not essential that the sequence to be assessed is inserted directly (i.e. in an one-step cloning procedure) into a quasi ready-to-go screening construct or screening vector. It may for example—first be linked to the additional sequence and then inserted into an appropriate construct or vector thus constituting the final screening construct or screening vector to be employed in the evaluation procedure. In principle, the ways and possibilities to assembly the various parts of a screening construct or screening vector are uncountable but well known and established to the person skilled in the art.

For the purpose of insertion into the insertion site the DNA sequence to be inserted may be linked to adapters providing the appropriate recognition sequences for restriction endonuclease or recombinase, respectively. However, in the case of restriction endonucleases adapters are not required in cases where a digestion of genomes is employed as a library of DNA sequences. Here the restriction enzyme employed for the digest should create DNA ends compatible with those at the cleaved insertion site.

5. The in Vitro Screening System

When performed as an in vitro screening system, the expression of the additional sequences (which may preferably be located downstream (i.e. in 3'-direction) of the insertion site) may be—for example—easily detected at the RNA levels using sensitive fluorescence probes that recognize single strand nucleotides. Such features are also to be understood as readily detectable characteristics. In case an efficient transcription terminator sequence is inserted in front of these sequences a reduced, preferably no significant or at all observable signal will be obtained.

Within the in vitro screening system, transcription of sequences located downstream of the transcription termination sequence inserted into the insertion site can be detected at the RNA levels using commercially available in vitro transcription systems (such as wheat germ nuclear extracts, HeLa nuclear extracts, rabbit reticulocyte extracts, or nuclear extracts from plant of interest) preferably in combination with single strand recognizing florescence probes (e.g. beacon probes). Various suitable in vitro transcription/translation systems are known in the art and commercially available (e.g., ActivePro™, PROTEINscript™ II, Retic Lysate IVT™ (treated) and Retic Lysate IVr™-96, Wheat Germ IVT™; all available from Ambion, Inc., Austin, USA). In this case no plant transformation is involved. In consequence, the screening construct or screening vector can be constructed on a simple base (e.g., pUC based). Preferably, individual screening constructs or screening vectors comprising different transcription termination sequences are placed in 96 well plates for in vitro transcription. The fluorescent probe hybridizes when read through occurs. The tighter transcription termination occurs, the less fluorescent products in the read through region are detected. The amounts of read through products can be normalized by the expression of sequences located upstream of the transcription termination sequences but still under control of the promoter.

6. The in Vivo Screening System

In a preferred embodiment, the method of the invention is realized in vivo, preferably in the target organism in which an efficient transcription terminator is sought for. The in vivo screening system allows for evaluation of multiple DNA sequences for their performance as transcription terminator sequences in parallel. Thus, a library of DNA sequences can be employed and inserted into the screening construct or screening vector yielding a library of screening constructs or screening vectors comprising various different DNA sequences. Said library of screening constructs or screening vectors is inserted into cells or organisms in a way that each individual cell or organism preferably comprises only one screening constructs or screening vectors of said library (comprising one specific DNA sequence to be assessed for the transcription termination capability). In consequence—as described below in more detail—this preferred embodiment does not necessarily require the sorting of the various screening constructs or screening vectors prior to evaluation for the transcription termination capability, which makes the method even more efficient. Thus, in a preferred embodiment the method of the invention therefore relates to a method for identification and isolation of transcription termination sequences for comprising the steps of:

i) providing a screening construct or screening vector comprising
   a) a promoter sequence, and
   b) one or more insertion sites—preferably a restriction or recombination site—for insertion of DNA sequences, and
   c) at least one additional sequence which causes upon expression under said promoter sequence a readily detectable characteristic, wherein insertion of an efficient transcription terminator into said insertion site changes expression of said additional sequences by said promoter sequence in comparison to no insertion, and ii) providing one or more DNA sequences to be assessed for their transcription termination capability, and iii) inserting one or more copies of said DNA sequences into said insertion site of said screening construct or screening vector, and iv) introducing said screening construct or screening vector with said inserted DNA sequences into cells or organisms suitable to induce expression from said promoter sequence, and v) identifying and/or selecting cells or organisms with a changed readily detectable characteristic in comparison to no insertion, and vi) isolating the inserted DNA sequences from said identified and/or selected screening construct or screening vector for use as transcription termination sequences and—optionally—determining their sequence.

All the above specified preferred variations (such as Variation A, B, or C) can also be advantageously combined with said in vivo system. In the in vivo screening systems of the invention, the expression of the sequence located downstream (at the 3'-end) of the insertion site will preferably cause an easily detectable phenotype. "Causing" includes both initiating or suppressing an easily detectable phenotype. For example, the sequence located downstream (at the 3'-end) of the insertion site may either code for a phenotype causing protein, or it may code for RNA (e.g., antisense or double stranded RNA) which causes suppression of expression of a phenotype causing protein. Multiple examples are given above.

In an preferred embodiment of the in vivo screening systems of the invention, the expression of the sequence located downstream (at the 3'-end) of the insertion site will cause a phenotype which is inhibiting growth, propagation and/or or regeneration of said cells or organisms (e.g., plant cells or plants), and which is therefore understood within the context of this invention to be "toxic" to said cells and/organisms (e.g., plant cells or plants). In consequence, only cells (or organisms) will survive if a tight transcription termination sequence is inserted in front of said toxic phenotype causing sequence thereby preventing expression of this growth, propagation and/or or regeneration inhibiting sequences. The surviving cells can be isolated and the transcription terminator sequence can be identified and isolated, e.g., by amplification using PCR followed by sequencing.

For conducting the screening in the in vivo system the screening construct or screening vector in transformed preferably into a cell, tissue or organism. The generation of a transformed organism or a transformed cell requires introducing the DNA in question into the host cell in question. A multiplicity of methods is available for this procedure, which is termed transformation (see also Keown 1990). For example, the DNA can be introduced directly by microinjection or by bombardment via DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse.

The host cell or organism can be any prokaryotic or eukaryotic organism. Preferred are mammalian cells, non-human mammalian organism, plant cells and plant organisms as defined above.

The screening construct or screening vector of the invention is preferably introduced into a eukaryotic cell. It may be preferably inserted into the genome (e.g., plastids or chromosomal DNA) but may also be exist extra-chromosomal or epichromosomal. Preferred eukaryotic cells are mammalian cell, fungal cell, plant cell, insect cell, avian cell, and the like. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570, ATCC CRL 8544, ATCC CRL 10314), canine kidney cells (MDCK; ATCC CCL 34), Chinese hamster ovary cells (CHO-K1; ATCC CCL61; CHO DG44 (Chasin 1986), rat pituitary cells (GH1; ATCC CCL82), HeLa S3 cells (ATCC CCL2.2), rat hepatoma cells (H-A-II-E; ATCC CRL 1548) SV40-transformed monkey kidney cells (COS-1; ATCC CRL 1650) and murine embryonic cells (NIH-3T3; ATCC CRL 1658).

A screening construct or screening vector can be introduced into host cells using a variety of standard techniques including calcium phosphate transfection, liposome-mediated transfection, microprojectile-mediated delivery, electroporation, and the like. Transfected cells can be selected and propagated to provide recombinant host cells that comprise the gene of interest stably integrated in the host cell genome.

The screening vector may be a baculovirus expression vector to be employed in a baculovirus system. The baculovirus system provides an efficient means to introduce cloned genes of interest into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system (Luckow 1993). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the polypeptide of interest into a baculovirus genome maintained in *E. coli* as a large plasmid called a "bacemid" (see, Hill-Perkins 1990; Bonning 1994; and Chazenbalk 1995). In addition, transfer vectors can include an in-frame fusion with DNA encoding an epitope tag at the C- or N-terminus of the expressed polypeptide, for example, a Glu-Glu epitope tag (Grussenmeyer 1985). Using a technique known in the art, a transfer vector containing a gene of interest is transformed into *E. coli*, and screened for bacmids, which contain an interrupted lacZ gene indicative of recombinant baculovirus. The bacmid DNA containing the recombinant baculovirus genome is then isolated using common techniques. The recombinant virus or bacinid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVE™ cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express Five™ (Life Technologies) for the *T. ni* cells. When recombinant virus is used, the cells are typically grown up from an inoculation density of approximately 2-5.times.10.sup.5 cells to a density of 1-2.times.10.sup.6 cells at which time a recombinant viral stock is added at a multiplicity of infection of 0.1 to 10, more typically near 3. Established techniques for the baculovirus systems are provided by Bailey 1991, Patel 1995, Ausubel 1995 (at pages 16-37 to 16-57), Richardson 1995, and by Lucknow, 1996.

Fungal cells, including yeast cells, can also be used as host cells for transformation with the screening construct or screening vector of the invention. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available to be employed. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, U.S. Pat. No. 4,599,311, U.S. Pat. No. 4,931,373, U.S. Pat. No. 4,870,008, U.S. Pat. No. 5,037,743, and U.S. Pat. No. 4,845,075. Transformed cells are selected by phenotype determined by the selectable marker, commonly drug resistance or the ability to grow in the absence of a particular nutrient (e.g., leucine). An illustrative vector system for use in *Saccharomyces cerevisiae* is the POTI vector system (U.S. Pat. No. 4,931,373), which allows transformed cells to be selected by growth in glucose-containing media. Additional suitable promoters and terminators for use in yeast include those from glycolytic enzyme genes (see, e.g., U.S. Pat. Nos. 4,599,311, 4,615,974, and 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson 1986, and U.S. Pat. No. 4,882,279. *Aspergillus* cells may be utilized according to the methods of McKnight et al. (U.S. Pat. No. 4,935,349). Methods for transforming *Acremonium chrysogenum* are disclosed (U.S. Pat. No. 5,162,228). Methods for transforming *Neurospora* are disclosed (U.S. Pat. No. 4,486,533).

For example, the use of *Pichia methanolica* as host for the production of recombinant proteins is disclosed (U.S. Pat. Nos. 5,716,808, 5,736,383, Raymond 1998, WO 97/17450, WO 97/17451, WO 98/02536, and WO 98/02565). DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. For large-scale, industrial processes where it is desirable to minimize the use of methanol host cells can be used in which both methanol utilization genes (AUG1 and AUG2) are deleted. For production of secreted proteins, host cells can be used that are deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Standard methods for introducing nucleic acid molecules into bacterial, yeast, insect, mammalian, and plant cells are provided, for example, by Ausubel (1995). General methods for expressing and recovering foreign protein produced by a mammalian cell system are provided by, for example, in Etcheverry 1996. Established methods for isolating recombinant proteins from a baculovirus system are described (Richardson 1995).

Especially preferred in transfer of the screening construct or screening vector into plant cells, tissues and/or organism. Methods for introduction of a transgenic expression construct or vector into plant tissue may include but are not limited to, e.g., electroinjection (Nan 1995; Griesbach 1992); fusion with liposomes, lysosomes, cells, minicells or other fusible lipid-surfaced bodies (Fraley 1982); polyethylene glycol (Krens 1982); chemicals that increase free DNA uptake; transformation using virus, and the like. Furthermore, the biolistic method with the gene gun, electroporation, incubation of dry embryos in DNA-containing solution, and microinjection may be employed.

Protoplast based methods can be employed (e.g., for rice), where DNA is delivered to the protoplasts through liposomes, PEG, or electroporation (Shimamoto 1989; Datta 1990b). Transformation by electroporation involves the application of short, high-voltage electric fields to create "pores" in the cell membrane through which DNA is taken-up. These methods are—for example—used to produce stably transformed monocotyledonous plants (Paszkowski 1984; Shillito 1985; Fromm 1986) especially from rice (Shimamoto 1989; Datta 1990b; Hayakawa 1992).

Particle bombardment or "biolistics" is a widely used method for the transformation of plants, especially monocotyledonous plants. In the "biolistics" (microprojectile-mediated DNA delivery) method microprojectile particles are coated with DNA and accelerated by a mechanical device to a speed high enough to penetrate the plant cell wall and nucleus (WO 91/02071). The foreign DNA gets incorporated into the host DNA and results in a transformed cell. There are many variations on the "biolistics" method (Sanford 1990; Fromm 1990; Christou 1988; Sautter 1991). The method has been used to produce stably transformed monocotyledonous plants including rice, maize, wheat, barley, and oats (Christou 1991; Gordon-Kamm 1990; Vasil 1992; Wan 1994).

In addition to these "direct" transformation techniques, transformation can also be affected by bacterial infection by means of *Agrobacterium tumefaciens* or *Agrobacterium rhizogenes*. These strains contain a plasmid (Ti or Ri plasmid) which is transferred to the plant following *Agrobacterium* infection. Part of this plasmid, termed T-DNA (transferred DNA), is integrated into the genome of the plant cell (see above for description of vectors). To transfer the DNA to the plant cell, plant explants are cocultured with a transgenic *Agrobacterium tumefaciens* or *Agrobacterium rhizogenes*. Starting from infected plant material (for example leaf, root or stem sections, but also protoplasts or suspensions of plant cells), intact plants can be generated using a suitable medium which may contain, for example, antibiotics or biocides for selecting transformed cells. The plants obtained can then be screened for the presence of the DNA introduced, in this case the expression construct according to the invention. As soon as the DNA has integrated into the host genome, the genotype in question is, as a rule, stable and the insertion in question is also found in the subsequent generations. As a rule, the expression construct integrated contains a selection marker which imparts a resistance to a biocide (for example a herbicide) or an antibiotic such as kanamycin, G 418, bleomycin, hygromycin or phosphinotricin and the like to the transformed plant. The selection marker permits the selection of transformed cells from untransformed cells (McCormick 1986). The plants obtained can be cultured and hybridized in the customary fashion. Two or more generations should be grown in order to ensure that the genomic integration is stable and hereditary. The abovementioned methods are described in detail in the relevant art (for example, in Jenes 1993, and in Potrykus 1991).

One of skill in the art knows that the efficiency of transformation by *Agrobacterium* may be enhanced by using a number of methods known in the art. For example, the inclusion of a natural wound response molecule such as acetosyringone (AS) to the Agro bacterium culture has been shown to enhance transformation efficiency with *Agrobacterium tumefaciens* (Shahla 1987). Alternatively, transformation efficiency may be enhanced by wounding the target tissue to be transformed. Wounding of plant tissue may be achieved, for example, by punching, maceration, bombardment with microprojectiles, etc. (see, e.g., Bidney 1992).

A number of other methods have been reported for the transformation of plants (especially monocotyledonous plants) including, for example, the "pollen tube method" (WO 93/18168; Luo 1988), macro-injection of DNA into floral tillers (Du 1989; de la Pena 1987), injection of *Agrobacterium* into developing caryopses (WO 00/63398), and tissue incubation of seeds in DNA solutions (Topfer 1989). Direct injection of exogenous DNA into the fertilized plant ovule at the onset of embryogenesis was disclosed in WO 94/00583. WO 97/48814 disclosed a process for producing stably transformed fertile wheat and a system of transforming wheat via *Agrobacterium* based on freshly isolated or pre-cultured immature embryos, embryogenic callus and suspension cells.

It may be desirable to target the nucleic acid sequence of interest to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (U.S. Pat. No. 5,501,967). Replacement-type vectors generally contain two regions which are homologous with the targeted genomic sequence and which flank a heterologous nucleic acid sequence, e.g., a selectable marker gene sequence. Replacement-type vectors result in the insertion of the selectable marker gene which thereby disrupts the targeted gene. Insertion-type vectors contain a single region of homology with the targeted gene and result in the insertion of the entire targeting vector into the targeted gene.

Transformed cells, i.e. those which contain the introduced DNA integrated into the DNA of the host cell, can be selected from untransformed cells if a selectable marker is part of the introduced DNA. A selection marker gene may confer positive or negative selection.

A positive selection marker gene may be used in constructs for random integration and site-directed integration. Positive selection marker genes include antibiotic resistance genes, and herbicide resistance genes and the like. Transformed cells which express such a marker gene are capable of surviving in the presence of concentrations of the antibiotic or herbicide in question which kill an untransformed wild type. Examples are the bar gene, which imparts resistance to the herbicide phosphinotricin (bialaphos; Vasil 1992; Weeks 1993; Rathore 1993), the nptII gene, which imparts resistance to kanamycin, the hpt gene, which imparts resistance to hygromycin, or the EPSP gene, which imparts resistance to the herbicide glyphosate, geneticin (G-418) (aminoglycoside) (Nehra 1994), glyphosate (Della-Cioppa et al. 1987) and the ALS gene (chlorsulphuron resistance). Further preferred selectable and screenable marker genes are disclosed above.

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive. The choice of the negative selection marker gene is not critical to the invention as long as it encodes a functional polypeptide in the transformed plant cell. The negative selection gene may for instance be chosen from the aux-2 gene from the Ti-plasmid of *Agrobacterium*, the tk-gene from SV40, cytochrome P450 from *Streptomyces griseolus*, the Adh gene from Maize or *Arabidopsis*, etc. Any gene encoding an enzyme capable of converting a substance which is otherwise harmless to plant cells into a substance which is harmful to plant cells may be used. Further preferred negative selection markers are disclosed above.

However, insertion of an expression cassette or a vector into the chromosomal DNA can also be demonstrated and analyzed by various other methods (not based on selection marker) known in the art like including, but not limited to, restriction mapping of the genomic DNA, PCR-analysis, DNA-DNA hybridization, DNA-RNA hybridization, DNA sequence analysis and the like. More specifically such methods may include e.g., PCR analysis, Southern blot analysis, fluorescence in situ hybridization (FISH), and in situ PCR.

As soon as a transformed plant cell has been generated, an intact plant can be obtained using methods known to the skilled worker. Accordingly, the present invention provides transgenic plants. The transgenic plants of the invention are not limited to plants in which each and every cell expresses the nucleic acid sequence of interest under the control of the promoter sequences provided herein. Included within the scope of this invention is any plant which contains at least one cell which expresses the nucleic acid sequence of interest (e.g., chimeric plants). It is preferred, though not necessary, that the transgenic plant comprises the nucleic acid sequence of interest in more than one cell, and more preferably in one or more tissue.

Once transgenic plant tissue which contains an expression vector has been obtained, transgenic plants may be regenerated from this transgenic plant tissue using methods known in the art. The term "regeneration" as used herein, means growing a whole plant from a plant cell, a group of plant cells, a plant part or a plant piece (e.g., from a protoplast, callus, protocorm-like body, or tissue part).

Species from the following examples of genera of plants may be regenerated from transformed protoplasts: *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Pisum, Lolium, Zea, Triticum, Sorghum*, and *Datura.*

For regeneration of transgenic plants from transgenic protoplasts, a suspension of transformed protoplasts or a Petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. These three variables may be empirically controlled to result in reproducible regeneration.

Plants may also be regenerated from cultured cells or tissues. Dicotyledonous plants which have been shown capable of regeneration from transformed individual cells to obtain transgenic whole plants include, for example, apple (*Malus pumila*), blackberry (*Rubus*), Blackberry/raspberry hybrid (*Rubus*), red raspberry (*Rubus*), carrot (*Daucus carota*), cauliflower (*Brassica Oleracea*), celery (*Apium graveolens*), cucumber (*Cucumis sativus*), eggplant (*Solanum melongena*), lettuce (*Lactuca sativa*), potato (*Solanum tuberosum*), rape (*Brassica napus*), wild soybean (*Glycine canescens*), strawberry (*Fragaria ananassa*), tomato (*Lycopersicon esculentum*), walnut (*Juglans regia*), melon (*Cucumis melo*), grape (*Vitis vinifera*), and mango (*Mangifera indica*). Monocotyledonous plants which have been shown capable of regeneration from transformed individual cells to obtain transgenic whole plants include, for example, rice (*Oryza sativa*), rye (*Secale cereale*), and maize (*Zea mays*).

In addition, regeneration of whole plants from cells (not necessarily transformed) has also been observed in: apricot (*Prunus armeniaca*), asparagus (*Asparagus officinalis*), banana (hybrid *Musa*), bean (*Phaseolus vulgaris*), cherry (hybrid *Prunus*), grape (*Vitis vinifera*), mango (*Mangifera indica*), melon (*Cucumis melo*), ochra (*Abelmoschus esculentus*), onion (hybrid *Allium*), orange (*Citrus sinensis*), papaya (*Carrica papaya*), peach (*Prunus persica*), plum (*Prunus domestica*), pear (*Pyrus communis*), pineapple (*Ananas comosus*), watermelon (*Citrullus vulgaris*), and wheat (*Triticum aestivum*).

The regenerated plants are transferred to standard soil conditions and cultivated in a conventional manner. After the expression vector is stably incorporated into regenerated transgenic plants, it can be transferred to other plants by vegetative propagation or by sexual crossing. For example, in vegetatively propagated crops, the mature transgenic plants are propagated by the taking of cuttings or by tissue culture techniques to produce multiple identical plants. In seed propagated crops, the mature transgenic plants are self-crossed to produce a homozygous inbred plant which is capable of passing the transgene to its progeny by Mendelian inheritance. The inbred plant produces seed containing the nucleic acid sequence of interest. These seeds can be grown to produce plants that would produce the selected phenotype. The inbred plants can also be used to develop new hybrids by crossing the inbred plant with another inbred plant to produce a hybrid.

Confirmation of the transgenic nature of the cells, tissues, and plants may be performed by PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant. The resulting plants can be bred in the customary fashion. Two or more generations should be grown in order to ensure that the genomic integration is stable and hereditary. Corresponding methods are described, (Jenes 1993; Potrykus 1991).

7. Conduction the Screening, Isolation and Use of the Transcription Terminator Sequences Once one or more DNA sequences or even a library of sequences to be assessed for their transcription termination efficiency was inserted into the screening construct or screening vector these vectors are submitted to the appropriate in vitro or in vivo screening system.

The readily detectable characteristic or the change thereof can be monitored by various means well known to the person skilled in the art depending on the additional sequence employed. The "output" of the screening system (i.e. the number of different transcription terminator sequences) and their efficiency can be controlled by setting certain cut-off limits. For example a certain intensity of color or fluorescence (in case the characteristic is a color), a certain resistance against a toxic compound (in case the characteristic is a resistance).

Screening constructs, screening vectors, or cells or organisms comprising those, derived from the screening process can be employed to isolate and analyze the transcription termination sequences comprised therein. Isolation can be done by various means including but not limited to PCR mediated amplification of the sequence inserted into the insertion site using primers specific for the known regions flanking said insertion site.

The isolated transcription terminator sequence can be used for various purposes in biotechnology, preferably in constructing gene expression constructs which require a tight transcription termination control i.e. a low read-through frequency. Such expression cassettes (consisting for example in 5'/3'-direction of a promoter, a gene of interest, and the isolated transcription termination sequence) can be produced by means of customary recombination and cloning techniques as are described (for example, in Maniatis 1989; Silhavy 1984; and in Ausubel 1987). The person skilled in the art is aware of numerous sequences which may be utilized as gene of interest in this context, e.g. to increase quality of food and feed, to produce chemicals, fine chemicals or pharmaceuticals (e.g., vitamins, oils, carbohydrates; Dunwell 2000), conferring resistance to herbicides, or conferring male sterility. Furthermore, growth, yield, and resistance against abiotic and biotic stress factors (like e.g., fungi, viruses, nematodes, or insects) may be enhanced. Advantageous properties may be conferred either by over-expressing proteins or by decreasing expression of endogenous proteins by e.g., expressing a corresponding antisense (Sheehy 1988; U.S. Pat. No. 4,801,340; Mol 1990) or double-stranded RNA (Matzke 2000; Fire 1998; Waterhouse 1998; WO 99/32619; WO 99/53050; WO 00/68374; WO 00/44914; WO 00/44895; WO 00/49035; WO 00/63364).

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

| Sequences | |
|---|---|
| 1. SEQ ID NO: 1 | Binary expression vector Lo546b-pSUN1-R4-Lo484::Lo376::Lo522b |
| 2. SEQ ID NO: 2 | Binary expression vector Lo546a-pSUN1-R4-Lo484::Lo376::Lo522a |
| 3. SEQ ID NO: 3 | Nucleic acid construct Lo522b-pENTR-C1-STPT-nptII-IRnos |
| 4. SEQ ID NO: 4 | Nucleic acid construct Lo522a-pENTR-C1-STPT-nptII-IRnos |
| 5. SEQ ID NO: 5 | Binary expression vector Lo523b-pSUN1-R4-Lo484::Lo376::Lo503b |
| 6. SEQ ID NO: 6 | Binary expression vector Lo523a-pSUN1-R4-Lo484::Lo376::Lo503a |
| 7. SEQ ID NO: 7 | Nucleic acid construct Lo503b-pENTR-C1-STPT-nptII-IRnos |
| 8. SEQ ID NO: 8 | Nucleic acid construct Lo503a-pENTR-C1-STPT-nptII-IRnos |
| 9. SEQ ID NO: 9 | Nucleic acid construct Lo484-pENTR-A1-inv-35s-GFP-E9 |
| 10. SEQ ID NO: 10-46: | Nucleic acid sequence from rice (*Oryza sativa sbsp. japonica*) encoding sequences suitable as transcription terminators and expression cassette isolators. |
| 11. SEQ ID NO: 47: | Primer 1(SacI, AvrII, SpeI, OCS 5') 5'-CG GAGCTC CCTAGG ACTAGT tcgaccggcatgccc-3' |
| 12. SEQ ID NO: 48 | Primer 2 (NotI, OCS 3') 5'- CC GCGGCCGC agcttggacaatcag-3' |
| 13. SEQ ID NO: 49 | Primer 3 (AvrII, XmaI, RsrII, $Lu^F$ 5') 5'-CG CCTAGG CCCGGG CGGACCG cattaagaagggccc-3' |
| 14. SEQ ID NO: 50 | Primer 4 (SpeI $Lu^F$ 3') 5'-CG ACTAGT agagagttctcagagc-3' |
| 15. SEQ ID NO: 51 | Primer 5 (RsrII, BspEI, target gene seq 5') 5' CG CGGACCG TCCGGA-N-3' [N represents a gene-specific sequence of preferably 10 to 20 bases] |
| 16. SEQ ID NO: 52 | Primer 6 (SpeI, AgeI, target gene seq 3') 5' CG ACTAGT ACCGGT-N-3' [N represents a gene-specific sequence of preferably 10 to 20 bases] |
| 17. SEQ ID NO: 53 | pTOI3 |
| 18. SEQ ID NO: 54 | pTOI4 |
| 19. SEQ ID NO: 55 | Oligonucleotideprimer Loy482-NosT-upper-SalI 5'-AAATTTGTCGACCGATCGGTCAAACATT-3' |
| 20. SEQ ID NO: 56 | Oligonucleotideprimer Loy483-NosT-Lower-HindIII 5'-AAATTTAAGCTTCCCGATCTAGTAACATAGATGACA-3' |
| 21. SEQ ID NO: 57 | Oligonucleotideprimer Loy494-Gus_upper_SalI_Spacer 5'-TTTTAGTCGACACGCTGGACTGGCATGAACT-3' |
| 22. SEQ ID NO: 58 | Oligonucleotideprimer Loy492-NosT-lower-BglII SpeI 5'-TTTTAAGATCTACTAGTCCGATCTAGTAACATAGATGACA-3' |
| 23. SEQ ID NO: 59 | Oligonucleotideprimer Loy493_Gus_upper_SalI_Spacer 5'- TTTAAGTCGACAAGTCGGCGGCTTTTCTGCT-3' |
| 24. SEQ ID NO: 60 | Oligonucleotideprimer Loy492-NosT-lower-BglII SpeI 5'-TTTTAAGATCTACTAGTCCGATCTAGTAACATAGATGACA-3' |
| 25. SEQ ID NO: 61 | Oligonucleotideprimer JMTOIprim1 5'-GGTTCCAAGGTACCAAAACAATGGGCGCTGATGATGTTGTTGAT-3' |
| 26. SEQ ID NO: 62 | Oligonucleotideprimer JMTOIprim2 5'-AAGGTAGAAGCAGAAACTTACCTGGATACGTCACTTTGACCA-3' |
| 27. SEQ ID NO: 63 | Oligonucleotideprimer JMTOIprim3 5'-TGGTCAAAGTGACGTATCCAGGTAAGTTTCTGCTTCTACCTT-3' |
| 28. SEQ ID NO: 64 | Oligonucleotideprimer JMTOIprim4 5'-GGTTCCAAGGATCCATTTATTTTGAAAAAAATATTTG-3' |
| 29. SEQ ID NO: 65 | Oligonucleotideprimer JMTOIprim5 5'- GGTTCCAAGGATCCAGTATATAGCAATTGCTTTTC-3' |
| 30. SEQ ID NO: 66 | Oligonucleotideprimer JMTOIprim6 5'- CGAGAACCTTCGTCAGTCCTGCACATCAACAAATTTTGGTCATAAAAAAAAAAATATTAGAAAAGTTATAAATTAAAATATAC-3' |

-continued

| Sequences | |
|---|---|
| 31. SEQ ID NO: 67 | Oligonucleotideprimer JMTOIprim7 5'- CTAATATTTTTTTTTTTATGAC-CAAAATTTGTTGATGTGCAGGAC-TGACGAAGGTTCTCGCAC-3' |
| 32. SEQ ID NO: 68 | Oligonucleotideprimer JMTOIprim8 5'- TTGGAACCACTAGTTTATCGCCTGACAC-GATTTCCTGC-3' |
| 33. SEQ ID NO: 69 | Oligonucleotideprimer JMTOIprim9 5'- GGTTCCAAGGATCCGATCGTTCAAA-CATTTGGCAA-3' |
| 34. SEQ ID NO: 70 | Oligonucleotideprimer JMTOIprim10 5'- GGTTCCAAGGATCCGATCTAGTAACATA-GATGACA-3' |
| 35. SEQ ID NO: 71 | Screening construct pJMTOI1 |
| 36. SEQ ID NO: 72 | Screening construct pJMTOI2 |
| 37. SEQ ID NO: 73 | Screening construct pJMTOI3 |
| 38. SEQ ID NO: 74 | Screening construct pJMTOI4 |
| 39. SEQ ID NO: 75 | Screening construct pJMTOI5 |
| 40. SEQ ID NO: 76 | Lo376-pENTR-B2 |
| 41. SEQ ID NO: 77 | Lo442 pSUN1-R4R3-M20 (OCS10) (destination vector) |
| 42. SEQ ID NO: 78 | Binary vector Lo239-pSUN3-GWs-B1-BnAK700::GUS::nosT-B2 (10414 bp) |
| 43. SEQ ID NO: 79 | Binary vector Lo657-pSUN3-GWs-B1-BnAK700::GUS::E9::nosT::B2 (11153 bp) |
| 44. SEQ ID NO: 80 | GFP-Primer5: 5'-CGGCCTAGGGGCGCCCGGACCGagctgt-tcaccggca-3' |
| 45. SEQ ID NO: 81 | GFP-Primer 6: 5'-CGG ACT AGT gat gta gcc ctc agg-3' |
| 46. SEQ ID NO: 82 | Primer 7: 5'- CGA GCT CGT GCC TTT TGG ATC G-3' |
| 47. SEQ ID NO: 83 | Primer 8: 5'- CGG TCC GAA CGT GGT TGG-3' |
| 48. SEQ ID NO: 84 | Primer 9: 5'- CGA GCT CGG CCC TAT GAA TTG G-3' |
| 49. SEQ ID NO: 85 | Primer 10: 5'- CGG TCC GTC TCC TTC TGC ACA C-3' |
| 50. SEQ ID NO: 86 | Primer 11: 5'-CGA GCT CGA TGC ATT CCT TGG AT-3' |
| 51. SEQ ID NO: 87 | Primer 12: 5'-CCT AGG GTT TGG AGG TAT CAA G-3' |
| 52. SEQ ID NO: 88 | Primer 13: 5'-CGA GCT CCG TCC GAT GTG ATT CCG TC-3' |
| 53. SEQ ID NO: 89 | Primer 14: 5'- CCT AGG GGC AGT GTC GGC GGT T-3' |
| 54. SEQ ID NO: 90 | Primer 15: 5'- CGA GCT CCA GAG TGA CAG ACA GTG A-3' |
| 55. SEQ ID NO: 91 | Primer 16: 5'- CCT AGG TCT TCA ACT GTC CCC A-3' |
| 56. SEQ ID NO: 92 | *Oryza sativa* terminator BPST.3 (1,137 bp). This sequence is a functional equivalent of the sequence described by SEQ ID NO: 45. |
| 57. SEQ ID NO: 93 | *Oryza sativa* terminator BPST.4 (reverse complementary sequence of BPST.3) (1,137 bp). This sequence is a functional equivalent of the sequence described by SEQ ID NO: 45 |
| 58. SEQ ID NO: 94 | Artificial sequence, vector pRJB058 (6,849 bp)) |
| 59. SEQ ID NO: 95 | insert from pRJB062: Nos terminator (Nos-T) sequence inserted into SacI-RsrII fragment of pRJB058 (257 bp) |
| 60. SEQ ID NO: 96 | insert from pRJB064: ORF sequence inserted into SacI digested and T4 DNA Polymerase filled in fragment of pRJB058 (1,089 bp) |
| 61. SEQ ID NO: 97 | insert from pRJB066: *Oryza sativa* BPST.1 sequence inserted into Saci digested and T4 DNA polymerase filled in fragment of pRJB058 (1,420 bp) |
| 62. SEQ ID NO: 98 | insert from pRJB065: *Oryza sativa* BPST.2 sequence inserted into Saci digested and T4 DNA polymerase filled in fragment of pRJB058 (1,414 bp) |
| 63. SEQ ID NO: 99 | insert from pRJB067: *Oryza sativa* BPST.3 sequence inserted into Saci digested and T4 DNA polymerase filled in fragment of pRJB058 (1,165 bp) |
| 64. SEQ ID NO: 100 | insert from pRJB068: *Oryza sativa* BPST.4 (reverse completentary sequence of BPST.3) sequence inserted into SacI digested and T4 DNA polymerase filled in fragment of pRJB058 (1,165 bp) |
| 65. SEQ ID NO: 101 | BPST.5-MCS: *Oryza sativa* BPST.5 sequence with EcoRI and *AvrII* sites (1,305 bp) |
| 66. SEQ ID NO: 102 | BPST.6-MCS: *Oryza sativa* BPST.6 sequence with EcoRI and AvrII sites (1,350 bp) |
| 67. SEQ ID NO: 103 | BPST.7-MCS: *Oryza sativa* BPST.7 sequence with EcoRI and *SacI* sites (1,532 bp) |
| 68. SEQ ID NO: 104 | BPST.8-MCS: *Oryza sativa* BPST.8 sequence (reverse complementary sequence of BPST.7) with EcoRI site (1,532 bp) |
| 69. SEQ ID NO: 105 | binary vector pRLI024 derived from pRJB058 (16,914 bp) |
| 70. SEQ ID NO: 106 | binary vector pRLI031 derived from pRLI024 (15,919 bp) |
| 71. SEQ ID NO: 107 | *Oryza sativa* terminator BPST.7 (1,499 bp). This sequence is a functional equivalent of the sequence described by SEQ ID NO: 11. |
| 72. SEQ ID NO: 108 | *Oryza sativa* terminator BPST.8 (reverse complementary se- |

-continued

| Sequences |
| --- |
| quence of BPST.3) (1,499 bp). This sequence is a functional equivalent of the sequence described by SEQ ID NO: 11. |

EXAMPLES

Chemicals

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N. J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Development of Genomic Libraries for Identification of Transcription Terminators Genomic DNA from a target plant is prepared according to Qiagen plant DNA preparation kit (cat#12143). One μg of the genomic DNA is digested with four base pair cutting enzyme (e.g. Sau3A) overnight at 37° C. or mechanical shearing in a Hamilton syringe or sonication followed by electroporation (0.8% Agarose gel) and gel purification using the QIAEX II Gel Extraction Kit (cat#20021). Fragmented genomic DNAs (500 to 1,000 bp) are cloned in to the screening constructs or screening vectors described herein. The resulting library of constructs and vectors is batch transformed into plant cells (see below).

Example 2

In Silico Identification of Sequences to Evaluation as Transcription Terminators Beside other approaches described herein to provide sequences for evaluation of their suitability as transcription terminator sequences (e.g., genomic sequences as provided by Example 1), sequences can be provided by in silico search of genome databases, such as for example of *Arabidopsis thaliana* or rice. Accordingly, the whole rice genome sequences are screened for potential plant derived terminator candidates using the most updated data from the Institute of Genome Research (TIGR; PUB_tigr_rice_genome_v4.nt (v03212003), PUB_tigr_rice_cds_Oct022003.nt, pubOSest0603 (ncbi)). This screening system comprises three major components:

1) identification of paired genes meeting predefined (for example 700 to 2,000 bp) intergenic distance criteria;
2) determination of the expression levels and expression patterns of the identified paired genes;
3) selection of intergenic sequences for terminator candidates by genome mapping.

The genome mapping requires the following activities: (1) manual verification of the gene model, reading frame of the coding sequences (CDS), and the intergenic structures underlying the genomic sequences and (2) selection of potential transcription terminators of interest candidates based on the EST sequence alignment and CDS.

2.1 Identification of Paired Genes of Interest

Given the recently released rice japonica genome sequences and the 56,056 annotated rice CDS, the coordinators of the beginning and ending of those 56,056 annotated rice CDS from genomic regions are retrieved and the intergenic distances are calculated. A frequency distribution table of intergenic distances at 200 bp/interval is generated such that appropriate intergenic distance can be defined. In order to capture maximal values of potential terminator candidates, the distance between genes in the range of 700 to 2,000 bp is used, leading to identify 16,058 pairs of rice genes (consisting of paired genes in head-to-tail, tail-to-head, and tail-to-tail orientation).

First, each pair of the identified rice CDS is blasted against rice EST databases to retrieve EST homolog sequences. The identified sequences that are homologous to ESTs are mapped onto the same rice genomic regions from which the rice CDS are derived using the splice alignment gene identification application, GeneSeqer™ (Version 1.9 (Oct. 22, 2002), Department of Zoology & Genetics, Iowa State University, Ames, Iowa 50011-3260). The underlying gene model, including the 5' end exon, the 3' end exon, CDS reading frame, and intergenic structure between two genes is carefully verified by graphically displaying the GeneSeqer™ genome mapping results using MyGV (Version 1.0 (from NewLink Genetics, 2901 South Loop Drive, Suite 3900, Ames, Iowa 50010) application. Potential gene terminator candidates are 1) the paired CDS reading frames must be either head-to-tail, tail-to-tail, or tail-to-head orientated. The tail-to-tail orientation (i.e. from which expression from said genes is directed in opposite direction against each other) is the most desirable, as the intergenic sequences do not contain the promoter sequences and the intergenic sequence length can be minimized;
2) the annotated CDS and its gene model must be verified and supported by the EST sequences according to sequence alignment.

Of these intergenic regions preferably regions are identified for further analysis which are localized between genes which have a tail-to-tail localization (i.e. from which expression from said genes is directed in opposite direction against each other).

2.2 Determination of Gene Expression Levels and Expression Patterns

Each pair of the identified rice CDS (i.e. corresponding to the genes flanking the intergenic region) is used to identify the corresponding EST sequences of high identity to rice EST database using blastn searching with expectation value set to $1.0e^{-20}$. Those identified EST sequences, which presumably are considered as the same sequences as the rice CDS, are used to retrieve the gene expression profiling data derived from either the cDNA library clone distribution or microarray expression. Overall, a gene with a cluster/variant size of more than 100 clones derived from the cDNA libraries is considered as highly expressed, and so does the signal intensity beyond the top 25% quantile from the microarray expression studies. Highly expressed abundance for both of the paired genes is required as criteria for gene selection. Furthermore, the co-expression pattern of the paired genes can be assessed using the clone distribution across cDNA libraries or using the microarray expression data across different experiments. A linear correlation coefficient is calculated to determine the pattern of the gene expression. A pair of genes demonstrating unique expression pattern is desirable. Using those criteria, 5,279 pairs of rice CDs sequences are selected.

2.3 Determination of Transcript Length Variability

Preferably, the 3'-end of the EST sequence alignments corresponding to the genes flanking the intergenic region must demonstrate a low degree of variability with respect to transcript length. This is found to be predictive for a strong terminator signal.

Based on the above criteria, 37 rice potential intergenic genomic sequences (SEQ ID NO: 10 to 46) are selected for testing in the screening systems of the invention in order to identify terminators of interest. All of these sequences are localized in between genes which are orientated in the above mentioned preferred tail-to-tail orientation.

Example 3

In Vitro Screening System for Identifying Terminators of Interest

A high throughput screening method is developed to identify transcription terminators at the mRNA levels. The method includes in vitro transcription using single strand fluorescence probes such as beacon probes that hybridize polyadenylated RNA region and the read through region. The fluorescence amount of the read through products are compared with the amount of polyadenylated RNA. The stronger and tighter terminators will show the lesser amounts of read through products. Control vectors are constructed to establish the screening system (see FIG. 13 and agenda to this figure above).

A promoter for these constructs is preferably a strong constitutive promoter (e.g. maize ubiqutin promoter). In order to measure uncoupled transcription, SP6 or T7 phase promoter can be used for in vitro transcription. The coding sequence in the expression cassette can be any reporter gene or genomic DNA including start at the 5' end and stop codon at the 3' end, which do not have sequence homology to plant genome (e.g. intergenic sequences from yeast genome). Nopaline synthase terminator can be replaced with any other known terminator to use as a control or uncharacterized genomic DNA fragment to identify potential terminator candidates.

3.1 Vector Construction

Vector pBPSMM268 contains the GUS::potato intron gene followed by the NOS terminator region. To this vector, maize Ubiquitin promoter::intron is added by digestion of pMM268 with StuI and SmaI, followed by blunt ligation of the Ubiquitin promoter::intron fragment obtained from StuI digestion of pBPSCER043, which produces vector pTOI01.

In order to ensure efficient transcript processing of mRNAs that do not undergo transcriptional termination at putative transcription terminators, the OCS terminator region is cloned into pTOI01. pTOI02 is generated by digestion of pTOI01 with SacI and NotI, and ligation of the SacI/NotI fragment generated from the PCR amplification of the OCS terminator from vector p1bxSuperGusQC using primers 1 and 2 (SEQ ID NO 47 and 48).

```
Primer 1
(SacI, AvrII, SpeI, OCS 5'; SEQ ID NO: 47):
5'-CG GAGCTC CCTAGG ACTAGT tcgaccggcatgccc-3'

Primer 2
(NotI, OCS 3'; SEQ ID NO: 48):
5'- CC GCGGCCGC agcttggacaatcag-3'
```

A fragment of the firefly luciferase gene is cloned downstream of the transcription terminator sequences to be assessed insertion site in order to act as a unique sequence that is only transcribed in the presence of a poorly functioning terminator. pTOI03 is generated from the digestion of pTOI02 with AvrII and SpeI, and ligating in the AvrIISpeI fragment generated from the PCR amplification of a 240 bp fragment of the firefly luciferase gene ($Lu^F$) from vector pGL3 (R2.2) basic vector (Promega cat# E6441) using primers 3 and 4 (SEQ ID NO: 49 and 50).

Primer 3
(AvrII, XmaI, RsrII, $Lu^F$ 5'; SEQ ID NO: 49):
5'-CG CCTAGG CCCGGG CGGACCG cattaagaagggccc-3'

Primer 4
(SpeI $Lu^F$ 3'; SEQ ID NO: 50):
5'-CG ACTAGT agagagttctcagagc-3'

Vector pTOI03 is the base vector that is used to generate constructs testing putative transcription terminator sequences. Vector pTOI04 comprises pTOI03 with the addition of the NOS in forward orientation, and is generated by insertion of the NOS containing SacI fragment from pBPSCR043 into the unique SacI site of pTOI03. (Positive control—NOS). Vector pTOI05 comprises pTOI03 with the addition of the NOS in reverse orientation, and is generated by the insertion of the inverted NOS SacI fragment from pBPSCR043 into the unique SacI site of pTOI03. (Negative control—inverted NOS).

Vectors pTOI06-pTOI10 are generated by the PCR amplification of putative terminator sequences from rice genomic DNA (selected from the sequences described by SEQ ID NO: 10 to 46) such that a SacI site is generated on the 5' end of the sequence and a RsriII site is generated on the 3' end. (Note: if the sequence of individual genomic elements precludes the use of these two restriction enzymes, then the alternative enzymes AvrII or XmaI can be used for cloning purposes.) The source of transcription terminators can be from both the in silico screening system and the genomic libraries containing 500 to 1,000 bp fragments.

3.2 Preparation of BMS Suspension Cultures Cells

Black Mexican Sweetcorn (BMS) suspension cultured cells are propagated in Murashige and Skoog (MS) liquid medium containing 2% (w/v) sucrose and 2 mg/L 2,4-dichlorophenoxyacetic acid. Every week 5 mL of a culture of stationary cells are transferred to 125 mL of fresh medium and cultured on a rotary shaker operated at 130 rpm at 27° C. in a 500 mL flask in the dark.

3.3 Preparation of the Nuclear Extract

The HeLa nuclear extract are purchased from Promega (HeLaScribe® Nuclear Extract; cat# E3092). Nuclear extracts are prepared from BMS cells as described (Moreno et al., 1997). BMS suspension cultured cells at logarithmic phase are harvested three days after the start of a fresh culture by spinning down at 2 krpm for 500 mL tubes for 10 min at 4° C. (1,200 rpm for 800 mL glass conical bottles at 170×g). The cell pellet is loosened and resuspended in cold HBSS (Hank's Balanced Salt Solution; Sigma cat# H9269). The cells are transferred into 50 mL Corning tube and spanned down at 1,200 rpm at 4° C. Packed cell volume (PCV) is measured by eye. The pellet is loosened and resuspended in 5×PCV hypotonic buffer followed by swelling the cells on ice for 10 min. The cells are spanned down at 1,200 rpm for 10 min. The supernatants are removed. One volume of PCV hypotonic buffer including 0.1% NP-40 is added to the pellet followed by resuspending the cells. The resuspended cells are transferred into chilled dounce homogenizer and measured the total volume before adding 1×PMSF (500×: 8.71 mg/mL). The cells are dounced for 10 to 15 strokes and checked the cells to yield 80 to 90% cell lysis. It is critical to avoid overdouncing the cells. Trypan blue is added to a small portion of the cells to check cell lysis under microscope. Blue cells indicate cell lysis. The cell lysis is quickly transferred into Corex 30 mL tube. 0.1 volume of sucrose restore buffer is added and gently mixed. The rotor and centrifuge have to be pre-cold. The nuclei are immediately spanned down at 10 krpm for 2 min in Beckman JA-20 rotor with brake. The supernatants containing cytoplasm are carefully removed and saved by adding glycerol to 20% (v/v) and stored at −70° C. The pellet is detached using a pipette and transferred into the nuclear resuspension buffer (3 mL/$10^9$ cells) in an ultracentrifuge tube followed by adding N-α-tosyl-L-lysine chloromethyl ketone (TLCK) protease inhibitor (250×: 10 mg/mL in 1 mM HCl), leupeptin (2,000×: 1 mg/mL in $dH_2O$), aprotinin (Sigma cat# A1153; 1,000×: 1 mg/mL in $dH_2O$), and pepstatin A (Sigma cat# P4265; 2,000×: 1 mg/mL in MeOH) to 1×. The tubes are balanced, rocked gently for 30 min, and spanned at 35 krpm in Ti454 (or 42 krpm in Ti70.a) for 90 min at 2° C. (150,000×9). The supernatants are transferred into another ultracentrifuge tube and measured the volume by eye. 0.33 g $(NH_4)_2SO_4$/mL is sprinkled into the extract for over 30 min with stirring or rocking until salt is dissolved after each addition on ice. The solution turns milky as the protein precipitates and is stirred or rocked for an additional 20 min at 4° C. followed by spinning down at 35 krpm for 30 min in Ti45 (or 32 krpm in Ti70.1). The pellet is resuspended in less than 1 mL of dialysis buffer ($10^9$ cells/mL). The resuspended cells are dialyzed for one hour against more than 200 volume of dialysis buffer (2 L). The buffer should be changed during dialysis for an additional four hours. The dialyzed extract is spanned down at 35 krpm for one hour followed by storing small aliquots at −80° C.

Hypotonic Buffer
10 mM HEPES, pH 7.9 (KOH)
0.75 mM spermidine
0.15 mM spermine
0.1 mM EDTA
0.1 mM EGTA, pH7.5 (KOH)
1 mM DTT
10 mM KCl
(add protease inhibitors and DTT before use)

10× Sucrose Restore Buffer
500 mM HEPES, pH 7.9 (KOH)
7.5 mM spermidine
1.5 mM spermine
10 mM KCl
mM EDTA
10 mM DTT
1×Sucrose Restore Buffer=1 volume 10×salts+9 volume 75% (w/v) sucrose Nuclear Resuspension Buffer
20 mM HEPES, pH 7.9 (KOH)
0.75 mM spermidine
0.15 mM sermine
0.2 mM EDTA
2 mM EGTA, pH 7.5 (KOH)
1 mM DTT
25% glycerol
10% saturated ammonium sulfate
(add protease inhibitors and DTT before use)

Dialysis Buffer
20 mM HEPES, pH7.9 (KOH)
20% glycerol
100 mM KCl
0.2 mM EDTA
0.2 mM EGTA, pH 7.5 (KOH)
2 mM DTT
(add protease inhibitors and DTT before use)

3.4 An in Vitro Assay System

Primer sequences for molecular beacon probes are chosen (1) between GUS and NOS for detecting polyadenylated products and (2) within the truncated firefly luciferase gene for detecting read through products. The probes are designed by using Beacon Designer 3.0. Two different reporter dyes are chosen for this assay (e.g. Texas Red, Rhodamine Red, Tamra, Joe, Tox, Oregon green, etc.).

The constructs are linearized by restriction enzyme digestion with NotI enzyme at 37° C. overnight followed by electroporation (0.8% Agarose gel) and gel purification using the QIAEX II Gel Extraction Kit (cat#20021). One μg of the linearized single template is added into the reaction solution in a total volume of 25 μL (15 μL of a mixture of HeLa and BMS nuclear extracts at 1:1 ratio [v/v], 400 μM ATP, CTP, GTP, UTP, 400 nM final concentration of two beacon probes, 5 mM $MgCl_2$, mg/mL BSA). The reaction solution is incubated for 2 hour at room temperature. The reaction progress is monitored using a Cytofluor multiwell plate reader at an excitation wavelength of 485 nm and an emission wavelength of 530 nm. [Razik and Quatrano, 1997; Yammaguchi et al., 1998; Liu et al., 2002]. If a particular transcription terminator sequences to be assessed provides efficient transcriptional termination, the expression of sequences complimentary to probe 1 is much greater than the expression of probe 2-specific sequences. If a sequence does not terminate efficiently the ratio of probe 1:probe 2 expression is lower. A ratio of the yield obtained between polyadenylated RNA and the read through products is calculated to determine potential terminator candidates (see FIG. 13B and agenda to this figure above). In addition to using single strand fluorescence probes, the ratio of the yield can be detected using Reverse Transcriptase (RT)-PCR following the protocols in the art.

Example 4

In Vivo Screening System for Identifying Terminators of Interest 4.1 Vector Construction 4.1.1 pUC Expression Vectors Vector pBPSMM268 contains the GUS::potato intron gene followed by the NOS terminator region. To this vector, maize Ubiquitin promoter::intron was added by digestion of pMM268 with StuI and SmaI, followed by blunt ligation of the Ubiquitin promoter::intron fragment obtained from StuI digestion of pBPSCER043, which produced vector pRJB051.

A fragment of the green fluoresecent protein (GFP-f) gene was cloned downstream of the transcription terminator sequences to be assessed insertion site in order to act as a unique sequence that is only transcribed in the presence of a poorly functioning terminator. pRJB058 was generated from the digestion of pRJB051 with AvrII and SpeI, and ligation of the AvrII/SpeI fragment generated from the PCR amplification of a 260 bp fragment of the GFP gene (GFP-F) from vector pALGFP1 using GFP-primers 5 and 6 (SEQ ID NOs: 80 and 81).

```
GFP-Primer 5
(AvrII, KasI, RsrII, AKR GFP19 5'; SEQ ID NO: 80):
5'-CGG CCT AGG GGC GCC CGG ACC Gag ctg ttc acc ggc
a-3'

GFP-Primer 6
(SpeI, S GFP 281 3'; SEQ ID NO: 81):
5'-CGG ACT AGT gat gta gcc ctc agg-3'
```

Vector pRJB058 is the base vector that was used to generate constructs testing putative transcription terminator sequences. Vector pRJB062 (SEQ ID NO: 95) comprises pRJB058 (SEQ ID NO: 94) with the addition of the NOS in forward orientation, and was generated by insertion of the NOS containing SacI fragment from pBPSCR043 into the unique SacI site of pTOI03. (Positive control—NOS).

Vector pRJB063 (reverse complementary sequence of SEQ ID NO: 95) comprises pRJB058 with the addition of the NOS in reverse orientation, and is generated by the insertion of the inverted NOS SacI fragment from pBPSCR043 into the unique SacI site of pTOI03. (Negative control—inverted NOS).

Vector pRJB064 (SEQ ID NO: 96) comprises pRJB048 with the addition of the 1.1 Kb ORF fragment from pRJB018. This vector will serve as a negative control for specific transcriptional termination by putative TOIs, as the sequence comprises an internal fragment from a known open reading frame, and should therefore possess minimal intrinsic transcriptional termination activity. Vector pRJB064 was generated by ligation of the 1.1 Kb HpaI/StuI fragment from pRJB018 into SacI digested and 3'-5-exonuclease-treated pRJB058.

Vectors pRJB065 (SEQ ID NO: 98) and pRJB066 (SEQ ID NO: 97) comprise pRJB058 with the addition of the rice genomic DNA BPST.2 (reverse complementary sequence of SEQ ID NO:33) and BPST.1 (SEQ ID NO:33), respectively. The 1.4 Kb PCR product produced from amplification of rice genomic DNA with primers 7 and 8 (SEQ ID Nos 82 and 83):

```
Primer 7:    5'- CGA GCT CGT GCC TTT TGG ATC G-3'

Primer 8:    5'- CGG TCC GAA CGT GGT TGG-3'
```

The PCR product was TOPO cloned to produce pTOPO BPST.1 (SEQ ID NO:33) and BPST.2 (reverse complementary sequence of SEQ ID NO:33). The 1.4 Kb fragment resulting from EcoRI digestion and T4 DNA polymerase fill in reaction of pTOPO BPST.1 and BPST.2 was ligated into SacI digested and 3'-5-exonuclease-treated pRJB058. pRJB065 (SEQ ID NO: 98) represents the resulting vector comprising the BPST.2 putative terminator, and pRJB066 (SEQ ID NO: 97) represents the ligation product comprising the BPST.1 sequence.

Vectors pRJB067 (SEQ ID NO: 99) and pRJB068 (SEQ ID NO: 100) comprise pRJB058 with the addition of the rice genomic DNA BPST.3 (SEQ ID NO:92) and BPST.4 (reverse complementary sequence, SEQ ID NO:92), respectively. The 1.1 Kb PCR product produced from amplification of rice genomic DNA with primers 9 and 10 (SEQ ID NO: 84 and 85):

```
Primer 9:    5'- CGA GCT CGG CCC TAT GAA TTG G-3'

Primer 10:   5'- CGG TCC GTC TCC TTC TGC ACA C-3'
```

The PCR product was TOPO cloned to produce pTOPO BPST.3 and BPST.4. The 1.1 Kb fragment resulting from EcoRI digestion and T4 DNA polymerase fill in reaction of pTOPO BPST.3 and BPST.4 was ligated into SacI digested and 3'-5-exonuclease-treated pRJB058. pRJB067 (SEQ ID NO: 99) represents the resulting vector comprising the BPST.3 putative terminator, and pRJB068 (SEQ ID NO: 100) represents the ligation product comprising the BPST.4 sequence.

BPST.5 (SEQ ID NO:18) produced a 1.2 Kb PCR product from amplification of rice genomic DNA with primers 11 and 12 (SEQ ID NO: 86 and 87):

```
Primer11:    5'-CGA GCT CGA TGC ATT CCT TGG AT-3'

Primer12:    5'-CCT AGG GTT TGG AGG TAT CAA G-3'
```

BPST.6 (SEQ ID NO:10) produced a 1.3 Kb PCR product from amplification of rice genomic DNA with primers 13 and 14 (SEQ ID NO:88 and 89):

```
Primer 13:
5'-CGA GCT CCG TCC GAT GTG ATT CCG TC-3'

Primer 14:
5'- CCT AGG GGC AGT GTC GGC GGT T-3'
```

BPST.7 (SEQ ID NO:107) and BPST.8 (reverse complementary sequence of SEQ ID NO:108) produced a1.5 Kb PCR product from amplification of rice genomic DNA with primers 15 and 16 (SEQ ID NO:90 and 91):

```
Primer 15:
5'- CGA GCT CCA GAG TGA CAG ACA GTG A-3'

Primer 16:
5'- CCT AGG TCT TCA ACT GTC CCC A-3'
```

Additional TOI candidates will be isolated and cloned into pUC expression vectors as described above.

4. 1. 2 Binary Vectors

For evaluation of transcriptional termination by the putative TOI sequences in stably transformed maize plants, binary vectors were prepared for *Agrobacterium*-mediated maize transformation. The full-length T-DNA sequences for vectors pRLI024 and pRLI031 are provided in the attached sequence listing (SEQ ID NO: 105 and 106, respectively). The other vectors were derived therefrom by exchanging the terminator regions.

Vector pRLI024 (SEQ ID NO:105) was generated by ligation of the 4.9 Kb PvuII fragment from pRJB058 into pLM150 that had been digested with PmeI, generating pJB077. The 3.1 Kb DsRed2 expression cassette was liberated from vector pLM299 via FseI/PacI digestion, and ligated into FseI/PacI digested pRJB077 to generate pRLI024 (SEQ ID NO:105).

Vector pRLI025 was generated by ligation of the 4.9 Kb PvuII fragment from pRJB062 (SEQ ID NO:95) into pLM150 that had been digested with PmeI, generating pJB078. The 3.1 Kb DsRed2 expression cassette was liberated from vector pLM299 via FseI/PacI digestion, and ligated into FseI/PacI digested pRJB078 to generate pRLI025.

Vector pRLI026 was generated by ligation of the 4.9 Kb PvuII fragment from pRJB064 (SEQ ID NO:96) into pLM150 that had been digested with PmeI, generating pJB079. The 3.1 Kb DsRed expression cassette was liberated from vector pLM299 via FseI/PacI digestion, and ligated into FseI/PacI digested pRJB079 to generate pRLI026.

Vector pRLI027 was generated by ligation of the 4.9 Kb PvuII fragment from pRJB066 (SEQ ID NO: 97) into pLM150 that had been digested with PmeI, generating pJB080. The 3.1 Kb DsRed expression cassette was liberated from vector pLM299 via FseI/PacI digestion, and ligated into FseI/PacI digested pRJB080 to generate pRLI027.

Vector pRLI028 was generated by ligation of the 4.9 Kb PvuII fragment from pRJB065 (SEQ ID NO: 98) into pLM150 that had been digested with PmeI, generating pJB081. The 3.1 Kb DsRed expression cassette was liberated from vector pLM299 via FseI/PacI digestion, and ligated into FseI/PacI digested pRJB081 to generate pRLI028.

Vector pRLI029 was generated by ligation of the 4.9 Kb PvuII fragment from pRJB067 (SEQ ID NO:99) into pLM150 that had been digested with PmeI, generating pRLI022. The 3.1 Kb DsRed expression cassette was liberated from vector pLM299 via FseI/PacI digestion, and ligated into FseI/PacI digested pRLI022 to generate pRLI029.

Vector pRLI030 was generated by ligation of the 4.9 Kb PvuII fragment from pRJB068 (SEQ ID NO:100) into pLM150 that had been digested with PmeI, generating pRLI023. The 3.1 Kb DsRed expression cassette was liberated from vector pLM299 via FseI/PacI digestion, and ligated into FseI/PacI digested pRLI023 to generate pRLI030.

An alternative series of binary vectors was generated in order to evaluate putative TOIs with regard to their ability to direct bi-directional transcriptional termination. For these vectors, the TOI sequences were cloned between two reporter expression cassettes in tail-to-tail orientation.

Vector pLI024 (SEQ ID NO: 105) was digested with SacI to remove the 950 bp Nos-T and intervening sequences from between the DsRed ORF and the TOI MCS. The vector was recircularized to generate pLI031 (SEQ ID NO:106).

Vector pLI025 was digested with SacI to remove the 950 bp Nos-T and intervening sequences from between the DsRed ORF and the TOI MCS. The vector was recircularized to generate pLI032.

Vector pLI026 was digested with SacI to remove the 950 bp Nos-T and intervening sequences from between the DsRed ORF and the TOI MCS. The vector was recircularized to generate pLI033.

Vector pLI027 was digested with SacI to remove the 950 bp Nos-T and intervening sequences from between the DsRed ORF and the TOI MCS. The vector was recircularized to generate pLI034.

Vector pLI028 was digested with SacI to remove the 950 bp Nos-T and intervening sequences from between the DsRed ORF and the TOI MCS. The vector was recircularized to generate pLI035.

Vector pLI029 was digested with SacI to remove the 950 bp Nos-T and intervening sequences from between the DsRed ORF and the TOI MCS. The vector was recircularized to generate pLI036.

Vector pLI030 was digested with SacI to remove the 950 bp Nos-T and intervening sequences from between the DsRed ORF and the TOI MCS. The vector was recircularized to generate pLI037.

Additional TOI candidates will be isolated and cloned into binary vectors as described above.

4.2 Assays for Identifying Terminators of Interest

The test construct comprised a GUS reporter gene driven by the maize ubiquitin promoter, and enzyme sites to insert putative TOI and control sequences. The TOI functionality screen was based on the principle that in the absence of a functional terminator region the GUS mRNA will not be efficiently processed, and therefore will not be available to support high levels of translation of GUS protein. The results of these transient analyses are shown in Table 2 and FIG. 14. The experimental rationale was supported by the finding that the vector lacking an insertion at the TOI cloning site does not drive detectable GUS expression (pRJB058; SEQ ID NO: 94). The insertion of the nopaline synthase (Nos) terminator was able to rescue GUS expression (pRJB062; SEQ ID NO: 95). The insertion of sequence derived from an internal portion of an exogenous protein-coding gene (ORF sequence) did not result in GUS expression (pRJB064; SEQ ID NO: 96), signifying that the GUS expression seen with pRJB062 was due to intrinsic transcriptional termination activity by Nos, and not a non-specific effect due to insertion of any DNA sequence at that site. BPST.1 (SEQ ID NO:33) and BPST.2 (reverse complementary sequence of SEQ ID NO:33) showed GUS expression levels comparable to that seen with the Nos (+) control vector. BPST.3 (SEQ ID NO:92) and BPST.4 (reverse complementary sequence, SEQ ID NO:92) consistently resulted in significant GUS expression at levels that appeared to be slightly lower than observed with Nos.

TABLE 2

Transient GUS expression testing for terminator candidates

| Terminator candidates | GUS expression* | |
|---|---|---|
| BPST (null)-(pRJB058; SEQ ID NO: 94) | – | 0% |
| BPST (+)-Nos (pRJB062; SEQ ID NO: 95) | ++++ | 100% |
| BPST (–)-ORF (pRJB064; SEQ ID NO: 96) | – | 0% |
| BPST.1 (pRJB066; SEQ ID NO: 97) | ++++ | 100% |
| BPST.2 (pRJB065; SEQ ID NO: 98) | ++++ | 100% |
| BPST.3 (pRJB067; SEQ ID NO: 99) | +++ | 80% |
| BPST.4 (pRJB068; SEQ ID NO: 100) | +++ | 80% |

*GUS histochemical assays: a range of GUS activities (– no expression to ++++ high expression).

No GUS staining was observed in vectors that do not comprise a functional transcriptional terminator downstream of the GUS coding sequence (pRJB058 and pRJB064; SEQ ID NO: 94 and 96, respectively). The presence of a functional terminator rescued GUS expression in the (+) control (pRJB062; SEQ ID NO: 95) vector as well as all four TOI candidate sequences (pRJB065-pRJB068: SEQ ID indicated in Table 2) (FIG. 14).

4.3 Analysis of Terminator Candidates in Stably Transformed Maize

The binary vectors pBPSLI027, pBPSLI028, pBPSLI029, and pBPSLI030 will be transformed into maize using *Agrobacterium*-mediated transformation (Example 11.4). The levels and patterns of GUS expression controlled by BPST.1 (SEQ ID NO:33), BPST.2 (reverse complementary sequence of SEQ ID NO:33)., BPST.3 (SEQ ID NO: 92), or BPST.4 (reverse complementary sequence of SEQ ID NO:92) terminator will be compared with those controlled by NOS-t. BPST.1, BPST.2, BPST.3 and BPST.4 should show similar levels to that observed in transient assays (Table 2). This result will indicate that a transient assay can be used as a model system and is therefore one of the important screening systems to identify functional transcriptional terminators.

However, the results obtained with the transient assays should be validated by the production of stable transformed transgenic plants.

Example 5

In Vivo Screening System Using Gene Silencing for Identifying Potential Transcription Terminators A high throughput screening system is developed to identify and isolate tight transcriptional termination sequences. This method is time-efficient and does not involve RNA analysis. Since dsRNA molecules are efficient in even a small amount, only very tight terminators can be identified. (FIG. 13C)

As described above in more detail, the RNA may be preferably selected from a) RNAs encoding for an antisense or preferably double-stranded RNAs, which down-regulates expression of essential plant genes. In principle, any gene is suitable which has a lethal phenotype in a homozygous knockout (e.g. Phytoen desaturase, Nitrate reductase, HPPD, Acetohydroxyacid synthase, etc.)

b) RNAs encoding for toxic proteins, which expression causes lethal effect to the transgenic plants (negative selection markers like e.g., TK, codA, tyrA, Diphtheria toxin etc.). Furthermore, any endogenous gene suitable as herbicidal target can be employed in the above-mentioned approach (Table 1).

5.1 Vector Construction for RNAi

For experiments using RNAi down-regulation mechanism to evaluate transcription termination, vector pTOI03 is modified such that $Lu^F$ is replaced with an appropriate dsRNA cassette. An appropriate RNAi cassette comprises a 200 to 300 bp sequence that is specific to the targeted gene, followed by a spacer sequence of approximately 150-200 bp, followed by an inverted repeat of the gene specific sequence, such when transcribed, a hairpin structure is formed with the gene-specific sequence forming the dsRNA stem. The RNAi target can be any gene that provides lethality or a screenable phenotype under down-regulation (e.g. AHAS, bar, target genes of herbicides (see Table 1), or other essential endogenous genes such as housekeeping genes). Gene-specific sequences are generated via PCR with appropriate restriction sites for forward and reverse orientation via amplification with primers 5 and 6 (SEQ ID NO: 51 and 52):

```
Primer 5
(RsrII, BspEI, target gene seq 5'; SEQ ID NO: 51):
5' CG CGGACCG TCCGGA-N-3'
[N: gene-specific sequence of preferably 10 to 20
bases]

Primer 6
(SpeI, AgeI, target gene seq 3'; SEQ ID NO: 52):
5'-CG ACTAGT ACCGGT-N-3'
[N: gene-specific sequence of preferably 10 to 20
bases]
```

The RNAi vector (pTOI11) is produced via a four-way ligation between (1) pTOI03 digested with RsrII and SpeI, (2) target gene PCR product digested with RsrII and AgeI, (3) the spacer sequence with AgeI and BspEI ends, and (4) target gene PCR product digested with BspEI and SpeI.

5.2 Assays for Identifying Terminators of Interest

These experiments are performed by bombardment of plant tissues or culture cells (Example 9.1), by PEG-mediated (or similar methodology) introduction of DNA to plant protoplasts (Example 9.2), or by *Agrobacterium*-mediated transformation (Example 9.3). The target tissues for these experiments can be plant tissues (e.g. leaf or root), cultured cells (e.g. maize BMS), or plant tissues (e.g. immature embryos) for *Agrobacterium* protocols.

The sequences used as potential transcription terminator sequences can either be derived from the in silico transcription terminator sequence screen or from a library of random genomic fragments. Only plants can survive in subsequent regeneration in the case of stable transformation, which have an efficient terminator inserted in front of the sequence encoding the toxic RNA (thereby blocking its expression). The surviving plants are isolated and the terminator sequence amplified using PCR and sequencing.

Example 6

In Vivo Screening System Using Bicistronic RNA Detection

A system is developed that utilizes the internal ribosome entry site (IRES) from encephalomiocarditis virus (EMCV), a picornovirus, or any functional IRES in plants. EMCV IRES has been shown in plants to efficiently direct translation of internally encoded proteins in parallel with canonical cap-mediated translation (Urwin et al., 2000). This method allows the screening of potential terminator sequences in plant tissue and will provide a screen to compare relative termination efficiency between multiple sequences. For these experiments, potentially bicistronic elements are generated containing two distinguishable fluorescent proteins (FP1 and FP2) separated by the transcription terminator to be assessed and IRES. If a particular transcription terminator sequences to be assessed provides efficient transcriptional termination, the expression of FP1 is much greater than the expression of FP2. If a sequence does not terminate efficiently the ratio of FP1: FP2 expression is lower.

6.1 Vector Construction

Test constructs comprises the following elements, described in order 5' to 3'. A strong constitutive promoter for the target tissue is used to drive expression of the RNA, such as Ubiquitin or ScBV for expression in maize leaf tissue. The most proximal open reading frame encodes for FP1 (e.g. DsRed21), followed by restriction sites for insertion of potential transcription terminator sequence elements. Immediately downstream of the insertion site for the transcription terminator sequences to be assessed is the encephalomyocarditis virus (EMCV) IRES element, followed by the open reading frame for FP2 (e.g. GFP), and followed by a known plant transcriptional terminator. This downstream terminator needs to be present in order to stabilize transcripts that are not efficiently terminated by the transcription terminator sequence, thereby allowing detection of mRNAs that encode FP2. If *Agrobacterium* mediated transformation experiments will be performed, then the vectors will have to include the LB and RB T-DNA elements flanking the expression cassette and selectable marker genes. (FIG. 15)

Example 7

System Based on Inverted Repeat of Nos Terminator 7.1 Generation of the Positive and Negative Binary Vector Control Constructs for the Screening of Terminator Activity To test the transcription termination efficiency of a sequence a construct was generated with a strong constitutive promoter (STPT promoter) upstream of the nptII marker gene followed by a short MCS in which putative terminator sequences are cloned and an inverted repeat of the 3'-UTR region from the nos-gene of *Agrobacterium* tumefaciens, with the first repeat element being in the antisense orientation relative to the STPT promoter. This arrangement without a putative terminator sequence serves as a negative control: Both orientations of the nosT are incorporated into the resulting transcript, since the inverted nos element does not lead to transcript truncation and polyadenylation, which gives rise to a transcript with 3' hairpin structure leading to dsRNA-mediated, sequence-specific RNA-degradation and thus silencing of the nptII-gene. As a positive control the Ribulose-bisphosphat Carboxlase E9 terminator region is cloned in between the nptII-gene and the nos inverted repeat (nos-IR), which leads to the proper termination of nptII-transcripts and thus to the expression of nptII.

7.2 Cloning of pENTR-A1-inv-35s-GFP-E9

Insertion of terminator E9: Lo394-pENTR-A1-inv is opened with BamHI and KpnI. The E9 terminator is isolated from Lo424-pENTR-A1-inv-P2-E9 with BamHI and KpnI and ligated into the opened Lo394 in direct orientation. The resulting construct is named Lo483-pENTR-A1-inv-E9. The orientation of sites is attL4-E9-attR1.

7.3 Insertion of the CaMV 35s Promoter Together with the Gene for mGFP5er

The 35s promoter of CaMV and the *Aequorea victoria* gene for the green fluorescent protein mGFP5er-gene were isolated from Lo409-pENTR-35s-GFP5er-GUS with HindIII/SmaI and ligated into Lo483-pENTR-A1-Inv-E9 opened with HindIII/EcoRV in direct orientation. The orientation of sites is attL4-35s-mGFP5er-E9-attR1. The resulting construct is named Lo484-pENTR-A1-inv-35s-GFP-E9 (SEQ ID NO: 9).

7.4 Cloning of pENTR-C1-STPT-nptII-nosIR

Insertion of the STPT-promoter and the nptII-gene: Lo393-pENTR-C1 was opened with BamHI. The STPT promoter with the nptII-gene was cut out of Lo441-pENTR1A-STPT-nptII-CatpA with BamHI and ligated undirected in the opened Lo393. Clones with the correct orientation were identified via colony-PCR followed by control digests. The orientation of sites is attR2-STPT-nptII-attL3. The resulting construct is named Lo485-pENTR-C1-STPT-nptII.

7.5 Insertion of the Terminator nosT in Sense Orientation

The 257 bp 3'-UTR region of the nopaline synthase (nos) gene from *Agrobacterium tumefaciens* was amplified using PCR from Lo114-pSUN3-Gus-nos with the overhang primers Loy482-NosT-upper-SalI and Loy483-NosT-Lower-HindIII (SEQ ID NO: 55 and 56).

```
Loy482-NosT-upper-SalI (SEQ ID NO: 55):
5'-AAATTTGTCGACCGATCGGTCAAACATT-3'

Loy483-NosT-Lower-HindIII (SEQ ID NO: 56):
5'-AAATTTAAGCTTCCCGATCTAGTAACATAGATGACA-3'
```

The resulting 282 bp PCR fragment was digested with SalI/HindIII and cloned in direct orientation into Lo485-pENTR-C1-STPT-nptII opened with SalI/HindIII. The orientation of sites is aftR2-STPT-nptII-nosT-attL3. The resulting construct is named Lo486-pENTR-$C_1$-STPT-nptII-nos.

7.6 Insertion of a Second Nos-Terminator Element in Antisense Orientation Between the nptII Gene and the Sense NosT Together with a Stuffer Sequence Derived from the 3'-Region of the Gus-Gene The NosT was amplified together with a part of the 3'-region of the gus-gene out of Lo400-pENTR1A (B)-Ln-Prom2-TypDra-nosT. Thetefore primers were designed which added a SalI site at the gus sequence and a SpeI-site together with a BglII-site at the end of nosT. Two kinds of constructs were prepared one including a 129 bp gus-spacer sequence between the inverted repeat of nosT and the other consisting of 155 bp spacer between the IR. The shorter version was amplified with the primers Loy494-Gus-upper-SalI-Spacer and Loy492-NosT-lower-BglII-SpeI (SEQ ID NO: 57 and 58).

```
Loy494- Gus-upper-SalI-Spacer (SEQ ID NO: 57):
5'-TTTTAGTCGACACGCTGGACTGGCATGAACT-3'

Loy492-NosT-lower- BglII-SpeI (SEQ ID NO: 58):
5'-TTTTAAGATCTACTAGTCCGATCTAGTAACATAGATGACA-3'
```

The longer version was amplified with Loy493-Gus-upper-SalI-Spacer together with Loy492-NosT-lower-BglII-SpeI.

```
Loy493_Gus_upper_SalI_Spacer (SEQ ID NO: 59):
5'- TTTAAGTCGACAAGTCGGCGGCTTTTCTGCT-3'

Loy492-NosT-lower- BglII-SpeI (SEQ ID NO: 60):
5'-TTTTAAGATCTACTAGTCCGATCTAGTAACATAGATGACA-3'.
```

The resulting PCR-fragments were digested with SalI/BglII and ligated into Lo486-pENTR-C1-STPT-nptII-nos opened with SalI/BglII. This resulted in the nptII open-reading frame being followed by a nos 3'-UTR in the antisense orientation relative to the STPT promoter, a 129 bp-spacer region respectively 155 bp-spacer region of gus-sequence in the antisense orientation, and a second nosT in the sense orientation. The orientation of sites is attR2-STPT-nptII-as nosT-spacer-s nosT-attL3. The resulting constructs were named Lo503a-pENTR-C1-STPT-nptII-IRnos (SEQ ID NO: 8) with the shorter spacer between the IR) and Lo503b-pENTR-C1-STPT-nptII-IRnos (SEQ ID NO: 7) with the longer spacer between the IR).

7.7 Generation of the Negative Control Construct 7.7.1 Triple-LR Reaction to Create the Binary Expression Vector which Will Serve as the Negative Control The triple-LR-reaction is carried out with the plasmids Lo484-pENTR-A1-inv-35s-GFP-E9, Lo376-pENTR-B2 (without insert; SEQ ID NO: 76) and Lo503a-pENTR-C1-STPT-nptII-IRnos, or with Lo503b-pENTR-C1-STPT-nptII-IRnos and Lo442-pSUN1-R4R3 (SEQ ID NO: 77), respectively according to the instructions of the manufacturer, using LR plus recombinase mix. The resulting binary plant transformation vectors were named Lo523a-pSUN1-R4-Lo484::Lo376::Lo503a (SEQ ID NO: 6) and Lo523b-pSUN1-R4::Lo484::Lo376::Lo503b (SEQ ID NO: 5), respectively.

7.8 Generation of the Positive Control Construct 7.8.1 Insertion of the E9 Terminator Upstream of IRnos The E9 terminator was isolated from Lo444-pGST-δ-KpnI-LUC+with BamHI/EcoRV. Lo503 is opened with SpeI, the 5'-protruding ends were completely filled in with Pfu turbo polymerase and cut again with BglII. The BglII/EcoRV fragment of the E9 terminator is ligated into the opened vectors Lo503a and Lo503b (which were digested first with SpeI and blunted, and subsequently with BamHI), respectively, in direct orientation. The orientation of sites is attR2-STPT-nptII-E9-IRnos-attL3. The resulting constructs were named Lo522a-pENTR-C1-STPT-nptII-IRnos (SEQ ID NO: 4) with the shorter spacer between the IR) and Lo522b-pENTR-C1-STPT-nptII-IRnos (SEQ ID NO: 3) with the longer spacer between the IR).

7.8.2 Triple-LR Reaction to Create the Binary Expression Vector which Will Serve as the Positive Control The triple-LR-reaction is carried out with the plasmids Lo484-pENTR-A1-inv-35s-GFP-E9, Lo376-pENTR-B2 (without insert; SEQ ID NO: 76) and Lo522a-pENTR-C1-STPT-nptII-E9-IRnos or with Lo522b-pENTR-C1-STPT-nptII-E9-IRnos and Lo442-pSUN1-R4R3 (SEQ ID NO: 77), respectively, according to the instructions of the manufacturer, using LR plus recombinase mix. The resulting binary plant transformation vectors were named Lo546a-pSUN1-R4-Lo484::Lo376::Lo522a (SEQ ID NO: 2) and Lo546b-pSUN1-R4-Lo484::Lo376::Lo522b (SEQ ID NO: 1), respectively.

Example 8

System Based on Inverted Repeat of Nos Terminator Using Two Expression Cassettes in Head to Head Orientation 8.1 Generation of the Positive and Negative Binary Vector Control Constructs for the Screening of Terminator Activity To test the transcription termination efficiency of a putative terminator sequence a construct was generated with a strong seed specific promoter (BnAK promoter) upstream of the β-Glucuronidase (GUS) marker gene followed by a short MCS in which putative terminator sequences are cloned and the 3'-UTR region from the nos-gene of *Agrobacterium tumefaciens*. The second expression cassette in this construct contains the promoter of the nos-gene from *Agrobacterium tumefaciens* followed by the nptII marker gene and the 3' nos UTR. Both expression cassettes are oriented in a head to head manner. In transgenic plants this arrangement without a putative terminator sequence serves as a negative control: As the nos terminator is used for both the right hand and left hand expression cassette both orientations of the nosT are incorporated into the resulting transcripts, giving rise to GUS and nptII transcripts carrying complementary 3' sequences, leading to hybridization of the two mRNA species, thus resulting in sequence-specific RNA-degradation and total or partial silencing of the β-Glucuronidase and the nptII-gene. As a positive control the Ribulose-bisphosphate Carboxiase E9 terminator region is cloned in between the GUS-gene and the nosT, leading to correct truncation of the transcript and enabling high expression of GUS. Transcripts from the nptII marker gene, carrying the 3' Tnos UTR are not interacting with the GUS transcripts as there is no complementary sequence present and the nptII expression is not impaired (FIG. 1 A3).

8.2 Cloning of Lo239-pSUN3-GWs-B1-BnAK700::GUS::nosT-B2

Insertion of promoter: The seed specific promoter BnAK700 is isolated by HindIII/BamHI digestion of Lo229 and inserted into the vector Lo215 pENTR-MCS::GUS::nosT to create Lo235 pENTR-B-BnAK700::GUS::nosT.

Lo 239 (SEQ ID NO: 78) is created by LR reaction of Lo235 with the Gateway destination vector Lo125 pSUN3-GWs-NPTII (FIG. 10).

8.3 Cloning of Lo657-pSUN3-GWs-B1-BnAK700::GUS::E9::nosT::B2

Insertion of the E9 Terminator The Gateway Entry vector Lo235 is cut with Ecl136II to create blunt ends. The E9 insert is isolated by restriction of Lo489 with EcoRV and KpnI followed by fill in with Klenow fragment. The blunt ended insert is ligated to the linearized vector to create Lo654 pENTR-BnAK700::GUS::E9::nosT.

Lo657 (SEQ ID NO: 79) is created by LR reaction of Lo654 with the Gateway destination vector Lo125 pSUN3-GWs-NPTII (FIG. 10).

Example 9

Development of an in Vivo Screening System to Identify Terminators by Embedding Sequences of Interest within an Intron of a Lethal Gene or Reporter Gene A terminator of interest (TOI) is embedded within an intron of a lethal gene including, but not limited to, diphtheria toxin fragment A (DT-A) or a reporter gene including, but not limited to, green fluorescence protein (GFP) (see FIG. 16A). If efficiency of transcription termination is low ("leaky" TOI), there is some transcription of the full length lethal or reporter gene. The intron with the embedded TOI is removed from the transcribed RNA allowing for translation of the full length lethal or reporter protein. In the example using the lethal gene, expression of full length DT-A kills the cells. If the TOI does not allow read through RNA products because of efficient transcription termination ("tight" TOI), only a partial protein is translated and the plant cells are viable. In the example using GFP, a leaky TOI yields full length GFP and cells that fluoresce green. A tight TOI produces only a partial GFP protein and cells don't fluoresce. Control constructs are constructed without a TOI embedded in the intron (FIG. 16B) and with a known terminator, NOS, embedded in the intron (FIG. 16C). See also agenda to FIG. 16 above.

Preferably, a strong constitutive promoter is used for these constructs such as the maize ubiquitin promoter (Zmubi). An octopine synthase terminator (OCS) is added to the end of the cassette to stabilize the read through products. The intron sequence to be used is a potato intron (PIV2) modified here to improve intron splicing efficiency. The modified PIV2 intron contains the following elements to promote efficient intron recognition and splicing in plants (FIG. 17):

(1) Transition at the 5' splice site from moderate AU content (exon) to high AU content (intron).

(2) Transition at the 3' splice site from high AU content (intron) to moderate AU content (exon).

(3) A consensus 5' splice recognition sequence CAG/GUAAGU. '/' identifies the splice site.

(4) A consensus 3' recognition sequence GCAG/G.

(5) A consensus branchpoint sequence CURAY upstream of the 3' splice site.

(6) A polyU tract just downstream of the branchpoint sequence and upstream of the 3' splice site.

A BamHI restriction site is added near the center of the intron for insertion of the transcription terminator of interest (TOI). A BamHI site is compatible with Sau3AI and is therefore ideal for insertions of genomic DNA fragments generated by a partial Sau3AI digest. The BamHI site can be substituted with other restriction sites to accommodate TOI libraries generated by other means. The cassettes in FIG. 15 can be placed in a binary vector for *Agrobacterium*-mediated plant transformation or in a pUC based vector for biolistic transformation. See also agenda to FIG. 16 above.

9.1 Vector Construction

Construct 2 (DT-A version) in FIG. 16 is constructed using the parental vector pTOI03 described above. pTOI03 is digested with KpnI and SpeI to remove the GUSint gene but leaving the ZmUbi promoter and OCS terminator. The 3' end of the first half of the DT-A gene is fused to the 5' end of the first half of the PIV2 intron by overlap PCR using the following primers:

JMTOIprim1 (SEQ ID NO: 61)
5'-GGTTCCAAGGTACCAAAACAATGGGCGCTGATGATGTTGTTGAT-3'

JMTOIprim2 (SEQ ID NO: 62)
5'-AAGGTAGAAGCAGAAACTTACCTGGATACGTCACTTTGACCA-3'

JMTOIprim3 (SEQ ID NO: 63)
5'-TGGTCAAAGTGACGTATCCAGGTAAGTTTCTGCTTCTACCTT-3'

JMTOIprim4 (SEQ ID NO: 64)
5'-GGTTCCAAGGATCCATTTATTTTGAAAAAAATATTTG-3'

This overlap PCR places a KpnI site on the 5' end of the DT-A portion of the fused sequences followed by an ATG start codon preceded by the bases AAAACA to enhance translation. It also generates a consensus 5' splice site between the DT-A and intron sequences and a BamHI site 133 bp downstream of the 5' splice site. The 3' end of the second half of the PIV2 intron is fused to the 5' end of the second half of the DT-A gene by overlap PCR using the following primers:

JMTOIprim5 (SEQ ID NO: 65)
5'- GGTTCCAAGGATCCAGTATATAGCAATTGCTTTTC-3'

JMTOIprim6 (SEQ ID NO: 66)
5'- CGAGAACCTTCGTCAGTCCTGCACATCAACAAATTTTGGTCAT
AAAAAAAAAAATATTAGAAAAGTTATAAATTAAAATATAC-3'

JMTOIpnm7 (SEQ ID NO: 67)
5'- CTAATATTTTTTTTTTTATGACCAAAATTTGTTGATGTGCAGGA
CTGACGAAGGTTCTCGCAC-3'

JMTOIprim8 (SEQ ID NO: 68)
5'- TTGGAACCACTAGTTTATCGCCTGACACGATTTCCTGC-3'

This overlap PCR places a BamHI site on the 5' end of the PCR product. A tract of 11 consecutive Us at positions +36 to +26 relative to the 3' splice site and 2 bases down-stream of a natural CTAAT consensus branchpoint sequence in the PIV2 intron is added as well as a consensus 3' splice site between the PIV2 and DT-A sequences. This overlap PCR also generates a TAA stop codon at the end of the DT-A open reading frame followed by a SpeI restriction enzyme site. The first overlap PCR product is digested with KpnI and BamHI, the second PCR product is digested with BamHI and SpeI, and both PCR products are ligated to pTOI03 digested with KpnI and SpeI in a 3-way ligation to make pJMTOI1 (SEQ ID NO: 71). The construct comprises the following features:

| Feature | Location (base) |
|---|---|
| ZmUbi promoter | (1) . . . (1988) |
| DT-A 5' end of coding sequence | (2007) . . . (2268) |
| Intron | (2269) . . . (2488) |
| DTA-A 3' end of coding sequence | (2489) . . . (2811) |
| OCS terminator | (2818) . . . (3030) |

Construct 3 (DT-A version) in FIG. 16C will be constructed by first placing BamHI sites on the ends of the NOS terminator using the following PCR primers:

JMTOIprim9 (SEQ ID NO: 69)
5'- GGTTCCAAGGATCCGATCGTTCAAACATTTGGCAA-3'

JMTOIprim10 (SEQ ID NO: 70)
5'- GGTTCCAAGGATCCGATCTAGTAACATAGATGACA-3'

This PCR product is digested with BamHI and ligated into the unique BamHI site within the PIV2 intron of pJMTOI1. Plasmids generated from the ligation are screened to identify those with the correct NOS orientation, yielding pJMTOI2 (SEQ ID NO: 72). The construct comprises the following features:

| Feature | Location (base) |
|---|---|
| ZmUbi promoter | (1) . . . (1988) |
| DT-A 5' end of coding sequence | (2007) . . . (2268) |
| Intron 5' end | (2269) . . . (2380) |
| Nos terminator | (2387) . . . (2639) |
| Intron 3' end | (2646) . . . (2747) |
| DTA-A 3' end of coding sequence | (2748) . . . (3070) |
| OCS terminator | (3077) . . . (3289) |

Example 10

An in Vivo Selection of Efficient Terminators

In this example, a terminator of interest (TOI) is placed between a reporter gene such as the green fluorescence protein (GFP) and a sequence with little or no homology to plant genes and that is a target of dsRNA mediated RNA silencing (FIG. 18). Each of these elements is under control of a single promoter, in this example, the maize ubiquitin promoter (ZmUbi). When expressed in plants, and if the TOI does not terminate transcription (leaky TOI); the entire transcript (including the region encoding GFP) is degraded by RNA silencing. If the TOI is functional as a terminator, the RNA will not be a target of RNA silencing and GFP will be produced leading to plants that fluoresce green (FIG. 18). TOIs may be obtained by fragmentation of genomic DNA or by a more selective procedure.

A BamHI restriction site will be placed at the junction between GFP and the spacer in construct 3 of FIG. 18 for insertion of the TOI (construct 1) or the NOS terminator (construct 2; pJMTOI3, SEQ ID NO: 73). A BamHI site is compatible with Sau3AI and is therefore ideal for insertions of genomic DNA fragments generated by a partial Sau3AI digest. The BamHI site can be substituted with other restriction sites to accommodate TOI libraries generated by other means. The cassettes in FIG. 18 can be placed in a binary vector for *Agrobacterium*-mediated plant transformation. Construct 2 (pJMTOI3) comprises the following features:

| Feature | Location (base) |
|---|---|
| ZmUbi promoter | (1) . . . (1988) |
| GFP | (2001) . . . (2696) |
| NOS terminator | (2703) . . . (2955) |
| Spacer | (2962) . . . (3161) |
| RNAi target | (3162) . . . (3461) |
| OCS terminator | (3468) . . . (3680) |

To perform the terminator screen described in this example, a plant line must be established that can effectively silence RNAs that contain the RNAi target region. In this example, *Arabidopsis* will be used as the host plant although the screen can be used in any plant species that can be transformed. A plant that can effectively silence can be obtained with the following steps using established transformation and genetic screening techniques.

1) Wild-type *Arabidopsis* is transformed with construct 3 in FIG. 18 (pJMTOI4, SEQ ID NO: 74). A $T_1$ plant is selected that is single copy for construct 3 and has strong green fluorescence. Construct 3 (pJMTOI4) comprises the following features:

| Feature | Location (base) |
|---|---|
| ZmUbi promoter | (1) . . . (1988) |
| GFP | (2001) . . . (2696) |
| Spacer | (2703) . . . (2902) |
| RNAi target | (2903) . . . (3202) |
| OCS terminator | (3209) . . . (3421) |

2) This fluorescent $T_1$ plant is transformed with construct 4 in FIG. 18 (pJMTOI5; SEQ ID NO: 75). A $T_1$ plant from this transformation is selected that is single copy and hemizygous for construct 3 and single copy for construct 4, and that no longer fluoresces green (silencing plant). Construct 4 (pJMTOI5) comprises the following features:

| Feature | Location (base) |
|---|---|
| ZmUbi promoter | (1) . . . (1988) |
| RNAi target sense | (2001) . . . (2300) |
| Spacer | (2309) . . . (2595) |
| RNAi target anti-sense | (2602) . . . (2901) |
| NOS terminator | (2908) . . . (3160) |

3) A $T_2$ plant with respect to construct 4 (pJMTOI5) is obtained that is homozygous for construct 4 and null for construct 3. To generate additional silencing plants, $T_3$ plants can be obtained from the plant isolated in step 3.

After an *Arabidopsis* silencing line containing construct 4 has been established, this line can be transformed with plasmid TOI libraries containing construct 1 and with the control constructs 2 and 3 (pJMTOI3 and (pJMTOI4, respectively) in FIG. 18. $T_1$ plants that fluoresce to a similar extent, as plants transformed with construct 2 will be selected for further analysis. If a selected plant has a single integrant, quantitative RT-PCR targeting GFP and the RNAi target region can determine if the experimental TOI is acting as an efficient terminator. RT-PCR of plants transformed with construct 2 (pJMTOI3) and construct 3 (pJMTOI4) would serve as controls. If a selected plant has multiple integrants of construct 1, single integrants can be obtained from the $T_2$ generation. The TOIs from selected plants can be amplified and cloned by PCR.

Example 11

Assays for Identifying Terminators of Interest

These experiments are performed by bombardment of plant tissues or culture cells (Example 11.1), by PEG-mediated (or similar methodology) introduction of DNA to plant protoplasts (Example 11.2), or by *Agrobacterium*-mediated transformation (Example 11.3). The target tissue for these experiments can be plant tissues (e.g. leaf tissue has been described to best support IRES-mediated translation (Urwin et al., 2000), cultured plant cells (e.g. maize BMS), or plant embryos for *Agrobacterium* protocols.

The sequences used as potential transcription terminator sequences can either be derived from the in silico transcription terminator sequence screen or from a library of random genomic fragments. Ratio of expression of two different reporter genes is measured by quantification of expression of reporter genes or RT-PCR using the protocols in the art in order to determine potentially strong and tight terminator candidates.

11.1 Transient Assay Using Microprojectile Bombardment

The plasmid constructs are isolated using Qiagen plasmid kit (cat# 12143). DNA is precipitated onto 0.6 μM gold particles (Bio-Rad cat#165-2262) according to the protocol described by Sanford et al. (1993) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature.

Two mg of gold particles (2 mg/3 shots) are resuspended in 100% ethanol followed by centrifugation in a Beckman Microfuge 18 Centrifuge at 2000 rpm in an Eppendorf tube. The pellet is rinsed once in sterile distilled water, centrifuged, and resuspended in 25 μL of 1 μg/μL total DNA. The following reagents are added to the tube: 220 μL $H_2O$, 250 μL 2.5M $CaCl_2$, 50 μL 0.1M spermidine, free base. The DNA solution is briefly vortexed and placed on ice for 5 min followed by centrifugation at 500 rpm for 5 min in a Beckman Microfuge 18 Centrifuge. The supernatant is removed. The pellet is resuspended in 600 μL ethanol followed by centrifugation for 1 min at 14,000 rpm. The final pellet is resuspended in 36 μL of ethanol and used immediately or stored on ice for up to 4 hr prior to bombardment. For bombardment, two-week-old maize leaves are cut in approximately 1 cm in length and located on 2 inches diameter sterilized Whatman filter paper. In the case of BMS cultured cells, 5 mL of one-week-old suspension cells are slowly vacuum filtered onto the 2 inches diameter filter paper placed on a filter unit to remove excess liquid. The filter papers holding the plant materials are placed on osmotic induction media (N6 1-100-25, 0.2 M mannitol, 0.2 M sorbitol) at 27° C. in darkness for 2-3 hours prior to bombardment. A few minutes prior to shooting, filters are removed from the medium and placed onto sterile opened Petri dishes to allow the calli surface to partially dry. To keep the position of plant materials, a sterilized wire mesh screen is laid on top of the sample. Each plate is shot with 10 μL of gold-DNA solution once at 2,200 psi for the leaf materials and twice at 1,100 psi for the BMS cultured cells. Following bombardment, the filters holding the samples are transferred onto MS basal media and incubated for 2 days in darkness at 27° C. prior to transient assays. Transient expression levels of the reporter gene are determined quantification of expression of reporter genes or RT-PCR using the protocols in the art in order to determine potentially strong and tight terminator candidates.

11.2 Transient Assay Using Protoplasts

Isolation of protoplasts is conducted by following the protocol developed by Sheen (1990). Maize seedlings are kept in the dark at 25° C. for 10 days and illuminated for 20 hours before protoplast preparation. The middle part of the leaves are cut to 0.5 mm strips (about 6 cm in length) and incubated in an enzyme solution containing 1% (w/v) cellulose RS, 0.1% (w/v) macerozyme R10 (both from Yakult Honsha, Nishinomiya, Japan), 0.6 M mannitol, 10 mM Mes (pH 5.7), 1 mM $CaCl_2$, 1 mM $MgCl_2$, 10 mM β-mercaptoethanol, and 0.1% BSA (w/v) for 3 hr at 23° C. followed by gentle shaking at 80 rpm for 10 min to release protoplasts. Protoplasts are collected by centrifugation at 100×g for 2 min, washed once in cold 0.6 M mannitol solution, centrifuged, and resuspended in cold 0.6 M mannitol ($2\times10^6$/mL).

A total of 50 μg plasmid DNA in a total volume of 100 μL sterile water is added into 0.5 mL of a suspension of maize protoplasts ($1\times10^6$ cells/mL) and mix gently. 0.5 mL PEG solution (40% PEG 4000, 100 mM $CaNO_3$, 0.5 mannitol) is added and pre-warmed at 70° C. with gentle shaking followed by addition of 4.5 mL MM solution (0.6 M mannitol, 15 mM $MgCl_2$, and 0.1% MES). This mixture is incubated for 15 minutes at room temperature. The protoplasts are washed twice by pelleting at 600 rpm for 5 min and resuspending in 1.0 mL of MMB solution [0.6 M mannitol, 4 mM Mes (pH 5.7), and brome mosaic virus (BMV) salts (optional)] and incubated in the dark at 25° C. for 48 hr. After the final wash step, collect the protoplasts in 3 mL MMB medium, and incubate in the dark at 25° C. for 48 hr. Transient expression levels of the reporter gene are determined quantification of expression of reporter genes or RT-PCR using the protocols in the art in order to determine potentially strong and tight terminator candidates.

11.3 *Agrobacterium*-Mediated Transformation in Dicotyledonous and Monocotyledonous Plants 11.3.1 Transformation and Regeneration of Transgenic *Arabidopsis thaliana* (Columbia) Plants To generate transgenic *Arabidopsis plants, Agrobacterium tumefaciens* (strain C58C1 pGV2260) is transformed with the various vector constructs described above. The agrobacterial strains are subsequently used to generate transgenic plants. To this end, a single transformed *Agrobacterium* colony is incubated overnight at 28° C. in a 4 mL culture (medium: YEB medium with 50 μg/mL kanamycin and 25 μg/mL rifampicin). This culture is subsequently used to inoculate a 400 mL culture in the same medium, and this is incubated overnight (28° C., 220 rpm) and spun down (GSA rotor, 8,000 rpm, 20 min). The pellet is resuspended in infiltration medium (½ MS medium; 0.5 g/L MES, pH 5.8; 50 g/L sucrose). The suspension is introduced into a plant box (Duchefa), and 100 ml of SILWET L-77 (heptamethyltrisiloxan modified with polyalkylene oxide; Osi Specialties Inc., Cat. P30196) is added to a final concentration of 0.02%. In a desiccator, the plant box with 8 to 12 plants is exposed to a vacuum for 10 to 15 minutes, followed by spontaneous aeration. This is repeated twice or 3 times. Thereupon, all plants are planted into flowerpots with moist soil and grown under long-day conditions (daytime temperature 22 to 24° C., nighttime temperature 19° C.; relative atmospheric humidity 65%). The seeds are harvested after 6 weeks.

As an alternative, transgenic *Arabidopsis* plants can be obtained by root transformation. White root shoots of plants with a maximum age of 8 weeks are used. To this end, plants which are kept under sterile conditions in 1 MS medium (1% sucrose; 100 mg/L inositol; 1.0 mg/L thiamine; 0.5 mg/L pyridoxine; 0.5 mg/L nicotinic acid; 0.5 g MES, pH 5.7; 0.8% agar) are used. Roots are grown on callus-inducing medium for 3 days (1× Gamborg's B5 medium; 2% glucose; 0.5 g/L mercaptoethanol; 0.8% agar; 0.5 mg/L 2,4-D (2,4-dichlorophenoxyacetic acid); 0.05 mg/L kinetin). Root sections 0.5 cm in length are transferred into 10 to 20 mL of liquid callus-inducing medium (composition as described above, but without agar supplementation), inoculated with 1 mL of the above-described overnight *Agrobacterium* culture (grown at 28° C., 200 rpm in LB) and shaken for 2 minutes. After excess medium has been allowed to run off, the root explants are transferred to callus-inducing medium with agar, subsequently to callus-inducing liquid medium without agar (with 500 mg/L betabactyl, SmithKline Beecham Pharma GmbH, Munich), incubated with shaking and finally transferred to shoot-inducing medium (5 mg/L 2-isopentenyladenine phosphate; 0.15 mg/L indole-3-acetic acid; 50 mg/L kanamycin; 500 mg/L betabactyl). After 5 weeks, and after 1 or 2 medium changes, the small green shoots are transferred to germination medium (1 MS medium; 1% sucrose; 100 mg/L inositol; 1.0 mg/L thiamine; 0.5 mg/L pyridoxine; 0.5 mg/L nicotinic acid; 0.5 g MES, pH 5.7; 0.8% agar) and regenerated into plants.

11.3.2 Transformation and Regeneration of Crop Plants

The *Agrobacterium*-mediated plant transformation using standard transformation and regeneration techniques may also be carried out for the purposes of transforming crop plants (Gelvin 1995; Glick 1993). For example, oilseed rape can be transformed by cotyledon or hypocotyl transformation (Moloney 1989; De Block 1989). The use of anti-biotics for the selection of *Agrobacteria* and plants depends on the binary vector and the *Agrobacterium* strain used for the transformation. The selection of oilseed rape is generally carried out using kanamycin as selectable plant marker. The *Agrobacterium*-mediated gene transfer in linseed (*Linum usitatissimum*) can be carried out using for example a technique described by Mlynarova (1994). The transformation of soybean can be carried out using, for example, a technique described in EP-A1 0 424 047 or in EP-A1 0 397 687, U.S. Pat. No. 5,376,543, U.S. Pat. No. 5,169,770. The transformation of maize or other monocotyledonous plants can be carried out using, for example, a technique described in U.S. Pat. No. 5,591,616. The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag N.Y.).

REFERENCES

The references listed below and all references cited herein are incorporated herein by reference to the extent that they supplement, explain, provide a background for, or teach methodology, techniques, and/or compositions employed herein.

1. Abremski et al. (1986) J. Biol. Chem. 261(1):391
2. Allen et al. (1996) Plant Cell 8(5), 899-913
3. Allen et al. (2000) Plant Mol Biol 43(2-3):361-76
4. An et al. (1985) EMBO J. 4:277-287
5. Anandalakshmi et al. (1998) Proc Natl Acad Sci USA 95(22):13079-84
6. Andersen et al. (1989) Arch Microbiol 152:115-118
7. Anderson & Young (1985) Quantitative Filter Hybridization, in Nucleic Acid Hybridization
8. Angell et al. (1999) Plant J 20(3):357-362
9. Araki et al. (1992) J. Mol. Biol. 225(1):25
10. Argos et al. (1986) EMBO J. 5:433-440
11. Atanassova et al. (1992) Plant J 2(3): 291-300
12. Ausubel et al. (1995) Short Protocols in Molecular Biology, 3.sup.rd Edition (John Wiley & Sons
13. Bailey et al., "Manipulation of Baculovirus Vectors," in Methods in Molecular Biology, Volume 7: Gene Transfer and Expression Protocols, Murray (ed.), p. 147-168 (The Humana Press, Inc. 1991)
14. Bartel & Szostak (1993) Science 261:1411-1418
15. Bäumlein et al. (1991a) Mol Gen Genet 225(3):459-467
16. Bäumlein et al. (1991b) Mol Gen Genet 225:121-128
17. Bayley et al. (1992) Plant Mol Biol. 18(2):353-361
18. Beclin et al. (1993) Transgenics Res 2:4855
19. Beerli et al. (2000) Proc Natl Acad Sci USA 97(4):1495-500
20. Beerli et al. (1998) Proc Natl Acad Sci USA 95(25): 14628-14633
21. Beerli et al. (2000) J Biol Chem 275(42):32617-32627
22. Belfort & Roberts (1997) Nucleic Acids Res 25:3379-3388

23. Bennett (1990) in Goodman and Gilman: the Pharmacological Basis of Therapeutics. 8th ed. eds. Gilman A G et al. (Pergamon Press, New York) pp. 1165-1181
24. Benoist et al. (1981) Nature 290:304
25. Besnard et al. (1987) Mol Cell Biol 7:4139
26. Bevan et al. (1984) Nucl Acid Res 12, 8711-8720
27. Bidney et al. (1992) Plant Mol. Biol. 18:301-313
28. Blanc et al. (1996) Biochimie 78(6):511-517
29. Bonning et al. (1994) J. Gen. Virol. 75:1551 (1994)
30. Broach et al. (1982) Cell 29:227-234
31. Brown (1991) (ed.), Molecular Biology Labfax Academic Press
32. Bruce et al. (1989) Proc Natl Acad Sci USA 86:9692-9696
33. Brummell et al. (2003) Plant J. 33:793-800
34. Bustos et al. (1989) Plant Cell 1(9):839-53
35. Calabrisi & Chabner (1990) in Goodman and Gilman: the Pharmacological Basis of Therapeutics. 8th ed., eds. Gilman et al. (Pergamon Press, New York) pp. 1209-1263
36. Campbell (1992) J. Bacteriol. 174(23):7495
37. Canaday et al. (1992) Mol Gen Genet 235:292-303
38. Cecchini et al. (1998) Mutat Res 401(1-2):199-206
39. Chasin et al. (1986) Som. Cell. Mol. Genet. 12:555
40. Chazenbalk & Rapoport (1995) J. Biol. Chem. 270:1543
41. Chen & Winans (1991) J. Bacteriol. 173: 1139-1144
42. Christensen et al. (1989) Plant Mol. Biol. 12: 619-632
43. Christensen et al. (1992) Plant Mol Biol 18:675-689
44. Christou et al., (1988) Plant Physiol 87:671-674
45. Christou et al. (1991) Bio/Technology 9:957-962
46. Chui et al. (1996) Curr Biol 6:325-330
47. Coombs (1994) Dictionary of Biotechnology, Stockton Press, New York N.Y.]
48. Corneille et al., (2001) Plant J 27:171-178
49. Cornell et al., (1996) 317:285-290).
50. Cramer et al. (1999) Current Topics in Microbiology and Immunology 240:95-118
51. Cramer et al. (2001) FEBS Letters 498:179-182
52. Czako & Marton (1994) Plant Physiol 104:1067-1071
53. Dale & Ow (1991) Proc Nat'l Acad Sci USA 88:10558-10562
54. Damon et al. (1989) Pharmac Ther 43:155-189)
55. Datta et al. (1990b) Bio/Technology 8:736-740
56. DE 10212892
57. de Block et al. (1987) EMBO J 6:2513-2518
58. De Block et al. (1989) Plant Physiol. 91:694-701)
59. de Feyter et al., (1996) Mol Gen Genet. 250(3):329-338
60. De la Pena et al. (1987) Nature 325:274-276
61. Deblaere et al. (1985) Nucl Acids Res 13:4777-4788
62. Della-Cioppa et al. (1987) Bio/Technology 5:579-584
63. Dellaporta et al. (1988) In: Chromosome Structure and Function: Impact of New Concepts, 18th Stadler Genetics Symposium, 11:263-282
64. Depicker et al. (1988) Plant Cell rep 104:1067-1071
65. Dietert et al. (1982) Plant Science Letters 26:233-240
66. Donald et al. (1996) J Biol Chem 271(24):14010-14019
67. Dotson et al. (1996) J Biol Chem 271(42): 25754-25761
68. Dotson et al. (1996) Plant J 10(2):383-392
69. Dreier et al., (2000) J Mol Biol 303(4):489-502
70. Dreier et al. (2001) J Biol Chem 276(31):29466-78
71. Drocourt et al. (1990) Nucl. Acids Res. 18:4009
72. Du et al. (1989) Genet Manip Plants 5:8-12
73. Dunahay et al. (1995) J Phycol 31:10004-1012
74. Dunwell (2000) J Exp Bot 51 Spec No:487-96
75. Ebinuma et al. (2000a) Proc Natl Acad Sci USA 94:2117-2121
76. Ebinuma et al. (2000b) Selection of Marker-free transgenic plants using the oncogenes (ipt rol A, B, C) of *Agrobacterium* as selectable markers, In Molecular Biology of Woody Plants. Kluwer Academic Publishers
77. Eichholtz et al. (1987) Somatic Cell and Molecular Genetics 13, 67-76
78. Ellegren & Lȧȧs (1989) J. Chromatogr. 467, 217
79. EP-A1 0 120 516
80. EP-A1 0 270 615
81. EP-A1 0 321 201
82. EP-A1 0 333 033
83. EP-A1 0 335 528
84. EP-A1 0 388 186
85. EP-A1 0 397 687
86. EP-A1 0 424 047
87. EP-A1 0 595 837
88. EP-A1 0 595 873
89. EP-A1 0 601 092
90. EP-A1 0 807 836
91. EP-A1 0 291 533
92. EP-A1 0 360 257
93. Erikson et al. (2004) Nat Biotechnol. 22(4):455-8
94. Etcheverry (1996) "Expression of Engineered Proteins in Mammalian Cell Culture," in Protein Engineering: Principles and Practice, Cleland et al. (eds.), p. 163-181 (John Wiley & Sons, Inc.
95. Fagard & Vaucheret (2000) Plant Mol Biol 43(2-3):285-93
96. Falciatore et al. (1999) Marine Biotechnology 1(3):239-251
97. Famulok & Mayer (1999) Curr Top Microbiol Immunol 243:123-36
98. Fedoroff & Smith (1993) Plant J 3:273-289
99. Fire et al. (1998) Nature 391:806-811
100. Foecking et al., (1980) Gene 45:101
101. Fenwick (1985) The HGPRT system, in *Molecular Cell Genetics* 1st Ed. (ed Gottesman, M.) Wiley, New York, pp. 333-373
102. Fraley et al. (1982) Proc. Natl. Acad. Sci. USA 79:1859-1863
103. Fraley et al. (1983) Proc Natl Acad Sci USA 80:4803
104. Fraley et al. (1985) CRC Crit. Rev. Plant. Sci., 4:145
105. Franck et al., (1980) Cell 21:285-294
106. Franken et al. (1997) Curr Opin Biotechnol 8(4):411-416
107. Freeling & Walbot (1994) The Maize Handbook, Chapter 116, Eds., Springer, N.Y.
108. Fromm et al. (1986) Nature 319:791-793
109. Fromm et al. (1990) Bio/Technology 8:833-839
110. Gallego (1999) Plant Mol Biol 39(1):83-93
111. Gallie et al. (1987) Nucl Acids Res 15:8693-8711
112. Gardner et al. (1986) Plant Mol Biol 6:221-228
113. Gatignol et al. (1987) Mol. Gen. Genet. 207:342
114. Gatz et al. (1991) Mol Gen Genetics 227:229-237
115. Gatz et al., (1992) Plant J 2:397-404
116. Gatz et al. (1994) Mol Gen Genetics 243:32-38).
117. Gatz et al. (1997) Annu Rev Plant Physiol Plant Mol Biol 48:89-108
118. Gaudin & Jouanin (1995) Plant Mol. Biol. 28(1):123-36
119. Gautier et al. (1987) Nucleic Acids Res 15:6625-6641)
120. Gavilondo & Larrick (2000) Biotechniques 29(1):128-138
121. Gelvin et al. (Eds) (1990) Plant Molecular Biology Manual; Kluwer Academic Publisher, Dordrecht, The Netherlands
122. Gelvin & Schilperoort (1995) Plant Molecular Biology Manual, $2^{nd}$ Edition, Dordrecht Kluwer Academic Publ., ISBN 0-7923-27314
123. GenBank Acc. No.: AB025109

124. GenBank Acc. No.: U38846
125. GenBank Acc. No.: X03677
126. GenBank Acc.-No.: AB016260 (Protein_id="BAA87807.1)
127. GenBank Acc.-No.: AE009419
128. GenBank Acc.-No.: AF212863
129. GenBank Acc.-No.: AC079674
130. GenBank Acc.-No.: J01603
131. GenBankAcc.-No.: M13422
132. GenBank Acc.-No.: M60917
133. GenBankAcc.-No.: M61151
134. GenBank Acc.-No.: AF039169
135. GenBank Acc.-No.: AB025110
136. GenBank Acc.-No.: NC002147
137. GenBank Acc.-No.: U02443
138. GenBank Acc.-No.: U10247
139. GenBank Acc.-No.: U44852
140. GenBank Acc.-No.: X00221
141. GenBank Acc.-No.: X77943
142. GenBank Acc.-No.: M12196
143. GenBank Acc.-No.: AF172282
144. GenBank Acc.-No.: X04049
145. GenBank Acc.-No.: AF253472
146. GenBank Acc.-No: J02224
147. GenBank Acc.-No.: V00470
148. GenBank Acc.-No.: V00467
149. GenBank Acc.-No: M26950.
150. GenBank Acc.-No: M32238.
151. GenBank Acc.-No: NC__003308 (Protein_id="NP__536128.1),
152. GenBank Acc.-No: S56903,
153. GeneBank Acc.-No.: U60066
154. Gleave et al. (1999) Plant Mol Biol 40(2):223-235
155. Gleeson et al., (1986) J. Gen. Microbiol. 132:3459
156. Glick & Thompson (1993) Methods in Plant Molecular Biology and Biotechnology, Boca Raton: CRC Press, ISBN 0-8493-5164-2)
157. Glimelius (1984) Physiol Plant 61:38-44
158. Gordon-Kamm et al. (1990) Plant Cell 2:603-618
159. Goring et al. (1991) Proc. Nat'l Acad. Sci. USA 88:1770-1774
160. Gorman et al. (1982) Proc. Natl. Acad. Sci. USA 79:6777
161. Gottesman (1985) Molecular Cell Genetics, John Wiley and Sons, New York
162. Grant et al. (1995) Science 269, 843-846
163. Greener & Callahan (1994) Strategies 7:32-34
164. Griesbach (1992) HortScience 27:620
165. Gruber et al. (1993) "Vectors for Plant Transformation," in METHODS IN PLANT MOLECULAR BIOLOGY AND BIOTECHNOLOGY; pp. 89-119
166. Grussenmeyer et al. (1985) Proc. Nat'l Acad. Sci. 82:7952
167. Guerrero et al. (1993) Mol Gen Genet 224:161-168
168. Hajdukiewicz et al. (1994) Plant Mol Biol 25:989-994
169. Hamer et al. (1982) J. Molec. Appl. Genet. 1:273
170. Hansen et al. (1994) Proc. Natl. Acad. Sci. USA 91:7603-7607
171. Hardy (1985) "*Bacillus* Cloning Methods," in DNA Cloning: A Practical Approach, Glover (ed.) (IRL Press)
172. Hasegawa et al., (2003) The Plant journal 33:1063-1072
173. Haselhoff & Gerlach (1988) Nature 334:585-591
174. Haseloff et al. (1997) Proc Natl Acad Sci USA 94(6): 2122-2127
175. Hashida-Okado et al. (1998) FEBS Letters 425:117
176. Hayakawa et al. (1992) Proc Natl Acad Sci USA 89:9865-9869
177. Hayford et al. (1988) Plant Physiol. 86:1216
178. Hershey et al. (1991) Mol Gen Genetics 227:229-237
179. Hille et al. (1986) Plant Mol. Biol. 7:171
180. Hill-Perkins & Possee (1990) J. Gen. Virol. 71:971
181. Hoekema (1985) In: The Binary Plant Vector System, Offsetdrukkerij Kanters B. V., Alblasserdam, Chapter V
182. Hoekema et al. (1983) Nature 303:179-181
183. Hoess & Abremski (1990) In Nucleic Acids and Molecular Biology, vol. 4. Eds.: Eckstein and Lilley, Berlin-Heidelberg: Springer-Verlag; pp. 90-109
184. Hoess et al. (1986) Nucleic Acids Research 14(6):2287
185. Holliger & Bohlen (1999) Cancer & Metastasis Reviews 18(4):411-419
186. Holsters et al. (1978) Mol Gen Genet 163:181-187
187. Holtorf et al. (1995) Plant Mol Biol 29:637-649
188. Hood & Jilka (1999) Curr Opin Biotechnol. 10(4):382-6
189. Hood et al. (1986) J Bacteriol 168:1291-1301
190. http://rebase.neb.com/rebase/rebase.homing.html;
191. http://www.biomedcentral.com/1471-2180/1/15
192. Inze et al. (1984) Mol Gen Genet 194:265-274
193. Jacobs et al. (1988) Biochem Genet 26(1-2):105-22
194. Janssen (1989) J Bacteriol 171(12):6791-9)
195. Janssen et al. (1994) Annu Rev Microbiol 48: 163-191
196. Jasin (1996) Trends Genet 12:224-228
197. Bennett (1990) Chapter 50: Antifungal Agents, in Goodman and Gilman's the Pharmacological Basis of Therapeutics 8th ed., A. G. Gilman, ed., Pergamon Press, New York
198. Jefferson (1987b) Plant Mol. Bio. Rep. 5:387-405
199. Jefferson et al. (1987a) EMBO J. 6:3901-3907
200. Jenes et al. (1983) Techniques for Gene Transfer, in: Transgenic Plants, Vol. 1, Engineering and Utilization, edited by Kung & Wu, Academic Press 128-143
201. Jolly et al. (1983) Proc Natl Acad Sci USA 80:477
202. Jones et al. (1987) Mol Gen Genet 210:86
203. Jorgensen et al. (1996) Plant Mol Biol 31(5):957-973
204. Joseffson et al. (1987) J Biol Chem 262:12196-12201
205. Kado (1991) Crit Rev Plant Sci 10:1
206. Kang & Kim (2000) J Biol Chem 275(12):8742-8748
207. Karlin-Neumannn et al. (1991) Plant Cell 3:573-582
208. Kasuga et al. (1999) Nature Biotechnology 17:276-286
209. Kaufman (1990a) Meth. Enzymol. 185:487
210. Kaufman (1990b) Meth. Enzymol. 185:537
211. Kaufman et al. (1991) Nucl. Acids Res. 19:4485
212. Kavanagh (2002) Plant J. 32, 391-400
213. Keown (1990) Methods in Enzymology 185:527-637
214. Kilstrup et al. (1989) J Bacteriol 171:2124-2127
215. Kim et al. (2003) Biotechnology Progress 19:1620-1622
216. Kim et al. (1997) Proc Nat Acad Sci USA 94(8):3616-3620
217. Klapwijk et al. (1980) J. Bacteriol., 141, 128-136
218. Klug (1999) J Mol Biol 293(2):215-218
219. Knoll et al. (1998) Mol Cell Biol 18(2):807-814
220. Kobayashi et al. (1995) Jpn J Genet 70(3):409-422
221. Koechlin et al., (1966) Biochemical Pharmacology 15:434-446
222. Koncz & Schell (1986) Mol Gen Genet 204:383-396
223. Koprek et al. (1999) Plant J 19(6):719-726
224. Krens et al. (1982) Nature 296:72-74
225. Kuersten & Goodwin (2003) Nature Reviews Genetics 4:626-637
226. Landy (1989) Ann. Rev. Biochem. 58:913-949
227. Landy (1993) Curr Opin Genet Dev. 3(5):699-707
228. Last et al. (1991) Theor. Appl. Genet. 81:581-588
229. Lazzeri (1984) Annals of Botany 54:341-350
230. Leffel et al. (1997) Biotechniques. 23(5):912-8
231. Lepetit et al. (1992) Mol. Gen. Genet. 231:276-285
232. Li et al. (1992) Plant Mol Biol 20:1037-1048

233. Li (1982) Plant Cell Rep 1:209-211
234. Liu et al., (2002) Analytical Biochemistry 300:40-45
235. Lloyd & Davis et al. (1994) Mol Gen Genet 242(6):653-657
236. Lucknow (1996) "Insect Cell Expression Technology," in Protein Engineering: Principles and Practice, Cleland et al. (eds.), pages 183-218 (John Wiley & Sons, Inc.).
237. Luckow et al. 1993) J. Virol. 67:4566
238. Ludwig et al. (1990) Science 247:449
239. Luo & Wu (1988) Plant Mol. Biol. Rep. 6:165-174
240. Luo et al. (1996) Arch. Biochem. Biophys. 329:215
241. Ma & Vine (1999) Curr Top Microbiol. Immunol. 236: 275-92
242. Maniatis et al., (1989) Molecular Cloning: A Laboratory Manual, 2nd Ed., Cold Spring Harbor Laboratory, Cold Spring Harbor (N.Y.)
243. Mapp et al. (2000) Proc Natl Acad Sci USA 97(8):3930-3935
244. Margraff et al. (1980) Experimentia 36: 846)
245. Markie (1996) Methods Mol. Biol. 54:359
246. Matzke et al. (1994) Mol Gen Genet 244:219-229
247. Matzke et al. (2000) Plant Mol Biol 43:401-415
248. Matzke et al. (1989) The EMBO Journal 8(3):643-649
249. McElroy et al. (1990) Plant Cell 2:163171
250. McKnight (1982) Cell 31:355
251. McKnight et al. (1980) Nucl Acids Res 8(24):5931-5948
252. McKnight et al. (1980) Nucl Acids Res 8(24):5949-5964
253. Mett et al. (1993) PNAS 90: 4567-4571
254. Miki et al. (1993) "Procedures for Introducing Foreign DNA into Plants" in METHODS IN PLANT MOLECULAR BIOLOGY AND BIOTECHNOLOGY; pp. 67-88
255. Millar et al. (1992) Plant Mol Biol Rep 10:324-414
256. Mlynarova et al. (1994) Plant Cell Report 13:282-285
257. Mlynarova et al. (2003) Plant Cell. 15(9):2203-17
258. Mlynarova et al. (2002) Genetics 160, 727-40
259. Mol et al. (1990) FEBS Lett 268(2):427-430
260. Moloney et al. (1989) Plant Cell Reports 8:238-242
261. Moreno et al. (1997) J. Immunol. 158: 5841-5848
262. Morganti et al. (1996) Biotechnol. Appl. Biochem. 23:67
263. Mozo & Hooykaas (1991) Plant Mol. Biol. 16: 917-918.
264. Mullen et al. (1992) Proc Natl Acad Sci USA 89(1):33-37
265. Murai et al. (1983) Science 23: 476-482
266. Mzoz & Moolten (1993) Human Gene Therapy 4:589-595
267. Naested et al. (1999) Plant J 18(5):571-576
268. Nan et al. (1995) In "Biotechnology in Agriculture and Forestry," Ed. Y. P. S. Bajaj, Springer-Verlag Berlin Heidelberg, Vol 34:145-155
269. Napoli et al. (1990) The Plant Cell 2:279-289
270. Napoli et al. (1990) Plant Cell 2:279-289
271. Nehra et al. (1994) Plant J. 5:285-297
272. O'Keefe (1991) Biochemistry 30(2):447-55
273. O'Keefe et al. (1994) Plant Physiol 105:473-482
274. Odell et al. (1985) Nature 313:810-812
275. Olhoft et al. (2001) Plant Cell Rep 20: 706-711
276. Ono et al. (1997) Hum Gene Ther 8(17):2043-55
277. Ow et al. (1986) Science 234:856-859
278. Owen et al. (1992) Biotechnology (N Y) 10(7):790-794
279. Owens et al., (1973) Weed Science 21:63-66)
280. Padidam & Cao (2001) BioTechniqus 31:328-334
281. Paszkowski et al. (1984) EMBO J 3:2717-2722
282. Patel et al. (1995) "The baculovirus expression system," in DNA Cloning 2: Expression Systems, 2nd Edition, Glover et al. (eds.), pages 205-244 (Oxford University Press)
283. Perera et al. (1993) Plant Mol. Biol 23(4): 793-799;
284. Perl et al. (1996) Nature Biotechnol 14: 624-628
285. Pfeifer et al. (1997) Gene 188:183
286. Polak & Scholer (1975) Chemotherapy (Basel) 21:113-130
287. Polak et al. (1976) Chemotherapy 22:137-153
288. Potrykus (1991) Ann Rev Plant Physiol Plant Mol Biol 42:205-225
289. Prasher et al. (1985) Biochem Biophys Res Commun 126(3):1259-1268
290. Preston et al. (1981) J Virol 38(2):593-605
291. Proudfoot (1986) Nature 322:562-565
292. Qian et al. (1992) J. Biol. Chem. 267(11):7794
293. Randez-Gil et al. (1995) Yeast 11:1233-1240
294. Ratcliff F et al. (2001) Plant J 25(2):237-45
295. Rathore et al. (1993) Plant Mol Biol 21(5):871-884
296. Raymond et al., Yeast 14:11-23 (1998)
297. Razik & Quatrano (1997) Plant Cell 9:1791-1803
298. Richardson (ed.) (1995) Baculovirus Expression Protocols (The Humana Press, Inc.)
299. Risseeuw (1997) Plant J 11 (4):717-728
300. Roberts & Macelis (2001) Nucl Acids Res 29:268-269
301. Romanos et al. (1995) "Expression of Cloned Genes in Yeast," in DNA Cloning 2: Expression Systems, 2.sup.nd Edition, p. 123-167 (IRL Press)
302. Rouster et al. (1998) Plant J 15:435-440
303. Ruiz (1998) Plant Cell 10(6):93746)
304. Russel (1999), Current Topics in Microbiology and Immunology 240:119-138
305. Salomon & Puchta (1998) EMBO J 17(20):6086-6095
306. Sambrook et al. (1989) Cold Spring Harbor Laboratory Press; ISBN 0-87969-309-6
307. Sanford (1990) Physiologia Plantarium 79:206-209
308. Sanger et al. (1977) Proc Natl Acad Sci USA 74:5463-5467
309. Sauer (1994) Current Opinion in Biotechnology 5:521-527
310. Sautter et al. (1991) Bio/Technology 9:1080-1085
311. Scheeren-Groot et al. (1994) J. Bacteriol 176: 6418-6426
312. Schena et al. (1991) Proc Nat'l Acad Sci USA 88:10421
313. Schenbom & Groskreutz (1999) Mol Biotechnol 13(1): 29-44
314. Schlaman & Hooykaas (1997) Plant J 11:1377-1385
315. Schroder et al. (1984) Eur J Biochem 138:387-391
316. Schwartz (1981) Environ Health Perspect 37:75-7
317. Segal & Barbas 3rd. (2000) Curr Opin Chem Biol 4(1): 34-39
318. Sekowska et al. (2001) BMC Microbiol 1:15
319. Sengupta-Gopalan et al. (1985) Proc. Natl. Acad. Sci. USA 82: 3320-3324
320. Serino (1997) Plant J 12(3):697-701
321. Shah et al. (1986) Science 233: 478
322. Shahla et al. (1987) Plant Mole. Biol. 8:291-298
323. Sharrocks et al. (1997) Int J Biochem Cell Biol 29(12): 1371-1387
324. Sheehy et al. (1988) Proc Natl Acad Sci USA 85: 8805-8809
325. Sheen (1990) Plant Cell 2:1027-1038
326. Sheen (1995) Plant J 8(5):777-784
327. Shewmaker et al. (1985) Virology 140:281-288
328. Shillito et al. (1985) Bio/Technology, 3:1099-1103
329. Shimamoto et al. (1989) Nature 338:274-276
330. Shirsat et al. (1989) Mol Gen Genet 215(2):326-331
331. Sidorenko et al. (2003) Transgenic Research. 12(2):137-54
332. Silhavy et al. (1984) Experiments with Gene Fusions, Cold Spring Harbor Laboratory, Cold Spring Harbor, N.Y.

333. Simpson et al. (1985) EMBO J 4:2723-2729
334. Smith et al. (1990) Mol Gen Genet 224:447-481
335. Sorscher et al. (1994) Gene Therapy 1:233-238
336. Srivastava & Schlessinger (1991) Gene 103:53
337. St. Clair et al. (1987) Antimicrob Agents Chemother 31(6):844-849
338. Stalberg et al. (1996) Planta 199:515-519
339. Steinecke et al. (1992) EMBO J 11(4):1525-1530
340. Steinecke (1995) Ribozymes, Methods in Cell Biology 50, Galbraith et al. eds, Academic Press, Inc. p. 449-460
341. Stief et al. (1989) Nature 341:343
342. Stougaard (1993) Plant J 3:755-761
343. Stringham (1979) Z Pflanzenphysiol 92:459-462
344. Sundaresan et al. (1995) Gene Develop 9: 1797-1810
345. Sundaresan et al. (1995) Gene Develop 9:1797-1810
346. Svab et al. (1990) Plant Mol. Biol. 14:197
347. Tanner (1999) FEMS Microbiol Rev 23(3):257-275
348. Taylor et al. (1985) "The APRT System", pp., 311-332, M. Gottesman (ed.), Molecular Cell Genetics, John Wiley and Sons, New York
349. The Maize Handbook, Chapter 116, Freeling and Walbot, Eds., Springer, N.Y. (1994)
350. Thykjaer et al. (1997) Plant Mol Biol 35(4):523-530
351. Tian et al. (1997) Plant Cell Rep 16:267-271
352. Timko et al., (1985) Nature 318: 579-582
353. Tissier et al. (1999) Plant Cell 11:1841-1852
354. Tomashow et al. (1984) Proc Natl Acad Sci USA 81:5071-5075
355. Topfer et al. (1989) Plant Cell, 1:133-139
356. Tsai et al. (1998) Adv Drug Deliv Rev 30(1-3):23-31
357. Tucker & Burke (1997) Gene 199:25
358. Twell et al. (1983) Sex. Plant Reprod. 6: 217-224
359. Twell et al. (1989b) Mol Gen Genet 217:240-245
360. Ulmasov & Folk (1995) The Plant Cell 7:1723-1734
361. Upadhyaya et al. (2000) Plant Mol Biol Rep 18:227-223
362. Urwin et al. (2000) Plant J 24: 583-589
363. U.S. Pat. No. 4,486,533
364. U.S. Pat. No. 4,599,311
365. U.S. Pat. No. 4,615,974
366. U.S. Pat. No. 4,661,454
367. U.S. Pat. No. 4,801,340
368. U.S. Pat. No. 4,845,075
369. U.S. Pat. No. 4,870,008
370. U.S. Pat. No. 4,882,279
371. U.S. Pat. No. 4,931,373
372. U.S. Pat. No. 4,935,349
373. U.S. Pat. No. 4,962,028
374. U.S. Pat. No. 4,975,374
375. U.S. Pat. No. 4,977,092
376. U.S. Pat. No. 4,987,071
377. U.S. Pat. No. 4,990,446,
378. U.S. Pat. No. 4,940,838
379. U.S. Pat. No. 5,037,743
380. U.S. Pat. No. 5,037,743
381. U.S. Pat. No. 5,063,154
382. U.S. Pat. No. 5,139,936
383. U.S. Pat. No. 5,143,830
384. U.S. Pat. No. 5,162,228
385. U.S. Pat. No. 5,169,770
386. U.S. Pat. No. 5,180,873
387. U.S. Pat. No. 5,300,435
388. U.S. Pat. No. 5,334,575
389. U.S. Pat. No. 5,352,605
390. U.S. Pat. No. 5,358,866;
391. U.S. Pat. No. 5,376,543
392. U.S. Pat. No. 5,426,041
393. U.S. Pat. No. 5,501,967
394. U.S. Pat. No. 5,504,200
395. U.S. Pat. No. 5,584,807
396. U.S. Pat. No. 5,591,616
397. U.S. Pat. No. 5,608,152
398. U.S. Pat. No. 5,683,439
399. U.S. Pat. No. 5,716,808
400. U.S. Pat. No. 5,736,383,
401. U.S. Pat. No. 5,888,732
402. U.S. Pat. No. 5,034,323.
403. U.S. Pat. No. 5,116,742
404. U.S. Pat. No. 5,254,801
405. Vagner et al., (2001) EMBO Rep. 2(10):893-8
406. Van der Krol et al. (1990) Plant Cell 2:291-99
407. Van Laerebeke et al. (1974) Nature 252:169-170
408. Vancanneyt et al. (1990) Mol Gen Genet 220(2):245-250
409. Vanden Elzen et al. (1985) Plant Mol Biol. 5:299
410. VanOnckelen et al. (1986) FEBS Lett. 198: 357-360
411. Vasil et al. (1992) Bio/Technology, 10:667-674
412. Velten et al. (1984) EMBO J. 3(12): 2723-2730
413. Villemure et al. (2001) J. Mol. Biol. 312, 963-974
414. Wagner et al. (1981) Proc Natl Acad Sci USA 78(3): 1441-1445
415. Wan & Lemaux (1994) Plant Physiol. 104:3748
416. Ward et al. (1993) Plant Mol. Biol. 22:361-366
417. Waterhouse et al. (1998) Proc Natl Acad Sci USA 95:13959-64
418. Watson et al. (1975) J. Bacteriol 123:255-264
419. Watson et al. (1985) EMBO J 4(2):277-284
420. Weeks et al. (1993) Plant Physiol 102:1077-1084
421. Whitelam (1996) Trend Plant Sci 1:286-272)
422. Wigler et al. (1977) Cell 11(1):223-232;
423. Wigler et al. (1979) Proc Natl Acad Sci USA 76(3): 1373-6
424. Wisman et al. (1991) Mol Gen Genet 226(1-2):120-8
425. WO 00/26388
426. WO 00/44895
427. WO 00/44914
428. WO 00/49035
429. WO 00/63364
430. WO 00/68374
431. WO 02/00900
432. WO 03/060133
433. WO 03/078629
434. WO 03/052104
435. WO 84/02913
436. WO 91/02071
437. WO 91/13980
438. WO 91/13991
439. WO 91/15585
440. WO 93/01281
441. WO 93/01294
442. WO 93/18168
443. WO 93/21334
444. WO 94/00583
445. WO 95/19443
446. WO 97/17450
447. WO 97/17451
448. WO 97/41228
449. WO 97/48814
450. WO 98/01572
451. WO 98/02536
452. WO 98/02565
453. WO 98/45456
454. WO 98/45461
455. WO 99/32619
456. WO 99/53050
457. WO 00/44914

458. WO 00/49035
459. WO 00/63364
460. WO 00/68374
461. WO 99/53050
462. Wu et al. (1997) Methods in Gene Biotechnology (CRC Press, Inc.)
463. Xiaohui Wang et al. (2001) Gene 272(1-2): 249-255
464. Yamada et al. (1985) Proc Natl Acad Sci USA 82:6522-6526
465. Yarnell & Roberts (1999) Science 284:611-615
466. Yonaha & Proudfoot (1999) Molecular Cell 3:593-600
467. Yonaha & Proudfoot (2000) EMBO J. 19:3770-3777
468. Zhang et al. (2000) J Biol Chem 275(43):33850-33860
469. Zhao et al., (1999) Microbiol Mol Biol Rev 63:405-445
470. Zheng et al. (1997) Gene 186:55
471. Zhou et al. (1990) Mol. Cell. Biol. 10:4529
472. Zubko et al. (2000) Nat Biotechnol 18:442-445
473. Zupan et al. (2000) Plant J 23(1):11-28

---

What is claimed is:

1. A method for identification and isolation of transcription termination sequences from a plant comprising the steps of:

i) providing a screening construct or screening vector comprising a) a promoter sequence, b) one or more insertion sites for insertion of DNA sequences, and c) at least one additional sequence which causes upon expression under said promoter sequence a readily detectable characteristic, wherein insertion of an efficient transcription terminator into said insertion site changes expression of said additional sequence by said promoter sequence in comparison to no insertion, ii) providing one or more DNA sequences to be assessed for their transcription termination capability by a) identifying intergenic regions between paired genes having an intergenic distance of about 400 to 3,000 base pairs from a plant, b) identifying one or more DNA sequences which are flanked on both sides by genes having at least 5% of expression level of actin in said plant, and c) isolating the one or more DNA sequences identified in step b), iii) inserting one or more copies of said DNA sequences obtained from step ii) into said insertion site of said screening construct or screening vector, iv) introducing said screening construct or screening vector with said inserted DNA sequences into an in vitro or in vivo transcription system suitable to induce expression from said promoter sequence, v) identifying and/or selecting screening construct or screening vector with a changed readily detectable characteristic in comparison to no insertion, and vi) isolating the inserted DNA sequences from said identified and/or selected screening construct or screening vector for use as transcription termination sequences and, optionally, determining their sequence.

2. The method of claim 1, wherein said insertion site is localized in relation to said additional sequences at a position selected from the group consisting of:

i) upstream of the additional sequences between said promoter and said additional sequences, ii) downstream of the additional sequences, and iii) in between said additional sequences.

3. The method of claim 1, wherein said DNA sequences to be assessed for their transcription termination efficiency are inserted into said insertion site in form of an inverted repeat.

4. The method of claim 1, wherein the method for identification and isolation of transcription termination sequences from a plant comprises the steps of:

i) providing a screening construct or screening vector comprising in 5' to 3' direction a) a promoter sequence, b) at least one additional sequence which causes upon expression under said promoter sequence a readily detectable characteristic, and c) one or more insertion sites for insertion of DNA sequences, ii) providing one or more DNA sequences to be assessed for their transcription termination capability by a) identifying intergenic regions between paired genes having an intergenic distance of about 400 to 3,000 base pairs from a plant, b) identifying one or more DNA sequences which are flanked on both sides by genes having at least 5% of expression level of actin in said plant, and c) isolating the one or more DNA sequences identified in step b), iii) inserting at least two copies of a specific DNA sequence of said DNA sequences obtained from step ii) in form of an inverted repeat into said insertion site of said screening construct or screening vector, wherein insertion of an inverted repeat of an efficient transcription terminator into said insertion site allows expression of said additional sequences by said promoter sequence in comparison to no insertion, iv) introducing said screening construct or screening vector with said inserted DNA sequences into an in vitro or in vivo transcription system suitable to induce expression from said promoter sequence, v) identifying and/or selecting screening constructs or screening vectors with said readily detectable characteristic in comparison to no insertion, and vi) isolating the inserted DNA sequences from said identified and/or selected screening constructs or screening vectors for use as transcription termination sequences and, optionally, determining their sequence.

5. The method of claim 1, wherein the method for identification and isolation of transcription termination sequences from a plant comprises the steps of:

i) providing a screening construct or screening vector comprising in 5' to 3' direction a) a promoter sequence, b) one or more insertion sites for insertion of DNA sequences, and c) at least one additional sequence which causes upon expression under said promoter sequence a readily detectable characteristic, wherein insertion of an efficient transcription terminator into said insertion site suppresses expression of said additional sequences by said promoter sequence in comparison to no insertion, ii) providing one or more DNA sequences to be assessed for their transcription termination capability by a) identifying intergenic regions between paired genes having an intergenic distance of about 400 to 3,000 base pairs from a plant, b) identifying one or more DNA sequences which are flanked on both sides by genes having at least 5% of expression level of actin in said plant, and c) isolating the one or more DNA sequences identified in step b), iii) inserting one or more copies of said DNA sequences obtained from step ii) into said insertion site of said screening construct or screening vector, iv) introducing said screening construct or screening vector with said inserted DNA sequences into an in vitro or in vivo transcription system suitable to induce expression from said promoter sequence, v) identifying and/or selecting screening constructs or screening vectors with a changed readily detectable characteristic in comparison to no insertion, and vi) isolating the inserted DNA sequences from said identified and/or selected screening constructs or screening vectors for use as transcription termination sequences and, optionally, determining their sequence.

6. The method of claim 5, wherein said additional sequence is an inverted repeat of a known transcription terminator sequence localized in a way the second copy of said repeat downstream from said promoter sequence is in an orientation to constitute a functional transcription terminator, and wherein said screening construct or screening vector comprises further sequences between said insertion site and said promoter which result in an readily detectable phenotype, and wherein absence of an efficient transcription terminator in said insertion site will lead to silencing of expression of said further sequences in consequence of expression of said inverted repeat of said known transcription terminator.

7. The method of claim 1, wherein the method for identification and isolation of transcription termination sequences from a plant comprises the steps of:

i) providing a screening construct or screening vector comprising in 5' to 3' direction a) a promoter sequence, and b) at least one additional sequence which causes upon expression under said promoter sequence a readily detectable characteristic, and embedded into said additional sequences one or more insertion sites for insertion of DNA sequences, wherein insertion of an efficient transcription terminator into said insertion site suppresses full-length transcription of said additional sequences by said promoter sequence in comparison to no insertion, ii) providing one or more DNA sequences to be assessed for their transcription termination capability by a) identifying intergenic regions between paired genes having an intergenic distance of about 400 to 3,000 base pairs from a plant, b) identifying one or more DNA sequences which are flanked on both sides by genes having at least 5% of expression level of actin in said plant, and c) isolating the one or more DNA sequences identified in step b), iii) inserting one or more copies of said DNA sequences obtained from step ii) into said insertion site of said screening construct or screening vector, iv) introducing said screening construct or screening vector with said inserted DNA sequences into an in vitro or in vivo transcription system suitable to induce expression from said promoter sequence, v) identifying and/or selecting screening constructs or screening vectors with a changed readily detectable characteristic in comparison to no insertion, and vi) isolating the inserted DNA sequences from said identified and/or selected screening constructs or screening vectors for use as transcription termination sequences and, optionally, determining their sequence.

8. The method of claim 7, wherein said insertion site is localized within an intron comprised in said additional sequence.

9. The method of claim 7, wherein said additional sequence comprises a first 5'-part which is encoding for a marker protein and a second 3'-part which is not protein encoding and has less than 30% identity to sequences endogenous to said transcription system, and wherein said insertion site is localized between said 5'-part and said 3'-part, and wherein for the purpose of selection and/or identification, a second expression cassette is introduced into said transcription system comprising a promoter function in said transcription system and operably linked thereto a sequence encoding for an antisense or double-stranded RNA molecule complementary to said 3'-part.

10. The method of claim 1, wherein said additional sequence is selected from the group consisting of positive selection marker, negative selection marker, counter selection marker, reporter genes, and toxic genes.

11. The method of claim 10, wherein said toxic gene is a construct for gene silencing of an essential endogenous gene or a selectable marker.

12. The method of claim 1, wherein said DNA sequence to be assessed for their transcription termination efficiency is provided by a method selected from the group consisting of:

i) a method of selecting sequences by amplification from a host genome, ii) a method of selecting sequences from a library of sequences by fragmentation of a host genome, and iii) a method of selecting sequences from a library of synthetic sequences.

13. The method of claim 1, wherein said DNA sequences to be assessed for their transcription termination efficiency are inserted into said insertion site by a method selected from the group consisting of:

i) recombinational cloning, and ii) insertion by sequence specific restriction and ligation.

14. A method for identification and isolation of intergenic sequences with transcription termination potential from a plant comprising at least the steps of:

a) identifying intergenic regions between paired genes having an intergenic distance of about 400 to 3,000 base pairs from a plant, b) identifying intergenic sequences which are flanked on both sides by genes having at least 5% of expression level of actin in said plant, and c) isolating the intergenic sequences identified in step b).

15. The method of claim 14 further comprises the steps of:

d) identifying and/or isolating intergenic sequences which are flanked on both sides by genes having an expression pattern which is independent from the expression pattern of the other paired gene, and e) identifying and/or isolating intergenic sequences which are flanked on one or both sides by genes having a low variability in length of the mRNA transcript derived from said paired genes.

16. The method of claim 14, wherein said intergenic region a) is localized between genes which have a tail-to-tail localization, and/or b) has a length measured from the respective stop codons of the flanking genes from about 700 to about 2000 base pairs.

* * * * *

SEQUENCE LISTING

```
<160> NUMBER OF SEQ ID NOS: 108

<210> SEQ ID NO 1
<211> LENGTH: 12287
<212> TYPE: DNA
<213> ORGANISM: Unknown
<220> FEATURE:
<223> OTHER INFORMATION: Binary expression vector
      Lo546b-pSUN1-R4-Lo484::Lo376::Lo522b
<220> FEATURE:
<221> NAME/KEY: misc_feature
<222> LOCATION: (1)..(21)
<223> OTHER INFORMATION: attB4 recombination site
<220> FEATURE:
<221> NAME/KEY: promoter
<222> LOCATION: (49)..(905)
<223> OTHER INFORMATION: CaMV 35S
<220> FEATURE:
<221> NAME/KEY: misc_feature
<222> LOCATION: (912)..(1719)
<223> OTHER INFORMATION: coding for mGFP5er
<220> FEATURE:
<221> NAME/KEY: terminator
<222> LOCATION: (1762)..(2431)
<223> OTHER INFORMATION: E9 terminator
<220> FEATURE:
<221> NAME/KEY: misc_feature
<222> LOCATION: (2432)..(2455)
<223> OTHER INFORMATION: attB1 recombination site
<220> FEATURE:
<221> NAME/KEY: misc_feature
<222> LOCATION: (2542)..(2565)
<223> OTHER INFORMATION: attb2 recombination site
<220> FEATURE:
<221> NAME/KEY: promoter
<222> LOCATION: (2581)..(3899)
<223> OTHER INFORMATION: STPT promoter
<220> FEATURE:
<221> NAME/KEY: misc_feature
<222> LOCATION: (3930)..(4777)
<223> OTHER INFORMATION: coding for nptII
<220> FEATURE:
<221> NAME/KEY: terminator
<222> LOCATION: (4816)..(5494)
<223> OTHER INFORMATION: E9 terminator
<220> FEATURE:
<221> NAME/KEY: terminator
<222> LOCATION: (5500)..(5752)
<223> OTHER INFORMATION: complement: nos terminator
<220> FEATURE:
<221> NAME/KEY: terminator
<222> LOCATION: (5907)..(6169)
<223> OTHER INFORMATION: nos terminator
<220> FEATURE:
<221> NAME/KEY: misc_feature
<222> LOCATION: (6283)..(6303)
<223> OTHER INFORMATION: complement: attB3 recombination site
<220> FEATURE:
<221> NAME/KEY: misc_feature
<222> LOCATION: (8245)..(9352)
<223> OTHER INFORMATION: repA
<220> FEATURE:
<221> NAME/KEY: rep_origin
<222> LOCATION: (8245)..(9352)
<223> OTHER INFORMATION: complement: ColE1
```

-continued

<220> FEATURE:
<221> NAME/KEY: misc_feature
<222> LOCATION: (11116)..(11907)
<223> OTHER INFORMATION: aadA marker (Spectomycin)
<220> FEATURE:
<221> NAME/KEY: misc_feature
<222> LOCATION: (12081)..(12226)
<223> OTHER INFORMATION: RB

<400> SEQUENCE: 1

```
caactttgta tagaaaagtt ggccatgatt acgccaagct tgcatgcctg caggtcccca     60

gattagcctt ttcaatttca gaaagaatgc taacccacag atggttagag aggcttacgc    120

agcaggtctc atcaagacga tctacccgag caataatctc caggaaatca aataccttcc    180

caagaaggtt aaagatgcag tcaaaagatt caggactaac tgcatcaaga acacagagaa    240

agatatattt ctcaagatca gaagtactat tccagtatgg acgattcaag gcttgcttca    300

caaaccaagg caagtaatag agattggagt ctctaaaaag gtagttccca ctgaatcaaa    360

ggccatggag tcaaagattc aaatagagga cctaacagaa ctcgccgtaa agactggcga    420

acagttcata cagagtctct tacgactcaa tgacaagaag aaaatcttcg tcaacatggt    480

ggagcacgac acacttgtct actccaaaaa tatcaaagat acagtctcag aagaccaaag    540

ggcaattgag acttttcaac aaagggtaat atccggaaac ctcctcggat tccattgccc    600

agctatctgt cactttattg tgaagatagt ggaaaaggaa ggtggctcct acaaatgcca    660

tcattgcgat aaaggaaagg ccatcgttga agatgcctct gccgacagtg gtcccaaaga    720

tggaccccca cccacgagga gcatcgtgga aaaagaagac gttccaacca cgtcttcaaa    780

gcaagtggat tgatgtgata tctccactga cgtaagggat gacgcacaat cccactatcc    840

ttcgcaagac ccttcctcta tataaggaag ttcatttcat ttggagagaa cacgggggac    900

tctagaggat ccaaggagat ataacaatga agactaatct ttttctcttt ctcatctttt    960

cacttctcct atcattatcc tcggccgaat tcagtaaagg agaagaactt ttcactggag   1020

ttgtcccaat tcttgttgaa ttagatggtg atgttaatgg gcacaaattt tctgtcagtg   1080

gagagggtga aggtgatgca acatacggaa aacttaccct taaatttatt tgcactactg   1140

gaaaactacc tgttccatgg ccaacacttg tcactacttt ctcttatggt gttcaatgct   1200

tttcaagata cccagatcat atgaagcggc acgacttctt caagagcgcc atgcctgagg   1260

gatacgtgca ggagaggacc atcttcttca aggacgacgg gaactacaag acacgtgctg   1320

aagtcaagtt tgagggagac accctcgtca acaggatcga gcttaaggga atcgatttca   1380

aggaggacgg aaacatcctc ggccacaagt tggaatacaa ctacaactcc cacaacgtat   1440

acatcatggc cgacaagcaa aagaacggca tcaaagccaa cttcaagacc cgccacaaca   1500

tcgaagacgg cggcgtgcaa ctcgctgatc attatcaaca aaatactcca attggcgatg   1560

gccctgtcct tttaccagac aaccattacc tgtccacaca atctgccctt tcgaaagatc   1620

ccaacgaaaa gagagaccac atggtccttc ttgagtttgt aacagctgct gggattacac   1680

atggcatgga tgaactatac aaacatgatg agctttaaga gaacggatcc ccatctgcgg   1740

ccgcctcgag catatgctag aggatcctct agctagagct ttcgttcgta tcatcggttt   1800

cgacaacgtt cgtcaagttc aatgcatcag tttcattgcg cacacaccag aatcctactg   1860

agtttgagta ttatggcatt gggaaaactg tttttcttgt accatttgtt gtgcttgtaa   1920

tttactgtgt tttttattcg gttttcgcta tcgaactgtg aaatggaaat ggatggagaa   1980

gagttaatga atgatatggt ccttttgttc attctcaaat taatattatt tgttttttct   2040

cttatttgtt gtgtgttgaa tttgaaatta taagagatat gcaaacattt tgttttgagt   2100
```

```
aaaaatgtgt caaatcgtgg cctctaatga ccgaagttaa tatgaggagt aaaacacttg   2160
tagttgtacc attatgctta ttcactaggc aacaaatata ttttcagacc tagaaaagct   2220
gcaaatgtta ctgaatacaa gtatgtcctc ttgtgtttta gacatttatg aactttcctt   2280
tatgtaattt tccagaatcc ttgtcagatt ctaatcattg ctttataatt atagttatac   2340
tcatggattt gtagttgagt atgaaaatat tttttaatgc attttatgac ttgccaattg   2400
attgacaaca tgcatcaatc gaccgggtac ccaagtttgt acaaaaaagc aggctggtac   2460
ccggggatcc tctaggtcga ccagatctga tatctgcggc cgcctcgagc atatgggcat   2520
gcaagcttgg cgtaatcatg gacccagctt tcttgtacaa agtggggtac ccggggatcc   2580
tgatagctta tactcaaatt caacaagtta tatataaatg tatagatact acaatatcat   2640
taacaaaagt caccttaaat aaatacacat atcttttatg ttctctattg ttttgcgtac   2700
gctaacacaa tttctcatat gcaaaaggat gaatgagtaa caaattacct cataagaaca   2760
atcatctttg cttacatact aatacaataa tcactcaatc aaccaataac atcaatcaca   2820
taggtttaca tacaataatc actcaatcaa cttcataaga agaatcatgt ttacttaatt   2880
catcaattat ccccaaaaac accactatta agtataaact acaacatatt tgtagtgatg   2940
ggtcaacatt tttatcatat ttaaactcgg gttccctcaa atcgagaaat agtgaacatg   3000
taatattaat tttaaatcgc aattacagaa attaattgaa tttggtcaaa tggacagaat   3060
tttatagatt gggtggaact agaaaaaaaa aaaaaaagag tatagggtga attgagtaca   3120
tgaaagtaca tggtaatcct agttaaacgc ataatacatg tgggttcatt tgtatttttt   3180
tgtaacttac gagtaaactg gctacaacaa aaaaaaatta gaagattttt ttgttttgta   3240
gaaaacccta attttagtta tagttgtata actttgataa aattataaaa ttgtattacg   3300
aaaaaagtaa taagatattc aaaaaagcct agaataacgt atatgactat gagcatgaaa   3360
ctgcaagtca aatgctgaca gacaaccata aacaaaagaa attaaataga gatacccttta   3420
aaataagtaa aatttcattt ataaaaaatc tactttcttg tgaatctgtc acgttcaata   3480
atttgaagac cactcaacat acaaggtaaa taatgaaaaa taaaatctac caaaatttca   3540
atcattatta tcttccaaaa aaacaaaatt atacagatga tgatggtgat atggaacttc   3600
gattggctaa tattcactgt gtctctaaaa accatccact tatcaagata agatggaccc   3660
tacactcatc caatctaaac cagtatctca agattcttat ctaattacat cattctctac   3720
cgttagatga aattgaccat taaccctacc ataactccat acaccgcgag atactggatt   3780
aaccaaatcg agatcatcgt agccgtccga tcaacaagta ccatctcttg aaatactcga   3840
aatcctcata agtccgtccc tctttgctct cactatcaaa actctgaatt tcgatttcat   3900
ctagagtcga gcccgggcga tatcggatct cgactctagt cgagggccca tgggagcttg   3960
gattgaacaa gatggattgc acgcaggttc tccggccgct tgggtggaga ggctattcgg   4020
ctatgactgg gcacaacaga caatcggctg ctctgatgcc gccgtgttcc ggctgtcagc   4080
gcaggggcgc ccggttcttt ttgtcaagac cgacctgtcc ggtgccctga atgaactgca   4140
ggacgaggca gcgcggctat cgtggctggc cacgacgggc gttccttgcg cagctgtgct   4200
cgacgttgtc actgaagcgg gaagggactg gctgctattg ggcgaagtgc cggggcagga   4260
tctcctgtca tctcaccttg ctcctgccga gaaagtatcc atcatggctg atgcaatgcg   4320
gcggctgcat acgcttgatc cggctacctg cccattcgac caccaagcga aacatcgcat   4380
cgagcgagca cgtactcgga tggaagccgg tcttgtcgat caggatgatc tggacgaaga   4440
gcatcagggg ctcgcgccag ccgaactgtt cgccaggctc aaggcgcgca tgcccgacgg   4500
```

cgaggatctc gtcgtgaccc atggcgatgc ctgcttgccg aatatcatgg tggaaaatgg 4560
ccgcttttct ggattcatcg actgtggccg gctgggtgtg gcggaccgct atcaggacat 4620
agcgttggct acccgtgata ttgctgaaga gcttggcggc gaatgggctg accgcttcct 4680
cgtgctttac ggtatcgccg ctcccgattc gcagcgcatc gccttctatc gccttcttga 4740
cgagttcttc tgagcgggac ccaagctagc ttcgacggat cctctagcat atgctcgagg 4800
cggccgcaga tatcagatcc tctagctaga gctttcgttc gtatcatcgg tttcgacaac 4860
gttcgtcaag ttcaatgcat cagtttcatt gcgcacacac cagaatccta ctgagtttga 4920
gtattatggc attgggaaaa ctgtttttct tgtaccattt gttgtgcttg taatttactg 4980
tgttttttat tcggttttcg ctatcgaact gtgaaatgga aatggatgga gaagagttaa 5040
tgaatgatat ggtccttttg ttcattctca aattaatatt atttgttttt tctcttattt 5100
gttgtgtgtt gaatttgaaa ttataagaga tatgcaaaca ttttgttttg agtaaaaatg 5160
tgtcaaatcg tggcctctaa tgaccgaagt taatatgagg agtaaaacac ttgtagttgt 5220
accattatgc ttattcacta ggcaacaaat atattttcag acctagaaaa gctgcaaatg 5280
ttactgaata caagtatgtc ctcttgtgtt ttagacattt atgaactttc ctttatgtaa 5340
ttttccagaa tccttgtcag attctaatca ttgctttata attatagtta tactcatgga 5400
tttgtagttg agtatgaaaa tatttttaa tgcattttat gacttgccaa ttgattgaca 5460
acatgcatca atcgacctgc agcccaagct tgatctagtc cgatctagta acatagatga 5520
caccgcgcgc gataatttat cctagtttgc gcgctatatt ttgttttcta tcgcgtatta 5580
aatgtataat tgcgggactc taatcataaa aacccatctc ataaataacg tcatgcatta 5640
catgttaatt attacatgct taacgtaatt caacagaaat tatatgataa tcatcgcaag 5700
accggcaaca ggattcaatc ttaagaaact ttattgccaa atgtttgaac gatcggggaa 5760
attcgagctc ggtagcaatt cccgaggctg tagccgacga tggtgcgcca ggagagttgt 5820
tgattcattg tttgcctccc tgctgcggtt tttcaccgaa gttcatgcca gtccagcgtt 5880
tttgcagcag aaaagccgcc gacttgtcga ccgatcggtc aaacatttgg caataaagtt 5940
tcttaagatt gaatcctgtt gccggtcttg cgatgattat catataattt ctgttgaatt 6000
acgttaagca tgtaataatt aacatgtaat gcatgacgtt atttatgaga tgggttttta 6060
tgattagagt cccgcaatta tacatttaat acgcgataga aaacaaaata tagcgcgcaa 6120
actaggataa attatcgcgc gcggtgtcat ctatgttact agatcgggaa gcttggcgta 6180
atcatggcaa ctttattata caaagttggc attataaaaa agcattgctt atcaatttgt 6240
tgcaacgaac aggtcactat cagtcaaaat aaaatcatta ttcaacttta ttatacatag 6300
ttgataattc actggccgga tctgcttggt aataattgtc attagattgt ttttatgcat 6360
agatgcactc gaaatcagcc aattttagac aagtatcaaa cggatgttaa ttcagtacat 6420
taaagacgtc cgcaatgtgt tattaagttg tctaagcgtc aatttgttta caccacaata 6480
tatcctgcca ccagccagcc aacagctccc cgaccggcag ctcggcacaa aatcaccacg 6540
cgttaccacc acgccggccg gccgcatggt gttgaccgtg ttcgccggca ttgccgagtt 6600
cgagcgttcc ctaatcatcg accgcacccg gagcgggcgc gaggccgcca aggcccgagg 6660
cgtgaagttt ggcccccgcc ctaccctcac cccggcacag atcgcgcacg cccgcgagct 6720
gatcgaccag gaaggccgca ccgtgaaaga ggcggctgca ctgcttggcg tgcatcgctc 6780
gaccctgtac cgcgcacttg agcgcagcga ggaagtgacg cccaccgagg ccaggcggcg 6840
cggtgccttc cgtgaggacg cattgaccga ggccgacgcc ctggcggccg ccgagaatga 6900
acgccaagag gaacaagcat gaaaccgcac caggacggcc aggacgaacc gtttttcatt 6960
accgaagaga tcgaggcgga gatgatcgcg gccgggtacg tgttcgagcc gcccgcgcac 7020
gtctcaaccg tgcggctgca tgaaatcctg gccggtttgt ctgatgccaa gctggcggcc 7080
tggccggcca gcttggccgc tgaagaaacc gagcgccgcc gtctaaaaag gtgatgtgta 7140
tttgagtaaa acagcttgcg tcatgcggtc gctgcgtata tgatgcgatg agtaaataaa 7200
caaatacgca aggggaacgc atgaaggtta tcgctgtact taaccagaaa ggcgggtcag 7260
gcaagacgac catcgcaacc catctagccc gcgccctgca actcgccggg gccgatgttc 7320
tgttagtcga ttccgatccc cagggcagtg cccgcgattg ggcggccgtg cgggaagatc 7380
aaccgctaac cgttgtcggc atcgaccgcc cgacgattga ccgcgacgtg aaggccatcg 7440
gccggcgcga cttcgtagtg atcgacggag cgccccaggc ggcggacttg gctgtgtccg 7500
cgatcaaggc agccgacttc gtgctgattc cggtgcagcc aagcccttac gacatatggg 7560
ccaccgccga cctggtggag ctggttaagc agcgcattga ggtcacggat ggaaggctac 7620
aagcggcctt tgtcgtgtcg cgggcgatca aaggcacgcg catcggcggt gaggttgccg 7680
aggcgctggc cgggtacgag ctgcccattc ttgagtcccg tatcacgcag cgcgtgagct 7740
acccaggcac tgccgccgcc ggcacaaccg ttcttgaatc agaacccgag ggcgacgctg 7800
cccgcgaggt ccaggcgctg gccgctgaaa ttaaatcaaa actcatttga gttaatgagg 7860
taaagagaaa atgagcaaaa gcacaaacac gctaagtgcc ggccgtccga gcgcacgcag 7920
cagcaaggct gcaacgttgg ccagcctggc agacacgcca gccatgaagc gggtcaactt 7980
tcagttgccg gcggaggatc acaccaagct gaagatgtac gcggtacgcc aaggcaagac 8040
cattaccgag ctgctatctg aatacatcgc gcagctacca gagtaaatga gcaaatgaat 8100
aaatgagtag atgaatttta gcggctaaag gaggcggcat ggaaaatcaa gaacaaccag 8160
gcaccgacgc cgtggaatgc cccatgtgtg gaggaacggg cggttggcca ggcgtaagcg 8220
gctgggttgt ctgccggccc tgcaatggca ctggaacccc caagcccgag gaatcggcgt 8280
gagcggtcgc aaaccatccg gcccggtaca aatcggcgcg gcgctgggtg atgacctggt 8340
ggagaagttg aaggccgcgc aggccgccca gcggcaacgc atcgaggcag aagcacgccc 8400
cggtgaatcg tggcaagcgg ccgctgatcg aatccgcaaa gaatcccggc aaccgccggc 8460
agccggtgcg ccgtcgatta ggaagccgcc caagggcgac gagcaaccag atttttcgt 8520
tccgatgctc tatgacgtgg gcacccgcga tagtcgcagc atcatggacg tggccgtttt 8580
ccgtctgtcg aagcgtgacc gacgagctgg cgaggtgatc cgctacgagc ttccagacgg 8640
gcacgtagag gtttccgcag ggccggccgg catggccagt gtgtgggatt acgacctggt 8700
actgatggcg gtttcccatc taaccgaatc catgaaccga taccgggaag ggaagggaga 8760
caagcccggc cgcgtgttcc gtccacacgt tgcggacgta ctcaagttct gccggcgagc 8820
cgatggcgga aagcagaaag acgacctggt agaaacctgc attcggttaa acaccacgca 8880
cgttgccatg cagcgtacga agaaggccaa gaacggccgc ctggtgacgg tatccgaggg 8940
tgaagccttg attagccgct acaagatcgt aaagagcgaa accgggcggc cggagtacat 9000
cgagatcgag ctagctgatt ggatgtaccg cgagatcaca gaaggcaaga acccggacgt 9060
gctgacggtt caccccgatt actttttgat cgatcccggc atcggccgtt ttctctaccg 9120
cctggcacgc cgcgccgcag gcaaggcaga agccagatgg ttgttcaaga cgatctacga 9180
acgcagtggc agcgccggag agttcaagaa gttctgtttc accgtgcgca agctgatcgg 9240
gtcaaatgac ctgccggagt acgatttgaa ggaggaggcg gggcaggctg gcccgatcct 9300

```
agtcatgcgc taccgcaacc tgatcgaggg cgaagcatcc gccggttcct aatgtacgga   9360
gcagatgcta gggcaaattg ccctagcagg ggaaaaaggt cgaaaaggtc tctttcctgt   9420
ggatagcacg tacattggga acccaaagcc gtacattggg aaccggaacc cgtacattgg   9480
gaacccaaag ccgtacattg ggaaccggtc acacatgtaa gtgactgata taaaagagaa   9540
aaaaggcgat ttttccgcct aaaactcttt aaaacttatt aaaactctta aaacccgcct   9600
ggcctgtgca taactgtctg gccagcgcac agccgaagag ctgcaaaaag cgcctaccct   9660
tcggtcgctg cgctccctac gccccgccgc ttcgcgtcgg cctatcgcgg ccgctggccg   9720
ctcaaaaatg gctggcctac ggccaggcaa tctaccaggg cgcggacaag ccgcgccgtc   9780
gccactcgac cgccggcgcc cacatcaagg caccctgcct cgcgcgtttc ggtgatgacg   9840
gtgaaaacct ctgacacatg cagctcccgg agacggtcac agcttgtctg taagcggatg   9900
ccgggagcag acaagcccgt cagggcgcgt cagcgggtgt tggcgggtgt cggggcgcag   9960
ccatgaccca gtcacgtagc gatagcggag tgtatactgg cttaactatg cggcatcaga  10020
gcagattgta ctgagagtgc accatatgcg gtgtgaaata ccgcacagat gcgtaaggag  10080
aaaataccgc atcaggcgct cttccgcttc ctcgctcact gactcgctgc gctcggtcgt  10140
tcggctgcgg cgagcggtat cagctcactc aaaggcggta atacggttat ccacagaatc  10200
aggggataac gcaggaaaga acatgtgagc aaaaggccag caaaaggcca ggaaccgtaa  10260
aaaggccgcg ttgctggcgt ttttccatag gctccgcccc cctgacgagc atcacaaaaa  10320
tcgacgctca agtcagaggt ggcgaaaccc gacaggacta taaagatacc aggcgtttcc  10380
ccctggaagc tccctcgtgc gctctcctgt tccgaccctg ccgcttaccg gatacctgtc  10440
cgcctttctc ccttcgggaa gcgtggcgct ttctcatagc tcacgctgta ggtatctcag  10500
ttcggtgtag gtcgttcgct ccaagctggg ctgtgtgcac gaaccccccg ttcagcccga  10560
ccgctgcgcc ttatccggta actatcgtct tgagtccaac ccggtaagac acgacttatc  10620
gccactggca gcagccactg gtaacaggat tagcagagcg aggtatgtag gcggtgctac  10680
agagttcttg aagtggtggc ctaactacgg ctacactaga aggacagtat ttggtatctg  10740
cgctctgctg aagccagtta ccttcggaaa aagagttggt agctcttgat ccggcaaaca  10800
aaccaccgct ggtagcggtg gtttttttgt ttgcaagcag cagattacgc gcagaaaaaa  10860
aggatctcaa gaagatcctt tgatcttttc tacggggtct gacgctcagt ggaacgaaaa  10920
ctcacgttaa gggattttgg tcatgcatga tatatctccc aatttgtgta gggcttatta  10980
tgcacgctta aaaataataa aagcagactt gacctgatag tttggctgtg agcaattatg  11040
tgcttagtgc atctaacgct tgagttaagc cgcgccgcga agcggcgtcg gcttgaacga  11100
atttctagct agacattatt tgccgactac cttggtgatc tcgcctttca cgtagtggac  11160
aaattcttcc aactgatctg cgcgcgaggc caagcgatct tcttcttgtc caagataagc  11220
ctgtctagct tcaagtatga cgggctgata ctgggccggc aggcgctcca ttgcccagtc  11280
ggcagcgaca tccttcggcg cgattttgcc ggttactgcg ctgtaccaaa tgcgggacaa  11340
cgtaagcact acatttcgct catcgccagc ccagtcgggc ggcgagttcc atagcgttaa  11400
ggtttcattt agcgcctcaa atagatcctg ttcaggaacc ggatcaaaga gttcctccgc  11460
cgctggacct accaaggcaa cgctatgttc tcttgctttt gtcagcaaga tagccagatc  11520
aatgtcgatc gtggctggct cgaagatacc tgcaagaatg tcattgcgct gccattctcc  11580
aaattgcagt tcgcgcttag ctggataacg ccacggaatg atgtcgtcgt gcacaacaat  11640
ggtgacttct acagcgcgga gaatctcgct ctctccaggg gaagccgaag tttccaaaag  11700
```

```
gtcgttgatc aaagctcgcc gcgttgtttc atcaagcctt acggtcaccg taaccagcaa  11760

atcaatatca ctgtgtggct tcaggccgcc atccactgcg gagccgtaca aatgtacggc  11820

cagcaacgtc ggttcgagat ggcgctcgat gacgccaact acctctgata gttgagtcga  11880

tacttcggcg atcaccgctt cccccatgat gtttaacttt gttttagggc gactgccctg  11940

ctgcgtaaca tcgttgctgc tccataacat caaacatcga cccacggcgt aacgcgcttg  12000

ctgcttggat gcccgaggca tagactgtac cccaaaaaaa cagtcataac aagccatgaa  12060

aaccgccact gcgttccatg gacatacaaa tggacgaacg gataaacctt ttcacgccct  12120

tttaaatatc cgattattct aataaacgct cttttctctt aggtttaccc gccaatatat  12180

cctgtcaaac actgatagtt taaactgaag gcgggaaacg acaatcagat ctagtaggaa  12240

acagctatga ccatgattac gccaagctat cgattacgcc aagctat               12287


<210> SEQ ID NO 2
<211> LENGTH: 12261
<212> TYPE: DNA
<213> ORGANISM: Unknown
<220> FEATURE:
<223> OTHER INFORMATION: Binary expression vector
      Lo546a-pSUN1-R4-Lo484::Lo376::Lo522a
<220> FEATURE:
<221> NAME/KEY: misc_feature
<222> LOCATION: (1)..(21)
<223> OTHER INFORMATION: attB4 recombination site
<220> FEATURE:
<221> NAME/KEY: promoter
<222> LOCATION: (49)..(905)
<223> OTHER INFORMATION: CaMV 35S promoter
<220> FEATURE:
<221> NAME/KEY: misc_feature
<222> LOCATION: (912)..(1719)
<223> OTHER INFORMATION: coding for mGFP5er
<220> FEATURE:
<221> NAME/KEY: terminator
<222> LOCATION: (1762)..(2431)
<223> OTHER INFORMATION: E9 terminator
<220> FEATURE:
<221> NAME/KEY: misc_feature
<222> LOCATION: (2432)..(2455)
<223> OTHER INFORMATION: attB1 recombination site
<220> FEATURE:
<221> NAME/KEY: misc_feature
<222> LOCATION: (2542)..(2565)
<223> OTHER INFORMATION: attb2 recombination site
<220> FEATURE:
<221> NAME/KEY: promoter
<222> LOCATION: (2581)..(3899)
<223> OTHER INFORMATION: STPT promoter
<220> FEATURE:
<221> NAME/KEY: misc_feature
<222> LOCATION: (3930)..(4777)
<223> OTHER INFORMATION: coding for nptII
<220> FEATURE:
<221> NAME/KEY: terminator
<222> LOCATION: (4816)..(5494)
<223> OTHER INFORMATION: E9 terminator
<220> FEATURE:
<221> NAME/KEY: terminator
<222> LOCATION: (5500)..(5752)
<223> OTHER INFORMATION: complement: nos terminator
<220> FEATURE:
<221> NAME/KEY: terminator
<222> LOCATION: (5881)..(6143)
<223> OTHER INFORMATION: nos terminator
<220> FEATURE:
<221> NAME/KEY: misc_feature
<222> LOCATION: (6257)..(6277)
<223> OTHER INFORMATION: complement: attB3 recombination site
<220> FEATURE:
<221> NAME/KEY: misc_feature
<222> LOCATION: (6296)..(6510)
```

-continued

<223> OTHER INFORMATION: LB
<220> FEATURE:
<221> NAME/KEY: misc_feature
<222> LOCATION: (8219)..(9326)
<223> OTHER INFORMATION: repA
<220> FEATURE:
<221> NAME/KEY: rep_origin
<222> LOCATION: (10075)..(10921)
<223> OTHER INFORMATION: complement: ColE1
<220> FEATURE:
<221> NAME/KEY: misc_feature
<222> LOCATION: (11090)..(11881)
<223> OTHER INFORMATION: complement: aadA marker (spectomycin)
<220> FEATURE:
<221> NAME/KEY: misc_feature
<222> LOCATION: (12055)..(12200)
<223> OTHER INFORMATION: RB

<400> SEQUENCE: 2
caactttgta tagaaaagtt ggccatgatt acgccaagct tgcatgcctg caggtcccca 60
gattagcctt ttcaatttca gaaagaatgc taacccacag atggttagag aggcttacgc 120
agcaggtctc atcaagacga tctacccgag caataatctc caggaaatca aataccttcc 180
caagaaggtt aaagatgcag tcaaaagatt caggactaac tgcatcaaga acacagagaa 240
agatatattt ctcaagatca gaagtactat tccagtatgg acgattcaag gcttgcttca 300
caaaccaagg caagtaatag agattggagt ctctaaaaag gtagttccca ctgaatcaaa 360
ggccatggag tcaaagattc aaatagagga cctaacagaa ctcgccgtaa agactggcga 420
acagttcata cagagtctct tacgactcaa tgacaagaag aaaatcttcg tcaacatggt 480
ggagcacgac acacttgtct actccaaaaa tatcaaagat acagtctcag aagaccaaag 540
ggcaattgag acttttcaac aaagggtaat atccggaaac ctcctcggat tccattgccc 600
agctatctgt cactttattg tgaagatagt ggaaaaggaa ggtggctcct acaaatgcca 660
tcattgcgat aaaggaaagg ccatcgttga agatgcctct gccgacagtg gtcccaaaga 720
tggaccccca cccacgagga gcatcgtgga aaaagaagac gttccaacca cgtcttcaaa 780
gcaagtggat tgatgtgata tctccactga cgtaagggat gacgcacaat cccactatcc 840
ttcgcaagac ccttcctcta tataaggaag ttcatttcat ttggagagaa cacgggggac 900
tctagaggat ccaaggagat ataacaatga agactaatct tttctcttt ctcatctttt 960 cacttctcct atcattatcc tcggccgaat tcagtaaagg agaagaactt ttcactggag 1020
ttgtcccaat tcttgttgaa ttagatggtg atgttaatgg gcacaaattt tctgtcagtg 1080
gagagggtga aggtgatgca acatacggaa aacttaccct taaatttatt tgcactactg 1140
gaaaactacc tgttccatgg ccaacacttg tcactacttt ctcttatggt gttcaatgct 1200
tttcaagata cccagatcat atgaagcggc acgacttctt caagagcgcc atgcctgagg 1260
gatacgtgca ggagaggacc atcttcttca aggacgacgg gaactacaag acacgtgctg 1320
aagtcaagtt tgagggagac accctcgtca acaggatcga gcttaaggga atcgatttca 1380
aggaggacgg aaacatcctc ggccacaagt tggaatacaa ctacaactcc cacaacgtat 1440
acatcatggc cgacaagcaa aagaacggca tcaaagccaa cttcaagacc cgccacaaca 1500
tcgaagacgg cggcgtgcaa ctcgctgatc attatcaaca aaatactcca attggcgatg 1560
gccctgtcct tttaccagac aaccattacc tgtccacaca atctgccctt tcgaaagatc 1620
ccaacgaaaa gagagaccac atggtccttc ttgagtttgt aacagctgct gggattacac 1680
atggcatgga tgaactatac aaacatgatg agctttaaga gaacggatcc ccatctgcgg 1740
ccgcctcgag catatgctag aggatcctct agctagagct ttcgttcgta tcatcggttt 1800

-continued

```
cgacaacgtt cgtcaagttc aatgcatcag tttcattgcg cacacaccag aatcctactg   1860
agtttgagta ttatggcatt gggaaaactg tttttcttgt accatttgtt gtgcttgtaa   1920
tttactgtgt tttttattcg gttttcgcta tcgaactgtg aaatggaaat ggatggagaa   1980
gagttaatga atgatatggt ccttttgttc attctcaaat taatattatt tgttttttct   2040
cttatttgtt gtgtgttgaa tttgaaatta taagagatat gcaaacattt tgttttgagt   2100
aaaaatgtgt caaatcgtgg cctctaatga ccgaagttaa tatgaggagt aaaacacttg   2160
tagttgtacc attatgctta ttcactaggc aacaaatata ttttcagacc tagaaaagct   2220
gcaaatgtta ctgaatacaa gtatgtcctc ttgtgtttta gacatttatg aactttcctt   2280
tatgtaattt tccagaatcc ttgtcagatt ctaatcattg ctttataatt atagttatac   2340
tcatggattt gtagttgagt atgaaaatat tttttaatgc attttatgac ttgccaattg   2400
attgacaaca tgcatcaatc gaccgggtac ccaagtttgt acaaaaaagc aggctggtac   2460
ccggggatcc tctaggtcga ccagatctga tatctgcggc cgcctcgagc atatgggcat   2520
gcaagcttgg cgtaatcatg gacccagctt tcttgtacaa agtggggtac ccggggatcc   2580
tgatagctta tactcaaatt caacaagtta tatataaatg tatagatact acaatatcat   2640
taacaaaagt caccttaaat aaatacacat atcttttatg ttctctattg ttttgcgtac   2700
gctaacacaa tttctcatat gcaaaaggat gaatgagtaa caaattacct cataagaaca   2760
atcatctttg cttacatact aatacaataa tcactcaatc aaccaataac atcaatcaca   2820
taggtttaca tacaataatc actcaatcaa cttcataaga agaatcatgt ttacttaatt   2880
catcaattat ccccaaaaac accactatta agtataaact acaacatatt tgtagtgatg   2940
ggtcaacatt tttatcatat ttaaactcgg gttccctcaa atcgagaaat agtgaacatg   3000
taatattaat tttaaatcgc aattacagaa attaattgaa tttggtcaaa tggacagaat   3060
tttatagatt gggtggaact agaaaaaaaa aaaaaaagag tatagggtga attgagtaca   3120
tgaaagtaca tggtaatcct agttaaacgc ataatacatg tgggttcatt tgtatttttt   3180
tgtaacttac gagtaaactg gctacaacaa aaaaaaatta gaagattttt ttgttttgta   3240
gaaaacccta attttagtta tagttgtata actttgataa aattataaaa ttgtattacg   3300
aaaaaagtaa taagatattc aaaaaagcct agaataacgt atatgactat gagcatgaaa   3360
ctgcaagtca aatgctgaca gacaaccata aacaaaagaa attaaataga gataccttta   3420
aaataagtaa aatttcattt ataaaaaatc tactttcttg tgaatctgtc acgttcaata   3480
atttgaagac cactcaacat acaaggtaaa taatgaaaaa taaaatctac caaaatttca   3540
atcattatta tcttccaaaa aaacaaaatt atacagatga tgatggtgat atggaacttc   3600
gattggctaa tattcactgt gtctctaaaa accatccact tatcaagata agatggaccc   3660
tacactcatc caatctaaac cagtatctca agattcttat ctaattacat cattctctac   3720
cgttagatga aattgaccat taaccctacc ataactccat acaccgcgag atactggatt   3780
aaccaaatcg agatcatcgt agccgtccga tcaacaagta ccatctcttg aaatactcga   3840
aatcctcata agtccgtccc tctttgctct cactatcaaa actctgaatt tcgatttcat   3900
ctagagtcga gcccgggcga tatcggatct cgactctagt cgagggccca tgggagcttg   3960
gattgaacaa gatggattgc acgcaggttc tccggccgct tgggtggaga ggctattcgg   4020
ctatgactgg gcacaacaga caatcggctg ctctgatgcc gccgtgttcc ggctgtcagc   4080
gcaggggcgc ccggttcttt ttgtcaagac cgacctgtcc ggtgccctga atgaactgca   4140
ggacgaggca gcgcggctat cgtggctggc cacgacgggc gttccttgcg cagctgtgct   4200
```

-continued

```
cgacgttgtc actgaagcgg gaagggactg gctgctattg ggcgaagtgc cggggcagga   4260
tctcctgtca tctcaccttg ctcctgccga gaaagtatcc atcatggctg atgcaatgcg   4320
gcggctgcat acgcttgatc cggctacctg cccattcgac caccaagcga aacatcgcat   4380
cgagcgagca cgtactcgga tggaagccgg tcttgtcgat caggatgatc tggacgaaga   4440
gcatcagggg ctcgcgccag ccgaactgtt cgccaggctc aaggcgcgca tgcccgacgg   4500
cgaggatctc gtcgtgaccc atggcgatgc ctgcttgccg aatatcatgg tggaaaatgg   4560
ccgcttttct ggattcatcg actgtggccg gctgggtgtg gcggaccgct atcaggacat   4620
agcgttggct acccgtgata ttgctgaaga gcttggcggc gaatgggctg accgcttcct   4680
cgtgctttac ggtatcgccg ctcccgattc gcagcgcatc gccttctatc gccttcttga   4740
cgagttcttc tgagcgggac ccaagctagc ttcgacggat cctctagcat atgctcgagg   4800
cggccgcaga tatcagatcc tctagctaga gctttcgttc gtatcatcgg tttcgacaac   4860
gttcgtcaag ttcaatgcat cagtttcatt gcgcacacac cagaatccta ctgagtttga   4920
gtattatggc attgggaaaa ctgtttttct tgtaccattt gttgtgcttg taatttactg   4980
tgtttttat tcggttttcg ctatcgaact gtgaaatgga aatggatgga gaagagttaa    5040
tgaatgatat ggtccttttg ttcattctca aattaatatt atttgttttt tctcttattt   5100
gttgtgtgtt gaatttgaaa ttataagaga tatgcaaaca ttttgttttg agtaaaaatg   5160
tgtcaaatcg tggcctctaa tgaccgaagt taatatgagg agtaaaacac ttgtagttgt   5220
accattatgc ttattcacta ggcaacaaat atattttcag acctagaaaa gctgcaaatg   5280
ttactgaata caagtatgtc ctcttgtgtt ttagacattt atgaactttc ctttatgtaa   5340
ttttccagaa tccttgtcag attctaatca ttgctttata attatagtta tactcatgga   5400
tttgtagttg agtatgaaaa tatttttaa tgcattttat gacttgccaa ttgattgaca    5460
acatgcatca atcgacctgc agcccaagct tgatctagtc cgatctagta acatagatga   5520
caccgcgcgc gataatttat cctagtttgc gcgctatatt ttgttttcta tcgcgtatta   5580
aatgtataat tgcgggactc taatcataaa aacccatctc ataaataacg tcatgcatta   5640
catgttaatt attacatgct taacgtaatt caacagaaat tatatgataa tcatcgcaag   5700
accggcaaca ggattcaatc ttaagaaact ttattgccaa atgtttgaac gatcggggaa   5760
attcgagctc ggtagcaatt cccgaggctg tagccgacga tggtgcgcca ggagagttgt   5820
tgattcattg tttgcctccc tgctgcggtt tttcaccgaa gttcatgcca gtccagcgtg   5880
tcgaccgatc ggtcaaacat ttggcaataa agtttcttaa gattgaatcc tgttgccggt   5940
cttgcgatga ttatcatata atttctgttg aattacgtta agcatgtaat aattaacatg   6000
taatgcatga cgttatttat gagatgggtt tttatgatta gagtcccgca attatacatt   6060
taatacgcga tagaaaacaa aatatagcgc gcaaactagg ataaattatc gcgcgcggtg   6120
tcatctatgt tactagatcg ggaagcttgg cgtaatcatg gcaactttat tatacaaagt   6180
tggcattata aaaaagcatt gcttatcaat ttgttgcaac gaacaggtca ctatcagtca   6240
aaataaaatc attattcaac tttattatac atagttgata attcactggc cggatctgct   6300
tggtaataat tgtcattaga ttgtttttat gcatagatgc actcgaaatc agccaatttt   6360
agacaagtat caaacggatg ttaattcagt acattaaaga cgtccgcaat gtgttattaa   6420
gttgtctaag cgtcaatttg tttacaccac aatatatcct gccaccagcc agccaacagc   6480
tccccgaccg gcagctcggc acaaaatcac cacgcgttac caccacgccg gccggccgca   6540
tggtgttgac cgtgttcgcc ggcattgccg agttcgagcg ttccctaatc atcgaccgca   6600
```

-continued

```
cccggagcgg gcgcgaggcc gccaaggccc gaggcgtgaa gtttggcccc cgccctaccc   6660
tcaccccggc acagatcgcg cacgcccgcg agctgatcga ccaggaaggc cgcaccgtga   6720
aagaggcggc tgcactgctt ggcgtgcatc gctcgaccct gtaccgcgca cttgagcgca   6780
gcgaggaagt gacgcccacc gaggccaggc ggcgcggtgc cttccgtgag gacgcattga   6840
ccgaggccga cgccctggcg gccgccgaga atgaacgcca agaggaacaa gcatgaaacc   6900
gcaccaggac ggccaggacg aaccgttttt cattaccgaa gagatcgagg cggagatgat   6960
cgcggccggg tacgtgttcg agccgcccgc gcacgtctca accgtgcggc tgcatgaaat   7020
cctggccggt ttgtctgatg ccaagctggc ggcctggccg gccagcttgg ccgctgaaga   7080
aaccgagcgc cgccgtctaa aaaggtgatg tgtatttgag taaaacagct tgcgtcatgc   7140
ggtcgctgcg tatatgatgc gatgagtaaa taaacaaata cgcaagggga acgcatgaag   7200
gttatcgctg tacttaacca gaaaggcggg tcaggcaaga cgaccatcgc aacccatcta   7260
gcccgcgccc tgcaactcgc cggggccgat gttctgttag tcgattccga tccccagggc   7320
agtgcccgcg attgggcggc cgtgcgggaa gatcaaccgc taaccgttgt cggcatcgac   7380
cgcccgacga ttgaccgcga cgtgaaggcc atcggccggc gcgacttcgt agtgatcgac   7440
ggagcgcccc aggcggcgga cttggctgtg tccgcgatca aggcagccga cttcgtgctg   7500
attccggtgc agccaagccc ttacgacata tgggccaccg ccgacctggt ggagctggtt   7560
aagcagcgca ttgaggtcac ggatggaagg ctacaagcgg cctttgtcgt gtcgcgggcg   7620
atcaaaggca cgcgcatcgg cggtgaggtt gccgaggcgc tggccgggta cgagctgccc   7680
attcttgagt cccgtatcac gcagcgcgtg agctacccag gcactgccgc cgccggcaca   7740
accgttcttg aatcagaacc cgagggcgac gctgcccgcg aggtccaggc gctggccgct   7800
gaaattaaat caaaactcat ttgagttaat gaggtaaaga gaaaatgagc aaaagcacaa   7860
acacgctaag tgccggccgt ccgagcgcac gcagcagcaa ggctgcaacg ttggccagcc   7920
tggcagacac gccagccatg aagcgggtca actttcagtt gccggcggag gatcacacca   7980
agctgaagat gtacgcggta cgccaaggca agaccattac cgagctgcta tctgaataca   8040
tcgcgcagct accagagtaa atgagcaaat gaataaatga gtagatgaat tttagcggct   8100
aaaggaggcg gcatggaaaa tcaagaacaa ccaggcaccg acgccgtgga atgccccatg   8160
tgtggaggaa cgggcggttg gccaggcgta agcggctggg ttgtctgccg gccctgcaat   8220
ggcactggaa cccccaagcc cgaggaatcg gcgtgagcgg tcgcaaacca tccggcccgg   8280
tacaaatcgg cgcggcgctg ggtgatgacc tggtggagaa gttgaaggcc gcgcaggccg   8340
cccagcggca acgcatcgag gcagaagcac gccccggtga atcgtggcaa gcggccgctg   8400
atcgaatccg caaagaatcc cggcaaccgc cggcagccgg tgcgccgtcg attaggaagc   8460
cgcccaaggg cgacgagcaa ccagattttt tcgttccgat gctctatgac gtgggcaccc   8520
gcgatagtcg cagcatcatg gacgtggccg ttttccgtct gtcgaagcgt gaccgacgag   8580
ctggcgaggt gatccgctac gagcttccag acgggcacgt agaggtttcc gcagggccgg   8640
ccggcatggc cagtgtgtgg gattacgacc tggtactgat ggcggtttcc catctaaccg   8700
aatccatgaa ccgataccgg gaagggaagg gagacaagcc cggccgcgtg ttccgtccac   8760
acgttgcgga cgtactcaag ttctgccggc gagccgatgg cggaaagcag aaagacgacc   8820
tggtagaaac ctgcattcgg ttaaacacca cgcacgttgc catgcagcgt acgaagaagg   8880
ccaagaacgg ccgcctggtg acggtatccg agggtgaagc cttgattagc cgctacaaga   8940
tcgtaaagag cgaaaccggg cggccggagt acatcgagat cgagctagct gattggatgt   9000
```

```
accgcgagat cacagaaggc aagaacccgg acgtgctgac ggttcacccc gattactttt   9060
tgatcgatcc cggcatcggc cgttttctct accgcctggc acgccgcgcc gcaggcaagg   9120
cagaagccag atggttgttc aagacgatct acgaacgcag tggcagcgcc ggagagttca   9180
agaagttctg tttcaccgtg cgcaagctga tcgggtcaaa tgacctgccg gagtacgatt   9240
tgaaggagga ggcggggcag gctggcccga tcctagtcat gcgctaccgc aacctgatcg   9300
agggcgaagc atccgccggt tcctaatgta cggagcagat gctagggcaa attgccctag   9360
caggggaaaa aggtcgaaaa ggtctctttc ctgtggatag cacgtacatt gggaacccaa   9420
agccgtacat tgggaaccgg aacccgtaca ttgggaaccc aaagccgtac attgggaacc   9480
ggtcacacat gtaagtgact gatataaaag agaaaaaagg cgatttttcc gcctaaaact   9540
ctttaaaact tattaaaact cttaaaaccc gcctggcctg tgcataactg tctggccagc   9600
gcacagccga agagctgcaa aaagcgccta cccttcggtc gctgcgctcc ctacgccccg   9660
ccgcttcgcg tcggcctatc gcggccgctg gccgctcaaa aatggctggc ctacggccag   9720
gcaatctacc agggcgcgga caagccgcgc cgtcgccact cgaccgccgg cgcccacatc   9780
aaggcaccct gcctcgcgcg tttcggtgat gacggtgaaa acctctgaca catgcagctc   9840
ccggagacgg tcacagcttg tctgtaagcg gatgccggga gcagacaagc ccgtcagggc   9900
gcgtcagcgg gtgttggcgg gtgtcggggc gcagccatga cccagtcacg tagcgatagc   9960
ggagtgtata ctggcttaac tatgcggcat cagagcagat tgtactgaga gtgcaccata  10020
tgcggtgtga aataccgcac agatgcgtaa ggagaaaata ccgcatcagg cgctcttccg  10080
cttcctcgct cactgactcg ctgcgctcgg tcgttcggct gcggcgagcg gtatcagctc  10140
actcaaaggc ggtaatacgg ttatccacag aatcagggga taacgcagga aagaacatgt  10200
gagcaaaagg ccagcaaaag gccaggaacc gtaaaaaggc cgcgttgctg gcgtttttcc  10260
ataggctccg cccccctgac gagcatcaca aaaatcgacg ctcaagtcag aggtggcgaa  10320
acccgacagg actataaaga taccaggcgt ttccccctgg aagctccctc gtgcgctctc  10380
ctgttccgac cctgccgctt accggatacc tgtccgcctt tctcccttcg ggaagcgtgg  10440
cgctttctca tagctcacgc tgtaggtatc tcagttcggt gtaggtcgtt cgctccaagc  10500
tgggctgtgt gcacgaaccc cccgttcagc ccgaccgctg cgccttatcc ggtaactatc  10560
gtcttgagtc caacccggta agacacgact tatcgccact ggcagcagcc actggtaaca  10620
ggattagcag agcgaggtat gtaggcggtg ctacagagtt cttgaagtgg tggcctaact  10680
acggctacac tagaaggaca gtatttggta tctgcgctct gctgaagcca gttaccttcg  10740
gaaaaagagt tggtagctct tgatccggca aacaaaccac cgctggtagc ggtggttttt  10800
ttgtttgcaa gcagcagatt acgcgcagaa aaaaaggatc tcaagaagat cctttgatct  10860
tttctacggg gtctgacgct cagtggaacg aaaactcacg ttaagggatt ttggtcatgc  10920
atgatatatc tcccaatttg tgtagggctt attatgcacg cttaaaaata ataaaagcag  10980
acttgacctg atagtttggc tgtgagcaat tatgtgctta gtgcatctaa cgcttgagtt  11040
aagccgcgcc gcgaagcggc gtcggcttga acgaatttct agctagacat tatttgccga  11100
ctaccttggt gatctcgcct ttcacgtagt ggacaaattc ttccaactga tctgcgcgcg  11160
aggccaagcg atcttcttct tgtccaagat aagcctgtct agcttcaagt atgacgggct  11220
gatactgggc cggcaggcgc tccattgccc agtcggcagc gacatccttc ggcgcgattt  11280
tgccggttac tgcgctgtac caaatgcggg acaacgtaag cactacattt cgctcatcgc  11340
cagcccagtc gggcggcgag ttccatagcg ttaaggtttc atttagcgcc tcaaatagat  11400
```

```
cctgttcagg aaccggatca aagagttcct ccgccgctgg acctaccaag gcaacgctat  11460

gttctcttgc ttttgtcagc aagatagcca gatcaatgtc gatcgtggct ggctcgaaga  11520

tacctgcaag aatgtcattg cgctgccatt ctccaaattg cagttcgcgc ttagctggat  11580

aacgccacgg aatgatgtcg tcgtgcacaa caatggtgac ttctacagcg cggagaatct  11640

cgctctctcc aggggaagcc gaagtttcca aaaggtcgtt gatcaaagct cgccgcgttg  11700

tttcatcaag ccttacggtc accgtaacca gcaaatcaat atcactgtgt ggcttcaggc  11760

cgccatccac tgcggagccg tacaaatgta cggccagcaa cgtcggttcg agatggcgct  11820

cgatgacgcc aactacctct gatagttgag tcgatacttc ggcgatcacc gcttccccca  11880

tgatgtttaa ctttgtttta gggcgactgc cctgctgcgt aacatcgttg ctgctccata  11940

acatcaaaca tcgacccacg gcgtaacgcg cttgctgctt ggatgcccga ggcatagact  12000

gtaccccaaa aaaacagtca taacaagcca tgaaaaccgc cactgcgttc catggacata  12060

caaatggacg aacggataaa ccttttcacg ccctttttaaa tatccgatta ttctaataaa  12120

cgctcttttc tcttaggttt acccgccaat atatcctgtc aaacactgat agtttaaact  12180

gaaggcggga aacgacaatc agatctagta ggaaacagct atgaccatga ttacgccaag  12240

ctatcgatta cgccaagcta t                                            12261
```

<210> SEQ ID NO 3
<211> LENGTH: 6256
<212> TYPE: DNA
<213> ORGANISM: Unknown
<220> FEATURE:
<223> OTHER INFORMATION: Nucleic acid construct
Lo522b-pENTR-C1-STPT-nptII-IRnos
<220> FEATURE:
<221> NAME/KEY: terminator
<222> LOCATION: (268)..(295)
<223> OTHER INFORMATION: complement
<220> FEATURE:
<221> NAME/KEY: terminator
<222> LOCATION: (427)..(470)
<223> OTHER INFORMATION: complement
<220> FEATURE:
<221> NAME/KEY: misc_feature
<222> LOCATION: (591)..(747)
<223> OTHER INFORMATION: attR2
<220> FEATURE:
<221> NAME/KEY: promoter
<222> LOCATION: (763)..(2081)
<223> OTHER INFORMATION: STPT promoter
<220> FEATURE:
<221> NAME/KEY: misc_feature
<222> LOCATION: (2112)..(2959)
<223> OTHER INFORMATION: nptII
<220> FEATURE:
<221> NAME/KEY: terminator
<222> LOCATION: (2998)..(3676)
<223> OTHER INFORMATION: E9 terminator
<220> FEATURE:
<221> NAME/KEY: terminator
<222> LOCATION: (3682)..(3934)
<223> OTHER INFORMATION: complement: nos terminator
<220> FEATURE:
<221> NAME/KEY: terminator
<222> LOCATION: (4089)..(4351)
<223> OTHER INFORMATION: nos terminator
<220> FEATURE:
<221> NAME/KEY: misc_feature
<222> LOCATION: (4370)..(4465)
<223> OTHER INFORMATION: complement: attL3
<220> FEATURE:
<221> NAME/KEY: misc_feature
<222> LOCATION: (4650)..(5459)
<223> OTHER INFORMATION: kanamycin resistance

<400> SEQUENCE: 3

-continued

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggggt acccggggat cctgatagct tatactcaaa    780
ttcaacaagt tatatataaa tgtatagata ctacaatatc attaacaaaa gtcaccttaa    840
ataaatacac atatctttta tgttctctat tgttttgcgt acgctaacac aatttctcat    900
atgcaaaagg atgaatgagt aacaaattac ctcataagaa caatcatctt tgcttacata    960
ctaatacaat aatcactcaa tcaaccaata acatcaatca cataggttta catacaataa   1020
tcactcaatc aacttcataa gaagaatcat gtttacttaa ttcatcaatt atccccaaaa   1080
acaccactat taagtataaa ctacaacata tttgtagtga tgggtcaaca tttttatcat   1140
atttaaactc gggttccctc aaatcgagaa atagtgaaca tgtaatatta attttaaatc   1200
gcaattacag aaattaattg aatttggtca aatggacaga attttataga ttgggtggaa   1260
ctagaaaaaa aaaaaaaaag agtatagggt gaattgagta catgaaagta catggtaatc   1320
ctagttaaac gcataataca tgtgggttca tttgtatttt tttgtaactt acgagtaaac   1380
tggctacaac aaaaaaaaat tagaagattt ttttgttttg tagaaaaccc taattttagt   1440
tatagttgta taactttgat aaaattataa aattgtatta cgaaaaaagt aataagatat   1500
tcaaaaaagc ctagaataac gtatatgact atgagcatga aactgcaagt caaatgctga   1560
cagacaacca taaacaaaag aaattaaata gagatacctt taaaataagt aaaatttcat   1620
ttataaaaaa tctactttct tgtgaatctg tcacgttcaa taatttgaag accactcaac   1680
atacaaggta aataatgaaa aataaaatct accaaaattt caatcattat tatcttccaa   1740
aaaaacaaaa ttatacagat gatgatggtg atatggaact tcgattggct aatattcact   1800
gtgtctctaa aaaccatcca cttatcaaga taagatggac cctacactca tccaatctaa   1860
accagtatct caagattctt atctaattac atcattctct accgttagat gaaattgacc   1920
attaacccta ccataactcc atacaccgcg agatactgga ttaaccaaat cgagatcatc   1980
gtagccgtcc gatcaacaag taccatctct tgaaatactc gaaatcctca taagtccgtc   2040
cctctttgct ctcactatca aaactctgaa tttcgatttc atctagagtc gagcccgggc   2100
gatatcggat ctcgactcta gtcgagggcc catgggagct tggattgaac aagatggatt   2160
gcacgcaggt tctccggccg cttgggtgga gaggctattc ggctatgact gggcacaaca   2220
gacaatcggc tgctctgatg ccgccgtgtt ccggctgtca gcgcaggggc gcccggttct   2280
ttttgtcaag accgacctgt ccggtgccct gaatgaactg caggacgagg cagcgcggct   2340
atcgtggctg gccacgacgg gcgttccttg cgcagctgtg ctcgacgttg tcactgaagc   2400
```

```
gggaagggac tggctgctat tgggcgaagt gccggggcag gatctcctgt catctcacct   2460
tgctcctgcc gagaaagtat ccatcatggc tgatgcaatg cggcggctgc atacgcttga   2520
tccggctacc tgcccattcg accaccaagc gaaacatcgc atcgagcgag cacgtactcg   2580
gatggaagcc ggtcttgtcg atcaggatga tctggacgaa gagcatcagg ggctcgcgcc   2640
agccgaactg ttcgccaggc tcaaggcgcg catgcccgac ggcgaggatc tcgtcgtgac   2700
ccatggcgat gcctgcttgc cgaatatcat ggtggaaaat ggccgctttt ctggattcat   2760
cgactgtggc cggctgggtg tggcggaccg ctatcaggac atagcgttgg ctacccgtga   2820
tattgctgaa gagcttggcg gcgaatgggc tgaccgcttc ctcgtgcttt acggtatcgc   2880
cgctcccgat tcgcagcgca tcgccttcta tcgccttctt gacgagttct tctgagcggg   2940
acccaagcta gcttcgacgg atcctctagc atatgctcga ggcggccgca gatatcagat   3000
cctctagcta gagctttcgt tcgtatcatc ggtttcgaca acgttcgtca agttcaatgc   3060
atcagtttca ttgcgcacac accagaatcc tactgagttt gagtattatg gcattgggaa   3120
aactgttttt cttgtaccat ttgttgtgct tgtaatttac tgtgtttttt attcggtttt   3180
cgctatcgaa ctgtgaaatg gaaatggatg gagaagagtt aatgaatgat atggtccttt   3240
tgttcattct caaattaata ttatttgttt tttctcttat ttgttgtgtg ttgaatttga   3300
aattataaga gatatgcaaa cattttgttt tgagtaaaaa tgtgtcaaat cgtggcctct   3360
aatgaccgaa gttaatatga ggagtaaaac acttgtagtt gtaccattat gcttattcac   3420
taggcaacaa atatattttc agacctagaa aagctgcaaa tgttactgaa tacaagtatg   3480
tcctcttgtg ttttagacat ttatgaactt tcctttatgt aattttccag aatccttgtc   3540
agattctaat cattgcttta taattatagt tatactcatg gatttgtagt tgagtatgaa   3600
aatatttttt aatgcatttt atgacttgcc aattgattga caacatgcat caatcgacct   3660
gcagcccaag cttgatctag tccgatctag taacatagat gacaccgcgc gcgataattt   3720
atcctagttt gcgcgctata ttttgttttc tatcgcgtat taaatgtata attgcgggac   3780
tctaatcata aaaacccatc tcataaataa cgtcatgcat tacatgttaa ttattacatg   3840
cttaacgtaa ttcaacagaa attatatgat aatcatcgca agaccggcaa caggattcaa   3900
tcttaagaaa ctttattgcc aaatgtttga acgatcgggg aaattcgagc tcggtagcaa   3960
ttcccgaggc tgtagccgac gatggtgcgc caggagagtt gttgattcat tgtttgcctc   4020
cctgctgcgg tttttcaccg aagttcatgc cagtccagcg tttttgcagc agaaaagccg   4080
ccgacttgtc gaccgatcgg tcaaacattt ggcaataaag tttcttaaga ttgaatcctg   4140
ttgccggtct tgcgatgatt atcatataat ttctgttgaa ttacgttaag catgtaataa   4200
ttaacatgta atgcatgacg ttatttatga gatgggtttt tatgattaga gtcccgcaat   4260
tatacattta atacgcgata gaaaacaaaa tatagcgcgc aaactaggat aaattatcgc   4320
gcgcggtgtc atctatgtta ctagatcggg aagcttggcg taatcatggc aactttatta   4380
tacaaagttg gcattataaa aaagcattgc ttatcaattt gttgcaacga acaggtcact   4440
atcagtcaaa ataaaatcat tatttggagc tccatggtag cgttaacgcg gccatcccct   4500
atagtgagtc gtattacatg gtcatagctg tttcctggca gctctggccc gtgtctcaaa   4560
atctctgatg ttacattgca caagataaaa atatatcatc atgaacaata aaactgtctg   4620
cttacataaa cagtaataca aggggtgtta tgagccatat tcaacgggaa acgtcgaggc   4680
cgcgattaaa ttccaacatg gatgctgatt tatatgggta taaatgggct cgcgataatg   4740
tcgggcaatc aggtgcgaca atctatcgct tgtatgggaa gcccgatgcg ccagagttgt   4800
```

```
ttctgaaaca tggcaaaggt agcgttgcca atgatgttac agatgagatg gtcagactaa   4860

actggctgac ggaatttatg cctcttccga ccatcaagca ttttatccgt actcctgatg   4920

atgcatggtt actcaccact gcgatccccg gaaaaacagc attccaggta ttagaagaat   4980

atcctgattc aggtgaaaat attgttgatg cgctggcagt gttcctgcgc cggttgcatt   5040

cgattcctgt ttgtaattgt ccttttaaca gcgatcgcgt atttcgtctc gctcaggcgc   5100

aatcacgaat gaataacggt ttggttgatg cgagtgattt tgatgacgag cgtaatggct   5160

ggcctgttga acaagtctgg aaagaaatgc ataaactttt gccattctca ccggattcag   5220

tcgtcactca tggtgatttc tcacttgata accttatttt tgacgagggg aaattaatag   5280

gttgtattga tgttggacga gtcggaatcg cagaccgata ccaggatctt gccatcctat   5340

ggaactgcct cggtgagttt tctccttcat tacagaaacg gctttttcaa aaatatggta   5400

ttgataatcc tgatatgaat aaattgcagt ttcatttgat gctcgatgag tttttctaat   5460

cagaattggt taattggttg taacactggc agagcattac gctgacttga cgggacggcg   5520

caagctcatg accaaaatcc cttaacgtga gttacgcgtc gttccactga gcgtcagacc   5580

ccgtagaaaa gatcaaagga tcttcttgag atcctttttt tctgcgcgta atctgctgct   5640

tgcaaacaaa aaaaccaccg ctaccagcgg tggtttgttt gccggatcaa gagctaccaa   5700

ctctttttcc gaaggtaact ggcttcagca gagcgcagat accaaatact gtccttctag   5760

tgtagccgta gttaggccac cacttcaaga actctgtagc accgcctaca tacctcgctc   5820

tgctaatcct gttaccagtg gctgctgcca gtggcgataa gtcgtgtctt accgggttgg   5880

actcaagacg atagttaccg gataaggcgc agcggtcggg ctgaacgggg ggttcgtgca   5940

cacagcccag cttggagcga acgacctaca ccgaactgag atacctacag cgtgagcatt   6000

gagaaagcgc cacgcttccc gaagggagaa aggcggacag gtatccggta agcggcaggg   6060

tcggaacagg agagcgcacg agggagcttc caggggggaaa cgcctggtat ctttatagtc   6120

ctgtcgggtt tcgccacctc tgacttgagc gtcgattttt gtgatgctcg tcaggggggc   6180

ggagcctatg gaaaaacgcc agcaacgcgg cctttttacg gttcctggcc ttttgctggc   6240

cttttgctca catgtt                                                   6256
```

```
<210> SEQ ID NO 4
<211> LENGTH: 6230
<212> TYPE: DNA
<213> ORGANISM: Unknown
<220> FEATURE:
<223> OTHER INFORMATION: Nucleic acid construct
      Lo522a-pENTR-C1-STPT-nptII-IRnos
<220> FEATURE:
<221> NAME/KEY: terminator
<222> LOCATION: (268)..(295)
<223> OTHER INFORMATION: complement: terminator
<220> FEATURE:
<221> NAME/KEY: terminator
<222> LOCATION: (427)..(470)
<223> OTHER INFORMATION: complement: terminator
<220> FEATURE:
<221> NAME/KEY: misc_feature
<222> LOCATION: (591)..(747)
<223> OTHER INFORMATION: attR2 recombination site
<220> FEATURE:
<221> NAME/KEY: promoter
<222> LOCATION: (763)..(2081)
<223> OTHER INFORMATION: STPT promoter
<220> FEATURE:
<221> NAME/KEY: misc_feature
<222> LOCATION: (2112)..(2959)
<223> OTHER INFORMATION: nptII
<220> FEATURE:
```

<221> NAME/KEY: terminator
<222> LOCATION: (2998)..(3676)
<223> OTHER INFORMATION: E9 terminator
<220> FEATURE:
<221> NAME/KEY: terminator
<222> LOCATION: (3682)..(3934)
<223> OTHER INFORMATION: complement: nos terminator
<220> FEATURE:
<221> NAME/KEY: terminator
<222> LOCATION: (4063)..(4325)
<223> OTHER INFORMATION: nos terminator
<220> FEATURE:
<221> NAME/KEY: misc_feature
<222> LOCATION: (4344)..(4439)
<223> OTHER INFORMATION: complement: attL3 recombination site
<220> FEATURE:
<221> NAME/KEY: misc_feature
<222> LOCATION: (4624)..(5433)
<223> OTHER INFORMATION: kanamycin resistance

<400> SEQUENCE: 4

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggggt acccggggat cctgatagct tatactcaaa    780
ttcaacaagt tatatataaa tgtatagata ctacaatatc attaacaaaa gtcaccttaa    840
ataaatacac atatctttta tgttctctat tgttttgcgt acgctaacac aatttctcat    900
atgcaaaagg atgaatgagt aacaaattac ctcataagaa caatcatctt tgcttacata    960
ctaatacaat aatcactcaa tcaaccaata acatcaatca cataggttta catacaataa   1020
tcactcaatc aacttcataa gaagaatcat gtttacttaa ttcatcaatt atccccaaaa   1080
acaccactat taagtataaa ctacaacata tttgtagtga tgggtcaaca tttttatcat   1140
atttaaactc gggttccctc aaatcgagaa atagtgaaca tgtaatatta attttaaatc   1200
gcaattacag aaattaattg aatttggtca aatggacaga attttataga ttgggtggaa   1260
ctagaaaaaa aaaaaaaaag agtatagggt gaattgagta catgaaagta catggtaatc   1320
ctagttaaac gcataataca tgtgggttca tttgtatttt tttgtaactt acgagtaaac   1380
tggctacaac aaaaaaaaat tagaagattt ttttgttttg tagaaaaccc taattttagt   1440
tatagttgta taactttgat aaaattataa aattgtatta cgaaaaaagt aataagatat   1500
tcaaaaaagc ctagaataac gtatatgact atgagcatga aactgcaagt caaatgctga   1560
cagacaacca taaacaaaag aaattaaata gagatacctt taaaataagt aaaatttcat   1620
ttataaaaaa tctactttct tgtgaatctg tcacgttcaa taatttgaag accactcaac   1680
atacaaggta aataatgaaa aataaaatct accaaaattt caatcattat tatcttccaa   1740
```

-continued

```
aaaaacaaaa ttatacagat gatgatggtg atatggaact tcgattggct aatattcact   1800
gtgtctctaa aaaccatcca cttatcaaga taagatggac cctacactca tccaatctaa   1860
accagtatct caagattctt atctaattac atcattctct accgttagat gaaattgacc   1920
attaacccta ccataactcc atacaccgcg agatactgga ttaaccaaat cgagatcatc   1980
gtagccgtcc gatcaacaag taccatctct tgaaatactc gaaatcctca taagtccgtc   2040
cctctttgct ctcactatca aaactctgaa tttcgatttc atctagagtc gagcccgggc   2100
gatatcggat ctcgactcta gtcgagggcc catgggagct tggattgaac aagatggatt   2160
gcacgcaggt tctccggccg cttgggtgga gaggctattc ggctatgact gggcacaaca   2220
gacaatcggc tgctctgatg ccgccgtgtt ccggctgtca gcgcaggggc gcccggttct   2280
ttttgtcaag accgacctgt ccggtgccct gaatgaactg caggacgagg cagcgcggct   2340
atcgtggctg gccacgacgg gcgttccttg cgcagctgtg ctcgacgttg tcactgaagc   2400
gggaagggac tggctgctat tgggcgaagt gccggggcag gatctcctgt catctcacct   2460
tgctcctgcc gagaaagtat ccatcatggc tgatgcaatg cggcggctgc atacgcttga   2520
tccggctacc tgcccattcg accaccaagc gaaacatcgc atcgagcgag cacgtactcg   2580
gatggaagcc ggtcttgtcg atcaggatga tctggacgaa gagcatcagg ggctcgcgcc   2640
agccgaactg ttcgccaggc tcaaggcgcg catgcccgac ggcgaggatc tcgtcgtgac   2700
ccatggcgat gcctgcttgc cgaatatcat ggtggaaaat ggccgctttt ctggattcat   2760
cgactgtggc cggctgggtg tggcggaccg ctatcaggac atagcgttgg ctacccgtga   2820
tattgctgaa gagcttggcg gcgaatgggc tgaccgcttc ctcgtgcttt acggtatcgc   2880
cgctcccgat tcgcagcgca tcgccttcta tcgccttctt gacgagttct tctgagcggg   2940
acccaagcta gcttcgacgg atcctctagc atatgctcga ggcggccgca gatatcagat   3000
cctctagcta gagctttcgt tcgtatcatc ggtttcgaca acgttcgtca agttcaatgc   3060
atcagtttca ttgcgcacac accagaatcc tactgagttt gagtattatg gcattgggaa   3120
aactgttttt cttgtaccat ttgttgtgct tgtaatttac tgtgtttttt attcggtttt   3180
cgctatcgaa ctgtgaaatg gaaatggatg gagaagagtt aatgaatgat atggtccttt   3240
tgttcattct caaattaata ttatttgttt tttctcttat ttgttgtgtg ttgaatttga   3300
aattataaga gatatgcaaa cattttgttt tgagtaaaaa tgtgtcaaat cgtggcctct   3360
aatgaccgaa gttaatatga ggagtaaaac acttgtagtt gtaccattat gcttattcac   3420
taggcaacaa atatatttc agacctagaa aagctgcaaa tgttactgaa tacaagtatg   3480
tcctcttgtg ttttagacat ttatgaactt tcctttatgt aattttccag aatccttgtc   3540
agattctaat cattgcttta taattatagt tatactcatg gatttgtagt tgagtatgaa   3600
aatatttttt aatgcatttt atgacttgcc aattgattga caacatgcat caatcgacct   3660
gcagcccaag cttgatctag tccgatctag taacatagat gacaccgcgc gcgataattt   3720
atcctagttt gcgcgctata ttttgttttc tatcgcgtat taaatgtata attgcgggac   3780
tctaatcata aaaacccatc tcataaataa cgtcatgcat tacatgttaa ttattacatg   3840
cttaacgtaa ttcaacagaa attatatgat aatcatcgca agaccggcaa caggattcaa   3900
tcttaagaaa ctttattgcc aaatgtttga acgatcgggg aaattcgagc tcggtagcaa   3960
ttcccgaggc tgtagccgac gatggtgcgc caggagagtt gttgattcat tgtttgcctc   4020
cctgctgcgg tttttcaccg aagttcatgc cagtccagcg tgtcgaccga tcggtcaaac   4080
atttggcaat aaagtttctt aagattgaat cctgttgccg gtcttgcgat gattatcata   4140
```

-continued

```
taatttctgt tgaattacgt taagcatgta ataattaaca tgtaatgcat gacgttattt   4200

atgagatggg tttttatgat tagagtcccg caattataca tttaatacgc gatagaaaac   4260

aaaatatagc gcgcaaacta ggataaatta tcgcgcgcgg tgtcatctat gttactagat   4320

cgggaagctt ggcgtaatca tggcaacttt attatacaaa gttggcatta taaaaaagca   4380

ttgcttatca atttgttgca acgaacaggt cactatcagt caaaataaaa tcattatttg   4440

gagctccatg gtagcgttaa cgcggccatc ccctatagtg agtcgtatta catggtcata   4500

gctgtttcct ggcagctctg gcccgtgtct caaaatctct gatgttacat tgcacaagat   4560

aaaaatatat catcatgaac aataaaactg tctgcttaca taaacagtaa tacaaggggt   4620

gttatgagcc atattcaacg ggaaacgtcg aggccgcgat taaattccaa catggatgct   4680

gatttatatg ggtataaatg ggctcgcgat aatgtcgggc aatcaggtgc gacaatctat   4740

cgcttgtatg ggaagcccga tgcgccagag ttgtttctga aacatggcaa aggtagcgtt   4800

gccaatgatg ttacagatga gatggtcaga ctaaactggc tgacggaatt tatgcctctt   4860

ccgaccatca agcattttat ccgtactcct gatgatgcat ggttactcac cactgcgatc   4920

cccggaaaaa cagcattcca ggtattagaa gaatatcctg attcaggtga aaatattgtt   4980

gatgcgctgg cagtgttcct gcgccggttg cattcgattc ctgtttgtaa ttgtcctttt   5040

aacagcgatc gcgtatttcg tctcgctcag gcgcaatcac gaatgaataa cggtttggtt   5100

gatgcgagtg attttgatga cgagcgtaat ggctggcctg ttgaacaagt ctggaaagaa   5160

atgcataaac ttttgccatt ctcaccggat tcagtcgtca ctcatggtga tttctcactt   5220

gataacctta tttttgacga ggggaaatta ataggttgta ttgatgttgg acgagtcgga   5280

atcgcagacc gataccagga tcttgccatc ctatggaact gcctcggtga gttttctcct   5340

tcattacaga aacggctttt tcaaaaatat ggtattgata atcctgatat gaataaattg   5400

cagtttcatt tgatgctcga tgagtttttc taatcagaat tggttaattg gttgtaacac   5460

tggcagagca ttacgctgac ttgacgggac ggcgcaagct catgaccaaa atcccttaac   5520

gtgagttacg cgtcgttcca ctgagcgtca gaccccgtag aaaagatcaa aggatcttct   5580

tgagatcctt tttttctgcg cgtaatctgc tgcttgcaaa caaaaaaacc accgctacca   5640

gcggtggttt gtttgccgga tcaagagcta ccaactcttt ttccgaaggt aactggcttc   5700

agcagagcgc agataccaaa tactgtcctt ctagtgtagc cgtagttagg ccaccacttc   5760

aagaactctg tagcaccgcc tacatacctc gctctgctaa tcctgttacc agtggctgct   5820

gccagtggcg ataagtcgtg tcttaccggg ttggactcaa gacgatagtt accggataag   5880

gcgcagcggt cgggctgaac ggggggttcg tgcacacagc ccagcttgga gcgaacgacc   5940

tacaccgaac tgagatacct acagcgtgag cattgagaaa gcgccacgct tcccgaaggg   6000

agaaaggcgg acaggtatcc ggtaagcggc agggtcggaa caggagagcg cacgagggag   6060

cttccagggg gaaacgcctg gtatctttat agtcctgtcg ggtttcgcca cctctgactt   6120

gagcgtcgat ttttgtgatg ctcgtcaggg gggcggagcc tatggaaaaa cgccagcaac   6180

gcggcctttt tacggttcct ggccttttgc tggccttttg ctcacatgtt              6230
```

<210> SEQ ID NO 5
<211> LENGTH: 11614
<212> TYPE: DNA
<213> ORGANISM: Unknown
<220> FEATURE:
<223> OTHER INFORMATION: Binary expression vector
      Lo523b-pSUN1-R4-Lo484::Lo376::Lo503b
<220> FEATURE:
<221> NAME/KEY: misc_feature
<222> LOCATION: (1)..(21)
<223> OTHER INFORMATION: attB3 recombination site
<220> FEATURE:
<221> NAME/KEY: promoter
<222> LOCATION: (49)..(905)
<223> OTHER INFORMATION: CaMVC 35S promoter
<220> FEATURE:
<221> NAME/KEY: misc_feature
<222> LOCATION: (912)..(1719)
<223> OTHER INFORMATION: coding for mGFP5er
<220> FEATURE:
<221> NAME/KEY: terminator
<222> LOCATION: (1762)..(2431)
<223> OTHER INFORMATION: E9 terminator
<220> FEATURE:
<221> NAME/KEY: misc_feature
<222> LOCATION: (2432)..(2455)
<223> OTHER INFORMATION: attB1 recombination site
<220> FEATURE:
<221> NAME/KEY: misc_feature
<222> LOCATION: (2542)..(2565)
<223> OTHER INFORMATION: attb2 recombination site
<220> FEATURE:
<221> NAME/KEY: promoter
<222> LOCATION: (2581)..(3899)
<223> OTHER INFORMATION: STPT promoter
<220> FEATURE:
<221> NAME/KEY: misc_feature
<222> LOCATION: (3930)..(4777)
<223> OTHER INFORMATION: coding for nptII
<220> FEATURE:
<221> NAME/KEY: terminator
<222> LOCATION: (4827)..(5079)
<223> OTHER INFORMATION: complement: nos terminator
<220> FEATURE:
<221> NAME/KEY: terminator
<222> LOCATION: (5234)..(5496)
<223> OTHER INFORMATION: nos terminator
<220> FEATURE:
<221> NAME/KEY: misc_feature
<222> LOCATION: (5610)..(5630)
<223> OTHER INFORMATION: complement: attB3 recombination site
<220> FEATURE:
<221> NAME/KEY: misc_feature
<222> LOCATION: (5649)..(5863)
<223> OTHER INFORMATION: LB
<220> FEATURE:
<221> NAME/KEY: misc_feature
<222> LOCATION: (7572)..(8679)
<223> OTHER INFORMATION: repA
<220> FEATURE:
<221> NAME/KEY: rep_origin
<222> LOCATION: (9428)..(10274)
<223> OTHER INFORMATION: complement: ColE1
<220> FEATURE:
<221> NAME/KEY: misc_feature
<222> LOCATION: (10443)..(11234)
<223> OTHER INFORMATION: complement: aadA marker (spectomycin)
<220> FEATURE:
<221> NAME/KEY: misc_feature
<222> LOCATION: (11408)..(11553)
<223> OTHER INFORMATION: RB

<400> SEQUENCE: 5
caactttgta tagaaaagtt ggccatgatt acgccaagct tgcatgcctg caggtcccca 60
gattagcctt ttcaatttca gaaagaatgc taacccacag atggttagag aggcttacgc 120
agcaggtctc atcaagacga tctacccgag caataatctc caggaaatca aataccttcc 180
caagaaggtt aaagatgcag tcaaaagatt caggactaac tgcatcaaga acacagagaa 240
agatatattt ctcaagatca gaagtactat tccagtatgg acgattcaag gcttgcttca 300
caaaccaagg caagtaatag agattggagt ctctaaaaag gtagttccca ctgaatcaaa 360
ggccatggag tcaaagattc aaatagagga cctaacagaa ctcgccgtaa agactggcga 420
acagttcata cagagtctct tacgactcaa tgacaagaag aaaatcttcg tcaacatggt 480

-continued

```
ggagcacgac acacttgtct actccaaaaa tatcaaagat acagtctcag aagaccaaag    540
ggcaattgag acttttcaac aaagggtaat atccggaaac ctcctcggat tccattgccc    600
agctatctgt cactttattg tgaagatagt ggaaaaggaa ggtggctcct acaaatgcca    660
tcattgcgat aaaggaaagg ccatcgttga agatgcctct gccgacagtg gtcccaaaga    720
tggaccccca cccacgagga gcatcgtgga aaaagaagac gttccaacca cgtcttcaaa    780
gcaagtggat tgatgtgata tctccactga cgtaagggat gacgcacaat cccactatcc    840
ttcgcaagac ccttcctcta tataaggaag ttcatttcat ttggagagaa cacgggggac    900
tctagaggat ccaaggagat ataacaatga agactaatct tttctcttt ctcatctttt    960
cacttctcct atcattatcc tcggccgaat tcagtaaagg agaagaactt ttcactggag   1020
ttgtcccaat tcttgttgaa ttagatggtg atgttaatgg gcacaaattt tctgtcagtg   1080
gagagggtga aggtgatgca acatacggaa aacttaccct taaatttatt tgcactactg   1140
gaaaactacc tgttccatgg ccaacacttg tcactacttt ctcttatggt gttcaatgct   1200
tttcaagata cccagatcat atgaagcggc acgacttctt caagagcgcc atgcctgagg   1260
gatacgtgca ggagaggacc atcttcttca aggacgacgg gaactacaag acacgtgctg   1320
aagtcaagtt tgagggagac accctcgtca acaggatcga gcttaaggga atcgatttca   1380
aggaggacgg aaacatcctc ggccacaagt tggaatacaa ctacaactcc cacaacgtat   1440
acatcatggc cgacaagcaa aagaacggca tcaaagccaa cttcaagacc cgccacaaca   1500
tcgaagacgg cggcgtgcaa ctcgctgatc attatcaaca aaatactcca attggcgatg   1560
gccctgtcct tttaccagac aaccattacc tgtccacaca atctgccctt tcgaaagatc   1620
ccaacgaaaa gagagaccac atggtccttc ttgagtttgt aacagctgct gggattacac   1680
atggcatgga tgaactatac aaacatgatg agctttaaga gaacggatcc ccatctgcgg   1740
ccgcctcgag catatgctag aggatcctct agctagagct ttcgttcgta tcatcggttt   1800
cgacaacgtt cgtcaagttc aatgcatcag tttcattgcg cacacaccag aatcctactg   1860
agtttgagta ttatggcatt gggaaaactg tttttcttgt accatttgtt gtgcttgtaa   1920
tttactgtgt tttttattcg gttttcgcta tcgaactgtg aaatggaaat ggatggagaa   1980
gagttaatga atgatatggt ccttttgttc attctcaaat taatattatt tgttttttct   2040
cttatttgtt gtgtgttgaa tttgaaatta taagagatat gcaaacattt tgttttgagt   2100
aaaaatgtgt caaatcgtgg cctctaatga ccgaagttaa tatgaggagt aaaacacttg   2160
tagttgtacc attatgctta ttcactaggc aacaaatata ttttcagacc tagaaaagct   2220
gcaaatgtta ctgaatacaa gtatgtcctc ttgtgtttta gacatttatg aactttcctt   2280
tatgtaattt tccagaatcc ttgtcagatt ctaatcattg ctttataatt atagttatac   2340
tcatggattt gtagttgagt atgaaaatat tttttaatgc attttatgac ttgccaattg   2400
attgacaaca tgcatcaatc gaccgggtac ccaagtttgt acaaaaaagc aggctggtac   2460
ccggggatcc tctaggtcga ccagatctga tatctgcggc cgcctcgagc atatgggcat   2520
gcaagcttgg cgtaatcatg gacccagctt tcttgtacaa agtggggtac ccggggatcc   2580
tgatagctta tactcaaatt caacaagtta tatataaatg tatagatact acaatatcat   2640
taacaaaagt caccttaaat aaatacacat atcttttatg ttctctattg ttttgcgtac   2700
gctaacacaa tttctcatat gcaaaaggat gaatgagtaa caaattacct cataagaaca   2760
atcatctttg cttacatact aatacaataa tcactcaatc aaccaataac atcaatcaca   2820
taggtttaca tacaataatc actcaatcaa cttcataaga agaatcatgt ttacttaatt   2880
```

-continued catcaattat ccccaaaaac accactatta agtataaact acaacatatt tgtagtgatg 2940
ggtcaacatt tttatcatat ttaaactcgg gttccctcaa atcgagaaat agtgaacatg 3000
taatattaat tttaaatcgc aattacagaa attaattgaa tttggtcaaa tggacagaat 3060
tttatagatt gggtggaact agaaaaaaaa aaaaaaagag tatagggtga attgagtaca 3120
tgaaagtaca tggtaatcct agttaaacgc ataatacatg tgggttcatt tgtatttttt 3180
tgtaacttac gagtaaactg gctacaacaa aaaaaaatta gaagattttt ttgttttgta 3240
gaaaacccta attttagtta tagttgtata actttgataa aattataaaa ttgtattacg 3300
aaaaaagtaa taagatattc aaaaaagcct agaataacgt atatgactat gagcatgaaa 3360
ctgcaagtca aatgctgaca gacaaccata aacaaaagaa attaaataga gataccttta 3420
aaataagtaa aatttcattt ataaaaaatc tactttcttg tgaatctgtc acgttcaata 3480
atttgaagac cactcaacat acaaggtaaa taatgaaaaa taaaatctac caaaatttca 3540
atcattatta tcttccaaaa aaacaaaatt atacagatga tgatggtgat atggaacttc 3600
gattggctaa tattcactgt gtctctaaaa accatccact tatcaagata agatggaccc 3660
tacactcatc caatctaaac cagtatctca agattcttat ctaattacat cattctctac 3720
cgttagatga aattgaccat taaccctacc ataactccat acaccgcgag atactggatt 3780
aaccaaatcg agatcatcgt agccgtccga tcaacaagta ccatctcttg aaatactcga 3840
aatcctcata agtccgtccc tctttgctct cactatcaaa actctgaatt tcgatttcat 3900
ctagagtcga gcccgggcga tatcggatct cgactctagt cgagggccca tgggagcttg 3960
gattgaacaa gatggattgc acgcaggttc tccggccgct tgggtggaga ggctattcgg 4020
ctatgactgg gcacaacaga caatcggctg ctctgatgcc gccgtgttcc ggctgtcagc 4080
gcaggggcgc ccggttcttt ttgtcaagac cgacctgtcc ggtgccctga atgaactgca 4140
ggacgaggca gcgcggctat cgtggctggc cacgacgggc gttccttgcg cagctgtgct 4200
cgacgttgtc actgaagcgg gaagggactg gctgctattg ggcgaagtgc cggggcagga 4260
tctcctgtca tctcaccttg ctcctgccga gaaagtatcc atcatggctg atgcaatgcg 4320
gcggctgcat acgcttgatc cggctacctg cccattcgac caccaagcga aacatcgcat 4380
cgagcgagca cgtactcgga tggaagccgg tcttgtcgat caggatgatc tggacgaaga 4440
gcatcagggg ctcgcgccag ccgaactgtt cgccaggctc aaggcgcgca tgcccgacgg 4500
cgaggatctc gtcgtgaccc atggcgatgc ctgcttgccg aatatcatgg tggaaaatgg 4560
ccgcttttct ggattcatcg actgtggccg gctgggtgtg gcggaccgct atcaggacat 4620
agcgttggct acccgtgata ttgctgaaga gcttggcggc gaatgggctg accgcttcct 4680
cgtgctttac ggtatcgccg ctcccgattc gcagcgcatc gccttctatc gccttcttga 4740
cgagttcttc tgagcgggac ccaagctagc ttcgacggat cctctagcat atgctcgagg 4800
cggccgcaga tatcagatct actagtccga tctagtaaca tagatgacac cgcgcgcgat 4860
aatttatcct agtttgcgcg ctatattttg ttttctatcg cgtattaaat gtataattgc 4920
gggactctaa tcataaaaac ccatctcata aataacgtca tgcattacat gttaattatt 4980
acatgcttaa cgtaattcaa cagaaattat atgataatca tcgcaagacc ggcaacagga 5040
ttcaatctta agaaacttta ttgccaaatg tttgaacgat cggggaaatt cgagctcggt 5100
agcaattccc gaggctgtag ccgacgatgg tgcgccagga gagttgttga ttcattgttt 5160
gcctccctgc tgcggttttt caccgaagtt catgccagtc cagcgttttt gcagcagaaa 5220
agccgccgac ttgtcgaccg atcggtcaaa catttggcaa taaagtttct taagattgaa 5280

-continued

```
tcctgttgcc ggtcttgcga tgattatcat ataatttctg ttgaattacg ttaagcatgt   5340
aataattaac atgtaatgca tgacgttatt tatgagatgg gtttttatga ttagagtccc   5400
gcaattatac atttaatacg cgatagaaaa caaaatatag cgcgcaaact aggataaatt   5460
atcgcgcgcg gtgtcatcta tgttactaga tcgggaagct tggcgtaatc atggcaactt   5520
tattatacaa agttggcatt ataaaaaagc attgcttatc aatttgttgc aacgaacagg   5580
tcactatcag tcaaaataaa atcattattc aactttatta tacatagttg ataattcact   5640
ggccggatct gcttggtaat aattgtcatt agattgtttt tatgcataga tgcactcgaa   5700
atcagccaat tttagacaag tatcaaacgg atgttaattc agtacattaa agacgtccgc   5760
aatgtgttat taagttgtct aagcgtcaat ttgtttacac cacaatatat cctgccacca   5820
gccagccaac agctccccga ccggcagctc ggcacaaaat caccacgcgt taccaccacg   5880
ccggccggcc gcatggtgtt gaccgtgttc gccggcattg ccgagttcga gcgttcccta   5940
atcatcgacc gcacccggag cgggcgcgag gccgccaagg cccgaggcgt gaagtttggc   6000
ccccgcccta ccctcacccc ggcacagatc gcgcacgccc gcgagctgat cgaccaggaa   6060
ggccgcaccg tgaaagaggc ggctgcactg cttggcgtgc atcgctcgac cctgtaccgc   6120
gcacttgagc gcagcgagga agtgacgccc accgaggcca ggcggcgcgg tgccttccgt   6180
gaggacgcat tgaccgaggc cgacgccctg gcggccgccg agaatgaacg ccaagaggaa   6240
caagcatgaa accgcaccag gacggccagg acgaaccgtt tttcattacc gaagagatcg   6300
aggcggagat gatcgcggcc gggtacgtgt tcgagccgcc cgcgcacgtc tcaaccgtgc   6360
ggctgcatga aatcctggcc ggtttgtctg atgccaagct ggcggcctgg ccggccagct   6420
tggccgctga agaaaccgag cgccgccgtc taaaaaggtg atgtgtattt gagtaaaaca   6480
gcttgcgtca tgcggtcgct gcgtatatga tgcgatgagt aaataaacaa atacgcaagg   6540
ggaacgcatg aaggttatcg ctgtacttaa ccagaaaggc gggtcaggca agacgaccat   6600
cgcaacccat ctagcccgcg ccctgcaact cgccggggcc gatgttctgt tagtcgattc   6660
cgatccccag ggcagtgccc gcgattgggc ggccgtgcgg gaagatcaac cgctaaccgt   6720
tgtcggcatc gaccgcccga cgattgaccg cgacgtgaag gccatcggcc ggcgcgactt   6780
cgtagtgatc gacggagcgc cccaggcggc ggacttggct gtgtccgcga tcaaggcagc   6840
cgacttcgtg ctgattccgg tgcagccaag cccttacgac atatgggcca ccgccgacct   6900
ggtggagctg gttaagcagc gcattgaggt cacggatgga aggctacaag cggcctttgt   6960
cgtgtcgcgg gcgatcaaag gcacgcgcat cggcggtgag gttgccgagg cgctggccgg   7020
gtacgagctg cccattcttg agtcccgtat cacgcagcgc gtgagctacc caggcactgc   7080
cgccgccggc acaaccgttc ttgaatcaga acccgagggc gacgctgccc gcgaggtcca   7140
ggcgctggcc gctgaaatta aatcaaaact catttgagtt aatgaggtaa agagaaaatg   7200
agcaaaagca caaacacgct aagtgccggc cgtccgagcg cacgcagcag caaggctgca   7260
acgttggcca gcctggcaga cacgccagcc atgaagcggg tcaactttca gttgccggcg   7320
gaggatcaca ccaagctgaa gatgtacgcg gtacgccaag gcaagaccat taccgagctg   7380
ctatctgaat acatcgcgca gctaccagag taaatgagca aatgaataaa tgagtagatg   7440
aattttagcg gctaaaggag gcggcatgga aaatcaagaa caaccaggca ccgacgccgt   7500
ggaatgcccc atgtgtggag gaacgggcgg ttggccaggc gtaagcggct gggttgtctg   7560
ccggccctgc aatggcactg gaacccccaa gcccgaggaa tcggcgtgag cggtcgcaaa   7620
ccatccggcc cggtacaaat cggcgcggcg ctgggtgatg acctggtgga gaagttgaag   7680
```

-continued

```
gccgcgcagg ccgcccagcg gcaacgcatc gaggcagaag cacgccccgg tgaatcgtgg   7740
caagcggccg ctgatcgaat ccgcaaagaa tcccggcaac cgccggcagc cggtgcgccg   7800
tcgattagga agccgcccaa gggcgacgag caaccagatt ttttcgttcc gatgctctat   7860
gacgtgggca cccgcgatag tcgcagcatc atggacgtgg ccgttttccg tctgtcgaag   7920
cgtgaccgac gagctggcga ggtgatccgc tacgagcttc cagacgggca cgtagaggtt   7980
tccgcagggc cggccggcat ggccagtgtg tgggattacg acctggtact gatggcggtt   8040
tcccatctaa ccgaatccat gaaccgatac cgggaaggga agggagacaa gcccggccgc   8100
gtgttccgtc cacacgttgc ggacgtactc aagttctgcc ggcgagccga tggcggaaag   8160
cagaaagacg acctggtaga aacctgcatt cggttaaaca ccacgcacgt tgccatgcag   8220
cgtacgaaga aggccaagaa cggccgcctg gtgacggtat ccgagggtga agccttgatt   8280
agccgctaca agatcgtaaa gagcgaaacc gggcggccgg agtacatcga gatcgagcta   8340
gctgattgga tgtaccgcga gatcacagaa ggcaagaacc cggacgtgct gacggttcac   8400
cccgattact ttttgatcga tcccggcatc ggccgttttc tctaccgcct ggcacgccgc   8460
gccgcaggca aggcagaagc cagatggttg ttcaagacga tctacgaacg cagtggcagc   8520
gccggagagt tcaagaagtt ctgtttcacc gtgcgcaagc tgatcgggtc aaatgacctg   8580
ccggagtacg atttgaagga ggaggcgggg caggctggcc cgatcctagt catgcgctac   8640
cgcaacctga tcgagggcga agcatccgcc ggttcctaat gtacggagca gatgctaggg   8700
caaattgccc tagcagggga aaaaggtcga aaaggtctct ttcctgtgga tagcacgtac   8760
attgggaacc caaagccgta cattgggaac cggaacccgt acattgggaa cccaaagccg   8820
tacattggga accggtcaca catgtaagtg actgatataa aagagaaaaa aggcgatttt   8880
tccgcctaaa actctttaaa acttattaaa actcttaaaa cccgcctggc ctgtgcataa   8940
ctgtctggcc agcgcacagc cgaagagctg caaaaagcgc ctacccttcg gtcgctgcgc   9000
tccctacgcc ccgccgcttc gcgtcggcct atcgcggccg ctggccgctc aaaaatggct   9060
ggcctacggc caggcaatct accagggcgc ggacaagccg cgccgtcgcc actcgaccgc   9120
cggcgcccac atcaaggcac cctgcctcgc gcgtttcggt gatgacggtg aaaacctctg   9180
acacatgcag ctcccggaga cggtcacagc ttgtctgtaa gcggatgccg ggagcagaca   9240
agcccgtcag ggcgcgtcag cgggtgttgg cgggtgtcgg ggcgcagcca tgacccagtc   9300
acgtagcgat agcggagtgt atactggctt aactatgcgg catcagagca gattgtactg   9360
agagtgcacc atatgcggtg tgaaataccg cacagatgcg taaggagaaa ataccgcatc   9420
aggcgctctt ccgcttcctc gctcactgac tcgctgcgct cggtcgttcg gctgcggcga   9480
gcggtatcag ctcactcaaa ggcggtaata cggttatcca cagaatcagg ggataacgca   9540
ggaaagaaca tgtgagcaaa aggccagcaa aaggccagga accgtaaaaa ggccgcgttg   9600
ctggcgtttt tccataggct ccgcccccct gacgagcatc acaaaaatcg acgctcaagt   9660
cagaggtggc gaaacccgac aggactataa agataccagg cgtttccccc tggaagctcc   9720
ctcgtgcgct ctcctgttcc gaccctgccg cttaccggat acctgtccgc ctttctccct   9780
tcgggaagcg tggcgctttc tcatagctca cgctgtaggt atctcagttc ggtgtaggtc   9840
gttcgctcca agctgggctg tgtgcacgaa ccccccgttc agcccgaccg ctgcgcctta   9900
tccggtaact atcgtcttga gtccaacccg gtaagacacg acttatcgcc actggcagca   9960
gccactggta acaggattag cagagcgagg tatgtaggcg gtgctacaga gttcttgaag  10020
tggtggccta actacggcta cactagaagg acagtatttg gtatctgcgc tctgctgaag  10080
```

```
ccagttacct tcggaaaaag agttggtagc tcttgatccg gcaaacaaac caccgctggt  10140
agcggtggtt tttttgtttg caagcagcag attacgcgca gaaaaaaagg atctcaagaa  10200
gatcctttga tcttttctac ggggtctgac gctcagtgga acgaaaactc acgttaaggg  10260
attttggtca tgcatgatat atctcccaat ttgtgtaggg cttattatgc acgcttaaaa  10320
ataataaaag cagacttgac ctgatagttt ggctgtgagc aattatgtgc ttagtgcatc  10380
taacgcttga gttaagccgc gccgcgaagc ggcgtcggct tgaacgaatt tctagctaga  10440
cattatttgc cgactacctt ggtgatctcg cctttcacgt agtggacaaa ttcttccaac  10500
tgatctgcgc gcgaggccaa gcgatcttct tcttgtccaa gataagcctg tctagcttca  10560
agtatgacgg gctgatactg ggccggcagg cgctccattg cccagtcggc agcgacatcc  10620
ttcggcgcga ttttgccggt tactgcgctg taccaaatgc gggacaacgt aagcactaca  10680
tttcgctcat cgccagccca gtcgggcggc gagttccata gcgttaaggt ttcatttagc  10740
gcctcaaata gatcctgttc aggaaccgga tcaaagagtt cctccgccgc tggacctacc  10800
aaggcaacgc tatgttctct tgcttttgtc agcaagatag ccagatcaat gtcgatcgtg  10860
gctggctcga agatacctgc aagaatgtca ttgcgctgcc attctccaaa ttgcagttcg  10920
cgcttagctg gataacgcca cggaatgatg tcgtcgtgca caacaatggt gacttctaca  10980
gcgcggagaa tctcgctctc tccaggggaa gccgaagttt ccaaaaggtc gttgatcaaa  11040
gctcgccgcg ttgtttcatc aagccttacg gtcaccgtaa ccagcaaatc aatatcactg  11100
tgtggcttca ggccgccatc cactgcggag ccgtacaaat gtacggccag caacgtcggt  11160
tcgagatggc gctcgatgac gccaactacc tctgatagtt gagtcgatac ttcggcgatc  11220
accgcttccc ccatgatgtt taactttgtt ttagggcgac tgccctgctg cgtaacatcg  11280
ttgctgctcc ataacatcaa acatcgaccc acggcgtaac gcgcttgctg cttggatgcc  11340
cgaggcatag actgtacccc aaaaaaacag tcataacaag ccatgaaaac cgccactgcg  11400
ttccatggac atacaaatgg acgaacggat aaaccttttc acgccctttt aaatatccga  11460
ttattctaat aaacgctctt ttctcttagg tttacccgcc aatatatcct gtcaaacact  11520
gatagtttaa actgaaggcg ggaaacgaca atcagatcta gtaggaaaca gctatgacca  11580
tgattacgcc aagctatcga ttacgccaag ctat                              11614
```

<210> SEQ ID NO 6
<211> LENGTH: 11588
<212> TYPE: DNA
<213> ORGANISM: Unknown
<220> FEATURE:
<223> OTHER INFORMATION: Binary expression vector
Lo523a-pSUN1-R4-Lo484::Lo376::Lo503a
<220> FEATURE:
<221> NAME/KEY: misc_feature
<222> LOCATION: (1)..(21)
<223> OTHER INFORMATION: attB4 recombination site
<220> FEATURE:
<221> NAME/KEY: promoter
<222> LOCATION: (49)..(905)
<223> OTHER INFORMATION: CaMV 35S promoter
<220> FEATURE:
<221> NAME/KEY: misc_feature
<222> LOCATION: (912)..(1719)
<223> OTHER INFORMATION: coding for mGFP5er
<220> FEATURE:
<221> NAME/KEY: terminator
<222> LOCATION: (1762)..(2431)
<223> OTHER INFORMATION: Ep terminator
<220> FEATURE:
<221> NAME/KEY: misc_feature
<222> LOCATION: (2432)..(2455)

<223> OTHER INFORMATION: attB1 recombination site
<220> FEATURE:
<221> NAME/KEY: misc_feature
<222> LOCATION: (2542)..(2565)
<223> OTHER INFORMATION: attb2 recombination site
<220> FEATURE:
<221> NAME/KEY: promoter
<222> LOCATION: (2581)..(3899)
<223> OTHER INFORMATION: STPT promoter
<220> FEATURE:
<221> NAME/KEY: misc_feature
<222> LOCATION: (3930)..(4777)
<223> OTHER INFORMATION: coding for nptII
<220> FEATURE:
<221> NAME/KEY: terminator
<222> LOCATION: (4827)..(5079)
<223> OTHER INFORMATION: complement: nos terminator
<220> FEATURE:
<221> NAME/KEY: terminator
<222> LOCATION: (5208)..(5470)
<223> OTHER INFORMATION: nos terminator
<220> FEATURE:
<221> NAME/KEY: misc_feature
<222> LOCATION: (5323)..(5837)
<223> OTHER INFORMATION: LB
<220> FEATURE:
<221> NAME/KEY: misc_feature
<222> LOCATION: (5584)..(5604)
<223> OTHER INFORMATION: complement: attB3 recombination site
<220> FEATURE:
<221> NAME/KEY: misc_feature
<222> LOCATION: (7546)..(8653)
<223> OTHER INFORMATION: repA
<220> FEATURE:
<221> NAME/KEY: rep_origin
<222> LOCATION: (9402)..(10248)
<223> OTHER INFORMATION: complement: ColE1
<220> FEATURE:
<221> NAME/KEY: misc_feature
<222> LOCATION: (10417)..(11208)
<223> OTHER INFORMATION: complement: aadA marker (spectomycin)
<220> FEATURE:
<221> NAME/KEY: misc_feature
<222> LOCATION: (11382)..(11527)
<223> OTHER INFORMATION: RB

<400> SEQUENCE: 6
caactttgta tagaaaagtt ggccatgatt acgccaagct tgcatgcctg caggtcccca 60
gattagcctt ttcaatttca gaaagaatgc taacccacag atggttagag aggcttacgc 120
agcaggtctc atcaagacga tctacccgag caataatctc caggaaatca aataccttcc 180
caagaaggtt aaagatgcag tcaaaagatt caggactaac tgcatcaaga acacagagaa 240
agatatattt ctcaagatca gaagtactat tccagtatgg acgattcaag gcttgcttca 300
caaaccaagg caagtaatag agattggagt ctctaaaaag gtagttccca ctgaatcaaa 360
ggccatggag tcaaagattc aaatagagga cctaacagaa ctcgccgtaa agactggcga 420
acagttcata cagagtctct tacgactcaa tgacaagaag aaaatcttcg tcaacatggt 480
ggagcacgac acacttgtct actccaaaaa tatcaaagat acagtctcag aagaccaaag 540
ggcaattgag acttttcaac aaagggtaat atccggaaac ctcctcggat tccattgccc 600
agctatctgt cactttattg tgaagatagt ggaaaaggaa ggtggctcct acaaatgcca 660
tcattgcgat aaaggaaagg ccatcgttga agatgcctct gccgacagtg gtcccaaaga 720
tggaccccca cccacgagga gcatcgtgga aaaagaagac gttccaacca cgtcttcaaa 780
gcaagtggat tgatgtgata tctccactga cgtaagggat gacgcacaat cccactatcc 840
ttcgcaagac ccttcctcta tataaggaag ttcatttcat ttggagagaa cacgggggac 900
tctagaggat ccaaggagat ataacaatga agactaatct tttctctttc tcatctttt 960

-continued

```
cacttctcct atcattatcc tcggccgaat tcagtaaagg agaagaactt ttcactggag   1020
ttgtcccaat tcttgttgaa ttagatggtg atgttaatgg gcacaaattt tctgtcagtg   1080
gagagggtga aggtgatgca acatacggaa aacttaccct taaatttatt tgcactactg   1140
gaaaactacc tgttccatgg ccaacacttg tcactacttt ctcttatggt gttcaatgct   1200
tttcaagata cccagatcat atgaagcggc acgacttctt caagagcgcc atgcctgagg   1260
gatacgtgca ggagaggacc atcttcttca aggacgacgg gaactacaag acacgtgctg   1320
aagtcaagtt tgagggagac accctcgtca acaggatcga gcttaaggga atcgatttca   1380
aggaggacgg aaacatcctc ggccacaagt tggaatacaa ctacaactcc cacaacgtat   1440
acatcatggc cgacaagcaa aagaacggca tcaaagccaa cttcaagacc cgccacaaca   1500
tcgaagacgg cggcgtgcaa ctcgctgatc attatcaaca aaatactcca attggcgatg   1560
gccctgtcct tttaccagac aaccattacc tgtccacaca atctgccctt tcgaaagatc   1620
ccaacgaaaa gagagaccac atggtccttc ttgagtttgt aacagctgct gggattacac   1680
atggcatgga tgaactatac aaacatgatg agctttaaga gaacggatcc ccatctgcgg   1740
ccgcctcgag catatgctag aggatcctct agctagagct ttcgttcgta tcatcggttt   1800
cgacaacgtt cgtcaagttc aatgcatcag tttcattgcg cacacaccag aatcctactg   1860
agtttgagta ttatggcatt gggaaaactg tttttcttgt accatttgtt gtgcttgtaa   1920
tttactgtgt tttttattcg gttttcgcta tcgaactgtg aaatggaaat ggatggagaa   1980
gagttaatga atgatatggt ccttttgttc attctcaaat taatattatt tgttttttct   2040
cttatttgtt gtgtgttgaa tttgaaatta taagagatat gcaaacattt tgttttgagt   2100
aaaaatgtgt caaatcgtgg cctctaatga ccgaagttaa tatgaggagt aaaacacttg   2160
tagttgtacc attatgctta ttcactaggc aacaaatata ttttcagacc tagaaaagct   2220
gcaaatgtta ctgaatacaa gtatgtcctc ttgtgtttta gacatttatg aactttcctt   2280
tatgtaattt tccagaatcc ttgtcagatt ctaatcattg ctttataatt atagttatac   2340
tcatggattt gtagttgagt atgaaaatat tttttaatgc attttatgac ttgccaattg   2400
attgacaaca tgcatcaatc gaccgggtac ccaagtttgt acaaaaaagc aggctggtac   2460
ccggggatcc tctaggtcga ccagatctga tatctgcggc cgcctcgagc atatgggcat   2520
gcaagcttgg cgtaatcatg gacccagctt tcttgtacaa agtggggtac ccggggatcc   2580
tgatagctta tactcaaatt caacaagtta tatataaatg tatagatact acaatatcat   2640
taacaaaagt caccttaaat aaatacacat atcttttatg ttctctattg ttttgcgtac   2700
gctaacacaa tttctcatat gcaaaaggat gaatgagtaa caaattacct cataagaaca   2760
atcatctttg cttacatact aatacaataa tcactcaatc aaccaataac atcaatcaca   2820
taggtttaca tacaataatc actcaatcaa cttcataaga agaatcatgt ttacttaatt   2880
catcaattat ccccaaaaac accactatta agtataaact acaacatatt tgtagtgatg   2940
ggtcaacatt tttatcatat ttaaactcgg gttccctcaa atcgagaaat agtgaacatg   3000
taatattaat tttaaatcgc aattacagaa attaattgaa tttggtcaaa tggacagaat   3060
tttatagatt gggtggaact agaaaaaaaa aaaaaaagag tatagggtga attgagtaca   3120
tgaaagtaca tggtaatcct agttaaacgc ataatacatg tgggttcatt tgtatttttt   3180
tgtaacttac gagtaaactg gctacaacaa aaaaaaatta gaagattttt ttgttttgta   3240
gaaaacccta attttagtta tagttgtata actttgataa aattataaaa ttgtattacg   3300
aaaaaagtaa taagatattc aaaaaagcct agaataacgt atatgactat gagcatgaaa   3360
```

-continued

```
ctgcaagtca aatgctgaca gacaaccata aacaaaagaa attaaataga gatacccttta   3420
aaataagtaa aatttcattt ataaaaaatc tactttcttg tgaatctgtc acgttcaata   3480
atttgaagac cactcaacat acaaggtaaa taatgaaaaa taaaatctac caaaatttca   3540
atcattatta tcttccaaaa aaacaaaatt atacagatga tgatggtgat atggaacttc   3600
gattggctaa tattcactgt gtctctaaaa accatccact tatcaagata agatggaccc   3660
tacactcatc caatctaaac cagtatctca agattcttat ctaattacat cattctctac   3720
cgttagatga aattgaccat taaccctacc ataactccat acaccgcgag atactggatt   3780
aaccaaatcg agatcatcgt agccgtccga tcaacaagta ccatctcttg aaatactcga   3840
aatcctcata agtccgtccc tctttgctct cactatcaaa actctgaatt tcgatttcat   3900
ctagagtcga gcccgggcga tatcggatct cgactctagt cgagggccca tgggagcttg   3960
gattgaacaa gatggattgc acgcaggttc tccggccgct tgggtggaga ggctattcgg   4020
ctatgactgg gcacaacaga caatcggctg ctctgatgcc gccgtgttcc ggctgtcagc   4080
gcaggggcgc ccggttcttt ttgtcaagac cgacctgtcc ggtgccctga atgaactgca   4140
ggacgaggca gcgcggctat cgtggctggc cacgacgggc gttccttgcg cagctgtgct   4200
cgacgttgtc actgaagcgg gaagggactg gctgctattg ggcgaagtgc cggggcagga   4260
tctcctgtca tctcaccttg ctcctgccga gaaagtatcc atcatggctg atgcaatgcg   4320
gcggctgcat acgcttgatc cggctacctg cccattcgac caccaagcga aacatcgcat   4380
cgagcgagca cgtactcgga tggaagccgg tcttgtcgat caggatgatc tggacgaaga   4440
gcatcagggg ctcgcgccag ccgaactgtt cgccaggctc aaggcgcgca tgcccgacgg   4500
cgaggatctc gtcgtgaccc atggcgatgc ctgcttgccg aatatcatgg tggaaaatgg   4560
ccgcttttct ggattcatcg actgtggccg gctgggtgtg gcggaccgct atcaggacat   4620
agcgttggct acccgtgata ttgctgaaga gcttggcggc gaatgggctg accgcttcct   4680
cgtgctttac ggtatcgccg ctcccgattc gcagcgcatc gccttctatc gccttcttga   4740
cgagttcttc tgagcgggac ccaagctagc ttcgacggat cctctagcat atgctcgagg   4800
cggccgcaga tatcagatct actagtccga tctagtaaca tagatgacac cgcgcgcgat   4860
aatttatcct agtttgcgcg ctatattttg ttttctatcg cgtattaaat gtataattgc   4920
gggactctaa tcataaaaac ccatctcata aataacgtca tgcattacat gttaattatt   4980
acatgcttaa cgtaattcaa cagaaattat atgataatca tcgcaagacc ggcaacagga   5040
ttcaatctta agaaacttta ttgccaaatg tttgaacgat cggggaaatt cgagctcggt   5100
agcaattccc gaggctgtag ccgacgatgg tgcgccagga gagttgttga ttcattgttt   5160
gcctccctgc tgcggttttt caccgaagtt catgccagtc cagcgtgtcg accgatcggt   5220
caaacatttg gcaataaagt ttcttaagat tgaatcctgt tgccggtctt gcgatgatta   5280
tcatataatt tctgttgaat tacgttaagc atgtaataat taacatgtaa tgcatgacgt   5340
tatttatgag atgggttttt atgattagag tcccgcaatt atacatttaa tacgcgatag   5400
aaaacaaaat atagcgcgca aactaggata aattatcgcg cgcggtgtca tctatgttac   5460
tagatcggga agcttggcgt aatcatggca actttattat acaaagttgg cattataaaa   5520
aagcattgct tatcaatttg ttgcaacgaa caggtcacta tcagtcaaaa taaaatcatt   5580
attcaacttt attatacata gttgataatt cactggccgg atctgcttgg taataattgt   5640
cattagattg tttttatgca tagatgcact cgaaatcagc caattttaga caagtatcaa   5700
acggatgtta attcagtaca ttaaagacgt ccgcaatgtg ttattaagtt gtctaagcgt   5760
```

-continued caatttgttt acaccacaat atatcctgcc accagccagc caacagctcc ccgaccggca 5820
gctcggcaca aaatcaccac gcgttaccac cacgccggcc ggccgcatgg tgttgaccgt 5880
gttcgccggc attgccgagt tcgagcgttc cctaatcatc gaccgcaccc ggagcgggcg 5940
cgaggccgcc aaggcccgag gcgtgaagtt tggcccccgc cctaccctca ccccggcaca 6000
gatcgcgcac gcccgcgagc tgatcgacca ggaaggccgc accgtgaaag aggcggctgc 6060
actgcttggc gtgcatcgct cgaccctgta ccgcgcactt gagcgcagcg aggaagtgac 6120
gcccaccgag gccaggcggc gcggtgcctt ccgtgaggac gcattgaccg aggccgacgc 6180
cctggcggcc gccgagaatg aacgccaaga ggaacaagca tgaaaccgca ccaggacggc 6240
caggacgaac cgtttttcat taccgaagag atcgaggcgg agatgatcgc ggccgggtac 6300
gtgttcgagc cgcccgcgca cgtctcaacc gtgcggctgc atgaaatcct ggccggtttg 6360
tctgatgcca agctggcggc ctggccggcc agcttggccg ctgaagaaac cgagcgccgc 6420
cgtctaaaaa ggtgatgtgt atttgagtaa aacagcttgc gtcatgcggt cgctgcgtat 6480
atgatgcgat gagtaaataa acaaatacgc aaggggaacg catgaaggtt atcgctgtac 6540
ttaaccagaa aggcgggtca ggcaagacga ccatcgcaac ccatctagcc cgcgccctgc 6600
aactcgccgg ggccgatgtt ctgttagtcg attccgatcc ccagggcagt gcccgcgatt 6660
gggcggccgt gcgggaagat caaccgctaa ccgttgtcgg catcgaccgc ccgacgattg 6720
accgcgacgt gaaggccatc ggccggcgcg acttcgtagt gatcgacgga gcgccccagg 6780
cggcggactt ggctgtgtcc gcgatcaagg cagccgactt cgtgctgatt ccggtgcagc 6840
caagccctta cgacatatgg gccaccgccg acctggtgga gctggttaag cagcgcattg 6900
aggtcacgga tggaaggcta caagcggcct ttgtcgtgtc gcgggcgatc aaaggcacgc 6960
gcatcggcgg tgaggttgcc gaggcgctgg ccgggtacga gctgcccatt cttgagtccc 7020
gtatcacgca gcgcgtgagc tacccaggca ctgccgccgc cggcacaacc gttcttgaat 7080
cagaacccga gggcgacgct gcccgcgagg tccaggcgct ggccgctgaa attaaatcaa 7140
aactcatttg agttaatgag gtaaagagaa aatgagcaaa agcacaaaca cgctaagtgc 7200
cggccgtccg agcgcacgca gcagcaaggc tgcaacgttg gccagcctgg cagacacgcc 7260
agccatgaag cgggtcaact ttcagttgcc ggcggaggat cacaccaagc tgaagatgta 7320
cgcggtacgc caaggcaaga ccattaccga gctgctatct gaatacatcg cgcagctacc 7380
agagtaaatg agcaaatgaa taaatgagta gatgaatttt agcggctaaa ggaggcggca 7440
tggaaaatca agaacaacca ggcaccgacg ccgtggaatg ccccatgtgt ggaggaacgg 7500
gcggttggcc aggcgtaagc ggctgggttg tctgccggcc ctgcaatggc actggaaccc 7560
ccaagcccga ggaatcggcg tgagcggtcg caaaccatcc ggcccggtac aaatcggcgc 7620
ggcgctgggt gatgacctgg tggagaagtt gaaggccgcg caggccgccc agcggcaacg 7680
catcgaggca gaagcacgcc ccggtgaatc gtggcaagcg gccgctgatc gaatccgcaa 7740
agaatcccgg caaccgccgg cagccggtgc gccgtcgatt aggaagccgc ccaagggcga 7800
cgagcaacca gatttttcg ttccgatgct ctatgacgtg ggcacccgcg atagtcgcag 7860
catcatggac gtggccgttt tccgtctgtc gaagcgtgac cgacgagctg gcgaggtgat 7920
ccgctacgag cttccagacg ggcacgtaga ggtttccgca gggccggccg gcatggccag 7980
tgtgtgggat tacgacctgg tactgatggc ggtttcccat ctaaccgaat ccatgaaccg 8040
ataccgggaa gggaagggag acaagcccgg ccgcgtgttc cgtccacacg ttgcggacgt 8100
actcaagttc tgccggcgag ccgatggcgg aaagcagaaa gacgacctgg tagaaacctg 8160

-continued

```
cattcggtta aacaccacgc acgttgccat gcagcgtacg aagaaggcca agaacggccg   8220
cctggtgacg gtatccgagg gtgaagcctt gattagccgc tacaagatcg taaagagcga   8280
aaccgggcgg ccggagtaca tcgagatcga gctagctgat tggatgtacc gcgagatcac   8340
agaaggcaag aacccggacg tgctgacggt tcaccccgat tactttttga tcgatcccgg   8400
catcggccgt tttctctacc gcctggcacg ccgcgccgca ggcaaggcag aagccagatg   8460
gttgttcaag acgatctacg aacgcagtgg cagcgccgga gagttcaaga agttctgttt   8520
caccgtgcgc aagctgatcg ggtcaaatga cctgccggag tacgatttga aggaggaggc   8580
ggggcaggct ggcccgatcc tagtcatgcg ctaccgcaac ctgatcgagg gcgaagcatc   8640
cgccggttcc taatgtacgg agcagatgct agggcaaatt gccctagcag gggaaaaagg   8700
tcgaaaaggt ctctttcctg tggatagcac gtacattggg aacccaaagc cgtacattgg   8760
gaaccggaac ccgtacattg ggaacccaaa gccgtacatt gggaaccggt cacacatgta   8820
agtgactgat ataaaagaga aaaaaggcga tttttccgcc taaaactctt taaaacttat   8880
taaaactctt aaaacccgcc tggcctgtgc ataactgtct ggccagcgca cagccgaaga   8940
gctgcaaaaa gcgcctaccc ttcggtcgct gcgctcccta cgccccgccg cttcgcgtcg   9000
gcctatcgcg gccgctggcc gctcaaaaat ggctggccta cggccaggca atctaccagg   9060
gcgcggacaa gccgcgccgt cgccactcga ccgccggcgc ccacatcaag gcaccctgcc   9120
tcgcgcgttt cggtgatgac ggtgaaaacc tctgacacat gcagctcccg gagacggtca   9180
cagcttgtct gtaagcggat gccgggagca gacaagcccg tcagggcgcg tcagcgggtg   9240
ttggcgggtg tcggggcgca gccatgaccc agtcacgtag cgatagcgga gtgtatactg   9300
gcttaactat gcggcatcag agcagattgt actgagagtg caccatatgc ggtgtgaaat   9360
accgcacaga tgcgtaagga gaaaataccg catcaggcgc tcttccgctt cctcgctcac   9420
tgactcgctg cgctcggtcg ttcggctgcg gcgagcggta tcagctcact caaaggcggt   9480
aatacggtta tccacagaat caggggataa cgcaggaaag aacatgtgag caaaaggcca   9540
gcaaaaggcc aggaaccgta aaaaggccgc gttgctggcg tttttccata ggctccgccc   9600
ccctgacgag catcacaaaa atcgacgctc aagtcagagg tggcgaaacc cgacaggact   9660
ataaagatac caggcgtttc cccctggaag ctccctcgtg cgctctcctg ttccgaccct   9720
gccgcttacc ggatacctgt ccgcctttct cccttcggga agcgtggcgc tttctcatag   9780
ctcacgctgt aggtatctca gttcggtgta ggtcgttcgc tccaagctgg gctgtgtgca   9840
cgaacccccc gttcagcccg accgctgcgc cttatccggt aactatcgtc ttgagtccaa   9900
cccggtaaga cacgacttat cgccactggc agcagccact ggtaacagga ttagcagagc   9960
gaggtatgta ggcggtgcta cagagttctt gaagtggtgg cctaactacg gctacactag  10020
aaggacagta tttggtatct gcgctctgct gaagccagtt accttcggaa aaagagttgg  10080
tagctcttga tccggcaaac aaaccaccgc tggtagcggt ggtttttttg tttgcaagca  10140
gcagattacg cgcagaaaaa aaggatctca agaagatcct ttgatctttt ctacggggtc  10200
tgacgctcag tggaacgaaa actcacgtta agggattttg gtcatgcatg atatatctcc  10260
caatttgtgt agggcttatt atgcacgctt aaaaataata aaagcagact tgacctgata  10320
gtttggctgt gagcaattat gtgcttagtg catctaacgc ttgagttaag ccgcgccgcg  10380
aagcggcgtc ggcttgaacg aatttctagc tagacattat ttgccgacta ccttggtgat  10440
ctcgcctttc acgtagtgga caaattcttc caactgatct gcgcgcgagg ccaagcgatc  10500
ttcttcttgt ccaagataag cctgtctagc ttcaagtatg acgggctgat actgggccgg  10560
```

```
caggcgctcc attgcccagt cggcagcgac atccttcggc gcgattttgc cggttactgc  10620

gctgtaccaa atgcgggaca acgtaagcac tacatttcgc tcatcgccag cccagtcggg  10680

cggcgagttc catagcgtta aggtttcatt tagcgcctca aatagatcct gttcaggaac  10740

cggatcaaag agttcctccg ccgctggacc taccaaggca acgctatgtt ctcttgcttt  10800

tgtcagcaag atagccagat caatgtcgat cgtggctggc tcgaagatac ctgcaagaat  10860

gtcattgcgc tgccattctc caaattgcag ttcgcgctta gctggataac gccacggaat  10920

gatgtcgtcg tgcacaacaa tggtgacttc tacagcgcgg agaatctcgc tctctccagg  10980

ggaagccgaa gtttccaaaa ggtcgttgat caaagctcgc cgcgttgttt catcaagcct  11040

tacggtcacc gtaaccagca aatcaatatc actgtgtggc ttcaggccgc catccactgc  11100

ggagccgtac aaatgtacgg ccagcaacgt cggttcgaga tggcgctcga tgacgccaac  11160

tacctctgat agttgagtcg atacttcggc gatcaccgct tcccccatga tgtttaactt  11220

tgttttaggg cgactgccct gctgcgtaac atcgttgctg ctccataaca tcaaacatcg  11280

acccacggcg taacgcgctt gctgcttgga tgcccgaggc atagactgta ccccaaaaaa  11340

acagtcataa caagccatga aaaccgccac tgcgttccat ggacatacaa atggacgaac  11400

ggataaacct tttcacgccc ttttaaatat ccgattattc taataaacgc tcttttctct  11460

taggtttacc cgccaatata tcctgtcaaa cactgatagt ttaaactgaa ggcgggaaac  11520

gacaatcaga tctagtagga aacagctatg accatgatta cgccaagcta tcgattacgc  11580

caagctat                                                           11588
```

```
<210> SEQ ID NO 7
<211> LENGTH: 5583
<212> TYPE: DNA
<213> ORGANISM: Unknown
<220> FEATURE:
<223> OTHER INFORMATION: Nucleic acid construct
      Lo503b-pENTR-C1-STPT-nptII-IRnos
<220> FEATURE:
<221> NAME/KEY: terminator
<222> LOCATION: (268)..(295)
<223> OTHER INFORMATION: complement
<220> FEATURE:
<221> NAME/KEY: terminator
<222> LOCATION: (427)..(470)
<223> OTHER INFORMATION: complement
<220> FEATURE:
<221> NAME/KEY: misc_feature
<222> LOCATION: (591)..(747)
<223> OTHER INFORMATION: attR2 recombination site
<220> FEATURE:
<221> NAME/KEY: promoter
<222> LOCATION: (763)..(2081)
<223> OTHER INFORMATION: STPT promoter
<220> FEATURE:
<221> NAME/KEY: misc_feature
<222> LOCATION: (2112)..(2959)
<223> OTHER INFORMATION: nptII
<220> FEATURE:
<221> NAME/KEY: terminator
<222> LOCATION: (3009)..(3261)
<223> OTHER INFORMATION: complement: nos terminator
<220> FEATURE:
<221> NAME/KEY: terminator
<222> LOCATION: (3416)..(3678)
<223> OTHER INFORMATION: nos terminator
<220> FEATURE:
<221> NAME/KEY: misc_feature
<222> LOCATION: (3697)..(3792)
<223> OTHER INFORMATION: complement: attL3 recombination site
<220> FEATURE:
<221> NAME/KEY: misc_feature
<222> LOCATION: (3977)..(4786)
<223> OTHER INFORMATION: kanamycin resistance
```

<400> SEQUENCE: 7
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggccctg cagctctaga gctcgaattc tacaggtcac 600
taataccatc taagtagttg gttcatagtg actgcatatg ttgtgtttta cagtattatg 660
tagtctgttt tttatgcaaa atctaattta atatattgat atttatatca ttttacgttt 720
ctcgttcaac tttcttgtac aaagtggggt acccggggat cctgatagct tatactcaaa 780
ttcaacaagt tatatataaa tgtatagata ctacaatatc attaacaaaa gtcaccttaa 840
ataaatacac atatctttta tgttctctat tgttttgcgt acgctaacac aatttctcat 900
atgcaaaagg atgaatgagt aacaaattac ctcataagaa caatcatctt tgcttacata 960
ctaatacaat aatcactcaa tcaaccaata acatcaatca cataggttta catacaataa 1020
tcactcaatc aacttcataa gaagaatcat gtttacttaa ttcatcaatt atccccaaaa 1080
acaccactat taagtataaa ctacaacata tttgtagtga tgggtcaaca tttttatcat 1140
atttaaactc gggttccctc aaatcgagaa atagtgaaca tgtaatatta attttaaatc 1200
gcaattacag aaattaattg aatttggtca aatggacaga attttataga ttgggtggaa 1260
ctagaaaaaa aaaaaaaaag agtatagggt gaattgagta catgaaagta catggtaatc 1320
ctagttaaac gcataataca tgtgggttca tttgtatttt tttgtaactt acgagtaaac 1380
tggctacaac aaaaaaaaat tagaagattt ttttgttttg tagaaaaccc taattttagt 1440
tatagttgta taactttgat aaaattataa aattgtatta cgaaaaaagt aataagatat 1500
tcaaaaaagc ctagaataac gtatatgact atgagcatga aactgcaagt caaatgctga 1560
cagacaacca taaacaaaag aaattaaata gagatacctt taaaataagt aaaatttcat 1620
ttataaaaaa tctactttct tgtgaatctg tcacgttcaa taatttgaag accactcaac 1680
atacaaggta aataatgaaa aataaaatct accaaaattt caatcattat tatcttccaa 1740
aaaaacaaaa ttatacagat gatgatggtg atatggaact tcgattggct aatattcact 1800
gtgtctctaa aaaccatcca cttatcaaga taagatggac cctacactca tccaatctaa 1860
accagtatct caagattctt atctaattac atcattctct accgttagat gaaattgacc 1920
attaacccta ccataactcc atacaccgcg agatactgga ttaaccaaat cgagatcatc 1980
gtagccgtcc gatcaacaag taccatctct tgaaatactc gaaatcctca taagtccgtc 2040
cctctttgct ctcactatca aaactctgaa tttcgatttc atctagagtc gagcccgggc 2100
gatatcggat ctcgactcta gtcgagggcc catgggagct tggattgaac aagatggatt 2160
gcacgcaggt tctccggccg cttgggtgga gaggctattc ggctatgact gggcacaaca 2220
gacaatcggc tgctctgatg ccgccgtgtt ccggctgtca gcgcaggggc gcccggttct 2280
ttttgtcaag accgacctgt ccggtgccct gaatgaactg caggacgagg cagcgcggct 2340
atcgtggctg gccacgacgg gcgttccttg cgcagctgtg ctcgacgttg tcactgaagc 2400
gggaagggac tggctgctat tgggcgaagt gccggggcag gatctcctgt catctcacct 2460
tgctcctgcc gagaaagtat ccatcatggc tgatgcaatg cggcggctgc atacgcttga 2520
tccggctacc tgcccattcg accaccaagc gaaacatcgc atcgagcgag cacgtactcg 2580
gatggaagcc ggtcttgtcg atcaggatga tctggacgaa gagcatcagg ggctcgcgcc 2640
agccgaactg ttcgccaggc tcaaggcgcg catgcccgac ggcgaggatc tcgtcgtgac 2700
ccatggcgat gcctgcttgc cgaatatcat ggtggaaaat ggccgctttt ctggattcat 2760
cgactgtggc cggctgggtg tggcggaccg ctatcaggac atagcgttgg ctacccgtga 2820
tattgctgaa gagcttggcg gcgaatgggc tgaccgcttc ctcgtgcttt acggtatcgc 2880
cgctcccgat tcgcagcgca tcgccttcta tcgccttctt gacgagttct tctgagcggg 2940
acccaagcta gcttcgacgg atcctctagc atatgctcga ggcggccgca gatatcagat 3000
ctactagtcc gatctagtaa catagatgac accgcgcgcg ataatttatc ctagtttgcg 3060
cgctatattt tgttttctat cgcgtattaa atgtataatt gcgggactct aatcataaaa 3120
acccatctca taaataacgt catgcattac atgttaatta ttacatgctt aacgtaattc 3180
aacagaaatt atatgataat catcgcaaga ccggcaacag gattcaatct taagaaactt 3240
tattgccaaa tgtttgaacg atcggggaaa ttcgagctcg gtagcaattc ccgaggctgt 3300
agccgacgat ggtgcgccag gagagttgtt gattcattgt ttgcctccct gctgcggttt 3360
ttcaccgaag ttcatgccag tccagcgttt ttgcagcaga aaagccgccg acttgtcgac 3420
cgatcggtca aacatttggc aataaagttt cttaagattg aatcctgttg ccggtcttgc 3480
gatgattatc atataatttc tgttgaatta cgttaagcat gtaataatta acatgtaatg 3540
catgacgtta tttatgagat gggtttttat gattagagtc ccgcaattat acatttaata 3600
cgcgatagaa aacaaaatat agcgcgcaaa ctaggataaa ttatcgcgcg cggtgtcatc 3660
tatgttacta gatcgggaag cttggcgtaa tcatggcaac tttattatac aaagttggca 3720
ttataaaaaa gcattgctta tcaatttgtt gcaacgaaca ggtcactatc agtcaaaata 3780
aaatcattat ttggagctcc atggtagcgt taacgcggcc atcccctata gtgagtcgta 3840
ttacatggtc atagctgttt cctggcagct ctggcccgtg tctcaaaatc tctgatgtta 3900
cattgcacaa gataaaaata tatcatcatg aacaataaaa ctgtctgctt acataaacag 3960
taatacaagg ggtgttatga gccatattca acgggaaacg tcgaggccgc gattaaattc 4020
caacatggat gctgatttat atgggtataa atgggctcgc gataatgtcg ggcaatcagg 4080
tgcgacaatc tatcgcttgt atgggaagcc cgatgcgcca gagttgtttc tgaaacatgg 4140
caaaggtagc gttgccaatg atgttacaga tgagatggtc agactaaact ggctgacgga 4200
atttatgcct cttccgacca tcaagcattt tatccgtact cctgatgatg catggttact 4260
caccactgcg atccccggaa aaacagcatt ccaggtatta gaagaatatc ctgattcagg 4320
tgaaaatatt gttgatgcgc tggcagtgtt cctgcgccgg ttgcattcga ttcctgtttg 4380
taattgtcct tttaacagcg atcgcgtatt tcgtctcgct caggcgcaat cacgaatgaa 4440
taacggtttg gttgatgcga gtgattttga tgacgagcgt aatggctggc ctgttgaaca 4500
agtctggaaa gaaatgcata aacttttgcc attctcaccg gattcagtcg tcactcatgg 4560
tgatttctca cttgataacc ttatttttga cgaggggaaa ttaataggtt gtattgatgt 4620
tggacgagtc ggaatcgcag accgatacca ggatcttgcc atcctatgga actgcctcgg 4680
tgagttttct ccttcattac agaaacggct tttttcaaaaa tatggtattg ataatcctga 4740

```
tatgaataaa ttgcagtttc atttgatgct cgatgagttt ttctaatcag aattggttaa   4800

ttggttgtaa cactggcaga gcattacgct gacttgacgg gacggcgcaa gctcatgacc   4860

aaaatccctt aacgtgagtt acgcgtcgtt ccactgagcg tcagaccccg tagaaaagat   4920

caaaggatct tcttgagatc cttttttttct gcgcgtaatc tgctgcttgc aaacaaaaaa   4980

accaccgcta ccagcggtgg tttgtttgcc ggatcaagag ctaccaactc tttttccgaa   5040

ggtaactggc ttcagcagag cgcagatacc aaatactgtc cttctagtgt agccgtagtt   5100

aggccaccac ttcaagaact ctgtagcacc gcctacatac ctcgctctgc taatcctgtt   5160

accagtggct gctgccagtg gcgataagtc gtgtcttacc gggttggact caagacgata   5220

gttaccggat aaggcgcagc ggtcgggctg aacggggggt tcgtgcacac agcccagctt   5280

ggagcgaacg acctacaccg aactgagata cctacagcgt gagcattgag aaagcgccac   5340

gcttcccgaa gggagaaagg cggacaggta tccggtaagc ggcagggtcg gaacaggaga   5400

gcgcacgagg gagcttccag ggggaaacgc ctggtatctt tatagtcctg tcgggtttcg   5460

ccacctctga cttgagcgtc gatttttgtg atgctcgtca ggggggcgga gcctatggaa   5520

aaacgccagc aacgcggcct ttttacggtt cctggccttt tgctggcctt ttgctcacat   5580

gtt                                                                  5583
```

```
<210> SEQ ID NO 8
<211> LENGTH: 5557
<212> TYPE: DNA
<213> ORGANISM: Unknown
<220> FEATURE:
<223> OTHER INFORMATION: Nucleic acid construct
      Lo503a-pENTR-C1-STPT-nptII-IRnos
<220> FEATURE:
<221> NAME/KEY: terminator
<222> LOCATION: (268)..(295)
<223> OTHER INFORMATION: complement
<220> FEATURE:
<221> NAME/KEY: terminator
<222> LOCATION: (427)..(470)
<223> OTHER INFORMATION: complement
<220> FEATURE:
<221> NAME/KEY: misc_feature
<222> LOCATION: (591)..(747)
<223> OTHER INFORMATION: attR2 recombination site
<220> FEATURE:
<221> NAME/KEY: promoter
<222> LOCATION: (763)..(2081)
<223> OTHER INFORMATION: STPT promoter
<220> FEATURE:
<221> NAME/KEY: misc_feature
<222> LOCATION: (2112)..(2959)
<223> OTHER INFORMATION: nptII
<220> FEATURE:
<221> NAME/KEY: terminator
<222> LOCATION: (3009)..(3261)
<223> OTHER INFORMATION: complement: nos terminator
<220> FEATURE:
<221> NAME/KEY: terminator
<222> LOCATION: (3390)..(3652)
<223> OTHER INFORMATION: nos terminator
<220> FEATURE:
<221> NAME/KEY: misc_feature
<222> LOCATION: (3671)..(3766)
<223> OTHER INFORMATION: complement: attL3 recombination site
<220> FEATURE:
<221> NAME/KEY: misc_feature
<222> LOCATION: (3951)..(4760)
<223> OTHER INFORMATION: kanamycin resistance

<400> SEQUENCE: 8

ctttcctgcg ttatcccctg attctgtgga taaccgtatt accgcctttg agtgagctga     60
```

-continued

```
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggggt acccggggat cctgatagct tatactcaaa    780
ttcaacaagt tatatataaa tgtatagata ctacaatatc attaacaaaa gtcaccttaa    840
ataaatacac atatctttta tgttctctat tgttttgcgt acgctaacac aatttctcat    900
atgcaaaagg atgaatgagt aacaaattac ctcataagaa caatcatctt tgcttacata    960
ctaatacaat aatcactcaa tcaaccaata acatcaatca cataggttta catacaataa   1020
tcactcaatc aacttcataa gaagaatcat gtttacttaa ttcatcaatt atccccaaaa   1080
acaccactat taagtataaa ctacaacata tttgtagtga tgggtcaaca tttttatcat   1140
atttaaactc gggttccctc aaatcgagaa atagtgaaca tgtaatatta attttaaatc   1200
gcaattacag aaattaattg aatttggtca aatggacaga attttataga ttgggtggaa   1260
ctagaaaaaa aaaaaaaaag agtatagggt gaattgagta catgaaagta catggtaatc   1320
ctagttaaac gcataataca tgtgggttca tttgtatttt tttgtaactt acgagtaaac   1380
tggctacaac aaaaaaaaat tagaagattt ttttgttttg tagaaaaccc taattttagt   1440
tatagttgta taactttgat aaaattataa aattgtatta cgaaaaaagt aataagatat   1500
tcaaaaaagc ctagaataac gtatatgact atgagcatga aactgcaagt caaatgctga   1560
cagacaacca taaacaaaag aaattaaata gagatacctt taaaataagt aaaatttcat   1620
ttataaaaaa tctactttct tgtgaatctg tcacgttcaa taatttgaag accactcaac   1680
atacaaggta aataatgaaa aataaaatct accaaaattt caatcattat tatcttccaa   1740
aaaaacaaaa ttatacagat gatgatggtg atatggaact tcgattggct aatattcact   1800
gtgtctctaa aaaccatcca cttatcaaga taagatggac cctacactca tccaatctaa   1860
accagtatct caagattctt atctaattac atcattctct accgttagat gaaattgacc   1920
attaacccta ccataactcc atacaccgcg agatactgga ttaaccaaat cgagatcatc   1980
gtagccgtcc gatcaacaag taccatctct tgaaatactc gaaatcctca taagtccgtc   2040
cctctttgct ctcactatca aaactctgaa tttcgatttc atctagagtc gagcccgggc   2100
gatatcggat ctcgactcta gtcgagggcc catgggagct tggattgaac aagatggatt   2160
gcacgcaggt tctccggccg cttgggtgga gaggctattc ggctatgact gggcacaaca   2220
gacaatcggc tgctctgatg ccgccgtgtt ccggctgtca gcgcaggggc gcccggttct   2280
ttttgtcaag accgacctgt ccggtgccct gaatgaactg caggacgagg cagcgcggct   2340
atcgtggctg gccacgacgg gcgttccttg cgcagctgtg ctcgacgttg tcactgaagc   2400
gggaagggac tggctgctat tgggcgaagt gccggggcag gatctcctgt catctcacct   2460
```

-continued

```
tgctcctgcc gagaaagtat ccatcatggc tgatgcaatg cggcggctgc atacgcttga   2520
tccggctacc tgcccattcg accaccaagc gaaacatcgc atcgagcgag cacgtactcg   2580
gatggaagcc ggtcttgtcg atcaggatga tctggacgaa gagcatcagg ggctcgcgcc   2640
agccgaactg ttcgccaggc tcaaggcgcg catgcccgac ggcgaggatc tcgtcgtgac   2700
ccatggcgat gcctgcttgc cgaatatcat ggtggaaaat ggccgctttt ctggattcat   2760
cgactgtggc cggctgggtg tggcggaccg ctatcaggac atagcgttgg ctacccgtga   2820
tattgctgaa gagcttggcg gcgaatgggc tgaccgcttc ctcgtgcttt acggtatcgc   2880
cgctcccgat tcgcagcgca tcgccttcta tcgccttctt gacgagttct tctgagcggg   2940
acccaagcta gcttcgacgg atcctctagc atatgctcga ggcggccgca gatatcagat   3000
ctactagtcc gatctagtaa catagatgac accgcgcgcg ataatttatc ctagtttgcg   3060
cgctatattt tgttttctat cgcgtattaa atgtataatt gcgggactct aatcataaaa   3120
acccatctca taaataacgt catgcattac atgttaatta ttacatgctt aacgtaattc   3180
aacagaaatt atatgataat catcgcaaga ccggcaacag gattcaatct taagaaactt   3240
tattgccaaa tgtttgaacg atcggggaaa ttcgagctcg gtagcaattc ccgaggctgt   3300
agccgacgat ggtgcgccag gagagttgtt gattcattgt ttgcctccct gctgcggttt   3360
ttcaccgaag ttcatgccag tccagcgtgt cgaccgatcg gtcaaacatt tggcaataaa   3420
gtttcttaag attgaatcct gttgccggtc ttgcgatgat tatcatataa tttctgttga   3480
attacgttaa gcatgtaata attaacatgt aatgcatgac gttatttatg agatgggttt   3540
ttatgattag agtcccgcaa ttatacattt aatacgcgat agaaaacaaa atatagcgcg   3600
caaactagga taaattatcg cgcgcggtgt catctatgtt actagatcgg gaagcttggc   3660
gtaatcatgg caactttatt atacaaagtt ggcattataa aaaagcattg cttatcaatt   3720
tgttgcaacg aacaggtcac tatcagtcaa aataaaatca ttatttggag ctccatggta   3780
gcgttaacgc ggccatcccc tatagtgagt cgtattacat ggtcatagct gtttcctggc   3840
agctctggcc cgtgtctcaa aatctctgat gttacattgc acaagataaa aatatatcat   3900
catgaacaat aaaactgtct gcttacataa acagtaatac aaggggtgtt atgagccata   3960
ttcaacggga aacgtcgagg ccgcgattaa attccaacat ggatgctgat ttatatgggt   4020
ataaatgggc tcgcgataat gtcgggcaat caggtgcgac aatctatcgc ttgtatggga   4080
agcccgatgc gccagagttg tttctgaaac atggcaaagg tagcgttgcc aatgatgtta   4140
cagatgagat ggtcagacta aactggctga cggaatttat gcctcttccg accatcaagc   4200
attttatccg tactcctgat gatgcatggt tactcaccac tgcgatcccc ggaaaaacag   4260
cattccaggt attagaagaa tatcctgatt caggtgaaaa tattgttgat gcgctggcag   4320
tgttcctgcg ccggttgcat tcgattcctg tttgtaattg tccttttaac agcgatcgcg   4380
tatttcgtct cgctcaggcg caatcacgaa tgaataacgg tttggttgat gcgagtgatt   4440
ttgatgacga gcgtaatggc tggcctgttg aacaagtctg gaaagaaatg cataaacttt   4500
tgccattctc accggattca gtcgtcactc atggtgattt ctcacttgat aaccttattt   4560
ttgacgaggg gaaattaata ggttgtattg atgttggacg agtcggaatc gcagaccgat   4620
accaggatct tgccatccta tggaactgcc tcggtgagtt ttctccttca ttacagaaac   4680
ggctttttca aaaatatggt attgataatc ctgatatgaa taaattgcag tttcatttga   4740
tgctcgatga gtttttctaa tcagaattgg ttaattggtt gtaacactgg cagagcatta   4800
cgctgacttg acgggacggc gcaagctcat gaccaaaatc ccttaacgtg agttacgcgt   4860
```

cgttccactg agcgtcagac cccgtagaaa agatcaaagg atcttcttga gatccttttt 4920
ttctgcgcgt aatctgctgc ttgcaaacaa aaaaaccacc gctaccagcg gtggtttgtt 4980
tgccggatca agagctacca actctttttc cgaaggtaac tggcttcagc agagcgcaga 5040
taccaaatac tgtccttcta gtgtagccgt agttaggcca ccacttcaag aactctgtag 5100
caccgcctac atacctcgct ctgctaatcc tgttaccagt ggctgctgcc agtggcgata 5160
agtcgtgtct taccgggttg gactcaagac gatagttacc ggataaggcg cagcggtcgg 5220
gctgaacggg gggttcgtgc acacagccca gcttggagcg aacgacctac accgaactga 5280
gatacctaca gcgtgagcat tgagaaagcg ccacgcttcc cgaagggaga aaggcggaca 5340
ggtatccggt aagcggcagg gtcggaacag gagagcgcac gagggagctt ccagggggaa 5400
acgcctggta tctttatagt cctgtcgggt ttcgccacct ctgacttgag cgtcgatttt 5460
tgtgatgctc gtcagggggg cggagcctat ggaaaaacgc cagcaacgcg gcctttttac 5520
ggttcctggc cttttgctgg ccttttgctc acatgtt 5557

<210> SEQ ID NO 9
<211> LENGTH: 5047
<212> TYPE: DNA
<213> ORGANISM: Unknown
<220> FEATURE:
<223> OTHER INFORMATION: Nucleic acid construct
Lo484-pENTR-A1-inv-35s-GFP-E9
<220> FEATURE:
<221> NAME/KEY: terminator
<222> LOCATION: (268)..(295)
<223> OTHER INFORMATION: complement
<220> FEATURE:
<221> NAME/KEY: terminator
<222> LOCATION: (427)..(470)
<223> OTHER INFORMATION: complement
<220> FEATURE:
<221> NAME/KEY: misc_feature
<222> LOCATION: (593)..(687)
<223> OTHER INFORMATION: attL4 recombination site
<220> FEATURE:
<221> NAME/KEY: promoter
<222> LOCATION: (715)..(1571)
<220> FEATURE:
<221> NAME/KEY: terminator
<222> LOCATION: (2428)..(3097)
<223> OTHER INFORMATION: E9 terminator
<220> FEATURE:
<221> NAME/KEY: misc_feature
<222> LOCATION: (3098)..(3254)
<223> OTHER INFORMATION: complement: attR1 recombination site
<220> FEATURE:
<221> NAME/KEY: misc_feature
<222> LOCATION: (3441)..(4250)
<223> OTHER INFORMATION: kanamycin resistance

<400> SEQUENCE: 9
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540

-continued

```
aacgacggcc agtcttaagc tcgggcccga gttaacgcta ccatggagct ccaaataatg    600
attttatttt gactgatagt gacctgttcg ttgcaacaaa ttgataagca atgctttttt    660
ataatgccaa ctttgtatag aaaagttgcc atgattacgc caagcttgca tgcctgcagg    720
tccccagatt agccttttca atttcagaaa gaatgctaac ccacagatgg ttagagaggc    780
ttacgcagca ggtctcatca agacgatcta cccgagcaat aatctccagg aaatcaaata    840
ccttcccaag aaggttaaag atgcagtcaa aagattcagg actaactgca tcaagaacac    900
agagaaagat atatttctca agatcagaag tactattcca gtatggacga ttcaaggctt    960
gcttcacaaa ccaaggcaag taatagagat tggagtctct aaaaaggtag ttcccactga   1020
atcaaaggcc atggagtcaa agattcaaat agaggaccta acagaactcg ccgtaaagac   1080
tggcgaacag ttcatacaga gtctcttacg actcaatgac aagaagaaaa tcttcgtcaa   1140
catggtggag cacgacacac ttgtctactc caaaaatatc aaagatacag tctcagaaga   1200
ccaaagggca attgagactt ttcaacaaag ggtaatatcc ggaaacctcc tcggattcca   1260
ttgcccagct atctgtcact ttattgtgaa gatagtggaa aaggaaggtg gctcctacaa   1320
atgccatcat tgcgataaag gaaaggccat cgttgaagat gcctctgccg acagtggtcc   1380
caaagatgga cccccaccca cgaggagcat cgtggaaaaa gaagacgttc caaccacgtc   1440
ttcaaagcaa gtggattgat gtgatatctc cactgacgta agggatgacg cacaatccca   1500
ctatccttcg caagaccctt cctctatata aggaagttca tttcatttgg agagaacacg   1560
ggggactcta gaggatccaa ggagatataa caatgaagac taatcttttt ctctttctca   1620
tcttttcact tctcctatca ttatcctcgg ccgaattcag taaaggagaa gaacttttca   1680
ctggagttgt cccaattctt gttgaattag atggtgatgt taatgggcac aaattttctg   1740
tcagtggaga gggtgaaggt gatgcaacat acggaaaact tacccttaaa tttatttgca   1800
ctactggaaa actacctgtt ccatggccaa cacttgtcac tactttctct tatggtgttc   1860
aatgcttttc aagataccca gatcatatga agcggcacga cttcttcaag agcgccatgc   1920
ctgagggata cgtgcaggag aggaccatct tcttcaagga cgacgggaac tacaagacac   1980
gtgctgaagt caagtttgag ggagacaccc tcgtcaacag gatcgagctt aagggaatcg   2040
atttcaagga ggacggaaac atcctcggcc acaagttgga atacaactac aactcccaca   2100
acgtatacat catggccgac aagcaaaaga acggcatcaa agccaacttc aagacccgcc   2160
acaacatcga agacggcggc gtgcaactcg ctgatcatta tcaacaaaat actccaattg   2220
gcgatggccc tgtcctttta ccagacaacc attacctgtc cacacaatct gccctttcga   2280
aagatcccaa cgaaaagaga gaccacatgg tccttcttga gtttgtaaca gctgctggga   2340
ttacacatgg catggatgaa ctatacaaac atgatgagct ttaagagaac ggatccccat   2400
ctgcggccgc ctcgagcata tgctagagga tcctctagct agagctttcg ttcgtatcat   2460
cggtttcgac aacgttcgtc aagttcaatg catcagtttc attgcgcaca caccagaatc   2520
ctactgagtt tgagtattat ggcattggga aaactgtttt tcttgtacca tttgttgtgc   2580
ttgtaattta ctgtgttttt tattcggttt tcgctatcga actgtgaaat ggaaatggat   2640
ggagaagagt taatgaatga tatggtcctt ttgttcattc tcaaattaat attatttgtt   2700
ttttctctta tttgttgtgt gttgaatttg aaattataag agatatgcaa acattttgtt   2760
ttgagtaaaa atgtgtcaaa tcgtggcctc taatgaccga agttaatatg aggagtaaaa   2820
cacttgtagt tgtaccatta tgcttattca ctaggcaaca aatatatttt cagacctaga   2880
aaagctgcaa atgttactga atacaagtat gtcctcttgt gttttagaca tttatgaact   2940
```

-continued

```
ttcctttatg taattttcca gaatccttgt cagattctaa tcattgcttt ataattatag   3000
ttatactcat ggatttgtag ttgagtatga aaatattttt taatgcattt tatgacttgc   3060
caattgattg acaacatgca tcaatcgacc gggtacccaa gtttgtacaa aaaagttgaa   3120
cgagaaacgt aaaatgatat aaatatcaat atattaaatt agattttgca taaaaaacag   3180
actacataat actgtaaaac acaacatatg cagtcactat gaaccaacta cttagatggt   3240
attagtgacc tgtagaattc gagctctaga gctgcagggc ggccatcccc tatagtgagt   3300
cgtattacat ggtcatagct gtttcctggc agctctggcc cgtgtctcaa aatctctgat   3360
gttacattgc acaagataaa aatatatcat catgaacaat aaaactgtct gcttacataa   3420
acagtaatac aaggggtgtt atgagccata ttcaacggga aacgtcgagg ccgcgattaa   3480
attccaacat ggatgctgat ttatatgggt ataaatgggc tcgcgataat gtcgggcaat   3540
caggtgcgac aatctatcgc ttgtatggga agcccgatgc gccagagttg tttctgaaac   3600
atggcaaagg tagcgttgcc aatgatgtta cagatgagat ggtcagacta aactggctga   3660
cggaatttat gcctcttccg accatcaagc attttatccg tactcctgat gatgcatggt   3720
tactcaccac tgcgatcccc ggaaaaacag cattccaggt attagaagaa tatcctgatt   3780
caggtgaaaa tattgttgat gcgctggcag tgttcctgcg ccggttgcat tcgattcctg   3840
tttgtaattg tccttttaac agcgatcgcg tatttcgtct cgctcaggcg caatcacgaa   3900
tgaataacgg tttggttgat gcgagtgatt ttgatgacga gcgtaatggc tggcctgttg   3960
aacaagtctg gaaagaaatg cataaacttt tgccattctc accggattca gtcgtcactc   4020
atggtgattt ctcacttgat aaccttattt ttgacgaggg gaaattaata ggttgtattg   4080
atgttggacg agtcggaatc gcagaccgat accaggatct tgccatccta tggaactgcc   4140
tcggtgagtt ttctccttca ttacagaaac ggctttttca aaaatatggt attgataatc   4200
ctgatatgaa taaattgcag tttcatttga tgctcgatga gtttttctaa tcagaattgg   4260
ttaattggtt gtaacactgg cagagcatta cgctgacttg acgggacggc gcaagctcat   4320
gaccaaaatc ccttaacgtg agttacgcgt cgttccactg agcgtcagac cccgtagaaa   4380
agatcaaagg atcttcttga gatccttttt ttctgcgcgt aatctgctgc ttgcaaacaa   4440
aaaaaccacc gctaccagcg gtggtttgtt tgccggatca agagctacca actctttttc   4500
cgaaggtaac tggcttcagc agagcgcaga taccaaatac tgtccttcta gtgtagccgt   4560
agttaggcca ccacttcaag aactctgtag caccgcctac atacctcgct ctgctaatcc   4620
tgttaccagt ggctgctgcc agtggcgata agtcgtgtct taccgggttg gactcaagac   4680
gatagttacc ggataaggcg cagcggtcgg gctgaacggg gggttcgtgc acacagccca   4740
gcttggagcg aacgacctac accgaactga gatacctaca gcgtgagcat tgagaaagcg   4800
ccacgcttcc cgaagggaga aaggcggaca ggtatccggt aagcggcagg gtcggaacag   4860
gagagcgcac gagggagctt ccagggggaa acgcctggta tctttatagt cctgtcgggt   4920
ttcgccacct ctgacttgag cgtcgatttt tgtgatgctc gtcagggggg cggagcctat   4980
ggaaaaacgc cagcaacgcg gcctttttac ggttcctggc cttttgctgg ccttttgctc   5040
acatgtt                                                             5047
```

<210> SEQ ID NO 10
<211> LENGTH: 1313
<212> TYPE: DNA
<213> ORGANISM: Oryza sativa

<400> SEQUENCE: 10

```
cgtccgatgt gattccgtcc tcttgattgt tttccttccc cctaattttt gttgcatacg     60
cggagagaag ctttagcttt aagaggttaa ctggcggcac ctcaatttct ttgggcttca    120
gcatgggtta agaccaccta ataatcctgt cgcattcttg ctcttggaaa agtttcttcc    180
aacattgcag tccagtcaga gaatggcctg taataattag tgacaaaatt atagcagtag    240
atagaatctg ttcattcaag ttcttcaaat tactgggcca agcttcaatg tcattttttg    300
cttaactcgt gctcgtgctg ttatagttta caactatctt ctttacctgc ccataaccaa    360
tgtgaccatc gaatcaaacg tatgtggcgg tgaatcccgt tgcttgtgcg ttgctagatt    420
tttgaggtcg ccttctgttc caaattccaa tcatttgaat tcgaagggat tacctgtcga    480
ctgcgcatac gatcttttat tgagaatatt tgctaggtgt gggagttcct gcgtgtgttc    540
gtttagtgga cgtgcgtatg tgagcatgtg ctatatgttg tgcttcgtga aaactcagct    600
tcttttcatc aagatcggca cctctgctta tcacctaatc ccatcattcc aatagcaaca    660
taacatagat gtgacacatc ctatacatga tattgggatg gagagagtat tcctaagatg    720
catctctacc ctttctcttc gaatgcacat ttattgggag tcatttttaa tgtgcatttg    780
tgcaaactgg taccatggaa ccctagtgct accctaacag atatgctcca tcgtcactac    840
aaactcttgt ttacatccac aaactactgc ttggaagggc acgctgacat ttgatcagaa    900
gaaagaatga catgggtgcc aaagttatgg atcagtgtgg tgaaattcga gaataaccga    960
caagatactt ctcaatcttg tcacaataag agggttattt ttgtttagta cagtacaact   1020
aacgataccg cacaaaaaac ggtgaacgcg atatcgcaca aaaaaaagag caacacgttt   1080
gaattatatt caggtttgct actgcaatcc aacaccatct cataactaca ttatcctaat   1140
cgagcctttt taagtaatga ggccagtaca attaaaaaag gtgccgtaga caatagcaaa   1200
cccatgaaga actgaaaaca aatgaatgca aaactaaaat tgtcttagtt ctgtcgacaa   1260
atgccaactg ctataatcgt acatgcgtct ccgaagaaac cgccgacact gcc          1313
```

<210> SEQ ID NO 11
<211> LENGTH: 1498
<212> TYPE: DNA
<213> ORGANISM: Oryza sativa

<400> SEQUENCE: 11

```
cagagtgaca gacagtgata cttgctagcc ttttttatga gcaccctttt tggcctttta     60
gttcctcatt agctaagaga tgtgatgagt gaggttttat tttttggctt tgtttggagt    120
tttgctttgg aggaagatag agaagccttt agaatgagtt gtgatggagg atcacatagt    180
ttgtctcagg tttacaatgt gcggtaaaaa aaaggaagga aataaagtga tgttagaata    240
tacagttttt taatccattt ctacagcttc aaattctcga ttgagcggca cgttctttga    300
aatgttcata gcaaagcaaa tcaaacgaaa tggatgagat ttgaaactaa gaaactgcac    360
ttgacaaagc acgctgcgct ctctgaaatt catgttcagc agaacgcctt tcagaaattc    420
atgttctgct gctgcaggaa ggcagctaag aactccatgc aataaaaata taaaatgcag    480
tgcagttatt agttagtgta gtagtaatct aagaaacaac aggtttaaca gaatattacc    540
ttcaaaaaca tcccctcaaa tcaagactcg gaaatcaaca ccattctgaa actagatgca    600
atactgcgct cctaatggaa tcttcagtgg ttactcctac acgccactaa aaaaaacggg    660
ctttggaaaa acgtcaccct gaaacaaaag ctcagtaaaa ataccactct aaaatcttgc    720
agcatgcaat atcacaaaag cagatcaatc cgtaattgta tttatgctgc atataccgtg    780
atattttctg tgatcctctg cactatcttc agctcatcag ctgcatattt tgaagccgga    840
```

-continued ctgatggctc atcgctttgt ttcggcttat tgtgatagcc atccatgcgt tgacgaaaga 900
tttagatata tcacaatttt aaccaagttc agagcaatgt tagctttagc tgatgatata 960
cacggcgcac tgattgccgc cgttattttc agagccttgt aaaacctgaa acaaattgtg 1020
tctccaaatt cttactagta ctgcagacat agcggatttg ttttcaggat gaattatcac 1080
aaaggtaagt caattcatag ccatattacg caagttcaaa actgcaggcc acaccatacg 1140
tttctgaaag tagaaacaag agatcttgca gcagatcacc actaaagaag cagtaaccgc 1200
aaaaaattat aacataatcc agaattaaca cttcgcagca ttactgaatt cactttaata 1260
gcacttctca tcatgaacta gtacaacaac ataactgtcc agtggaaatg tgaaatgcat 1320
acaccaagta atggtccata acatgaacta tatggataca acaacgttct tatttcgctc 1380
atatatacat gaaataagtc ttgcacgtct tggttactta ataggtgcga taatcgccgt 1440
aggcttttag aagaagaaaa aaaagtgagc ctgcaaagtt cctggggaca gttgaaga 1498

<210> SEQ ID NO 12
<211> LENGTH: 1246
<212> TYPE: DNA
<213> ORGANISM: Oryza sativa

<400> SEQUENCE: 12
cccttgacag ctccagtttt actcttgtgc agtgtactga aattctggta ctgtagtaca 60
gtcttccact ggtttggttt gtcgctgagg cagcagaagg cttatggtta cacgtacacg 120
gtgacggtag gtcggtagct ggcttttggg tagaggaatc tgtatgtctg agtgaaataa 180
tactggattc gccatttggt gcgtttcctt ttttgtttcc ttttggctgg cctgctttct 240
tgcttcgtaa cttgaccaaa aagttctggc cgtcgcaaag agctggaact gtgaatacat 300
tttctactgc ataaaacgtt acacgcatca tgcatcacct acacggttac acccgataga 360
attcggttac agttcaatta caaggcactc ccgagtccca gaagctagca cgtcgagcag 420
acaaacccta cagataaaat ttctcctcgc catgctttta agctttacgc taaccacatg 480
cttataataa taacgagcat tgccgcgtca tttccagatt gaagtggcag tgaagggcaa 540
caaaatgatc atcaccttgc tgaaattagt gggcagcagc aaccatagcc gtgcgagcac 600
ccgtgaaagt tgatatcagc gcccccagct gtaacttgtc attgcaagca aagcttagcc 660
ggtacctgca cacagacgcc atgaacaacg tgccatctta agggaaaagg ccataaatgg 720
ttatactacc tacctttcca agaagactaa aggctaaaaa tatttggaat atttcataat 780
attaatcagt tattatactt ccataagtat tccagatagc caaaggtcaa ctttaggtaa 840
ttgcatcatg aaagcaaccc aaagactcat tttcccccca aatgcaaaca ttccacaagg 900
cacaaataag caattccaac atgtgaggtt tgcttaacaa ctattgcttt gcagtatgca 960
accatttaac tgtaatggct aaattgtgaa acacatacaa taaagtatgt tagctggttt 1020
aaattattta ttattatttt tcttacgtaa gatactccat actagttatt tgatgtgatg 1080
acataaatga ctatcttgaa gcatataata tgaataaatc agcaaaatgt tccgtcaaag 1140
ttttgaaaaa aaagggtact gagtagaaaa tcagccaaaa atcacaaatg atttatgatc 1200
aaataaaata ttatatgcaa gttctaggtg aactaagcaa ggcaca 1246

<210> SEQ ID NO 13
<211> LENGTH: 771
<212> TYPE: DNA
<213> ORGANISM: Oryza sativa

<400> SEQUENCE: 13

-continued

```
cgtggcaatg gctgtcatgc tttggcacat actaatagca aggtagaatg gtacagctat     60

ttcattattt ttgcccttgt atatttgtat cactacatga gtaaacgacg tttagttatc    120

gatagttttg ttatgagtga tgaatgatct gcatcgtact gccaatgcct tgcattctca    180

aatggttgca cacttgcact catacaaagt tagtacactc catcatatta taaattactt    240

ttttttcaag ttaaatttcc tgaaagtttg ataaaattta tagaaaaaat ataacgacgc    300

ttataacact aaattaattt cattacatct aacattaaac atattttgat tttttttgt     360

tttgtgttaa atatattact atgtttttct ataaacttga ttaaacatat aaaagtttaa    420

cttcaaaaaa aagttaaaat gacttgtaat ataaaacgta ggcagtacaa tgcgaatgta    480

gggtactcca tccagctgag gtaaaccaac tccaatatat atacaaacac aaacaacgta    540

cccaattttt actgttaaaa tacaggcaca atgcctggta tcacacgtta ttaagtagac    600

agactcgata accatgacac ggacagggac ttcttgccac tggtttacgc acggttaata    660

ttacagacca cacatagaga gacggcttag ctatttgcaa ataagcttga caagatagat    720

gatgctccaa aaggatgcga tctcagcagt tgagtactta cgctggttca t             771
```

<210> SEQ ID NO 14
<211> LENGTH: 755
<212> TYPE: DNA
<213> ORGANISM: Oryza sativa

<400> SEQUENCE: 14

```
ttctgagcac ctgacaaaat attcagtcct ggattggacg tatatattgt tggtaaactc     60

ctgagttgct gatgagggaa aagtattgaa atgaaatctt gaggttttac ataggcgatt    120

gtgttcatca cataaacgcc ttccttttcc ttgcccggaa tgcaagaacg agagatacct    180

tgaaaatgtt ttatcctgtc atgaatgtac ctcaatcgca agatgtacag tgtggttgga    240

ccggctggtt ggttaattat attggtcctg acatgttcct atcctaatta atctcctgtt    300

tgtggggaaa acgaagaata agtatgtcat tttcatctag ctgggttgcc tgcatctgca    360

tgctagctag ctactgtaaa tgatgcgtac gtatgctcat gaatgaattc gcaagcgatc    420

gccgcaccat acatcctttg ttcttgccat taatcaagca agataagcta cctagtagtg    480

ctataacttg cgttgattaa ttgcatcggt cgattacaat acaagctcgc tatacatact    540

cgtccgctga ttgatcagtt tctgcacttc tgcagtgata aacacaaaca ctacctcgat    600

cgatcgatca gttgtgcagt gggtttgggc cctccggcac cacccgcttg gacgcagaca    660

caccatgatc ctcctcctcc tcctgcatca tgcgcctgct gctgtagtaa tggccgggcg    720

gcgccgccat ctcctccgtc aaaaggccgc agccc                               755
```

<210> SEQ ID NO 15
<211> LENGTH: 1373
<212> TYPE: DNA
<213> ORGANISM: Oryza sativa

<400> SEQUENCE: 15

```
tgctctgatg tatgccttca aattcatcct tctgtgcaga aaatagctgt agagaaatgg     60

aaactgggct gtttttatcc gtgcccccta atatgagaaa ctatgcctcc ctcagatttt    120

tttggctaga ctaacagaaa tatgagaata gcccatatca ttgacattag atgcagagca    180

tgggaaatgc caatgtggat tggcttgtgt gtaacaactg acaaacatgt gctgtgcaat    240

tgtgaatact ggagttgtac aagtggtata ctgtaatact gttatagcat agcatcagaa    300

tacaaagaca gaaatgaaca catagcatcg atgtctcttt tctttatttt tttctttgga    360
```

-continued

```
cagcatgcct tgaattattt gccataatgt ctccgtcccg ctggcttcat cacaccttct    420

ttgctgggtt tagtttcagt tcatcgtttg gattagctgt ttatgaatag agatgctgtt    480

tctgtctatg ttcactctca gggatgaaca tagggcctgc actgtctatg ttcaaactca    540

gagaggaaca ttgggcctgc actgcagcgg tgaaatggat ccgtgtgttc gcgccaccag    600

aatgagcttg gggcgcaatg gaacatgtga tgtcagttaa agttgcaggt aaggcagtca    660

ccggtcaaat cacggcactc gccaaccagg ccggagcata tcggctctgc cgtttgtttg    720

ctcctatctg tacgtagcac gagctgtttt ccattggcaa cgcctgatcg atcaaggcgt    780

tctactcccc tcagcacatg acgccaacgg gttgcatctg ctgacgacaa atcgctacgc    840

agactccaga ttttacagct gtgttctgca tcaaccatgg ggaattggcg acccaaagtg    900

ccaaaccatc acacgcaagt tgccatgatc gatgcgtgaa ccggaaattg atcctctaac    960

ttgtccccat aatttatgag cctacgtatg agtaacccat agcatagtat cagagaacag   1020

taagtcagat aagccttttc gatctgcgac catcaaaatc gaacaaacgg cagcacattt   1080

tagccgaaac gaatcagaga tctgccccag atttgcaacc tacacacttg acaatctcaa   1140

cttggctgcc tgcaatctgc cattcccctt ccactgcaac atggagatag ccccacccac   1200

caacgcagcc accctacgga aaagcacacc gtaacgccgc ccaccaaccc ccctccgaat   1260

ctcctccgat cccgacgcct atagatgaat aaatctcctc cctcttctca ctagacaaag   1320

cccaaaccaa ggccaaaacc ctcctcccct cctctcctct ccattccgcc gcc          1373
```

```
<210> SEQ ID NO 16
<211> LENGTH: 1208
<212> TYPE: DNA
<213> ORGANISM: Oryza sativa

<400> SEQUENCE: 16

tgtaccatat ctccagtgag gcttgagggc gaaaattcgg aagccctctg ttttacaacc     60

tgcttgtatg ccatgttcca gttctgagga taccgggacc tatcaatttc gtgtcctctg    120

ctgtgctaga ctcgatcaca ttggtgaacc atgaatatca tgtccctttc aaagaaatcg    180

ttgtgcaagt actgatatac cgtactctat tttgttgatt gctttttgag cgtgtgttta    240

tctgttcagt cgtcttgctc tctttttttt ttttttgggg gggggggggg tgggggtgga    300

tttttcataa aattggtatg cggcactaac gatcatgata gcgtcgaaag aacacgattc    360

ggtttattag ccccgaaaat tatctccatt tttcttttta acattttggc ggctgtcatg    420

caaaattgcg caggaaatta gactagttag tttaatatca aaattggcca catttgagta    480

ttactttttg ttccccgact gcatggtaaa aagaaagata taaatataca gaaatacttc    540

tgaaaatcta ctgacatgat tttcattttt tttccatacg ttaacacacg aagtttaaga    600

acctctctta actgctagcg ttccaaagca agaaaaggac aaaccgcatt ttaaaacaaa    660

ctccatgtta ttttcaagga ccaattaatt tgcatatgtg agtgcattcg atgatcatgt    720

ttacgctacc tccaattttg ttgaaatgtg tgatagtagc ttaaggaggt agcaggaccc    780

aaagtgggtg tgcgtatcca caagtgcgtg taattgtgtt caccttgtac taggggaaaa    840

aaaaagaaga gcaagacggt atggggtaaa ctgagaagaa aaaacggaga aaacctctat    900

ttcttaaaat ccctttctca actcatttta ctcacgtcca tgctcaccac aaagaaatga    960

attcgcagtc aaacatcact aaaataggta atgctccgca agttcatcca ctacacctac   1020

ggaaaaaaaa aatgtggtgc ccaaatgccc aataatacaa actgttcccc tcccgtttct   1080

ttggctgtcc tgttccatgc tctttgccga gccagaacaa aacacaattg agcaagccaa   1140
```

-continued ccatggaaag ctcagcacat taaggcaggt caagatggaa cctgcacctc atgtacctac 1200
gctgtaag 1208

<210> SEQ ID NO 17
<211> LENGTH: 1494
<212> TYPE: DNA
<213> ORGANISM: Oryza sativa

<400> SEQUENCE: 17
aggtttctag tctactactg ctagtacatt gcccgtggta ctcttgtttt gcatctaggc 60
tagggccagt gtgaaccagc agactaccac tgtgagtcgc ctctgtaata aaatttgttc 120
ggcctatggc catcctcagt acgttgtcaa tgtctcggtg ggctgttatg ctcaactgca 180
atgctgcatc cactgaaacc tctttctaga tgtgttggta tgaaatgcgg tattgcgttc 240
ccgatttccc ctgctactgt cttgaacctg ccgtggtaca atccttgttt gctgcacttc 300
atttttagtt cgttctaatt ccgcctggaa tgacttttga gtgcttcacg ggctgactgc 360
ctgaccgtgt tgctgtacat gcctacccca tcagttcaaa aaaaaacaat cctacctacg 420
aaattcgttt tttattggga caggacatcg gctgagttta atttcaaaat ttttcaacaa 480
actttcaact tttccatcac atcaaaactt tccctataca cgtaaacttt caacttttct 540
gtcatatcgt ttcaatttca accaaacttt taattttgat gtgaactaaa cccacccatc 600
attggatgga cttggcaaaa catggcttga ccattgagat cgttttgggg attttgttca 660
gtcagctctt ccatggtgtc tatcagaaga gttggggccg tacaacgcaa attatttccc 720
agatggtgtt gatatcatca atgatcatgg caatttggca aaccatttct tatttcccag 780
atggggttgg tataataatt aatcatggca accccatttg tttggtgcta acttgatgaa 840
acatgaatgc cctcaacctc aacagatggg ctccagtccg gccggcgccg gccagcactc 900
ggtcaacaca atatgggcac gagtggggct caaggaagtg tggggcgcag cacaaggagc 960
caagagacaa ggagtcatgt tggtcctttc agtttcaggc aaaaaaggaa ccgaaaggag 1020
ccaaggatcg gaccctttcg aagctttttt gaccatttcg tccgacttgc aaggcaggcc 1080
cagaaacaaa aataacccaa ctgtctagtg gtaatatcat ttgggatctg ttaggatttt 1140
cagttcgaag aaactgtcct gattcagagt tcagacaaaa tacgccttca gtagttggtc 1200
ctgccgcccc tcgtagtttc actatcgaaa gggatcgctg ctgtcgtaat acgtttggtt 1260
ttggcaatac agaaatcaat ctgctcgcaa agtataatat cataatccaa agttccaaac 1320
ccttttattc gaacatagta ccatatatca tacaaagcag ccacaacttg cagagaatgt 1380
gggtttcgaa catcaacaaa caaacaaatg caatgttcag tctacccggc tctcaatctt 1440
gatcatatgt acaaagcagg tatagacggg atctcatttc catggtgatt caat 1494

<210> SEQ ID NO 18
<211> LENGTH: 1274
<212> TYPE: DNA
<213> ORGANISM: Oryza sativa

<400> SEQUENCE: 18
gatgcattcc ttggattgtt cccaatgtat tccagaaatc atagttttga tgccaaagtt 60
ggtcttcggt atttgttact tggagatggc aaatcgactt gagcaatgtt aaagttttgg 120
gcatttaaat tatagacctt tgcttggcac ggttagcttg tttcaaatcc gttgtttgtt 180
gtggaatgtg tttcacatat gtggtaggtg aagaatctca ttatggttcg ctgtttcatt 240
ctcttgcgtt tatcacccgc tgtctgctaa cttagggtgt gtttagtcct cgtcaaaatt 300

-continued

```
ggaagtttgg ttgaaattgg aacaatgtga cgaaaaagtt gaaatttttt ttgtgggtag    360
gaaagttttg atgtgataga aaagttggaa gtttaaaaaa aaagtttaga actaaactcg    420
gccctagtca atttaccctt actattaggc attatccccg ctgtctgcta acctagtcaa    480
tttacccttg tattattact aggcattatc cttgcctccg ttagtggttt gttcttgaga    540
gcggccaggt aggaaaattc cacttgaaga ggagtgcgtt acgccggcct cttgccatta    600
tcatcgtttg tattgatatg cagaaataga aagaaaaacc taggattttg atgaaaataa    660
atcggatata gatatcataa aacacattgg aacttgagat ggagagaact ctagatattt    720
tccatgagat tgttacctaa ttcctacttt cctacaaaat cttatgaaac tgccattcga    780
aaggaatatc gtaggattct cgagtcccaa tccgttccag aaaggtaaat cggaacaatg    840
gtacgaaaaa tctgtcccca ttggatcata agacttggac ggtctatccc atggtactaa    900
gggttttgga aagaattttg cagaatttga atggatgtat cctatacaca agttttctgt    960
gtacacatcg tacacatcaa ctaacaattt ttaccaaaaa tctaagaaca aattcacatg   1020
ttctatcatg agttatcaca cattcacacg ttcatatctt ggttaaatct gaacagcagg   1080
ctgtaaataa accacaaaag tctccaaatt atgggcctca acagtaatca atatcgtttc   1140
ctcagacggc aattgccagt ttgccacaac agccatgttg gctaacattt gatacattcg   1200
gagtactgct tgaatttgca ggctctccct aaccttatta tccctatagt ctttgactct   1260
tgatacctcc aaac                                                     1274

<210> SEQ ID NO 19
<211> LENGTH: 806
<212> TYPE: DNA
<213> ORGANISM: Oryza sativa

<400> SEQUENCE: 19

aaaacgcaga gatgtgaatt tttaacacaa gaactatata ttagtcttgc aatcatctcc     60
ttagcgacct agagtctctt ttcgtaattg atctgtattt aatagtagca gtctctaaaa    120
tggacaccac tttgagccat cataggagtg tcttctccat tgaattgtga ggaaactggg    180
caaagcttct tcatggcagc tgtaacagag agtttaagca aaagggagca ggagtttgca    240
tttgccgaac tcgttgtcac tgcccctgag agcaatattc tgtcatcttt gtgaagatct    300
acatcttctt gtgaccttac aatttgttaa atcaatgcaa gaatatggtt atctgcttac    360
atgatcatca atagttttga gatttttgaa ttccctagaa aacaaattgt cagtgatctc    420
catgattagt tgtataacat gtagatcagg cagtaacaat atggattgag caagctggat    480
acttcagttt atttttacag tcacgaacaa ttatgcaagt tccaaagtac aaggcaaatg    540
gaacatgcca ccaaaccgct atgagtaaaa gtatgaaaca cagaatggct ggatagcttt    600
gcaatggttg atgcaaatat ggcgattcac ataacagaac agtgtgcaat gcacaaagtt    660
ttttaacaaa atggagctac taaaccataa ctactacttt actttagtgg cagtgatcca    720
ctctccagag tttacaccaa aaaaatctta agacctggca gcgtcacaaa caagtcaagc    780
atagcgttct aaaactctca ggtatt                                         806

<210> SEQ ID NO 20
<211> LENGTH: 1435
<212> TYPE: DNA
<213> ORGANISM: Oryza sativa

<400> SEQUENCE: 20

ctgaactaca gtctcagcga gttttattag caaggagaag ctgtaattag tggccactgt     60
```

-continued

```
tgttcaatgt aaaaagaaag aagcgacacg gtatgatgta caagaaagca cagatgtgtg    120

atagaatggt attagggaat gatgtgtgct gcatttggtg aaaagaatac acaactgtag    180

gcctcataca aatgtggttg ttaatttgtg acagaactac tctgaattta atagagatca    240

acctatacaa ataccatcaa agaaagtgtc ggcacgtgac caaaagttcc aaaaacacgg    300

gataactcct gattaaacaa ggagaaaaaa aaattatttt ctgatttatc tatatagcct    360

tcagttcaga gtttgatact tatactggaa aagtggaaat ggacccagaa cacgaatcaa    420

ccggaattta agttcagttc cagcacaatt ccaggcatcc gcccgtttgt ctgatgtcta    480

cgtactgcaa aaatgtcgct catgtctgct agacgactac caaattaggc caagaaaaaa    540

aaaaccaagc attaagcctt gaacattcac aggacaaagt ctgcaaatgg tccaagcaaa    600

ctgatgcaac catgcaaatt tcagtcacag ttacactgcg gaaagaaggc atacatgtca    660

aggcaacatg gcatgccatc atcacgccag ttcactgata cagcatccag tcataatgga    720

gttgcacaga ccatattact acaagggcaa agtcaacttg cagcacattg ctgttcgttt    780

tgagtagcct cagtcacagc ttagccgcct ccaacctggc gtttccagga gtcctccaca    840

ataagctcgt caacgcccca gtcctcatag ctatatttga acacacagta aactattata    900

atgaggttac aaaatcagga aacacataaa tgtcttttat tcaaatctca ccttccgtca    960

ggtaagtacc gcctaattgt gaatgggatc ttgcgtgctc tcagctcttt catggcaatc   1020

taatttgcac aaagacaata gtttagcata gcaagtaatt tgaaagatag aataaaatca   1080

actgacaatt tctgacagaa agagagaaga aatctaagta gtatttataa tgagttgttg   1140

ataagtgcag tcaacattca tctcatcttg gttttgtggg agtactctac caaaatattt   1200

cagttaccat gcctaaaaca taccaaaata attttttatc cgggaaaagc aatctaagac   1260

ccttgtggaa ttctaaaaac atgtgaaaat ttttcatgac atggaggaag agggacacgt   1320

gtaaacatac aaaattttaa gattgagaaa catatgggag tcaacaaaaa ttgtattcat   1380

attcccggaa gaaatgaatt cctccaatct ctccctttct ctggccatca tgata         1435


<210> SEQ ID NO 21
<211> LENGTH: 889
<212> TYPE: DNA
<213> ORGANISM: Oryza sativa

<400> SEQUENCE: 21

tcgtcctagg tggtccattg ccctcaacta gacaatctat gcgcatcagg tatgtcaaat     60

ggtttcaaca attttacctg ttctatttcg ttttaaaatt tgaaacaggg aagggcctgc    120

tgaatttgat catgaagtga atttgatatc cagatttctt atcagcgcca actccaaagc    180

acatgcagca attataagta ctgactgact gcaagaatag actgtacttc tatgaagttg    240

gatctcttca cctatctgtt caccctaaac cttttcatgg tttataagaa tgcgggttgt    300

ttcttgcaaa attttgggta gaatggtgca aaaaagaatt tgttcgataa tgaagatagc    360

tgtggttttg ttagcttgtg ttatattgat gtaatttaag atcatgcgag tgtttatttt    420

cccggcgaca ttcttttgtt tattcattat atgcagtatc catttatctt ggctctcacc    480

tgcctgatga aaaacatgta tgtttatcca taccatatgt aacaccgtcg aatgttaatc    540

acttctgcgt aacaatgcaa atgtgccaaa actagtatag aagtattccg gtcaaaaatg    600

aaagaacatt aataaacaaa agaaaaaaaa catctggcca gtaatgcctc gtccgaaact    660

agtaaactac gcgaaacaat caactgaaaa ggacaggtga atcagccaac caagactatt    720

gccagtaaac gagaaagcca gtgcagtaac aaccatccat aaattgaagg taaacgggcg    780
```

cattttccag caccatgcca accaggctga ttacaaatcc caacacatca gatgttttca 840
gggaaatcaa tagaatatga tcgttgctcg cgacagccgg gaatcagta 889

<210> SEQ ID NO 22
<211> LENGTH: 1721
<212> TYPE: DNA
<213> ORGANISM: Oryza sativa

<400> SEQUENCE: 22
cattgccatg cctttcatga tcttgcaata tggacttgtc tattatggat ttgtgtgtca 60
ctataaattt ggtagtgtga gactgcttga tggtttgtgg gtttgttcat ggaaccatgg 120
agatatggct ctatcctgta tttcgttgtt gcgctcagaa tgtatgggcc tgtgatgcac 180
tgttccaagt ttaattgaga tgtgtcaatg ttcaagttac agaataaatt gctgatatgt 240
tctcagttct catggacacc ttgggaggat tgtatggttc tgactactca tggaggttga 300
gtaatgcagc gtttccgttc gtttgctctt tatttgataa agtataaaat gcttcgggag 360
gattgtgtgg tttatgttag ctcatcgagg ttaagcaata cagcatttca gttcgtttgc 420
tctttatttt gataaatatc aaatgttttg gatgatttgt gtggttctat gttattcatc 480
aaggttgagt gatgtagcgt ttcggttcgt ttgcttcttt gttggataaa atatgaaagt 540
gcggtttggg caaatgcact tgtgggacaa aattaaaaga taaagatagt tcccctcttt 600
ttgttggata caacgtgact ttggctttgg ccaaatgcac ttgtgggact aaattaaaag 660
ataacctctt gggcaaattc acttgtggga aaatatgatg tgtgattttg ggaaaatgcg 720
cttgtgggac aaaataaaaa cataatcaaa atatgaagtg ctaattttct ttggcaaaat 780
gcagaaaata ataataatct aaatatgaag tgtaaatttt ctttgggcaa atgcataaaa 840
attgggaaaa gacaaaaaaa taaaacataa tcaaaatatg aactggaaaa ggtttaaaaa 900
aaatacaaaa cacataatca aaatatgcaa atatgaacta taaattttct ttgggcaaac 960
gcaatgtttt taggaagatg tgagcttttt ttccttaacc aaatcagcct aaaggcaaag 1020
accatcagag aactgtcata atctgattat cctgatctca ctcgtcaact tttcttccag 1080
gaagataata tgagaataca gaacaatgag gacaactcga cgcaacagtc agtggggagg 1140
agcaagcttg gaggagtcaa atagctcaaa cagtcatgca caatacttga tatggcctgg 1200
tctaccaaag cagtttttct ggatgtctct cttgggaaga tacatcattt tgttccccca 1260
cgaaaggcta caacaccctg attaacacaa gcaaaagttt cacccaaata catcctacag 1320
aatcattcct caactcccag agagcaaaag gtataaaaga accgtttcgg tatagtcaag 1380
caagctatct aagcagaatc aatggaacaa tgcgaaattc cgagcatcag aaccagcagt 1440
gcgtatggat ggctgtcatc agaacctgcg gagcccacga tcaaacatcc ttgcagatgg 1500
gcactcatat gacatatgac ccctcccacc gcaggtgcca cagatcatgg ttgtcatgca 1560
gttgcggctg atgtgccctg gcttgccaca caagcggcag gtaatgtcac ggaaagggcc 1620
gccctgtatc tctgaagaaa tggtcgtttt ttgacagttc cgagcaagat gcccagagac 1680
attgcacagg ttgcaaacag gctcgttcgt gcactcccga g 1721

<210> SEQ ID NO 23
<211> LENGTH: 1599
<212> TYPE: DNA
<213> ORGANISM: Oryza sativa

<400> SEQUENCE: 23
acccatcaat taatctcttt tcttttctta atctattttt cttctctttg caatcactcc 60

```
tcctatttgt gcgatagcgt gcatgggcca tgtgacaatc tcttgtgatg aatggatgat    120

cacgcgtgct acctaaccta ccagatcgcc atatcaggct atcgctgatc gcgtgatctg    180

tagtatcaca tccgtttgtg tgggggtaaa atcagccatc ttcctgtaat aaaatagaat    240

gattttccat tagactcact gatcattggc tgtgaaattt gccggccgcc tgttcatcag    300

ttatctcgat caaggcttca acttttactg tggtatgccg gctcctagct ggaaaatgtt    360

gaggacaaaa actcttcttc aacccaaaga taacacaacc atcctgaatt tggttgtagg    420

ggacgcaaat tcaaaaccat aattttctgg tcacaataat tgatgtgttc aagataacct    480

gctctgctct gaattttctg tcatcttaat taattacagc tgccttgaat cgttcagaca    540

atacacgata tcttagttga ctcggaaata aaatgaacga atgaatctaa agacgagcct    600

tgcgtggatt gcaaattggc aaaggcagca cagatgctcc cgtcactcgc ttagaataac    660

aagccacaaa cacaacacaa gaacaaagag aatttgcttt gtgcaagatt cttctaatgc    720

gattacatca agaatctgtt actgtcagtg tcactgtcaa ccatttgcac aacgggcggg    780

ccttgacgtt ccagcatttt tgacgacgaa aaagtggaga aaagagagga gacaaaataa    840

cagtcttgcg tggcaccgcc tggagtccac gtcactttga acggctctgc tacaacgata    900

cacccggcaa gacagcaact tgcattgtgt ttatcattgg tggctcaaaa tcacagcaaa    960

acaagccatt gcaatatata atatgatgtc gacagacggc tgttcgcaaa gtaccatttt   1020

tcccacgata agctgaatct atcatactcg actgccagta tttggtcagt ttccatacac   1080

ggttagctga atcttgcctt cacaaattaa cagttttttt ccaccctgca agattgcatt   1140

ataataaacc tgtaacattt aagctatcga cagagacgtc agtaaaagga acaaccagcc   1200

agtttgcaat agcttatctg cttataatag gaagatgaac tctaactggc agtggcacag   1260

atcactgtga gaaataagaa ataacatgac tggttccatt tagcacaggc acatcaaagt   1320

atacctttttc ttcccagcta taccactaac tggaatgaat accatcgtat gtttcaatct   1380

tgtcaagaaa cgaataaaaa tatcttcatg cggacagggt tccaacaata gtaaaaaagg   1440

aaaaaagaat acagacgcat aattgccaat cctctacttt catctacata gctgtgcaac   1500

aaatgcttct ctgagctgca ccacatttta aactcaatac ggtattctgt gcaggtttgc   1560

caaaacaaaa aatgctaatg atctcgcccc atcaaccac                          1599


<210> SEQ ID NO 24
<211> LENGTH: 715
<212> TYPE: DNA
<213> ORGANISM: Oryza sativa

<400> SEQUENCE: 24

agtatcatgt tggcatgttc ggttgttctt gtttgttcgt gggtggaaac ttacattggt     60

tggaacataa caatacagaa tagggaatac tagtcagttt ggcatctgtt tagtttgatg    120

atatgacttg gtgatgatat atactcgaga tttgtttctc tcttctgcgt tttgaagaat    180

ttaggagctg taaatctgag ggcattatat atcgagatta cttctgcttc tgttgatcct    240

tttgcatgtt acttttcact gttaccaact agcagctgct cttatgcaca ggccctagcg    300

aacactaacc accattgcac tgacaaatca caaacaaaaa agaactccca tgcaaatttt    360

ggaatctata actcatcacc tctcattcgt aatagaatcg atcctgctag aaaagaggga    420

caaaaagagg gggaaaaaca aacatcaggt actccaaaaa gggccaagct taccaggact    480

acatctgaaa ttctgaatag acgtatatgc tacaattagt aaaccaatat caccactgct    540

ctcccttgcc acaaaacaag ggaagcttca atttatgacc cgatttttgc tgataatctc    600
```

```
tcacataaac ccaactcaac acataccctc ttcccgaatg ttgataattc caacccacga    660

aaatatcaaa ctttttcacc gacgcatagc aaccgaggca tagcaactaa ctcgc         715
```

<210> SEQ ID NO 25
<211> LENGTH: 1191
<212> TYPE: DNA
<213> ORGANISM: Oryza sativa

<400> SEQUENCE: 25

```
ggcagctggt cacgcttagc ggcggccggt ccggtgctag ccttctcctg agcttgtgtg     60

ttggcgatgt tggtgtgtgg gtggtggatt tttttctttt ttcctggtta cgaccctcca    120

gggttataat attgtaattt tttcctgctc tatcaatata attttgcacc gtctcgtgcg    180

agtcgttcaa aaaaaaataa aggtagtttt taaaaaaaaa aatctaattt acagatgtat    240

tggatgagtt tgaccatgtg acatatgcat ggataaatat gttaaaatca ttacttaaat    300

cttttgtttt tttatctact tgttctatct tccatacaaa taagtatcaa tataatatta    360

gtataaaatt attatataaa ttgagaactt atgattgata tattaatata ttatatcagt    420

tatttaaaac taaccgttta agtttctcaa ttcataaaac cacaatccaa aattacttta    480

gacggtaata taaagggtct tataaagttt aggaggctag atatccgata atttaaaatc    540

cagagcataa gatagactca catacaatgt ttatgtggta tacgcctata tggacttttt    600

ccaagctgta acgggtggca aatttgccac ccaagccgca attctctaaa atatattccc    660

tataaaaaaa tatttttcat ttcatagtag ccaccaatat ctggaatgct ggatgatact    720

caaatgaact ctgctgttgt ctattgtatc agagcaaatt catcagctct aacaagaaag    780

aaacaataag ctattaagca taccggccgt cctcttgctg tttttaacgc atttgtagac    840

atatgtggtt tgagtaccaa ttcaatacaa agcaagagga gcagtacaaa ctaaatggta    900

ctcacacaat gaagcaaggt gaacttccaa atatctgcaa ccattattta cagaagataa    960

tagctattta gacagctatg agcctcacac atgtaccttt gaatcgccaa acaaatactt   1020

ctagcgcatt tatatatgaa catataatgg agccaacaca tcatttacaa ccaacatccc   1080

agtgagttat ttgtttggat caccactaac ttcgcaggca acctatgatt tgctctataa   1140

tcagttccgc ctcggtgaca atccaaacct tcacgagttg cctgcaacca a            1191
```

<210> SEQ ID NO 26
<211> LENGTH: 791
<212> TYPE: DNA
<213> ORGANISM: Oryza sativa

<400> SEQUENCE: 26

```
actttggtct accttttgta tgatagatat taagttaaga agtatgagac atcgatattg     60

ttcttgcgga tgtgtggctg gctggaagtg tgtacatttg tgattattcg tcccttgttg    120

taatcaccaa ggttctagca accgaaaata tttgattctt cgcatcgggt gagacataac    180

ttgtctgaag gtgacatgca tatctatcta ccttactcaa gagggaaaac aaaattctgc    240

atcttgaact gaactgaact gaactgaact tgccttctct tgttctgcat ttgattgatc    300

tttgtgcaga agaaatgccc ccaaatttgt ccatattttc ttcccattac ctcagcattg    360

cagatttggg ccttggcacg gttgttcaga acaagtgcgt cctgtttgca tactgaacct    420

ctgaaatttt cagagttcag aatcaggaac tagctcaatc aactgaaaat gctaaagatt    480

agaacaagcg aaccatgcca gcattaacat aaccgcaacg cggccagaca taaattaagg    540

tagatctgta actacaatat tgcttaatta tgagcttaca taagctagca gcaactgcac    600
```

```
tacagtacta caatactaca gactaatctt ggatgtcggc aaattcagtt ggggcatcat    660

ctgacgactg atcatgcagc aatgacctac ttgactacat ctctggcttc ctgaactata    720

gactatgagc aaggtgctca cctaacactg gaatatacta ctaagtagca ttctttacac    780

aggatgctgt t                                                          791
```

<210> SEQ ID NO 27
<211> LENGTH: 1478
<212> TYPE: DNA
<213> ORGANISM: Oryza sativa

<400> SEQUENCE: 27

```
cgaaggccca ggttttcgct tttatgctgc agctagttcg ttctcatttg aggtgggaag     60

gaaaactgcc tcaaaaaagg aaatttttccc agcttacaag caccagcagc tgccttttct   120

gtgggtgtga ttttgcgttg gtaattgtta gcagttcagc agtttaattt ctcttttacc    180

ttattttgtt tctcatgtca ttaacaaccg ggtgtagcat ttaggaagtt ggatgatcat    240

gagctgtacc aaaatatttg tattgctgga agaatatatt gatggtagaa ttgtagctta    300

cacttcccaa aaatgtattt actggttgta caacagtcag cagtaaaatt aaatggaatt    360

taagtcaggg tcattcgttg tcctgctggt gaactatact cgagtacgtc tagggctcat    420

ctggtgaatg atcagaccaa tacgaaagaa ttccagctag taatttatca catcaaatta    480

atcataactc actttcagg gcttatttac ttcgttgcct aattttggta aggtattgta    540

tagaccgatg gtttttactt tgagacctta ccaaatttta atagaagttt tgagagtaga    600

aagttatgga attaccaaag tgaacaaact ggctggctgg atgcaaaacc ataggcgcag    660

ccaaagacgc gagctgtttt tacactctag tacattacag taatcagcca gatctgtcaa    720

accatttgtc tgcaccaaca attagagctc tgcatgctat tctggcacaa aacccatcag    780

tatcagtaca tcacacgcat ccacacatac aaagcatccc agaagggatt gcaacccaaa    840

acggaacagc acaaactacg gccagttcga agtgggtcaa gatatacact catgtcgcac    900

aggctgtaac actaacacga gaagcaaact tgaagaatgc tgaggaaacg catctagcac    960

tagagtggga acgagtcgag cagctgccat cgaactgatg accatcaggc aattagagtt   1020

gcattcttgt aggacctgca tgtacaagtc atagctcatg acaagaggtt taaaagacaa   1080

tattataacc ccttcgtcct aaattccagg tttcaaaatt ctactcacaa gcatacatca   1140

tttaataagg gacattactg tcttttattc ttaaacttaa tctatgctaa acaacataaa   1200

aggacaacta tattgggacg ggggagtagc taacagagtg aaaatcaaag gagtaacgaa   1260

tttagtagtg tcactgtcga tacacctaat ttaacaccat aatatctcca actctccaca   1320

acacaaggac tgctgataaa ataaatgcac ttctttagga gaataatgtg ctcatcaagg   1380

ccatgtacaa aatatttctc caaaaagttc aacaaaggtt ccaggtaccc gtacagcaag   1440

ctatatcagg aatggagtcc aatgcgttac cttcatat                           1478
```

<210> SEQ ID NO 28
<211> LENGTH: 1678
<212> TYPE: DNA
<213> ORGANISM: Oryza sativa

<400> SEQUENCE: 28

```
gaaagcagca atcgccctgg actgtgattc tgtgacagcg aagttttggg tggaagatgc     60

agattgatgg ttctctgcaa ctgttggtgg agctaggttc agcagctatg ttcgcgagtg    120

tattagcgct cttttggcgg tgctgggtag tagaatgtag aatcgtttct tgttgattcc    180
```

-continued

```
ctgaactgat ccagatcaaa catcttctaa aggttctgcg atgcaatgct agctgcagac    240
gggagatggt acagggggtc gttttgctac tttgccgccg atgttgtagg gtgtgtagac    300
agactgtaga tgaataatgt cagtaacacc tgtggggggt tcagtgctag tgggctgcaa    360
aacttgagca ctgcttcgat caaattgtgt ctttgattat gaaattatgg aatccagcac    420
aggcaggtaa taatttcgta atagagcata aacaatttgt gaccttaggt gcgaagaaca    480
taaagctgac caaggtgaag taatattgat gcattgtgcg ctgcatttaa tttggttgtt    540
gaattcagag tacgtattta aataggtgtc cggaggggaa aatgtacaca aatgtttact    600
ccgtttgctg tgcatctcgc agtgatacaa aaaaatacaa atcaaaccac gctaaaaaat    660
ttagtcagtt gctcgtcttc agaattcagt cctcaaatat ttttaatgtt tcctccatgg    720
ctgctcgtcc gttcattttg cactcgtttt gctctctgtg aactggagag ccccagaggt    780
tctctttttg catgtaatct gagtttctga tcaaccattc agcctggcta agaaaaccat    840
atggtggtgg cgttcttcta acttgtgtct gcgcggctgt tggcttcatc caattcatcg    900
atcgccagtt actacttact tactaacagc gtccgggaac aggagttgag ccaaagaggc    960
aggtttatct tccattaagc ttaagagaac tcggagatat ctcgaagttc ttggcacggc   1020
acgtcctgtt ttcactttca aacttgagca ttcagtttag acgaggtact tgattttttt   1080
tttgtgtgca cgccccagca ggtgttttaa gaaaaaaatt aggcaactta aaattgttgt   1140
cccttctcct gtgttttgcg ctaataattc catcctgcac atggcatctc tgaggaatca   1200
aagatcaact agcaacagca acaattagcc gcgatagatc agacatagac actggcactt   1260
tcggatgaac aacagctagc tagattaact gaaagcaagc acggttacaa aggacacacc   1320
cagcagaggc atcagttgga aacaagaagc tagcagctgc tggccatgaa aagccaaagc   1380
atcacctagc tagcattcag cccctgcctg accgatcctg caataaacta aaacacatac   1440
cctagctact gaccatgatc gatcagcacc taaaccaaac taccaaagct agctaaagct   1500
aagcacgcat caccatatga aacataacat agcaaatcat acgggcgcct aaatgcgtgc   1560
atccgtcaag acctacatta ttattgataa gagagctagc tagctaagac tgactcgatg   1620
actacaactg agacgactac gacacactgg cattcacgga tgcaaaagtg tgtgtagt     1678
```

<210> SEQ ID NO 29
<211> LENGTH: 781
<212> TYPE: DNA
<213> ORGANISM: Oryza sativa

<400> SEQUENCE: 29

```
gcgtattcca atttttgat ttacgaattc ttcccgtgag ctcaagcaaa gagtggctct      60
gcagaacagt taagatctga tgcatagcca agttatatgg gttatgtatg tcaacaaatc    120
attgctcccc cccccccccc cagagatgta ttagtctgta tttcggcatt actcatttgg    180
aaatttgttt caaggcttgt gctttgatct atgtacttct atttgttatt ggaaaaggaa    240
ttaatatggc gattggtgtt acttcgctat ttgattgggt tattattgta gcctgaatat    300
tacattacaa accttcaatt ctgtagcaat agctttttat tagagaaatt ttacgggctc    360
ttaacgagat accgagaggt accacatttt tctgtaatgt accaagaaca aaaaaagtga    420
tactctcttt ataatccttg taaaaacaaa aggtaccaaa atgataactt ggaatactta    480
tcaagagctg taaaaatgac ccttggagca acggtgtaat tatactttaa gacaaaacga    540
tatagctata acccgaaaca aaagatcaaa tgtaagccta aaattagcta ttgcaaggag    600
ctgaaaaggc acttatgttc caatcaaatt atgtaagaat catattcctt tattctttca    660
```

-continued

```
tattggtgaa gccgtaccgt gtcagtatag gctgattttt ttacattaaa gcaaaaaaaa    720

atgtctatgt tcacaaggta gagggtgatt catgtgtcct tttactcttc agtaacaccg    780

g                                                                   781


<210> SEQ ID NO 30
<211> LENGTH: 1260
<212> TYPE: DNA
<213> ORGANISM: Oryza sativa
<220> FEATURE:
<221> NAME/KEY: misc_feature
<222> LOCATION: (183)..(183)
<223> OTHER INFORMATION: may stand for any base (a,t,c,g)
<220> FEATURE:
<221> NAME/KEY: misc_feature
<222> LOCATION: (426)..(426)
<223> OTHER INFORMATION: may stand for any base (a,t,c,g)

<400> SEQUENCE: 30

ttattttcca gttctggtgg tcacttccag ttgtgttttt actgtacaat tagggctctg     60

ttgggaggca acatatccta tgcacacagg ccctcacgta tacacacgtg cacatcaact    120

aaaaaatgtc accaaaaaat ctagaaaaaa tcatacatat actttcaatt gtattacacc    180

tanggttaaa atcttaatgt caaattcatt atattttagc cgtaacaaaa aaaaaacaaa    240

aaatctgaca gttttaaggt tacaattttg tcagcatttt atcttttttg ttattctcta    300

tgtacaataa atttgaagat gcgactttgc atgtagatgt aatactattg aaagtacatg    360

tatgaatttt actagaattt tttgtgataa tttttagttg gtatacacgg tgtgtatacg    420

tgaggncctg tgtgcatagg atacgctccc ctgttgggac gactatttta agggattttt    480

tcaataggaa ttagtccaat tcataccaaa atccttaaaa aaaaaatcct ctattctgaa    540

ggccttaagg acctattcgt tttggagaaa tttcagagga tttggatttt taagaattaa    600

ttcctatcat tgccatttgg tttataggaa tgtagacata ggaaaatcaa ggaattcttc    660

ctttcctaca agttgtagag agaaaacata agaaattttt cgtcttctta aatctcttgg    720

aaaattcctg tggattgaag tgtgcgtata tttctatttc tccactttaa attccttaaa    780

aacaaatagg gtgcctaact atttcatctg gtcttgtatg acactgacat ggtttttcag    840

atgcacattt agctaataca gtacaattca tattgttgaa gttttgcgca tatttttatg    900

taggagtaaa tgagttttaa gtatcaattt aaatttaaaa tgatgctggt acatcttttc    960

aaatttgatc aaaagctcca acgagtatta ctcctatttg cacataattg gcagcgttgt   1020

gaattccaaa caagcaaata aagaaagaaa aagacagctt aaaacgaccg cataactaga   1080

gtcacagcta agcgataatt cacaacatca cgatgcaaat cataaatcag tttcgttttt   1140

ataaaaaccc tcgtaggttc cagcagactg ctcataaaaa cggagtattc aacatcgcag   1200

agaccatttc tctgacccat agcaaaatca cagcgacaaa atccgctgtt tacatttaat   1260


<210> SEQ ID NO 31
<211> LENGTH: 1529
<212> TYPE: DNA
<213> ORGANISM: Oryza sativa

<400> SEQUENCE: 31

ttcaagttgc atcgccactt atgaacactc catgaacact taattctgga ggcatgattg     60

gtccgtggga ttaagacatc ttgatagact gcagtggagc ccagcccata atctgaagaa    120

ctcattaccg actcttggct gaagtgcttc ggagtgattg atgccattct gtcatgtgat    180

caagttcatg tccatactac atacgtcgtc tggtccttta gagcaacatg acttcaggac    240
```

```
gttgctatca acggctattg atgataaact agtaataaaa tttgtcgatg aaattacttg    300
ccgtgataaa tgattccgtt gtcgccaggt tacagttatt caacgtaaga acttcatatt    360
cattctagaa accaacacta ttcatcacca ttttcctcat ccccgaaaaa ctttgaccag    420
tacctctgtt tttgccaccc ccctccctcc ccggccacaa ggtgtagaat caagtgccat    480
cgctgaccaa tttgagctgc tcccaattaa aatacaaact aaaataaaaa agtatagaaa    540
aaatgaaatt acctatggat aatattatgt caatggcatt aaaatttgtg aattttggca    600
tttggataat agtacctccg ccttaaaata tatggatttt tcggattagg cacgagtaat    660
aagaaagttg gtggaattaa atagaaaaat attatgattg gttgagaaga ggaaaagttc    720
gtgaaattaa acagaaaaat gttatgattg attagaagaa aagaatgtaa gtagttcgaa    780
tggtgtaagg ttgtgattgg ttgagaagag aatgtaggta gagaaattgt tatatgttag    840
gataaaattt gaaggataca agttgttacg ttaaggagag agtattatgt ctatgtacta    900
tcaaaattca attatgattt tttttcaact taagctgttt tcgtcaattg gacgggatct    960
tgctacgacc acgatcggtt tggtaaacga cctgccccaa tccttcccac gcacctcctc   1020
tcccttcccg cgatcagtcg tcgcctacca accaactaca taatgctcta ccgacacctc   1080
ataaagctct ctcctccccc accctacgct accgtctctc gtgcacgcac ttcacgacga   1140
cttcgccagc aagggaattg tactccagag caacagctca accgacgacg agagctcaca   1200
acattgcctt tgcaaaaaaa acaactcgcg tatttcccat tctttataca attcctgtta   1260
tagtgtggta aaaaatttac acgtattgat ctctaggctg cctggattga tcggcgtcag   1320
ccctctccag ggagctctcg atcctgcccg ttgtgacaaa aataacatac acaaggcaca   1380
ataggatcga ctattctaac aaaaaaaaaa cgaaaaaaga aagttaagaa aaaaaaaacg   1440
aacggcatgt tcttctccca tcattccatt ttgcacttga accgtctgga tgcgtctgat   1500
gcttggatat catcaatggc atcgagaca                                    1529
```

<210> SEQ ID NO 32
<211> LENGTH: 1277
<212> TYPE: DNA
<213> ORGANISM: Oryza sativa

<400> SEQUENCE: 32

```
cagaaggaga tcaagaatgt ctttggcgag acattgcttc gacattgctt cagtgtcaaa     60
atacaccatc atcattgaga tcagtgttct taaggcgaca aggcgaggca aggcgaccca    120
cccctgctca attgcctagg cgacgcttta agcgtttaag gcgagggtaa ggcgacgcct    180
tccacacaag cacaagaggc atactagaaa tatatgaggc aaaaaagaga ggaagaacat    240
gaaggggcga ggaagatcca ttggagaagg gagcagcagg agggagacaa ccatcttctc    300
tttccatctt tcccatgttt ccaatctctg ctcgccctat tctctactct ctttccatct    360
ttcacccttc cctctcccta aattggtgca ctgctatatc tattctcttt ccatctttcg    420
cccttccctc tccctaaatt gtcgcacatg cgatttccgt cctatcttca cgcgatttcc    480
ttcccagcat gcataaatcc ctaagcggtg gggacgctct gctccctgat ggcgctcaga    540
cgcctaggga cgctttttaa accatgattg agattcctcc acgacgatca cctccatcca    600
gtttctcgct ccacattcta tccggcgatg agaatttgtt ttttatcaaa taactatcac    660
aaagctgcta gcccttcccc aaatccaccc ctacctctct cactgttgct actgttgatt    720
tttgcctaga catcagcatc actggataga acatgcaatg aggaactaga tggagtgagc    780
ttggtaaagg aattaattgg tgattgccat actttagcag cagcaaagca atgtctgaca    840
```

-continued

```
ctaagaacca cttgattttc ttgaggacag gagtctctgt tcctctagtt atttgtagga    900

attggactag gagcttcaag aacatggtgt tatgcggttg aatttgccat aggcagatca    960

atggagctcc catagtggca gcaatgaggg tgaataatgg acttcaagca taagttcaaa   1020

gaccagaagt ggactatttc tgaatttagt ccgaaaaatg aactttggga cgaaaagtat   1080

ggacttcatc catatcaaaa ccatgaccaa acataacttc tttcgaaatc catactgcac   1140

aaacatacat gtgccttttt ttaaaagata ttgggtaaag tgtatttgtg ccatgaatgg   1200

ctgctatcag gaatgcaatc tccacatgtt gtagcattgt taaaagctaa aactgcaaga   1260

ttttgcacca agtaata                                                  1277
```

<210> SEQ ID NO 33
<211> LENGTH: 1381
<212> TYPE: DNA
<213> ORGANISM: Oryza sativa

<400> SEQUENCE: 33

```
tgccttttgg atcgaaagat gcagttgttt tgctgctgaa ggcatcctca tgtctgttac     60

tttgatatgg tcttgaaata aatcttcgtt tacaagagaa caacactctg ttttatcttg    120

ttttgtgtgc cagaagcctg ctgaacaatt ttatgtcaat ttctttgcta ctaagaaagt    180

tatgcaccaa aatgaaggga aattctgtga agtttgtaat tttcaagtga ttggcattat    240

tctgtttagt tcgtgcagtg ccatgttcct tatataatca cagaacatgt aaaaggccga    300

aatattttcc ttgtcatttt ccatgcgaga acggcctttc gatgagactg gaaagtcctg    360

caataactat tgtccaaaat aacacacggc tctctaccga ttcacatcaa aaccaaccca    420

aacgctctct ctgttgcttg tgttctggac ttctctgagc gcagttcagg agtctcgagt    480

gtgcctcaac agtacatgtt aaacataaaa ctgccattga agattaccac caaccatatt    540

ggaagtttat catggcatat acttgccttt caaagaccct aattttcaaa gtgaacatgg    600

gactttcaga ctacagataa cctcaatcga taacatcacc gaaaattcga tattactaca    660

aagattttgg ttgaaaactt ctctgaaccc aatttaaata caagtcgccc tcggtgatgg    720

ctactcgcca ttccacgctc acagttgcag ttcacacttg caaaatgaaa aaaaaaatct    780

tctgaacagc aatcatcaac cggttcgacc tcaggatcat cacagaaatg aaaaggacga    840

ggaatctcaa tttaagaaag ttcctatcca aatatccaac aaaaatctga ctgtctggct    900

attattaatt caacaggaga tgctcgttaa agacaatata gttctgtaat ttgtaacaac    960

acaagagcct gaggatataa cgagttacaa acatgctgcc gttgcagcat ggtcatcaat   1020

atacaacatt acaacaacat atggggatcg cagaacactc ccattccacg attttacaac   1080

atatgcttca caacacgtta taaatacatg gttgtaccga gctgtagaga gacagccagc   1140

acgtcccaac tacaaatgca cactagccaa cagcaaacat aaaaactact ctctggtaag   1200

tcactatata tacgcactat agcttcacat gactaaaatt ataacatgac ataatttctt   1260

tcgtataaat tagccccagg aagcttctgt ccgaatcgcc atcttgggag caataaatat   1320

actggcattc ttcacaatgg atgcattatt tacatatata tacttcttct ccaaccacgt   1380

t                                                                   1381
```

<210> SEQ ID NO 34
<211> LENGTH: 1172
<212> TYPE: DNA
<213> ORGANISM: Oryza sativa

<400> SEQUENCE: 34

```
gtaactccag caatttactc ccaaccaata caattgcaca attgtgccct aaatttaata     60
ccagataagc taataagtga tctcttaaaa tgtctgtgat ctagggacct ggccatttga    120
tggagaattt ggttagctat ataccttgtg aagagattga tacaaagatg ggctatgagt    180
tcaagggaac tagttatggt gatcccagac catactcagc agatacttaa gtgtgcttcc    240
aatgatttta gcttcatttt tgtatagtaa aagaaatggt ttgtaccgag ccacagtgat    300
tgagcaatag agaagtagct aggtaggcat ttctgctctc atgtggaacg acatacaata    360
caatacacac agaattttta gaaaagaaaa atacaggtgg cggtgtatca tagtcataga    420
taaccatatt aagaaaaata tggatggcgg tgtatcaaaa accataaaat aaggtgtttc    480
tgtctatttg gagttgtttt ggcatgcttt cctgaaaaca ccaggctctt gttttcagaa    540
atccatgata agagagttga tcacttgctg gttttcttgt gggctatgat atcggccgac    600
ggccaagtat ctaataaaag attcttgatc agggccatgt ggagtgatca taaaaccttc    660
ttcttcagtg gcacttattg ggcaggacat tattaccaga ttaggttttg ttggaaacat    720
ttccattact tgctaactga aggagcactc cctgcagaga gctggccttg agcacaaaat    780
tccatctatt gctagactac cccaaatata aaaatgaggc aggaatcaga tcaaccccat    840
ggtcaattca aaatatgacc agtcgatata gcaccttaag aacttaaaat attaacaaaa    900
agggtagggg agttgcaatc agcgttgttt ggatggccca ggaattgaag ggctgagatc    960
atagcagatc tcatactaga gcacccaagt aaacatctcc caaaagaaat gtacatgttt   1020
atcagtgatt ttatttatct aattagcata ccaatacaaa ggaaaagaag tgcacagact   1080
aaagaaaacc tcacttttct caaaatagaa aaaataaacc acaaaatctt cctggggcta   1140
agtgagatct tacaacagtg tatgggagtt tt                                 1172
```

<210> SEQ ID NO 35
<211> LENGTH: 790
<212> TYPE: DNA
<213> ORGANISM: Oryza sativa

<400> SEQUENCE: 35

```
aggcaagaac gaacatgtga aggcaacgtg ctacactaag atcttcacat gttggttttt     60
tgtataaatc ttattcgcga ttgtcgcgcc tatcaagctt aagctatggc gatgtcgccc    120
aggtgacctc ttatgtaaat atgtgcgaat aagacagcat tctggagttg ttcttcctgt    180
ggacctctac ttgtagtata tggactaatg tgttgtatga gtacgtgaag cagaattcgg    240
tattatcaag gcttgtaatg ttagatgctc ttatattaca ctatgaagtg tcaactttca    300
agtggccacg tttacacata tatttgctat gctgacttgc tgagacatgc ttggttttag    360
ggcggtttgc agcttaacat gtgttccttt caaagagcag tagatctgca gtttgcatgg    420
tattcctgtc caaactgtct agtatactct atactgatac tctggtataa agctccctgc    480
agtttgcaac tgatgtattc tggaaactgc taagacacct cagctacctt tgtttgtttt    540
aaagactatc tcaactacct ggaactctgc attttgttta gtacggcaat taaggactga    600
gttttcagca aacagacttc gatgctattt ttgattgaaa taaagcaggc aaagttcggt    660
ctctcacata aacgaaacac attcatggat gatgtcgaaa gtgcaacgga atgatacaca    720
tgacatgtaa catttagcct tagaatttta ttgattcgac gcagcaatcc aacttttgac    780
ggacttggcc                                                           790
```

<210> SEQ ID NO 36
<211> LENGTH: 1283
<212> TYPE: DNA

<213> ORGANISM: Oryza sativa

<400> SEQUENCE: 36

```
atcgacgacg acgacggcca tggtgatcac tgctatagtt gtagcagaag gaggaggagg     60
ctgctctgct ttcttgctgt gtgctgcgat cgagttgtcc atcagtgttg ctgttcttag    120
agaagaagac tgacatctct ctctctctct atatatatag aaaaccctta atctatagag    180
cattttgttt ctgcttatat tgctacatgc tctatctttt tggttgaact atctacatat    240
atatctatat ttctatctac tcactccttt ctccttatgt aacatacctc tcaaaactct    300
gaactggctt gtgctgatca tctgatgtat aatatataat atataaatat atatcgcccc    360
ttggacacca tcgcatatca atctcctgga tatacttggt agactggctt aaatcatttc    420
tgctcttctg ggtcattaca gcttgattat aattggataa ttatcaaaga gctgagtagc    480
tgacacagtt tttgcattga gctgtcccag tccagagtct acttcgaagt ttagaacacc    540
agtatcactg catctgcata tgcctgatgc gaggaaagcc aataaatatg gatctgatga    600
gcatgccatg cagaaaggat aagatacaga cggcacgcat gcatgcccac atacacgtgc    660
tgtatcaatc aagagaacat catccaaata tccaaaccaa aatgcaaagg atcaacatca    720
tcatcaatga ccagtgccac actgcacaag ttaaagaggc acagcggatg agatctggtt    780
cagttcaggt acccttgttg agagttggca gagttcttgc tgtatccaaa gtgaatcttc    840
cccaagggga aagcaacaat ttacacggtg gtcaataaat aagagtgcat gtacaagtca    900
aaaatatagt agtagtatac ataaggtcca caacatcagc taattaagtt actccttttt    960
tggcttatta tttcatatgc actggtgtta aaattcctgc ggcggaacaa gacttttgct   1020
ttttcggctg gaaagattga gctttccatg gagcatcagc agcacaacac aattgaacag   1080
ctagctattc tttttaagtc gatcttgaaa catacattac tatgatgctg ggattaaaga   1140
gctggagaag agcttctgtg tctctccatt tttttttaca tcattgaggg aatgatcttg   1200
gccgaaatga ccggctttta ctttaccaca ggggaagaaa accttcttca gtcaggtgtg   1260
ttgcctccac catgcattca ggg                                           1283
```

<210> SEQ ID NO 37
<211> LENGTH: 1072
<212> TYPE: DNA
<213> ORGANISM: Oryza sativa

<400> SEQUENCE: 37

```
cagctcggta gcaaagcaca tattgaatca tgctgccgat acaaaaatcc tgctgtttag     60
aagatacaag ctaggaatag aaaagcaagc gaagactcaa catcaacatt gataacatgt    120
gggaaaaatg attgttgagg aaaccataga taaattggcc gaactcaact gcccattttt    180
cccaaaactg gtttagcagg aaagtttaag cagcatgtac aatgaaattg tatgtgcagc    240
tccatttata ctagtcctgc atgcaatgag ttctagacaa ccgaagttga taaaagtttc    300
atgacactgc catacaaaca acaaacaaat ctgtttcagg tctaatgaga ggaaaatgat    360
tgttggagaa aacagaataa gcttaaccca actgcccact ttcctctaat tgatatagca    420
ggaaacactt tcggcaaaaa atgcatagca taaggcatta ggccgataca cactatcctg    480
cagggtaaca tgacaacgga aaaaacaaat gtaaaatcca tgaaaaagta aaacatttct    540
ttggtactgc tatctagaga gaaaactaaa agctacagaa gcacaataag gaataaataa    600
agcaagaatg caatttacag atcaccaaaa cagacataat gtcataatat aaaaatatgt    660
agagataaat gagaggaaaa tgattgttga aaaaagcaca aaagcttaac ccaactgccc    720
```

actttcccca gatcaatata gcaggaaaca cttttggcac aagacgcaca aaaaagcgtt 780
aagccgatac acactatcct gcaggatgaa gcatatacag tgggcagaat gattacctac 840
tatactaatc tcatgtaaaa aaatgagaaa tatatcagga actagaaagt gagacacacc 900
ataaatgtta ctgagcacca ggaagaaatt aatagtgacg aatcttgtat tagttgctga 960
tgtttgcaac ttaaaaacta gaactcttta ctagtaataa tgttaataat gaacattaca 1020
taactgaaaa aaacatgaag cgcatgcatc agatcaccta aacttattct at 1072

<210> SEQ ID NO 38
<211> LENGTH: 1549
<212> TYPE: DNA
<213> ORGANISM: Oryza sativa

<400> SEQUENCE: 38
ttggtttaga gcttgagatg ttttaaaatc gttcattcct gagttataat agcccaagaa 60
cctcttgcac tatgttcgat caatccaccc cagctacttt cagatttctc gagtaattgg 120
tgcaattttg catgaacatg ctgccttgtt tggaattctt ttttgagtac cggagaatta 180
ccatgttagt gtgttggttt atgttttgaa ggtggccttg ttattctgtt gctgtgttga 240
tgtttggacg caattgctgg attggtactt ggtagcatgc tagaggtttt ttactctgct 300
tcatttgagt tgctgggttg cagttgcagg catcggtgta aactcaactc gaagtcgttt 360
gctgctgcct atagtccagg cggtgtaaat tcaaccttat ttttttgta aaatgaaatt 420 ttaatttcag gagagcaaca gacagaccaa actcttaact gttatgacct gacaagttta 480
atttctacca aaatttgtac cgtcgttgtc gaggaatttc ttcttgccgt tcgaattcga 540
tttcttcggt attgggttgg tccggtctca atccgttccg attgtgtcag tcttgggcca 600
taaagcccat gtgttacaag cctaacagcc caattcgact ggcccacgac ttttgcaggc 660
gggcaccaat tccgggtgca ctccgacgcg gggcgcgtga tcaaatttct tttcacactt 720
tatatcctat caaaatttaa taattttcaa attttgttat attttggtat tatataaatt 780
cagtagtgct aaactagttt ggttcacgca gaaaaaaaac atttgaattc gaaaggattt 840
gtttattatg ggaaataatc atataaggga acatatgtta tacatatata gaagcttttg 900
cgtgtacacg ccaactaaga aaatatggct ggttctaaaa cttctacacg ttttaaaatc 960
caataggaat gcaaagcata tgacatttca gctctacgtt tatctctatc tcgtattcac 1020
aatcatatgt ttcaaaggta accttatcaa atccttttg gtggaaattt ccgaaattac 1080
aaaatacgaa caagcccttc agtactagcg ttggcgtact gcattttgcc catctcgctt 1140
ggccaagaaa gggggacaag ggggaaacgc atgtcgcagc ctggcacgtt ccaaacttcc 1200
aatcgcagag aaaaaaaaaa gagaagcaga tagagaggca tcgatcgtat ctacgagtac 1260
aaaagtaacc aagcaaacca tctagcttta ttttctcctg tccccaaggc caaacagcac 1320
agagctgagg ccccccttaaa aattcatcag aacacatcca tcaaaaaact tattacaaca 1380
cggcgagtat atatgctacc atatcctcga caactgccta tagtgccaag aacactcaac 1440
aaccaccata caaacatttg acagaacaca tgcagatatc accgccggcg agttgaaact 1500
attctacccc ctcctcccag tttcttttcc cttcccccgt ttcagcagt 1549

<210> SEQ ID NO 39
<211> LENGTH: 766
<212> TYPE: DNA
<213> ORGANISM: Oryza sativa

<400> SEQUENCE: 39

```
gtaggaattc actaaaactg tatacttcgg actgggaagg gaaaacaaaa caaagtttat     60
tcagtatatt gttttgttct tctttgccat ccacttcagc tgtaagttca atttaacacc    120
ctttttgttg agcaagatat gctgtttttt cttggtgtca tttacatgtg gaatcagatg    180
ccagaaactt actttgtcaa gattggaatg ttcacaatta aattactaag gtgttctcat    240
ttttaacttg ctactgtagt cacattggcc acattagcac actatttcgt gttggctaaa    300
ttcctgtttt tgtacagttg tcgtacatat gtaaagtatg gagtgaagga tcgtaatact    360
ctagtgtagt tttcttaaaa tagttactga tattctgtgt tcacaaccac ctgctttata    420
ttcctagtag gtatcaaata ctagtctgca aatgaacaag tgattaagtg acaataagta    480
acatattcca aagaaagaac ttctacccat gctccatttt tcattcacag gcaccctctt    540
tgttaaacac tgtatcctcg tgtatgtcat gttacaactt tttataaatt acataaattg    600
tacaagtctc aactctcaat tcagtgagac agaaggattt ctcctccttt tttgaatgca    660
ggatctgatt gatcaaacaa atttaccggt caattccttc aatcttgtct tcaacctcag    720
agtagagctc cctgagcttt tccaagtttt cctctgatgt ttccca                   766
```

<210> SEQ ID NO 40
<211> LENGTH: 1691
<212> TYPE: DNA
<213> ORGANISM: Oryza sativa

<400> SEQUENCE: 40

```
gttatctgtt caaggagccc tgaaagtctg aaactgaaaa acaacatgaa taacagtgaa     60
tgattagaac ccagaaacct gctaaattgt ttatcagtga acatcttcat aaaccgtagt    120
ggaacccttc tgaaatcaat ctgaactgaa gctggcatct gcctgttaat acattataca    180
taataaaatt accggatcat cattttgtgc agatcaacac actgtaactg tagtatgcag    240
aaatcccgat ctgcagttgt tcctgtgatc ctgtctagca ttttgtaaag aagaaagcac    300
tggagcatga aaaaaccaat ctgaagctgt tcctgtcaag cattttagtt gtttgtttgc    360
gttgatacgt tctttgtttc tctgtggtat tgtcaaccag tcaaattgca atataatatc    420
attgagcgtt atatttgacc aagttacttc tgaattcatg cagaccacta tcacttttga    480
ccaattactt ctgaattcat gttcctttct ctattatcac tttgaccaat tacttcattt    540
atgttcttca ccctacaatc acttttgagt tttgaccaac tacttctgaa ttcatgttct    600
tctccctagc ttgttttaga gacttgactg ctgaatcaac atggccttcc ataatttgct    660
acctaactga acctaaacca agacattctc ttgcacgata cattttgctt tcatgcttat    720
agtttagaaa ccatgtctta tcttgcattg catactaagt tctcaaataa tttaatgaca    780
gtttgacatg gctgagctgt atgcctgttt atgcaaagct ggcatgttca tcatacgaac    840
tcttcagttc aaagttgaga gagccaacca gaaattgaaa gccaacgtca agaataaatc    900
agctacctat tgttagaatg tctatggata tctctgcaac cttaacagcc agctgcagaa    960
atcaatctga acttaatgct gtttccgtct agcatttatc tgtgacacct cacacgtaga   1020
tattgctcct tgaatggtac ttatgttgct ttcatttcta aagttactaa atcatgacca   1080
attcgatggc gatttcggtc ccagttcgtc acatttccac actgatgtct ttcagaggct   1140
ttaaacttcc accttctttt cagagctccc aattaaatca tctttcttga tcagtcactt   1200
ccatttttgc tactgatgat gccagtaata aaccaccatc atcggcatcg cacatgatga   1260
caattgacaa accaaccacc aactttcgag atccaacaaa ttcacagaca acaaaagagc   1320
aggtttctac cagattctga agagagcaaa ggaataatca gaagttgaaa gattctaaac   1380
```

attagactgc ttgccatctt aatatatcca acattaacaa gggcggtagt agaatcatta 1440
gtacacatga ttctacatca ctctctattt ttgctttttt ttttctaaca cattttagat 1500
gatgcacctg aaactgaaca gaagctgctt tactactaca agggatgcag caccagaaag 1560
ctgcaatttt tccccctttt tttttcagtt tttatacaca gtgaagaaaa gcagagagac 1620
taaactctga aaactccaag gttatacact agacagcagc agcagcagca tcaccactca 1680
cccatggcgc t 1691

<210> SEQ ID NO 41
<211> LENGTH: 836
<212> TYPE: DNA
<213> ORGANISM: Oryza sativa

<400> SEQUENCE: 41
cctgctggta ttggagacgt taagaacatg acgttaggta atcctatctg tatttgaggc 60
aaactaggga cctcctgctg ctggcttaat gtattgcact gcatgacatt acatgacctc 120
catgtgttga acaagggctg aggctgttta actatagcac tagcagtacc gttttgcagc 180
tcgagagagc tagtagtgta tgtatgaatt cctcaggtgc tattcgtagt agtaagcgcg 240
aattgattat tatcagttca tgatggtgct actattcata ttcatgtttc tggttggcat 300
gggcggtgct agtgcaaact gcagagtgct gtaaatattc cccaaatctg caatgaattg 360
aacgagggtg catttgccct tatgactgtt gcggtgttgc aggtttttga atgagaagga 420
aagattacta tgtagaaaac gctgtgttgt atttgtcggt cgcaggcatc tggtggtaaa 480
ttctgttact gaagaaagtc cttgtcgcta tatatttgtg tgtttactta tgctcttgcc 540
tggaataaaa ctcgaggatc ttttcctttg caaaactggg aaaatccaga agtatatgct 600
atacgatcag ccgcattgca tttggttgat tgtattatag tgtacaaact cggcaacata 660
gttgaaattt ctgtggcatc cttattaaat aaatacttat tatacatacg tataaataac 720
tgctgcaagt aatctgcaag cagttgtttc tctcagctac tagtagtttg tgtgtgtgtg 780
tttccgtcga aaacccctgt gaaataacac aagccagggt taccgcaaca atgatt 836

<210> SEQ ID NO 42
<211> LENGTH: 1021
<212> TYPE: DNA
<213> ORGANISM: Oryza sativa

<400> SEQUENCE: 42
cggacttggg gagatctttt catgatgaaa agaaagttag gctcagtgtg taatatgtag 60
ggaattgttg gcatatccaa atgtatttcc tcttgaatac attattttgc tcgcatgcat 120
cctctccttt tccaattgta tgtttggttt atcgaatttt tgttgttccg acaaaaaaat 180
taggcccttg cagagtaatg gttcaggatt tcaagctgag cacagaatag aaagtttaac 240
aaaaaaaaga aagtgtagtc tgtagattgt aataccaata acatctgaaa accacaagct 300
atgtaattgt acctttatgc gtgtgatgtt tttaactaca atcaaacaat agtcagtgaa 360
accaagtcta agaggattga tcattgatgc cagttgatgt tgccttttca gattattcct 420
ggaatctaaa tgaaccatgg gatgcaacaa caagagtaac ccttttaaaa cctttttta 480 tatatacaaa aagaaaatga tattagctca ggaagaaagg aggaacacaa acatcatctg 540
aagccatcaa gccaatacta ttaaatgaat gggtaatatc taacattcta tgaccaaaag 600
aattgtgtaa tagtgaaacc catactgttt gctgaatgta tttggaactg gaagcatcac 660
atctggaaaa aaggaaaaac agagaaccaa accagaaaac aatgtcactg agatgactgc 720

-continued

```
caagtataca ttccaatcca actgaacaaa tatgttacac aactaattaa acaaaaaaac    780

atgctggtac ggtggtaaat aatatatgct tcatatgaac accaataaaa tttcttcaca    840

tatgctgtta tcgtacaaaa tttgtttagt tgcaaagtga aattgcattg gaaggtcttt    900

ccactttgtt gcaaatatct agccttaaag tttccctcag tctacaggtg ttcacaaagt    960

tacttcagcc tcagaggtac ccactttgcc atcaaccagt ctggaaatat ctgctagatg   1020

c                                                                   1021


<210> SEQ ID NO 43
<211> LENGTH: 798
<212> TYPE: DNA
<213> ORGANISM: Oryza sativa

<400> SEQUENCE: 43

atgaccttag agcttttctt tcacctgtca tgacttgaat ggaaggcaaa taatctgttt     60

cacctctttc cagatgtaat ttctacagat gtcttctggg tcattttatg gatgtacctt    120

ctgaatgatt ttctgttgga ttccataatt ttgattatgt gaatatcaat aaaaacatgt    180

ttcaggtttt tagattccct taaaaggtaa agggttgtca tttactgaat ccatggctat    240

ctgaacttgt caagaatcca agatacacca gaagattgga attagttgat tctggcaaac    300

cagaaaaaaa aggttaaatg gagatgcggg gtatcgatcc ccgtacctct cgcatgctaa    360

gcgagcgctc taccatctga gctacatccc catgttgggg tcatttctta ttagttcatt    420

ctactattgg acaacacaaa gaccaaatgt aggcagaaag gcagtggatc gaatgaaagt    480

cacacgggcg caaatgccat ttacgaacaa atgagagcga actgaacttg tcatgttcaa    540

aacattgtgc cccaaggatt gaacggtaca gtatttcagg aaagaataca ttgccttcta    600

agcggtttga gtgataaaaa aattgttaaa aacataaaac acactgaatt aaatgtcaac    660

ggttccatgg tttcaactat cccagaaaag cagggttggc atttcgagat cttccgtctc    720

ttaaaactga atggatgccc atgcttcaaa atgaaaccct tgaggcagca actgaaagca    780

tgaaaagaaa tcaccaat                                                  798


<210> SEQ ID NO 44
<211> LENGTH: 865
<212> TYPE: DNA
<213> ORGANISM: Oryza sativa

<400> SEQUENCE: 44

ctgtcctata tatagccaaa atctggaatg cctccctggt cattttgttc gttacggctt     60

gtgtagtgtt ttgattttgt ttcgatttct gtagtagtgt cgtgctgctg tgccttttgt    120

ttttgtggct gtgacttgtg agcatccatg gaacttgtta cgctgaccaa taacattgtg    180

actcgggtag tctttatgtg gtttgcgctc aacttgaaag agtcagaacc aattgctgta    240

tatgtttttt ttttgggtga aatatgcgct gtagaagcaa atgatctgca tttctctggt    300

gttttgatgc caaatcgact actaatcgag actttatcgt aggcaaggat aacaagttat    360

gccttttgat actatcgagg catgttaacg tccattccag aaatattact tggctcagat    420

atgcaataaa caggagaaaa tcagcagcat actcttcccg aattacccga attacgttca    480

cacaccaaaa ttagggggta gaaaaaaagc ttgcaacgga gcaatgccga gcttgtgtgc    540

cagttcaaaa gggcgcttca gtaccggatt ggaagtacag actacagttt ggggtataaa    600

aacacacaga tgcaactgca aggcatataa gactaacttc aagtttgtag gaattaaaac    660

aagtatccca tctggaattc atcctcaccg atcaacgagt atcgcagtta aacagcagaa    720
```

-continued

```
ccgacaaata caagtaagct gacaaactat gaaaactgaa gtatctgaaa tacactaaca    780

ttcttaaggc ataaagcacg agatatgatt attcataatg ccggtcccaa cgaagagtca    840

tctgattgag cacttggaaa atcac                                          865


<210> SEQ ID NO 45
<211> LENGTH: 1162
<212> TYPE: DNA
<213> ORGANISM: Oryza sativa

<400> SEQUENCE: 45

gccctatgaa ttggaatgta tttgaccata caaaaaccat acaaagtgta gggttctaat     60

tagcaaatgt aagtttgtaa ttcttctgtc taaatgtagt gtgttgaggt ggtcagttgc    120

cgtgactggc tctttcagat ggtaattaca aagaaatgta acattaatgt tgtaacaagg    180

gtgccatttt gtttctgatt ccagatgaaa aggaaaaact attccatatt ctgcaggatt    240

aaacgtttct gctgttcaca acaggtaaag tcactccact tcagggaaag acagcaaaat    300

catttctttt acacagactt tagataaccc ttttttttgg ggttcttggt atatgccaac    360

ttttgtagcc tgcaccagaa acaaaaatga agacttttgc taaagatgta aaagtggcat    420

gatgtcctgg atgaccaaat aattcatgac aaatggatta aaagagccca atatctgaaa    480

gagactggcc agcagccact aatgtcacca accacatatg taacacttgg tgcataattc    540

aagagggagc atctcctcca gaatcaggat tgaaaggtac aacctcatag taaatcctcg    600

gaatatagca tgtgcagcat aagaatatat cagtgttgtg ctgggtaaga aaccacatga    660

accaattagg aataaataat catgctgaaa ttatagcaat gcttgcaatt tgcaaacgat    720

aaagctagac gcgggttgct ggaataacaa tccatctcca acaaaatagt acagaatata    780

actgaatggc cagctcagac cctaacagaa ttgaaaagct ggattcatca gcactccatt    840

gagcaatcta gatcaggaaa gagcatagat gcataatgaa ctgagatccc ttcaaaatga    900

ctaactaata tttttttttc ttataaaaga gtttacaaca gtacaaccac gaagatcagc    960

actaccatta ctgattttgt taacatagag tgatttatca tgtgtgccag acaaacaaca   1020

gatacattca tacatagcat aacttacagc acatgataca gactacggag aacggttaat   1080

cttaaaataa aaacaaaaaa acaaggaggc aaagcttatt ttgcctggga ttcatctaaa   1140

tgcagttgtg tgcagaagga ga                                            1162


<210> SEQ ID NO 46
<211> LENGTH: 1297
<212> TYPE: DNA
<213> ORGANISM: Oryza sativa

<400> SEQUENCE: 46

tgttttgtca agctcccgct tgggaaaagc ttggtttttt tgttacgtgt tttgacctgg     60

aacaacattt gacacatgtc ttttgatctc attgtctgtt tttcaagccc aataagaatt    120

tgggtcgagc attgttttag gatcgaccat atacagtacc tctctttgca ttacaatgaa    180

gagcagttaa tttgggtcac tttttacatc tttactgaag tagaaacgcg tcctctgtct    240

gtgacagttt ttttgttctc cagattgttt gccgcttttt acttgcctga tacctgtgat    300

agtagtacta gatgtagatg gttgtactgg gcgaaattca gcgaggctag gagttttgga    360

ggattttggt tgaactagtt tctgcgagaa ttcaataaaa tttctgaatt atgatggagc    420

cacggagaac aagcaatctg aaagaagata cgcaggtact gcgagtgtag tgcagccaga    480

agcaagttat ccgtagcttg tgaaagcaca gttggcttct tctacccaaa atataagaac    540
```

-continued

```
ctattaacca aaatataaga acctattaac gaatgagata ttttctagta ctaagtatat    600

tttctagtac taagtccata ttcgtagtac taggaaatgc cccatccgat ttaagttcaa    660

attcgtagta ttaggaaatg tcctatccgg ttctaggtta ttgtacttaa gaacagatgg    720

agtaggaaac taggttattg tacttaagaa cggatggagt aggaaacaac ggtgtactca    780

cacagagctg attgtctgaa caatcttcca gaggtcatca aactgctgat cagatcagaa    840

aaaaagattg aaattttgga tctcaatacc atttttacct gtcttgaacg gattgcaaca    900

atatgcattc agaactttag acatgcatac atactgcatt ggaaatgcgt ggaacaaaaa    960

cccatacctg ccttatggga actataagaa atatgttgta cattagcaac aaagtgaatt   1020

tccaatacaa acataagatc atcaatatta tccatgataa ataaaaatac agggctggta   1080

taagcaacat acaatctccg cttgttcaga acctaaaatt tgtttacagt tgtaccacat   1140

ggtatgctct ctacaactaa tgctactaag gaaatttcac agcatcgcga cagaacaaac   1200

aacagatgac atatcagtaa ctaaaatcat gtgttctgat atgtccagct gatgaggcat   1260

gcaaaacttc aggagatcag aaccctctac ttcaaag                            1297
```

<210> SEQ ID NO 47
<211> LENGTH: 35
<212> TYPE: DNA
<213> ORGANISM: Unknown
<220> FEATURE:
<223> OTHER INFORMATION: Oligonucleotide primer Primer 1(SacI, AvrII, SpeI, OCS 5')

<400> SEQUENCE: 47

```
cggagctccc taggactagt tcgaccggca tgccc                               35
```

<210> SEQ ID NO 48
<211> LENGTH: 25
<212> TYPE: DNA
<213> ORGANISM: Unknown
<220> FEATURE:
<223> OTHER INFORMATION: Primer 2 (NotI, OCS 3')

<400> SEQUENCE: 48

```
ccgcggccgc agcttggaca atcag                                          25
```

<210> SEQ ID NO 49
<211> LENGTH: 36
<212> TYPE: DNA
<213> ORGANISM: Unknown
<220> FEATURE:
<223> OTHER INFORMATION: Primer 3 (AvrII, XmaI, RsrII, LuF 5')

<400> SEQUENCE: 49

```
cgcctaggcc cgggcggacc gcattaagaa gggccc                              36
```

<210> SEQ ID NO 50
<211> LENGTH: 24
<212> TYPE: DNA
<213> ORGANISM: Unknown
<220> FEATURE:
<223> OTHER INFORMATION: Primer 4 (SpeI LuF 3')

<400> SEQUENCE: 50

```
cgactagtag agagttctca gagc                                           24
```

<210> SEQ ID NO 51
<211> LENGTH: 16
<212> TYPE: DNA
<213> ORGANISM: Unknown

<220> FEATURE:
<223> OTHER INFORMATION: Primer 5 (RsrII, BspEI, target gene seq 5')
<220> FEATURE:
<221> NAME/KEY: misc_feature
<222> LOCATION: (16)..(16)
<223> OTHER INFORMATION: n stands for preferably 10 to 20 bases of
target sequence to be amplyfied

<400> SEQUENCE: 51
cgcggaccgt ccggan 16

<210> SEQ ID NO 52
<211> LENGTH: 15
<212> TYPE: DNA
<213> ORGANISM: Unknown
<220> FEATURE:
<223> OTHER INFORMATION: Primer 6 (SpeI, AgeI, target gene seq 3')
<220> FEATURE:
<221> NAME/KEY: misc_feature
<222> LOCATION: (15)..(15)
<223> OTHER INFORMATION: n stands for preferably 10 to 20 bases of
target sequence to be amplyfied

<400> SEQUENCE: 52
cgactagtac cggtn 15

<210> SEQ ID NO 53
<211> LENGTH: 4811
<212> TYPE: DNA
<213> ORGANISM: Unknown
<220> FEATURE:
<223> OTHER INFORMATION: pTOI3
<220> FEATURE:
<221> NAME/KEY: misc_feature
<222> LOCATION: (1)..(100)
<223> OTHER INFORMATION: attL2 recombination site
<220> FEATURE:
<221> NAME/KEY: promoter
<222> LOCATION: (147)..(2134)
<223> OTHER INFORMATION: ubiquitin promoter + intron
<220> FEATURE:
<221> NAME/KEY: Intron
<222> LOCATION: (2551)..(2739)
<223> OTHER INFORMATION: PIV2 intron
<220> FEATURE:
<221> NAME/KEY: misc_feature
<222> LOCATION: (4218)..(4242)
<223> OTHER INFORMATION: insertion site for transcription terminator of
interest
<220> FEATURE:
<221> NAME/KEY: misc_feature
<222> LOCATION: (4243)..(4482)
<223> OTHER INFORMATION: luciferase fragment (Lu-F)
<220> FEATURE:
<221> NAME/KEY: terminator
<222> LOCATION: (4489)..(4701)
<223> OTHER INFORMATION: ocs terminator
<220> FEATURE:
<221> NAME/KEY: misc_feature
<222> LOCATION: (4712)..(4811)
<223> OTHER INFORMATION: attL1 recombination site

<400> SEQUENCE: 53
caaataatga ttttattttg actgatagtg acctgttcgt tgcaacaaat tgataagcaa 60
tgctttctta taatgccaac tttgtacaag aaagctgggt cggcgcgcca agcttgcatg 120
cctgcaggca tgcaagcttc cgcggctgca gtgcagcgtg acccggtcgt gcccctctct 180
agagataatg agcattgcat gtctaagtta taaaaaatta ccacatattt tttttgtcac 240
acttgtttga agtgcagttt atctatcttt atacatatat ttaaacttta ctctacgaat 300
aatataatct atagtactac aataatatca gtgttttaga gaatcatata aatgaacagt 360

-continued

```
tagacatggt ctaaaggaca attgagtatt ttgacaacag gactctacag ttttatcttt    420
ttagtgtgca tgtgttctcc ttttttttg caaatagctt cacctatata atacttcatc    480
cattttatta gtacatccat ttagggttta gggttaatgg tttttataga ctaatttttt    540
tagtacatct attttattct attttagcct ctaaattaag aaaactaaaa ctctatttta    600
gttttttat ttaatagttt agatataaaa tagaataaaa taaagtgact aaaaattaaa    660
caaataccct ttaagaaatt aaaaaaacta aggaaacatt tttcttgttt cgagtagata    720
atgccagcct gttaaacgcc gtcgacgagt ctaacggaca ccaaccagcg aaccagcagc    780
gtcgcgtcgg gccaagcgaa gcagacggca cggcatctct gtcgctgcct ctggacccct    840
ctcgagagtt ccgctccacc gttggacttg ctccgctgtc ggcatccaga aattgcgtgg    900
cggagcggca gacgtgagcc ggcacggcag gcggcctcct cctcctctca cggcaccggc    960
agctacgggg gattcctttc ccaccgctcc ttcgctttcc cttcctcgcc cgccgtaata   1020
aatagacacc ccctccacac cctctttccc caacctcgtg ttgttcggag cgcacacaca   1080
cacaaccaga tctcccccaa atccacccgt cggcacctcc gcttcaaggt acgccgctcg   1140
tcctcccccc cccccccct ctctaccttc tctagatcgg cgttccggtc catggttagg   1200
gcccggtagt tctacttctg ttcatgtttg tgttagatcc gtgtttgtgt tagatccgtg   1260
ctgctagcgt tcgtacacgg atgcgacctg tacgtcagac acgttctgat tgctaacttg   1320
ccagtgtttc tctttgggga atcctgggat ggctctagcc gttccgcaga cgggatcgat   1380
ttcatgattt tttttgtttc gttgcatagg gtttggtttg cccttttcct ttatttcaat   1440
atatgccgtg cacttgtttg tcgggtcatc ttttcatgct ttttttgtc ttggttgtga    1500
tgatgtggtc tggttgggcg gtcgttctag atcggagtag aattctgttt caaactacct   1560
ggtggattta ttaattttgg atctgtatgt gtgtgccata catattcata gttacgaatt   1620
gaagatgatg gatggaaata tcgatctagg ataggtatac atgttgatgc gggttttact   1680
gatgcatata cagagatgct tttgttcgc ttggttgtga tgatgtggtg tggttgggcg    1740
gtcgttcatt cgttctagat cggagtagaa tactgtttca aactacctgg tgtatttatt   1800
aattttggaa ctgtatgtgt gtgtcataca tcttcatagt tacgagttta agatggatgg   1860
aaatatcgat ctaggatagg tatacatgtt gatgtgggtt ttactgatgc atatacatga   1920
tggcatatgc agcatctatt catatgctct aaccttgagt acctatctat tataataaac   1980
aagtatgttt tataattatt tcgatcttga tatacttgga tgatggcata tgcagcagct   2040
atatgtggat tttttagcc ctgccttcat acgctattta tttgcttggt actgtttctt    2100
ttgtcgatgc tcaccctgtt gtttggtgtt acttctgcag ggtacccccg ggtggtcagt   2160
cccttatgtt acgtcctgta gaaaccccaa cccgtgaaat caaaaaactc gacggcctgt   2220
gggcattcag tctggatcgc gaaaactgtg gaattgatca gcgttggtgg gaaagcgcgt   2280
tacaagaaag ccgggcaatt gctgtgccag gcagttttaa cgatcagttc gccgatgcag   2340
atattcgtaa ttatgcgggc aacgtctggt atcagcgcga agtctttata ccgaaaggtt   2400
gggcaggcca gcgtatcgtg ctgcgtttcg atgcggtcac tcattacggc aaagtgtggg   2460
tcaataatca ggaagtgatg gagcatcagg gcggctatac gccatttgaa gccgatgtca   2520
cgccgtatgt tattgccggg aaaagtgtac gtaagtttct gcttctacct ttgatatata   2580
tataataatt atcattaatt agtagtaata taatatttca aatatttttt tcaaaataaa   2640
agaatgtagt atatagcaat tgcttttctg tagtttataa gtgtgtatat tttaatttat   2700
aacttttcta atatatgacc aaaatttgtt gatgtgcagg tatcaccgtt tgtgtgaaca   2760
```

-continued acgaactgaa ctggcagact atcccgccgg gaatggtgat taccgacgaa aacggcaaga 2820
aaaagcagtc ttacttccat gatttcttta actatgccgg aatccatcgc agcgtaatgc 2880
tctacaccac gccgaacacc tgggtggacg atatcaccgt ggtgacgcat gtcgcgcaag 2940
actgtaacca cgcgtctgtt gactggcagg tggtggccaa tggtgatgtc agcgttgaac 3000
tgcgtgatgc ggatcaacag gtggttgcaa ctggacaagg cactagcggg actttgcaag 3060
tggtgaatcc gcacctctgg caaccgggtg aaggttatct ctatgaactg tgcgtcacag 3120
ccaaaagcca gacagagtgt gatatctacc cgcttcgcgt cggcatccgg tcagtggcag 3180
tgaagggcca acagttcctg attaaccaca aaccgttcta ctttactggc tttggtcgtc 3240
atgaagatgc ggacttacgt ggcaaaggat tcgataacgt gctgatggtg cacgaccacg 3300
cattaatgga ctggattggg gccaactcct accgtacctc gcattaccct tacgctgaag 3360
agatgctcga ctgggcagat gaacatggca tcgtggtgat tgatgaaact gctgctgtcg 3420
gctttaacct ctctttaggc attggtttcg aagcgggcaa caagccgaaa gaactgtaca 3480
gcgaagaggc agtcaacggg gaaactcagc aagcgcactt acaggcgatt aaagagctga 3540
tagcgcgtga caaaaaccac ccaagcgtgg tgatgtggag tattgccaac gaaccggata 3600
cccgtccgca agtgcacggg aatatttcgc cactggcgga agcaacgcgt aaactcgacc 3660
cgacgcgtcc gatcacctgc gtcaatgtaa tgttctgcga cgctcacacc gataccatca 3720
gcgatctctt tgatgtgctg tgcctgaacc gttattacgg atggtatgtc caaagcggcg 3780
atttggaaac ggcagagaag gtactggaaa aagaacttct ggcctggcag gagaaactgc 3840
atcagccgat tatcatcacc gaatacggcg tggatacgtt agccgggctg cactcaatgt 3900
acaccgacat gtggagtgaa gagtatcagt gtgcatggct ggatatgtat caccgcgtct 3960
ttgatcgcgt cagcgccgtc gtcggtgaac aggtatggaa tttcgccgat tttgcgacct 4020
cgcaaggcat attgcgcgtt ggcggtaaca agaaagggat cttcactcgc gaccgcaaac 4080
cgaagtcggc ggcttttctg ctgcaaaaac gctggactgg catgaacttc ggtgaaaaac 4140
cgcagcaggg aggcaaacaa tgaatcaaca actctcctgg cgcaccatcg tcggctacag 4200
cctcgggaat tgctaccgag ctccctaggc ccgggcggac cgcattaaga agggccctgc 4260
tcccttctac cctctggagg atggcaccgc tggcgagcag ctgcacaagg ccatgaagag 4320
gtatgccctg gtgcctggca ccattgcctt caccgatgcc cacattgagg tggacatcac 4380
ctatgccgag tacttcgaga tgtctgtgcg cctggccgag gccatgaaga ggtacggcct 4440
gaacaccaac caccgcatcg tggtgtgctc tgagaactct ctactagttc gaccggcatg 4500
ccctgcttta atgagatatg cgagacgcct atgatcgcat gatatttgct ttcaattctg 4560
ttgtgcacgt tgtaaaaaac ctgagcatgt gtagctcaga tccttaccgc cggtttcggt 4620
tcattctaat gaatatatca cccgttacta tcgtattttt atgaataata ttctccgttc 4680
aatttactga ttgtccaagc tgcggccgcg gagcctgctt ttttgtacaa agttggcatt 4740
ataaaaaagc attgctcatc aatttgttgc aacgaacagg tcactatcag tcaaaataaa 4800
atcattattt g 4811

<210> SEQ ID NO 54
<211> LENGTH: 5053
<212> TYPE: DNA
<213> ORGANISM: Unknown
<220> FEATURE:
<223> OTHER INFORMATION: pTOI4
<220> FEATURE:
<221> NAME/KEY: misc_feature
<222> LOCATION: (1)..(100)

<223> OTHER INFORMATION: attL2 recombination site
<220> FEATURE:
<221> NAME/KEY: promoter
<222> LOCATION: (147)..(2134)
<223> OTHER INFORMATION: ubiquitin promotor + intron
<220> FEATURE:
<221> NAME/KEY: misc_feature
<222> LOCATION: (2158)..(4163)
<223> OTHER INFORMATION: coding for glucuronidase (GUS) + intron
<220> FEATURE:
<221> NAME/KEY: Intron
<222> LOCATION: (2551)..(2739)
<223> OTHER INFORMATION: PIV2 intron
<220> FEATURE:
<221> NAME/KEY: terminator
<222> LOCATION: (4225)..(4478)
<223> OTHER INFORMATION: nos terminator
<220> FEATURE:
<221> NAME/KEY: misc_feature
<222> LOCATION: (4485)..(4724)
<223> OTHER INFORMATION: luciferase fragment (Lu-F)
<220> FEATURE:
<221> NAME/KEY: terminator
<222> LOCATION: (4731)..(4943)
<223> OTHER INFORMATION: ocs terminator
<220> FEATURE:
<221> NAME/KEY: misc_feature
<222> LOCATION: (4954)..(5053)
<223> OTHER INFORMATION: attL1 recombination site

<400> SEQUENCE: 54
caaataatga ttttattttg actgatagtg acctgttcgt tgcaacaaat tgataagcaa 60
tgctttctta taatgccaac tttgtacaag aaagctgggt cggcgcgcca agcttgcatg 120
cctgcaggca tgcaagcttc cgcggctgca gtgcagcgtg acccggtcgt gcccctctct 180
agagataatg agcattgcat gtctaagtta taaaaaatta ccacatattt tttttgtcac 240
acttgtttga agtgcagttt atctatcttt atacatatat ttaaacttta ctctacgaat 300
aatataatct atagtactac aataatatca gtgttttaga gaatcatata aatgaacagt 360
tagacatggt ctaaaggaca attgagtatt ttgacaacag gactctacag ttttatcttt 420
ttagtgtgca tgtgttctcc tttttttttg caaatagctt cacctatata atacttcatc 480
cattttatta gtacatccat ttagggttta gggttaatgg tttttataga ctaatttttt 540
tagtacatct attttattct attttagcct ctaaattaag aaaactaaaa ctctatttta 600
gtttttttat ttaatagttt agatataaaa tagaataaaa taaagtgact aaaaattaaa 660
caaataccct ttaagaaatt aaaaaaacta aggaaacatt tttcttgttt cgagtagata 720
atgccagcct gttaaacgcc gtcgacgagt ctaacggaca ccaaccagcg aaccagcagc 780
gtcgcgtcgg gccaagcgaa gcagacggca cggcatctct gtcgctgcct ctggacccct 840
ctcgagagtt ccgctccacc gttggacttg ctccgctgtc ggcatccaga aattgcgtgg 900
cggagcggca gacgtgagcc ggcacggcag gcggcctcct cctcctctca cggcaccggc 960
agctacgggg gattcctttc ccaccgctcc ttcgctttcc cttcctcgcc cgccgtaata 1020
aatagacacc ccctccacac cctctttccc caacctcgtg ttgttcggag cgcacacaca 1080
cacaaccaga tctcccccaa atccacccgt cggcacctcc gcttcaaggt acgccgctcg 1140
tcctcccccc ccccccccct ctctaccttc tctagatcgg cgttccggtc catggttagg 1200
gcccggtagt tctacttctg ttcatgtttg tgttagatcc gtgtttgtgt tagatccgtg 1260
ctgctagcgt tcgtacacgg atgcgacctg tacgtcagac acgttctgat tgctaacttg 1320
ccagtgtttc tctttgggga atcctgggat ggctctagcc gttccgcaga cgggatcgat 1380
ttcatgattt tttttgtttc gttgcatagg gtttggtttg cccttttcct ttatttcaat 1440

-continued

```
atatgccgtg cacttgtttg tcgggtcatc ttttcatgct ttttttgtc ttggttgtga   1500
tgatgtggtc tggttgggcg gtcgttctag atcggagtag aattctgttt caaactacct   1560
ggtggattta ttaattttgg atctgtatgt gtgtgccata catattcata gttacgaatt   1620
gaagatgatg gatggaaata tcgatctagg ataggtatac atgttgatgc gggttttact   1680
gatgcatata cagagatgct ttttgttcgc ttggttgtga tgatgtggtg tggttgggcg   1740
gtcgttcatt cgttctagat cggagtagaa tactgtttca aactacctgg tgtatttatt   1800
aattttggaa ctgtatgtgt gtgtcataca tcttcatagt tacgagttta agatggatgg   1860
aaatatcgat ctaggatagg tatacatgtt gatgtgggtt ttactgatgc atatacatga   1920
tggcatatgc agcatctatt catatgctct aaccttgagt acctatctat tataataaac   1980
aagtatgttt tataattatt tcgatcttga tatacttgga tgatggcata tgcagcagct   2040
atatgtggat ttttttagcc ctgccttcat acgctattta tttgcttggt actgtttctt   2100
ttgtcgatgc tcaccctgtt gtttggtgtt acttctgcag ggtacccccg ggtggtcagt   2160
cccttatgtt acgtcctgta gaaaccccaa cccgtgaaat caaaaaactc gacggcctgt   2220
gggcattcag tctggatcgc gaaaactgtg gaattgatca gcgttggtgg gaaagcgcgt   2280
tacaagaaag ccgggcaatt gctgtgccag gcagttttaa cgatcagttc gccgatgcag   2340
atattcgtaa ttatgcgggc aacgtctggt atcagcgcga agtctttata ccgaaaggtt   2400
gggcaggcca gcgtatcgtg ctgcgtttcg atgcggtcac tcattacggc aaagtgtggg   2460
tcaataatca ggaagtgatg gagcatcagg gcggctatac gccatttgaa gccgatgtca   2520
cgccgtatgt tattgccggg aaaagtgtac gtaagtttct gcttctacct ttgatatata   2580
tataataatt atcattaatt agtagtaata taatatttca aatatttttt tcaaaataaa   2640
agaatgtagt atatagcaat tgcttttctg tagtttataa gtgtgtatat tttaatttat   2700
aacttttcta atatatgacc aaaatttgtt gatgtgcagg tatcaccgtt tgtgtgaaca   2760
acgaactgaa ctggcagact atcccgccgg gaatggtgat taccgacgaa aacggcaaga   2820
aaaagcagtc ttacttccat gatttcttta actatgccgg aatccatcgc agcgtaatgc   2880
tctacaccac gccgaacacc tgggtggacg atatcaccgt ggtgacgcat gtcgcgcaag   2940
actgtaacca cgcgtctgtt gactggcagg tggtggccaa tggtgatgtc agcgttgaac   3000
tgcgtgatgc ggatcaacag gtggttgcaa ctggacaagg cactagcggg actttgcaag   3060
tggtgaatcc gcacctctgg caaccgggtg aaggttatct ctatgaactg tgcgtcacag   3120
ccaaaagcca gacagagtgt gatatctacc cgcttcgcgt cggcatccgg tcagtggcag   3180
tgaagggcca acagttcctg attaaccaca aaccgttcta ctttactggc tttggtcgtc   3240
atgaagatgc ggacttacgt ggcaaaggat tcgataacgt gctgatggtg cacgaccacg   3300
cattaatgga ctggattggg gccaactcct accgtacctc gcattaccct tacgctgaag   3360
agatgctcga ctgggcagat gaacatggca tcgtggtgat tgatgaaact gctgctgtcg   3420
gctttaacct ctctttaggc attggtttcg aagcgggcaa caagccgaaa gaactgtaca   3480
gcgaagaggc agtcaacggg gaaactcagc aagcgcactt acaggcgatt aaagagctga   3540
tagcgcgtga caaaaaccac ccaagcgtgg tgatgtggag tattgccaac gaaccggata   3600
cccgtccgca agtgcacggg aatatttcgc cactggcgga agcaacgcgt aaactcgacc   3660
cgacgcgtcc gatcacctgc gtcaatgtaa tgttctgcga cgctcacacc gataccatca   3720
gcgatctctt tgatgtgctg tgcctgaacc gttattacgg atggtatgtc caaagcggcg   3780
atttggaaac ggcagagaag gtactggaaa aagaacttct ggcctggcag gagaaactgc   3840
```

atcagccgat tatcatcacc gaatacggcg tggatacgtt agccgggctg cactcaatgt 3900
acaccgacat gtggagtgaa gagtatcagt gtgcatggct ggatatgtat caccgcgtct 3960
ttgatcgcgt cagcgccgtc gtcggtgaac aggtatggaa tttcgccgat tttgcgacct 4020
cgcaaggcat attgcgcgtt ggcggtaaca agaaagggat cttcactcgc gaccgcaaac 4080
cgaagtcggc ggcttttctg ctgcaaaaac gctggactgg catgaacttc ggtgaaaaac 4140
cgcagcaggg aggcaaacaa tgaatcaaca actctcctgg cgcaccatcg tcggctacag 4200
cctcgggaat tgctaccgag ctccgatcgt tcaaacattt ggcaataaag tttcttaaga 4260
ttgaatcctg ttgccggtct tgcgatgatt atcatataat ttctgttgaa ttacgttaag 4320
catgtaataa ttaacatgta atgcatgacg ttatttatga gatgggtttt tatgattaga 4380
gtcccgcaat tatacattta atacgcgata gaaaacaaaa tatagcgcgc aaactaggat 4440
aaattatcgc gcgcggtgtc atctatgtta ctagatccgg accgcattaa gaagggccct 4500
gctcccttct accctctgga ggatggcacc gctggcgagc agctgcacaa ggccatgaag 4560
aggtatgccc tggtgcctgg caccattgcc ttcaccgatg cccacattga ggtggacatc 4620
acctatgccg agtacttcga gatgtctgtg cgcctggccg aggccatgaa gaggtacggc 4680
ctgaacacca accaccgcat cgtggtgtgc tctgagaact ctctactagt tcgaccggca 4740
tgccctgctt taatgagata tgcgagacgc ctatgatcgc atgatatttg ctttcaattc 4800
tgttgtgcac gttgtaaaaa acctgagcat gtgtagctca gatccttacc gccggtttcg 4860
gttcattcta atgaatatat cacccgttac tatcgtattt ttatgaataa tattctccgt 4920
tcaatttact gattgtccaa gctgcggccg cggagcctgc ttttttgtac aaagttggca 4980
ttataaaaaa gcattgctca tcaatttgtt gcaacgaaca ggtcactatc agtcaaaata 5040
aaatcattat ttg 5053

<210> SEQ ID NO 55
<211> LENGTH: 28
<212> TYPE: DNA
<213> ORGANISM: Unknown
<220> FEATURE:
<223> OTHER INFORMATION: Oligonucleotideprimer Loy482-NosT-upper-SalI

<400> SEQUENCE: 55
aaatttgtcg accgatcggt caaacatt 28

<210> SEQ ID NO 56
<211> LENGTH: 36
<212> TYPE: DNA
<213> ORGANISM: Unknown
<220> FEATURE:
<223> OTHER INFORMATION: Oligonucleotideprimer Loy483-NosT-Lower-HindIII

<400> SEQUENCE: 56
aaatttaagc ttcccgatct agtaacatag atgaca 36

<210> SEQ ID NO 57
<211> LENGTH: 31
<212> TYPE: DNA
<213> ORGANISM: Unknown
<220> FEATURE:
<223> OTHER INFORMATION: Oligonucleotideprimer
Loy494-Gus_upper_SalI_Spacer

<400> SEQUENCE: 57
ttttagtcga cacgctggac tggcatgaac t 31

<210> SEQ ID NO 58
<211> LENGTH: 40
<212> TYPE: DNA
<213> ORGANISM: Unknown
<220> FEATURE:
<223> OTHER INFORMATION: Oligonucleotideprimer
Loy492-NosT-lower-BglII SpeI

<400> SEQUENCE: 58
ttttaagatc tactagtccg atctagtaac atagatgaca 40

<210> SEQ ID NO 59
<211> LENGTH: 31
<212> TYPE: DNA
<213> ORGANISM: Unknown
<220> FEATURE:
<223> OTHER INFORMATION: Oligonucleotideprimer
Loy493_Gus_upper_SalI_Spacer

<400> SEQUENCE: 59
tttaagtcga caagtcggcg gcttttctgc t 31

<210> SEQ ID NO 60
<211> LENGTH: 40
<212> TYPE: DNA
<213> ORGANISM: Unknown
<220> FEATURE:
<223> OTHER INFORMATION: Oligonucleotideprimer
Loy492-NosT-lower-BglII SpeI

<400> SEQUENCE: 60
ttttaagatc tactagtccg atctagtaac atagatgaca 40

<210> SEQ ID NO 61
<211> LENGTH: 44
<212> TYPE: DNA
<213> ORGANISM: Unknown
<220> FEATURE:
<223> OTHER INFORMATION: Oligonucleotideprimer JMTOIprim1

<400> SEQUENCE: 61
ggttccaagg taccaaaaca atgggcgctg atgatgttgt tgat 44

<210> SEQ ID NO 62
<211> LENGTH: 42
<212> TYPE: DNA
<213> ORGANISM: Unknown
<220> FEATURE:
<223> OTHER INFORMATION: Oligonucleotideprimer JMTOIprim2

<400> SEQUENCE: 62
aaggtagaag cagaaactta cctggatacg tcactttgac ca 42

<210> SEQ ID NO 63
<211> LENGTH: 42
<212> TYPE: DNA
<213> ORGANISM: Unknown
<220> FEATURE:
<223> OTHER INFORMATION: Oligonucleotideprimer JMTOIprim3

<400> SEQUENCE: 63
tggtcaaagt gacgtatcca ggtaagtttc tgcttctacc tt 42

<210> SEQ ID NO 64
<211> LENGTH: 37
<212> TYPE: DNA
<213> ORGANISM: Unknown
<220> FEATURE:

<223> OTHER INFORMATION: Oligonucleotideprimer JMTOIprim4

<400> SEQUENCE: 64
ggttccaagg atccatttat tttgaaaaaa atatttg 37

<210> SEQ ID NO 65
<211> LENGTH: 35
<212> TYPE: DNA
<213> ORGANISM: Unknown
<220> FEATURE:
<223> OTHER INFORMATION: Oligonucleotideprimer JMTOIprim5

<400> SEQUENCE: 65
ggttccaagg atccagtata tagcaattgc ttttc 35

<210> SEQ ID NO 66
<211> LENGTH: 83
<212> TYPE: DNA
<213> ORGANISM: Unknown
<220> FEATURE:
<223> OTHER INFORMATION: Oligonucleotideprimer JMTOIprim6

<400> SEQUENCE: 66
cgagaacctt cgtcagtcct gcacatcaac aaattttggt cataaaaaaa aaaatattag 60
aaaagttata aattaaaata tac 83

<210> SEQ ID NO 67
<211> LENGTH: 63
<212> TYPE: DNA
<213> ORGANISM: Unknown
<220> FEATURE:
<223> OTHER INFORMATION: Oligonucleotideprimer JMTOIprim7

<400> SEQUENCE: 67
ctaatatttt ttttttatg accaaaattt gttgatgtgc aggactgacg aaggttctcg 60
cac 63

<210> SEQ ID NO 68
<211> LENGTH: 38
<212> TYPE: DNA
<213> ORGANISM: Unknown
<220> FEATURE:
<223> OTHER INFORMATION: Oligonucleotideprimer JMTOIprim8

<400> SEQUENCE: 68
ttggaaccac tagtttatcg cctgacacga tttcctgc 38

<210> SEQ ID NO 69
<211> LENGTH: 35
<212> TYPE: DNA
<213> ORGANISM: Unknown
<220> FEATURE:
<223> OTHER INFORMATION: Oligonucleotideprimer JMTOIprim9

<400> SEQUENCE: 69
ggttccaagg atccgatcgt tcaaacattt ggcaa 35

<210> SEQ ID NO 70
<211> LENGTH: 35
<212> TYPE: DNA
<213> ORGANISM: Unknown
<220> FEATURE:
<223> OTHER INFORMATION: Oligonucleotideprimer JMTOIprim10

<400> SEQUENCE: 70

```
ggttccaagg atccgatcta gtaacataga tgaca                          35


<210> SEQ ID NO 71
<211> LENGTH: 3030
<212> TYPE: DNA
<213> ORGANISM: Unknown
<220> FEATURE:
<223> OTHER INFORMATION: pJMTOI1
<220> FEATURE:
<221> NAME/KEY: promoter
<222> LOCATION: (1)..(1988)
<223> OTHER INFORMATION: Zea mays ubiquitin promoter
<220> FEATURE:
<221> NAME/KEY: misc_feature
<222> LOCATION: (2007)..(2268)
<223> OTHER INFORMATION: 5'-part of sequence encoding diphtheria toxin A
<220> FEATURE:
<221> NAME/KEY: Intron
<222> LOCATION: (2269)..(2488)
<220> FEATURE:
<221> NAME/KEY: misc_feature
<222> LOCATION: (2489)..(2811)
<223> OTHER INFORMATION: 3'-part of sequence encoding diphtheria toxin A
<220> FEATURE:
<221> NAME/KEY: terminator
<222> LOCATION: (2818)..(3030)
<223> OTHER INFORMATION: ocs terminator

<400> SEQUENCE: 71

tgcagtgcag cgtgacccgg tcgtgcccct ctctagagat aatgagcatt gcatgtctaa     60

gttataaaaa attaccacat attttttttg tcacacttgt ttgaagtgca gtttatctat    120

ctttatacat atatttaaac tttactctac gaataatata atctatagta ctacaataat    180

atcagtgttt tagagaatca tataaatgaa cagttagaca tggtctaaag gacaattgag    240

tattttgaca acaggactct acagttttat ctttttagtg tgcatgtgtt ctcctttttt    300

tttgcaaata gcttcaccta tataatactt catccatttt attagtacat ccatttaggg    360

tttagggtta atggttttta tagactaatt tttttagtac atctatttta ttctatttta    420

gcctctaaat taagaaaact aaaactctat tttagttttt ttatttaata gtttagatat    480

aaaatagaat aaaataaagt gactaaaaat taaacaaata ccctttaaga aattaaaaaa    540

actaaggaaa catttttctt gtttcgagta gataatgcca gcctgttaaa cgccgtcgac    600

gagtctaacg gacaccaacc agcgaaccag cagcgtcgcg tcgggccaag cgaagcagac    660

ggcacggcat ctctgtcgct gcctctggac ccctctcgag agttccgctc caccgttgga    720

cttgctccgc tgtcggcatc cagaaattgc gtggcggagc ggcagacgtg agccggcacg    780

gcaggcggcc tcctcctcct ctcacggcac cggcagctac gggggattcc tttcccaccg    840

ctccttcgct ttcccttcct cgcccgccgt aataaataga caccccctcc acaccctctt    900

tccccaacct cgtgttgttc ggagcgcaca cacacacaac cagatctccc ccaaatccac    960

ccgtcggcac ctccgcttca aggtacgccg ctcgtcctcc cccccccccc ccctctctac   1020

cttctctaga tcggcgttcc ggtccatggt tagggcccgg tagttctact tctgttcatg   1080

tttgtgttag atccgtgttt gtgttagatc cgtgctgcta gcgttcgtac acggatgcga   1140

cctgtacgtc agacacgttc tgattgctaa cttgccagtg tttctctttg gggaatcctg   1200

ggatggctct agccgttccg cagacgggat cgatttcatg attttttttg tttcgttgca   1260

tagggtttgg tttgcccttt tcctttattt caatatatgc cgtgcacttg tttgtcgggt   1320

catcttttca tgcttttttt tgtcttggtt gtgatgatgt ggtctggttg ggcggtcgtt   1380

ctagatcgga gtagaattct gtttcaaact acctggtgga tttattaatt ttggatctgt   1440

atgtgtgtgc catacatatt catagttacg aattgaagat gatggatgga aatatcgatc   1500
```

```
taggataggt atacatgttg atgcgggttt tactgatgca tatacagaga tgctttttgt   1560
tcgcttggtt gtgatgatgt ggtgtggttg ggcggtcgtt cattcgttct agatcggagt   1620
agaatactgt ttcaaactac ctggtgtatt tattaatttt ggaactgtat gtgtgtgtca   1680
tacatcttca tagttacgag tttaagatgg atggaaatat cgatctagga taggtataca   1740
tgttgatgtg ggttttactg atgcatatac atgatggcat atgcagcatc tattcatatg   1800
ctctaacctt gagtacctat ctattataat aaacaagtat gttttataat tatttcgatc   1860
ttgatatact tggatgatgg catatgcagc agctatatgt ggattttttt agccctgcct   1920
tcatacgcta tttatttgct tggtactgtt tcttttgtcg atgctcaccc tgttgtttgg   1980
tgttacttct gcagggtacc aaaacaatgg gcgctgatga tgttgttgat tcttctaaat   2040
cttttgtgat ggaaaacttt tcttcgtacc acgggactaa acctggttat gtagattcca   2100
ttcaaaaagg tatacaaaag ccaaaatctg gtacacaagg aaattatgac gatgattgga   2160
aagggtttta tagtaccgac aataaatacg acgctgcggg atactctgta gataatgaaa   2220
acccgctctc tggaaaagct ggaggcgtgg tcaaagtgac gtatccaggt aagtttctgc   2280
ttctaccttg taagtttctg cttctacctt tgatatatat ataataatta tcattaatta   2340
gtagtaatat aatatttcaa atattttttt caaaataaat ggatccagta tatagcaatt   2400
gcttttctgt agtttataag tgtgtatatt ttaatttata acttttctaa tatttttttt   2460
tttatgacca aaatttgttg atgtgcagga ctgacgaagg ttctcgcact aaaagtggat   2520
aatgccgaaa ctattaagaa agagttaggt ttaagtctca ctgaaccgtt gatggagcaa   2580
gtcggaacgg aagagtttat caaaaggttc ggtgatggtg cttcgcgtgt agtgctcagc   2640
cttcccttcg ctgaggggag ttctagcgtt gaatatatta ataactggga acaggcgaaa   2700
gcgttaagcg tagaacttga gattaatttt gaaacccgtg gaaaacgtgg ccaagatgcg   2760
atgtatgagt atatggctca agcctgtgca ggaaatcgtg tcaggcgata aactagttcg   2820
accggcatgc cctgctttaa tgagatatgc gagacgccta tgatcgcatg atatttgctt   2880
tcaattctgt tgtgcacgtt gtaaaaaacc tgagcatgtg tagctcagat ccttaccgcc   2940
ggtttcggtt cattctaatg aatatatcac ccgttactat cgtattttta tgaataatat   3000
tctccgttca atttactgat tgtccaagct                                    3030
```

<210> SEQ ID NO 72
<211> LENGTH: 3289
<212> TYPE: DNA
<213> ORGANISM: Unknown
<220> FEATURE:
<223> OTHER INFORMATION: pJMTOI2
<220> FEATURE:
<221> NAME/KEY: promoter
<222> LOCATION: (1)..(1988)
<223> OTHER INFORMATION: Zea mays ubiquitin promoter
<220> FEATURE:
<221> NAME/KEY: misc_feature
<222> LOCATION: (2007)..(2268)
<223> OTHER INFORMATION: 5'-part of sequence encoding diphtheria toxin A
<220> FEATURE:
<221> NAME/KEY: Intron
<222> LOCATION: (2269)..(2380)
<223> OTHER INFORMATION: 5'-part of intron
<220> FEATURE:
<221> NAME/KEY: terminator
<222> LOCATION: (2387)..(2639)
<223> OTHER INFORMATION: nos terminator
<220> FEATURE:
<221> NAME/KEY: Intron
<222> LOCATION: (2646)..(2747)
<223> OTHER INFORMATION: 3'-part of intron
<220> FEATURE:
<221> NAME/KEY: misc_feature
<222> LOCATION: (2747)..(3070)
<223> OTHER INFORMATION: 3'-part of sequence encoding diphtheria toxin A
<220> FEATURE:
<221> NAME/KEY: terminator
<222> LOCATION: (3077)..(3289)
<223> OTHER INFORMATION: ocs terminator

<400> SEQUENCE: 72

```
tgcagtgcag cgtgacccgg tcgtgcccct ctctagagat aatgagcatt gcatgtctaa     60
gttataaaaa attaccacat atttttttttg tcacacttgt ttgaagtgca gtttatctat    120
ctttatacat atatttaaac tttactctac gaataatata atctatagta ctacaataat    180
atcagtgttt tagagaatca tataaatgaa cagttagaca tggtctaaag gacaattgag    240
tattttgaca acaggactct acagttttat ctttttagtg tgcatgtgtt ctcctttttt    300
tttgcaaata gcttcaccta tataatactt catccatttt attagtacat ccatttaggg    360
tttagggtta atggttttta tagactaatt tttttagtac atctatttta ttctatttta    420
gcctctaaat taagaaaact aaaactctat tttagttttt ttatttaata gtttagatat    480
aaaatagaat aaaataaagt gactaaaaat taaacaaata ccctttaaga aattaaaaaa    540
actaaggaaa catttttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
ctccttcgct ttcccttcct cgcccgccgt aataaataga caccccctcc acaccctctt    900
tccccaacct cgtgttgttc ggagcgcaca cacacacaac cagatctccc ccaaatccac    960
ccgtcggcac ctccgcttca aggtacgccg ctcgtcctcc cccccccccc ccctctctac   1020
cttctctaga tcggcgttcc ggtccatggt tagggcccgg tagttctact tctgttcatg   1080
tttgtgttag atccgtgttt gtgttagatc cgtgctgcta gcgttcgtac acggatgcga   1140
cctgtacgtc agacacgttc tgattgctaa cttgccagtg tttctctttg gggaatcctg   1200
ggatggctct agccgttccg cagacgggat cgatttcatg atttttttttg tttcgttgca   1260
tagggtttgg tttgcccttt tcctttattt caatatatgc cgtgcacttg tttgtcgggt   1320
catcttttca tgcttttttt tgtcttggtt gtgatgatgt ggtctggttg ggcggtcgtt   1380
ctagatcgga gtagaattct gtttcaaact acctggtgga tttattaatt ttggatctgt   1440
atgtgtgtgc catacatatt catagttacg aattgaagat gatggatgga aatatcgatc   1500
taggataggt atacatgttg atgcgggttt tactgatgca tatacagaga tgctttttgt   1560
tcgcttggtt gtgatgatgt ggtgtggttg ggcggtcgtt cattcgttct agatcggagt   1620
agaatactgt ttcaaactac ctggtgtatt tattaatttt ggaactgtat gtgtgtgtca   1680
tacatcttca tagttacgag tttaagatgg atggaaatat cgatctagga taggtataca   1740
tgttgatgtg ggttttactg atgcatatac atgatggcat atgcagcatc tattcatatg   1800
ctctaacctt gagtacctat ctattataat aaacaagtat gttttataat tatttcgatc   1860
ttgatatact tggatgatgg catatgcagc agctatatgt ggattttttt agccctgcct   1920
tcatacgcta tttatttgct tggtactgtt tcttttgtcg atgctcaccc tgttgtttgg   1980
tgttacttct gcagggtacc aaaacaatgg gcgctgatga tgttgttgat tcttctaaat   2040
cttttgtgat ggaaaacttt tcttcgtacc acgggactaa acctggttat gtagattcca   2100
```

```
ttcaaaaagg tatacaaaag ccaaaatctg gtacacaagg aaattatgac gatgattgga   2160

aagggtttta tagtaccgac aataaatacg acgctgcggg atactctgta gataatgaaa   2220

acccgctctc tggaaaagct ggaggcgtgg tcaaagtgac gtatccaggt aagtttctgc   2280

ttctaccttg taagtttctg cttctacctt tgatatatat ataataatta tcattaatta   2340

gtagtaatat aatatttcaa atattttttt caaaataaat ggatccgatc gttcaaacat   2400

ttggcaataa agtttcttaa gattgaatcc tgttgccggt cttgcgatga ttatcatata   2460

atttctgttg aattacgtta agcatgtaat aattaacatg taatgcatga cgttatttat   2520

gagatgggtt tttatgatta gagtcccgca attatacatt taatacgcga tagaaaacaa   2580

aatatagcgc gcaaactagg ataaattatc gcgcgcggtg tcatctatgt tactagatcg   2640

gatccagtat atagcaattg cttttctgta gtttataagt gtgtatattt taatttataa   2700

cttttctaat attttttttt ttatgaccaa aatttgttga tgtgcaggac tgacgaaggt   2760

tctcgcacta aaagtggata atgccgaaac tattaagaaa gagttaggtt taagtctcac   2820

tgaaccgttg atggagcaag tcggaacgga agagtttatc aaaaggttcg gtgatggtgc   2880

ttcgcgtgta gtgctcagcc ttcccttcgc tgaggggagt tctagcgttg aatatattaa   2940

taactgggaa caggcgaaag cgttaagcgt agaacttgag attaattttg aaacccgtgg   3000

aaaacgtggc caagatgcga tgtatgagta tatggctcaa gcctgtgcag gaaatcgtgt   3060

caggcgataa actagttcga ccggcatgcc ctgctttaat gagatatgcg agacgcctat   3120

gatcgcatga tatttgcttt caattctgtt gtgcacgttg taaaaaacct gagcatgtgt   3180

agctcagatc cttaccgccg gtttcggttc attctaatga atatatcacc cgttactatc   3240

gtatttttat gaataatatt ctccgttcaa tttactgatt gtccaagct              3289
```

<210> SEQ ID NO 73
<211> LENGTH: 3680
<212> TYPE: DNA
<213> ORGANISM: Unknown
<220> FEATURE:
<223> OTHER INFORMATION: pJMTOI3
<220> FEATURE:
<221> NAME/KEY: promoter
<222> LOCATION: (1)..(1988)
<223> OTHER INFORMATION: Zea mays ubiquitin promoter
<220> FEATURE:
<221> NAME/KEY: misc_feature
<222> LOCATION: (2001)..(2696)
<223> OTHER INFORMATION: coding for green fluorescence protein (GFP)
<220> FEATURE:
<221> NAME/KEY: terminator
<222> LOCATION: (2703)..(2955)
<223> OTHER INFORMATION: nos terminator
<220> FEATURE:
<221> NAME/KEY: misc_feature
<222> LOCATION: (2962)..(3161)
<223> OTHER INFORMATION: spacer
<220> FEATURE:
<221> NAME/KEY: misc_feature
<222> LOCATION: (3162)..(3461)
<223> OTHER INFORMATION: dsRNAi target sequence
<220> FEATURE:
<221> NAME/KEY: terminator
<222> LOCATION: (3468)..(3680)
<223> OTHER INFORMATION: ocs terminator

<400> SEQUENCE: 73

```
tgcagtgcag cgtgacccgg tcgtgcccct ctctagagat aatgagcatt gcatgtctaa     60

gttataaaaa attaccacat attttttttg tcacacttgt ttgaagtgca gtttatctat    120

ctttatacat atatttaaac tttactctac gaataatata atctatagta ctacaataat    180
```

```
atcagtgttt tagagaatca tataaatgaa cagttagaca tggtctaaag gacaattgag    240
tattttgaca acaggactct acagttttat ctttttagtg tgcatgtgtt ctcctttttt    300
tttgcaaata gcttcaccta tataatactt catccatttt attagtacat ccatttaggg    360
tttagggtta atggttttta tagactaatt tttttagtac atctatttta ttctatttta    420
gcctctaaat taagaaaact aaaactctat tttagttttt ttatttaata gtttagatat    480
aaaatagaat aaaataaagt gactaaaaat taaacaaata ccctttaaga aattaaaaaa    540
actaaggaaa catttttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
ctccttcgct ttcccttcct cgcccgccgt aataaataga cacccccctcc acaccctctt   900
tccccaacct cgtgttgttc ggagcgcaca cacacacaac cagatctccc ccaaatccac    960
ccgtcggcac ctccgcttca aggtacgccg ctcgtcctcc cccccccccc ccctctctac   1020
cttctctaga tcggcgttcc ggtccatggt tagggcccgg tagttctact tctgttcatg   1080
tttgtgttag atccgtgttt gtgttagatc cgtgctgcta gcgttcgtac acggatgcga   1140
cctgtacgtc agacacgttc tgattgctaa cttgccagtg tttctctttg gggaatcctg   1200
ggatggctct agccgttccg cagacgggat cgatttcatg attttttttg tttcgttgca   1260
tagggtttgg tttgcccttt tcctttattt caatatatgc cgtgcacttg tttgtcgggt   1320
catcttttca tgcttttttt tgtcttggtt gtgatgatgt ggtctggttg ggcggtcgtt   1380
ctagatcgga gtagaattct gtttcaaact acctggtgga tttattaatt ttggatctgt   1440
atgtgtgtgc catacatatt catagttacg aattgaagat gatggatgga aatatcgatc   1500
taggataggt atacatgttg atgcgggttt tactgatgca tatacagaga tgctttttgt   1560
tcgcttggtt gtgatgatgt ggtgtggttg ggcggtcgtt cattcgttct agatcggagt   1620
agaatactgt ttcaaactac ctggtgtatt tattaatttt ggaactgtat gtgtgtgtca   1680
tacatcttca tagttacgag tttaagatgg atggaaatat cgatctagga taggtataca   1740
tgttgatgtg ggttttactg atgcatatac atgatggcat atgcagcatc tattcatatg   1800
ctctaacctt gagtacctat ctattataat aaacaagtat gttttataat tatttcgatc   1860
ttgatatact tggatgatgg catatgcagc agctatatgt ggattttttt agccctgcct   1920
tcatacgcta tttatttgct tggtactgtt tcttttgtcg atgctcaccc tgttgtttgg   1980
tgttacttct gcagggtacc atggctcagt caaagcacgg tctaacaaaa gaaatgacaa   2040
tgaaataccg tatggaaggg tgcgtcgatg gacataaatt tgtgatcacg ggagagggca   2100
ttggatatcc gttcaaaggg aaacaggcta ttaatctgtg tgtggtcgaa ggtggaccat   2160
tgccatttgc cgaagacata ttgtcagctg cctttatgta cggaaacagg gttttcactg   2220
aatatcctca agacatagct gactatttca agaactcgtg tcctgctggt tatacatggg   2280
acaggtcttt tctctttgag gatggagcag tttgcatatg taatgcagat ataacagtga   2340
gtgttgaaga aaactgcatg tatcatgagt ccaaatttta tggagtgaat tttcctgctg   2400
atggacctgt gatgaaaaag atgacagata actgggagcc atcctgcgag aagatcatac   2460
cagtacctaa gcaggggata ttgaaagggg atgtctccat gtacctcctt ctgaaggatg   2520
gtgggcgttt acggtgccaa ttcgacacag tttacaaagc aaagtctgtg ccaagaaaga   2580
```

tgccggactg gcacttcatc cagcataagc tcacccgtga agaccgcagc gatgctaaga 2640
atcagaaatg gcatctgaca gaacatgcta ttgcatccgg atctgcattg ccctgaggat 2700
ccgatcgttc aaacatttgg caataaagtt tcttaagatt gaatcctgtt gccggtcttg 2760
cgatgattat catataattt ctgttgaatt acgttaagca tgtaataatt aacatgtaat 2820
gcatgacgtt atttatgaga tgggttttta tgattagagt cccgcaatta tacatttaat 2880
acgcgataga aaacaaaata tagcgcgcaa actaggataa attatcgcgc gcggtgtcat 2940
ctatgttact agatcggatc catcaccgtt tgtgtgaaca acgaactgaa ctggcagact 3000
atcccgccgg gaatggtgat taccgacgaa aacggcaaga aaaagcagtc ttacttccat 3060
gatttcttta actatgccgg aatccatcgc agcgtaatgc tctacaccac gccgaacacc 3120
tgggtggacg atatcaccgt ggtgacgcat gtcgcgcaag actgtaacca cgcgtctgtt 3180
gactggcagg tggtggccaa tggtgatgtc agcgttgaac tgcgtgatgc ggatcaacag 3240
gtggttgcaa ctggacaagg cactagcggg actttgcaag tggtgaatcc gcacctctgg 3300
caaccgggtg aaggttatct ctatgaactg tgcgtcacag ccaaaagcca gacagagtgt 3360
gatatctacc cgcttcgcgt cggcatccgg tcagtggcag tgaagggcga acagttcctg 3420
attaaccaca aaccgttcta ctttactggc tttggtcgtc aactagttcg accggcatgc 3480
cctgctttaa tgagatatgc gagacgccta tgatcgcatg atatttgctt tcaattctgt 3540
tgtgcacgtt gtaaaaaacc tgagcatgtg tagctcagat ccttaccgcc ggtttcggtt 3600
cattctaatg aatatatcac ccgttactat cgtattttta tgaataatat tctccgttca 3660
atttactgat tgtccaagct 3680

<210> SEQ ID NO 74
<211> LENGTH: 3421
<212> TYPE: DNA
<213> ORGANISM: Unknown
<220> FEATURE:
<223> OTHER INFORMATION: pJMTOI4
<220> FEATURE:
<221> NAME/KEY: promoter
<222> LOCATION: (1)..(1988)
<223> OTHER INFORMATION: Zea may ubiquitin promoter
<220> FEATURE:
<221> NAME/KEY: misc_feature
<222> LOCATION: (2001)..(2696)
<223> OTHER INFORMATION: coding for green fluorescence protein (GFP)
<220> FEATURE:
<221> NAME/KEY: misc_feature
<222> LOCATION: (2703)..(2902)
<223> OTHER INFORMATION: spacer
<220> FEATURE:
<221> NAME/KEY: misc_feature
<222> LOCATION: (2903)..(3202)
<223> OTHER INFORMATION: dsRNAi target
<220> FEATURE:
<221> NAME/KEY: terminator
<222> LOCATION: (3209)..(3421)
<223> OTHER INFORMATION: ocs terminator

<400> SEQUENCE: 74
tgcagtgcag cgtgacccgg tcgtgcccct ctctagagat aatgagcatt gcatgtctaa 60
gttataaaaa attaccacat attttttttg tcacacttgt ttgaagtgca gtttatctat 120
ctttatacat atatttaaac tttactctac gaataatata atctatagta ctacaataat 180
atcagtgttt tagagaatca tataaatgaa cagttagaca tggtctaaag gacaattgag 240
tattttgaca acaggactct acagttttat ctttttagtg tgcatgtgtt ctcctttttt 300
tttgcaaata gcttcaccta tataatactt catccatttt attagtacat ccatttaggg 360

```
tttagggtta atggttttta tagactaatt tttttagtac atctatttta ttctatttta    420
gcctctaaat taagaaaact aaaactctat tttagttttt ttatttaata gtttagatat    480
aaaatagaat aaaataaagt gactaaaaat taaacaaata ccctttaaga aattaaaaaa    540
actaaggaaa catttttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
ctccttcgct ttcccttcct cgcccgccgt aataaataga cacccccctcc acaccctctt    900
tccccaacct cgtgttgttc ggagcgcaca cacacacaac cagatctccc ccaaatccac    960
ccgtcggcac ctccgcttca aggtacgccg ctcgtcctcc cccccccccc ccctctctac   1020
cttctctaga tcggcgttcc ggtccatggt tagggcccgg tagttctact tctgttcatg   1080
tttgtgttag atccgtgttt gtgttagatc cgtgctgcta gcgttcgtac acggatgcga   1140
cctgtacgtc agacacgttc tgattgctaa cttgccagtg tttctctttg gggaatcctg   1200
ggatggctct agccgttccg cagacgggat cgatttcatg attttttttg tttcgttgca   1260
tagggtttgg tttgcccttt tcctttattt caatatatgc cgtgcacttg tttgtcgggt   1320
catcttttca tgcttttttt tgtcttggtt gtgatgatgt ggtctggttg ggcggtcgtt   1380
ctagatcgga gtagaattct gtttcaaact acctggtgga tttattaatt ttggatctgt   1440
atgtgtgtgc catacatatt catagttacg aattgaagat gatggatgga aatatcgatc   1500
taggataggt atacatgttg atgcgggttt tactgatgca tatacagaga tgcttttttgt   1560
tcgcttggtt gtgatgatgt ggtgtggttg ggcggtcgtt cattcgttct agatcggagt   1620
agaatactgt ttcaaactac ctggtgtatt tattaatttt ggaactgtat gtgtgtgtca   1680
tacatcttca tagttacgag tttaagatgg atggaaatat cgatctagga taggtataca   1740
tgttgatgtg ggttttactg atgcatatac atgatggcat atgcagcatc tattcatatg   1800
ctctaacctt gagtacctat ctattataat aaacaagtat gttttataat tatttcgatc   1860
ttgatatact tggatgatgg catatgcagc agctatatgt ggattttttt agccctgcct   1920
tcatacgcta tttatttgct tggtactgtt tcttttgtcg atgctcaccc tgttgtttgg   1980
tgttacttct gcagggtacc atggctcagt caaagcacgg tctaacaaaa gaaatgacaa   2040
tgaaataccg tatggaaggg tgcgtcgatg gacataaatt tgtgatcacg ggagagggca   2100
ttggatatcc gttcaaaggg aaacaggcta ttaatctgtg tgtggtcgaa ggtggaccat   2160
tgccatttgc cgaagacata ttgtcagctg cctttatgta cggaaacagg gttttcactg   2220
aatatcctca agacatagct gactatttca agaactcgtg tcctgctggt tatacatggg   2280
acaggtcttt tctctttgag gatggagcag tttgcatatg taatgcagat ataacagtga   2340
gtgttgaaga aaactgcatg tatcatgagt ccaaatttta tggagtgaat tttcctgctg   2400
atggacctgt gatgaaaaag atgacagata actgggagcc atcctgcgag aagatcatac   2460
cagtacctaa gcaggggata ttgaaagggg atgtctccat gtacctcctt ctgaaggatg   2520
gtgggcgttt acggtgccaa ttcgacacag tttacaaagc aaagtctgtg ccaagaaaga   2580
tgccggactg gcacttcatc cagcataagc tcacccgtga agaccgcagc gatgctaaga   2640
atcagaaatg gcatctgaca gaacatgcta ttgcatccgg atctgcattg ccctgaggat   2700
ccatcaccgt ttgtgtgaac aacgaactga actggcagac tatcccgccg ggaatggtga   2760
```

```
ttaccgacga aaacggcaag aaaaagcagt cttacttcca tgatttcttt aactatgccg   2820

gaatccatcg cagcgtaatg ctctacacca cgccgaacac ctgggtggac gatatcaccg   2880

tggtgacgca tgtcgcgcaa gactgtaacc acgcgtctgt tgactggcag gtggtggcca   2940

atggtgatgt cagcgttgaa ctgcgtgatg cggatcaaca ggtggttgca actggacaag   3000

gcactagcgg gactttgcaa gtggtgaatc cgcacctctg gcaaccgggt gaaggttatc   3060

tctatgaact gtgcgtcaca gccaaaagcc agacagagtg tgatatctac ccgcttcgcg   3120

tcggcatccg gtcagtggca gtgaagggcg aacagttcct gattaaccac aaaccgttct   3180

actttactgg ctttggtcgt caactagttc gaccggcatg ccctgcttta atgagatatg   3240

cgagacgcct atgatcgcat gatatttgct ttcaattctg ttgtgcacgt tgtaaaaaac   3300

ctgagcatgt gtagctcaga tccttaccgc cggtttcggt tcattctaat gaatatatca   3360

cccgttacta tcgtattttt atgaataata ttctccgttc aatttactga ttgtccaagc   3420

t                                                                   3421
```

<210> SEQ ID NO 75
<211> LENGTH: 3160
<212> TYPE: DNA
<213> ORGANISM: Unknown
<220> FEATURE:
<223> OTHER INFORMATION: pJMTOI5
<220> FEATURE:
<221> NAME/KEY: promoter
<222> LOCATION: (1)..(1988)
<223> OTHER INFORMATION: Zea mays ubiquitin promoter
<220> FEATURE:
<221> NAME/KEY: misc_feature
<222> LOCATION: (2001)..(2300)
<223> OTHER INFORMATION: sense strand of dsRNA for dsRNAi target
<220> FEATURE:
<221> NAME/KEY: misc_feature
<222> LOCATION: (2309)..(2595)
<223> OTHER INFORMATION: spacer
<220> FEATURE:
<221> NAME/KEY: misc_feature
<222> LOCATION: (2602)..(2901)
<223> OTHER INFORMATION: antisense strand of dsRNA for dsRNAi target
<220> FEATURE:
<221> NAME/KEY: terminator
<222> LOCATION: (2908)..(3160)
<223> OTHER INFORMATION: nos terminator

<400> SEQUENCE: 75

```
tgcagtgcag cgtgacccgg tcgtgcccct ctctagagat aatgagcatt gcatgtctaa     60

gttataaaaa attaccacat atttttttg tcacacttgt ttgaagtgca gtttatctat    120

ctttatacat atatttaaac tttactctac gaataatata atctatagta ctacaataat    180

atcagtgttt tagagaatca tataaatgaa cagttagaca tggtctaaag gacaattgag    240

tattttgaca acaggactct acagttttat ctttttagtg tgcatgtgtt ctcctttttt    300

tttgcaaata gcttcaccta tataatactt catccatttt attagtacat ccatttaggg    360

tttagggtta atggttttta tagactaatt tttttagtac atctatttta ttctatttta    420

gcctctaaat taagaaaact aaaactctat tttagttttt ttatttaata gtttagatat    480

aaaatagaat aaaataaagt gactaaaaat taaacaaata ccctttaaga aattaaaaaa    540

actaaggaaa catttttctt gtttcgagta gataatgcca gcctgttaaa cgccgtcgac    600

gagtctaacg gacaccaacc agcgaaccag cagcgtcgcg tcgggccaag cgaagcagac    660

ggcacggcat ctctgtcgct gcctctggac ccctctcgag agttccgctc caccgttgga    720

cttgctccgc tgtcggcatc cagaaattgc gtggcggagc ggcagacgtg agccggcacg    780
```

-continued gcaggcggcc tcctcctcct ctcacggcac cggcagctac gggggattcc tttcccaccg 840
ctccttcgct ttcccttcct cgcccgccgt aataaataga caccccctcc acaccctctt 900
tccccaacct cgtgttgttc ggagcgcaca cacacacaac cagatctccc ccaaatccac 960
ccgtcggcac ctccgcttca aggtacgccg ctcgtcctcc cccccccccc ccctctctac 1020
cttctctaga tcggcgttcc ggtccatggt tagggcccgg tagttctact tctgttcatg 1080
tttgtgttag atccgtgttt gtgttagatc cgtgctgcta gcgttcgtac acggatgcga 1140
cctgtacgtc agacacgttc tgattgctaa cttgccagtg tttctctttg gggaatcctg 1200
ggatggctct agccgttccg cagacgggat cgatttcatg attttttttg tttcgttgca 1260
tagggtttgg tttgcccttt tcctttattt caatatatgc cgtgcacttg tttgtcgggt 1320
catcttttca tgcttttttt tgtcttggtt gtgatgatgt ggtctggttg ggcggtcgtt 1380
ctagatcgga gtagaattct gtttcaaact acctggtgga tttattaatt ttggatctgt 1440
atgtgtgtgc catacatatt catagttacg aattgaagat gatggatgga aatatcgatc 1500
taggataggt atacatgttg atgcgggttt tactgatgca tatacagaga tgctttttgt 1560
tcgcttggtt gtgatgatgt ggtgtggttg ggcggtcgtt cattcgttct agatcggagt 1620
agaatactgt ttcaaactac ctggtgtatt tattaatttt ggaactgtat gtgtgtgtca 1680
tacatcttca tagttacgag tttaagatgg atggaaatat cgatctagga taggtataca 1740
tgttgatgtg ggttttactg atgcatatac atgatggcat atgcagcatc tattcatatg 1800
ctctaacctt gagtacctat ctattataat aaacaagtat gttttataat tatttcgatc 1860
ttgatatact tggatgatgg catatgcagc agctatatgt ggattttttt agccctgcct 1920
tcatacgcta tttatttgct tggtactgtt tcttttgtcg atgctcaccc tgttgtttgg 1980
tgttacttct gcagggtacc ctgtaaccac gcgtctgttg actggcaggt ggtggccaat 2040
ggtgatgtca gcgttgaact gcgtgatgcg gatcaacagg tggttgcaac tggacaaggc 2100
actagcggga ctttgcaagt ggtgaatccg cacctctggc aaccgggtga aggttatctc 2160
tatgaactgt gcgtcacagc caaaagccag acagagtgtg atatctaccc gcttcgcgtc 2220
ggcatccggt cagtggcagt gaagggcgaa cagttcctga ttaaccacaa accgttctac 2280
tttactggct ttggtcgtca ggcgcgccta ctccccgagt ctgaaccgct cgatcgaacc 2340
tcactcaaca ttgacgagag cgagtcgtct aactcttgca gcctctttgc gtcgtgaaag 2400
ctctctggaa gaagaagatt ctcatcagga tccccgagaa actcggataa gagactcaca 2460
gagtagccat gctcggtcac aacgctacaa tggtccaagc tcgtaagctc gaagccgaag 2520
tccagatctg tgctggcgaa gtcgatgtcg gacttaagaa cttcctccaa atggcggtcg 2580
cagtcttcaa attcgctcga gtgacgacca aagccagtaa agtagaacgg tttgtggtta 2640
atcaggaact gttcgccctt cactgccact gaccggatgc cgacgcgaag cgggtagata 2700
tcacactctg tctggctttt ggctgtgacg cacagttcat agagataacc ttcacccggt 2760
tgccagaggt gcggattcac cacttgcaaa gtcccgctag tgccttgtcc agttgcaacc 2820
acctgttgat ccgcatcacg cagttcaacg ctgacatcac cattggccac cacctgccag 2880
tcaacagacg cgtggttaca gactagtgat cgttcaaaca tttggcaata aagtttctta 2940
agattgaatc ctgttgccgg tcttgcgatg attatcatat aatttctgtt gaattacgtt 3000
aagcatgtaa taattaacat gtaatgcatg acgttattta tgagatgggt ttttatgatt 3060
agagtcccgc aattatacat ttaatacgcg atagaaaaca aaatatagcg cgcaaactag 3120
gataaattat cgcgcgcggt gtcatctatg ttactagatc 3160

<210> SEQ ID NO 76
<211> LENGTH: 2665
<212> TYPE: DNA
<213> ORGANISM: Unknown
<220> FEATURE:
<223> OTHER INFORMATION: Lo376-pENTR-B2
<220> FEATURE:
<221> NAME/KEY: terminator
<222> LOCATION: (269)..(295)
<223> OTHER INFORMATION: complement: T2 terminator
<220> FEATURE:
<221> NAME/KEY: terminator
<222> LOCATION: (427)..(470)
<223> OTHER INFORMATION: complement: T1 terminator
<220> FEATURE:
<221> NAME/KEY: misc_feature
<222> LOCATION: (569)..(668)
<223> OTHER INFORMATION: attL1 recombination site
<220> FEATURE:
<221> NAME/KEY: misc_feature
<222> LOCATION: (755)..(853)
<223> OTHER INFORMATION: complement: attL2 recombination site
<220> FEATURE:
<221> NAME/KEY: misc_feature
<222> LOCATION: (1059)..(1868)
<223> OTHER INFORMATION: kanamycin resistance

<400> SEQUENCE: 76

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggctgg tacccgggga tcctctaggt cgaccagatc tgatatctgc ggccgcctcg    720

agcatatggg catgcaagct tggcgtaatc atggacccag ctttcttgta caaagttggc    780

attataagaa agcattgctt atcaatttgt tgcaacgaac aggtcactat cagtcaaaat    840

aaaatcatta tttgccatcc agctgatccg gtgcaggttg gcggcggcgt gcgtagcgaa    900

gaatccccta tagtgagtcg tattacatgg tcatagctgt ttcctggcag ctctggcccg    960

tgtctcaaaa tctctgatgt tacattgcac aagataaaaa tatatcatca tgaacaataa   1020

aactgtctgc ttacataaac agtaatacaa ggggtgttat gagccatatt caacgggaaa   1080

cgtcgaggcc gcgattaaat tccaacatgg atgctgattt atatgggtat aaatgggctc   1140

gcgataatgt cgggcaatca ggtgcgacaa tctatcgctt gtatgggaag cccgatgcgc   1200

cagagttgtt tctgaaacat ggcaaaggta gcgttgccaa tgatgttaca gatgagatgg   1260

tcagactaaa ctggctgacg gaatttatgc ctcttccgac catcaagcat tttatccgta   1320

ctcctgatga tgcatggtta ctcaccactg cgatccccgg aaaaacagca ttccaggtat   1380

tagaagaata tcctgattca ggtgaaaata ttgttgatgc gctggcagtg ttcctgcgcc   1440

ggttgcattc gattcctgtt tgtaattgtc cttttaacag cgatcgcgta tttcgtctcg   1500
```

```
ctcaggcgca atcacgaatg aataacggtt tggttgatgc gagtgatttt gatgacgagc   1560

gtaatggctg gcctgttgaa caagtctgga aagaaatgca taaacttttg ccattctcac   1620

cggattcagt cgtcactcat ggtgatttct cacttgataa ccttattttt gacgagggga   1680

aattaatagg ttgtattgat gttggacgag tcggaatcgc agaccgatac caggatcttg   1740

ccatcctatg gaactgcctc ggtgagtttt ctccttcatt acagaaacgg ctttttcaaa   1800

aatatggtat tgataatcct gatatgaata aattgcagtt tcatttgatg ctcgatgagt   1860

ttttctaatc agaattggtt aattggttgt aacactggca gagcattacg ctgacttgac   1920

gggacggcgc aagctcatga ccaaaatccc ttaacgtgag ttacgcgtcg ttccactgag   1980

cgtcagaccc cgtagaaaag atcaaaggat cttcttgaga tccttttttt ctgcgcgtaa   2040

tctgctgctt gcaaacaaaa aaaccaccgc taccagcggt ggtttgtttg ccggatcaag   2100

agctaccaac tctttttccg aaggtaactg gcttcagcag agcgcagata ccaaatactg   2160

ttcttctagt gtagccgtag ttaggccacc acttcaagaa ctctgtagca ccgcctacat   2220

acctcgctct gctaatcctg ttaccagtgg ctgctgccag tggcgataag tcgtgtctta   2280

ccgggttgga ctcaagacga tagttaccgg ataaggcgca gcggtcgggc tgaacggggg   2340

gttcgtgcac acagcccagc ttggagcgaa cgacctacac cgaactgaga tacctacagc   2400

gtgagctatg agaaagcgcc acgcttcccg aagggagaaa ggcggacagg tatccggtaa   2460

gcggcagggt cggaacagga gagcgcacga gggagcttcc agggggaaac gcctggtatc   2520

tttatagtcc tgtcgggttt cgccacctct gacttgagcg tcgatttttg tgatgctcgt   2580

caggggggcg gagcctatgg aaaaacgcca gcaacgcggc ctttttacgg ttcctggcct   2640

tttgctggcc ttttgctcac atgtt                                          2665
```

<210> SEQ ID NO 77
<211> LENGTH: 7686
<212> TYPE: DNA
<213> ORGANISM: Unknown
<220> FEATURE:
<223> OTHER INFORMATION: Lo442 pSUN1-R4R3-M20 (OCS10) (destination vector)
<220> FEATURE:
<221> NAME/KEY: misc_feature
<222> LOCATION: (8)..(153)
<223> OTHER INFORMATION: RB (right border)
<220> FEATURE:
<221> NAME/KEY: misc_feature
<222> LOCATION: (215)..(339)
<223> OTHER INFORMATION: attR4 recombination site
<220> FEATURE:
<221> NAME/KEY: misc_feature
<222> LOCATION: (1004)..(1684)
<223> OTHER INFORMATION: complement: Chloramphenicol resistance
<220> FEATURE:
<221> NAME/KEY: misc_feature
<222> LOCATION: (1792)..(1916)
<223> OTHER INFORMATION: complement: attR3 recombination site
<220> FEATURE:
<221> NAME/KEY: misc_feature
<222> LOCATION: (1935)..(2149)
<223> OTHER INFORMATION: LB (left border)
<220> FEATURE:
<221> NAME/KEY: misc_feature
<222> LOCATION: (3858)..(4965)
<223> OTHER INFORMATION: coding for repA
<220> FEATURE:
<221> NAME/KEY: rep_origin
<222> LOCATION: (5715)..(6560)
<223> OTHER INFORMATION: complement: ColE1 origin
<220> FEATURE:
<221> NAME/KEY: misc_feature
<222> LOCATION: (6729)..(7520)

<223> OTHER INFORMATION: complement: aadA marker (spectomycin)

<400> SEQUENCE: 77

```
ttccatggac atacaaatgg acgaacggat aaaccttttc acgccctttt aaatatccga     60
ttattctaat aaacgctctt ttctcttagg tttacccgcc aatatatcct gtcaaacact    120
gatagtttaa actgaaggcg ggaaacgaca atcagatcta gtaggaaaca gctatgacca    180
tgattacgcc aagctatcga ttacgccaag ctatcaactt tgtatagaaa agttgaacga    240
gaaacgtaaa atgatataaa tatcaatata ttaaattaga ttttgcataa aaaacagact    300
acataatact gtaaaacaca acatatccag tcactatggt cgacctgcag actggctgtg    360
tataagggag cctgacattt atattcccca gaacatcagg ttaatggcgt ttttgatgtc    420
attttcgcgg tggctgagat cagccacttc ttccccgata acggagaccg gcacactggc    480
catatcggtg gtcatcatgc gccagctttc atccccgata tgcaccaccg ggtaaagttc    540
acgggggact ttatctgaca gcagacgtgc actggccagg gggatcacca tccgtcgccc    600
gggcgtgtca ataatatcac tctgtacatc cacaaacaga cgataacggc tctctctttt    660
ataggtgtaa accttaaact gcatttcacc agcccctgtt ctcgtcggca aaagagccgt    720
tcatttcaat aaaccgggcg acctcagcca tcccttcctg attttccgct ttccagcgtt    780
cggcacgcag acgacgggct tcattctgca tggttgtgct taccgaaccg gagatattga    840
catcatatat gccttgagca actgatagct gtcgctgtca actgtcactg taatacgctg    900
cttcatagca tacctctttt tgacatactt cgggtataca tatcagtata tattcttata    960
ccgcaaaaat cagcgcgcaa atacgcatac tgttatctgg cttttagtaa gccggatcct   1020
ctagattacg ccccgcctgc cactcatcgc agtactgttg taattcatta agcattctgc   1080
cgacatggaa gccatcacaa acggcatgat gaacctgaat cgccagcggc atcagcacct   1140
tgtcgccttg cgtataatat ttgcccatgg tgaaaacggg ggcgaagaag ttgtccatat   1200
tggccacgtt taaatcaaaa ctggtgaaac tcacccaggg attggctgag acgaaaaaca   1260
tattctcaat aaacccttta gggaaatagg ccaggttttc accgtaacac gccacatctt   1320
gcgaatatat gtgtagaaac tgccggaaat cgtcgtggta ttcactccag agcgatgaaa   1380
acgtttcagt ttgctcatgg aaaacggtgt aacaagggtg aacactatcc catatcacca   1440
gctcaccgtc tttcattgcc atacggaatt ccggatgagc attcatcagg cgggcaagaa   1500
tgtgaataaa ggccggataa aacttgtgct tatttttctt tacggtcttt aaaaaggccg   1560
taatatccag ctgaacggtc tggttatagg tacattgagc aactgactga aatgcctcaa   1620
aatgttcttt acgatgccat tgggatatat caacggtggt atatccagtg atttttttct   1680
ccattttagc ttccttagct cctgaaaatc tcgacggatc ctaactcaaa atccacacat   1740
tatacgagcc ggaagcataa agtgtaaagc ctggggtgcc taatgcggcc gccatagtga   1800
ctggatatgt tgtgttttac agtattatgt agtctgtttt ttatgcaaaa tctaatttaa   1860
tatattgata tttatatcat tttacgtttc tcgttcaact ttattataca tagttgataa   1920
ttcactggcc ggatctgctt ggtaataatt gtcattagat tgtttttatg catagatgca   1980
ctcgaaatca gccaatttta gacaagtatc aaacggatgt taattcagta cattaaagac   2040
gtccgcaatg tgttattaag ttgtctaagc gtcaatttgt ttacaccaca atatatcctg   2100
ccaccagcca gccaacagct ccccgaccgg cagctcggca caaaatcacc acgcgttacc   2160
accacgccgg ccggccgcat ggtgttgacc gtgttcgccg gcattgccga gttcgagcgt   2220
tccctaatca tcgaccgcac ccggagcggg cgcgaggccg ccaaggcccg aggcgtgaag   2280
```

-continued

```
tttggccccc gccctaccct caccccggca cagatcgcgc acgcccgcga gctgatcgac   2340
caggaaggcc gcaccgtgaa agaggcggct gcactgcttg gcgtgcatcg ctcgaccctg   2400
taccgcgcac ttgagcgcag cgaggaagtg acgcccaccg aggccaggcg gcgcggtgcc   2460
ttccgtgagg acgcattgac cgaggccgac gccctggcgg ccgccgagaa tgaacgccaa   2520
gaggaacaag catgaaaccg caccaggacg gccaggacga accgtttttc attaccgaag   2580
agatcgaggc ggagatgatc gcggccgggt acgtgttcga gccgcccgcg cacgtctcaa   2640
ccgtgcggct gcatgaaatc ctggccggtt tgtctgatgc caagctggcg gcctggccgg   2700
ccagcttggc cgctgaagaa accgagcgcc gccgtctaaa aaggtgatgt gtatttgagt   2760
aaaacagctt gcgtcatgcg gtcgctgcgt atatgatgcg atgagtaaat aaacaaatac   2820
gcaaggggaa cgcatgaagg ttatcgctgt acttaaccag aaaggcgggt caggcaagac   2880
gaccatcgca acccatctag cccgcgccct gcaactcgcc ggggccgatg ttctgttagt   2940
cgattccgat ccccagggca gtgcccgcga ttgggcggcc gtgcgggaag atcaaccgct   3000
aaccgttgtc ggcatcgacc gcccgacgat tgaccgcgac gtgaaggcca tcggccggcg   3060
cgacttcgta gtgatcgacg gagcgcccca ggcggcggac ttggctgtgt ccgcgatcaa   3120
ggcagccgac ttcgtgctga ttccggtgca gccaagccct tacgacatat gggccaccgc   3180
cgacctggtg gagctggtta agcagcgcat tgaggtcacg gatggaaggc tacaagcggc   3240
ctttgtcgtg tcgcgggcga tcaaaggcac gcgcatcggc ggtgaggttg ccgaggcgct   3300
ggccgggtac gagctgccca ttcttgagtc ccgtatcacg cagcgcgtga gctacccagg   3360
cactgccgcc gccggcacaa ccgttcttga atcagaaccc gagggcgacg ctgcccgcga   3420
ggtccaggcg ctggccgctg aaattaaatc aaaactcatt tgagttaatg aggtaaagag   3480
aaaatgagca aaagcacaaa cacgctaagt gccggccgtc cgagcgcacg cagcagcaag   3540
gctgcaacgt tggccagcct ggcagacacg ccagccatga agcgggtcaa ctttcagttg   3600
ccggcggagg atcacaccaa gctgaagatg tacgcggtac gccaaggcaa gaccattacc   3660
gagctgctat ctgaatacat cgcgcagcta ccagagtaaa tgagcaaatg aataaatgag   3720
tagatgaatt ttagcggcta aaggaggcgg catggaaaat caagaacaac caggcaccga   3780
cgccgtggaa tgccccatgt gtggaggaac gggcggttgg ccaggcgtaa gcggctgggt   3840
tgtctgccgg ccctgcaatg gcactggaac ccccaagccc gaggaatcgg cgtgagcggt   3900
cgcaaaccat ccggcccggt acaaatcggc gcggcgctgg gtgatgacct ggtggagaag   3960
ttgaaggccg cgcaggccgc ccagcggcaa cgcatcgagg cagaagcacg ccccggtgaa   4020
tcgtggcaag cggccgctga tcgaatccgc aaagaatccc ggcaaccgcc ggcagccggt   4080
gcgccgtcga ttaggaagcc gcccaagggc gacgagcaac cagatttttt cgttccgatg   4140
ctctatgacg tgggcacccg cgatagtcgc agcatcatgg acgtggccgt tttccgtctg   4200
tcgaagcgtg accgacgagc tggcgaggtg atccgctacg agcttccaga cgggcacgta   4260
gaggtttccg cagggccggc cggcatggcc agtgtgtggg attacgacct ggtactgatg   4320
gcggtttccc atctaaccga atccatgaac cgataccggg aagggaaggg agacaagccc   4380
ggccgcgtgt tccgtccaca cgttgcggac gtactcaagt tctgccggcg agccgatggc   4440
ggaaagcaga aagacgacct ggtagaaacc tgcattcggt taaacaccac gcacgttgcc   4500
atgcagcgta cgaagaaggc caagaacggc cgcctggtga cggtatccga gggtgaagcc   4560
ttgattagcc gctacaagat cgtaaagagc gaaaccgggc ggccggagta catcgagatc   4620
gagctagctg attggatgta ccgcgagatc acagaaggca agaacccgga cgtgctgacg   4680
```

-continued

```
gttcaccccg attacttttt gatcgatccc ggcatcggcc gttttctcta ccgcctggca   4740
cgccgcgccg caggcaaggc agaagccaga tggttgttca agacgatcta cgaacgcagt   4800
ggcagcgccg gagagttcaa gaagttctgt ttcaccgtgc gcaagctgat cgggtcaaat   4860
gacctgccgg agtacgattt gaaggaggag gcggggcagg ctggcccgat cctagtcatg   4920
cgctaccgca acctgatcga gggcgaagca tccgccggtt cctaatgtac ggagcagatg   4980
ctagggcaaa ttgccctagc aggggaaaaa ggtcgaaaag gtctctttcc tgtggatagc   5040
acgtacattg ggaacccaaa gccgtacatt gggaaccgga acccgtacat tgggaaccca   5100
aagccgtaca ttgggaaccg gtcacacatg taagtgactg atataaaaga gaaaaaaggc   5160
gatttttccg cctaaaactc tttaaaactt attaaaactc ttaaaacccg cctggcctgt   5220
gcataactgt ctggccagcg cacagccgaa gagctgcaaa aagcgcctac ccttcggtcg   5280
ctgcgctccc tacgccccgc cgcttcgcgt cggcctatcg cggccgctgg ccgctcaaaa   5340
atggctggcc tacggccagg caatctacca gggcgcggac aagccgcgcc gtcgccactc   5400
gaccgccggc gcccacatca aggcaccctg cctcgcgcgt ttcggtgatg acggtgaaaa   5460
cctctgacac atgcagctcc cggagacggt cacagcttgt ctgtaagcgg atgccgggag   5520
cagacaagcc cgtcagggcg cgtcagcggg tgttggcggg tgtcggggcg cagccatgac   5580
ccagtcacgt agcgatagcg gagtgtatac tggcttaact atgcggcatc agagcagatt   5640
gtactgagag tgcaccatat gcggtgtgaa ataccgcaca gatgcgtaag gagaaaatac   5700
cgcatcaggc gctcttccgc ttcctcgctc actgactcgc tgcgctcggt cgttcggctg   5760
cggcgagcgg tatcagctca ctcaaaggcg gtaatacggt tatccacaga atcaggggat   5820
aacgcaggaa agaacatgtg agcaaaaggc cagcaaaagg ccaggaaccg taaaaaggcc   5880
gcgttgctgg cgtttttcca taggctccgc ccccctgacg agcatcacaa aaatcgacgc   5940
tcaagtcaga ggtggcgaaa cccgacagga ctataaagat accaggcgtt tccccctgga   6000
agctccctcg tgcgctctcc tgttccgacc ctgccgctta ccggatacct gtccgccttt   6060
ctcccttcgg gaagcgtggc gctttctcat agctcacgct gtaggtatct cagttcggtg   6120
taggtcgttc gctccaagct gggctgtgtg cacgaacccc ccgttcagcc cgaccgctgc   6180
gccttatccg gtaactatcg tcttgagtcc aacccggtaa gacacgactt atcgccactg   6240
gcagcagcca ctggtaacag gattagcaga gcgaggtatg taggcggtgc tacagagttc   6300
ttgaagtggt ggcctaacta cggctacact agaaggacag tatttggtat ctgcgctctg   6360
ctgaagccag ttaccttcgg aaaaagagtt ggtagctctt gatccggcaa acaaaccacc   6420
gctggtagcg gtggtttttt tgtttgcaag cagcagatta cgcgcagaaa aaaaggatct   6480
caagaagatc ctttgatctt ttctacgggg tctgacgctc agtggaacga aaactcacgt   6540
taagggattt tggtcatgca tgatatatct cccaatttgt gtagggctta ttatgcacgc   6600
ttaaaaataa taaaagcaga cttgacctga tagtttggct gtgagcaatt atgtgcttag   6660
tgcatctaac gcttgagtta agccgcgccg cgaagcggcg tcggcttgaa cgaatttcta   6720
gctagacatt atttgccgac taccttggtg atctcgcctt tcacgtagtg gacaaattct   6780
tccaactgat ctgcgcgcga ggccaagcga tcttcttctt gtccaagata agcctgtcta   6840
gcttcaagta tgacgggctg atactgggcc ggcaggcgct ccattgccca gtcggcagcg   6900
acatccttcg gcgcgatttt gccggttact gcgctgtacc aaatgcggga caacgtaagc   6960
actacatttc gctcatcgcc agcccagtcg ggcggcgagt tccatagcgt taaggtttca   7020
tttagcgcct caaatagatc ctgttcagga accggatcaa agagttcctc cgccgctgga   7080
```

```
cctaccaagg caacgctatg ttctcttgct tttgtcagca agatagccag atcaatgtcg   7140

atcgtggctg gctcgaagat acctgcaaga atgtcattgc gctgccattc tccaaattgc   7200

agttcgcgct tagctggata acgccacgga atgatgtcgt cgtgcacaac aatggtgact   7260

tctacagcgc ggagaatctc gctctctcca ggggaagccg aagtttccaa aaggtcgttg   7320

atcaaagctc gccgcgttgt ttcatcaagc cttacggtca ccgtaaccag caaatcaata   7380

tcactgtgtg gcttcaggcc gccatccact gcggagccgt acaaatgtac ggccagcaac   7440

gtcggttcga gatggcgctc gatgacgcca actacctctg atagttgagt cgatacttcg   7500

gcgatcaccg cttcccccat gatgtttaac tttgttttag ggcgactgcc ctgctgcgta   7560

acatcgttgc tgctccataa catcaaacat cgacccacgg cgtaacgcgc ttgctgcttg   7620

gatgcccgag gcatagactg taccccaaaa aaacagtcat aacaagccat gaaaaccgcc   7680

actgcg                                                              7686
```

<210> SEQ ID NO 78
<211> LENGTH: 10414
<212> TYPE: DNA
<213> ORGANISM: Artificial sequence
<220> FEATURE:
<223> OTHER INFORMATION: binary vector
      Lo239-pSUN3-GWs-B1-BnAK700::GUS::nosT-B2
<220> FEATURE:
<221> NAME/KEY: misc_recomb
<222> LOCATION: (4)..(28)
<223> OTHER INFORMATION: attB1 Gateway recombination site
<220> FEATURE:
<221> NAME/KEY: promoter
<222> LOCATION: (56)..(724)
<223> OTHER INFORMATION: p-BnAK promoter
<220> FEATURE:
<221> NAME/KEY: misc_feature
<222> LOCATION: (749)..(2560)
<223> OTHER INFORMATION: cds encoding c-GUS (E.coli)
<220> FEATURE:
<221> NAME/KEY: terminator
<222> LOCATION: (2631)..(2883)
<223> OTHER INFORMATION: t-NOS nopaline synthase terminator
<220> FEATURE:
<221> NAME/KEY: misc_recomb
<222> LOCATION: (2895)..(2919)
<223> OTHER INFORMATION: attB2 Gateway recombination site
<220> FEATURE:
<221> NAME/KEY: terminator
<222> LOCATION: (2972)..(3224)
<223> OTHER INFORMATION: complement: t-NOS nopaline synthase terminator
<220> FEATURE:
<221> NAME/KEY: misc_feature
<222> LOCATION: (3300)..(4094)
<223> OTHER INFORMATION: complement: cds encoding c-NptII confers
      kanamycin resistance
<220> FEATURE:
<221> NAME/KEY: promoter
<222> LOCATION: (4126)..(4413)
<223> OTHER INFORMATION: complement: p-NOS promoter from the noplaine
      synthase gene
<220> FEATURE:
<221> NAME/KEY: misc_structure
<222> LOCATION: (4464)..(4678)
<223> OTHER INFORMATION: complement: b-LB Left T-DNA border
<220> FEATURE:
<221> NAME/KEY: misc_structure
<222> LOCATION: (10227)..(10372)
<223> OTHER INFORMATION: complement: b-RB Right T-DNA border

<400> SEQUENCE: 78

```
atcacaagtt tgtacaaaaa agcaggcttt aaaggaacca attcagtcga cacgaagctt     60

tcgaggctaa cgttggtgga gatgttaagg cacggcatct tctcttcttc ttcttttttg    120

tttgtttgtt tgtttcgctc tctatcactc actcgatcga tccccagtct tcttttcggg    180
```

-continued

```
aaagctgtgt cagaccaatt atattccatc tttaatttgg cccttttttat tattcgctat    240
ggcccaacat ttcaggccca atttatacga ttataaatat aaccacttga ttgtgctgcc    300
gctcagctga atagtactcc ctccgttttt taatataaat cgttttacag ttatgcacgt    360
aaattaagaa aaccattaac tttttatatt ttctaaacaa aaacatcatt aattatttac    420
ttactcacaa ttcaaccaat agaaaaatag aagatatatt accattggtc atacaacatt    480
aattattaat aaattttaca tagaaaaccg aaaacgacat ataatttgga acaaaaaaat    540
ttctctaaaa ctacttatat taaaaaacgg agagagtata tttaactagt tcgtcttact    600
gacaaattga agaggcagac caagacacgc ggctcctcga tggctgtctt atgccaagtg    660
gcggtgcctg cttctgcatt aaataggtag aagaactcta attacagaag ctcgaggtag    720
ataggatccc cgggtaggtc agtcccttat gttacgtcct gtagaaaccc caacccgtga    780
aatcaaaaaa ctcgacggcc tgtgggcatt cagtctggat cgcgaaaact gtggaattga    840
tcagcgttgg tgggaaagcg cgttacaaga aagccgggca attgctgtgc caggcagttt    900
taacgatcag ttcgccgatg cagatattcg taattatgcg ggcaacgtct ggtatcagcg    960
cgaagtcttt ataccgaaag gttgggcagg ccagcgtatc gtgctgcgtt tcgatgcggt   1020
cactcattac ggcaaagtgt gggtcaataa tcaggaagtg atggagcatc agggcggcta   1080
tacgccattt gaagccgatg tcacgccgta tgttattgcc gggaaaagtg tacgtatcac   1140
cgtttgtgtg aacaacgaac tgaactggca gactatcccg ccgggaatgg tgattaccga   1200
cgaaaacggc aagaaaaagc agtcttactt ccatgatttc tttaactatg ccggaatcca   1260
tcgcagcgta atgctctaca ccacgccgaa cacctgggtg gacgatatca ccgtggtgac   1320
gcatgtcgcg caagactgta accacgcgtc tgttgactgg caggtggtgg ccaatggtga   1380
tgtcagcgtt gaactgcgtg atgcggatca acaggtggtt gcaactggac aaggcactag   1440
cgggactttg caagtggtga atccgcacct ctggcaaccg ggtgaaggtt atctctatga   1500
actgtgcgtc acagccaaaa gccagacaga gtgtgatatc tacccgcttc gcgtcggcat   1560
ccggtcagtg gcagtgaagg gcgaacagtt cctgattaac cacaaaccgt tctactttac   1620
tggctttggt cgtcatgaag atgcggactt gcgtggcaaa ggattcgata acgtgctgat   1680
ggtgcacgac cacgcattaa tggactggat tggggccaac tcctaccgta cctcgcatta   1740
cccttacgct gaagagatgc tcgactgggc agatgaacat ggcatcgtgg tgattgatga   1800
aactgctgct gtcggcttta acctctcttt aggcattggt ttcgaagcgg gcaacaagcc   1860
gaaagaactg tacagcgaag aggcagtcaa cggggaaact cagcaagcgc acttacaggc   1920
gattaaagag ctgatagcgc gtgacaaaaa ccacccaagc gtggtgatgt ggagtattgc   1980
caacgaaccg gatacccgtc cgcaaggtgc acgggaatat ttcgcgccac tggcggaagc   2040
aacgcgtaaa ctcgacccga cgcgtccgat cacctgcgtc aatgtaatgt tctgcgacgc   2100
tcacaccgat accatcagcg atctctttga tgtgctgtgc ctgaaccgtt attacggatg   2160
gtatgtccaa agcggcgatt tggaaacggc agagaaggta ctggaaaaag aacttctggc   2220
ctggcaggag aaactgcatc agccgattat catcaccgaa tacggcgtgg atacgttagc   2280
cgggctgcac tcaatgtaca ccgacatgtg gagtgaagag tatcagtgtg catggctgga   2340
tatgtatcac cgcgtctttg atcgcgtcag cgccgtcgtc ggtgaacagg tatggaattt   2400
cgccgatttt gcgacctcgc aaggcatatt gcgcgttggc ggtaacaaga aagggatctt   2460
cactcgcgac cgcaaaccga agtcggcggc ttttctgctg caaaaacgct ggactggcat   2520
gaacttcggt gaaaaaccgc agcagggagg caaacaatga atcaacaact ctcctggcgc   2580
```

```
accatcgtcg gctacagcct cgggaattgc taccgagctc gaatttcccc gatcgttcaa   2640
acatttggca ataaagtttc ttaagattga atcctgttgc cggtcttgcg atgattatca   2700
tataatttct gttgaattac gttaagcatg taataattaa catgtaatgc atgacgttat   2760
ttatgagatg ggtttttatg attagagtcc cgcaattata catttaatac gcgatagaaa   2820
acaaaatata gcgcgcaaac taggataaat tatcgcgcgc ggtgtcatct atgttactag   2880
atcgggaatt ctagacccag ctttcttgta caaagtggtg ataattcact ggccgtcgtt   2940
ttacaacgac tcagagcttg acaggaggcc cgatctagta acatagatga caccgcgcgc   3000
gataatttat cctagtttgc gcgctatatt ttgttttcta tcgcgtatta aatgtataat   3060
tgcgggactc taatcataaa aacccatctc ataaataacg tcatgcatta catgttaatt   3120
attacatgct taacgtaatt caacagaaat tatatgataa tcatcgcaag accggcaaca   3180
ggattcaatc ttaagaaact ttattgccaa atgtttgaac gatcggggat catccgggtc   3240
tgtggcggga actccacgaa aatatccgaa cgcagcaaga tctagagctt gggtcccgct   3300
cagaagaact cgtcaagaag gcgatagaag gcgatgcgct gcgaatcggg agcggcgata   3360
ccgtaaagca cgaggaagcg gtcagcccat tcgccgccaa gctcttcagc aatatcacgg   3420
gtagccaacg ctatgtcctg atagcggtcc gccacaccca gccggccaca gtcgatgaat   3480
ccagaaaagc ggccattttc caccatgata ttcggcaagc aggcatcgcc atgggtcacg   3540
acgagatcct cgccgtcggg catgcgcgcc ttgagcctgg cgaacagttc ggctggcgcg   3600
agcccctgat gctcttcgtc cagatcatcc tgatcgacaa gaccggcttc catccgagta   3660
cgtgctcgct cgatgcgatg tttcgcttgg tggtcgaatg ggcaggtagc cggatcaagc   3720
gtatgcagcc gccgcattgc atcagccatg atggatactt tctcggcagg agcaaggtga   3780
gatgacagga gatcctgccc cggcacttcg cccaatagca gccagtccct tcccgcttca   3840
gtgacaacgt cgagcacagc tgcgcaagga acgcccgtcg tggccagcca cgatagccgc   3900
gctgcctcgt cctgcagttc attcagggca ccggacaggt cggtcttgac aaaaagaacc   3960
gggcgcccct gcgctgacag ccggaacacg gcggcatcag agcagccgat tgtctgttgt   4020
gcccagtcat agccgaatag cctctccacc caagcggccg gagaacctgc gtgcaatcca   4080
tcttgttcaa tcatgcgaaa cgatccagat ccggtgcaga ttatttggat tgagagtgaa   4140
tatgagactc taattggata ccgaggggaa tttatggaac gtcagtggag catttttgac   4200
aagaaatatt tgctagctga tagtgacctt aggcgacttt tgaacgcgca ataatggttt   4260
ctgacgtatg tgcttagctc attaaactcc agaaacccgc ggctgagtgg ctccttcaac   4320
gttgcggttc tgtcagttcc aaacgtaaaa cggcttgtcc cgcgtcatcg gcgggggtca   4380
taacgtgact cccttaattc tccgctcatg atcagattgt cgtttcccgc cttcagttta   4440
aactatcagt gtttgacagg atcctgcttg gtaataattg tcattagatt gtttttatgc   4500
atagatgcac tcgaaatcag ccaattttag acaagtatca aacggatgtt aattcagtac   4560
attaaagacg tccgcaatgt gttattaagt tgtctaagcg tcaatttgtt tacaccacaa   4620
tatatcctgc caccagccag ccaacagctc cccgaccggc agctcggcac aaaatcacca   4680
cgcgttacca ccacgccggc cggccgcatg gtgttgaccg tgttcgccgg cattgccgag   4740
ttcgagcgtt ccctaatcat cgaccgcacc cggagcgggc gcgaggccgc caaggcccga   4800
ggcgtgaagt ttggcccccg ccctaccctc accccggcac agatcgcgca cgcccgcgag   4860
ctgatcgacc aggaaggccg caccgtgaaa gaggcggctg cactgcttgg cgtgcatcgc   4920
tcgaccctgt accgcgcact tgagcgcagc gaggaagtga cgcccaccga ggccaggcgg   4980
```

-continued

```
cgcggtgcct tccgtgagga cgcattgacc gaggccgacg ccctggcggc cgccgagaat   5040
gaacgccaag aggaacaagc atgaaaccgc accaggacgg ccaggacgaa ccgtttttca   5100
ttaccgaaga gatcgaggcg gagatgatcg cggccgggta cgtgttcgag ccgcccgcgc   5160
acgtctcaac cgtgcggctg catgaaatcc tggccggttt gtctgatgcc aagctggcgg   5220
cctggccggc cagcttggcc gctgaagaaa ccgagcgccg ccgtctaaaa aggtgatgtg   5280
tatttgagta aaacagcttg cgtcatgcgg tcgctgcgta tatgatgcga tgagtaaata   5340
aacaaatacg caaggggaac gcatgaaggt tatcgctgta cttaaccaga aaggcgggtc   5400
aggcaagacg accatcgcaa cccatctagc ccgcgccctg caactcgccg ggccgatgt    5460
tctgttagtc gattccgatc cccagggcag tgcccgcgat tgggcggccg tgcgggaaga   5520
tcaaccgcta accgttgtcg gcatcgaccg cccgacgatt gaccgcgacg tgaaggccat   5580
cggccggcgc gacttcgtag tgatcgacgg agcgccccag gcggcggact tggctgtgtc   5640
cgcgatcaag gcagccgact tcgtgctgat tccggtgcag ccaagccctt acgacatatg   5700
ggccaccgcc gacctggtgg agctggttaa gcagcgcatt gaggtcacgg atggaaggct   5760
acaagcggcc tttgtcgtgt cgcgggcgat caaaggcacg cgcatcggcg gtgaggttgc   5820
cgaggcgctg gccgggtacg agctgcccat tcttgagtcc cgtatcacgc agcgcgtgag   5880
ctacccaggc actgccgccg ccggcacaac cgttcttgaa tcagaacccg agggcgacgc   5940
tgcccgcgag gtccaggcgc tggccgctga aattaaatca aaactcattt gagttaatga   6000
ggtaaagaga aaatgagcaa aagcacaaac acgctaagtg ccggccgtcc gagcgcacgc   6060
agcagcaagg ctgcaacgtt ggccagcctg gcagacacgc cagccatgaa gcgggtcaac   6120
tttcagttgc cggcggagga tcacaccaag ctgaagatgt acgcggtacg ccaaggcaag   6180
accattaccg agctgctatc tgaatacatc gcgcagctac cagagtaaat gagcaaatga   6240
ataaatgagt agatgaattt tagcggctaa aggaggcggc atggaaaatc aagaacaacc   6300
aggcaccgac gccgtggaat gccccatgtg tggaggaacg ggcggttggc caggcgtaag   6360
cggctgggtt gtctgccggc cctgcaatgg cactggaacc cccaagcccg aggaatcggc   6420
gtgagcggtc gcaaaccatc cggcccggta caaatcggcg cggcgctggg tgatgacctg   6480
gtggagaagt tgaaggccgc gcaggccgcc cagcggcaac gcatcgaggc agaagcacgc   6540
cccggtgaat cgtggcaagc ggccgctgat cgaatccgca aagaatcccg gcaaccgccg   6600
gcagccggtg cgccgtcgat taggaagccg cccaagggcg acgagcaacc agattttttc   6660
gttccgatgc tctatgacgt gggcacccgc gatagtcgca gcatcatgga cgtggccgtt   6720
ttccgtctgt cgaagcgtga ccgacgagct ggcgaggtga tccgctacga gcttccagac   6780
gggcacgtag aggtttccgc agggccggcc ggcatggcca gtgtgtggga ttacgacctg   6840
gtactgatgg cggtttccca tctaaccgaa tccatgaacc gataccggga agggaaggga   6900
gacaagcccg gccgcgtgtt ccgtccacac gttgcggacg tactcaagtt ctgccggcga   6960
gccgatggcg gaaagcagaa agacgacctg gtagaaacct gcattcggtt aaacaccacg   7020
cacgttgcca tgcagcgtac gaagaaggcc aagaacggcc gcctggtgac ggtatccgag   7080
ggtgaagcct tgattagccg ctacaagatc gtaaagagcg aaaccgggcg gccggagtac   7140
atcgagatcg agctagctga ttggatgtac cgcgagatca cagaaggcaa gaacccggac   7200
gtgctgacgg ttcaccccga ttactttttg atcgatcccg gcatcggccg ttttctctac   7260
cgcctggcac gccgcgccgc aggcaaggca gaagccagat ggttgttcaa gacgatctac   7320
gaacgcagtg gcagcgccgg agagttcaag aagttctgtt tcaccgtgcg caagctgatc   7380
```

-continued

```
gggtcaaatg acctgccgga gtacgatttg aaggaggagg cggggcaggc tggcccgatc   7440
ctagtcatgc gctaccgcaa cctgatcgag ggcgaagcat ccgccggttc ctaatgtacg   7500
gagcagatgc tagggcaaat tgccctagca ggggaaaaag gtcgaaaagg tctctttcct   7560
gtggatagca cgtacattgg gaacccaaag ccgtacattg ggaaccggaa cccgtacatt   7620
gggaacccaa agccgtacat tgggaaccgg tcacacatgt aagtgactga tataaaagag   7680
aaaaaaggcg atttttccgc ctaaaactct ttaaaactta ttaaaactct taaaacccgc   7740
ctggcctgtg cataactgtc tggccagcgc acagccgaag agctgcaaaa agcgcctacc   7800
cttcggtcgc tgcgctccct acgccccgcc gcttcgcgtc ggcctatcgc ggccgctggc   7860
cgctcaaaaa tggctggcct acggccaggc aatctaccag ggcgcggaca agccgcgccg   7920
tcgccactcg accgccggcg cccacatcaa ggcaccctgc ctcgcgcgtt tcggtgatga   7980
cggtgaaaac ctctgacaca tgcagctccc ggagacggtc acagcttgtc tgtaagcgga   8040
tgccgggagc agacaagccc gtcagggcgc gtcagcgggt gttggcgggt gtcggggcgc   8100
agccatgacc cagtcacgta gcgatagcgg agtgtatact ggcttaacta tgcggcatca   8160
gagcagattg tactgagagt gcaccatatg cggtgtgaaa taccgcacag atgcgtaagg   8220
agaaaatacc gcatcaggcg ctcttccgct tcctcgctca ctgactcgct gcgctcggtc   8280
gttcggctgc ggcgagcggt atcagctcac tcaaaggcgg taatacggtt atccacagaa   8340
tcaggggata acgcaggaaa gaacatgtga gcaaaaggcc agcaaaaggc caggaaccgt   8400
aaaaaggccg cgttgctggc gtttttccat aggctccgcc cccctgacga gcatcacaaa   8460
aatcgacgct caagtcagag gtggcgaaac ccgacaggac tataaagata ccaggcgttt   8520
ccccctggaa gctccctcgt gcgctctcct gttccgaccc tgccgcttac cggatacctg   8580
tccgcctttc tcccttcggg aagcgtggcg ctttctcata gctcacgctg taggtatctc   8640
agttcggtgt aggtcgttcg ctccaagctg ggctgtgtgc acgaaccccc cgttcagccc   8700
gaccgctgcg ccttatccgg taactatcgt cttgagtcca acccggtaag acacgactta   8760
tcgccactgg cagcagccac tggtaacagg attagcagag cgaggtatgt aggcggtgct   8820
acagagttct tgaagtggtg gcctaactac ggctacacta gaaggacagt atttggtatc   8880
tgcgctctgc tgaagccagt taccttcgga aaaagagttg gtagctcttg atccggcaaa   8940
caaaccaccg ctggtagcgg tggttttttt gtttgcaagc agcagattac gcgcagaaaa   9000
aaaggatctc aagaagatcc tttgatcttt tctacggggt ctgacgctca gtggaacgaa   9060
aactcacgtt aagggatttt ggtcatgcat gatatatctc ccaatttgtg tagggcttat   9120
tatgcacgct taaaaataat aaaagcagac ttgacctgat agtttggctg tgagcaatta   9180
tgtgcttagt gcatctaacg cttgagttaa gccgcgccgc gaagcggcgt cggcttgaac   9240
gaatttctag ctagacatta tttgccgact accttggtga tctcgccttt cacgtagtgg   9300
acaaattctt ccaactgatc tgcgcgcgag gccaagcgat cttcttcttg tccaagataa   9360
gcctgtctag cttcaagtat gacgggctga tactgggccg gcaggcgctc cattgcccag   9420
tcggcagcga catccttcgg cgcgattttg ccggttactg cgctgtacca aatgcgggac   9480
aacgtaagca ctacatttcg ctcatcgcca gcccagtcgg gcggcgagtt ccatagcgtt   9540
aaggtttcat ttagcgcctc aaatagatcc tgttcaggaa ccggatcaaa gagttcctcc   9600
gccgctggac ctaccaaggc aacgctatgt tctcttgctt ttgtcagcaa gatagccaga   9660
tcaatgtcga tcgtggctgg ctcgaagata cctgcaagaa tgtcattgcg ctgccattct   9720
ccaaattgca gttcgcgctt agctggataa cgccacggaa tgatgtcgtc gtgcacaaca   9780
```

atggtgactt ctacagcgcg gagaatctcg ctctctccag gggaagccga agtttccaaa 9840
aggtcgttga tcaaagctcg ccgcgttgtt tcatcaagcc ttacggtcac cgtaaccagc 9900
aaatcaatat cactgtgtgg cttcaggccg ccatccactg cggagccgta caaatgtacg 9960
gccagcaacg tcggttcgag atggcgctcg atgacgccaa ctacctctga tagttgagtc 10020
gatacttcgg cgatcaccgc ttcccccatg atgtttaact ttgttttagg gcgactgccc 10080
tgctgcgtaa catcgttgct gctccataac atcaaacatc gacccacggc gtaacgcgct 10140
tgctgcttgg atgcccgagg catagactgt accccaaaaa aacagtcata acaagccatg 10200
aaaaccgcca ctgcgggggt tccatggaca tacaaatgga cgaacggata aaccttttca 10260
cgccctttta aatatccgat tattctaata aacgctcttt tctcttaggt ttacccgcca 10320
atatatcctg tcaaacactg atagtttaaa ctgaaggcgg gaaacgacaa tcagatctag 10380
taggaaacag ctatgaccat gattacgcca agct 10414

<210> SEQ ID NO 79
<211> LENGTH: 11152
<212> TYPE: DNA
<213> ORGANISM: Artificial sequence
<220> FEATURE:
<223> OTHER INFORMATION: binary vector
      Lo657-pSUN3-GWs-B1-BnAK700::GUS::E9::nosT::B2
<220> FEATURE:
<221> NAME/KEY: misc_recomb
<222> LOCATION: (4)..(28)
<223> OTHER INFORMATION: attB1 Gateway recombination site
<220> FEATURE:
<221> NAME/KEY: promoter
<222> LOCATION: (56)..(724)
<223> OTHER INFORMATION: p-BnAK promoter
<220> FEATURE:
<221> NAME/KEY: misc_feature
<222> LOCATION: (749)..(2560)
<223> OTHER INFORMATION: cds encoding c-GUS (E.coli)
<220> FEATURE:
<221> NAME/KEY: terminator
<222> LOCATION: (2691)..(3355)
<223> OTHER INFORMATION: t-E9 terminator
<220> FEATURE:
<221> NAME/KEY: terminator
<222> LOCATION: (3369)..(3621)
<223> OTHER INFORMATION: t-NOS nopaline synthase terminator
<220> FEATURE:
<221> NAME/KEY: misc_recomb
<222> LOCATION: (3633)..(3657)
<223> OTHER INFORMATION: attB2 Gateway recombination site
<220> FEATURE:
<221> NAME/KEY: terminator
<222> LOCATION: (3710)..(3962)
<223> OTHER INFORMATION: complement: t-NOS nopaline synthase terminator
<220> FEATURE:
<221> NAME/KEY: misc_feature
<222> LOCATION: (4038)..(4832)
<223> OTHER INFORMATION: complement: cds encoding c-NptII confers
      kanamycin resistance
<220> FEATURE:
<221> NAME/KEY: promoter
<222> LOCATION: (4864)..(5151)
<223> OTHER INFORMATION: complement: p-NOS promoter from the noplaine
      synthase gene
<220> FEATURE:
<221> NAME/KEY: misc_structure
<222> LOCATION: (5202)..(5416)
<223> OTHER INFORMATION: complement: b-LB Left T-DNA border
<220> FEATURE:
<221> NAME/KEY: misc_structure
<222> LOCATION: (10965)..(11109)
<223> OTHER INFORMATION: complement: b-RB Right T-DNA border

<400> SEQUENCE: 79

```
atcacaagtt tgtacaaaaa agcaggcttt aaaggaacca attcagtcga cacgaagctt      60
tcgaggctaa cgttggtgga gatgttaagg cacggcatct tctcttcttc ttcttttttg     120
tttgtttgtt tgtttcgctc tctatcactc actcgatcga tccccagtct tcttttcggg     180
aaagctgtgt cagaccaatt atattccatc tttaatttgg ccctttttat tattcgctat     240
ggcccaacat ttcaggccca atttatacga ttataaatat aaccacttga ttgtgctgcc     300
gctcagctga atagtactcc ctccgttttt taatataaat cgttttacag ttatgcacgt     360
aaattaagaa aaccattaac tttttatatt ttctaaacaa aaacatcatt aattatttac     420
ttactcacaa ttcaaccaat agaaaaatag aagatatatt accattggtc atacaacatt     480
aattattaat aaattttaca tagaaaaccg aaaacgacat ataatttgga acaaaaaaat     540
ttctctaaaa ctacttatat taaaaaacgg agagagtata tttaactagt tcgtcttact     600
gacaaattga agaggcagac caagacacgc ggctcctcga tggctgtctt atgccaagtg     660
gcggtgcctg cttctgcatt aaataggtag aagaactcta attacagaag ctcgaggtag     720
ataggatccc cgggtaggtc agtcccttat gttacgtcct gtagaaaccc caacccgtga     780
aatcaaaaaa ctcgacggcc tgtgggcatt cagtctggat cgcgaaaact gtggaattga     840
tcagcgttgg tgggaaagcg cgttacaaga aagccgggca attgctgtgc caggcagttt     900
taacgatcag ttcgccgatg cagatattcg taattatgcg ggcaacgtct ggtatcagcg     960
cgaagtcttt ataccgaaag gttgggcagg ccagcgtatc gtgctgcgtt tcgatgcggt    1020
cactcattac ggcaaagtgt gggtcaataa tcaggaagtg atggagcatc agggcggcta    1080
tacgccattt gaagccgatg tcacgccgta tgttattgcc gggaaaagtg tacgtatcac    1140
cgtttgtgtg aacaacgaac tgaactggca gactatcccg ccgggaatgg tgattaccga    1200
cgaaaacggc aagaaaaagc agtcttactt ccatgatttc tttaactatg ccggaatcca    1260
tcgcagcgta atgctctaca ccacgccgaa cacctgggtg gacgatatca ccgtggtgac    1320
gcatgtcgcg caagactgta accacgcgtc tgttgactgg caggtggtgg ccaatggtga    1380
tgtcagcgtt gaactgcgtg atgcggatca acaggtggtt gcaactggac aaggcactag    1440
cgggactttg caagtggtga atccgcacct ctggcaaccg ggtgaaggtt atctctatga    1500
actgtgcgtc acagccaaaa gccagacaga gtgtgatatc tacccgcttc gcgtcggcat    1560
ccggtcagtg gcagtgaagg gcgaacagtt cctgattaac cacaaaccgt tctactttac    1620
tggctttggt cgtcatgaag atgcggactt gcgtggcaaa ggattcgata acgtgctgat    1680
ggtgcacgac cacgcattaa tggactggat tggggccaac tcctaccgta cctcgcatta    1740
cccttacgct gaagagatgc tcgactgggc agatgaacat ggcatcgtgg tgattgatga    1800
aactgctgct gtcggcttta acctctcttt aggcattggt ttcgaagcgg gcaacaagcc    1860
gaaagaactg tacagcgaag aggcagtcaa cggggaaact cagcaagcgc acttacaggc    1920
gattaaagag ctgatagcgc gtgacaaaaa ccacccaagc gtggtgatgt ggagtattgc    1980
caacgaaccg gatacccgtc cgcaaggtgc acgggaatat ttcgcgccac tggcggaagc    2040
aacgcgtaaa ctcgacccga cgcgtccgat cacctgcgtc aatgtaatgt tctgcgacgc    2100
tcacaccgat accatcagcg atctctttga tgtgctgtgc ctgaaccgtt attacggatg    2160
gtatgtccaa agcggcgatt tggaaacggc agagaaggta ctggaaaaag aacttctggc    2220
ctggcaggag aaactgcatc agccgattat catcaccgaa tacggcgtgg atacgttagc    2280
cgggctgcac tcaatgtaca ccgacatgtg gagtgaagag tatcagtgtg catggctgga    2340
tatgtatcac cgcgtctttg atcgcgtcag cgccgtcgtc ggtgaacagg tatggaattt    2400
```

-continued

```
cgccgatttt gcgacctcgc aaggcatatt gcgcgttggc ggtaacaaga aagggatctt   2460
cactcgcgac cgcaaaccga agtcggcggc ttttctgctg caaaaacgct ggactggcat   2520
gaacttcggt gaaaaaccgc agcagggagg caaacaatga atcaacaact ctcctggcgc   2580
accatcgtcg gctacagcct cgggaattgc taccgagatc tgcggccgcg gcgcgccaat   2640
tgactagtag gcctatcgat taattaaggc cgcctcgagc atatgctaga ggatcctcta   2700
gctagagctt tcgttcgtat catcggtttc gacaacgttc gtcaagttca atgcatcagt   2760
ttcattgcgc acacaccaga atcctactga gtttgagtat tatggcattg ggaaaactgt   2820
ttttcttgta ccatttgttg tgcttgtaat ttactgtgtt ttttattcgg ttttcgctat   2880
cgaactgtga aatggaaatg gatggagaag agttaatgaa tgatatggtc cttttgttca   2940
ttctcaaatt aatattattt gttttttctc ttatttgttg tgtgttgaat ttgaaattat   3000
aagagatatg caaacatttt gttttgagta aaaatgtgtc aaatcgtggc ctctaatgac   3060
cgaagttaat atgaggagta aaacacttgt agttgtacca ttatgcttat tcactaggca   3120
acaaatatat tttcagacct agaaaagctg caaatgttac tgaatacaag tatgtcctct   3180
tgtgttttag acatttatga actttccttt atgtaatttt ccagaatcct tgtcagattc   3240
taatcattgc tttataatta tagttatact catggatttg tagttgagta tgaaaatatt   3300
ttttaatgca ttttatgact tgccaattga ttgacaacat gcatcaatcg accggctcga   3360
atttccccga tcgttcaaac atttggcaat aaagtttctt aagattgaat cctgttgccg   3420
gtcttgcgat gattatcata taatttctgt tgaattacgt taagcatgta ataattaaca   3480
tgtaatgcat gacgttattt atgagatggg tttttatgat tagagtcccg caattataca   3540
tttaatacgc gatagaaaac aaaatatagc gcgcaaacta ggataaatta tcgcgcgcgg   3600
tgtcatctat gttactagat cgggaattct agacccagct ttcttgtaca aagtggtgat   3660
aattcactgg ccgtcgtttt acaacgactc agagcttgac aggaggcccg atctagtaac   3720
atagatgaca ccgcgcgcga taatttatcc tagtttgcgc gctatatttt gttttctatc   3780
gcgtattaaa tgtataattg cgggactcta atcataaaaa cccatctcat aaataacgtc   3840
atgcattaca tgttaattat tacatgctta acgtaattca acagaaatta tatgataatc   3900
atcgcaagac cggcaacagg attcaatctt aagaaacttt attgccaaat gtttgaacga   3960
tcggggatca tccgggtctg tggcgggaac tccacgaaaa tatccgaacg cagcaagatc   4020
tagagcttgg gtcccgctca gaagaactcg tcaagaaggc gatagaaggc gatgcgctgc   4080
gaatcgggag cggcgatacc gtaaagcacg aggaagcggt cagcccattc gccgccaagc   4140
tcttcagcaa tatcacgggt agccaacgct atgtcctgat agcggtccgc cacacccagc   4200
cggccacagt cgatgaatcc agaaaagcgg ccattttcca ccatgatatt cggcaagcag   4260
gcatcgccat gggtcacgac gagatcctcg ccgtcgggca tgcgcgcctt gagcctggcg   4320
aacagttcgg ctggcgcgag cccctgatgc tcttcgtcca gatcatcctg atcgacaaga   4380
ccggcttcca tccgagtacg tgctcgctcg atgcgatgtt tcgcttggtg gtcgaatggg   4440
caggtagccg gatcaagcgt atgcagccgc cgcattgcat cagccatgat ggatactttc   4500
tcggcaggag caaggtgaga tgacaggaga tcctgccccg gcacttcgcc caatagcagc   4560
cagtcccttc ccgcttcagt gacaacgtcg agcacagctg cgcaaggaac gcccgtcgtg   4620
gccagccacg atagccgcgc tgcctcgtcc tgcagttcat tcagggcacc ggacaggtcg   4680
gtcttgacaa aaagaaccgg gcgcccctgc gctgacagcc ggaacacggc ggcatcagag   4740
cagccgattg tctgttgtgc ccagtcatag ccgaatagcc tctccaccca agcggccgga   4800
```

-continued

```
gaacctgcgt gcaatccatc ttgttcaatc atgcgaaacg atccagatcc ggtgcagatt   4860
atttggattg agagtgaata tgagactcta attggatacc gaggggaatt tatggaacgt   4920
cagtggagca tttttgacaa gaaatatttg ctagctgata gtgaccttag gcgacttttg   4980
aacgcgcaat aatggtttct gacgtatgtg cttagctcat taaactccag aaacccgcgg   5040
ctgagtggct ccttcaacgt tgcggttctg tcagttccaa acgtaaaacg gcttgtcccg   5100
cgtcatcggc gggggtcata acgtgactcc cttaattctc cgctcatgat cagattgtcg   5160
tttcccgcct tcagtttaaa ctatcagtgt ttgacaggat cctgcttggt aataattgtc   5220
attagattgt ttttatgcat agatgcactc gaaatcagcc aattttagac aagtatcaaa   5280
cggatgttaa ttcagtacat taaagacgtc cgcaatgtgt tattaagttg tctaagcgtc   5340
aatttgttta caccacaata tatcctgcca ccagccagcc aacagctccc cgaccggcag   5400
ctcggcacaa aatcaccacg cgttaccacc acgccggccg gccgcatggt gttgaccgtg   5460
ttcgccggca ttgccgagtt cgagcgttcc ctaatcatcg accgcacccg gagcgggcgc   5520
gaggccgcca aggcccgagg cgtgaagttt ggcccccgcc ctaccctcac cccggcacag   5580
atcgcgcacg cccgcgagct gatcgaccag gaaggccgca ccgtgaaaga ggcggctgca   5640
ctgcttggcg tgcatcgctc gaccctgtac cgcgcacttg agcgcagcga ggaagtgacg   5700
cccaccgagg ccaggcggcg cggtgccttc cgtgaggacg cattgaccga ggccgacgcc   5760
ctggcggccg ccgagaatga acgccaagag gaacaagcat gaaaccgcac caggacggcc   5820
aggacgaacc gtttttcatt accgaagaga tcgaggcgga gatgatcgcg gccgggtacg   5880
tgttcgagcc gcccgcgcac gtctcaaccg tgcggctgca tgaaatcctg gccggtttgt   5940
ctgatgccaa gctggcggcc tggccggcca gcttggccgc tgaagaaacc gagcgccgcc   6000
gtctaaaaag gtgatgtgta tttgagtaaa acagcttgcg tcatgcggtc gctgcgtata   6060
tgatgcgatg agtaaataaa caaatacgca aggggaacgc atgaaggtta tcgctgtact   6120
taaccagaaa ggcgggtcag gcaagacgac catcgcaacc catctagccc gcgccctgca   6180
actcgccggg gccgatgttc tgttagtcga ttccgatccc cagggcagtg cccgcgattg   6240
ggcggccgtg cgggaagatc aaccgctaac cgttgtcggc atcgaccgcc cgacgattga   6300
ccgcgacgtg aaggccatcg gccggcgcga cttcgtagtg atcgacggag cgccccaggc   6360
ggcggacttg gctgtgtccg cgatcaaggc agccgacttc gtgctgattc cggtgcagcc   6420
aagcccttac gacatatggg ccaccgccga cctggtggag ctggttaagc agcgcattga   6480
ggtcacggat ggaaggctac aagcggcctt tgtcgtgtcg cgggcgatca aaggcacgcg   6540
catcggcggt gaggttgccg aggcgctggc cgggtacgag ctgcccattc ttgagtcccg   6600
tatcacgcag cgcgtgagct acccaggcac tgccgccgcc ggcacaaccg ttcttgaatc   6660
agaacccgag ggcgacgctg cccgcgaggt ccaggcgctg gccgctgaaa ttaaatcaaa   6720
actcatttga gttaatgagg taaagagaaa atgagcaaaa gcacaaacac gctaagtgcc   6780
ggccgtccga gcgcacgcag cagcaaggct gcaacgttgg ccagcctggc agacacgcca   6840
gccatgaagc gggtcaactt tcagttgccg gcggaggatc acaccaagct gaagatgtac   6900
gcggtacgcc aaggcaagac cattaccgag ctgctatctg aatacatcgc gcagctacca   6960
gagtaaatga gcaaatgaat aaatgagtag atgaatttta gcggctaaag gaggcggcat   7020
ggaaaatcaa gaacaaccag gcaccgacgc cgtggaatgc cccatgtgtg gaggaacggg   7080
cggttggcca ggcgtaagcg gctgggttgt ctgccggccc tgcaatggca ctggaacccc   7140
caagcccgag gaatcggcgt gagcggtcgc aaaccatccg gcccggtaca aatcggcgcg   7200
```

-continued

```
gcgctgggtg atgacctggt ggagaagttg aaggccgcgc aggccgccca gcggcaacgc   7260
atcgaggcag aagcacgccc cggtgaatcg tggcaagcgg ccgctgatcg aatccgcaaa   7320
gaatcccggc aaccgccggc agccggtgcg ccgtcgatta ggaagccgcc caagggcgac   7380
gagcaaccag atttttcgt tccgatgctc tatgacgtgg gcacccgcga tagtcgcagc   7440
atcatggacg tggccgtttt ccgtctgtcg aagcgtgacc gacgagctgg cgaggtgatc   7500
cgctacgagc ttccagacgg gcacgtagag gtttccgcag ggccggccgg catggccagt   7560
gtgtgggatt acgacctggt actgatggcg gtttcccatc taaccgaatc catgaaccga   7620
taccgggaag ggaagggaga caagcccggc cgcgtgttcc gtccacacgt tgcggacgta   7680
ctcaagttct gccggcgagc cgatggcgga aagcagaaag acgacctggt agaaacctgc   7740
attcggttaa acaccacgca cgttgccatg cagcgtacga agaaggccaa gaacggccgc   7800
ctggtgacgg tatccgaggg tgaagccttg attagccgct acaagatcgt aaagagcgaa   7860
accgggcggc cggagtacat cgagatcgag ctagctgatt ggatgtaccg cgagatcaca   7920
gaaggcaaga acccggacgt gctgacggtt caccccgatt actttttgat cgatcccggc   7980
atcggccgtt ttctctaccg cctggcacgc cgcgccgcag gcaaggcaga agccagatgg   8040
ttgttcaaga cgatctacga acgcagtggc agcgccggag agttcaagaa gttctgtttc   8100
accgtgcgca agctgatcgg gtcaaatgac ctgccggagt acgatttgaa ggaggaggcg   8160
gggcaggctg gcccgatcct agtcatgcgc taccgcaacc tgatcgaggg cgaagcatcc   8220
gccggttcct aatgtacgga gcagatgcta gggcaaattg ccctagcagg ggaaaaaggt   8280
cgaaaaggtc tctttcctgt ggatagcacg tacattggga acccaaagcc gtacattggg   8340
aaccggaacc cgtacattgg gaacccaaag ccgtacattg ggaaccggtc acacatgtaa   8400
gtgactgata taaaagagaa aaaaggcgat tttccgcct aaaactcttt aaaacttatt   8460
aaaactctta aaacccgcct ggcctgtgca taactgtctg gccagcgcac agccgaagag   8520
ctgcaaaaag cgcctaccct tcggtcgctg cgctccctac gccccgccgc ttcgcgtcgg   8580
cctatcgcgg ccgctggccg ctcaaaaatg gctggcctac ggccaggcaa tctaccaggg   8640
cgcggacaag ccgcgccgtc gccactcgac cgccggcgcc cacatcaagg caccctgcct   8700
cgcgcgtttc ggtgatgacg gtgaaaacct ctgacacatg cagctcccgg agacggtcac   8760
agcttgtctg taagcggatg ccgggagcag acaagcccgt cagggcgcgt cagcgggtgt   8820
tggcgggtgt cggggcgcag ccatgaccca gtcacgtagc gatagcggag tgtatactgg   8880
cttaactatg cggcatcaga gcagattgta ctgagagtgc accatatgcg gtgtgaaata   8940
ccgcacagat gcgtaaggag aaaataccgc atcaggcgct cttccgcttc ctcgctcact   9000
gactcgctgc gctcggtcgt tcggctgcgg cgagcggtat cagctcactc aaaggcggta   9060
atacggttat ccacagaatc aggggataac gcaggaaaga acatgtgagc aaaaggccag   9120
caaaaggcca ggaaccgtaa aaaggccgcg ttgctggcgt ttttccatag gctccgcccc   9180
cctgacgagc atcacaaaaa tcgacgctca agtcagaggt ggcgaaaccc gacaggacta   9240
taaagatacc aggcgtttcc ccctggaagc tccctcgtgc gctctcctgt tccgaccctg   9300
ccgcttaccg gatacctgtc cgcctttctc ccttcgggaa gcgtggcgct ttctcatagc   9360
tcacgctgta ggtatctcag ttcggtgtag gtcgttcgct ccaagctggg ctgtgtgcac   9420
gaaccccccg ttcagcccga ccgctgcgcc ttatccggta actatcgtct tgagtccaac   9480
ccggtaagac acgacttatc gccactggca gcagccactg gtaacaggat tagcagagcg   9540
aggtatgtag gcggtgctac agagttcttg aagtggtggc ctaactacgg ctacactaga   9600
```

-continued

```
aggacagtat ttggtatctg cgctctgctg aagccagtta ccttcggaaa aagagttggt   9660

agctcttgat ccggcaaaca aaccaccgct ggtagcggtg gtttttttgt ttgcaagcag   9720

cagattacgc gcagaaaaaa aggatctcaa gaagatcctt tgatcttttc tacggggtct   9780

gacgctcagt ggaacgaaaa ctcacgttaa gggattttgg tcatgcatga tatatctccc   9840

aatttgtgta gggcttatta tgcacgctta aaaataataa aagcagactt gacctgatag   9900

tttggctgtg agcaattatg tgcttagtgc atctaacgct tgagttaagc cgcgccgcga   9960

agcggcgtcg gcttgaacga atttctagct agacattatt tgccgactac cttggtgatc  10020

tcgcctttca cgtagtggac aaattcttcc aactgatctg cgcgcgaggc caagcgatct  10080

tcttcttgtc caagataagc ctgtctagct tcaagtatga cgggctgata ctgggccggc  10140

aggcgctcca ttgcccagtc ggcagcgaca tccttcggcg cgattttgcc ggttactgcg  10200

ctgtaccaaa tgcgggacaa cgtaagcact acatttcgct catcgccagc ccagtcgggc  10260

ggcgagttcc atagcgttaa ggtttcattt agcgcctcaa atagatcctg ttcaggaacc  10320

ggatcaaaga gttcctccgc cgctggacct accaaggcaa cgctatgttc tcttgctttt  10380

gtcagcaaga tagccagatc aatgtcgatc gtggctggct cgaagatacc tgcaagaatg  10440

tcattgcgct gccattctcc aaattgcagt tcgcgcttag ctggataacg ccacggaatg  10500

atgtcgtcgt gcacaacaat ggtgacttct acagcgcgga gaatctcgct ctctccaggg  10560

gaagccgaag tttccaaaag gtcgttgatc aaagctcgcc gcgttgtttc atcaagcctt  10620

acggtcaccg taaccagcaa atcaatatca ctgtgtggct tcaggccgcc atccactgcg  10680

gagccgtaca aatgtacggc cagcaacgtc ggttcgagat ggcgctcgat gacgccaact  10740

acctctgata gttgagtcga tacttcggcg atcaccgctt cccccatgat gtttaacttt  10800

gttttagggc gactgccctg ctgcgtaaca tcgttgctgc tccataacat caaacatcga  10860

cccacggcgt aacgcgcttg ctgcttggat gcccgaggca tagactgtac cccaaaaaaa  10920

cagtcataac aagccatgaa aaccgccact gcgggggttc catggacata caaatggacg  10980

aacggataaa ccttttcacg ccctttttaaa tatccgatta ttctaataaa cgctcttttc  11040

tcttaggttt acccgccaat atatcctgtc aaacactgat agtttaaact gaaggcggga  11100

aacgacaatc agatctagta ggaaacagct atgaccatga ttacgccaag ct          11152
```

<210> SEQ ID NO 80
<211> LENGTH: 37
<212> TYPE: DNA
<213> ORGANISM: Unknown
<220> FEATURE:
<223> OTHER INFORMATION: Oligonucleotide primer 5

<400> SEQUENCE: 80

```
cggcctaggg gcgcccggac cgagctgttc accggca                              37
```

<210> SEQ ID NO 81
<211> LENGTH: 24
<212> TYPE: DNA
<213> ORGANISM: Unknown
<220> FEATURE:
<223> OTHER INFORMATION: oligonucleotide primer 6

<400> SEQUENCE: 81

```
cggactagtg atgtagccct cagg                                            24
```

<210> SEQ ID NO 82
<211> LENGTH: 22
<212> TYPE: DNA

<213> ORGANISM: Unknown
<220> FEATURE:
<223> OTHER INFORMATION: oligonucleotide primer 7

<400> SEQUENCE: 82
cgagctcgtg ccttttggat cg 22

<210> SEQ ID NO 83
<211> LENGTH: 18
<212> TYPE: DNA
<213> ORGANISM: Unknown
<220> FEATURE:
<223> OTHER INFORMATION: oligonucleotide primer 8

<400> SEQUENCE: 83
cggtccgaac gtggttgg 18

<210> SEQ ID NO 84
<211> LENGTH: 22
<212> TYPE: DNA
<213> ORGANISM: Unknown
<220> FEATURE:
<223> OTHER INFORMATION: oligonucleotide primer 9

<400> SEQUENCE: 84
cgagctcggc cctatgaatt gg 22

<210> SEQ ID NO 85
<211> LENGTH: 22
<212> TYPE: DNA
<213> ORGANISM: Unknown
<220> FEATURE:
<223> OTHER INFORMATION: oligonucleotide primer 10

<400> SEQUENCE: 85
cggtccgtct ccttctgcac ac 22

<210> SEQ ID NO 86
<211> LENGTH: 23
<212> TYPE: DNA
<213> ORGANISM: Unknown
<220> FEATURE:
<223> OTHER INFORMATION: oligonucleotide primer 11

<400> SEQUENCE: 86
cgagctcgat gcattccttg gat 23

<210> SEQ ID NO 87
<211> LENGTH: 22
<212> TYPE: DNA
<213> ORGANISM: Unknown
<220> FEATURE:
<223> OTHER INFORMATION: oligonucleotide primer 12

<400> SEQUENCE: 87
cctagggttt ggaggtatca ag 22

<210> SEQ ID NO 88
<211> LENGTH: 26
<212> TYPE: DNA
<213> ORGANISM: Unknown
<220> FEATURE:
<223> OTHER INFORMATION: oligonucleotide primer 13

<400> SEQUENCE: 88
cgagctccgt ccgatgtgat tccgtc 26

<210> SEQ ID NO 89
<211> LENGTH: 22
<212> TYPE: DNA
<213> ORGANISM: Unknown
<220> FEATURE:
<223> OTHER INFORMATION: oligonucleotide primter 14

<400> SEQUENCE: 89
cctaggggca gtgtcggcgg tt 22

<210> SEQ ID NO 90
<211> LENGTH: 25
<212> TYPE: DNA
<213> ORGANISM: Unknown
<220> FEATURE:
<223> OTHER INFORMATION: oligonucleotide primer 15

<400> SEQUENCE: 90
cgagctccag agtgacagac agtga 25

<210> SEQ ID NO 91
<211> LENGTH: 22
<212> TYPE: DNA
<213> ORGANISM: Unknown
<220> FEATURE:
<223> OTHER INFORMATION: oligonucleotide primer 16

<400> SEQUENCE: 91
cctaggtctt caactgtccc ca 22

<210> SEQ ID NO 92
<211> LENGTH: 1137
<212> TYPE: DNA
<213> ORGANISM: Oryza sativa
<220> FEATURE:
<221> NAME/KEY: terminator
<222> LOCATION: (1)..(1137)
<223> OTHER INFORMATION: BPST.3

<400> SEQUENCE: 92
ggaatgtatt tgaccataca aaaaccgtac aaagtgtagg gttctaatta gcaaatgtaa 60
gtttgtaatt cttctgtcta aatgtagtgt gttgaggtgg tcagttgccg tgactggctc 120
tttcagatgg taattacaaa gaaatgtaac attaatgttg taacaagggt gccattttgt 180
ttctgattcc agatgaaaag gaaaaactat tccatattct gcaggattaa acgtttctgc 240
tgttcacaac aggtaaagtc actccacttc agggaaagac agcaaaatca tttcttttac 300
acagacttta gataaccctt ttttttgggg ttcttggtat atgccaactt ttgtagcctg 360
caccagaaac aaaaatgaag acttttgcta aagatgtaaa agtggcatga tgtcctggat 420
gaccaaataa ttcatgacaa atggattaaa agagcccaat atctgaaaga gactggccag 480
cagccactaa tgtcaccaac cacatatgta acacttggtg cataattcaa gagggagcat 540
ctcctccaga atcaggattg aaaggtacaa cctcatagta aatcctcgga atatagcatg 600
tgcagcataa gaatatatca gtgttgtgct gggtaagaaa ccacatgaac caattaggaa 660
taaataatca tgctgaaatt atagcaatgc ttgcaatttg caaacgataa agctagacgc 720
gggttgctgg aataacaatc catctccaac aaaatagtac agaatataac tgaatggcca 780
gctcagaccc taacagaatt gaaaagctgg attcatcagc actccattga gcaatctaga 840
tcaggaaaga gcatagatgc ataatgaact gagatccctt caaaatgact aactaatatt 900
tttttttctt ataaaagagt ttacaacagt acaaccacga agatcagcac taccattact 960

```
gattttgtta acatagagtg atttatcatg tgtgccagac aaacaacaga tacattcata   1020

catagcataa cttacagcac atgatacaga ctacggagaa cggttaatct taaaataaaa   1080

acaaaaaaac aaggaggcaa agcttatttt gcctgggatt catctaaatg cagttgt      1137


<210> SEQ ID NO 93
<211> LENGTH: 1137
<212> TYPE: DNA
<213> ORGANISM: Oryza sativa
<220> FEATURE:
<221> NAME/KEY: terminator
<222> LOCATION: (1)..(1137)
<223> OTHER INFORMATION: BPST.4

<400> SEQUENCE: 93

acaactgcat ttagatgaat cccaggcaaa ataagctttg cctccttgtt tttttgtttt     60

tattttaaga ttaaccgttc tccgtagtct gtatcatgtg ctgtaagtta tgctatgtat    120

gaatgtatct gttgtttgtc tggcacacat gataaatcac tctatgttaa caaaatcagt    180

aatggtagtg ctgatcttcg tggttgtact gttgtaaact cttttataag aaaaaaaaat    240

attagttagt cattttgaag ggatctcagt tcattatgca tctatgctct ttcctgatct    300

agattgctca atggagtgct gatgaatcca gcttttcaat tctgttaggg tctgagctgg    360

ccattcagtt atattctgta ctattttgtt ggagatggat tgttattcca gcaacccgcg    420

tctagcttta tcgtttgcaa attgcaagca ttgctataat ttcagcatga ttatttattc    480

ctaattggtt catgtggttt cttacccagc acaacactga tatattctta tgctgcacat    540

gctatattcc gaggatttac tatgaggttg tacctttcaa tcctgattct ggaggagatg    600

ctccctcttg aattatgcac caagtgttac atatgtggtt ggtgacatta gtggctgctg    660

gccagtctct ttcagatatt gggctctttt aatccatttg tcatgaatta tttggtcatc    720

caggacatca tgccactttt acatctttag caaaagtctt catttttgtt tctggtgcag    780

gctacaaaag ttggcatata ccaagaaccc caaaaaaaag ggttatctaa agtctgtgta    840

aaagaaatga ttttgctgtc tttccctgaa gtggagtgac tttacctgtt gtgaacagca    900

gaaacgttta atcctgcaga atatggaata gtttttcctt ttcatctgga atcagaaaca    960

aaatggcacc cttgttacaa cattaatgtt acatttcttt gtaattacca tctgaaagag   1020

ccagtcacgg caactgacca cctcaacaca ctacatttag acagaagaat tacaaactta   1080

catttgctaa ttagaaccct acactttgta cggtttttgt atggtcaaat acattcc      1137


<210> SEQ ID NO 94
<211> LENGTH: 6849
<212> TYPE: DNA
<213> ORGANISM: Artificial sequence
<220> FEATURE:
<223> OTHER INFORMATION: vector pRJB058
<220> FEATURE:
<221> NAME/KEY: promoter
<222> LOCATION: (204)..(2191)
<223> OTHER INFORMATION: ZmUbi
<220> FEATURE:
<221> NAME/KEY: Intron
<222> LOCATION: (1186)..(2191)
<223> OTHER INFORMATION: i-ZmUbi
<220> FEATURE:
<221> NAME/KEY: misc_feature
<222> LOCATION: (2224)..(4224)
<223> OTHER INFORMATION: cds encoding GUS
<220> FEATURE:
<221> NAME/KEY: Intron
<222> LOCATION: (2609)..(2797)
<223> OTHER INFORMATION: i-PIV2
<220> FEATURE:
```

<221> NAME/KEY: misc_feature
<222> LOCATION: (4284)..(4299)
<223> OTHER INFORMATION: TOI cloning site
<220> FEATURE:
<221> NAME/KEY: misc_feature
<222> LOCATION: (4304)..(4567)
<223> OTHER INFORMATION: GFP-fragment

<400> SEQUENCE: 94

```
caggaaacag ctatgaccat gtaatacgac tcactatagg ggatatcagc tggatggcaa     60
ataatgattt tattttgact gatagtgacc tgttcgttgc aacaaattga taagcaatgc    120
tttcttataa tgccaacttt gtacaagaaa gctgggtcgg cgcgccaagc ttgcatgcct    180
gcaggcatgc aagcttccgc ggctgcagtg cagcgtgacc cggtcgtgcc cctctctaga    240
gataatgagc attgcatgtc taagttataa aaaattacca catatttttt ttgtcacact    300
tgtttgaagt gcagtttatc tatctttata catatattta aactttactc tacgaataat    360
ataatctata gtactacaat aatatcagtg ttttagagaa tcatataaat gaacagttag    420
acatggtcta aaggacaatt gagtattttg acaacaggac tctacagttt tatcttttta    480
gtgtgcatgt gttctccttt ttttttgcaa atagcttcac ctatataata cttcatccat    540
tttattagta catccattta gggtttaggg ttaatggttt ttatagacta atttttttag    600
tacatctatt ttattctatt ttagcctcta aattaagaaa actaaaactc tattttagtt    660
tttttattta atagtttaga tataaaatag aataaaataa agtgactaaa aattaaacaa    720
ataccettta agaaattaaa aaaactaagg aaacattttt cttgtttcga gtagataatg    780
ccagcctgtt aaacgccgtc gacgagtcta acggacacca accagcgaac cagcagcgtc    840
gcgtcgggcc aagcgaagca gacggcacgg catctctgtc gctgcctctg gacccctctc    900
gagagttccg ctccaccgtt ggacttgctc cgctgtcggc atccagaaat tgcgtggcgg    960
agcggcagac gtgagccggc acggcaggcg gcctcctcct cctctcacgg caccggcagc   1020
tacgggggat tcctttccca ccgctccttc gctttccctt cctcgcccgc cgtaataaat   1080
agacaccccc tccacaccct ctttccccaa cctcgtgttg ttcggagcgc acacacacac   1140
aaccagatct cccccaaatc cacccgtcgg cacctccgct tcaaggtacg ccgctcgtcc   1200
tccccccccc ccccctctc taccttctct agatcggcgt tccggtccat ggttagggcc   1260
cggtagttct acttctgttc atgtttgtgt tagatccgtg tttgtgttag atccgtgctg   1320
ctagcgttcg tacacggatg cgacctgtac gtcagacacg ttctgattgc taacttgcca   1380
gtgtttctct ttggggaatc ctgggatggc tctagccgtt ccgcagacgg gatcgatttc   1440
atgatttttt ttgtttcgtt gcatagggtt tggtttgccc ttttccttta tttcaatata   1500
tgccgtgcac ttgtttgtcg ggtcatcttt tcatgctttt ttttgtcttg gttgtgatga   1560
tgtggtctgg ttgggcggtc gttctagatc ggagtagaat tctgtttcaa actacctggt   1620
ggatttatta attttggatc tgtatgtgtg tgccatacat attcatagtt acgaattgaa   1680
gatgatggat ggaaatatcg atctaggata ggtatacatg ttgatgcggg ttttactgat   1740
gcatatacag agatgctttt tgttcgcttg gttgtgatga tgtggtgtgg ttgggcggtc   1800
gttcattcgt tctagatcgg agtagaatac tgtttcaaac tacctggtgt atttattaat   1860
tttggaactg tatgtgtgtg tcatacatct tcatagttac gagtttaaga tggatggaaa   1920
tatcgatcta ggataggtat acatgttgat gtgggtttta ctgatgcata tacatgatgg   1980
catatgcagc atctattcat atgctctaac cttgagtacc tatctattat aataaacaag   2040
tatgttttat aattatttcg atcttgatat acttggatga tggcatatgc agcagctata   2100
```

-continued

```
tgtggatttt tttagccctg ccttcatacg ctatttattt gcttggtact gtttcttttg   2160
tcgatgctca ccctgttgtt tggtgttact tctgcagggt acccccgggt aggtcagtcc   2220
cttatgttac gtcctgtaga aaccccaacc cgtgaaatca aaaaactcga cggcctgtgg   2280
gcattcagtc tggatcgcga aaactgtgga attggtcagc gttggtggga aagcgcgtta   2340
caagaaagcc gggcaattgc tgtgccaggc agttttaacg atcagttcgc cgatgcagat   2400
attcgtaatt atgcgggcaa cgtctggtat cagcgcgaag tctttatacc gaaaggttgg   2460
gcaggccagc gtatcgtgct gcgtttcgat gcggtcactc attacggcaa agtgtgggtc   2520
aataatcagg aagtgatgga gcatcagggc ggctatacgc catttgaagc cgatgtcacg   2580
ccgtatgtta ttgccgggaa aagtgtacgt aagtttctgc ttctaccttt gatatatata   2640
taataattat cattaattag tagtaatata atatttcaaa tatttttttc aaaataaaag   2700
aatgtagtat atagcaattg cttttctgta gtttataagt gtgtatattt taatttataa   2760
cttttctaat atatgaccaa aatttgttga tgtgcaggta tcaccgtttg tgtgaacaac   2820
gaactgaact ggcagactat cccgccggga atggtgatta ccgacgaaaa cggcaagaaa   2880
aagcagtctt acttccatga tttctttaac tatgccggaa tccatcgcag cgtaatgctc   2940
tacaccacgc cgaacacctg ggtggacgat atcaccgtgg tgacgcatgt cgcgcaagac   3000
tgtaaccacg cgtctgttga ctggcaggtg gtggccaatg gtgatgtcag cgttgaactg   3060
cgtgatgcgg atcaacaggt ggttgcaact ggacaaggca ctagcgggac tttgcaagtg   3120
gtgaatccgc acctctggca accgggtgaa ggttatctct atgaactgtg cgtcacagcc   3180
aaaagccaga cagagtgtga tatctacccg cttcgcgtcg gcatccggtc agtggcagtg   3240
aagggcgaac agttcctgat taaccacaaa ccgttctact ttactggctt tggtcgtcat   3300
gaagatgcgg acttgcgtgg caaaggattc gataacgtgc tgatggtgca cgaccacgca   3360
ttaatggact ggattggggc caactcctac cgtacctcgc attaccctta cgctgaagag   3420
atgctcgact gggcagatga acatggcatc gtggtgattg atgaaactgc tgctgtcggc   3480
tttaacctct ctttaggcat tggtttcgaa gcgggcaaca agccgaaaga actgtacagc   3540
gaagaggcag tcaacgggga aactcagcaa gcgcacttac aggcgattaa agagctgata   3600
gcgcgtgaca aaaaccaccc aagcgtggtg atgtggagta ttgccaacga accggatacc   3660
cgtccgcaag gtgcacggga atatttcgcg ccactggcgg aagcaacgcg taaactcgac   3720
ccgacgcgtc cgatcacctg cgtcaatgta atgttctgcg acgctcacac cgataccatc   3780
agcgatctct ttgatgtgct gtgcctgaac cgttattacg gatggtatgt ccaaagcggc   3840
gatttggaaa cggcagagaa ggtactggaa aaagaacttc tggcctggca ggagaaactg   3900
catcagccga ttatcatcac cgaatacggc gtggatacgt tagccgggct gcactcaatg   3960
tacaccgaca tgtggagtga agagtatcag tgtgcatggc tggatatgta tcaccgcgtc   4020
tttgatcgcg tcagcgccgt cgtcggtgaa caggtatgga atttcgccga ttttgcgacc   4080
tcgcaaggca tattgcgcgt tggcggtaac aagaaaggga tcttcactcg cgaccgcaaa   4140
ccgaagtcgg cggcttttct gctgcaaaaa cgctggactg gcatgaactt cggtgaaaaa   4200
ccgcagcagg gaggcaaaca atgaatcaac aactctcctg gcgcaccatc gtcggctaca   4260
gcctcgggaa ttgctaccga gctccctagg gggcgcccgg accgagctgt tcaccggcat   4320
cgtgcccatc ctgatcgagc tgaatggcga tgtgaatggc cacaagttca gcgtgagcgg   4380
cgagggcgag ggcgatgcca cctacggcaa gctgaccctg aagttcatct gcaccaccgg   4440
caagctgcct gtgccctggc ccaccctggt gaccaccctg agctacggcg tgcagtgctt   4500
```

-continued

```
ctcacgctac cccgatcaca tgaagcagca cgacttcttc aagagcgcca tgcctgaggg   4560
ctacatcact agttaagact ggccgtcgtt ttacaacgtc gtgactggga aaacatccat   4620
gctagcgtta acgcgagagt agggaactgc caggcatcaa ataaaacgaa aggctcagtc   4680
ggaagactgg gcctttcgtt ttatctgttg tttgtcggtg aacgctctcc tgagtaggac   4740
aaatccgccg ggagcggatt tgaacgttgt gaagcaacgg cccggagggt ggcgggcagg   4800
acgcccgcca taaactgcca ggcatcaaac taagcagaag gccatcctga cggatggcct   4860
ttttgcgttt ctacaaactc ttcctggcta gcggtacgcg tattaattgc gttgcgctca   4920
ctgcccgctt tccagtcggg aaacctgtcg tgccagctgc attaatgaat cggccaacgc   4980
gcggggagag gcggtttgcg tattgggcgc tcttccgctt cctcgctcac tgactcgctg   5040
cgctcggtcg ttcggctgcg gcgagcggta tcagctcact caaaggcggt aatacggtta   5100
tccacagaat caggggataa cgcaggaaag aacatgtgag caaaaggcca gcaaaaggcc   5160
aggaaccgta aaaaggccgc gttgctggcg tttttccata ggctccgccc ccctgacgag   5220
catcacaaaa atcgacgctc aagtcagagg tggcgaaacc cgacaggact ataaagatac   5280
caggcgtttc cccctggaag ctccctcgtg cgctctcctg ttccgaccct gccgcttacc   5340
ggatacctgt ccgcctttct cccttcggga agcgtggcgc tttctcatag ctcacgctgt   5400
aggtatctca gttcggtgta ggtcgttcgc tccaagctgg gctgtgtgca cgaacccccc   5460
gttcagcccg accgctgcgc cttatccggt aactatcgtc ttgagtccaa cccggtaaga   5520
cacgacttat cgccactggc agcagccact ggtaacagga ttagcagagc gaggtatgta   5580
ggcggtgcta cagagttctt gaagtggtgg cctaactacg gctacactag aagaacagta   5640
tttggtatct gcgctctgct gaagccagtt accttcggaa aaagagttgg tagctcttga   5700
tccggcaaac aaaccaccgc tggtagcggt ggtttttttg tttgcaagca gcagattacg   5760
cgcagaaaaa aaggatctca agaagatcct ttgatctttt ctacggggtc tgacgctcag   5820
tggaacgacg cgtaactcac gttaagggat tttggtcatg agcttgcgcc gtcccgtcaa   5880
gtcagcgtaa tgctctgcca gtgttacaac caattaacca attctgatta gaaaaactca   5940
tcgagcatca aatgaaactg caatttattc atatcaggat tatcaatacc atatttttga   6000
aaaagccgtt tctgtaatga aggagaaaac tcaccgaggc agttccatag gatggcaaga   6060
tcctggtatc ggtctgcgat tccgactcgt ccaacatcaa tacaacctat taatttcccc   6120
tcgtcaaaaa taaggttatc aagtgagaaa tcaccatgag tgacgactga atccggtgag   6180
aatggcaaaa gtttatgcat ttctttccag acttgttcaa caggccagcc attacgctcg   6240
tcatcaaaat cactcgcatc aaccaaaccg ttattcattc gtgattgcgc ctgagcgaga   6300
cgaaatacgc gatcgctgtt aaaaggacaa ttacaaacag gaatcgaatg caaccggcgc   6360
aggaacactg ccagcgcatc aacaatattt tcacctgaat caggatattc ttctaatacc   6420
tggaatgctg tttttccggg gatcgcagtg gtgagtaacc atgcatcatc aggagtacgg   6480
ataaaatgct tgatggtcgg aagaggcata aattccgtca gccagtttag tctgaccatc   6540
tcatctgtaa catcattggc aacgctacct ttgccatgtt tcagaaacaa ctctggcgca   6600
tcgggcttcc catacaagcg atagattgtc gcacctgatt gcccgacatt atcgcgagcc   6660
catttatacc catataaatc agcatccatg ttggaattta atcgcggcct cgacgtttcc   6720
cgttgaatat ggctcataac accccttgta ttactgttta tgtaagcaga cagttttatt   6780
gttcatgatg atatattttt atcttgtgca atgtaacatc agagattttg agacacgggc   6840
cagagctgc                                                           6849
```

<210> SEQ ID NO 95
<211> LENGTH: 257
<212> TYPE: DNA
<213> ORGANISM: Artificial sequence
<220> FEATURE:
<223> OTHER INFORMATION: Nos-T sequence inserted into SacI-RsrII fragment of pRJB058
<220> FEATURE:
<221> NAME/KEY: terminator
<222> LOCATION: (3)..(254)
<223> OTHER INFORMATION: Nos terminator inserted into the SacI-RsrII sites of pJB058

<400> SEQUENCE: 95

```
cgatcgttca aacatttggc aataaagttt cttaagattg aatcctgttg ccggtcttgc     60

gatgattatc atataatttc tgttgaatta cgttaagcat gtaataatta acatgtaatg    120

catgacgtta tttatgagat gggtttttat gattagagtc ccgcaattat acatttaata    180

cgcgatagaa aacaaaatat agcgcgcaaa ctaggataaa ttatcgcgcg cggtgtcatc    240

tatgttacta gatccgg                                                   257
```

<210> SEQ ID NO 96
<211> LENGTH: 1089
<212> TYPE: DNA
<213> ORGANISM: Artificial sequence
<220> FEATURE:
<223> OTHER INFORMATION: ORF sequence inserted into SacI digested and T4 DNA Polymerase filled in fragment of pRJB058
<220> FEATURE:
<221> NAME/KEY: misc_feature
<222> LOCATION: (3)..(1088)
<223> OTHER INFORMATION: internal ORF sequence cloned into filled-in SacI site of pRJB058

<400> SEQUENCE: 96

```
cgaacaacaa aaaaaccatc ccgaacaacc tggttgaaaa ctacctgacc ccgatgtctc     60

tggcatactg gttcatggat gatggtggta aatgggatta caacaaaaac tctaccaaca    120

aatcgatcgt actgaacacc cagtctttca ctttcgaaga agtagaatac ctggttaagg    180

gtctgcgtaa caaattccaa ctgaactgtt acgtaaaaat caacaaaaac aaaccgatca    240

tctacatcga ttctatgtct tacctgatct tctacaacct gatcaaaccg tacctgatcc    300

cgcagatgat gtacaaactg ccgaacacta tctcctccga aactttcctg aaaggtacca    360

aaggtgggat acgaaaagac cgaagaggag ggagaatgtt gaaacacaag cgccagagag    420

atgatgggga gggcaggggt gaagtggggt ctgctggaga catgagagct gccaaccttt    480

ggccaagccc gctcatgatc aaacgctcta agaagaacag cctggccttg tccctgacgg    540

ccgaccagat ggtcagtgcc ttgttggatg ctgagccccc catacctcta ttccgagtat    600

gatcctacca gacccttcag tgaagcttcg atgatgggct tactgaccaa cctggcagac    660

agggagctgg ttcacatgat caactgggcg aagagggtgc caggctttgt ggatttgacc    720

ctccatgatc aggtccacct tctagaatgt gcctggctag agatcctgat gattggtctc    780

gtctggcgct ccatggaaca cccggggaag ctcctgtttg ctcctaactt gctcctggac    840

aggaatcaag gtaaatgtgt ggaaggcatg gtggagatct tcgacatgct gctggctaca    900

tcatctcggt tccgcatgat gaatctgcag ggagaggagt ttgtgtgcct caaatctatt    960

attttgctta attctggagt gtacacattt ctgtccagca ccctgaagtc tctggaagag   1020

aaggaccata tccaccgagt cctggacaag atcacagaca ctttgatcca cctgatggcc   1080

aaggcaggc                                                           1089
```

<210> SEQ ID NO 97
<211> LENGTH: 1414
<212> TYPE: DNA
<213> ORGANISM: Artificial sequence
<220> FEATURE:
<223> OTHER INFORMATION: Oryza sativa BPST.1 sequence inserted into SacI digested and T4 DNA Polymerase filled in fragment of pRJB058
<220> FEATURE:
<221> NAME/KEY: misc_feature
<222> LOCATION: (1)..(18)
<223> OTHER INFORMATION: EcoRI/SacI MCS
<220> FEATURE:
<221> NAME/KEY: terminator
<222> LOCATION: (19)..(1402)
<223> OTHER INFORMATION: BPST.1 sequence inserted into SacI site of pRJB058
<220> FEATURE:
<221> NAME/KEY: misc_feature
<222> LOCATION: (1403)..(1414)
<223> OTHER INFORMATION: RsrII/EcoRI MCS

<400> SEQUENCE: 97
aattcgccct tcggaccgtg ccttttggat cgaaagatgc agttgttttg ctgctgaagg 60
catcctcatg tctgttactt tgatatggtc ttgaaataaa tcttcgttta caagagaaca 120
acactctgtt ttatcttgtt ttgtgtgcca gaagcctgct gaacaatttt atgtcaattt 180
ctttgctact aagaaagtta tgcaccaaaa tgaagggaaa ttctgtgaag tttgtaattt 240
tcaagtgatt ggcattattc tgtttagttc gtgcagtgcc atgttcctta tataatcaca 300
gaacatgtaa aaggccgaaa tattttcctt gtcattttcc atgcgagaac ggcctttcga 360
tgagactgga aagtcctgca ataactattg tccaaaataa cacacggctc tctaccgatt 420
cacatcaaaa ccaacccaaa cgctctctct gttgcttgtg ttctggactt ctctgagcgc 480
agttcaggag tctcgagtgt gcctcaacag tacatgttaa acataaaact gccattgaag 540
attaccacca accatattgg aagtttatca tggcatatac ttgcctttca aagaccctaa 600
ttttcaaagt gaacatggga ctttcagact acagataacc tcaatcgata acatcaccga 660
aaattcgata ttactacaaa gattttggtt gaaaacttct ctgaacccaa tttaaataca 720
agtcgccctc ggtgatggct actcgccatt ccacgctcac agttgcagtt cacacttgca 780
aaatgaaaaa aaaaatcttc tgaacagcaa tcatcaaccg gttcgacctc aggatcatca 840
cagaaatgaa aaggacgagg aatctcaatt taagaaagtt cctatccaaa tatccaacaa 900
aaatctgact gtctggctat tattaattca acaggagatg ctcgttaaag acaatatagt 960
tctgtaattt gtaacaacac aagagcctga ggatataacg agttacaaac atgctgccgt 1020
tgcagcatgg tcatcaatat acaacattac aacaacatat ggggatcgca gaacactccc 1080
attccacgat tttacaacat atgcttcaca acacgttata aatacatggt tgtaccgagc 1140
tgtagagaga cagccagcac gtcccaacta caaatgcaca ctagccaaca gcaaacataa 1200
aaactactct ctggtaagtc actatatata cgcactatag cttcacatga ctaaaattat 1260
aacatgacat aatttctttc gtataaatta gccccaggaa gcttctgtcc gaatcgccat 1320
cttgggagca ataaatatac tggcattctt cacaatggat gcattattta catatatata 1380
cttcttctcc aaccacgttc gagctcgaag ggcg 1414

<210> SEQ ID NO 98
<211> LENGTH: 1414
<212> TYPE: DNA
<213> ORGANISM: Artificial sequence
<220> FEATURE:
<223> OTHER INFORMATION: Oryza sativa BPST.2 sequence inserted into SacI digested and T4 DNA Polymerase filled in fragment of pRJB058

<220> FEATURE:
<221> NAME/KEY: misc_feature
<222> LOCATION: (1)..(14)
<223> OTHER INFORMATION: EcoRI/SacI MCS
<220> FEATURE:
<221> NAME/KEY: terminator
<222> LOCATION: (15)..(1398)
<223> OTHER INFORMATION: BPST.2 sequence inserted into the filled-in SacI site of pRJB058
<220> FEATURE:
<221> NAME/KEY: misc_feature
<222> LOCATION: (1399)..(1414)
<223> OTHER INFORMATION: RsrII/EcoRI MCS

<400> SEQUENCE: 98

```
cgcccttcga gctcgaacgt ggttggagaa gaagtatata tatgtaaata atgcatccat     60

tgtgaagaat gccagtatat ttattgctcc caagatggcg attcggacag aagcttcctg    120

gggctaattt atacgaaaga aattatgtca tgttataatt ttagtcatgt gaagctatag    180

tgcgtatata tagtgactta ccagagagta gtttttatgt ttgctgttgg ctagtgtgca    240

tttgtagttg ggacgtgctg gctgtctctc tacagctcgg tacaaccatg tatttataac    300

gtgttgtgaa gcatatgttg taaaatcgtg gaatgggagt gttctgcgat ccccatatgt    360

tgttgtaatg ttgtatattg atgaccatgc tgcaacggca gcatgtttgt aactcgttat    420

atcctcaggc tcttgtgttg ttacaaatta cagaactata ttgtctttaa cgagcatctc    480

ctgttgaatt aataatagcc agacagtcag atttttgttg gatatttgga taggaacttt    540

cttaaattga gattcctcgt ccttttcatt tctgtgatga tcctgaggtc gaaccggttg    600

atgattgctg ttcagaagat ttttttttc attttgcaag tgtgaactgc aactgtgagc     660

gtggaatggc gagtagccat caccgagggc gacttgtatt taaattgggt tcagagaagt    720

tttcaaccaa aatctttgta gtaatatcga attttcggtg atgttatcga ttgaggttat    780

ctgtagtctg aaagtcccat gttcactttg aaaattaggg tctttgaaag gcaagtatat    840

gccatgataa acttccaata tggttggtgg taatcttcaa tggcagtttt atgtttaaca    900

tgtactgttg aggcacactc gagactcctg aactgcgctc agagaagtcc agaacacaag    960

caacagagag agcgtttggg ttggttttga tgtgaatcgg tagagagccg tgtgttattt   1020

tggacaatag ttattgcagg actttccagt ctcatcgaaa ggccgttctc gcatggaaaa   1080

tgacaaggaa aatatttcgg ccttttacat gttctgtgat tatataagga acatggcact   1140

gcacgaacta aacagaataa tgccaatcac ttgaaaatta caaacttcac agaatttccc   1200

ttcattttgg tgcataactt tcttagtagc aaagaaattg acataaaatt gttcagcagg   1260

cttctggcac acaaaacaag ataaaacaga gtgttgttct cttgtaaacg aagatttatt   1320

tcaagaccat atcaaagtaa cagacatgag gatgccttca gcagcaaaac aactgcatct   1380

ttcgatccaa aaggcacggt ccgaagggcg aatt                                1414
```

<210> SEQ ID NO 99
<211> LENGTH: 1165
<212> TYPE: DNA
<213> ORGANISM: Artificial sequence
<220> FEATURE:
<223> OTHER INFORMATION: Oryza sativa BPST.3 sequence inserted into SacI digested and T4 DNA Polymerase filled in fragment of pRJB058
<220> FEATURE:
<221> NAME/KEY: misc_feature
<222> LOCATION: (1)..(13)
<223> OTHER INFORMATION: EcoRI/SacI MCS
<220> FEATURE:
<221> NAME/KEY: terminator
<222> LOCATION: (14)..(1150)
<223> OTHER INFORMATION: BPST.3 sequence inserted into the SacI site of pRJB058
<220> FEATURE:
<221> NAME/KEY: misc_feature
<222> LOCATION: (1151)..(1165)
<223> OTHER INFORMATION: RsrII/EcoRI MCS

<400> SEQUENCE: 99
ggccctatga attggaatgt atttgaccat acaaaaaccg tacaaagtgt agggttctaa 60
ttagcaaatg taagtttgta attcttctgt ctaaatgtag tgtgttgagg tggtcagttg 120
ccgtgactgg ctctttcaga tggtaattac aaagaaatgt aacattaatg ttgtaacaag 180
ggtgccattt tgtttctgat tccagatgaa aaggaaaaac tattccatat tctgcaggat 240
taaacgtttc tgctgttcac aacaggtaaa gtcactccac ttcagggaaa gacagcaaaa 300
tcatttcttt tacacagact ttagataacc cttttttttg gggttcttgg tatatgccaa 360
cttttgtagc ctgcaccaga aacaaaaatg aagacttttg ctaaagatgt aaaagtggca 420
tgatgtcctg gatgaccaaa taattcatga caaatggatt aaaagagccc aatatctgaa 480
agagactggc cagcagccac taatgtcacc aaccacatat gtaacacttg gtgcataatt 540
caagagggag catctcctcc agaatcagga ttgaaaggta caacctcata gtaaatcctc 600
ggaatatagc atgtgcagca taagaatata tcagtgttgt gctgggtaag aaaccacatg 660
aaccaattag gaataaataa tcatgctgaa attatagcaa tgcttgcaat ttgcaaacga 720
taaagctaga cgcgggttgc tggaataaca atccatctcc aacaaaatag tacagaatat 780
aactgaatgg ccagctcaga ccctaacaga attgaaaagc tggattcatc agcactccat 840
tgagcaatct agatcaggaa agagcataga tgcataatga actgagatcc cttcaaaatg 900
actaactaat attttttttt cttataaaag agtttacaac agtacaacca cgaagatcag 960
cactaccatt actgattttg ttaacataga gtgatttatc atgtgtgcca gacaaacaac 1020
agatacattc atacatagca taacttacag cacatgatac agactacgga gaacggttaa 1080
tcttaaaata aaaacaaaaa aacaaggagg caaagcttat tttgcctggg attcatctaa 1140
atgcagttgt gtgcagaagg agacg 1165

<210> SEQ ID NO 100
<211> LENGTH: 1165
<212> TYPE: DNA
<213> ORGANISM: Artificial sequence
<220> FEATURE:
<223> OTHER INFORMATION: Oryza sativa BPST.4 sequence inserted into SacI
      digested and T4 DNA Polymerase filled in fragment of pRJB058
<220> FEATURE:
<221> NAME/KEY: misc_feature
<222> LOCATION: (1)..(15)
<220> FEATURE:
<221> NAME/KEY: misc_feature
<222> LOCATION: (1)..(15)
<223> OTHER INFORMATION: EcoRI/SacI
<220> FEATURE:
<221> NAME/KEY: terminator
<222> LOCATION: (16)..(1152)
<223> OTHER INFORMATION: BPST.4 sequence inserted into the SacI site of
      pRJB058
<220> FEATURE:
<221> NAME/KEY: misc_feature
<222> LOCATION: (1153)..(1165)
<223> OTHER INFORMATION: AvrII/EcoRI

<400> SEQUENCE: 100
cgtctccttc tgcacacaac tgcatttaga tgaatcccag gcaaaataag ctttgcctcc 60
ttgttttttt gtttttattt taagattaac cgttctccgt agtctgtatc atgtgctgta 120
agttatgcta tgtatgaatg tatctgttgt ttgtctggca cacatgataa atcactctat 180

```
gttaacaaaa tcagtaatgg tagtgctgat cttcgtggtt gtactgttgt aaactctttt    240

ataagaaaaa aaaatattag ttagtcattt tgaagggatc tcagttcatt atgcatctat    300

gctctttcct gatctagatt gctcaatgga gtgctgatga atccagcttt tcaattctgt    360

tagggtctga gctggccatt cagttatatt ctgtactatt ttgttggaga tggattgtta    420

ttccagcaac ccgcgtctag ctttatcgtt tgcaaattgc aagcattgct ataatttcag    480

catgattatt tattcctaat tggttcatgt ggtttcttac ccagcacaac actgatatat    540

tcttatgctg cacatgctat attccgagga tttactatga ggttgtacct ttcaatcctg    600

attctggagg agatgctccc tcttgaatta tgcaccaagt gttacatatg tggttggtga    660

cattagtggc tgctggccag tctctttcag atattgggct cttttaatcc atttgtcatg    720

aattatttgg tcatccagga catcatgcca cttttacatc tttagcaaaa gtcttcattt    780

ttgtttctgg tgcaggctac aaaagttggc atataccaag aaccccaaaa aaaagggtta    840

tctaaagtct gtgtaaaaga aatgattttg ctgtctttcc ctgaagtgga gtgactttac    900

ctgttgtgaa cagcagaaac gtttaatcct gcagaatatg gaatagtttt tccttttcat    960

ctggaatcag aaacaaaatg gcacccttgt tacaacatta atgttacatt tctttgtaat   1020

taccatctga aagagccagt cacggcaact gaccacctca acacactaca tttagacaga   1080

agaattacaa acttacattt gctaattaga accctacact ttgtacggtt tttgtatggt   1140

caaatacatt ccaattcata gggcc                                         1165
```

<210> SEQ ID NO 101
<211> LENGTH: 1305
<212> TYPE: DNA
<213> ORGANISM: Artificial sequence
<220> FEATURE:
<223> OTHER INFORMATION: terminator sequence from Orzza sativa with 5' and 3'-multiple cloning site linkers
<220> FEATURE:
<221> NAME/KEY: misc_feature
<222> LOCATION: (1)..(18)
<223> OTHER INFORMATION: EcoRI/SacI MCS
<220> FEATURE:
<221> NAME/KEY: terminator
<222> LOCATION: (19)..(1292)
<223> OTHER INFORMATION: BPST.5
<220> FEATURE:
<221> NAME/KEY: misc_feature
<222> LOCATION: (1294)..(1305)
<223> OTHER INFORMATION: AvrII/EcoRI MCS

<400> SEQUENCE: 101

```
aattcgccct tcgagctcga tgcattcctt ggattgttcc caatgtattc cagaaatcat     60

agttttgatg ccaaagttgg tcttcggtat ttgttacttg gagatggcaa atcgacttga    120

gcaatgttaa agttttgggc atttaaatta tagacctttg cttggcacgg ttagcttgtt    180

tcaaatccgt tgtttgttgt ggaatgtgtt tcacatatgt ggtaggtgaa gaatctcatt    240

atggttcgct gtttcattct cttgcgttta tcacccgctg tctgctaact tagggtgtgt    300

ttagtcctcg tcaaaattgg aagtttggtt gaaattggaa caatgtgacg aaaaagttga    360

aatttttttt gtgggtagga aagttttgat gtgatagaaa agttggaagt ttaaaaaaaa    420

agtttagaac taaactcggc cctagtcaat ttacccttac tattaggcat tatccccgct    480

gtctgctaac ctagtcaatt taccettgta ttattactag gcattatcct tgcctccgtt    540

agtggtttgt tcttgagagc ggccaggtag gaaaattcca cttgaagagg agtgcgttac    600

gccggcctct tgccattatc atcgtttgta ttgatatgca gaaatagaaa gaaaaaccta    660
```

```
ggattttgat gaaaataaat cggatataga tatcataaaa cacattggaa cttgagatgg    720

agagaactct agatattttc catgagattg ttacctaatt cctactttcc tacaaaatct    780

tatgaaactg ccattcgaaa ggaatatcgt aggattctcg agtcccaatc cgttccagaa    840

aggtaaatcg gaacaatggt acgaaaaatc tgtccccatt ggatcataag acttggacgg    900

tctatcccat ggtactaagg gttttggaaa gaattttgca gaatttgaat ggatgtatcc    960

tatacacaag ttttctgtgt acacatcgta cacatcaact aacaattttt accaaaaatc   1020

taggaacaaa ttcacatgtt ctatcatgag ttatcacaca ttcacacgtt catatcttgg   1080

ttaaatctga acagcaggct gtaaataaac cacaaaagtc tccaaattat gggcctcaac   1140

agtaatcaat atcgtttcct cagacggcaa ttgccagttt gccacaacag ccatgttggc   1200

taacatttga tacattcgga gtactgcttg aatttgcagg ctctccctaa ccttattatc   1260

cctatagtct ttgactcttg atacctccaa accctaggaa gggcg                   1305
```

<210> SEQ ID NO 102
<211> LENGTH: 1350
<212> TYPE: DNA
<213> ORGANISM: Artificial sequence
<220> FEATURE:
<223> OTHER INFORMATION: terminator sequence from Orzza sativa with 5' and 3'-multiple cloning site linkers
<220> FEATURE:
<221> NAME/KEY: misc_feature
<222> LOCATION: (1)..(18)
<223> OTHER INFORMATION: EcoRI/SacI MCS
<220> FEATURE:
<221> NAME/KEY: terminator
<222> LOCATION: (19)..(1332)
<220> FEATURE:
<221> NAME/KEY: misc_feature
<222> LOCATION: (1333)..(1350)
<223> OTHER INFORMATION: AvrII/EcoRI MCS

<400> SEQUENCE: 102

```
gaattcgccc ttcgagctcc gtccgatgtg attccgtcct cttgattgtt ttccttcccc     60

ctaatttttg ttgcatacgc ggagagaagc tttagcttta agaggttaac tggcggcacc    120

tcaatttctt tgggcttcag catgggttaa gaccacctaa taatcctgtc gcattcttgc    180

tcttggaaaa gtttcttcca acattgcagt ccagtcagag aatggcctgt aataattagt    240

gacaaaatta tagcagtaga tagaatctgt tcattcaagt tcttcaaatt actgggccaa    300

gcttcaatgt catttttttgc ttaactcgtg ctcgtgctgt tatagtttac aactatcttc    360

tttacctgcc cataaccaat gtgaccatcg aatcaaacgt atgtggcggt gaatcccgtt    420

gcttgtgcgt tgctagattt ttgaggtcgc cttctgttcc aaattccaat catttgaatt    480

cgaagggatt acctgtcgac tgcgcatacg atcttttatt gagaatattt gctaggtgtg    540

ggagttcctg cgtgtgttcg tttagtggac gtgcgtatgt gagcatgtgc tatatgttgt    600

gcttcgtgaa aactcagctt cttttcatca agatcggcac ctctgcttat cacctaatcc    660

catcattcca atagcaacat aacatagatg tgacacatcc tatacatgat attgggatgg    720

agagagtatt cctaagatgc atctctaccc tttctcttcg aatgcacatt tattgggagt    780

catttttaat gtgcatttgt gcaaactggt accatggaac cctagtgcta ccctaacaga    840

tatgctccat cgtcactaca aactcttgtt tacatccaca aactactgct tggaagggca    900

cgctgacatt tgatcagaag aaagaatgac atgggtgcca aagttatgga tcagtgtggt    960

gaaattcgag aataaccgac aagatacttc tcaatcttgt cacaataaga gggttatttt   1020

tgtttagtac agtacaacta acgataccgc acaaaaaacg gtgaacgcga tatcgcacaa   1080
```

-continued

```
aaaaaagagc aacacgtttg aattatattc aggtttgcta ctgcaatcca acaccatctc   1140

ataactacat tatcctaatc gagccttttt aagtaatgag gccagtacaa ttaaaaaagg   1200

tgccgtagac aatagcaaac ccatgaagaa ctgaaaacaa atgaatgcaa aactaaaatt   1260

gtcttagttc tgtcgacaaa tgccaactgc tataatcgta catgcgtctc cgaagaaacc   1320

gccgacactg cccctaggaa gggcgaattc                                    1350
```

<210> SEQ ID NO 103
<211> LENGTH: 1532
<212> TYPE: DNA
<213> ORGANISM: Artificial sequence
<220> FEATURE:
<223> OTHER INFORMATION: terminator sequence from Orzza sativa with 5' and 3'-multiple cloning site linkers
<220> FEATURE:
<221> NAME/KEY: misc_feature
<222> LOCATION: (1)..(19)
<223> OTHER INFORMATION: EcoRI/SacI MCS
<220> FEATURE:
<221> NAME/KEY: terminator
<222> LOCATION: (20)..(1518)
<220> FEATURE:
<221> NAME/KEY: misc_feature
<222> LOCATION: (1519)..(1532)
<223> OTHER INFORMATION: EcoRI site

<400> SEQUENCE: 103

```
gaattcgccc ttcgagctcc agagtgatag acagtgctac ttgctagcct tttttatgag     60

cacccttttt ggccttttag ttcctcatta gctaagagat gtgatgagtg aggttttatt    120

ttttggcttt gtttggagtt ttgctttgga ggaagataga gaagccttta gaatgagttg    180

tgatggagga tcacatagtt tgtctcaggt ttacaatgtg cggtaaaaaa aaggaaggaa    240

ataaagtgat gttagaatat acagtttttt aatccatttc tacagcttca aattctcgat    300

tgagcggcac gttctttgaa atgttcatag caaagcaaat caaacgaaat ggatgagatt    360

tgaaactaag aaactgcact tgacaaagca cgctgcgctc tctgaaattc atgttcagca    420

gaacgccttt cagaaattca tgttctgctg ctgcaggaag gcagctaaga actccatgca    480

ataaaaatat aaaatgcagt gcagttatta gttagtgtag tagtaatcta agaaacaaca    540

ggtttaacag aatattacct tcaaaaacat cccctcaaat caagactcgg aaatcaacac    600

cattctgaaa ctagatgcaa tactgcgctc ctaatggaat cttcagtggt tactcctaca    660

cgccactaaa aaaaacgggc tttggaaaaa cgtcaccctg aaaacaagag ctcagtaaaa    720

ataccactct aaaatcttgc agcatgcatt atcacaaaag cagatcaatc cgtaattgta    780

tttatgctgc atataccgtg atattttctg tgatcctctg cactatcttc agctcatcag    840

ctgcatattt tgaagccgga ctgatggctc atcgctttgt ttcggcttat tgtgatagcc    900

atccatgcgt tgacgaaaga tttagatata tcacaatttt aaccaagttc agagcaatgt    960

tagctttagc tgatgatata cacggcgcac tgattgccgc cgttattttc agagccttgt   1020

aaaacctgaa acaaattgtg tctccaaatt cttactagta ctgcagacat agcggatttg   1080

ttttcaggat gaattatcac aaaggtaagt caattcatag ccatattacg caagttcaaa   1140

actgcaggcc acaccatacg tttctgaaag tagaaacaag agatcttgca gcagatcacc   1200

actaaagaag cagtaaccgc aaaaaattat aacataatcc agaattaaca cttcgcagca   1260

ttactgaatt cactttaata gcacttctca tcatgaacta gtacaacaac ataactgtcc   1320

agtggaaatg tgaaatgcat acaccaagta atggtccata acatgaacta tatggataca   1380

acaacgttct tatttcgctc atatatacat gaaataagtc ttgcacgtct tggttactta   1440
```

-continued

```
ataggtgcga taatcgccgt aggcttttag aagaagaaaa aaaagtgagc ctgcaaagtt   1500

cctggggaca gttgaagacc aagggcgaat tc                                 1532
```

<210> SEQ ID NO 104
<211> LENGTH: 1532
<212> TYPE: DNA
<213> ORGANISM: Artificial sequence
<220> FEATURE:
<223> OTHER INFORMATION: terminator sequence from Orzza sativa with 5' and 3'-multiple cloning site linkers
<220> FEATURE:
<221> NAME/KEY: misc_feature
<222> LOCATION: (1)..(15)
<223> OTHER INFORMATION: EcoRI site
<220> FEATURE:
<221> NAME/KEY: terminator
<222> LOCATION: (16)..(1514)
<220> FEATURE:
<221> NAME/KEY: misc_feature
<222> LOCATION: (1515)..(1532)
<223> OTHER INFORMATION: EcoRI/SacI MCS

<400> SEQUENCE: 104

```
cgaattcgcc cttggtcttc aactgtcccc aggaactttg caggctcact ttttttcttt     60

cttctaaaag cctacggcga ttatcgcacc tattaagtaa ccaagacgtg caagacttat    120

ttcatgtata tatgagcgaa ataagaacgt tgttgtatcc atatagttca tgttatggac    180

cattacttgg tgtatgcatt tcacatttcc actggacagt tatgttgttg tactagttca    240

tgatgagaag tgctattaaa gtgaattcag taatgctgcg aagtgttaat tctggattat    300

gttataattt tttgcggtta ctgcttcttt agtggtgatc tgctgcaaga tctcttgttt    360

ctactttcag aaacgtatgg tgtggcctgc agttttgaac ttgcgtaata tggctatgaa    420

ttgacttacc tttgtgataa ttcatcctga aaacaaatcc gctatgtctg cagtactagt    480

aagaatttgg agacacaatt tgtttcaggt tttacaaggc tctgaaaata acggcggcaa    540

tcagtgcgcc gtgtatatca tcagctaaag ctaacattgc tctgaacttg gttaaaattg    600

tgatatatct aaatctttcg tcaacgcatg gatggctatc acaataagcc gaaacaaagc    660

gatgagccat cagtccggct tcaaaatatg cagctgatga gctgaagata gtgcagagga    720

tcacagaaaa tatcacggta tatgcagcat aaatacaatt acggattgat ctgcttttgt    780

gataatgcat gctgcaagat tttagagtgg tatttttact gagctcttgt tttcagggtg    840

acgtttttcc aaagcccgtt ttttttagtg gcgtgtagga gtaaccactg aagattccat    900

taggagcgca gtattgcatc tagtttcaga atggtgttga tttccgagtc ttgatttgag    960

gggatgtttt tgaaggtaat attctgttaa acctgttgtt tcttagatta ctactacact   1020

aactaataac tgcactgcat tttatatttt tattgcatgg agttcttagc tgccttcctg   1080

cagcagcaga acatgaattt ctgaaaggcg ttctgctgaa catgaatttc agagagcgca   1140

gcgtgctttg tcaagtgcag tttcttagtt tcaaatctca tccatttcgt ttgatttgct   1200

ttgctatgaa catttcaaag aacgtgccgc tcaatcgaga atttgaagct gtagaaatgg   1260

attaaaaaac tgtatattct aacatcactt tatttccttc cttttttttta ccgcacattg   1320

taaacctgag acaaactatg tgatcctcca tcacaactca ttctaaaggc ttctctatct   1380

tcctccaaag caaaactcca aacaaagcca aaaaataaaa cctcactcat cacatctctt   1440

agctaatgag gaactaaaag gccaaaaagg gtgctcataa aaaaggctag caagtagcac   1500

tgtctatcac tctggagctc gaagggcgaa tt                                 1532
```

<210> SEQ ID NO 105

<211> LENGTH: 16914
<212> TYPE: DNA
<213> ORGANISM: Artificial sequence
<220> FEATURE:
<223> OTHER INFORMATION: binary vector derived from pRJB058
<220> FEATURE:
<221> NAME/KEY: misc_feature
<222> LOCATION: (47)..(71)
<223> OTHER INFORMATION: complement of LB
<220> FEATURE:
<221> NAME/KEY: promoter
<222> LOCATION: (187)..(986)
<223> OTHER INFORMATION: ZmAHAS
<220> FEATURE:
<221> NAME/KEY: misc_feature
<222> LOCATION: (987)..(2903)
<223> OTHER INFORMATION: cds encoding ZmAHAS
<220> FEATURE:
<221> NAME/KEY: terminator
<222> LOCATION: (2902)..(4112)
<223> OTHER INFORMATION: complement of ZmAHAS
<220> FEATURE:
<221> NAME/KEY: promoter
<222> LOCATION: (4177)..(6164)
<223> OTHER INFORMATION: ZmUbi
<220> FEATURE:
<221> NAME/KEY: Intron
<222> LOCATION: (5159)..(6164)
<223> OTHER INFORMATION: ZmUbi
<220> FEATURE:
<221> NAME/KEY: misc_feature
<222> LOCATION: (6209)..(6886)
<223> OTHER INFORMATION: cds encoding DsRed2
<220> FEATURE:
<221> NAME/KEY: terminator
<222> LOCATION: (6918)..(7170)
<223> OTHER INFORMATION: NOS
<220> FEATURE:
<221> NAME/KEY: misc_feature
<222> LOCATION: (7614)..(7877)
<223> OTHER INFORMATION: complement of GFP fragment
<220> FEATURE:
<221> NAME/KEY: misc_feature
<222> LOCATION: (7879)..(7901)
<223> OTHER INFORMATION: complement of TOI cloning site
<220> FEATURE:
<221> NAME/KEY: misc_feature
<222> LOCATION: (7957)..(9957)
<223> OTHER INFORMATION: complement: cds encoding GUS
<220> FEATURE:
<221> NAME/KEY: Intron
<222> LOCATION: (9384)..(9572)
<223> OTHER INFORMATION: complement of PIV2
<220> FEATURE:
<221> NAME/KEY: Intron
<222> LOCATION: (9990)..(10995)
<223> OTHER INFORMATION: complement of ZmUbi
<220> FEATURE:
<221> NAME/KEY: promoter
<222> LOCATION: (9990)..(11977)
<223> OTHER INFORMATION: complement of ZmUbi
<220> FEATURE:
<221> NAME/KEY: misc_feature
<222> LOCATION: (12147)..(12170)
<223> OTHER INFORMATION: complement of RB

<400> SEQUENCE: 105
gtgattttgt gccgagctgc cggtcgggga gctgttggct ggctggtggc aggatatatt 60
gtggtgtaaa caaattgacg cttagacaac ttaataacac attgcggacg tttttaatgt 120
actgaattgg atccgcccgg gcggtacccg gggatcctct agaactagtg gatcccccgg 180
gctgcaggtc aacggatcac ctatcaacat cccagctaaa aacagtaaaa agggggaaaa 240
cgtgggtgag ttgagtctgt cttgtggaaa aaacgtttta gtttctcctg gaattaacaa 300
taaaaacagt tgaacaagat tgactgttcc tccgggaggg tttggaacat cgttacagat 360

-continued

```
gtgagcgaaa ggtgaggaaa cagagcggag ggcttggagg tgacctcggt agtcgacgcc    420
ggagttgagc ttgatgacga caccgtactg gcgtaccagg cctagtagtg aacaccgggc    480
ctgaagctgt cgccgccgct gctcatcttg tgggctgtgc ccggtgtccc tgttgcggat    540
tgcgggtggc agcctggcag gtgggtgcga cccgtttgga ctccctgatc tgggcccttt    600
gtgtcagtac cgtctgtact ccgatgacat gcacaccgtc gtccacagtc aagtccacaa    660
tctcccctct ttttttaacg gaatagttca aaatctcctt gacgcacgct atcgtgtacc    720
agcgctcact ggacaccacg tttgtaatcc acgccgacac gtcggtccca cgtcgacagg    780
ccccaccgtc cggtctgtag cgtgtacgta ttcgggcgac ggacgtgtcg tcgtcgtctt    840
gcgagtccca ttcccatcac catctgagcc acacatcctc tgaacaaaag cagggaggcc    900
tctacgcaca tccccctttc tcccactccg tgtccgtggc acccacccca aaccctcgcg    960
ccgcctccga gacagccgcc gcaaccatgg ccaccgccgc cgccgcgtct accgcgctca   1020
ctggcgccac taccgctgcg cccaaggcga ggcgccgggc gcacctcctg gccacccgcc   1080
gcgccctcgc cgcgcccatc aggtgctcag cggcgtcacc cgccatgccg atggctcccc   1140
cggccacccc gctccggccg tggggcccca ccgatccccg caagggcgcc gacatcctcg   1200
tcgagtccct cgagcgctgc ggcgtccgcg acgtcttcgc ctacccccggc ggcgcgtcca  1260
tggagatcca ccaggcactc acccgctccc ccgtcatcgc caaccacctc ttccgccacg   1320
agcaagggga ggcctttgcg gcctccggct acgcgcgctc ctcgggccgc gtcggcgtct   1380
gcatcgccac ctccggcccc ggcgccacca accttgtctc cgcgctcgcc gacgcgctgc   1440
tcgattccgt ccccatggtc gccatcacgg gacaggtgcc gcgacgcatg attggcaccg   1500
acgccttcca ggagacgccc atcgtcgagg tcacccgctc catcaccaag cacaactacc   1560
tggtcctcga cgtcgacgac atcccccgcg tcgtgcagga ggctttcttc ctcgcctcct   1620
ctggtcgacc ggggccggtg cttgtcgaca tccccaagga catccagcag cagatggcgg   1680
tgcctgtctg ggacaagccc atgagtctgc ctgggtacat tgcgcgcctt cccaagcccc   1740
ctgcgactga gttgcttgag caggtgctgc gtcttgttgg tgaatcccgg cgccctgttc   1800
tttatgttgg cggtggctgc gcagcatctg gtgaggagtt gcgacgcttt gtggagctga   1860
ctggaatccc ggtcacaact actcttatgg gcctcggcaa cttccccagc gacgacccac   1920
tgtctctgcg catgctaggt atgcatggca cggtgtatgc aaattatgca gtggataagg   1980
ccgatctgtt gcttgcactt ggtgtgcggt ttgatgatcg tgtgacaggg aagattgagg   2040
cttttgcaag cagggctaag attgtgcacg ttgatattga tccggctgag attggcaaga   2100
acaagcagcc acatgtgtcc atctgtgcag atgttaagct tgctttgcag ggcatgaatg   2160
ctcttcttga aggaagcaca tcaaagaaga gctttgactt tggctcatgg aacgatgagt   2220
tggatcagca gaagagggaa ttcccccttg ggtataaaac atctaatgag gagatccagc   2280
cacaatatgc tattcaggtt cttgatgagc tgacgaaagg cgaggccatc atcggcacag   2340
gtgttgggca gcaccagatg tgggcggcac agtactacac ttacaagcgg ccaaggcagt   2400
ggttgtcttc agctggtctt ggggctatgg gatttggttt gccggctgct gctggtgctt   2460
ctgtggccaa cccaggtgtt actgttgttg acatcgatgg agatggtagc tttctcatga   2520
acgttcagga gctagctatg atccgaattg agaacctccc ggtgaaggtc tttgtgctaa   2580
acaaccagca cctggggatg gtggtgcagt gggaggacag gttctataag gccaacagag   2640
cgcacacata cttgggaaac ccagagaatg aaagtgagat atatccagat ttcgtgacga   2700
tcgccaaagg gttcaacatt ccagcggtcc gtgtgacaaa gaagaacgaa gtccgcgcag   2760
```

-continued

```
cgataaagaa gatgctcgag actccagggc cgtacctctt ggatataatc gtcccacacc   2820
aggagcatgt gttgcctatg atccctaatg gtggggcttt caaggatatg atcctggatg   2880
gtgatggcag gactgtgtac tgatctaaaa tccagcaagc aactgatcta aaatccagca   2940
agcaccgcct ccctgctagt acaagggtga tatgttttta tctgtgtgat gttctcctgt   3000
attctatctt tttttgtagg ccgtcagcta tctgttatgg taatcctatg tagcttccga   3060
ccttgtaatt gtgtagtctg ttgttttcct tctggcatgt gtcataagag atcatttaag   3120
tgccttttgc tacatataaa taagataata agcactgcta tgcagtggtt ctgaattggc   3180
ttctgttgcc aaatttaagt gtccaactgg tccttgcttt tgttttcgct attttttttcc   3240
tttttagtt  attattatat tggtaatttc aactcaacat atgatgtatg gaataatgct   3300
agggctgcaa tttcaaacta ttttacaaac cagaatggca ttttcgtggt ttgaggggag   3360
tgaaaaaaaa tgaggcattt gactgaatta gttacctgat ccattttcgt ggtttggatc   3420
attggaatta aattccattc taataatagt aattttggca tatatcaatt aagttaattc   3480
ggttttatgc aaaatatatt tgtatactat tattatcaag atgtcggaga tatttatatg   3540
ctacattttt actatacagg agtgagatga agagtgtcat gtaagttaca cagtagaaac   3600
aaattctatt aatgcataaa atcatttcca tcatccaccc tatgaatttg agatagacct   3660
atatctaaac tttgaaaagt ggttgaatat caaattccaa attaaataag ttattttatt   3720
gagtgaattc taatttctct aaaacgaagg gatctaaacg ccctctaaag ctaatttgga   3780
aactcaaact ttcttagcat tggaggggat tgagaaaaaa tattaattca ttttcatctc   3840
aatcattcaa tctccaaaga gatttgagtt ccttattagt ctgttccatg catcaaatcg   3900
gctcaatgtg tcattatttg ccatgacgat tgacgagttg ttctggggcc tagcgctttc   3960
cacgccgatg tgctggggcc tggtcctgga gaagacagct tgatatttaa agctatcaat   4020
tgtttcaatt gattcccact tcatttttct aaatgtagaa aacggtgacg tataagaaaa   4080
agaatgaatt aggactttta ttccgtacac taatctagag cggccgcaag cttgtacaac   4140
gcgtaccggt taattaaggt accaagcttc cgcggctgca gtgcagcgtg acccggtcgt   4200
gcccctctct agagataatg agcattgcat gtctaagtta taaaaaatta ccacatattt   4260
tttttgtcac acttgtttga agtgcagttt atctatcttt atacatatat ttaaacttta   4320
ctctacgaat aatataatct atagtactac aataatatca gtgttttaga gaatcatata   4380
aatgaacagt tagacatggt ctaaaggaca attgagtatt ttgacaacag gactctacag   4440
ttttatcttt ttagtgtgca tgtgttctcc ttttttttg caaatagctt cacctatata   4500
atacttcatc cattttatta gtacatccat ttagggttta gggttaatgg tttttataga   4560
ctaatttttt tagtacatct attttattct attttagcct ctaaattaag aaaactaaaa   4620
ctctatttta gtttttttat ttaatagttt agatataaaa tagaataaaa taaagtgact   4680
aaaaattaaa caaataccct ttaagaaatt aaaaaaaacta aggaaacatt tttcttgttt   4740
cgagtagata atgccagcct gttaaacgcc gtcgacgagt ctaacggaca ccaaccagcg   4800
aaccagcagc gtcgcgtcgg gccaagcgaa gcagacggca cggcatctct gtcgctgcct   4860
ctggacccct ctcgagagtt ccgctccacc gttggacttg ctccgctgtc ggcatccaga   4920
aattgcgtgg cggagcggca gacgtgagcc ggcacggcag gcggcctcct cctcctctca   4980
cggcaccggc agctacgggg gattcctttc ccaccgctcc ttcgctttcc cttcctcgcc   5040
cgccgtaata aatagacacc ccctccacac cctctttccc caacctcgtg ttgttcggag   5100
cgcacacaca cacaaccaga tctcccccaa atccacccgt cggcacctcc gcttcaaggt   5160
```

-continued acgccgctcg tcctcccccc cccccccccct ctctaccttc tctagatcgg cgttccggtc 5220
catggttagg gcccggtagt tctacttctg ttcatgtttg tgttagatcc gtgtttgtgt 5280
tagatccgtg ctgctagcgt tcgtacacgg atgcgacctg tacgtcagac acgttctgat 5340
tgctaacttg ccagtgtttc tctttgggga atcctgggat ggctctagcc gttccgcaga 5400
cgggatcgat ttcatgattt tttttgtttc gttgcatagg gtttggtttg cccttttcct 5460
ttatttcaat atatgccgtg cacttgtttg tcgggtcatc ttttcatgct ttttttgtc 5520
ttggttgtga tgatgtggtc tggttgggcg gtcgttctag atcggagtag aattctgttt 5580
caaactacct ggtggattta ttaattttgg atctgtatgt gtgtgccata catattcata 5640
gttacgaatt gaagatgatg gatggaaata tcgatctagg ataggtatac atgttgatgc 5700
gggttttact gatgcatata cagagatgct ttttgttcgc ttggttgtga tgatgtggtg 5760
tggttgggcg gtcgttcatt cgttctagat cggagtagaa tactgtttca aactacctgg 5820
tgtatttatt aattttggaa ctgtatgtgt gtgtcataca tcttcatagt tacgagttta 5880
agatggatgg aaatatcgat ctaggatagg tatacatgtt gatgtgggtt ttactgatgc 5940
atatacatga tggcatatgc agcatctatt catatgctct aaccttgagt acctatctat 6000
tataataaac aagtatgttt tataattatt tcgatcttga tatacttgga tgatggcata 6060
tgcagcagct atatgtggat ttttttagcc ctgccttcat acgctattta tttgcttggt 6120
actgtttctt ttgtcgatgc tcaccctgtt gtttggtgtt acttctgcag ggtacggatc 6180
cggcgcgcca ctagtcccgg tcgccaccat ggcctcctcc gagaacgtca tcaccgagtt 6240
catgcgcttc aaggtgcgca tggagggcac cgtgaacggc cacgagttcg agatcgaggg 6300
cgagggcgag ggccgcccct acgagggcca caacaccgtg aagctgaagg tgaccaaggg 6360
cggccccctg cccttcgcct gggacatcct gtcccccccag ttccagtacg gctccaaggt 6420
gtacgtgaag caccccgccg acatccccga ctacaagaag ctgtccttcc ccgagggctt 6480
caagtgggag cgcgtgatga acttcgagga cggcggcgtg gcgaccgtga cccaggactc 6540
ctccctgcag gacggctgct tcatctacaa ggtgaagttc atcggcgtga acttcccctc 6600
cgacggcccc gtgatgcaga agaagaccat gggctgggag gcctccaccg agcgcctgta 6660
cccccgcgac ggcgtgctga agggcgagac ccacaaggcc ctgaagctga aggacggcgg 6720
ccactacctg gtggagttca agtccatcta catggccaag aagcccgtgc agctgcccgg 6780
ctactactac gtggacgcca agctggacat cacctcccac aacgaggact acaccatcgt 6840
ggagcagtac gagcgcaccg agggccgcca ccacctgttc ctgtagcggc cgccctgcag 6900
ggagctcgaa tttccccgat cgttcaaaca tttggcaata aagtttctta agattgaatc 6960
ctgttgccgg tcttgcgatg attatcatat aatttctgtt gaattacgtt aagcatgtaa 7020
taattaacat gtaatgcatg acgttattta tgagatgggt ttttatgatt agagtcccgc 7080
aattatacat ttaatacgcg atagaaaaca aaatatagcg cgcaaactag gataaattat 7140
cgcgcgcggt gtcatctatg ttactagatc gggaattcgg gcccggccgg ccagatcttg 7200
attgtcgttt cccgccttca gtttctggca cgacaggttt cccgactgga aagcgggcag 7260
tgagcgcaac gcaattaata cgcgtaccgc tagccaggaa gagtttgtag aaacgcaaaa 7320
aggccatccg tcaggatggc cttctgctta gtttgatgcc tggcagttta tggcgggcgt 7380
cctgcccgcc accctccggg ccgttgcttc acaacgttca aatccgctcc cggcggattt 7440
gtcctactca ggagagcgtt caccgacaaa caacagataa aacgaaaggc ccagtcttcc 7500
gactgagcct ttcgttttat ttgatgcctg gcagttccct actctcgcgt taacgctagc 7560

-continued

```
atggatgttt tcccagtcac gacgttgtaa aacgacggcc agtcttaact agtgatgtag   7620
ccctcaggca tggcgctctt gaagaagtcg tgctgcttca tgtgatcggg gtagcgtgag   7680
aagcactgca cgccgtagct cagggtggtc accagggtgg gccagggcac aggcagcttg   7740
ccggtggtgc agatgaactt cagggtcagc ttgccgtagg tggcatcgcc ctcgccctcg   7800
ccgctcacgc tgaacttgtg gccattcaca tcgccattca gctcgatcag gatgggcacg   7860
atgccggtga acagctcggt ccgggcgccc cctagggagc tcggtagcaa ttcccgaggc   7920
tgtagccgac gatggtgcgc caggagagtt gttgattcat tgtttgcctc cctgctgcgg   7980
tttttcaccg aagttcatgc cagtccagcg tttttgcagc agaaaagccg ccgacttcgg   8040
tttgcggtcg cgagtgaaga tccctttctt gttaccgcca acgcgcaata tgccttgcga   8100
ggtcgcaaaa tcggcgaaat tccatacctg ttcaccgacg acggcgctga cgcgatcaaa   8160
gacgcggtga tacatatcca gccatgcaca ctgatactct tcactccaca tgtcggtgta   8220
cattgagtgc agcccggcta acgtatccac gccgtattcg gtgatgataa tcggctgatg   8280
cagtttctcc tgccaggcca gaagttcttt ttccagtacc ttctctgccg tttccaaatc   8340
gccgctttgg acataccatc cgtaataacg gttcaggcac agcacatcaa agagatcgct   8400
gatggtatcg gtgtgagcgt cgcagaacat tacattgacg caggtgatcg gacgcgtcgg   8460
gtcgagttta cgcgttgctt ccgccagtgg cgcgaaatat tcccgtgcac cttgcggacg   8520
ggtatccggt tcgttggcaa tactccacat caccacgctt gggtggtttt tgtcacgcgc   8580
tatcagctct ttaatcgcct gtaagtgcgc ttgctgagtt tccccgttga ctgcctcttc   8640
gctgtacagt tctttcggct tgttgcccgc ttcgaaacca atgcctaaag agaggttaaa   8700
gccgacagca gcagtttcat caatcaccac gatgccatgt tcatctgccc agtcgagcat   8760
ctcttcagcg taagggtaat gcgaggtacg gtaggagttg gccccaatcc agtccattaa   8820
tgcgtggtcg tgcaccatca gcacgttatc gaatcctttg ccacgcaagt ccgcatcttc   8880
atgacgacca aagccagtaa agtagaacgg tttgtggtta atcaggaact gttcgccctt   8940
cactgccact gaccggatgc cgacgcgaag cgggtagata tcacactctg tctggctttt   9000
ggctgtgacg cacagttcat agagataacc ttcacccggt tgccagaggt gcggattcac   9060
cacttgcaaa gtcccgctag tgccttgtcc agttgcaacc acctgttgat ccgcatcacg   9120
cagttcaacg ctgacatcac cattggccac cacctgccag tcaacagacg cgtggttaca   9180
gtcttgcgcg acatgcgtca ccacggtgat atcgtccacc caggtgttcg gcgtggtgta   9240
gagcattacg ctgcgatgga ttccggcata gttaaagaaa tcatggaagt aagactgctt   9300
tttcttgccg ttttcgtcgg taatcaccat tcccggcggg atagtctgcc agttcagttc   9360
gttgttcaca caaacggtga tacctgcaca tcaacaaatt ttggtcatat attagaaaag   9420
ttataaatta aaatatacac acttataaac tacagaaaag caattgctat atactacatt   9480
cttttatttt gaaaaaaata tttgaaatat tatattacta ctaattaatg ataattatta   9540
tatatatatc aaaggtagaa gcagaaactt acgtacactt ttcccggcaa taacatacgg   9600
cgtgacatcg gcttcaaatg gcgtatagcc gccctgatgc tccatcactt cctgattatt   9660
gacccacact ttgccgtaat gagtgaccgc atcgaaacgc agcacgatac gctggcctgc   9720
ccaacctttc ggtataaaga cttcgcgctg ataccagacg ttgcccgcat aattacgaat   9780
atctgcatcg gcgaactgat cgttaaaact gcctggcaca gcaattgccc ggctttcttg   9840
taacgcgctt tcccaccaac gctgaccaat tccacagttt tcgcgatcca gactgaatgc   9900
ccacaggccg tcgagttttt tgatttcacg ggttggggtt tctacaggac gtaacataag   9960
```

-continued

```
ggactgacct acccgggggt accctgcaga agtaacacca aacaacaggg tgagcatcga  10020
caaaagaaac agtaccaagc aaataaatag cgtatgaagg cagggctaaa aaaatccaca  10080
tatagctgct gcatatgcca tcatccaagt atatcaagat cgaaataatt ataaaacata  10140
cttgtttatt ataatagata ggtactcaag gttagagcat atgaatagat gctgcatatg  10200
ccatcatgta tatgcatcag taaaacccac atcaacatgt atacctatcc tagatcgata  10260
tttccatcca tcttaaactc gtaactatga agatgtatga cacacacata cagttccaaa  10320
attaataaat acaccaggta gtttgaaaca gtattctact ccgatctaga acgaatgaac  10380
gaccgcccaa ccacaccaca tcatcacaac caagcgaaca aaaagcatct ctgtatatgc  10440
atcagtaaaa cccgcatcaa catgtatacc tatcctagat cgatatttcc atccatcatc  10500
ttcaattcgt aactatgaat atgtatggca cacacataca gatccaaaat taataaatcc  10560
accaggtagt ttgaaacaga attctactcc gatctagaac gaccgcccaa ccagaccaca  10620
tcatcacaac caagacaaaa aaaagcatga aaagatgacc cgacaaacaa gtgcacggca  10680
tatattgaaa taaaggaaaa gggcaaacca aaccctatgc aacgaaacaa aaaaaatcat  10740
gaaatcgatc ccgtctgcgg aacggctaga gccatcccag gattccccaa agagaaacac  10800
tggcaagtta gcaatcagaa cgtgtctgac gtacaggtcg catccgtgta cgaacgctag  10860
cagcacggat ctaacacaaa cacggatcta acacaaacat gaacagaagt agaactaccg  10920
ggccctaacc atggaccgga acgccgatct agagaaggta gagagggggg gggggggga  10980
ggacgagcgg cgtaccttga agcggaggtg ccgacgggtg gatttggggg agatctggtt  11040
gtgtgtgtgt gcgctccgaa caacacgagg ttggggaaag agggtgtgga gggggtgtct  11100
atttattacg gcgggcgagg aagggaaagc gaaggagcgg tgggaaagga atcccccgta  11160
gctgccggtg ccgtgagagg aggaggaggc cgcctgccgt gccggctcac gtctgccgct  11220
ccgccacgca atttctggat gccgacagcg gagcaagtcc aacggtggag cggaactctc  11280
gagaggggtc cagaggcagc gacagagatg ccgtgccgtc tgcttcgctt ggcccgacgc  11340
gacgctgctg gttcgctggt tggtgtccgt tagactcgtc gacggcgttt aacaggctgg  11400
cattatctac tcgaaacaag aaaaatgttt ccttagtttt tttaatttct taaagggtat  11460
ttgtttaatt tttagtcact ttattttatt ctattttata tctaaactat taaataaaaa  11520
aactaaaata gagttttagt tttcttaatt tagaggctaa aatagaataa aatagatgta  11580
ctaaaaaaat tagtctataa aaaccattaa ccctaaaccc taaatggatg tactaataaa  11640
atggatgaag tattatatag gtgaagctat ttgcaaaaaa aaaggagaac acatgcacac  11700
taaaaagata aaactgtaga gtcctgttgt caaaatactc aattgtcctt tagaccatgt  11760
ctaactgttc atttatatga ttctctaaaa cactgatatt attgtagtac tatagattat  11820
attattcgta gagtaaagtt taaatatatg tataaagata gataaactgc acttcaaaca  11880
agtgtgacaa aaaaaatatg tggtaatttt ttataactta gacatgcaat gctcattatc  11940
tctagagagg ggcacgaccg ggtcacgctg cactgcagcc gcggaagctt gcatgcctgc  12000
aggcatgcaa gcttggcgcg ccgacccagc tttcttgtac aaagttggca ttataagaaa  12060
gcattgctta tcaatttgtt gcaacgaaca ggtcactatc agtcaaaata aaatcattat  12120
ttgccatcca gaaactatca gtgtttgaca ggatatattg gcgggtaaac ctaagagaaa  12180
agagcgttta ttagaataat cggatattta aaagggcgtg aaaaggttta tccgttcgtc  12240
catttgtatg tgcatgccaa ccacagggtt cccctcggga gtgcttggca ttccgtgcga  12300
taatgacttc tgttcaacca cccaaacgtc ggaaagcctg acgacggagc agcattccaa  12360
```

```
aaagatccct tggctcgtct gggtcggcta gaaggtcgag tgggctgctg tggcttgatc  12420
cctcaacgcg gtcgcggacg tagcgcagcg ccgaaaaatc ctcgatcgca aatccgacgc  12480
tgtcgaaaag cgtgatctgc ttgtcgctct ttcggccgac gtcctggcca gtcatcacgc  12540
gccaaagttc cgtcacagga tgatctggcg cgagttgctg gatctcgcct tcaatccggg  12600
tctgtggcgg gaactccacg aaaatatccg aacgcagcaa gatcgtcgac caattcttga  12660
agacgaaagg gcctcgtgat acgcctattt ttataggtta atgtcatgat aataatggtt  12720
tcttagacgt caggtggcac ttttcgggga aatgtgcgcg gaacccctat ttgtttattt  12780
ttctaaatac attcaaatat gtatccgctc atgagacaat aaccctgata aatgcttcaa  12840
taatattgaa aaaggaagag tatgagtatt caacatttcc gtgtcgccct tattcccttt  12900
tttgcggcat tttgccttcc tgtttttgct cacccagaaa cgctggtgaa agtaaaagat  12960
gctgaagatc agttgggtgc acgagtgggt tacatcgaac tggatctcaa cagcggtaag  13020
atccttgaga gttttcgccc cgaagaacgt tttccaatga tgagcacttt taaagttctg  13080
ctatgtggcg cggtattatc ccgtgttgac gccgggcaag agcaactcgg tcgccgcata  13140
cactattctc agaatgactt ggttgagtac tcaccagtca cagaaaagca tcttacggat  13200
ggcatgacag taagagaatt atgcagtgct gccataacca tgagtgataa cactgcggcc  13260
aacttacttc tgacaacgat cggaggaccg aaggagctaa ccgctttttt gcacaacatg  13320
ggggatcatg taactcgcct tgatcgttgg gaaccggagc tgaatgaagc cataccaaac  13380
gacgagcgtg acaccacgat gccggggggg gggggggggg acatgaggtt gccccgtatt  13440
cagtgtcgct gatttgtatt gtctgaagtt gtttttacgt taagttgatg cagatcaatt  13500
aatacgatac ctgcgtcata attgattatt tgacgtggtt tgatggcctc cacgcacgtt  13560
gtgatatgta gatgataatc attatcactt tacgggtcct ttccggtgat ccgacaggtt  13620
acggggcggc gacctcgcgg gttttcgcta tttatgaaaa ttttccggtt taaggcgttt  13680
ccgttcttct tcgtcataac ttaatgtttt tatttaaaat accctctgaa aagaaaggaa  13740
acgacaggtg ctgaaagcga gctttttggc ctctgtcgtt tcctttctct gtttttgtcc  13800
gtggaatgaa caatggaacc cccccccccc cccccctgcag caatggcaac aacgttgcgc  13860
aaactattaa ctggcgaact acttactcta gcttcccggc aacaattaat agactggatg  13920
gaggcggata aagttgcagg accacttctg cgctcggccc ttccggctgg ctggtttatt  13980
gctgataaat ctggagccgg tgagcgtggg tctcgcggta tcattgcagc actggggcca  14040
gatggtaagc cctcccgtat cgtagttatc tacacgacgg ggagtcaggc aactatggat  14100
gaacgaaata gacagatcgc tgagataggt gcctcactga ttaagcattg gtaactgtca  14160
gaccaagttt actcatatat actttagatt gatttaaaac ttcattttta atttaaaagg  14220
atctaggtga agatcctttt tgataatctc atgaccaaaa tcccttaacg tgagttttcg  14280
ttccactgag cgtcagaccc cgtagaaaag atcaaaggat cttcttgaga tccttttttt  14340
ctgcgcgtaa tctgctgctt gcaaacaaaa aaaccaccgc taccagcggt ggtttgtttg  14400
ccggatcaag agctaccaac tctttttccg aaggtaactg gcttcagcag agcgcagata  14460
ccaaatactg tccttctagt gtagccgtag ttaggccacc acttcaagaa ctctgtagca  14520
ccgcctacat acctcgctct gctaatcctg ttaccagtgg ctgctgccag tggcgataag  14580
tcgtgtctta ccgggttgga ctcaagacga tagttaccgg ataaggcgca gcggtcgggc  14640
tgaacggggg gttcgtgcac acagcccagc ttggagcgaa cgacctacac cgaactgaga  14700
tacctacagc gtgagctatg agaaagcgcc acgcttcccg aagggagaaa ggcggacagg  14760
```

-continued

```
tatccggtaa gcggcagggt cggaacagga gagcgcacga gggagcttcc agggggaaac  14820
gcctggtatc tttatagtcc tgtcgggttt cgccacctct gacttgagcg tcgatttttg  14880
tgatgctcgt caggggggcg gagcctatgg aaaaacgcca gcaacgcggc ctttttacgg  14940
ttcctggcct tttgctggcc ttttgctcac atgttctttc ctgcgttatc ccctgattct  15000
gtggataacc gtattaccgc ctttgagtga gctgataccg ctcgccgcag ccgaacgacc  15060
gagcgcagcg agtcagtgag cgaggaagcg gaagagcgcc tgatgcggta ttttctcctt  15120
acgcatctgt gcggtatttc acaccgcata tggtgcactc tcagtacaat ctgctctgat  15180
gccgcatagt taagccagta tacactccgc tatcgctacg tgactgggtc atggctgcgc  15240
cccgacaccc gccaacaccc gctgacgcgc cctgacgggc ttgtctgctc ccggcatccg  15300
cttacagaca agctgtgacc gtctccggga gctgcatgtg tcagaggttt tcaccgtcat  15360
caccgaaacg cgcgaggcag cagatccccc gatcaagtag atacactaca tatatctaca  15420
atagacatcg agccggaagg tgatgtttac tttcctgaaa tccccagcaa ttttaggcca  15480
gtttttaccc aagacttcgc ctctaacata aattatagtt accaaatctg gcaaaagggt  15540
tgaccggggg ggggggggaaa gccacgttgt gtctcaaaat ctctgatgtt acattgcaca  15600
agataaaaat atatcatcat gaacaataaa actgtctgct tacataaaca gtaatacaag  15660
gggtgttatg agccatattc aacgggaaac gtcttgctcg aggccgcgat taaattccaa  15720
catggatgct gatttatatg ggtataaatg ggctcgcgat aatgtcgggc aatcaggtgc  15780
gacaatctat cgattgtatg ggaagcccga tgcgccagag ttgtttctga aacatggcaa  15840
aggtagcgtt gccaatgatg ttacagatga gatggtcaga ctaaactggc tgacggaatt  15900
tatgcctctt ccgaccatca agcattttat ccgtactcct gatgatgcat ggttactcac  15960
cactgcgatc cccgggaaaa cagcattcca ggtattagaa gaatatcctg attcaggtga  16020
aaatattgtt gatgcgctgg cagtgttcct gcgccggttg cattcgattc ctgtttgtaa  16080
ttgtcctttt aacagcgatc gcgtatttcg tctcgctcag gcgcaatcac gaatgaataa  16140
cggtttggtt gatgcgagtg attttgatga cgagcgtaat ggctggcctg ttgaacaagt  16200
ctggaaagaa atgcataagc ttttgccatt ctcaccggat tcagtcgtca ctcatggtga  16260
tttctcactt gataacctta tttttgacga ggggaaatta ataggttgta ttgatgttgg  16320
acgagtcgga atcgcagacc gataccagga tcttgccatc ctatggaact gcctcggtga  16380
gttttctcct tcattacaga aacggctttt tcaaaaatat ggtattgata atcctgatat  16440
gaataaattg cagtttcatt tgatgctcga tgagtttttc taatcagaat tggttaattg  16500
gttgtaacac tggcagagca ttacgctgac ttgacgggac ggcggctttg ttgaataaat  16560
cgaacttttg ctgagttgaa ggatcagatc acgcatcttc ccgacaacgc agaccgttcc  16620
gtggcaaagc aaaagttcaa aatcaccaac tggtccacct acaacaaagc tctcatcaac  16680
cgtggctccc tcactttctg gctggatgat ggggcgattc aggatcaca ggcagcaacg  16740
ctctgtcatc gttacaatca acatgctacc ctccgcgaga tcatccgtgt ttcaaacccg  16800
gcagcttagt tgccgttctt ccgaatagca tcggtaacat gagcaaagtc tgccgcctta  16860
caacggctct cccgctgacg ccgtcccgga ctgatgggct gcctgtatcg agtg        16914
```

<210> SEQ ID NO 106
<211> LENGTH: 15919
<212> TYPE: DNA
<213> ORGANISM: Artificial sequence
<220> FEATURE:
<223> OTHER INFORMATION: binary vector derived from pRLI024
<220> FEATURE:

<221> NAME/KEY: misc_feature
<222> LOCATION: (47)..(71)
<223> OTHER INFORMATION: complement of LB
<220> FEATURE:
<221> NAME/KEY: promoter
<222> LOCATION: (187)..(986)
<223> OTHER INFORMATION: ZmAHAS
<220> FEATURE:
<221> NAME/KEY: misc_feature
<222> LOCATION: (987)..(2903)
<223> OTHER INFORMATION: cds encoding ZmAHAS
<220> FEATURE:
<221> NAME/KEY: terminator
<222> LOCATION: (2902)..(4112)
<223> OTHER INFORMATION: ZmAHAS
<220> FEATURE:
<221> NAME/KEY: promoter
<222> LOCATION: (4177)..(6164)
<223> OTHER INFORMATION: ZmUbi
<220> FEATURE:
<221> NAME/KEY: Intron
<222> LOCATION: (5159)..(6164)
<223> OTHER INFORMATION: ZmUbi
<220> FEATURE:
<221> NAME/KEY: misc_feature
<222> LOCATION: (6209)..(6886)
<223> OTHER INFORMATION: cds encoding DsRed2
<220> FEATURE:
<221> NAME/KEY: misc_feature
<222> LOCATION: (6902)..(6907)
<223> OTHER INFORMATION: complement of TOI cloning site
<220> FEATURE:
<221> NAME/KEY: misc_feature
<222> LOCATION: (6962)..(8962)
<223> OTHER INFORMATION: complement: cds encoding GUS
<220> FEATURE:
<221> NAME/KEY: Intron
<222> LOCATION: (8389)..(8577)
<223> OTHER INFORMATION: complement of PIV2
<220> FEATURE:
<221> NAME/KEY: Intron
<222> LOCATION: (8995)..(10000)
<223> OTHER INFORMATION: complement of ZmUbi
<220> FEATURE:
<221> NAME/KEY: promoter
<222> LOCATION: (8995)..(10982)
<223> OTHER INFORMATION: complement of ZmUbi
<220> FEATURE:
<221> NAME/KEY: misc_feature
<222> LOCATION: (11152)..(11175)
<223> OTHER INFORMATION: complement of RB

<400> SEQUENCE: 106
gtgattttgt gccgagctgc cggtcgggga gctgttggct ggctggtggc aggatatatt 60
gtggtgtaaa caaattgacg cttagacaac ttaataacac attgcggacg tttttaatgt 120
actgaattgg atccgcccgg gcggtacccg gggatcctct agaactagtg gatcccccgg 180
gctgcaggtc aacggatcac ctatcaacat cccagctaaa aacagtaaaa agggggaaaa 240
cgtgggtgag ttgagtctgt cttgtggaaa aaacgtttta gtttctcctg gaattaacaa 300
taaaaacagt tgaacaagat tgactgttcc tccgggaggg tttggaacat cgttacagat 360
gtgagcgaaa ggtgaggaaa cagagcggag ggcttggagg tgacctcggt agtcgacgcc 420
ggagttgagc ttgatgacga caccgtactg gcgtaccagg cctagtagtg aacaccgggc 480
ctgaagctgt cgccgccgct gctcatcttg tgggctgtgc ccggtgtccc tgttgcggat 540
tgcgggtggc agcctggcag gtgggtgcga cccgtttgga ctccctgatc tgggcccttt 600
gtgtcagtac cgtctgtact ccgatgacat gcacaccgtc gtccacagtc aagtccacaa 660
tctcccctct ttttttaacg gaatagttca aaatctcctt gacgcacgct atcgtgtacc 720
agcgctcact ggacaccacg tttgtaatcc acgccgacac gtcggtccca cgtcgacagg 780

-continued

```
ccccaccgtc cggtctgtag cgtgtacgta ttcgggcgac ggacgtgtcg tcgtcgtctt    840
gcgagtccca ttcccatcac catctgagcc acacatcctc tgaacaaaag cagggaggcc    900
tctacgcaca tccccctttc tcccactccg tgtccgtggc acccacccca aaccctcgcg    960
ccgcctccga gacagccgcc gcaaccatgg ccaccgccgc cgccgcgtct accgcgctca   1020
ctggcgccac taccgctgcg cccaaggcga ggcgccgggc gcacctcctg gccacccgcc   1080
gcgccctcgc cgcgcccatc aggtgctcag cggcgtcacc cgccatgccg atggctcccc   1140
cggccacccc gctccggccg tggggcccca ccgatccccg caagggcgcc gacatcctcg   1200
tcgagtccct cgagcgctgc ggcgtccgcg acgtcttcgc ctaccccggc ggcgcgtcca   1260
tggagatcca ccaggcactc acccgctccc ccgtcatcgc caaccacctc ttccgccacg   1320
agcaagggga ggcctttgcg gcctccggct acgcgcgctc ctcgggccgc gtcggcgtct   1380
gcatcgccac ctccggcccc ggcgccacca accttgtctc cgcgctcgcc gacgcgctgc   1440
tcgattccgt ccccatggtc gccatcacgg gacaggtgcc gcgacgcatg attggcaccg   1500
acgccttcca ggagacgccc atcgtcgagg tcacccgctc catcaccaag cacaactacc   1560
tggtcctcga cgtcgacgac atcccccgcg tcgtgcagga ggctttcttc ctcgcctcct   1620
ctggtcgacc ggggccggtg cttgtcgaca tccccaagga catccagcag cagatggcgg   1680
tgcctgtctg ggacaagccc atgagtctgc ctgggtacat tgcgcgcctt cccaagcccc   1740
ctgcgactga gttgcttgag caggtgctgc gtcttgttgg tgaatcccgg cgccctgttc   1800
tttatgttgg cggtggctgc gcagcatctg gtgaggagtt gcgacgcttt gtggagctga   1860
ctggaatccc ggtcacaact actcttatgg gcctcggcaa cttccccagc gacgacccac   1920
tgtctctgcg catgctaggt atgcatggca cggtgtatgc aaattatgca gtggataagg   1980
ccgatctgtt gcttgcactt ggtgtgcggt ttgatgatcg tgtgacaggg aagattgagg   2040
cttttgcaag cagggctaag attgtgcacg ttgatattga tccggctgag attggcaaga   2100
acaagcagcc acatgtgtcc atctgtgcag atgttaagct tgctttgcag ggcatgaatg   2160
ctcttcttga aggaagcaca tcaaagaaga gctttgactt tggctcatgg aacgatgagt   2220
tggatcagca gaagagggaa ttcccccttg ggtataaaac atctaatgag gagatccagc   2280
cacaatatgc tattcaggtt cttgatgagc tgacgaaagg cgaggccatc atcggcacag   2340
gtgttgggca gcaccagatg tgggcggcac agtactacac ttacaagcgg ccaaggcagt   2400
ggttgtcttc agctggtctt ggggctatgg gatttggttt gccggctgct gctggtgctt   2460
ctgtggccaa cccaggtgtt actgttgttg acatcgatgg agatggtagc tttctcatga   2520
acgttcagga gctagctatg atccgaattg agaacctccc ggtgaaggtc tttgtgctaa   2580
acaaccagca cctggggatg gtggtgcagt gggaggacag gttctataag gccaacagag   2640
cgcacacata cttgggaaac ccagagaatg aaagtgagat atatccagat ttcgtgacga   2700
tcgccaaagg gttcaacatt ccagcggtcc gtgtgacaaa gaagaacgaa gtccgcgcag   2760
cgataaagaa gatgctcgag actccagggc cgtacctctt ggatataatc gtcccacacc   2820
aggagcatgt gttgcctatg atccctaatg gtggggcttt caaggatatg atcctggatg   2880
gtgatggcag gactgtgtac tgatctaaaa tccagcaagc aactgatcta aaatccagca   2940
agcaccgcct ccctgctagt acaagggtga tatgttttta tctgtgtgat gttctcctgt   3000
attctatctt tttttgtagg ccgtcagcta tctgttatgg taatcctatg tagcttccga   3060
ccttgtaatt gtgtagtctg ttgttttcct tctggcatgt gtcataagag atcatttaag   3120
tgccttttgc tacatataaa taagataata agcactgcta tgcagtggtt ctgaattggc   3180
```

-continued

```
ttctgttgcc aaatttaagt gtccaactgg tccttgcttt tgttttcgct attttttttcc   3240
tttttagtt attattatat tggtaatttc aactcaacat atgatgtatg gaataatgct   3300
agggctgcaa tttcaaacta ttttacaaac cagaatggca ttttcgtggt ttgaggggag   3360
tgaaaaaaaa tgaggcattt gactgaatta gttacctgat ccattttcgt ggtttggatc   3420
attggaatta aattccattc taataatagt aattttggca tatatcaatt aagttaattc   3480
ggttttatgc aaaatatatt tgtatactat tattatcaag atgtcggaga tatttatatg   3540
ctacattttt actatacagg agtgagatga agagtgtcat gtaagttaca cagtagaaac   3600
aaattctatt aatgcataaa atcatttcca tcatccaccc tatgaatttg agatagacct   3660
atatctaaac tttgaaaagt ggttgaatat caaattccaa attaaataag ttattttatt   3720
gagtgaattc taatttctct aaaacgaagg gatctaaacg ccctctaaag ctaatttgga   3780
aactcaaact ttcttagcat tggaggggat tgagaaaaaa tattaattca ttttcatctc   3840
aatcattcaa tctccaaaga gatttgagtt ccttattagt ctgttccatg catcaaatcg   3900
gctcaatgtg tcattatttg ccatgacgat tgacgagttg ttctggggcc tagcgctttc   3960
cacgccgatg tgctggggcc tggtcctgga gaagacagct tgatatttaa agctatcaat   4020
tgtttcaatt gattcccact tcatttttct aaatgtagaa aacggtgacg tataagaaaa   4080
agaatgaatt aggactttta ttccgtacac taatctagag cggccgcaag cttgtacaac   4140
gcgtaccggt taattaaggt accaagcttc cgcggctgca gtgcagcgtg acccggtcgt   4200
gcccctctct agagataatg agcattgcat gtctaagtta taaaaaatta ccacatattt   4260
tttttgtcac acttgtttga agtgcagttt atctatcttt atacatatat ttaaacttta   4320
ctctacgaat aatataatct atagtactac aataatatca gtgttttaga gaatcatata   4380
aatgaacagt tagacatggt ctaaaggaca attgagtatt ttgacaacag gactctacag   4440
ttttatcttt ttagtgtgca tgtgttctcc tttttttttg caaatagctt cacctatata   4500
atacttcatc cattttatta gtacatccat ttagggttta gggttaatgg tttttataga   4560
ctaatttttt tagtacatct attttattct attttagcct ctaaattaag aaaactaaaa   4620
ctctatttta gtttttttat ttaatagttt agatataaaa tagaataaaa taaagtgact   4680
aaaaattaaa caaataccct ttaagaaatt aaaaaaaacta aggaaacatt tttcttgttt   4740
cgagtagata atgccagcct gttaaacgcc gtcgacgagt ctaacggaca ccaaccagcg   4800
aaccagcagc gtcgcgtcgg gccaagcgaa gcagacggca cggcatctct gtcgctgcct   4860
ctggacccct ctcgagagtt ccgctccacc gttggacttg ctccgctgtc ggcatccaga   4920
aattgcgtgg cggagcggca gacgtgagcc ggcacggcag gcggcctcct cctcctctca   4980
cggcaccggc agctacgggg gattcctttc ccaccgctcc ttcgctttcc cttcctcgcc   5040
cgcccgtaata aatagacacc ccctccacac cctctttccc caacctcgtg ttgttcggag   5100
cgcacacaca cacaaccaga tctcccccaa atccacccgt cggcacctcc gcttcaaggt   5160
acgccgctcg tcctcccccc cccccccct ctctaccttc tctagatcgg cgttccggtc   5220
catggttagg gcccggtagt tctacttctg ttcatgtttg tgttagatcc gtgtttgtgt   5280
tagatccgtg ctgctagcgt tcgtacacgg atgcgacctg tacgtcagac acgttctgat   5340
tgctaacttg ccagtgtttc tctttgggga atcctgggat ggctctagcc gttccgcaga   5400
cgggatcgat ttcatgattt tttttgtttc gttgcatagg gtttggtttg ccctttttcct   5460
ttatttcaat atatgccgtg cacttgtttg tcgggtcatc ttttcatgct tttttttgtc   5520
ttggttgtga tgatgtggtc tggttgggcg gtcgttctag atcggagtag aattctgttt   5580
```

-continued

```
caaactacct ggtggattta ttaattttgg atctgtatgt gtgtgccata catattcata   5640
gttacgaatt gaagatgatg gatggaaata tcgatctagg ataggtatac atgttgatgc   5700
gggttttact gatgcatata cagagatgct tttgttcgc ttggttgtga tgatgtggtg    5760
tggttgggcg gtcgttcatt cgttctagat cggagtagaa tactgtttca aactacctgg   5820
tgtatttatt aattttggaa ctgtatgtgt gtgtcataca tcttcatagt tacgagttta   5880
agatggatgg aaatatcgat ctaggatagg tatacatgtt gatgtgggtt ttactgatgc   5940
atatacatga tggcatatgc agcatctatt catatgctct aaccttgagt acctatctat   6000
tataataaac aagtatgttt tataattatt tcgatcttga tatacttgga tgatggcata   6060
tgcagcagct atatgtggat tttttagcc ctgccttcat acgctattta tttgcttggt    6120
actgtttctt ttgtcgatgc tcaccctgtt gtttggtgtt acttctgcag ggtacggatc   6180
cggcgcgcca ctagtcccgg tcgccaccat ggcctcctcc gagaacgtca tcaccgagtt   6240
catgcgcttc aaggtgcgca tggagggcac cgtgaacggc cacgagttcg agatcgaggg   6300
cgagggcgag ggccgcccct acgagggcca caacaccgtg aagctgaagg tgaccaaggg   6360
cggccccctg cccttcgcct gggacatcct gtccccccag ttccagtacg gctccaaggt   6420
gtacgtgaag caccccgccg acatccccga ctacaagaag ctgtccttcc ccgagggctt   6480
caagtgggag cgcgtgatga acttcgagga cggcggcgtg gcgaccgtga cccaggactc   6540
ctccctgcag gacggctgct tcatctacaa ggtgaagttc atcggcgtga acttcccctc   6600
cgacggcccc gtgatgcaga agaagaccat gggctgggag gcctccaccg agcgcctgta   6660
cccccgcgac ggcgtgctga agggcgagac ccacaaggcc ctgaagctga aggacggcgg   6720
ccactacctg gtggagttca agtccatcta catggccaag aagcccgtgc agctgcccgg   6780
ctactactac gtggacgcca agctggacat cacctcccac aacgaggact acaccatcgt   6840
ggagcagtac gagcgcaccg agggccgcca ccacctgttc ctgtagcggc cgccctgcag   6900
ggagctcggt agcaattccc gaggctgtag ccgacgatgg tgcgccagga gagttgttga   6960
ttcattgttt gcctccctgc tgcggttttt caccgaagtt catgccagtc cagcgttttt   7020
gcagcagaaa agccgccgac ttcggtttgc ggtcgcgagt gaagatccct ttcttgttac   7080
cgccaacgcg caatatgcct tgcgaggtcg caaaatcggc gaaattccat acctgttcac   7140
cgacgacggc gctgacgcga tcaaagacgc ggtgatacat atccagccat gcacactgat   7200
actcttcact ccacatgtcg gtgtacattg agtgcagccc ggctaacgta tccacgccgt   7260
attcggtgat gataatcggc tgatgcagtt tctcctgcca ggccagaagt tctttttcca   7320
gtaccttctc tgccgtttcc aaatcgccgc tttggacata ccatccgtaa taacggttca   7380
ggcacagcac atcaaagaga tcgctgatgg tatcggtgtg agcgtcgcag aacattacat   7440
tgacgcaggt gatcggacgc gtcgggtcga gtttacgcgt tgcttccgcc agtggcgcga   7500
aatattcccg tgcaccttgc ggacgggtat ccggttcgtt ggcaatactc cacatcacca   7560
cgcttgggtg gtttttgtca cgcgctatca gctctttaat cgcctgtaag tgcgcttgct   7620
gagtttcccc gttgactgcc tcttcgctgt acagttcttt cggcttgttg cccgcttcga   7680
aaccaatgcc taaagagagg ttaaagccga cagcagcagt ttcatcaatc accacgatgc   7740
catgttcatc tgcccagtcg agcatctctt cagcgtaagg gtaatgcgag gtacggtagg   7800
agttggcccc aatccagtcc attaatgcgt ggtcgtgcac catcagcacg ttatcgaatc   7860
ctttgccacg caagtccgca tcttcatgac gaccaaagcc agtaaagtag aacggtttgt   7920
ggttaatcag gaactgttcg cccttcactg ccactgaccg gatgccgacg cgaagcgggt   7980
```

-continued

```
agatatcaca ctctgtctgg cttttggctg tgacgcacag ttcatagaga taaccttcac   8040
ccggttgcca gaggtgcgga ttcaccactt gcaaagtccc gctagtgcct tgtccagttg   8100
caaccacctg ttgatccgca tcacgcagtt caacgctgac atcaccattg gccaccacct   8160
gccagtcaac agacgcgtgg ttacagtctt gcgcgacatg cgtcaccacg gtgatatcgt   8220
ccacccaggt gttcggcgtg gtgtagagca ttacgctgcg atggattccg gcatagttaa   8280
agaaatcatg gaagtaagac tgcttttttct tgccgttttc gtcggtaatc accattcccg   8340
gcgggatagt ctgccagttc agttcgttgt tcacacaaac ggtgatacct gcacatcaac   8400
aaattttggt catatattag aaaagttata aattaaaata tacacactta taaactacag   8460
aaaagcaatt gctatatact acattctttt attttgaaaa aaatatttga aatattatat   8520
tactactaat taatgataat tattatatat atatcaaagg tagaagcaga aacttacgta   8580
cacttttccc ggcaataaca tacggcgtga catcggcttc aaatggcgta tagccgccct   8640
gatgctccat cacttcctga ttattgaccc acactttgcc gtaatgagtg accgcatcga   8700
aacgcagcac gatacgctgg cctgcccaac ctttcggtat aaagacttcg cgctgatacc   8760
agacgttgcc cgcataatta cgaatatctg catcggcgaa ctgatcgtta aaactgcctg   8820
gcacagcaat tgcccggctt tcttgtaacg cgctttccca ccaacgctga ccaattccac   8880
agttttcgcg atccagactg aatgcccaca ggccgtcgag tttttgatt tcacgggttg   8940
gggtttctac aggacgtaac ataagggact gacctacccg gggtaccct gcagaagtaa   9000
caccaaacaa cagggtgagc atcgacaaaa gaaacagtac caagcaaata aatagcgtat   9060
gaaggcaggg ctaaaaaaat ccacatatag ctgctgcata tgccatcatc caagtatatc   9120
aagatcgaaa taattataaa acatacttgt ttattataat agataggtac tcaaggttag   9180
agcatatgaa tagatgctgc atatgccatc atgtatatgc atcagtaaaa cccacatcaa   9240
catgtatacc tatcctagat cgatatttcc atccatctta aactcgtaac tatgaagatg   9300
tatgacacac acatacagtt ccaaaattaa taaatacacc aggtagtttg aaacagtatt   9360
ctactccgat ctagaacgaa tgaacgaccg cccaaccaca ccacatcatc acaaccaagc   9420
gaacaaaaag catctctgta tatgcatcag taaaacccgc atcaacatgt atacctatcc   9480
tagatcgata tttccatcca tcatcttcaa ttcgtaacta tgaatatgta tggcacacac   9540
atacagatcc aaaattaata aatccaccag gtagtttgaa acagaattct actccgatct   9600
agaacgaccg cccaaccaga ccacatcatc acaaccaaga caaaaaaaag catgaaaaga   9660
tgacccgaca aacaagtgca cggcatatat tgaaataaag gaaaagggca aaccaaaccc   9720
tatgcaacga aacaaaaaaa atcatgaaat cgatcccgtc tgcggaacgg ctagagccat   9780
cccaggattc cccaaagaga aacactggca agttagcaat cagaacgtgt ctgacgtaca   9840
ggtcgcatcc gtgtacgaac gctagcagca cggatctaac acaaacacgg atctaacaca   9900
aacatgaaca gaagtagaac taccgggccc taaccatgga ccggaacgcc gatctagaga   9960
aggtagagag gggggggggg ggggaggacg agcggcgtac cttgaagcgg aggtgccgac  10020
gggtggattt gggggagatc tggttgtgtg tgtgtgcgct ccgaacaaca cgaggttggg  10080
gaaagagggt gtggaggggg tgtctattta ttacggcggg cgaggaaggg aaagcgaagg  10140
agcggtggga aaggaatccc ccgtagctgc cggtgccgtg agaggaggag gaggccgcct  10200
gccgtgccgg ctcacgtctg ccgctccgcc acgcaatttc tggatgccga cagcggagca  10260
agtccaacgg tggagcggaa ctctcgagag gggtccagag gcagcgacag agatgccgtg  10320
ccgtctgctt cgcttggccc gacgcgacgc tgctggttcg ctggttggtg tccgttagac  10380
```

-continued tcgtcgacgg cgtttaacag gctggcatta tctactcgaa acaagaaaaa tgtttcctta 10440
gtttttttaa tttcttaaag ggtatttgtt taatttttag tcactttatt ttattctatt 10500
ttatatctaa actattaaat aaaaaaacta aaatagagtt ttagttttct taatttagag 10560
gctaaaatag aataaaatag atgtactaaa aaaattagtc tataaaaacc attaacccta 10620
aaccctaaat ggatgtacta ataaaatgga tgaagtatta tataggtgaa gctatttgca 10680
aaaaaaaagg agaacacatg cacactaaaa agataaaact gtagagtcct gttgtcaaaa 10740
tactcaattg tcctttagac catgtctaac tgttcattta tatgattctc taaaacactg 10800
atattattgt agtactatag attatattat tcgtagagta aagtttaaat atatgtataa 10860
agatagataa actgcacttc aaacaagtgt gacaaaaaaa atatgtggta atttttttata 10920 acttagacat gcaatgctca ttatctctag agaggggcac gaccgggtca cgctgcactg 10980
cagccgcgga agcttgcatg cctgcaggca tgcaagcttg gcgcgccgac ccagctttct 11040
tgtacaaagt tggcattata agaaagcatt gcttatcaat ttgttgcaac gaacaggtca 11100
ctatcagtca aaataaaatc attatttgcc atccagaaac tatcagtgtt tgacaggata 11160
tattggcggg taaacctaag agaaaagagc gtttattaga ataatcggat atttaaaagg 11220
gcgtgaaaag gtttatccgt tcgtccattt gtatgtgcat gccaaccaca gggttcccct 11280
cgggagtgct tggcattccg tgcgataatg acttctgttc aaccacccaa acgtcggaaa 11340
gcctgacgac ggagcagcat tccaaaaaga tcccttggct cgtctgggtc ggctagaagg 11400
tcgagtgggc tgctgtggct tgatccctca acgcggtcgc ggacgtagcg cagcgccgaa 11460
aaatcctcga tcgcaaatcc gacgctgtcg aaaagcgtga tctgcttgtc gctctttcgg 11520
ccgacgtcct ggccagtcat cacgcgccaa agttccgtca caggatgatc tggcgcgagt 11580
tgctggatct cgccttcaat ccgggtctgt ggcgggaact ccacgaaaat atccgaacgc 11640
agcaagatcg tcgaccaatt cttgaagacg aaagggcctc gtgatacgcc tatttttata 11700
ggttaatgtc atgataataa tggtttctta gacgtcaggt ggcacttttc ggggaaatgt 11760
gcgcggaacc cctatttgtt tatttttcta aatacattca aatatgtatc cgctcatgag 11820
acaataaccc tgataaatgc ttcaataata ttgaaaaagg aagagtatga gtattcaaca 11880
tttccgtgtc gcccttattc ccttttttgc ggcattttgc cttcctgttt ttgctcaccc 11940
agaaacgctg gtgaaagtaa aagatgctga agatcagttg ggtgcacgag tgggttacat 12000
cgaactggat ctcaacagcg gtaagatcct tgagagtttt cgccccgaag aacgttttcc 12060
aatgatgagc acttttaaag ttctgctatg tggcgcggta ttatcccgtg ttgacgccgg 12120
gcaagagcaa ctcggtcgcc gcatacacta ttctcagaat gacttggttg agtactcacc 12180
agtcacagaa aagcatctta cggatggcat gacagtaaga gaattatgca gtgctgccat 12240
aaccatgagt gataacactg cggccaactt acttctgaca acgatcggag gaccgaagga 12300
gctaaccgct tttttgcaca acatggggga tcatgtaact cgccttgatc gttgggaacc 12360
ggagctgaat gaagccatac caaacgacga gcgtgacacc acgatgccgg gggggggggg 12420
gggggacatg aggttgcccc gtattcagtg tcgctgattt gtattgtctg aagttgtttt 12480
tacgttaagt tgatgcagat caattaatac gatacctgcg tcataattga ttatttgacg 12540
tggtttgatg gcctccacgc acgttgtgat atgtagatga taatcattat cactttacgg 12600
gtcctttccg gtgatccgac aggttacggg gcggcgacct cgcgggtttt cgctatttat 12660
gaaaattttc cggtttaagg cgtttccgtt cttcttcgtc ataacttaat gtttttattt 12720
aaaataccct ctgaaaagaa aggaaacgac aggtgctgaa agcgagcttt ttggcctctg 12780
tcgtttcctt tctctgtttt tgtccgtgga atgaacaatg gaaccccccc cccccccccc 12840
tgcagcaatg gcaacaacgt tgcgcaaact attaactggc gaactactta ctctagcttc 12900
ccggcaacaa ttaatagact ggatggaggc ggataaagtt gcaggaccac ttctgcgctc 12960
ggcccttccg gctggctggt ttattgctga taaatctgga gccggtgagc gtgggtctcg 13020
cggtatcatt gcagcactgg ggccagatgg taagccctcc cgtatcgtag ttatctacac 13080
gacggggagt caggcaacta tggatgaacg aaatagacag atcgctgaga taggtgcctc 13140
actgattaag cattggtaac tgtcagacca agtttactca tatatacttt agattgattt 13200
aaaacttcat ttttaattta aaaggatcta ggtgaagatc ctttttgata atctcatgac 13260
caaaatccct taacgtgagt tttcgttcca ctgagcgtca gaccccgtag aaaagatcaa 13320
aggatcttct tgagatcctt tttttctgcg cgtaatctgc tgcttgcaaa caaaaaaacc 13380
accgctacca gcggtggttt gtttgccgga tcaagagcta ccaactcttt ttccgaaggt 13440
aactggcttc agcagagcgc agataccaaa tactgtcctt ctagtgtagc cgtagttagg 13500
ccaccacttc aagaactctg tagcaccgcc tacatacctc gctctgctaa tcctgttacc 13560
agtggctgct gccagtggcg ataagtcgtg tcttaccggg ttggactcaa gacgatagtt 13620
accggataag gcgcagcggt cgggctgaac ggggggttcg tgcacacagc ccagcttgga 13680
gcgaacgacc tacaccgaac tgagatacct acagcgtgag ctatgagaaa gcgccacgct 13740
tcccgaaggg agaaaggcgg acaggtatcc ggtaagcggc agggtcggaa caggagagcg 13800
cacgagggag cttccagggg gaaacgcctg gtatctttat agtcctgtcg ggtttcgcca 13860
cctctgactt gagcgtcgat ttttgtgatg ctcgtcaggg gggcggagcc tatggaaaaa 13920
cgccagcaac gcggcctttt tacggttcct ggccttttgc tggccttttg ctcacatgtt 13980
ctttcctgcg ttatcccctg attctgtgga taaccgtatt accgcctttg agtgagctga 14040
taccgctcgc cgcagccgaa cgaccgagcg cagcgagtca gtgagcgagg aagcggaaga 14100
gcgcctgatg cggtattttc tccttacgca tctgtgcggt atttcacacc gcatatggtg 14160
cactctcagt acaatctgct ctgatgccgc atagttaagc cagtatacac tccgctatcg 14220
ctacgtgact gggtcatggc tgcgccccga cacccgccaa cacccgctga cgcgccctga 14280
cgggcttgtc tgctcccggc atccgcttac agacaagctg tgaccgtctc cgggagctgc 14340
atgtgtcaga ggttttcacc gtcatcaccg aaacgcgcga ggcagcagat cccccgatca 14400
agtagataca ctacatatat ctacaataga catcgagccg gaaggtgatg tttactttcc 14460
tgaaatcccc agcaatttta ggccagtttt tacccaagac ttcgcctcta acataaatta 14520
tagttaccaa atctggcaaa agggttgacc gggggggggg ggaaagccac gttgtgtctc 14580
aaaatctctg atgttacatt gcacaagata aaaatatatc atcatgaaca ataaaactgt 14640
ctgcttacat aaacagtaat acaaggggtg ttatgagcca tattcaacgg gaaacgtctt 14700
gctcgaggcc gcgattaaat tccaacatgg atgctgattt atatgggtat aaatgggctc 14760
gcgataatgt cgggcaatca ggtgcgacaa tctatcgatt gtatgggaag cccgatgcgc 14820
cagagttgtt tctgaaacat ggcaaaggta gcgttgccaa tgatgttaca gatgagatgg 14880
tcagactaaa ctggctgacg gaatttatgc ctcttccgac catcaagcat tttatccgta 14940
ctcctgatga tgcatggtta ctcaccactg cgatccccgg gaaaacagca ttccaggtat 15000
tagaagaata tcctgattca ggtgaaaata ttgttgatgc gctggcagtg ttcctgcgcc 15060
ggttgcattc gattcctgtt tgtaattgtc cttttaacag cgatcgcgta tttcgtctcg 15120
ctcaggcgca atcacgaatg aataacggtt tggttgatgc gagtgatttt gatgacgagc 15180
gtaatggctg gcctgttgaa caagtctgga aagaaatgca taagcttttg ccattctcac 15240
cggattcagt cgtcactcat ggtgatttct cacttgataa ccttattttt gacgagggga 15300
aattaatagg ttgtattgat gttggacgag tcggaatcgc agaccgatac caggatcttg 15360
ccatcctatg gaactgcctc ggtgagtttt ctccttcatt acagaaacgg ctttttcaaa 15420
aatatggtat tgataatcct gatatgaata aattgcagtt tcatttgatg ctcgatgagt 15480
ttttctaatc agaattggtt aattggttgt aacactggca gagcattacg ctgacttgac 15540
gggacggcgg ctttgttgaa taaatcgaac ttttgctgag ttgaaggatc agatcacgca 15600
tcttcccgac aacgcagacc gttccgtggc aaagcaaaag ttcaaaatca ccaactggtc 15660
cacctacaac aaagctctca tcaaccgtgg ctccctcact ttctggctgg atgatggggc 15720
gattcaggga tcacaggcag caacgctctg tcatcgttac aatcaacatg ctaccctccg 15780
cgagatcatc cgtgtttcaa acccggcagc ttagttgccg ttcttccgaa tagcatcggt 15840
aacatgagca aagtctgccg ccttacaacg gctctcccgc tgacgccgtc ccggactgat 15900
gggctgcctg tatcgagtg 15919

<210> SEQ ID NO 107
<211> LENGTH: 1499
<212> TYPE: DNA
<213> ORGANISM: Oryza sativa
<220> FEATURE:
<221> NAME/KEY: terminator
<222> LOCATION: (1)..(1499)

<400> SEQUENCE: 107
cagagtgata gacagtgcta cttgctagcc ttttttatga gcaccctttt tggcctttta 60
gttcctcatt agctaagaga tgtgatgagt gaggttttat tttttggctt tgtttggagt 120
tttgctttgg aggaagatag agaagccttt agaatgagtt gtgatggagg atcacatagt 180
ttgtctcagg tttacaatgt gcggtaaaaa aaaggaagga aataaagtga tgttagaata 240
tacagttttt taatccattt ctacagcttc aaattctcga ttgagcggca cgttctttga 300
aatgttcata gcaaagcaaa tcaaacgaaa tggatgagat ttgaaactaa gaaactgcac 360
ttgacaaagc acgctgcgct ctctgaaatt catgttcagc agaacgcctt tcagaaattc 420
atgttctgct gctgcaggaa ggcagctaag aactccatgc aataaaaata taaaatgcag 480
tgcagttatt agttagtgta gtagtaatct aagaaacaac aggtttaaca gaatattacc 540
ttcaaaaaca tcccctcaaa tcaagactcg gaaatcaaca ccattctgaa actagatgca 600
atactgcgct cctaatggaa tcttcagtgg ttactcctac acgccactaa aaaaaacggg 660
ctttggaaaa acgtcaccct gaaaacaaga gctcagtaaa aataccactc taaaatcttg 720
cagcatgcat tatcacaaaa gcagatcaat ccgtaattgt atttatgctg catataccgt 780
gatattttct gtgatcctct gcactatctt cagctcatca gctgcatatt ttgaagccgg 840
actgatggct catcgctttg tttcggctta ttgtgatagc catccatgcg ttgacgaaag 900
atttagatat atcacaattt taaccaagtt cagagcaatg ttagctttag ctgatgatat 960
acacggcgca ctgattgccg ccgttatttt cagagccttg taaaacctga aacaaattgt 1020
gtctccaaat tcttactagt actgcagaca tagcggattt gttttcagga tgaattatca 1080
caaaggtaag tcaattcata gccatattac gcaagttcaa aactgcaggc cacaccatac 1140
gtttctgaaa gtagaaacaa gagatcttgc agcagatcac cactaaagaa gcagtaaccg 1200
caaaaaatta taacataatc cagaattaac acttcgcagc attactgaat tcactttaat 1260
agcacttctc atcatgaact agtacaacaa cataactgtc cagtggaaat gtgaaatgca 1320

-continued

```
tacaccaagt aatggtccat aacatgaact atatggatac aacaacgttc ttatttcgct   1380

catatataca tgaaataagt cttgcacgtc ttggttactt aataggtgcg ataatcgccg   1440

taggctttta gaagaagaaa aaaaagtgag cctgcaaagt tcctggggac agttgaaga    1499


<210> SEQ ID NO 108
<211> LENGTH: 1499
<212> TYPE: DNA
<213> ORGANISM: Oryza sativa
<220> FEATURE:
<221> NAME/KEY: terminator
<222> LOCATION: (1)..(1499)

<400> SEQUENCE: 108

gagacaaact atgtgatcct ccatcacaac tcattctaaa ggcttctcta tcttcctcca     60

aagcaaaact ccaaacaaag ccaaaaaata aaacctcact catcacatct cttagctaat    120

gaggaactaa aaggccaaaa agggtgctca taaaaaaggc tagcaagtag cactgtctat    180

cactctgtct tcaactgtcc ccaggaactt tgcaggctca cttttttttc ttcttctaaa    240

agcctacggc gattatcgca cctattaagt aaccaagacg tgcaagactt atttcatgta    300

tatatgagcg aaataagaac gttgttgtat ccatatagtt catgttatgg accattactt    360

ggtgtatgca tttcacattt ccactggaca gttatgttgt tgtactagtt catgatgaga    420

agtgctatta aagtgaattc agtaatgctg cgaagtgtta attctggatt atgttataat    480

tttttgcggt tactgcttct ttagtggtga tctgctgcaa gatctcttgt ttctactttc    540

agaaacgtat ggtgtggcct gcagttttga acttgcgtaa tatggctatg aattgactta    600

cctttgtgat aattcatcct gaaaacaaat ccgctatgtc tgcagtacta gtaagaattt    660

ggagacacaa tttgtttcag gttttacaag gctctgaaaa taacggcggc aatcagtgcg    720

ccgtgtatat catcagctaa agctaacatt gctctgaact tggttaaaat tgtgatatat    780

ctaaatcttt cgtcaacgca tggatggcta tcacaataag ccgaaacaaa gcgatgagcc    840

atcagtccgg cttcaaaata tgcagctgat gagctgaaga tagtgcagag gatcacagaa    900

aatatcacgg tatatgcagc ataaatacaa ttacggattg atctgctttt gtgataatgc    960

atgctgcaag attttagagt ggtatttta ctgagctctt gttttcaggg tgacgttttt    1020

ccaaagcccg tttttttag tggcgtgtag gagtaaccac tgaagattcc attaggagcg    1080

cagtattgca tctagtttca gaatggtgtt gatttccgag tcttgatttg aggggatgtt   1140

tttgaaggta atattctgtt aaacctgttg tttcttagat tactactaca ctaactaata   1200

actgcactgc attttatatt tttattgcat ggagttctta gctgccttcc tgcagcagca   1260

gaacatgaat ttctgaaagg cgttctgctg aacatgaatt tcagagagcg cagcgtgctt   1320

tgtcaagtgc agtttcttag tttcaaatct catccatttc gtttgatttg ctttgctatg   1380

aacatttcaa agaacgtgcc gctcaatcga gaatttgaag ctgtagaaat ggattaaaaa   1440

actgtatatt ctaacatcac tttatttcct tcctttttt taccgcacat tgtaaacct     1499
```